US011291655B2

(12) United States Patent
Castro et al.

(10) Patent No.: US 11,291,655 B2
(45) Date of Patent: Apr. 5, 2022

(54) RAD51 INHIBITORS

(71) Applicant: Cyteir Therapeutics, Inc., Lexington, MA (US)

(72) Inventors: Alfredo C. Castro, Woburn, MA (US); Casey Cameron McComas, Phoenixville, PA (US); Joseph Vacca, Telford, PA (US)

(73) Assignee: Cyteir Therapeutics, Inc., Lexington, MA (US)

( * ) Notice: Subject to any disclaimer, the term of this patent is extended or adjusted under 35 U.S.C. 154(b) by 0 days.

(21) Appl. No.: 16/623,850

(22) PCT Filed: Jul. 11, 2018

(86) PCT No.: PCT/US2018/041588
§ 371 (c)(1),
(2) Date: Dec. 18, 2019

(87) PCT Pub. No.: WO2019/014315
PCT Pub. Date: Jan. 17, 2019

(65) Prior Publication Data
US 2020/0129484 A1   Apr. 30, 2020

Related U.S. Application Data

(60) Provisional application No. 62/530,972, filed on Jul. 11, 2017.

(51) Int. Cl.
| | | |
|---|---|---|
| *A61K 31/427* | (2006.01) | |
| *A61K 31/426* | (2006.01) | |
| *A61K 31/496* | (2006.01) | |
| *A61K 45/06* | (2006.01) | |
| *C07D 277/28* | (2006.01) | |
| *C07D 417/10* | (2006.01) | |
| *C07D 417/12* | (2006.01) | |

(52) U.S. Cl.
CPC .......... *A61K 31/427* (2013.01); *A61K 31/426* (2013.01); *A61K 31/496* (2013.01); *A61K 45/06* (2013.01); *C07D 277/28* (2013.01); *C07D 417/10* (2013.01); *C07D 417/12* (2013.01)

(58) Field of Classification Search
None
See application file for complete search history.

(56) References Cited

U.S. PATENT DOCUMENTS

| | | | | |
|---|---|---|---|---|
| 7,067,537 | B2 * | 6/2006 | Kuroda | A61K 31/4439 514/342 |
| 10,336,746 | B1 | 7/2019 | Castro et al. | |
| 10,590,122 | B2 | 3/2020 | Castro et al. | |
| 17,363,099 | | 6/2021 | Castro et al. | |
| 11,084,812 | B2 | 8/2021 | Castro et al. | |
| 2002/0086840 | A1 | 7/2002 | Zarling et al. | |
| 2020/0291014 | A1 | 9/2020 | LaPierre et al. | |

FOREIGN PATENT DOCUMENTS

| | | | |
|---|---|---|---|
| WO | WO 2013/105985 A1 | 7/2013 | |
| WO | WO 2016/140971 A1 | 9/2016 | |

OTHER PUBLICATIONS

Database Registry Chemical Abstracts Service, Columbus, Ohio, Accession No. RN 1465351-63-6, Entered STN: Oct. 29, 2013.*
Budke, B. et al. (2016) "Recent developments using small molecules to target RAD51: How to best modulate RAD51 for anticancer therapy?" ChemMedChem, 11:2468-2473.
Chen, C-F. et al. (1999) "Expression of BRC Repeats in Breast Cancer Cells Dismpts the BRCA2-Rad51 Complex and Leads to Radiation Hypersensitivity and Loss of $G_2$/M Checkpoint Control" J Biol Chem, 274(46):32931-32935.
Collis, S.J. et al. (2001) "Ribozyme minigene-mediated RAD51 down-regulation increases radiosensitivity of human prostate cancer cells" Nucleic Acids Res, 29(7):1534-1538.
Connell, P.P. et al. (2004) "A Hot Spot for RAD51C Interaction Revealed by a Peptide That Sensitizes Cells to Cisplatin" Cancer Research, 64:3002-3005.
Cui, X. et al. (1999) "The XRCC2 and XRCC3 repair genes are required for chromosome stability in mammalian cells" Mutat Res, 434:75-88.
Godthelp, B.C. et al. (2002) "Mammalian Rad51C contributes to DNA cross-link resistance, sister chromatid cohesion and genomic stability" Nucleic Acids Res, 30(10):2172-2182.
Hansen, L.T. et al. (2003) "The Role of RAD51 in etoposide (VP16) Resistance in Small Cell Lung Cancer" Int J Cancer, 105:472-479.
Ito, M. et al. (2005) "Rad51 siRNA delivered by HVJ envelope vector enhances the anti-cancer effect of cisplatin" J Gene Med, 7:1044-1052.
Liu, N. et al. (2002) "Involvement of Rad51C in two distinct protein complexes of Rad51 paralogs in human cells" Nucleic Acids Res, 30:1009-1015.
Liu, N. et al. (May 1998) "XRCC2 and XRCC3, New Human Rad51-Family Members, Promote Chromosome Stability and Protect against DNA Cross-Links and Other Damages" Molecular Cell, 1:783-793.
Ohnishi, T. et al. (1998) "In Vitro and in Vivo Potentiation of Radiosensitivity of Malignant Gliomas by Antisense Inhibition of the RAD51 Gene" Biochemical and Biophysical Research Communications, 245:319-324.
Russell, J.S. et al. (Nov. 1, 2003) "Gleevec-Mediated Inhibition of Rad51 Expression and Enhancement of Tumor Cell Radiosensitivity" Cancer Research, 63:7377-7383.

(Continued)

*Primary Examiner* — Samantha L Shterengarts
(74) *Attorney, Agent, or Firm* — Cooley LLP; Matthew Pavao; Chen Chen

(57) ABSTRACT

This application is directed to inhibitors of RAD51, and methods for their use, such as to treat or prevent conditions involving mitochondrial defects.

20 Claims, No Drawings

(56) References Cited

OTHER PUBLICATIONS

Takata, M. et al. (2001) "Chromosome Instability and Defective Recombinational Repair in Knockout Mutants of the Five Rad51 Paralogs" Molecular and Cellular Biology, 21(8):2858-2866.
Tebbs, R.S. et al. (Jul. 1995) "Correction of chromosomal instability and sensitivity to diverse mutagens by a cloned cDNA of the XRCC3 DNA repair gene" Proc Natl Acad Sci USA, 92:6354-6358.
Thompson, L.H. and D. Schild (2001) "Homologous recombinational repair of DNA ensures mammalian chromosome stability" Mutat Res, 477:131-153.

* cited by examiner

RAD51 INHIBITORS

CROSS-REFERENCES TO RELATED APPLICATIONS

This application is a U.S. National Phase application, filed under 35 U.S.C. § 371, of International Application No. PCT/US2018/041588, filed on Jul. 11, 2018, which claims the benefit of U.S. Provisional Application No. 62/530,972, filed on Jul. 11, 2017. The entire teachings of the aforementioned applications are incorporated herein by reference.

FIELD OF THE INVENTION

This application is directed to inhibitors of RAD51, and methods for their use, such as to treat conditions such as cancer, autoimmune disease, immune deficiency, or neurodegenerative disease.

BACKGROUND OF THE INVENTION

Homologous recombination (HR) has multiple roles in DNA repair including the repair of DNA double-strand breaks (DSBs) and recovery from the replication blocking lesions formed by DNA cross-linking agents. HR repairs DSBs by locating a homologous stretch of DNA and replicating the missing genetic information from the homologous template. Numerous studies have also shown HR to be critically important in the maintenance of genomic stability (Thompson and Schild, "Homologous recombinational repair of DNA ensures mammalian chromosome stability," Mutat. Res., 477:131-153, 2001; Godthelp et al., "Mammalian Rad51C contributes to DNA cross-link resistance, sister chromatid cohesion and genomic stability," Nucleic Acids Res., 30:2172-2182, 2002; Tebbs et al., "Correction of chromosomal instability and sensitivity to diverse mutagens by a cloned cDNA of the XRCC3 DNA repair gene," Proc. Natl. Acad. Sci. USA, 92:6354-6358, 1995; Takata et al., "Chromosome instability and defective recombinational repair in knockout mutants of the five Rad51 paralogs," Mol. Cell Biol., 21:2858-2866, 2001; Liu et al., "Involvement of Rad51C in two distinct protein complexes of Rad51 paralogs in human cells," Nucleic Acids Res., 30:1009-1015, 2002; Cui et al., "The XRCC2 and XRCC3 repair genes are required for chromosome stability in mammalian cells," Mutat. Res., 434:75-88, 1999; Thompson and Schild, "Homologous recombinational repair of DNA ensures mammalian chromosome stability," Mutat. Res., 477:131-153, 2001).

RAD51 is a eukaryote gene. The protein encoded by this gene is a member of the RAD51 protein family which assists in repair of DNA double strand breaks. RAD51 family members are homologous to the bacterial RecA, Archaeal RadA and yeast Rad51. The protein is highly conserved in most eukaryotes, from yeast to humans. In humans, RAD51 is a 339-amino acid protein that plays a major role in homologous recombination of DNA during double strand break (DSB) repair. RAD51 catalyzes strand transfer between a broken sequence and its undamaged homologue to allow re-synthesis of the damaged region (see homologous recombination models).

Studies have demonstrated a sensitization to certain DNA damaging therapies associated with cellular defects in proteins that promote HR DNA repair. This sensitization is particularly dramatic for DNA cross-linking chemotherapeutic drugs (30-100 times) and ionizing radiation (3-5 times) (Godthelp et al., "Mammalian Rad51C contributes to DNA cross-link resistance, sister chromatid cohesion and genomic stability," Nucleic Acids Res., 30:2172-2182, 2002; Tebbs et al., "Correction of chromosomal instability and sensitivity to diverse mutagens by a cloned cDNA of the XRCC3 DNA repair gene," Proc. Natl. Acad. Sci. USA, 92:6354-6358, 1995; Takata et al., "Chromosome instability and defective recombinational repair in knockout mutants of the five Rad51 paralogs," Mol. Cell Biol., 21:2858-2866, 2001; Liu et al., "XRCC2 and XRCC3, new human Rad51-family members, promote chromosome stability and protect against DNA cross-links and other damages," Mol. Cell, 1:783-793, 1998).

Several groups have recently demonstrated that HR can be partially inhibited in order to sensitize cells to DNA damaging therapies. Inhibition of XRCC3 (a RAD51 paralog protein), has been demonstrated using a synthetic peptide corresponding to another paralog protein. This peptide sensitized Chinese Hamster Ovary (CHO) cells to cisplatin and inhibited the formation of sub-nuclear RAD51 foci in response to DNA damage (Connell et al., Cancer Res., 64:3002-3005, 2004). Other researchers have inhibited the expression of the RAD51 protein itself (Russell et al., Cancer Res., 63:7377-7383, 2003; Hansen et al., Int. J. Cancer, 105:472-479, 2003; Ohnishi et al., Biochem. Biophys. Res. Commun., 245:319-324, 1998; Ito et al., J. Gene Med., 7(8):1044-1052, 2005; Collins et al., Nucleic Acids Res., 29:1534-1538, 2001) or blocked its function by over-expressing a dominant negative BRC peptide fragment derived from BRCA2 (Chen et al., J. Biol. Chem., 274: 32931-32935, 1999).

In view of the connection between increased sensitivity to certain DNA damaging therapies and cellular defects in HR DNA repair-related proteins, there is a need for additional compounds that inhibit RAD51.

SUMMARY OF THE INVENTION

Applicant has now discovered novel compounds which are effective inhibitors of RAD51 (see Examples 1-18).

The present invention provides a compound represented by Structural Formula I:

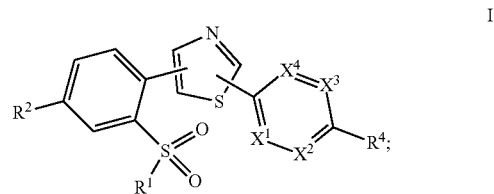

or a pharmaceutically acceptable salt thereof. The definition of each variable is provided below.

The present invention also provides a pharmaceutical composition comprising a compound as described herein and a pharmaceutically acceptable carrier or diluent.

The present invention further provides a method of treating cancer, autoimmune disease, immune deficiency, or neurodegenerative disease, the method comprises administering to a subject in need thereof an effective amount of a compound of disclosed herein or a pharmaceutically acceptable salt thereof or a corresponding pharmaceutical composition.

Also provided herein is the use of one or more of the disclosed compounds, or a pharmaceutically acceptable salt thereof, or the pharmaceutical compositions disclosed herein, for the preparation of a medicament for the treatment of cancer, autoimmune disease, immune deficiency, or neurodegenerative disease.

In another embodiment provided herein, the disclosed compounds, or a pharmaceutically acceptable salt thereof, or the pharmaceutical compositions disclosed herein are for use in treating cancer, autoimmune disease, immune deficiency, or neurodegenerative disease.

In another embodiment, the present invention provides a method of treating a subject with cancer, the method comprises administering to a subject in need thereof an effective amount of a compound of disclosed herein or a pharmaceutically acceptable salt thereof or a corresponding pharmaceutical composition, wherein the cancer is selected from the group consisting of lymphoma, leukemia, and a plasma cell neoplasm.

Also provided herein is the use of one or more of the disclosed compounds, or a pharmaceutically acceptable salt thereof, or the pharmaceutical compositions disclosed herein, for the preparation of a medicament for the treatment of cancer, wherein the cancer is selected from the group consisting of lymphoma, leukemia, and a plasma cell neoplasm.

In another embodiment, provided herein the disclosed compounds, or a pharmaceutically acceptable salt thereof, or the pharmaceutical compositions disclosed herein are for use in treating cancer, wherein the cancer is selected from the group consisting of lymphoma, leukemia, and a plasma cell neoplasm.

DETAILED DESCRIPTION

In a first embodiment, the invention provides a compound represented by Structural Formula I:

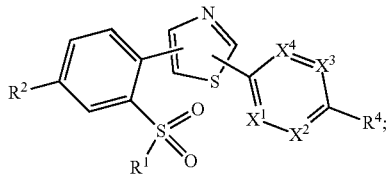

I or a pharmaceutically acceptable salt thereof, wherein:
the thiazole ring is optionally substituted with —F or —Cl. Alternatively, the thiazole ring is unsubstituted;
$X^1$, $X^2$, $X^3$, and $X^4$ are independently N or $CR^5$, provided that no more than two of $X^1$, $X^2$, $X^3$, and $X^4$ are N;
$R^1$ is —$OR^a$; —$NH_2$, —$N((C_1-C_5)alkyl)_2$; —$NR^a(C_1-C_5)$alkyl; —$NR^a$—$(C_3-C_6)$cycloalkyl, —$NR^a$-phenyl; —$NR^a$-monocyclic 3-7 membered heterocyclic ring; —N-monocyclic 4-7 membered nitrogen containing heterocyclic ring (wherein the nitrogen atom of the heterocyclic ring is attached to the sulfur atom), or —N-5-8 membered nitrogen containing bridged bicyclic heterocyclyl (wherein the nitrogen atom of the bridged bicyclic heterocyclyl is attached to the sulfur atom);
wherein the $(C_1-C_5)$alkyl represented by $R^1$ or a $(C_1-C_5)$alkyl in the group represented by $R^1$ is optionally substituted with —$OR^a$, —$OC(C_1-C_3)$alkylene-OH, —$CO(O)CH_3$, —$NR^aR^a$, —$(C_3-C_6)$cycloalkyl, phenyl, monocyclic 3-7 membered heterocyclic ring, or monocyclic 5-6 membered heteroaromatic ring;
wherein the —$(C_3-C_6)$cycloalkyl represented by $R^1$ or a $(C_3-C_6)$cycloalkyl in the group represented by $R^1$ is optionally substituted with halogen or —$OR^a$; wherein the phenyl represented by $R^1$ or a phenyl in the group represented by $R^1$ is optionally substituted with halogen, —$CH_3$, halomethyl, halomethoxy, —OH, or —$NH_2$;
$R^2$ is —H, —$(C_1-C_4)$alkyl; —$NH_2$, —$NO_2$, —$OR^a$; —$(CH_2)_mC(O)NH_2$; —$(CH_2)_mNR^aC(O)NH_2$;
—$(CH_2)_mC(O)NR^a(C_1-C_4)$alkyl; —$(CH_2)_mC(O)NR^a(C_2-C_4)$alkenyl; —$(CH_2)_mC(O)NR^a$—$(C_3-C_6)$cycloalkyl; —$(CH_2)_mC(O)NR^a$-phenyl; —$(CH_2)_mC(O)NR^a$-monocyclic 3-7 membered heterocyclic ring; —$(CH_2)_mC(O)NR^a$-5-10 membered heteroaromatic ring;
—$(CH_2)_mNR^a(C_1-C_4)$alkyl; —$(CH_2)_mNR^a(C_2-C_4)$alkenyl; —$(CH_2)_mNR^a$—$(C_3-C_6)$cycloalkyl; —$(CH_2)_mNR^a$-phenyl; —$(CH_2)_mNR^a$-monocyclic 3-7 membered heterocyclic ring; —$(CH_2)_mNR^a$-5-10 membered heteroaromatic ring;
—$(CH_2)_mNR^aC(O)(C_1-C_4)$alkyl; —$(CH_2)_mNR^aC(O)(C_2-C_4)$alkenyl; —$(CH_2)_mNR^aC(O)$—$(C_3-C_6)$cycloalkyl; —$(CH_2)_mNR^aC(O)$-phenyl; —$(CH_2)_mNR^aC(O)$-monocyclic 3-7 membered heterocyclic ring; —$(CH_2)_mNR^aC(O)$-5-10 membered heteroaromatic ring;
—$(CH_2)_mNR^aC(O)O(C_1-C_4)$alkyl; —$(CH_2)_mNR^aC(O)O(C_2-C_4)$alkenyl; —$(CH_2)_mNR^aC(O)O$—$(C_3-C_6)$cycloalkyl; —$(CH_2)_mNR^aC(O)O$-phenyl; —$(CH_2)_mNR^aC(O)O$-monocyclic 3-7 membered heterocyclic ring; —$(CH_2)_mNR^aC(O)O$-5-10 membered heteroaromatic ring;
—$(CH_2)_mNR^aC(O)NR^a(C_1-C_4)$alkyl; —$(CH_2)_mNR^aC(O)NR^a(C_2-C_4)$alkenyl; —$(CH_2)_mNR^aC(O)NR^a$—$(C_3-C_6)$cycloalkyl; —$(CH_2)_mNR^aC(O)NR^a$-phenyl; —$(CH_2)_mNR^aC(O)NR^a$-monocyclic 3-7 membered heterocyclic ring; —$(CH_2)_mNR^aC(O)NR^a$-5-10 membered heteroaromatic ring;
—$(CH_2)_mNR^aC(S)(C_1-C_4)$alkyl; —$(CH_2)_mNR^aC(S)(C_2-C_4)$alkenyl; —$(CH_2)_mNR^aC(S)$—$(C_3-C_6)$cycloalkyl; —$(CH_2)_mNR^aC(S)$-phenyl; —$(CH_2)_mNR^aC(S)$-monocyclic 3-7 membered heterocyclic ring; —$(CH_2)_mNR^aC(S)$-5-10 membered heteroaromatic ring;
—$(CH_2)_mNR^aC(S)NR^a(C_1-C_4)$alkyl; —$(CH_2)_mNR^aC(S)NR^a(C_2-C_4)$alkenyl; —$(CH_2)_mNR^aC(S)NR^a$—$(C_3-C_6)$cycloalkyl; —$(CH_2)_mNR^aC(S)NR^a$-phenyl; —$(CH_2)_mNR^aC(S)NR^a$-monocyclic 3-7 membered heterocyclic ring; —$(CH_2)_mNR^aC(S)NR^a$-5-10 membered heteroaromatic ring;
—$(CH_2)_mNR^aS(O)_2$—$(C_1-C_4)$alkyl; —$(CH_2)_mNR^aS(O)_2$—$(C_2-C_4)$alkenyl; —$(CH_2)_mNR^aS(O)_2$—$(C_3-C_6)$cycloalkyl; —$(CH_2)_mNR^aS(O)_2$-phenyl; —$(CH_2)_mNR^aS(O)_2$-monocyclic 3-7 membered heterocyclic ring; —$(CH_2)_mNR^aS(O)_2$-5-10 membered heteroaromatic ring;
monocyclic 3-10 membered heterocyclic ring; 5-10 membered heteroaromatic ring;
wherein the $(C_1-C_4)$alkyl represented by $R^2$ or a $(C_1-C_4)$alkyl in the group represented by $R^2$ is optionally substituted with halogen, —$OR^a$, —$NR^aR^a$, —$(C_3-C_6)$cycloalkyl, phenyl, monocyclic 3-7 membered heterocyclic ring, or monocyclic 5-6 membered heteroaromatic ring; wherein the —$(C_3-C_6)$cycloalkyl represented by $R^2$ or a $(C_3-C_6)$cycloalkyl in the group represented by $R^2$ is optionally substituted with halogen, —$OR^a$ or —$NR^aR^a$; wherein the phenyl represented by $R^2$ or a phenyl in the group represented by $R^2$ is optionally substituted with halogen, —$CH_3$, halomethyl, halomethoxy, —$OR^a$, or —$N_3$; wherein the heterocyclic ring represented by R² or a heterocyclic ring in the group represented by R² is optionally substituted with =O, —CH₃, halomethyl, halomethoxy, phenyl, or benzyl; wherein the heteroaromatic ring represented by R² or a heteroaromatic ring in the group represented by R² is optionally substituted with halogen, —CH₃, halomethyl, or halomethoxy;

R⁴ is —H; —NH₂; —NO₂; —NRᵃ(C₁-C₄)alkyl; —NRᵃC(O)(C₁-C₄)alkyl; —NRᵃC(O)O(C₁-C₄)alkyl; —NRᵃC(O)NRᵃ(C₁-C₄)alkyl; —NRᵃC(S)NRᵃ(C₁-C₄)alkyl; —NRᵃS(O)₂(C₁-C₄)alkyl; —NRᵃS(O)₂NRᵃ(C₁-C₄)alkyl; —NRᵃS(O)₂-phenyl; —OC(O)NRᵃ(C₁-C₄)alkyl; —NRᵃC(S)O(C₁-C₄)alkyl; —NRᵃ-monocyclic 5 or 6 membered nitrogen containing heteroaromatic ring; —NRᵃC(S)—N-monocyclic 4-7 membered nitrogen containing heterocyclic ring; —NRᵃC(S)NRᵃ-monocyclic 3-7 membered heterocyclic ring; —NRᵃC(S)NRᵃ-monocyclic 5 or 6 membered nitrogen containing heteroaromatic ring; monocyclic 5 or 6 membered nitrogen containing heterocyclic ring; or —NRᵃ—(C₃-C₆)cycloalkenyl optionally substituted with =O or —NRᵃ(C₁-C₄)alkyl;

wherein the (C₁-C₄)alkyl represented by R⁴ or a (C₁-C₄)alkyl in the group represented by R⁴ is optionally substituted with —ORᵃ, phenyl, —C(O)NRᵃRᵃ, or —NRᵃRᵃ; wherein the heterocyclic ring represented by R⁴ or a heterocyclic ring in the group represented by R⁴ is optionally substituted with —CH₃, halomethyl, halomethoxy, or —ORᵃ;

each R⁵ is independently —H, —(C₁-C₄)alkyl, —O(C₁-C₄)alkyl, halogen, —CN, halomethyl, halomethoxy, —OCH₂CH₂R¹, —C(O)O(C₁-C₄)alkyl, —S(O)₂NH₂, or —SO₂NRᵃ(C₁-C₄)alkyl;

each Rᵃ is independently —H or —CH₃;

m is 0 or 1.

In a second embodiment, the invention provides a compound represented by Structural Formula II:

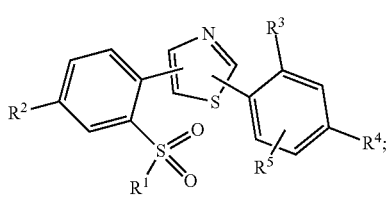

II or a pharmaceutically acceptable salt thereof, wherein R³ is —H, halogen, —C(O)O(C₁-C₄)alkyl, —S(O)₂NH₂, or —SO₂NRᵃ(C₁-C₄)alkyl; and the remaining variables are as defined in the first embodiment.

In a third embodiment, the invention provides a compound represented by Structural Formula III:

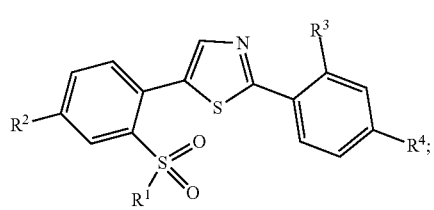

III or a pharmaceutically acceptable salt thereof, wherein R³ is —H, halogen, —C(O)O(C₁-C₄)alkyl, —S(O)₂NH₂, or —SO₂NRᵃ(C₁-C₄)alkyl; and the remaining variables are as defined in the first embodiment.

In a fourth embodiment, the invention provides a compound according to Structural Formula I, II, or III, or a pharmaceutically acceptable salt thereof, wherein:

the thiazole ring is optionally substituted with —F or —Cl. Alternatively, the thiazole ring is unsubstituted;

R¹ is —NH₂, —NRᵃ(C₁-C₅)alkyl, —NRᵃ—(C₃-C₆)cycloalkyl, —N-monocyclic 4-7 membered nitrogen containing heterocyclic ring (wherein the nitrogen atom of the heterocyclic ring is attached to the sulfur atom), or —N-5-8 membered nitrogen containing bridged bicyclic heterocyclyl (wherein the nitrogen atom of the bridged bicyclic heterocyclyl is attached to the sulfur atom);

wherein the (C₁-C₅)alkyl represented by R¹ or a (C₁-C₅)alkyl in the group represented by R¹ is optionally substituted with —ORᵃ, —OC(C₁-C₃)alkylene-OH, —CO(O)CH₃, —NRᵃRᵃ, —(C₃-C₆)cycloalkyl, phenyl, monocyclic 3-7 membered heterocyclic ring, or monocyclic 5-6 membered heteroaromatic ring; wherein the —(C₃-C₆)cycloalkyl represented by R¹ or a (C₃-C₆)cycloalkyl in the group represented by R¹ is optionally substituted with —ORᵃ; wherein the phenyl represented by R¹ or a phenyl in the group represented by R¹ is optionally substituted with halogen, —CH₃, halomethyl, halomethoxy, —OH, or —NH₂;

R² is —H, —(C₁-C₄)alkyl; —(CH₂)ₘC(O)NH₂; —(CH₂)ₘC(O)NRᵃ(C₁-C₄)alkyl; —ORᵃ; —(CH₂)ₘNRᵃC(O)NRᵃRᵃ; —(CH₂)ₘNRᵃ(C₁-C₄)alkyl; —(CH₂)ₘNRᵃC(O)(C₁-C₄)alkyl; —(CH₂)ₘNRᵃC(O)O(C₁-C₄)alkyl; —(CH₂)ₘNRᵃC(O)O(C₂-C₄)alkenyl; —(CH₂)ₘNRᵃC(O)NRᵃ(C₁-C₄)alkyl; —(CH₂)ₘNRᵃC(O)—(C₃-C₆)cycloalkyl; —(CH₂)ₘNRᵃC(O)NRᵃ—(C₃-C₆)cycloalkyl; —(CH₂)ₘNRᵃC(O)-phenyl; —(CH₂)ₘNRᵃC(O)O-phenyl; —(CH₂)ₘNRᵃ-monocyclic 3-7 membered heterocyclic ring; —(CH₂)ₘNRᵃ-monocyclic 5-6 membered heteroaromatic ring; —(CH₂)ₘNRᵃC(O)-monocyclic 3-7 membered heterocyclic ring; —(CH₂)ₘNRᵃC(O)-monocyclic 5-6 membered heteroaromatic ring; —(CH₂)ₘNRᵃC(O)O-monocyclic 3-7 membered heterocyclic ring; —(CH₂)ₘNRᵃC(O)O-monocyclic 5-6 membered heteroaromatic ring; monocyclic 3-7 membered heterocyclic ring; monocyclic 5-6 membered heteroaromatic ring; —(CH₂)ₘ—NRᵃC(O)NRᵃ-monocyclic 3-7 membered heterocyclic ring; —(CH₂)ₘ—NRᵃC(O)NRᵃ-monocyclic 5-6 membered heteroaromatic ring; —NRᵃC(S)NRᵃ(C₁-C₄)alkyl; —(CH₂)ₘNRᵃS(O)₂—(C₁-C₄)alkyl; —CH₂NRᵃS(O)₂-phenyl;

wherein the (C₁-C₄)alkyl represented by R² or a (C₁-C₄)alkyl in the group represented by R² is optionally substituted with halogen, —ORᵃ, —NRᵃRᵃ, —(C₃-C₆)cycloalkyl, phenyl, monocyclic 3-7 membered heterocyclic ring, or monocyclic 5-6 membered heteroaromatic ring; wherein the —(C₃-C₆)cycloalkyl represented by R² or a (C₃-C₆)cycloalkyl in the group represented by R² is optionally substituted with halogen, —ORᵃ or —NRᵃRᵃ; wherein the phenyl represented by R² or a phenyl in the group represented by R² is optionally substituted with halogen, —CH₃, halomethyl, halomethoxy, —ORᵃ, or —N₃; wherein the monocyclic 3-7 membered heterocyclic ring represented by R² or a monocyclic 3-7 membered heterocyclic ring in the group represented by $R^2$ is optionally substituted with =O, —CH$_3$, halomethyl, halomethoxy, phenyl, or benzyl; wherein the 5-6 membered heteroaromatic ring represented by $R^2$ or a 5-6 membered heteroaromatic ring in the group represented by $R^2$ is optionally substituted with halogen, —CH$_3$, halomethyl, or halomethoxy;

$R^3$ is —H, halogen, or —SO$_2$NR$^a$(C$_1$-C$_4$)alkyl;

$R^4$ is —H; —NH$_2$; —NR$^a$(C$_1$-C$_4$)alkyl; —NR$^a$C(O)(C$_1$-C$_4$)alkyl; —NR$^a$C(O)O(C$_1$-C$_4$)alkyl; —NR$^a$C(O)NR$^a$(C$_1$-C$_4$)alkyl; —NR$^a$C(S)NR$^a$(C$_1$-C$_4$)alkyl; —NR$^a$S(O)$_2$(C$_1$-C$_4$)alkyl; —NR$^a$S(O)$_2$NR$^a$(C$_1$-C$_4$)alkyl; —NR$^a$S(O)$_2$-phenyl; —OC(O)NR$^a$(C$_1$-C$_4$)alkyl; or monocyclic 5 or 6 membered nitrogen containing heterocyclic ring optionally substituted with methyl; wherein the (C$_1$-C$_4$)alkyl represented by $R^4$ or a (C$_1$-C$_4$)alkyl in the group represented by $R^4$ is optionally substituted with —OR$^a$ or phenyl;

each $R^a$ is independently —H or —CH$_3$;

and the remaining variables are as defined in the first embodiment.

In a fifth embodiment, the invention provides a compound according to Structural Formula I, II, or III, or a pharmaceutically acceptable salt thereof, wherein:

$R^1$ is —NH$_2$, —NHCH$_3$, —NHCH$_2$CH$_3$, —N(CH$_3$)$_2$, —NHC(CH$_3$)$_3$, —NHCH$_2$CH$_2$NH$_2$, —NHCH$_2$CH$_2$NHCH$_3$, —NHCH$_2$CH$_2$N(CH$_3$)$_2$, —NHCH$_2$CH$_2$CH$_2$NH$_2$, —NHCH$_2$CH$_2$CH$_2$NHCH$_3$, —NHCH$_2$CH$_2$CH$_2$N(CH$_3$)$_2$, —NHCH$_2$C(O)OCH$_3$, —NHCH(CH(CH$_3$)(CH$_2$)C(O)OCH$_3$, —NHCH$_2$-phenyl, —NHCH$_2$-pyridyl, —NHCH$_2$CH$_2$OH, —NHCH$_2$CH$_2$OCH$_3$, —NHCH$_2$C(CH$_3$)$_2$CH$_2$OH, —NHCH(CH$_3$)CH$_2$OH, —NHCH$_2$CH$_2$OCH$_2$CH$_2$OH, —NHCH(CH$_2$OH)C(O)OCH$_3$, —NHCH(CH$_2$OH)$_2$, —NH—cyclohexyl (wherein the cyclohexyl is optionally substituted with —OH); N-morpholinyl, N-piperidinyl, N-piperazinyl, N-pyrrolidinyl, or 7-azabicyclo[2.2.1]heptanyl;

$R^2$ is —H, —CH$_2$OH, —CH$_2$NHC(O)CH$_3$, —CH$_2$NHC(O)OCH$_3$, —CH$_2$NHC(O)CH$_2$CH$_3$, —CH$_2$NHC(O)CH$_2$CH$_2$OH, —CH$_2$NHC(O)CH$_2$CH$_2$OCH$_3$, —CH$_2$NHC(O)OCH$_2$CH$_3$, —CH$_2$NHC(O)CH(CH$_3$)$_2$, —CH$_2$NHC(O)OCH(CH$_3$)$_2$, —CH$_2$NHC(O)C(CH$_3$)$_3$, —CH$_2$NHC(O)-phenyl, —CH$_2$NHC(O)-piperidinyl, —CH$_2$NHC(O)-pyridyl, —CH$_2$NHC(O)-pyrimidinyl, —CH$_2$NHC(O)CH$_2$-phenyl, —CH$_2$NHC(O)CH$_2$-pyridyl, —CH$_2$NHC(O)OCH$_2$-phenyl, —CH$_2$NHS(O)$_2$CH$_3$, —CH$_2$NHS(O)$_2$-phenyl, —CF$_3$, —C(O)NH$_2$, —C(O)NHCH$_3$, —C(O)NHCH$_2$-phenyl, —OH, —NHCH$_2$CH$_3$, —NHCH$_2$CF$_3$, —NHCH(CH$_3$)CF$_3$, —NHCH$_2$CH(OH)CH$_3$, —NH-oxetanyl substituted with methyl, —NHC(O)CH$_3$, —NHC(O)CH$_2$CH$_3$, —N(CH$_3$)C(O)CH$_3$, —NHC(O)CH(CH$_3$)$_2$, —NHC(O)—cyclopropyl, —NHC(O)-pyrrolidinyl, —NHC(O)-phenyl, —NHC(O)—CH$_2$—CH$_2$-phenyl, —NHC(O)NH—CH$_2$CH$_2$NH$_2$, —NHC(O)N(CH$_3$)$_2$, —NHC(O)NH—CH$_2$CH$_2$NHCH$_3$, —NHC(O)NH-azetidinyl, —NHC(O)NH-cyclohexyl (wherein the cyclohexyl is optionally substituted with —NH$_2$ or —N(CH$_3$)$_2$), —NHC(O)NHCH$_2$-azepanyl, —NHC(O)NHCH$_2$-azetidinyl, —NHC(O)NH—CH$_2$-phenyl (wherein the phenyl is optionally substituted with —OH or N$_3$), —NHC(O)NH—CH(CH$_3$)-phenyl, —NHC(O)N(CH$_3$)—CH$_2$-phenyl, —N(CH$_3$)C(O)NH—CH$_2$-phenyl, —N(CH$_3$)C(O)N(CH$_3$)—CH$_2$-phenyl, —NHC(O)NH—CH$_2$-imidazolyl, —NHC(O)NH—CH$_2$-pyrazolyl, —NHC(O)NH—CH$_2$-pyridyl, —NHC(O)NH—CH$_2$-pyrimidinyl, —NHC(O)NH—CH$_2$-pyrrolidinyl (wherein the pyrrolidinyl is optionally substituted with —CH$_3$), —NHC(O)N(CH$_3$)—CH$_2$-pyrrolidinyl, —NHC(O)NH—CH$_2$-thiazolyl, —NHC(O)OCH$_3$, —NHC(O)OCH$_2$CH$_3$, —NHC(O)OCH(CH$_3$)$_2$, —NHC(O)OCH$_2$CH$_3$, —NHC(O)OCH$_2$CH$_2$NH$_2$, —NHC(O)OCH$_2$C(CH$_3$)=CH$_2$, —NHC(O)OCH=CH(CH$_3$), —NHC(O)OCH$_2$CH$_2$OH, —NHC(O)OCH$_2$CH$_2$OCH$_3$, —NHC(O)O—CH$_2$-cyclohexyl, —NHC(O)O—CH$_2$-imidazolyl, —NHC(O)O—CH$_2$-phenyl, —NHC(O)O—CH(CH$_3$)-phenyl, —NHC(O)O—CH$_2$—CH$_2$-phenyl, —NHC(O)O—CH$_2$-pyridyl, —NHC(O)O—CH$_2$-pyrrolidinyl, —NHC(O)O—CH$_2$—CH$_2$-thiazolyl, —NHC(S)NHCH(CH$_3$)$_2$, —NHC(S)NHCH$_2$-phenyl, —NH-thiazolyl, —NH-imidazolyl (substituted with methyl), —NHS(O)$_2$CH$_3$, —NHS(O)$_2$-phenyl, —NHS(O)$_2$—CH$_2$-phenyl, —N(CH$_3$)S(O)$_2$CH$_3$, imidazolyl, pyrazolyl, triazolyl,

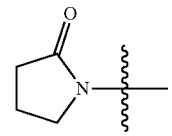 [SMILES: *N1CCCC1=O]

optionally substituted with benzyl;

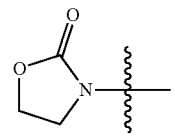 [SMILES: *N1CCOC1=O]

optionally substituted with methyl, phenyl, or benzyl;

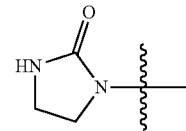

optionally substituted with benzyl,

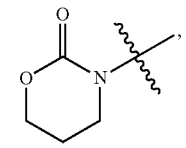

$R^3$ is —H, —F, or —SO$_2$NHC(CH$_3$)$_3$;

$R^4$ is —H, —NH$_2$, —NHCH$_2$CH(OH)CH$_3$, —NHCH$_2$C(CH$_3$)$_2$OH, —NHC(O)CH$_3$, —NHC(O)CH$_2$CH(CH$_3$)$_2$, —NHC(O)OCH$_3$, —NHC(O)OC(CH$_3$)$_3$, —NHC(O)OCH$_2$CH$_3$, —NHC(O)OCH(CH$_3$)$_2$, —NHC(O)OCH$_2$CH(CH$_3$)$_2$, —NHC(O)NHCH(CH$_3$)$_2$, —NHC(O)N(CH$_3$)CH(CH$_3$)$_2$, —N(CH$_3$)C(O)NHCH(CH$_3$)$_2$, —NHC(S)NHCH(CH$_3$)$_2$, —NHC(S)NHCH$_2$-phenyl, —NHS(O)$_2$CH$_3$, —NHS(O)$_2$CH$_2$CH$_3$, —NHS(O)$_2$CH$_2$CH$_2$OCH$_3$, —NHS(O)$_2$-phenyl, —NHS(O)$_2$NHCH$_3$, —OC(O)NHCH(CH$_3$)$_2$, or

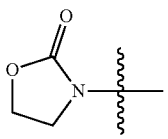 [SMILES: *N1CCOC1=O]

optionally substituted with one or two methyl;
and the remaining variables are as defined in the first embodiment.

In a sixth embodiment, the invention provides a compound according to Structural Formula I, II, or III, or a pharmaceutically acceptable salt thereof, wherein:

$R^1$ is —NH($C_1$-$C_4$)alkyl; —N-monocyclic 5 or 6 membered nitrogen containing heterocyclic ring (wherein the nitrogen atom of the heterocyclic ring is attached to the sulfur atom); or —N-5-8 membered nitrogen containing bridged bicyclic heterocyclyl (wherein the nitrogen atom of the bridged bicyclic heterocyclyl is attached to the sulfur atom);

$R^2$ is —H; —$CH_2OR^a$; —C(O)$NR^aR^a$; —$OR^a$; —$(CH_2)_m$NHC(O)($C_1$-$C_4$)alkyl; —NHC(O)$NR^aR^a$; —NH($C_1$-$C_4$)alkyl; —NHC(O)($C_1$-$C_4$)alkyl; —NHC(O)NH($C_1$-$C_4$)alkyl; —NHC(O)O($C_1$-$C_4$)alkyl; —NHC(O)O($C_2$-$C_4$)alkenyl; —NHC(O)—($C_3$-$C_6$)cycloalkyl; —NHC(O)O$CH_2$—($C_3$-$C_6$)cycloalkyl; —NHC(O)NH—$(CH_2)_n$—($C_3$-$C_6$)cycloalkyl; —$NR^a$C(O)—$(CHR^a)_n$-phenyl; —$NR^a$C(O)O—$(CHR^a)_n$-phenyl; —$NR^a$C(O)$NR^a$—$(CHR^a)_n$-phenyl; —$NR^a$C(S)$NR^a$—$(CH_2)$-phenyl; —NH-monocyclic 3-7 membered heterocyclic ring optionally substituted with —$CH_3$; —NH-monocyclic 5-6 membered heteroaromatic ring; —NHC(O)-monocyclic 3-7 membered heterocyclic ring; —NHC(O)-monocyclic 5-6 membered heteroaromatic ring; —$(CH_2)_m$NHC(O)—$(CH_2)_n$-monocyclic 5 or 6 membered nitrogen containing heterocyclic or heteroaromatic ring; —NHC(O)O—$(CH_2)_n$-monocyclic 5 or 6 membered nitrogen containing heterocyclic or heteroaromatic ring optionally substituted with —$CH_3$; monocyclic 5 or 6 membered nitrogen containing heteroaromatic ring; —$NR^a$C(O)$NR^a$—$(CH_2)_n$-monocyclic 3-7 membered heterocyclic ring; —$NR^a$C(O)$NR^a$—$(CH_2)_n$-monocyclic 5 or 6 membered nitrogen containing heteroaromatic ring; —$NR^a$C(S)$NR^a$($C_1$-$C_4$)alkyl; —$NR^a$C(S)$NR^a$—$(CHR^a)_n$-phenyl; —$NR^a$S(O)$_2$—($C_1$-$C_4$)alkyl;

wherein the ($C_1$-$C_4$)alkyl represented by $R^2$ or a ($C_1$-$C_4$)alkyl in the group represented by $R^2$ is optionally substituted with halogen, —$OR^a$, or —$NR^aR^a$; wherein the ($C_3$-$C_6$)cycloalkyl represented by $R^2$ or a ($C_3$-$C_6$)cycloalkyl in the group represented by $R^2$ is optionally substituted with —$NR^aR^a$; wherein the phenyl represented by $R^2$ or a phenyl in the group represented by $R^2$ is optionally substituted with halogen, —$OR^a$ or —$N_3$;

$R^3$ is —H or halogen;

$R^4$ is —H, —$NR^a$C(O)O($C_1$-$C_4$)alkyl, —OC(O)$NR^a$($C_1$-$C_4$)alkyl, or —$NR^a$C(S)$NR^a$($C_1$-$C_4$)alkyl optionally substituted with phenyl;

each $R^a$ is independently —H or —$CH_3$;

m is 0 or 1; and n is 0, 1, or 2;

and the remaining variables are as defined in the first embodiment.

In an seventh embodiment, the invention provides a compound according to Structural Formula I, II, or III, or a pharmaceutically acceptable salt thereof, wherein:

$R^1$ is —N($CH_3$)$_2$, —NHC($CH_3$)$_3$, —N-piperazinyl, or 7-azabicyclo[2.2.1]heptanyl;

$R^2$ is —H, —$CH_2OH$, —$CH_2$NHC(O)CH($CH_3$)$_2$, —$CH_2$NHC(O)-pyridyl, —$CH_2$NHC(O)$CH_2$-pyridyl, —C(O)$NH_2$, —C(O)$NHCH_3$, —OH, —$NHCH_2CH_3$, —$NHCH_2CF_3$, —NHCH($CH_3$)$CF_3$, —$NHCH_2$CH(OH)$CH_3$, —NH-oxetanyl substituted with methyl, —NHC(O)$CH_3$, —NHC(O)$CH_2CH_3$, —NHC(O)CH($CH_3$)$_2$, —NHC(O)-cyclopropyl, —NHC(O)-pyrrolidinyl, —NHC(O)-phenyl, —NHC(O)—$CH_2$—$CH_2$-phenyl, —NHC(O)NH—$CH_2CH_2NH_2$, —NHC(O)N($CH_3$)$_2$, —NHC(O)NH—$CH_2CH_2NHCH_3$, —NHC(O)NH— azetidinyl, —NHC(O)NH-cyclohexyl (wherein the cyclohexyl is optionally substituted with —$NH_2$ or —N($CH_3$)$_2$), —NHC(O)$NHCH_2$-azepanyl, —NHC(O)$NHCH_2$-azetidinyl, —NHC(O)NH—$CH_2$-phenyl (wherein the phenyl is optionally substituted with —OH or $N_3$), —NHC(O)NH—CH($CH_3$)-phenyl, —N($CH_3$)C(O)NH—$CH_2$-phenyl, —N($CH_3$)C(O)N($CH_3$)—$CH_2$-phenyl, —NHC(O)NH—$CH_2$-pyridyl, —NHC(O)NH—$CH_2$-pyrrolidinyl (wherein the pyrrolidinyl is optionally substituted with —$CH_3$), —NHC(O)N($CH_3$)—$CH_2$-pyrrolidinyl, —NHC(O)O$CH_3$, —NHC(O)O$CH_2CH_3$, —NHC(O)OCH($CH_3$)$_2$, —NHC(O)O$CH_2CH_3$, —NHC(O)O$CH_2CH_2NH_2$, —NHC(O)O$CH_2$C($CH_3$)=$CH_2$, —NHC(O)OCH=CH($CH_3$), —NHC(O)O$CH_2CH_2OH$, —NHC(O)O$CH_2CH_2OCH_3$, —NHC(O)O—$CH_2$-cyclohexyl, —NHC(O)O—$CH_2$-phenyl, —NHC(O)O—CH($CH_3$)-phenyl, —NHC(O)O—$CH_2$—$CH_2$-phenyl, —NHC(O)O—$CH_2$-pyridyl, —NHC(O)O—$CH_2$-pyrrolidinyl, —NHC(O)O—$CH_2$—$CH_2$-thiazolyl, —NHC(S)NHCH($CH_3$)$_2$, —NHC(S)$NHCH_2$-phenyl, —N($CH_3$)S(O)$_2CH_3$, imidazolyl, pyrazolyl, triazolyl, $R^3$ is —H or —F;

$R^4$ is —H, —NHC(O)O$CH_2CH_3$, —NHC(O)OCH($CH_3$)$_2$, —NHC(O)O$CH_2$CH($CH_3$)$_2$, —NHC(S)NHCH($CH_3$)$_2$, —NHC(S)$NHCH_2$-phenyl, or —OC(O)NHCH($CH_3$)$_2$;

and the remaining variables are as defined in the first embodiment.

In a eighth embodiment, the invention provides a compound according to Structural Formula I, II, or III, or a pharmaceutically acceptable salt thereof, wherein:

$R^1$ is —NH($C_1$-$C_4$)alkyl or 7-azabicyclo[2.2.1]heptanyl;

$R^2$ is —H, —NHC(O)($C_1$-$C_4$)alkyl; —NHC(O)O($C_1$-$C_4$)alkyl; —NHC(O)O($C_2$-$C_4$)alkenyl; —NHC(O)O$CH_2$—($C_3$-$C_6$)cycloalkyl; —NHC(O)NH—$(CH_2)_n$—($C_3$-$C_6$)cycloalkyl; —$NR^a$C(O)—$(CHR^a)_n$-phenyl; —$NR^a$C(O)O—$(CHR^a)_n$-phenyl; —$NR^a$C(O)$NR^a$—$(CHR^a)_n$-phenyl; —$NR^a$C(S)$NR^a$—$(CHR^a)_n$-phenyl; —NHC(O)O—$(CH_2)_n$-monocyclic 5 or 6 membered nitrogen containing heterocyclic or heteroaromatic ring optionally substituted with —$CH_3$; —$NR^a$C(O)$NR^a$—$(CH_2)_n$-monocyclic 5 or 6 membered nitrogen containing heterocyclic or heteroaromatic ring;

wherein the ($C_1$-$C_4$)alkyl represented by $R^2$ or a ($C_1$-$C_4$)alkyl in the group represented by $R^2$ is optionally substituted with —$OR^a$; wherein the ($C_3$-$C_6$)cycloalkyl represented by $R^2$ or a ($C_3$-$C_6$)cycloalkyl in the group represented by $R^2$ is optionally substituted with —$NR^a$; wherein the phenyl represented by $R^2$ or a phenyl in the group represented by $R^2$ is optionally substituted with —$OR^a$ or —$N_3$;

$R^3$ is —H or halogen;
$R^4$ is —H, —NR$^a$C(O)O(C$_1$-C$_4$)alkyl or —NR$^a$C(S)NR$^a$ (C$_1$-C$_4$)alkyl;
each $R^a$ is independently —H or —CH$_3$; and
n is 0, 1, or 2;
and the remaining variables are as defined in the first embodiment.

In a ninth embodiment, the invention provides a compound according to Structural Formula I, II, or III, or a pharmaceutically acceptable salt thereof, wherein:
$R^1$ is —N(CH$_3$)$_2$, —NHC(CH$_3$)$_3$, or 7-azabicyclo[2.2.1]heptanyl;
$R^2$ is —H; —NHC(O)CH$_3$; —NHC(O)CH$_2$CH$_3$; —NHC(O)CH(CH$_3$)$_2$; —NHC(O)-phenyl; —NHC(O)—CH$_2$—CH$_2$-phenyl; —NHC(O)NH-cyclohexyl (wherein the cyclohexyl is optionally substituted with —NH$_2$ or —N(CH$_3$)$_2$); —NHC(O)NH—CH$_2$-phenyl (wherein the phenyl is optionally substituted with —OH or N$_3$); —NHC(O)NH—CH(CH$_3$)-phenyl; —N(CH$_3$)C(O)NH—CH$_2$-phenyl, —N(CH$_3$)C(O)N(CH$_3$)—CH$_2$-phenyl; —NHC(O)NH—CH$_2$-pyrrolidinyl (wherein the pyrrolidinyl is optionally substituted with —CH$_3$); —NHC(O)OCH$_3$; —NHC(O)OCH(CH$_3$)$_2$; —NHC(O)OCH$_2$CH$_3$; —NHC(O)OCH$_2$C(CH$_3$)=CH$_2$; —NHC(O)OCH=CH(CH$_3$); —NHC(O)OCH$_2$CH$_2$OCH$_3$; —NHC(O)O—CH$_2$-cyclohexyl; —NHC(O)O—CH$_2$-phenyl; —NHC(O)O—CH(CH$_3$)-phenyl; —NHC(O)O—CH$_2$—CH$_2$-phenyl; —NHC(O)O—CH$_2$-pyridyl; —NHC(O)O—CH$_2$—CH$_2$-thiazolyl; or —NHC(S)NHCH$_2$-phenyl;
$R^3$ is —H or —F;
$R^4$ is —H, —NHC(O)OCH$_2$CH$_3$, —NHC(O)OCH(CH$_3$)$_2$, or —NHC(S)NHCH(CH$_3$)$_2$;
and the remaining variables are as defined in the first embodiment.

In a tenth embodiment, the invention provides a compound represented by Structural Formula IV or V:

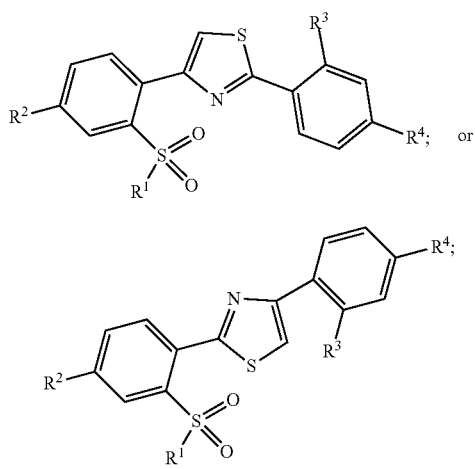

or a pharmaceutically acceptable salt thereof, wherein the thiazole ring is optionally substituted with —F or —Cl. Alternatively, the thiazole ring is unsubstituted; $R^3$ is —H, halogen, —C(O)O(C$_1$-C$_4$)alkyl, —S(O)$_2$NH$_2$, or —SO$_2$NR$^a$(C$_1$-C$_4$)alkyl; and the remainder of the variables are as defined in the first embodiment.

In an eleventh embodiment, the invention provides a compound according to Structural Formula IV or V, or a pharmaceutically acceptable salt thereof, wherein:

the thiazole ring is optionally substituted with —F or —Cl. Alternatively, the thiazole ring is unsubstituted;
$R^1$ is —NR$^a$R$^a$, —NR$^a$(C$_1$-C$_5$)alkyl, or —N-monocyclic 4-7 membered nitrogen containing heterocyclic ring (wherein the nitrogen atom of the heterocyclic ring is attached to the sulfur atom);
wherein the (C$_1$-C$_5$)alkyl represented by $R^1$ or a (C$_1$-C$_5$)alkyl in the group represented by $R^1$ is optionally substituted with —OR$^a$, —OC(C$_1$-C$_3$)alkylene-OH, —CO(O)CH$_3$, —NR$^a$R$^a$, —(C$_3$-C$_6$)cycloalkyl, phenyl, or monocyclic 5-6 membered heteroaromatic ring; wherein the phenyl represented by $R^1$ or a phenyl in the group represented by $R^1$ is optionally substituted with halogen, —CH$_3$, halomethyl, halomethoxy, —OH, or —NH$_2$;
$R^2$ is —H, —NH$_2$, —NO$_2$, —NR$^a$C(O)(C$_1$-C$_4$)alkyl, —NR$^a$C(O)O(C$_1$-C$_4$)alkyl, or —NR$^a$C(S)NR$^a$(C$_1$-C$_4$)alkyl;
$R^3$ is —H or —S(O)$_2$NR$^a$(C$_1$-C$_4$)alkyl;
$R^4$ is —H, —NH$_2$, —NO$_2$, —NR$^a$C(O)(C$_1$-C$_4$)alkyl, —NR$^a$C(O)O(C$_1$-C$_4$)alkyl, or —NR$^a$C(S)NR$^a$(C$_1$-C$_4$)alkyl; and
each $R^a$ is independently —H or —CH$_3$;
and the remaining variables are as defined in the first embodiment.

In a twelfth embodiment, the invention provides a compound according to Structural Formula IV or V, or a pharmaceutically acceptable salt thereof, wherein:
the thiazole ring is optionally substituted with —F or —Cl. Alternatively, the thiazole ring is unsubstituted;
$R^1$ is —NHCH$_3$, —NHCH$_2$CH$_3$, —N(CH$_3$)$_2$, —NHC(CH$_3$)$_3$, —NHCH$_2$CH$_2$OH, —NHCH(CH$_3$)CH$_2$OH, —NHCH$_2$C(CH$_3$)$_2$CH$_2$OH, —NHCH$_2$CH$_2$OCH$_3$, —NHCH$_2$C(O)OCH$_3$, —NHCH$_2$CH$_2$OCH$_2$CH$_2$OH, —NHCH(CH$_2$OH)$_2$, —NHCH$_2$CH$_2$NH$_2$, —NHCH$_2$CH$_2$NHCH$_3$, —NHCH$_2$CH$_2$N(CH$_3$)$_2$, —NHCH$_2$CH$_2$CH$_2$NH$_2$, —NHCH$_2$CH$_2$CH$_2$NHCH$_3$, —NHCH$_2$CH$_2$CH$_2$N(CH$_3$)$_2$, —NHCH$_2$-phenyl, —NHCH$_2$-pyridyl, —NH-cyclobutyl, or —N-pyrrolidinyl;
$R^2$ is —H, —NH$_2$, —NO$_2$, —NHC(O)CH$_3$, —NHC(O)OCH(CH$_3$)$_2$, or —NHC(S)NHCH(CH$_3$)$_2$;
$R^3$ is —H or —S(O)$_2$NHC(CH$_3$)$_3$; and
$R^4$ is —H, —NH$_2$, —NO$_2$, —NHC(O)CH$_3$, —NHC(O)OCH(CH$_3$)$_2$, or —NHC(S)NHCH(CH$_3$)$_2$;
and the remaining variables are as defined in the first embodiment.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids).

Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Definitions

The term "halo" as used herein means halogen and includes fluoro, chloro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. ($C_1$-$C_5$)alkyl. As used herein, a "($C_1$-$C_5$)alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The terms "haloalkyl" and "haloalkoxy" means alkyl or alkoxy, as the case may be, substituted with one or more halogen atoms.

An "alkylene group" is a saturated aliphatic branched or straight-chain divalent hydrocarbon radical. Unless otherwise specified, an alkylene group typically has 2-6 carbon atoms, i.e. ($C_2$-$C_6$)alkylene.

The term "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e. ($C_2$-$C_6$)alkenyl. For example, "($C_2$-$C_4$)alkenyl" means a radical having from 2-4 carbon atoms in a linear or branched arrangement.

The term "cycloalkyl" means a monocyclic saturated hydrocarbon ring system. For example, a $C_{3-6}$ cycloalkyl includes cyclopropyl, cyclobutyl, cyclopentyl and cyclohexyl. Unless otherwise described, a "cycloalkyl" has from three to seven carbon atoms.

The term "cycloalkenyl" means a non-aromatic monocyclic ring system containing a carbon-carbon double bond and having 3 to 7 ring carbon atoms.

The term "heterocyclyl" or "heterocyclic ring" means a saturated or unsaturated non-aromatic 3-12 membered ring radical containing from 1 to 4 ring heteroatoms, which may be the same or different, selected from N, O or S. It can be monocyclic, bicyclic or tricyclic (e.g., a fused or bridged bicyclic or tricyclic ring). A heterocyclyl optionally contains one or more double bonds and/or is optionally fused with one or more aromatic rings (for example, tetrahydronaphthyridine, indolinone, dihydropyrrolotriazole, imidazopyrimidine, quinolinone, dioxaspirodecane).

"3-7 membered monocyclic heterocyclic ring" means a radical having from 3-7 atoms arranged in a monocyclic ring. The term "heterocyclyl" is intended to include all the possible isomeric forms. Examples of 3-7 membered monocyclic heterocyclic ring include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

Examples of bicyclic heterocyclic groups include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, chroman, chromene, isochroman and isochromene.

The term "bridged bicyclic group" refers to a ring system which includes two rings that share at least three adjacent ring atoms. "Nitrogen-containing bridged bicyclic groups" are bridged bicyclic groups with a ring nitrogen atom. Examples include azabicyclo[3.2.1]octane, azabicyclo [2.2.1]heptane, azabicyclo[3.1.0]hexane, and the like.

The term "fused bicyclic group" refers to a ring system which includes two rings that share at two adjacent ring atoms.

"—N-nitrogen containing heterocyclyl ring" means that the nitrogen containing heterocyclic is attached to the reminder of the compound through a ring nitrogen atom. For example, N-piperidinyl means that the piperidinyl is connected with the remaining part of a compound through the ring nitrogen ring atom in the piperidinyl.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to ten ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. "Heteroaryl" includes monocyclic and bicyclic ring systems.

"Monocyclic 5-6 membered heteroaryl" means a monocyclic aromatic ring system having five or six ring atoms selected from carbon and at least one (typically 1 to 3, more typically 1 or 2) heteroatoms (e.g., oxygen, nitrogen or sulfur). Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

Examples of bicyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl.

The term "phenylene" refers to a group ($C_6H_4$) based on a di-substituted benzene ring.

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, alkylene, cycloalkyl, cycloalkylene, aryl, arylene, heteroaryl, heteroarylene, heterocyclyl or heterocyclylene) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant disclosure. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art.

Suitable substituents are those which do not have a significant adverse effect on the ability of the compound to inhibit RAD51. Where suitable substituents are not specifically enumerated, exemplary substituents include, but are not limited to: halo, —CN, alkyl, alkoxy, halomethyl, halomethoxy, $(C_1-C_5)$alkyl, halo$(C_1-C_5)$alkyl, $(C_1-C_5)$alkoxy, —$NO_2$, —$OR^{c'}$, —$NR^{a'}R^{b'}$, —$S(O)_iR^{a'}$, —$NR^aS(O)_iR^{b'}$, —$S(O)_iNR^{a'}R^{b'}$,
—$C(=O)OR^{a'}$, —$OC(=O)OR^{a'}$, —$C(=S)OR^{a'}$, —$O(C=S)R^{a'}$, —$C(=O)NR^{a'}R^{b'}$, —$NR^{a'}C(=O)R^{b'}$, —$C(=S)NR^{a'}R^{b'}$,
—$NR^{a'}C(=S)R^{b'}$, —$NR^{a'}(C=O)OR^{b'}$, —$O(C=O)NR^{a'}R^{b'}$, —$NR^{a'}(C=S)OR^{b'}$, —$O(C=S)NR^{a'}R^{b'}$, —$NR^{a'}(C=O)NR^{a'}R^{b'}$, —$NR^{a'}(C=S)NR^{a'}R^{b'}$, —$C(=S)R^{a'}$, —$C(=O)R^{a'}$, $(C_3-C_6)$cycloalkyl, monocyclic heteroaryl and phenyl, wherein the $(C_3-C_6)$cycloalkyl, monocyclic heteroaryl and phenyl substituents are optionally and independently substituted with —$CH_3$, halomethyl, halo, methoxy or halomethoxy. Each $R^{a'}$ and each $R^{b'}$ are independently selected from —H and $(C_1-C_5)$alkyl, wherein the $(C_1-C_5)$alkyl group represented by $R^{a'}$ or $R^{b'}$ is optionally substituted with hydroxyl or $(C_1-C_3)$alkoxy; $R^{c'}$ is —H, halo$(C_1-C_5)$alkyl or $(C_1-C_5)$alkyl, wherein the $(C_1-C_5)$alkyl group represented by $R^{c'}$ is optionally substituted with hydroxyl or $(C_1-C_3)$alkoxy; and i is 0, 1, or 2. =O is also a suitable substituent for alkyl, cycloalkyl, cycloalkenyl and hetercyclyl.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Pharmaceutical Compositions

The compounds disclosed therein are RAD51 inhibitors. The pharmaceutical composition of the present invention comprises one or more RAD51 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present invention provides a method of treating a subject with a disease which can be ameliorated by inhibition of RAD51, by administering to the subject an effective amount of one or more disclosed compounds, or a pharmaceutically acceptable salt thereof, or the corresponding pharmaceutical composition.

The present invention also provides a method of treating cancer, autoimmune disease, immune deficiency, or neurodegenerative disease, by administering to the subject in need thereof an effective amount of one or more disclosed compounds, or a pharmaceutically acceptable salt thereof, or the pharmaceutical composition thereof.

In one embodiment, cancers that can be treated by methods and compositions of the invention include cancer of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Another embodiment is a method of treating a cancer selected from the group consisting of lymphoma, leukemia, and a plasma cell neoplasm.

In one aspect of this embodiment, the cancer is lymphoma and the lymphoma is selected from the group consisting of Non-Hodgkin's lymphoma; Burkitt's lymphoma; small lymphocytic lymphoma; lymphoplasmacylic lymphoma; MALT lymphoma; follicular lymphoma; diffuse large B-celllymphoma; and T-cell lymphoma.

In another aspect of this embodiment, the cancer is leukemia and the leukemia is selected from the group consisting of acute lymphoblastic leukemia (ALL); Burkitt's leukemia; B-cellieukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

In another aspect of this embodiment, the cancer is plasma cell neoplasm and the plasma cell neoplasm is selected from the group consisting of multiple myeloma; plasma cell myeloma; plasma cell leukemia; and plasmacytoma.

In another embodiment, the method is a method of treating cancer and the cancer is selected from the group consisting of epithelial cell cancer; colon cancer; liver cancer; gastric cancer; intestinal cancer; esophageal cancer; breast cancer; ovarian cancer; head and neck cancer; lung cancer; and thyroid cancer.

In yet another embodiment, the method is a method of treating autoimmune disease and the autoimmune disease is selected from the group consisting of lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; inflammatory chronic rhinosinusitis; colitis; celiac disease; inflammatory bowel disease; Barrett's esophagus; inflammatory gastritis; autoimmune nephritis; autoimmune vasculitis; autoimmune hepatitis; autoimmune carditis; autoimmune encephalitis; autoimmune diabetes; autoimmune diabetes nephritis; and autoimmune mediated hematological disease.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In certain embodiments, the methods disclosed herein further comprise co-administering an effective amount of a DNA damaging agent to the subject being treated for cancer, in addition to an effective amount of a disclosed RAD51 inhibitor. The term "DNA damaging agent" refers to any agent that directly or indirectly damages DNA for which homologous recombination could repair the damage. The DNA damaging agents is selected from the group consisting of: exposure to a DNA damaging chemical; exposure to a chemotherapeutic agent; exposure to a radiochemotherapy, and exposure to ionizing or ultraviolet radiation. Specific examples of DNA-damaging chemotherapeutic agents include alkylating agents, nitrosoureas, anti-metabolites, plant alkaloids, plant extracts and radioisotopes. Specific examples of the chemotherapeutic agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or .alpha.-, .beta.-, or .gamma.-radiation, as well as environmental shock, e.g., hyperthermia.

In certain embodiments, the subject is determined to have an increased level and/or activity of a DNA damage process or DNA editing enzyme. A "DNA editing enzyme" refers to an enzyme which normally catalyzes the mutation, exchange or excision of DNA segments, particularly enzymes which can generate or promote the generation of point mutations, DNA single strand breaks, DNA double strained breaks or protein-DNA adducts. In one aspect of this embodiment, the DNA editing enzyme is selected from the group consisting of activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG 1), and Recombination Activating Gene 2 (RAG2).

In certain embodiments, blood cells obtained from the subject have been determined to have a detectable level of activation-induced cytidine deaminase (AID).

In certain embodiments, B cells obtained from the subject have been determined to have a detectable level of activation-induced cytidine deaminase (AID).

In certain embodiments, the detectable level of activation-induced cytidine deaminase (AID) is statistically significantly higher than the level of AID expressed in unactivated B-cells or normal non-immune cells from a healthy subject.

In certain embodiments, the invention provides methods for using the compounds of the invention, or the pharmaceutically acceptable salts, or the pharmaceutical compositions thereof. The compounds of the invention, or the pharmaceutically acceptable salts, or the pharmaceutical compositions thereof may be useful for a variety of therapeutic applications including treating and/or reducing a wide variety of diseases and disorders including, for example, cancer, autoimmune disease, immune deficiency, or neurodegenerative disease. The methods comprise administering to a subject in need thereof an effective amount of one or more compounds of the invention, or a pharmaceutically acceptable salt thereof, or the pharmaceutical compositions thereof.

Methods of Administration and Dosage Forms

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the Physician's Desk Reference (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and *Remington's, Pharmaceutical Sciences* (current edition), Mack Publishing Co., Easton, Pa.

In addition, the disclosed RAD51 inhibitors can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a a RAD51 mediated disease using the disclosed RAD51 inhibitors for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

EXEMPLIFICATION

Synthetic Protocols

Example 1

Scheme 1.1

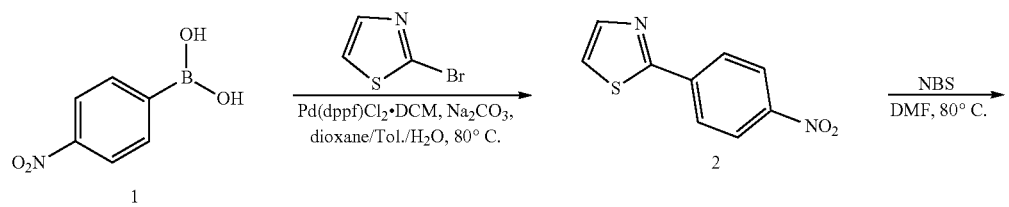

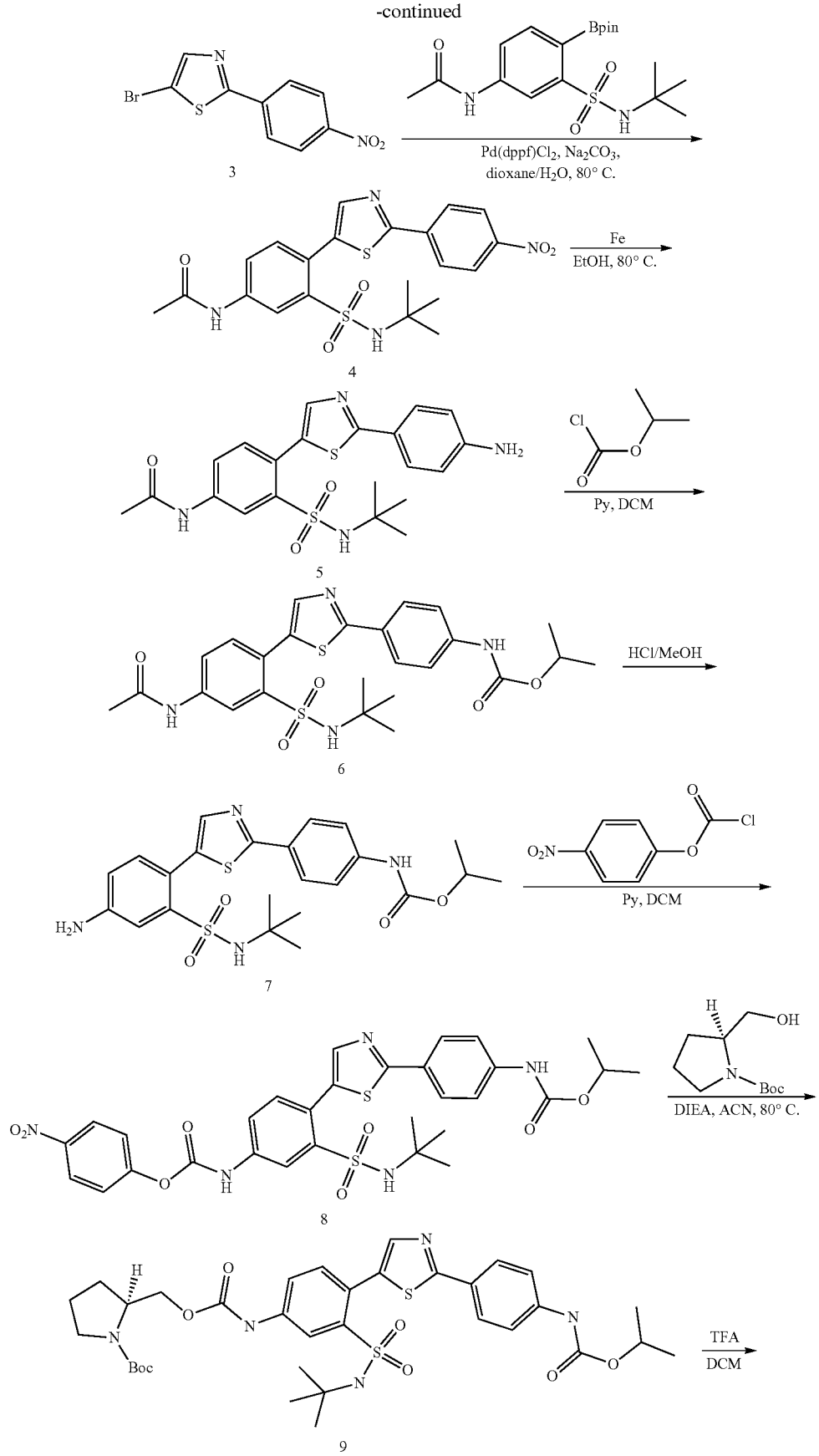

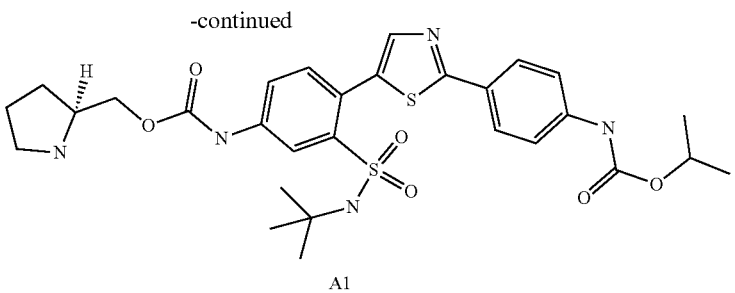

A1

Intermediate Compound 2

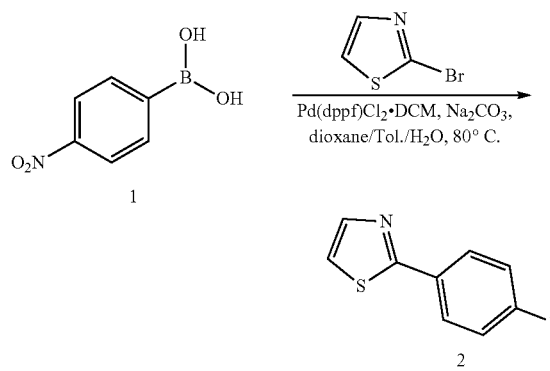

A mixture of 4-nitrophenyl)boronic acid (23.00 g, 137.78 mmol, 1.00 eq.), 2-bromothiazole (25.54 g, 155.69 mmol, 14.03 mL, 1.13 eq.), $Na_2CO_3$ (36.51 g, 344.45 mmol, 2.50 eq.) and $Pd(dppf)Cl_2 \cdot CH_2Cl_2$ (6.75 g, 8.27 mmol, 0.06 eq.) in Tol. (250.00 mL)/$H_2O$ (100.00 mL)/dioxane (250.00 mL) was degassed and purged with $N_2$ for 3 times. The mixture was stirred at 80° C. for 12 hrs under $N_2$ atmosphere and LCMS showed the reaction was complete. The mixture was concentrated and the residue was purified by column chromatography (Petroleum ether:Ethyl acetate=50:1 to 5:1) to give 2-(4-nitrophenyl)thiazole (14.00 g, 67.89 mmol, 56.00% yield) as a yellow solid. $^1$H NMR (400 MHz, CHLOROFORM-d) δ=8.35-8.29 (m, 2H), 8.21-8.12 (m, 2H), 7.99 (d, J=3.2 Hz, 1H), 7.50 (d, J=3.2 Hz, 1H).

Intermediate Compound 3

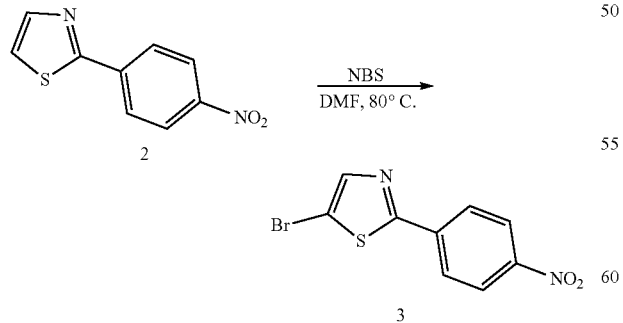

To a solution of 2-(4-nitrophenyl)thiazole (6 g, 29.10 mmol, 1 eq.) in DMF (50 mL), was added NBS (15.54 g, 87.29 mmol, 3 eq.). The mixture was stirred at 80° C. for 15 mins and LCMS showed the reaction was complete. The mixture was poured into water (1 L) and filtered. The filter cake was washed with MeOH (50 mL) and dried to give 5-bromo-2-(4-nitrophenyl)thiazole (7.3 g, crude) as a yellow solid. $^1$H NMR (400 MHz, METHANOL-d4) δ=8.35 (br s, 2H), 8.18 (br s, 2H), 8.07-7.88 (m, 1H).

General Method A: Intermediate Compound 4

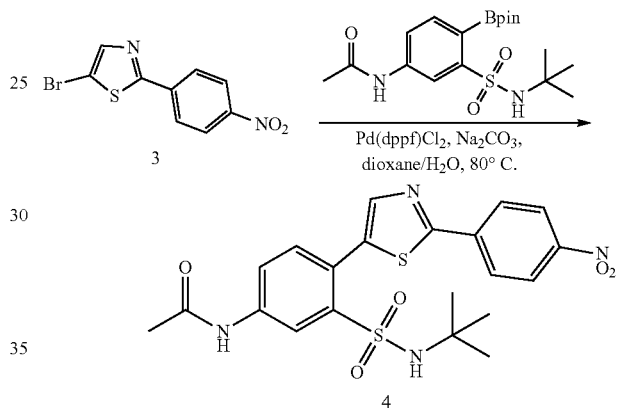

A mixture of N-[3-(tert-butylsulfamoyl)-4-(4,4,5,5-tetramethyl-1,3,2-dioxaborolan-2-yl)phenyl]acetamide (5 g, 12.62 mmol, 1 eq.), 5-bromo-2-(4-nitrophenyl)thiazole (4.32 g, 15.14 mmol, 1.2 eq.), $Na_2CO_3$ (4.01 g, 37.85 mmol, 3 eq.) and $Pd(dppf)Cl_2$ (923.16 mg, 1.26 mmol, 0.1 eq.) in dioxane (50 mL) and $H_2O$ (10 mL) was degassed and purged with $N_2$ for 3 times. Then the mixture was stirred at 80° C. for 12 hrs under $N_2$ atmosphere and LCMS showed the reaction was complete. The mixture was concentrated, diluted with $H_2O$ (50 mL) and extracted with EtOAc (40 mL×3). The combined organic layers were washed with brine (40 mL), dried over $Na_2SO_4$, filtered and concentrated to give N-[3-(tert-butylsulfamoyl)-4-[2-(4-nitrophenyl)thiazol-5-yl]phenyl]acetamide (8.9 g, crude) as black brown oil, which was used directly without further purification. ESI [M+H]=475.1

General Method B: Intermediate Compound 5

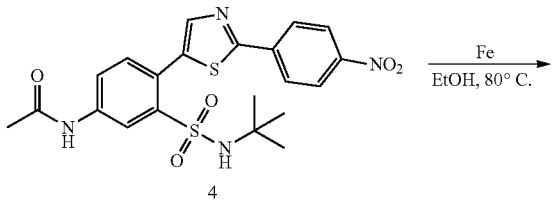

-continued

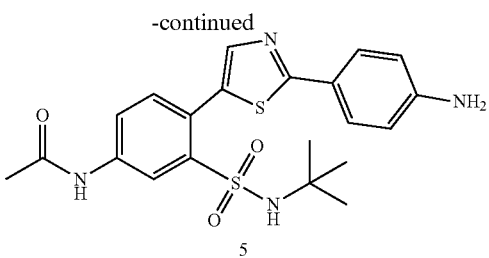
5

A mixture of N-[3-(tert-butylsulfamoyl)-4-[2-(4-nitrophenyl)thiazol-5-yl]phenyl] acetamide (800 mg, 1.69 mmol, 1 eq.), NH₄Cl (450.87 mg, 8.43 mmol, 294.68 ul, 5 eq.) and Fe (470.76 mg, 8.43 mmol, 5 eq.) in EtOH (20 mL), THF (20 mL) and H₂O (10 mL) was stirred at 80° C. for 2 hrs and LCMS showed the reaction was complete. The mixture was filtered, the filtrate was diluted with H₂O (20 mL) and extracted with EtOAc (20 mL×3). The combined organic layers were washed with brine (20 mL), dried over Na₂SO₄, filtered and concentrated. The residue was purified by column chromatography (Petroleum ether:Ethyl acetate=10:1-1:2) to give N-[4-[2-(4-aminophenyl)thiazol-5-yl]-3-(tert-butylsulfamoyl)phenyl]acetamide (0.6 g, 1.35 mmol, 80.06% yield) as a yellow solid. ESI [M+H]=445.1

General Method C: Intermediate Compound 6

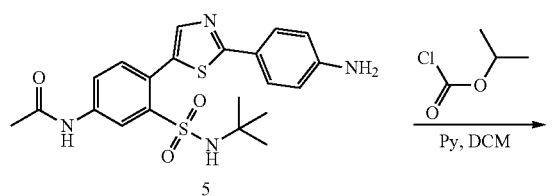
5

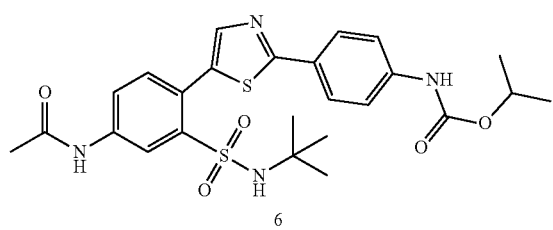
6

A mixture of N-[4-[2-(4-aminophenyl)thiazol-5-yl]-3-(tert-butylsulfamoyl) phenyl]acetamide (1.3 g, 2.92 mmol, 1 eq.), DMAP (35.72 mg, 292.42 µmol, 0.1 eq.) and Pyridine (1.16 g, 14.62 mmol, 1.18 mL, 5 eq.) in DCM (20 mL) was added isopropyl carbonochloridate (716.72 mg, 5.85 mmol, 811.68 ul, 2 eq.) at 0° C. Then the mixture was stirred at 20° C. for 1 hr under N₂ atmosphere. TLC (Petroleum ether:Ethyl acetate=1:1, R_f=0.3) indicated the reaction was complete. The reaction mixture was washed with 1N HCl (50 mL) and sat.aq.Na₂CO₃ (50 mL), dried over Na₂SO₄, filtered and concentrated. The residue was purified by column chromatography (Petroleum ether:Ethyl acetate=1:1) to give isopropyl N-[4-[5-[4-acetamido-2-(tert-butylsulfamoyl)phenyl]thiazol-2-yl]phenyl]carbamate (1.5 g, 2.83 mmol, 96.67% yield) as a yellow solid.

Intermediate Compound 7

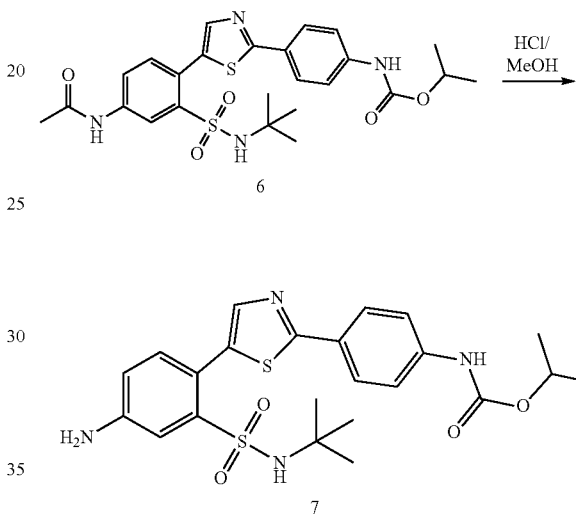
6

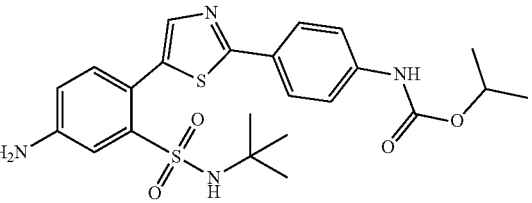
7

Isopropyl N-[4-[5-[4-acetamido-2-(tert-butylsulfamoyl)phenyl]thiazol-2-yl]phenyl]carbamate (1.5 g, 2.83 mmol, 1 eq.) was dissolved into HCl/MeOH (4 M, 17.65 mL, 24.97 eq.) and the mixture was stirred at 30° C. for 2 hrs. LCMS showed the reaction was complete. The mixture concentrated and the residue was dissolved into sat.aq.Na₂CO₃ (50 mL) and extracted with EtOAc (50 mL×3). The combined organic phase was dried over Na₂SO₄, filtered and concentrated to give intermediate compound 7 (1.3 g, 2.66 mmol, 94.12% yield) as a yellow solid, which was used directly without further purification. ESI [M+H]=489.1

Intermediate Compound 8

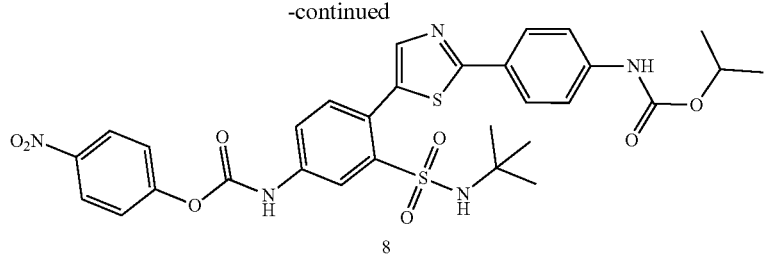

8

To a mixture of isopropyl N-[4-[5-[4-amino-2-(tert-butylsulfamoyl)phenyl] thiazol-2-yl]phenyl]carbamate (0.5 g, 1.02 mmol, 1 eq.), DMAP (12.50 mg, 102.33 μmol, 0.1 eq.) and Pyridine (404.71 mg, 5.12 mmol, 412.97 ul, 5 eq.) in DCM (10 mL) was added (4-nitrophenyl) carbonochloridate (412.52 mg, 2.05 mmol, 2 eq.) at 0° C., and then the mixture was stirred at 20° C. for 2 hrs under $N_2$ atmosphere. LCMS showed the reaction was complete. The mixture was used for next step without any purification. ESI [M+H]=654.1

General Method D: Intermediate Compound 9

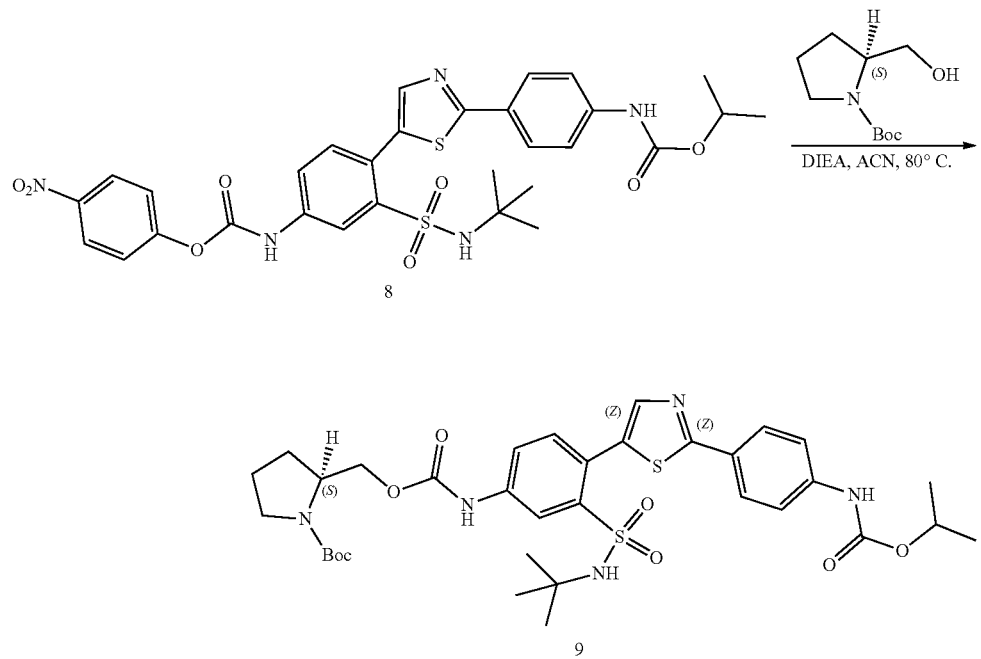

A mixture of tert-butyl (2S)-2-(hydroxymethyl)pyrrolidine-1-carboxylate (60 mg, 298.12 mol, 3.90 eq.), DIEA (25 mg, 193.43 μmol, 33.69 ul, 2.53 eq.) and (4-nitrophenyl) N-[3-(tert-butylsulfamoyl)-4-[2-[4-(isopropoxycarbonylamino) phenyl]thiazol-5-yl]phenyl]carbamate (50 mg, 76.48 μmol, 1 eq.) in MeCN (2 mL) was stirred at 80° C. for 1 hour. LCMS showed the reaction was complete. The mixture was diluted with EtOAc (4 mL) and THF (1 mL), washed with $H_2O$ (5 mL), dried over $Na_2SO_4$, filtered and concentrated to give tert-butyl (2S)-2-[[3-(tert-butylsulfamoyl)-4-[2-[4-(isopropoxycarbonylamino)phenyl]thiazol-5-yl]phenyl]carbamoyloxymethyl]pyrrolidine-1-carboxylate (80 mg, crude) as a yellow gum, which was used directly. ESI [M+H]=716.2

General Method E: Compound A1

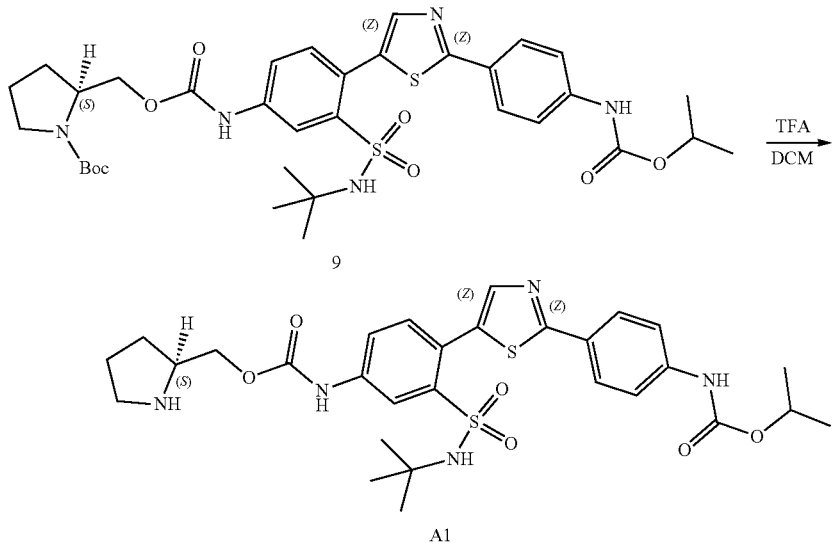

To a solution of tert-butyl (2S)-2-[[3-(tert-butylsulfamoyl)-4-[2-[4-(isopropoxycarbonylamino)phenyl]thiazol-5-yl]phenyl]carbamoyloxymethyl]pyrrolidine-1-carboxylate (80 mg, 111.75 μmol, 1 eq.) in DCM (1 mL) was added TFA (1 mL) dropwise and the mixture was stirred at 15° C. for 1 hour. LCMS showed the reaction was complete. The mixture was concentrated and the residue was purified by prep-HPLC (column: Luna C18 100*30 5u; mobile phase: [water (0.1% TFA)-ACN]; B %: 20%-60%, 10 min) to give compound A1 (4.54 mg, 6.10 μmol, 5.46% yield, 98.064% purity, TFA) as a brown solid. 1H NMR (400 MHz, METHANOL-d4) δ=8.41 (d, J=2.2 Hz, 1H), 7.91-7.84 (m, 3H), 7.75 (dd, J=2.0, 8.4 Hz, 1H), 7.57 (d, J=8.8 Hz, 2H), 7.50 (d, J=8.4 Hz, 1H), 5.02-4.93 (m, 1H), 4.50 (dd, J=3.3, 12.6 Hz, 1H), 4.35 (dd, J=7.8, 12.5 Hz, 1H), 3.95 (dq, J=3.4, 8.1 Hz, 1H), 3.42-3.33 (m, 2H), 2.31-2.02 (m, 3H), 1.93-1.81 (m, 1H), 1.32 (d, J=6.4 Hz, 6H), 1.12 (s, 9H). ESI [M+H]=616.2

General Method F: Compound A2

To a solution of phenylmethanamine (14.47 g, 135.06 mmol, 14.72 mL, 3 eq.) and DIEA (23.27 g, 180.08 mmol, 31.37 mL, 4 eq.) in DCM (500 mL) was added (4-nitrophenyl) N-[3-(tert-butylsulfamoyl)-4-[2-[4-(isopoxycarbonylamino) phenyl]thiazol-5-yl]phenyl]carbamate (29.43 g, 45.02 mmol, 1 eq.) in DCM (500 mL). The mixture was stirred at 20° C. for 15 mins and LCMS showed the reaction was complete. The mixture was washed with 1 N HCl (500 mL) and sat.aq.Na2CO3 (500 mL). Then the organic phase was dried over $Na_2SO_4$, filtered and concentrated. The residue was purified by silica gel chromatography eluted with Petroleum ether:Ethyl acetate=3:1 to give compound A2 (10.23 g, 15.47 mmol, 34.37% yield, 94.09% purity) as a yellow solid. 1H NMR (400 MHz, METHANOL-d4) δ=8.29 (d, J=2.4 Hz, 1H), 7.93-7.84 (m, 3H), 7.74 (dd, J=2.2, 8.6 Hz, 1H), 7.59 (d, J=8.8 Hz, 2H), 7.45 (d, J=8.3 Hz, 1H), 7.40-7.32 (m, 4H), 7.27 (dt, J=2.7, 5.7 Hz, 1H), 5.07-4.95 (m, 1H), 4.44 (s, 2H), 1.33 (d, J=6.4 Hz, 6H), 1.15 (s, 9H). ESI [M+H]=622.2

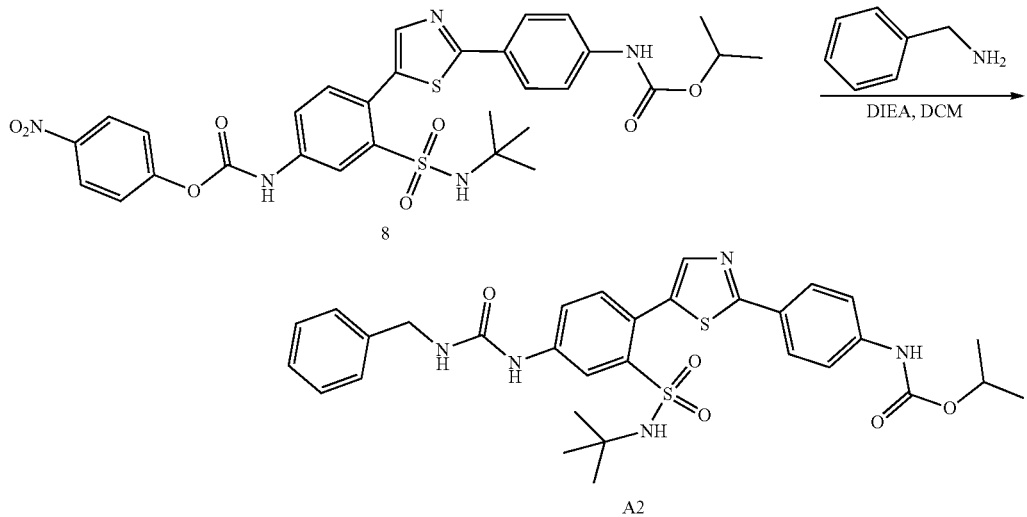

Scheme 1.2

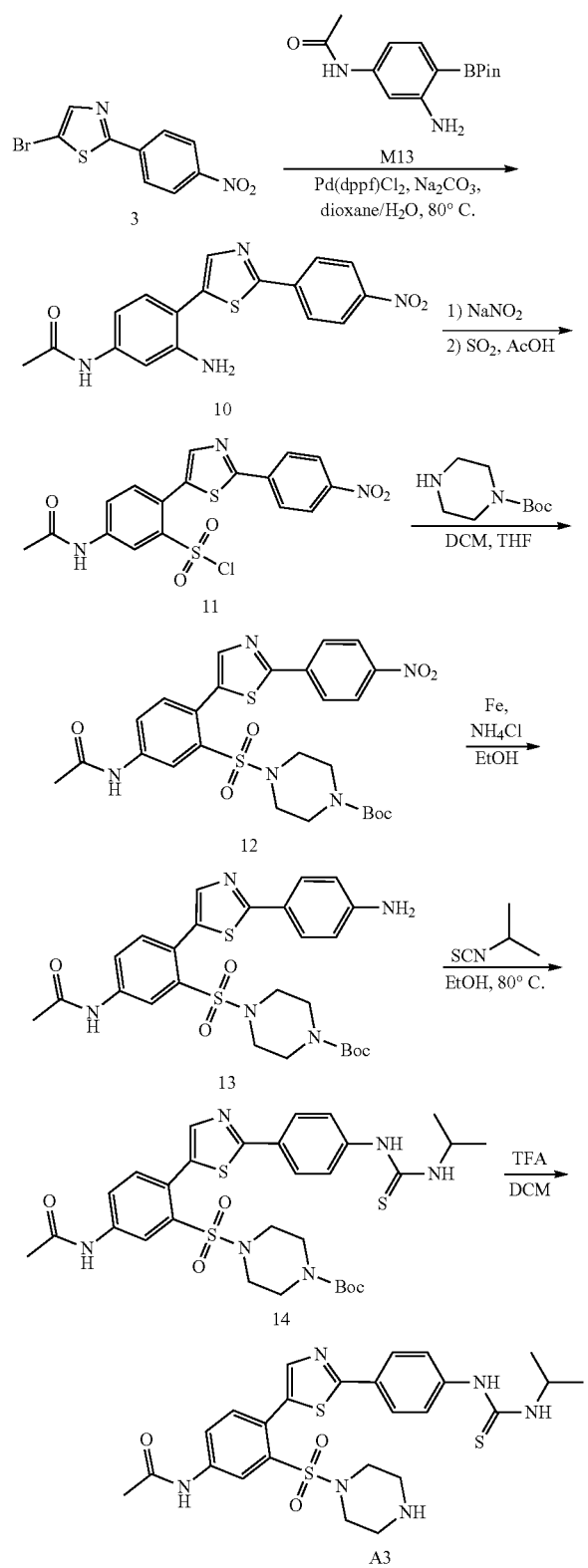

Intermediate Compound 10

Intermediate compound 10 was prepared from intermediate compound 3 via general method A (supra).

$^1$H NMR (400 MHz, DMSO-d6) δ=9.85 (s, 1H), 8.36-8.31 (m, 2H), 8.22-8.16 (m, 2H), 8.10 (s, 1H), 7.24-7.16 (m, 2H), 6.84 (dd, J=2.0, 8.4 Hz, 1H), 5.35 (s, 2H), 2.02 (s, 3H).

Intermediate Compound 11

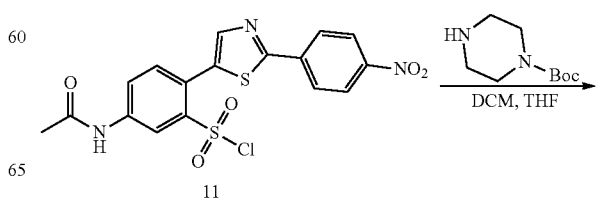

To a mixture of N-[3-amino-4-[2-(4-nitrophenyl)thiazol-5-yl]phenyl]acetamide (2.00 g, 5.64 mmol, 1.00 eq.) in H$_2$O (5 mL) and AcOH (15 mL) was added conc. HCl (20.00 mL) at 0° C. followed by a solution of NaNO$_2$ (2.00 g, 28.99 mmol, 1.57 mL, 5.14 eq.) in H$_2$O (5 mL). The mixture was stirred at 0° C. for 2.5 hrs (mixture 1). Another mixture of CuCl$_2$ (758.79 mg, 5.64 mmol, 1.00 eq.) in a solution of SO$_2$ in AcOH (15 g in 20 mL) and H$_2$O (5 mL) was stirred at 20° C. for 1 hour (mixture 2). Then the mixture 2 was cooled to 0° C. and mixture 1 was added into dropwise. The reaction mixture was stirred at 0° C. for another 0.5 hour. HPLC showed the reaction was complete. The mixture was poured into ice-water mixture (70 mL) and the resulting precipitate was collected by filtration, then washed with water (10 mL×3) and dried to give 5-acetamido-2-[2-(4-nitrophenyl)thiazol-5-yl]benzenesulfonyl chloride (2.50 g, crude) as a black brown solid, which was used directly.

Intermediate Compound 12

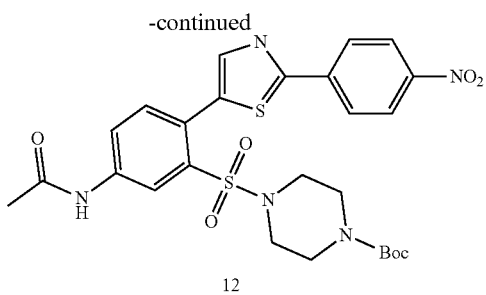

12

To a solution of tert-butyl piperazine-1-carboxylate (191.41 mg, 1.03 mmol, 3.00 eq.) and DMAP (4.19 mg, 34.26 μmol, 0.10 eq.) in DCM (1.00 mL) was added a solution of 5-acetamido-2-[2-(4-nitrophenyl)thiazol-5-yl]benzenesulfonyl chloride (150.00 mg, 342.56 mol, 1.00 eq.) in THF (5.00 mL) dropwise. The mixture was stirred at 25° C. for 1 hour and LCMS showed the reaction was complete. The mixture was poured into 0.5 N HCl (6 mL) and extracted with EtOAc/THF (3 mL/1 mL×3). The combined organic layers were washed with brine (3 mL×2), dried over Na$_2$SO$_4$, filtered and concentrated to give tert-butyl 4-[5-acetamido-2-[2-(4-nitrophenyl)thiazol-5-yl]phenyl] sulfonylpiperazine-1-carboxylate (200.00 mg, crude) without any purification. ESI [M+Na]=610.2

Intermediate Compound 13

Intermediate Compound 13 was prepared from intermediate compound 12 via general method B (supra)

General Method G: Intermediate Compound 14

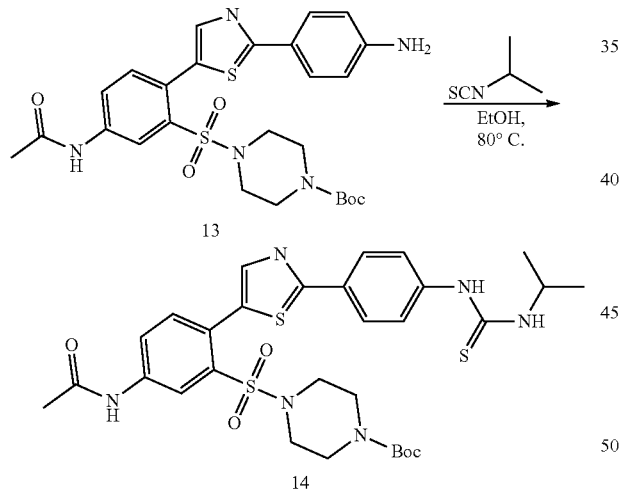

A mixture of 2-isothiocyanatopropane (261.23 mg, 2.58 mmol, 274.98 ul, 10.00 eq.) and tert-butyl 4-[5-acetamido-2-[2-(4-aminophenyl)thiazol-5-yl]phenyl]sulfonyl piperazine-1-carboxylate (180.00 mg, 258.21 μmol, 1.00 eq.) in EtOH (3.00 mL) was stirred at 80° C. for 2 hrs and LCMS showed the reaction was complete. The mixture was concentrated and the residue was purified by prep-TLC (Petroleum ether: Ethyl acetate=1:2) to give tert-butyl 4-[5-acetamido-2-[2-[4-(isopropylcarbamo thioylamino)phenyl]thiazol-5-yl]phenyl]sulfonylpiperazine-1-carboxylate (90.00 mg, crude) as a yellow solid. ESI [M+H]=659.3

Compound A3

Compound A3 was prepared from intermediate compound 14 via general method E (supra).

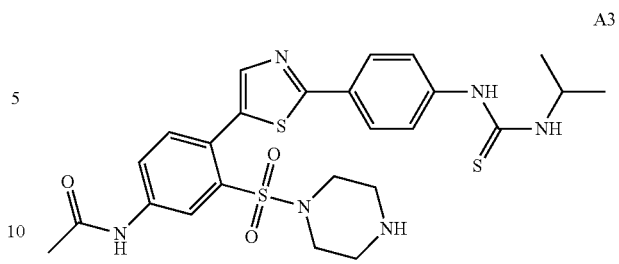

$^1$H NMR (400 MHz, DMSO-d6) δ=10.54 (s, 1H), 9.70 (br s, 1H), 8.75 (br s, 2H), 8.42 (d, J=1.8 Hz, 1H), 8.00-7.80 (m, 5H), 7.68 (d, J=8.6 Hz, 2H), 7.61 (d, J=8.4 Hz, 1H), 4.39 (br d, J=6.4 Hz, 1H), 3.12 (br s, 4H), 3.05-2.97 (m, 4H), 2.11 (s, 3H), 1.18 (d, J=6.6 Hz, 6H). ESI [M+H]=558.9

General Method H: Compound A4

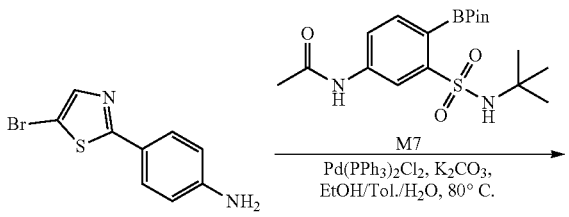

A mixture of 4-(5-bromothiazol-2-yl)aniline (80.00 mg, 313.57 μmol, 1.00 eq.), N-[3-(tert-butylsulfamoyl)-4-(4,4,5,5-tetramethyl-1,3,2-dioxaborolan-2-yl)phenyl]acetamide (149.13 mg, 376.28 μmol, 1.20 eq.), Pd(PPh$_3$)$_2$Cl$_2$ (22.01 mg, 31.36 μmol, 0.10 eq.) and K$_2$CO$_3$ (86.68 mg, 627.14 μmol, 2.00 eq.) in the mixture of EtOH (900.00 ul), toluene (900.00 ul) and H$_2$O (300.00 ul) was heated to 80° C. for 16 hrs under N$_2$. LCMS showed the reaction was complete. The mixture was diluted with EtOAc (20 mL) and washed with H$_2$O (7 mL). The aqueous phase was extracted with EtOAc (7 mL×2). The combined organic phase was dried over Na$_2$SO$_4$, filtered, concentrated in vacuum and purified by acidic prep-HPLC to give compound A4 (90.00 mg, 143.73 μmol, 45.84% yield, 71% purity) as a yellow solid. 1H NMR (400 MHz, DMSO-d6) δ=10.36 (s, 1H), 8.39 (d, J=2.2 Hz, 1H), 7.81 (dd, J=2.0, 8.6 Hz, 1H), 7.73 (s, 1H), 7.65 (br d, J=6.6 Hz, 2H), 7.45 (d, J=8.3 Hz, 1H), 7.09 (s, 1H), 6.76-6.64 (m, 2H), 2.08 (s, 3H), 1.07 (s, 9H). ESI [M+H]=445.2

General Method I: Compound A5

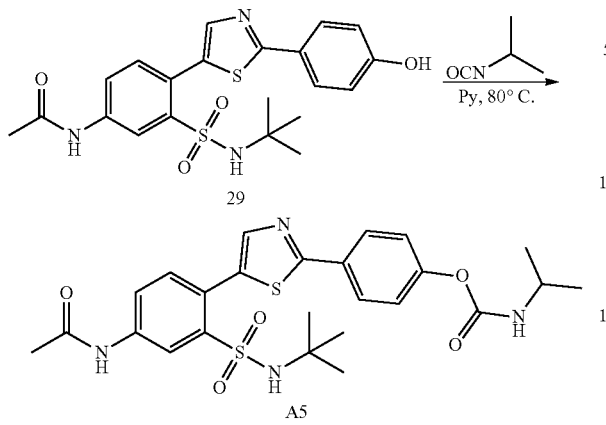

To a solution of N-[3-(tert-butylsulfamoyl)-4-[2-(4-hydroxyphenyl)thiazol-5-yl]phenyl]acetamide (50.00 mg, 112.22 μmol, 1.00 eq.) in Py (2.00 mL) was added 2-isocyanatopropane (28.65 mg, 336.66 μmol, 32.93 ul, 3.00 eq.) and the mixture was stirred at 80° C. for 16 hrs. LCMS showed the reaction was complete. The mixture was concentrated and the residue was purified by acidic prep-HPLC to give compound A5 (3.68 mg, 6.84 μmol, 6.09% yield, 98.6% purity) as a brown solid. $^1$H NMR (400 MHz, METHANOL-d4) δ=8.48 (s, 1H), 7.98 (d, J=8.8 Hz, 2H), 7.91-7.84 (m, 2H), 7.50 (d, J=8.3 Hz, 1H), 7.24 (d, J=8.8 Hz, 2H), 3.78 (br d, J=7.9 Hz, 1H), 2.17 (s, 3H), 1.22 (d, J=6.6 Hz, 6H), 1.13 (s, 9H). ESI [M+H]=530.9

Scheme 1.3

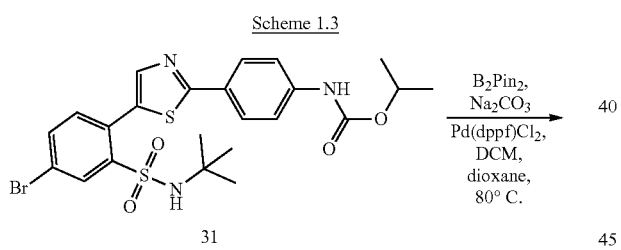

General Method J: Intermediate Compound 34

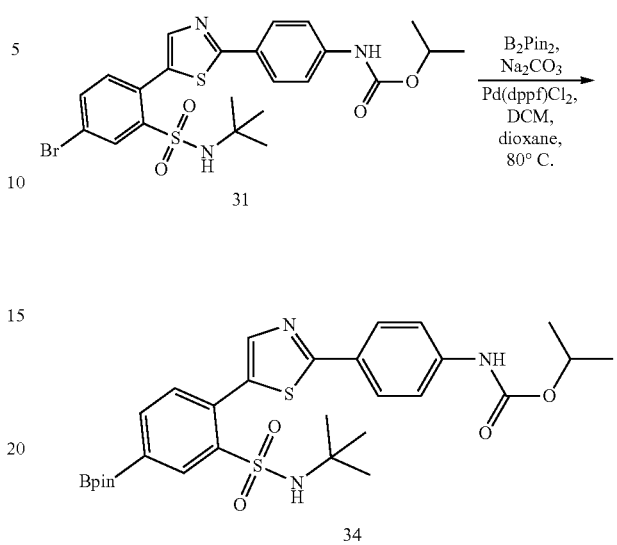

To a solution of isopropyl N-[4-[5-[4-bromo-2-(tert-butylsulfamoyl)phenyl] thiazol-2-yl]phenyl]carbamate (100.00 mg, 181.00 μmol, 1.00 eq.) in dioxane (3.00 mL) was added 4,4,5,5-tetramethyl-2-(4,4,5,5-tetramethyl-1,3,2-dioxaborolan-2-yl)-1,3,2-dioxaborolane (183.85 mg, 724.00 μmol, 4.00 eq.), Na$_2$CO$_3$ (38.37 mg, 362.00 μmol, 2.00 eq.) and Pd(dppf)Cl$_2$.CH$_2$Cl$_2$ (14.78 mg, 18.10 μmol, 0.10 eq.) and the mixture was stirred at 80° C. under N$_2$ for 16 hrs. LCMS showed the reaction was complete. The mixture was diluted with water (30 mL) and extracted with EtOAc (30 mL×3). The combined organic phase was dried, filtered and concentrated. The residue was purified by prep-TLC (PE: EtOAc=2:1) to give intermediate compound 34 (90.00 mg, 150.11 μmol, 82.93% yield) as a yellow solid. ESI [M+H]=600.3

Compound A6

Compound A6 was prepared from intermediate compound 34 via general method A (supra).

$^1$H NMR (400 MHz, METHANOL-d4) δ=9.05 (s, 1H), 8.60 (d, J=2.0 Hz, 1H), 8.13 (d, J=1.2 Hz, 1H), 8.04 (dd, J=2.0, 7.9 Hz, 1H), 8.00 (s, 1H), 7.96-7.92 (m, 2H), 7.75 (d, J=8.1 Hz, 1H), 7.61 (d, J=8.7 Hz, 2H), 5.01 (td, J=6.2, 12.5 Hz, 1H), 1.34 (d, J=6.2 Hz, 6H), 1.12 (s, 9H). ESI [M+H]=540.2

General Method K: Compound A7

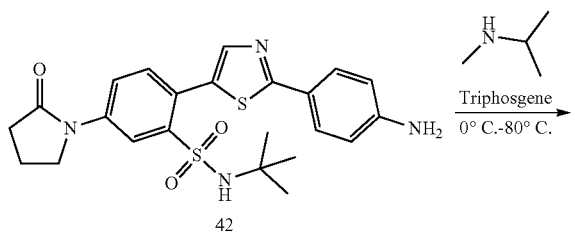

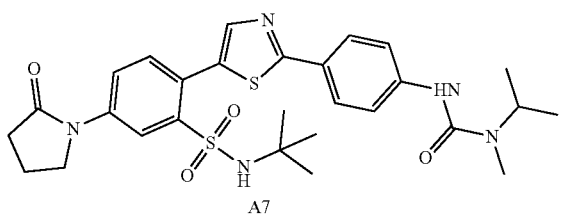

To a solution of N-methylpropan-2-amine (124.33 mg, 1.70 mmol, 177.61 ul, 10.00 eq.) in DCM (2.00 mL) was added DIPEA (109.85 mg, 849.95 μmol, 148.45 ul, 5.00 eq.) and bis(trichloromethyl)carbonate (227.00 mg, 764.96 μmol, 4.50 eq.) at 0° C. The mixture was stirred at 0° C. for 0.5 hr and then added 2-[2-(4-aminophenyl) thiazol-5-yl]-N-tert-butyl-5-(2-oxopyrrolidin-1-yl)benzenesulfonamide (80.00 mg, 169.99 μmol, 1.00 eq.) in DMF (2.00 mL). The mixture was stirred at 80° C. for another 0.5 hr and LCMS showed the reaction was complete. The mixture was concentrated and the residue was purified by acidic prep-HPLC to give compound A7 (4.83 mg, 8.27 μmol, 4.87% yield, 97.6% purity) as a yellow solid. 1H NMR (400 MHz, METHANOL-d4) δ=8.66 (d, J=2.2 Hz, 1H), 7.92-7.80 (m, 4H), 7.60-7.49 (m, 3H), 4.54 (td, J=6.7, 13.5 Hz, 1H), 3.99 (t, J=7.1 Hz, 2H), 2.90 (s, 3H), 2.65 (t, J=8.0 Hz, 2H), 2.22 (quin, J=7.6 Hz, 2H), 1.19 (d, J=6.6 Hz, 6H), 1.14 (s, 9H). ESI [M+H]=570.2

Example 2

The following compounds were synthesized via reacting intermediate 8 with different alcohols via general method D and E (shown in Example 1), unless otherwise noted.

Compound B1

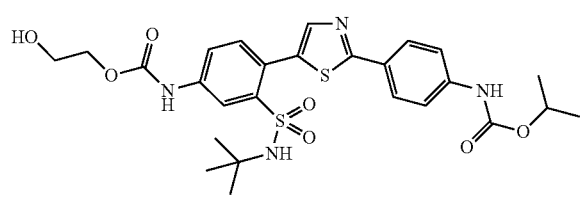

$^1$H NMR (400 MHz, METHANOL-d4) δ=8.39 (d, J=2.0 Hz, 1H), 7.93-7.86 (m, 3H), 7.75 (dd, J=2.0, 8.3 Hz, 1H), 7.61-7.57 (m, 2H), 7.49 (d, J=8.8 Hz, 1H), 5.00 (td, J=6.2, 12.6 Hz, 1H), 4.32-4.22 (m, 2H), 3.87-3.76 (m, 2H), 1.34 (d, J=6.4 Hz, 6H), 1.16 (s, 9H). ESI [M+H]=577.2

Compound B2

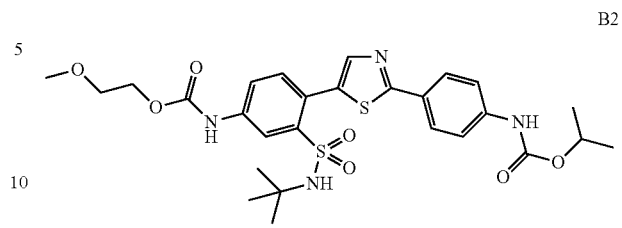

$^1$H NMR (400 MHz, METHANOL-d4) δ=8.37 (d, J=2.2 Hz, 1H), 7.90-7.82 (m, 3H), 7.70 (dd, J=2.2, 8.4 Hz, 1H), 7.56 (d, J=8.6 Hz, 2H), 7.45 (d, J=8.4 Hz, 1H), 5.04-4.93 (m, 1H), 4.34-4.26 (m, 2H), 3.66 (dd, J=3.9, 5.4 Hz, 2H), 3.40 (s, 3H), 1.31 (d, J=6.2 Hz, 6H), 1.13 (s, 9H). ESI [M+H]=591.2

Compound B3

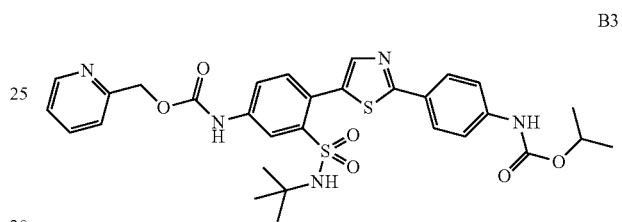

$^1$H NMR (400 MHz, METHANOL-d4) δ=8.69 (d, J=5.3 Hz, 1H), 8.39 (d, J=2.2 Hz, 1H), 8.25 (dt, J=1.5, 7.8 Hz, 1H), 7.91-7.81 (m, 4H), 7.77-7.66 (m, 2H), 7.57 (d, J=8.8 Hz, 2H), 7.48 (d, J=8.3 Hz, 1H), 5.43 (s, 2H), 4.97 (quin, J=6.2 Hz, 1H), 1.31 (d, J=6.1 Hz, 6H), 1.12 (s, 9H). ESI [M+H]=624.0

Compound B4

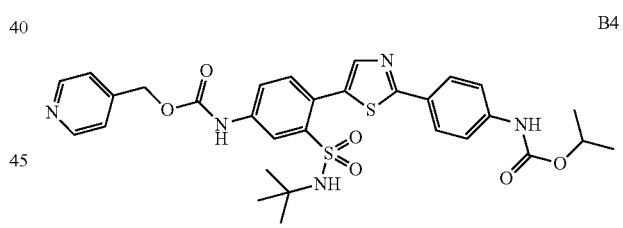

$^1$H NMR (400 MHz, METHANOL-d4) δ=8.81 (d, J=7.0 Hz, 2H), 8.40 (d, J=2.2 Hz, 1H), 8.02 (d, J=6.6 Hz, 2H), 7.91-7.83 (m, 3H), 7.77-7.72 (m, 1H), 7.57 (d, J=8.8 Hz, 2H), 7.50 (d, J=8.3 Hz, 1H), 5.53 (s, 2H), 4.98 (quin, J=6.2 Hz, 1H), 1.31 (d, J=6.1 Hz, 6H), 1.12 (s, 9H). ESI [M+H]=624.1

Compound B5

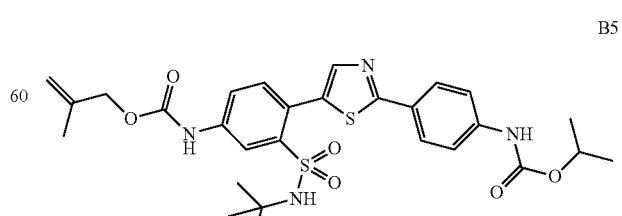

¹H NMR (400 MHz, METHANOL-d4) δ=8.38 (d, J=2.2 Hz, 1H), 7.90-7.83 (m, 3H), 7.72 (dd, J=2.2, 8.3 Hz, 1H), 7.57 (d, J=8.8 Hz, 2H), 7.45 (d, J=8.3 Hz, 1H), 5.05 (s, 1H), 5.01-4.93 (m, 2H), 4.61 (s, 2H), 1.81 (s, 3H), 1.31 (d, J=6.6 Hz, 6H), 1.14 (s, 9H). ESI [M+H]=587.1

Compound B6

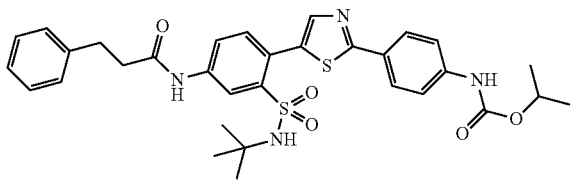

¹H NMR (400 MHz, METHANOL-d4) δ=8.46 (d, J=2.0 Hz, 1H), 7.94-7.84 (m, 4H), 7.59 (d, J=8.8 Hz, 2H), 7.50 (d, J=8.8 Hz, 1H), 7.35-7.25 (m, 4H), 7.23-7.15 (m, 1H), 5.00 (td, J=6.2, 12.6 Hz, 1H), 3.04 (t, J=7.6 Hz, 2H), 2.80-2.66 (m, 2H), 1.33 (d, J=5.9 Hz, 6H), 1.16 (s, 9H). ESI [M+H]=621.1

Compound B7

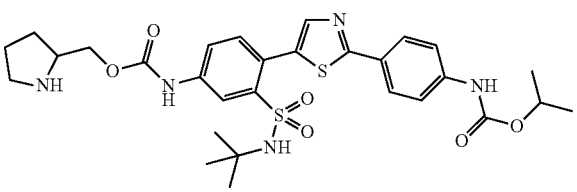

¹H NMR (400 MHz, METHANOL-d4) δ=8.43 (d, J=1.5 Hz, 1H), 7.94-7.85 (m, 3H), 7.77 (dd, J=2.0, 8.3 Hz, 1H), 7.59 (d, J=8.3 Hz, 2H), 7.51 (d, J=8.3 Hz, 1H), 5.00 (spt, J=6.2 Hz, 1H), 4.52 (dd, J=3.4, 12.7 Hz, 1H), 4.37 (dd, J=7.8, 12.7 Hz, 1H), 3.97 (dq, J=3.4, 8.0 Hz, 1H), 3.46-3.35 (m, 2H), 2.35-2.23 (m, 1H), 2.21-2.01 (m, 2H), 1.89 (qd, J=8.4, 12.9 Hz, 1H), 1.34 (d, J=6.4 Hz, 6H), 1.14 (s, 9H). ESI [M+H]=616.2

Compound B8

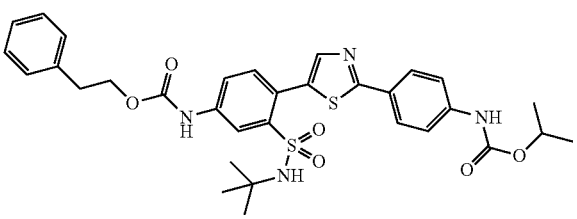

¹H NMR (400 MHz, METHANOL-d4) δ=8.37 (s, 1H), 7.91-7.85 (m, 3H), 7.70 (br d, J=8.6 Hz, 1H), 7.58 (d, J=8.6 Hz, 2H), 7.45 (d, J=8.2 Hz, 1H), 7.36-7.25 (m, 4H), 7.22 (qd, J=4.2, 8.7 Hz, 1H), 4.98 (td, J=6.3, 12.5 Hz, 1H), 4.39 (t, J=6.8 Hz, 2H), 3.01 (t, J=6.8 Hz, 2H), 1.35-1.29 (m, 6H), 1.14 (s, 9H). ESI [M+H]=637.2

Compound B9

¹H NMR (400 MHz, METHANOL-d4) δ=8.89 (s, 1H), 8.75 (br d, J=5.5 Hz, 1H), 8.49 (br d, J=8.6 Hz, 1H), 8.39 (d, J=1.8 Hz, 1H), 7.96-7.85 (m, 4H), 7.73 (br d, J=7.9 Hz, 1H), 7.58 (d, J=8.6 Hz, 2H), 7.49 (d, J=8.4 Hz, 1H), 5.42 (s, 2H), 4.98 (td, J=6.2, 12.3 Hz, 1H), 1.32 (d, J=6.2 Hz, 6H), 1.12 (s, 9H). ESI [M+H]=624.2

Compound B10

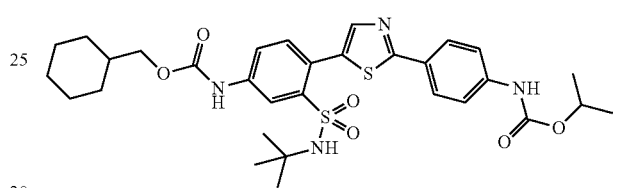

¹H NMR (400 MHz, METHANOL-d₄) δ=8.38 (d, J=2.0 Hz, 1H), 7.91-7.82 (m, 3H), 7.70 (br d, J=7.3 Hz, 1H), 7.57 (d, J=8.6 Hz, 2H), 7.45 (d, J=8.4 Hz, 1H), 5.02-4.92 (m, 1H), 3.98 (d, J=6.4 Hz, 2H), 1.87-1.63 (m, 6H), 1.39-1.19 (m, 9H), 1.16-0.94 (m, 11H). ESI [M+H]=629.2

Compound B11

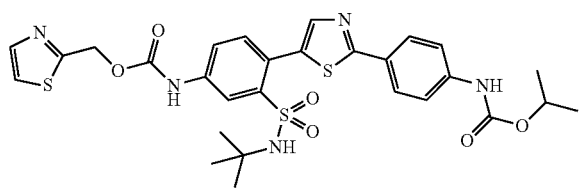

¹H NMR (400 MHz, METHANOL-d4) δ=8.39 (s, 1H), 7.92-7.85 (m, 3H), 7.82 (d, J=3.1 Hz, 1H), 7.75 (br d, J=6.6 Hz, 1H), 7.66 (d, J=3.3 Hz, 1H), 7.58 (d, J=8.6 Hz, 2H), 7.49 (d, J=8.6 Hz, 1H), 5.51 (s, 2H), 5.02-4.91 (m, 1H), 1.31 (d, J=6.2 Hz, 6H), 1.14 (s, 9H). ESI [M+H]=630.1

Compound B12

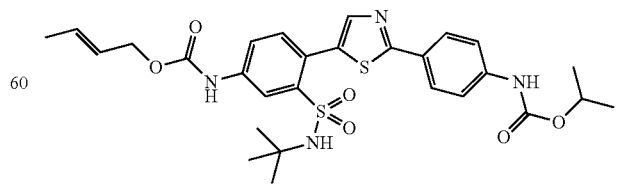

¹H NMR (400 MHz, METHANOL-d4) δ=8.38 (d, J=1.8 Hz, 1H), 7.96-7.84 (m, 3H), 7.73 (dd, J=2.0, 8.3 Hz, 1H), 7.58 (d, J=8.7 Hz, 2H), 7.48 (d, J=8.3 Hz, 1H), 5.98-5.81 (m, 1H), 5.75-5.63 (m, 1H), 4.99 (td, J=6.3, 12.5 Hz, 1H), 4.61 (d, J=6.4 Hz, 2H), 1.76 (d, J=6.1 Hz, 3H), 1.33 (d, J=6.2 Hz, 6H), 1.16 (s, 9H). ESI [M+H]=587.2

Compound B13

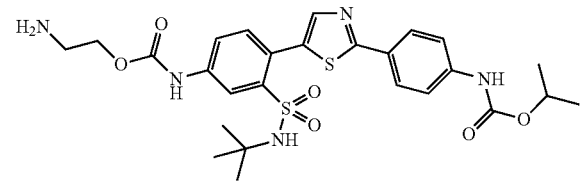

¹H NMR (400 MHz, METHANOL-d4) δ=8.41 (d, J=2.0 Hz, 1H), 7.96-7.83 (m, 3H), 7.77 (dd, J=2.1, 8.4 Hz, 1H), 7.59 (d, J=8.7 Hz, 2H), 7.51 (d, J=8.3 Hz, 1H), 5.00 (td, J=6.2, 12.5 Hz, 1H), 4.50-4.43 (m, 2H), 3.31 (br s, 2H), 1.33 (d, J=6.2 Hz, 6H), 1.14 (s, 9H). ESI [M+H]=576.1

Compound B14

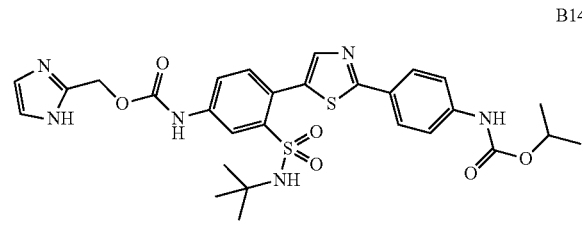 [SMILES: CC(C)OC(=O)Nc1ccc(-c2ncc(-c3ccc(NC(=O)OCc4nccs4)cc3S(=O)(=O)NC(C)(C)C)s2)cc1]

¹H NMR (400 MHz, METHANOL-d4) δ=8.42 (s, 1H), 7.94-7.86 (m, 3H), 7.75 (br d, J=8.3 Hz, 1H), 7.65-7.50 (m, 5H), 5.49 (s, 2H), 5.00 (td, J=6.3, 12.5 Hz, 1H), 1.34 (d, J=6.2 Hz, 6H), 1.13 (s, 9H). ESI [M+H]=613.2

Compound B15

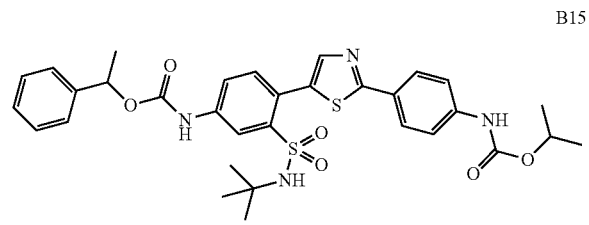 [SMILES: CC(C)OC(=O)Nc1ccc(-c2ncc(-c3ccc(NC(=O)OC(C)c4ccccc4)cc3S(=O)(=O)NC(C)(C)C)s2)cc1]

¹H NMR (400 MHz, DMSO-d6) δ=10.25 (s, 1H), 9.84 (s, 1H), 8.33 (d, J=2.2 Hz, 1H), 7.87 (d, J=8.8 Hz, 2H), 7.81 (s, 1H), 7.67 (dd, J=2.2, 8.4 Hz, 1H), 7.60 (d, J=8.8 Hz, 2H), 7.42 (dt, J=8.1, 14.1 Hz, 5H), 7.35-7.29 (m, 1H), 7.14-7.09 (m, 1H), 5.85 (q, J=6.6 Hz, 1H), 4.92 (td, J=6.2, 12.5 Hz, 1H), 1.57 (d, J=6.6 Hz, 3H), 1.27 (d, J=6.2 Hz, 6H), 1.08 (s, 9H). ESI [M+H]=637.2

Compound B16

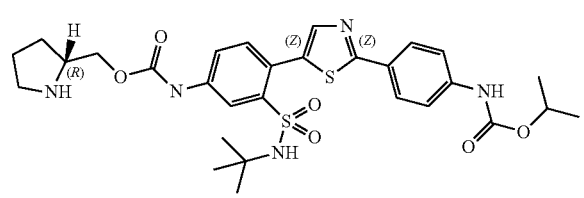

¹H NMR (400 MHz, METHANOL-d4) δ=8.43 (d, J=1.96 Hz, 1H), 7.87-7.94 (m, 3H), 7.77 (br d, J=8.44 Hz, 1H), 7.60 (d, J=8.68 Hz, 2H), 7.52 (d, J=8.44 Hz, 1H), 5.00 (td, J=6.28, 12.50 Hz, 1H), 4.52 (dd, J=3.36, 12.53 Hz, 1H), 4.37 (br dd, J=7.83, 10.88 Hz, 1H), 3.97 (dq, J=3.30, 8.03 Hz, 1H), 3.36-3.44 (m, 2H), 2.05-2.34 (m, 3H), 1.84-1.94 (m, 1H), 1.34 (d, J=6.24 Hz, 6H), 1.14 (s, 9H). ESI [M+H]=616.2

Compound B17

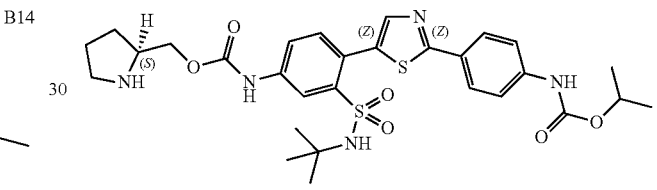

¹H NMR (400 MHz, METHANOL-d4) δ=8.41 (d, J=2.2 Hz, 1H), 7.91-7.84 (m, 3H), 7.75 (dd, J=2.0, 8.4 Hz, 1H), 7.57 (d, J=8.8 Hz, 2H), 7.50 (d, J=8.4 Hz, 1H), 5.02-4.93 (m, 1H), 4.50 (dd, J=3.3, 12.6 Hz, 1H), 4.35 (dd, J=7.8, 12.5 Hz, 1H), 3.95 (dq, J=3.4, 8.1 Hz, 1H), 3.42-3.33 (m, 2H), 2.31-2.02 (m, 3H), 1.93-1.81 (m, 1H), 1.32 (d, J=6.4 Hz, 6H), 1.12 (s, 9H). ESI [M+H]=616.2

Compound B18

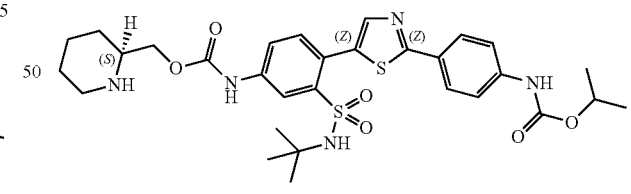

¹H NMR (400 MHz, METHANOL-d4) δ=8.44 (d, J=2.08 Hz, 1H), 7.88-7.94 (m, 3H), 7.78 (dd, J=1.90, 8.38 Hz, 1H), 7.61 (d, J=8.68 Hz, 2H), 7.53 (d, J=8.44 Hz, 1H), 5.01 (td, J=6.21, 12.53 Hz, 1H), 4.42-4.49 (m, 1H), 4.33 (dd, J=7.21, 12.59 Hz, 1H), 3.42-3.55 (m, 2H), 3.01-3.11 (m, 1H), 1.91-2.06 (m, 3H), 1.58-1.76 (m, 3H), 1.35 (d, J=6.24 Hz, 6H), 1.14 (s, 9H). ESI [M+H]=630.2

Compound B19

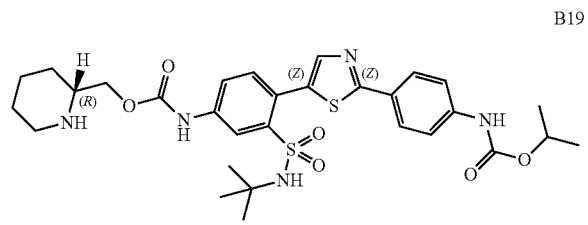

¹H NMR (400 MHz, METHANOL-d4) δ=8.43 (d, J=2.2 Hz, 1H), 7.87-7.94 (m, 3H), 7.77 (dd, J=8.3, 2.0 Hz, 1H), 7.60 (d, J=8.7 Hz, 2H), 7.53 (d, J=8.4 Hz, 1H), 5.00 (dt, J=12.5, 6.3 Hz, 1H), 4.42-4.48 (m, 1H), 4.29-4.36 (m, 1H), 3.41-3.53 (m, 2H), 3.01-3.10 (m, 1H), 1.92-2.06 (m, 3H), 1.58-1.75 (m, 3H), 1.34 (d, J=6.2 Hz, 6H), 1.13 (s, 9H). SI [M+H]=630.2

Example 3

The following compounds were synthesized via reacting intermediate 8 with different amines via general method D and E (shown in Example 1), unless otherwise noted.

Compound C1

¹H NMR (400 MHz, DMSO-d6) δ=9.84 (s, 1H), 8.96 (s, 1H), 8.24 (d, J=2.3 Hz, 1H), 7.86 (d, J=8.7 Hz, 2H), 7.80 (s, 1H), 7.63-7.55 (m, 3H), 7.41-7.32 (m, 5H), 7.28-7.20 (m, 1H), 7.07 (s, 1H), 6.76 (d, J=7.8 Hz, 1H), 4.98-4.80 (m, 2H), 1.42 (d, J=6.8 Hz, 3H), 1.27 (d, J=6.2 Hz, 6H), 1.08 (s, 9H). ESI [M+H]=636.3

Compound C2

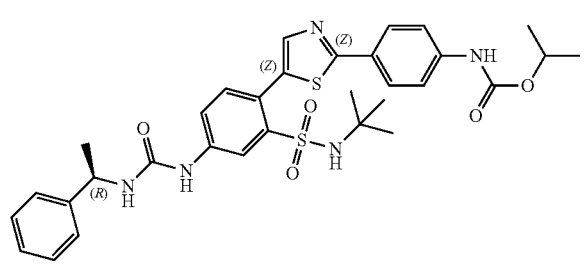

¹H NMR (400 MHz, METHANOL-d4) δ=8.25 (d, J=2.3 Hz, 1H), 7.87-7.91 (m, 3H), 7.68-7.72 (m, 1H), 7.60 (d, J=8.7 Hz, 2H), 7.33-7.45 (m, 5H), 7.23-7.29 (m, 1H), 4.94-5.03 (m, 2H), 1.51 (d, J=6.8 Hz, 3H), 1.33 (d, J=6.2 Hz, 6H), 1.14 (s, 9H). ESI [M+H]=636.2

Compound C3

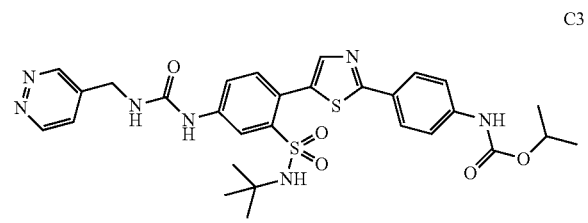 [SMILES: CC(C)OC(=O)Nc1ccc(-c2ncc(-c3ccc(NC(=O)NCc4ccnnc4)cc3S(=O)(=O)NC(C)(C)C)s2)cc1]

¹H NMR (400 MHz, DMSO-d6) δ=9.84 (s, 1H), 9.39 (s, 1H), 9.23-9.15 (m, 2H), 8.25 (d, J=2.4 Hz, 1H), 7.85 (d, J=8.8 Hz, 2H), 7.79 (s, 1H), 7.67-7.56 (m, 4H), 7.39 (d, J=8.4 Hz, 1H), 7.07 (s, 1H), 6.97 (t, J=6.0 Hz, 1H), 4.90 (quin, J=6.3 Hz, 1H), 4.39 (d, J=5.5 Hz, 2H), 1.26 (d, J=6.2 Hz, 6H), 1.05 (s, 9H). ESI [M+H]=624.2

Compound C4

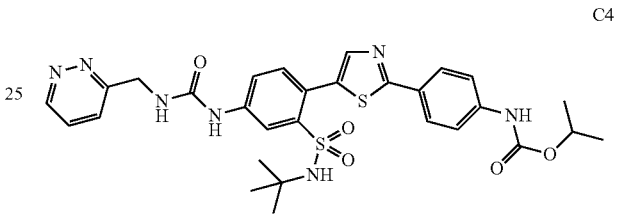

¹H NMR (400 MHz, METHANOL-d4) δ=9.23 (br s, 1H), 8.31 (d, J=2.2 Hz, 1H), 8.08-8.02 (m, 1H), 8.01-7.95 (m, 1H), 7.86 (t, J=4.3 Hz, 3H), 7.70 (dd, J=2.2, 8.4 Hz, 1H), 7.57 (d, J=8.6 Hz, 2H), 7.43 (d, J=8.4 Hz, 1H), 4.97 (td, J=6.2, 12.5 Hz, 1H), 4.77 (s, 2H), 1.30 (d, J=6.2 Hz, 6H), 1.11 (s, 9H). ESI [M+H]=624.2

Compound C5

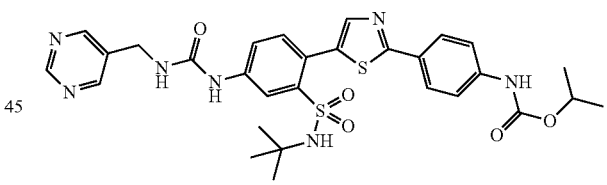

¹H NMR (400 MHz, METHANOL-d4) δ=9.07 (s, 1H), 8.82 (s, 2H), 8.28 (d, J=2.2 Hz, 1H), 7.91-7.84 (m, 3H), 7.71 (dd, J=2.3, 8.3 Hz, 1H), 7.57 (d, J=8.8 Hz, 2H), 7.44 (d, J=8.4 Hz, 1H), 4.97 (td, J=6.1, 12.5 Hz, 1H), 4.46 (s, 2H), 1.31 (d, J=6.4 Hz, 6H), 1.12 (s, 9H). ESI [M+H]=624.2

Compound C6

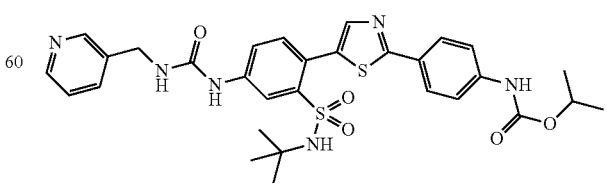

¹H NMR (400 MHz, METHANOL-d4) δ=8.84 (br s, 1H), 8.75 (br d, J=5.1 Hz, 1H), 8.60 (br d, J=8.2 Hz, 1H), 8.33 (d,

J=2.2 Hz, 1H), 8.04 (dd, J=6.0, 7.7 Hz, 1H), 7.91-7.82 (m, 3H), 7.67 (dd, J=2.3, 8.3 Hz, 1H), 7.56 (d, J=8.6 Hz, 2H), 7.43 (d, J=8.2 Hz, 1H), 5.02-4.95 (m, 1H), 4.61 (s, 2H), 1.30 (d, J=6.2 Hz, 6H), 1.10 (s, 9H). ESI [M+H]=623.4

Compound C7

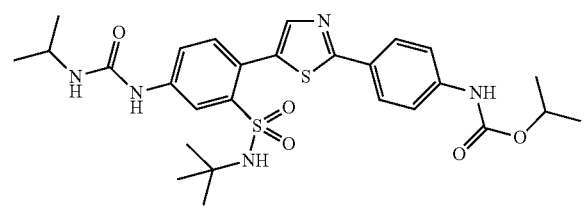

¹H NMR (400 MHz, METHANOL-d4) δ=8.25 (d, J=2.2 Hz, 1H), 7.90-7.84 (m, 3H), 7.69 (dd, J=2.3, 8.5 Hz, 1H), 7.58 (d, J=8.8 Hz, 2H), 7.43 (d, J=8.4 Hz, 1H), 5.04-4.92 (m, 1H), 3.91 (quin, J=6.6 Hz, 1H), 1.32 (d, J=6.2 Hz, 6H), 1.20 (d, J=6.6 Hz, 6H), 1.13 (s, 9H). ESI [M+H]=574.1

Compound C8

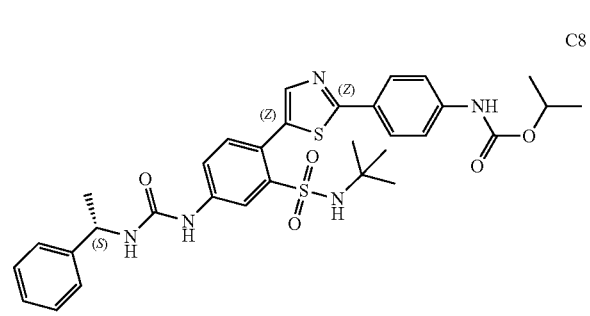

¹H NMR (400 MHz, METHANOL-d4) δ=8.22 (d, J=2.2 Hz, 1H), 7.91-7.83 (m, 3H), 7.69 (dd, J=2.2, 8.4 Hz, 1H), 7.57 (d, J=8.8 Hz, 2H), 7.44-7.32 (m, 5H), 7.28-7.21 (m, 1H), 5.02-4.91 (m, 2H), 1.50 (d, J=6.8 Hz, 3H), 1.31 (d, J=6.2 Hz, 6H), 1.12 (s, 9H). ESI [M+H]=636.2

Compound C9

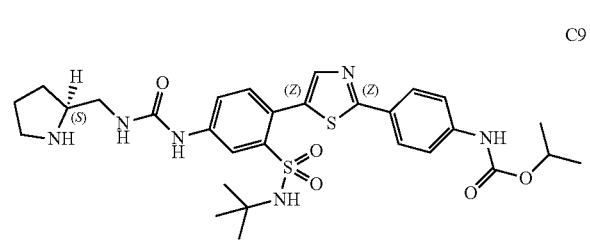

¹H NMR (400 MHz, METHANOL-d4) δ=8.38 (d, J=2.2 Hz, 1H), 7.90-7.83 (m, 3H), 7.70 (dd, J=2.2, 8.4 Hz, 1H), 7.57 (d, J=8.6 Hz, 2H), 7.45 (d, J=8.4 Hz, 1H), 4.98 (td, J=6.1, 12.5 Hz, 1H), 3.79-3.68 (m, 1H), 3.59-3.47 (m, 2H), 3.40-3.32 (m, 1H), 3.30-3.25 (m, 1H), 2.24-1.96 (m, 3H), 1.89-1.75 (m, 1H), 1.32 (d, J=6.4 Hz, 6H), 1.11 (s, 9H). ESI [M+H]=615.2

Compound C10

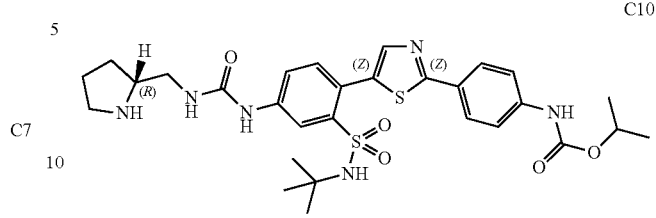

¹H NMR (400 MHz, METHANOL-d4) δ=8.39 (d, J=2.32 Hz, 1H), 7.88-7.93 (m, 2H), 7.87 (s, 1H), 7.72 (dd, J=2.32, 8.31 Hz, 1H), 7.59 (d, J=8.68 Hz, 2H), 7.47 (d, J=8.31 Hz, 1H), 5.00 (td, J=6.28, 12.50 Hz, 1H), 3.72-3.79 (m, 1H), 3.53-3.57 (m, 2H), 3.36-3.42 (m, 1H), 3.27-3.32 (m, 1H), 2.00-2.26 (m, 3H), 1.75-1.90 (m, 1H), 1.34 (d, J=6.24 Hz, 6H), 1.13 (s, 9H). ESI [M+H]=615.2

Compound C11

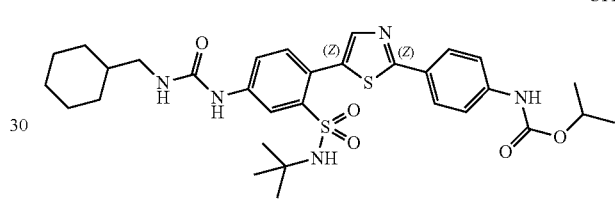

¹H NMR (400 MHz, METHANOL-d4) δ=8.27 (d, J=2.4 Hz, 1H), 7.93-7.85 (m, 3H), 7.71 (dd, J=2.4, 8.3 Hz, 1H), 7.60 (d, J=8.3 Hz, 2H), 7.45 (d, J=8.3 Hz, 1H), 5.06-4.95 (m, 1H), 3.08 (d, J=6.4 Hz, 2H), 1.86-1.68 (m, 5H), 1.52 (ttd, J=3.5, 7.3, 14.5 Hz, 1H), 1.33 (d, J=5.9 Hz, 9H), 1.15 (s, 9H), 1.07-0.93 (m, 2H). ESI [M+H]=628.2

Compound C12

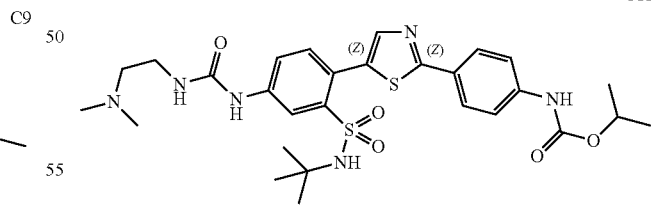

¹H NMR (400 MHz, METHANOL-d4) δ=8.36 (d, J=2.4 Hz, 1H), 7.91-7.82 (m, 3H), 7.70 (dd, J=2.4, 8.4 Hz, 1H), 7.57 (d, J=8.8 Hz, 2H), 7.45 (d, J=8.4 Hz, 1H), 4.98 (td, J=6.3, 12.4 Hz, 1H), 3.61 (t, J=5.6 Hz, 2H), 3.35-3.31 (m, 2H), 2.98 (s, 6H), 1.31 (d, J=6.4 Hz, 6H), 1.11 (s, 9H). ESI [M+H]=603.2

Compound C13

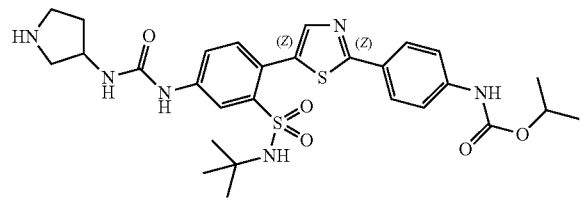

¹H NMR (400 MHz, METHANOL-d4) δ=8.34 (d, J=2.2 Hz, 1H), 7.92-7.82 (m, 3H), 7.67 (dd, J=2.2, 8.4 Hz, 1H), 7.57 (d, J=8.6 Hz, 2H), 7.44 (d, J=8.4 Hz, 1H), 4.97 (td, J=6.3, 12.4 Hz, 1H), 4.46-4.32 (m, 1H), 3.56-3.47 (m, 2H), 3.39-3.32 (m, 2H), 2.45-2.32 (m, 1H), 2.15-2.00 (m, 1H), 1.31 (d, J=6.4 Hz, 6H), 1.11 (s, 9H). ESI [M+H]=601.3

Compound C14

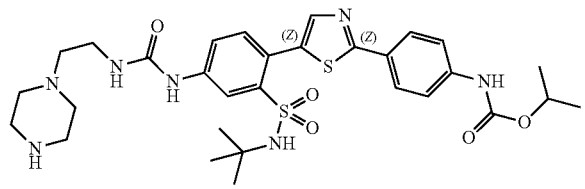

¹H NMR (400 MHz, METHANOL-d4) δ=8.37 (d, J=1.8 Hz, 1H), 7.93-7.86 (m, 3H), 7.71 (dd, J=1.9, 8.3 Hz, 1H), 7.60 (d, J=8.6 Hz, 2H), 7.46 (d, J=8.3 Hz, 1H), 5.03-4.98 (m, 1H), 3.65-3.46 (m, 10H), 3.27 (br s, 2H), 1.33 (d, J=6.2 Hz, 6H), 1.13 (s, 9H). ESI [M+H]=644.2

Compound C15

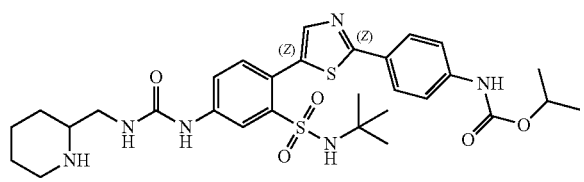

¹H NMR (400 MHz, METHANOL-d4) δ=8.40 (d, J=2.3 Hz, 1H), 7.93-7.85 (m, 3H), 7.73 (dd, J=2.3, 8.3 Hz, 1H), 7.59 (d, J=8.7 Hz, 2H), 7.47 (d, J=8.4 Hz, 1H), 5.00 (td, J=6.2, 12.5 Hz, 1H), 3.46 (d, J=5.5 Hz, 2H), 3.40 (br d, J=12.8 Hz, 1H), 3.28-3.19 (m, 1H), 3.03-2.93 (m, 1H), 2.01-1.86 (m, 3H), 1.75-1.47 (m, 3H), 1.34 (d, J=6.2 Hz, 6H), 1.13 (s, 9H). ESI [M+H]=629.3

Compound C16

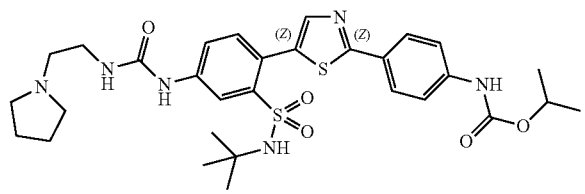

¹H NMR (400 MHz, METHANOL-d4) δ=8.38 (d, J=2.32 Hz, 1H), 7.90 (d, J=8.80 Hz, 2H), 7.74 (d, J=2.4 Hz, 1H), 7.73 (dd, J=2.32, 8.31 Hz, 1H), 7.59 (d, J=8.68 Hz, 2H), 7.47 (d, J=8.44 Hz, 1H), 5.00 (td, J=6.24, 12.47 Hz, 1H), 3.81 (br d, J=5.26 Hz, 2H), 3.62 (t, J=5.75 Hz, 2H), 3.39 (t, J=5.62 Hz, 2H), 3.11-3.21 (m, 2H), 2.00-2.24 (m, 4H), 1.33 (d, J=6.24 Hz, 6H), 1.14 (s, 9H). ESI [M+H]=629.3

Compound C17

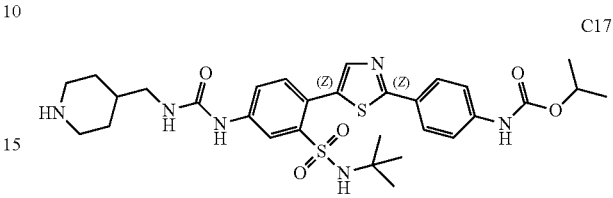

¹H NMR (400 MHz, METHANOL-d4) δ=8.32 (d, J=2.2 Hz, 1H), 7.91-7.82 (m, 3H), 7.66 (dd, J=2.4, 8.6 Hz, 1H), 7.57 (d, J=8.8 Hz, 2H), 7.42 (d, J=8.3 Hz, 1H), 4.97 (td, J=6.2, 12.6 Hz, 1H), 3.41 (br d, J=12.7 Hz, 2H), 3.18 (d, J=6.6 Hz, 2H), 3.04-2.92 (m, 2H), 1.99 (br d, J=13.6 Hz, 2H), 1.92-1.80 (m, 1H), 1.51-1.36 (m, 2H), 1.31 (d, J=6.1 Hz, 6H), 1.11 (s, 9H). ESI [M+H]=629.2

Compound C18

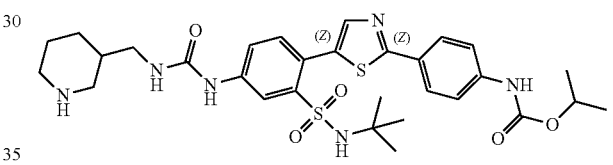

¹H NMR (400 MHz, METHANOL-d4) δ=8.33 (s, 1H), 7.90-7.82 (m, 3H), 7.65 (br d, J=7.5 Hz, 1H), 7.57 (br d, J=8.3 Hz, 2H), 7.43 (br d, J=8.3 Hz, 1H), 5.01-4.94 (m, 1H), 3.43-3.32 (m, 2H), 3.20 (br d, J=6.1 Hz, 2H), 2.92 (br t, J=12.5 Hz, 1H), 2.74 (br t, J=12.1 Hz, 1H), 2.08-1.87 (m, 3H), 1.73 (br d, J=11.8 Hz, 1H), 1.31 (br d, J=6.1 Hz, 7H), 1.11 (s, 9H). ESI [M+H]=629.2

Compound C19

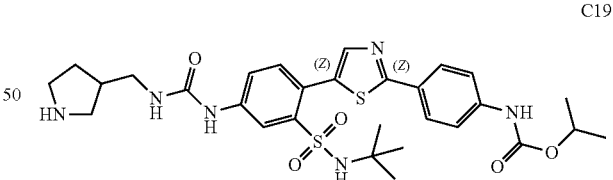

¹H NMR (400 MHz, METHANOL-d4) δ=8.24 (d, J=2.2 Hz, 1H), 7.81-7.73 (m, 3H), 7.57 (dd, J=2.3, 8.4 Hz, 1H), 7.47 (d, J=8.6 Hz, 2H), 7.34 (d, J=8.4 Hz, 1H), 4.91-4.85 (m, 1H), 3.36-3.26 (m, 2H), 3.24 (s, 1H), 3.20-3.15 (m, 2H), 2.95 (dd, J=8.1, 11.7 Hz, 1H), 2.51 (spt, J=7.5 Hz, 1H), 2.14-2.03 (m, 1H), 1.71 (qd, J=8.1, 13.2 Hz, 1H), 1.22 (d, J=6.2 Hz, 6H), 1.02 (s, 9H). ESI [M+H]=615.2

Example 4

The following compounds were synthesized via reacting intermediate 11 with different amines via general methods E and G (shown in Example 1), unless otherwise noted.

Compound D1

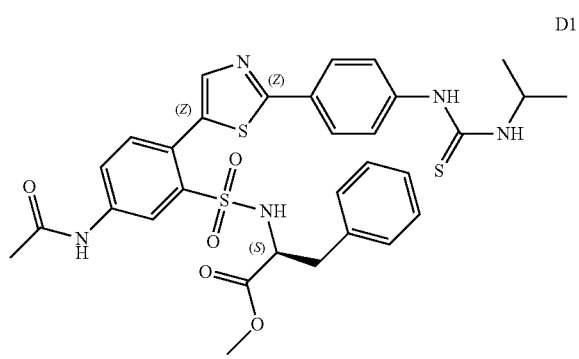

¹H NMR (400 MHz, DMSO-d6) δ=10.36 (s, 1H), 9.55 (br s, 1H), 8.31 (d, J=8.8 Hz, 1H), 8.18 (s, 1H), 7.91-7.77 (m, 4H), 7.70 (s, 1H), 7.64 (d, J=8.8 Hz, 2H), 7.41 (d, J=8.3 Hz, 1H), 7.18-7.07 (m, 3H), 7.03 (br d, J=6.1 Hz, 2H), 4.37 (br s, 1H), 3.92-3.80 (m, 1H), 3.43 (br s, 3H), 2.96-2.80 (m, 2H), 2.09 (s, 3H), 1.17 (d, J=6.6 Hz, 6H). ESI [M+H]=652.2

Compound D2

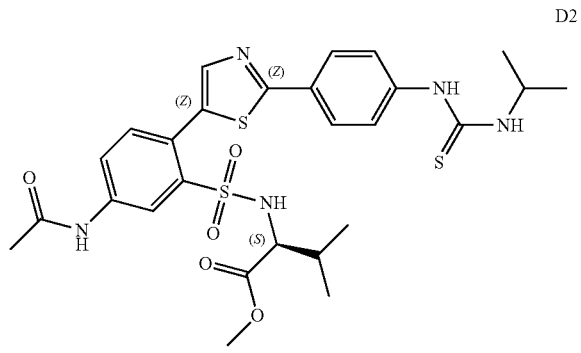

¹H NMR (400 MHz, DMSO-d6) δ=10.39 (s, 1H), 9.55 (br s, 1H), 8.25 (d, J=1.8 Hz, 1H), 8.14 (d, J=9.6 Hz, 1H), 7.93-7.77 (m, 5H), 7.64 (d, J=8.3 Hz, 2H), 7.48 (d, J=8.3 Hz, 1H), 4.37 (br s, 1H), 3.58 (br s, 1H), 3.43 (s, 3H), 2.08 (s, 3H), 1.89 (br dd, J=6.4, 13.4 Hz, 1H), 1.17 (d, J=6.6 Hz, 6H), 0.83-0.69 (m, 6H). ESI [M+H]=604.2

Compound D3

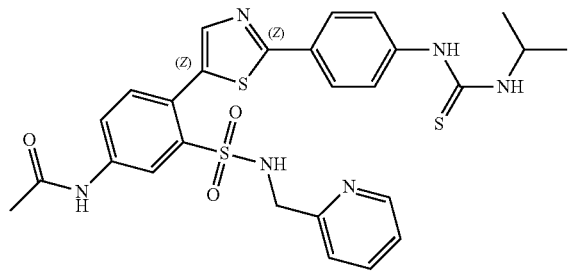

¹H NMR (400 MHz, DMSO-d6) δ=10.40 (s, 1H), 9.56 (br s, 1H), 8.43 (d, J=4.2 Hz, 1H), 8.28 (d, J=2.2 Hz, 1H), 8.19 (t, J=6.2 Hz, 1H), 7.89-7.78 (m, 6H), 7.64 (d, J=8.8 Hz, 2H), 7.49 (d, J=8.4 Hz, 1H), 7.38 (d, J=7.9 Hz, 1H), 7.33-7.26 (m, 1H), 4.38 (br s, 1H), 4.15 (d, J=6.2 Hz, 2H), 2.09 (s, 3H), 1.16 (d, J=6.6 Hz, 6H). ESI [M+H]=581.2

Compound D4

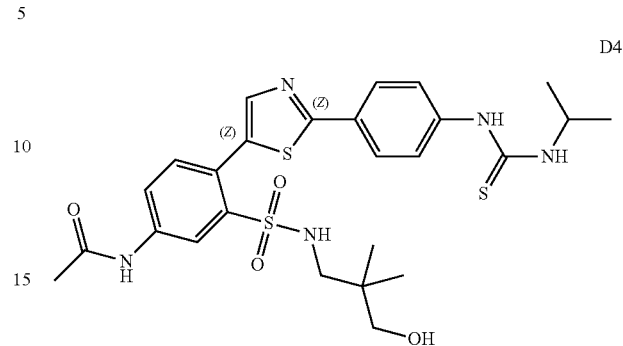

¹H NMR (400 MHz, DMSO-d6) δ=10.41 (s, 1H), 9.56 (br s, 1H), 8.20 (d, J=2.0 Hz, 1H), 7.89-7.80 (m, 5H), 7.63 (d, J=8.8 Hz, 2H), 7.52 (d, J=8.4 Hz, 1H), 7.39 (t, J=6.5 Hz, 1H), 4.42-4.33 (m, 1H), 3.05 (s, 2H), 2.70 (d, J=6.4 Hz, 2H), 2.09 (s, 3H), 1.17 (d, J=6.6 Hz, 6H), 0.70 (s, 6H). ESI [M+H]=576.3

Compound D5

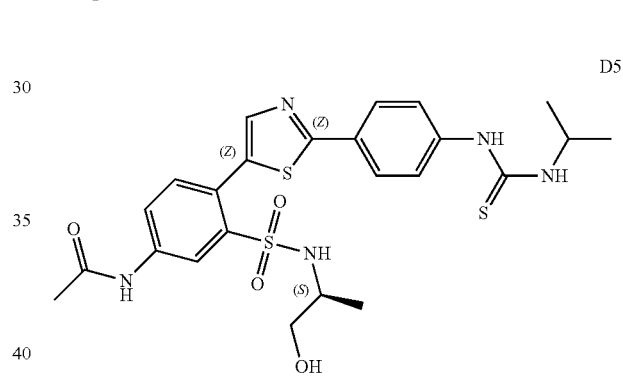

¹H NMR (400 MHz, DMSO-d6) δ=10.41 (s, 1H), 9.56 (br s, 1H), 8.35 (d, J=2.2 Hz, 1H), 7.90-7.79 (m, 5H), 7.63 (d, J=8.8 Hz, 2H), 7.50 (d, J=8.2 Hz, 1H), 7.26 (d, J=7.7 Hz, 1H), 4.38 (br d, J=6.6 Hz, 1H), 3.32-3.24 (m, 1H), 3.12-2.97 (m, 2H), 2.08 (s, 3H), 1.17 (d, J=6.4 Hz, 6H), 0.94 (d, J=6.4 Hz, 3H). ESI [M+H]=548.2

Compound D6

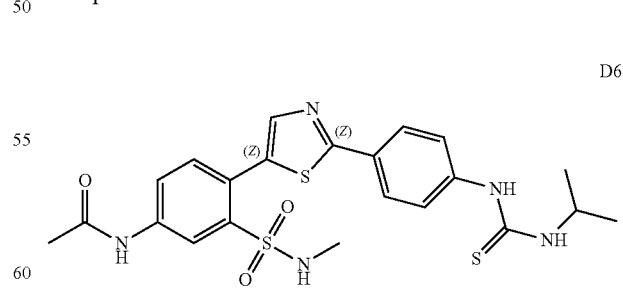

¹H NMR (400 MHz, DMSO-d6) δ=10.41 (s, 1H), 9.55 (br s, 1H), 8.24 (d, J=2.0 Hz, 1H), 7.92-7.76 (m, 5H), 7.62 (d, J=8.8 Hz, 2H), 7.50 (d, J=8.2 Hz, 1H), 7.35 (br d, J=4.6 Hz, 1H), 4.36 (br d, J=7.1 Hz, 1H), 2.43 (d, J=4.9 Hz, 3H), 2.07 (s, 3H), 1.15 (d, J=6.6 Hz, 6H). ESI [M+H]=503.8

Compound D7

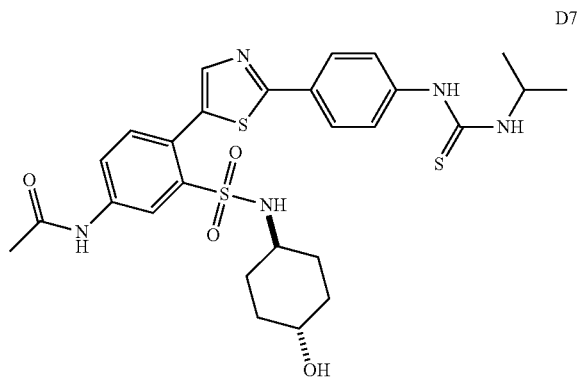

¹H NMR (400 MHz, DMSO-d6) δ=10.49-10.34 (m, 1H), 9.67-9.48 (m, 1H), 8.36 (s, 1H), 7.97-7.79 (m, 5H), 7.65 (d, J=8.8 Hz, 2H), 7.49 (dd, J=8.2, 17.6 Hz, 2H), 4.39 (br d, J=7.5 Hz, 1H), 3.29-3.17 (m, 1H), 2.81 (br d, J=7.5 Hz, 1H), 2.10 (s, 3H), 1.67 (br t, J=14.2 Hz, 4H), 1.18 (d, J=6.6 Hz, 8H), 1.08-0.94 (m, 2H). ESI [M+H]=587.9

Compound D8

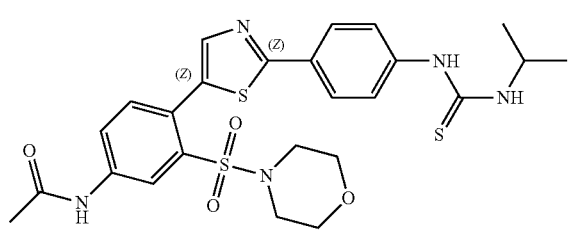

¹H NMR (400 MHz, METHANOL-d4) δ=8.47-8.39 (m, 1H), 7.96-7.86 (m, 4H), 7.59 (d, J=8.4 Hz, 3H), 4.66-4.40 (m, 1H), 3.54-3.48 (m, 4H), 3.05-2.98 (m, 4H), 2.18 (s, 3H), 1.25 (d, J=6.6 Hz, 6H). ESI [M+H]=559.8

Compound D9

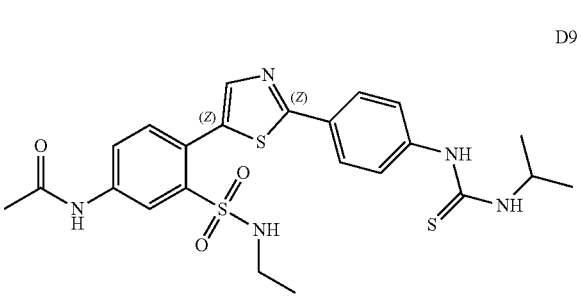 [SMILES: CCNS(=O)(=O)c1cc(NC(C)=O)ccc1-c1cnc(-c2ccc(NC(=S)NC(C)C)cc2)s1]

¹H NMR (400 MHz, DMSO-d6) δ=10.41 (s, 1H), 9.56 (br s, 1H), 8.29 (d, J=2.2 Hz, 1H), 7.90-7.79 (m, 5H), 7.63 (d, J=8.8 Hz, 2H), 7.53-7.47 (m, 2H), 4.46-4.30 (m, 1H), 2.90-2.74 (m, 2H), 2.08 (s, 3H), 1.17 (d, J=6.6 Hz, 6H), 0.95 (t, J=7.2 Hz, 3H). ESI [M+H]=517.9

Compound D10

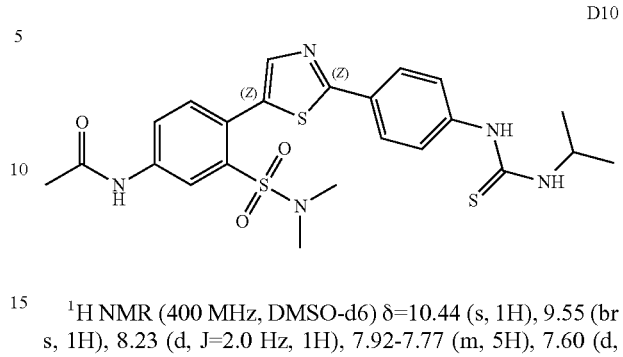

¹H NMR (400 MHz, DMSO-d6) δ=10.44 (s, 1H), 9.55 (br s, 1H), 8.23 (d, J=2.0 Hz, 1H), 7.92-7.77 (m, 5H), 7.60 (d, J=8.6 Hz, 2H), 7.53 (d, J=8.4 Hz, 1H), 4.36 (br d, J=6.8 Hz, 1H), 2.60 (s, 6H), 2.08 (s, 3H), 1.15 (d, J=6.4 Hz, 6H). ESI [M+H]=517.9

Compound D11

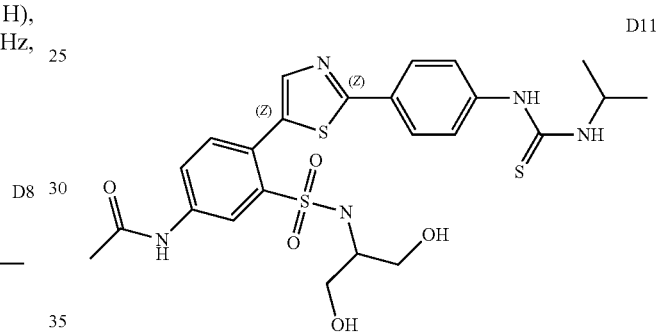

¹H NMR (400 MHz, METHANOL-d4) δ=8.42 (s, 1H), 7.96-7.84 (m, 4H), 7.57 (br d, J=8.2 Hz, 2H), 7.50 (d, J=7.9 Hz, 1H), 4.52 (br s, 1H), 3.55-3.44 (m, 4H), 3.23-3.18 (m, 1H), 2.16 (s, 3H), 1.23 (d, J=6.6 Hz, 6H). ESI [M+H]=563.9

Compound D12

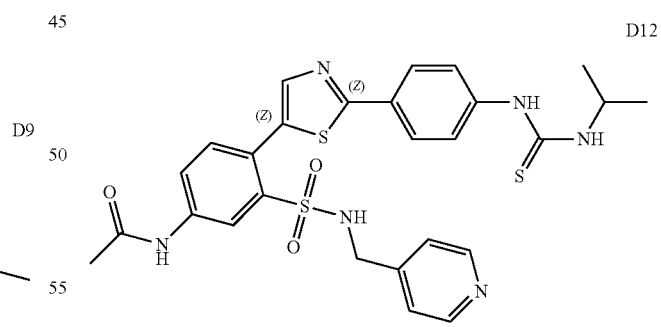

¹H NMR (400 MHz, DMSO-d6) δ=10.45 (s, 1H), 9.61 (br s, 1H), 8.68 (d, J=6.2 Hz, 2H), 8.45 (t, J=6.3 Hz, 1H), 8.36 (s, 1H), 7.88 (br t, J=4.3 Hz, 5H), 7.72-7.60 (m, 4H), 7.58-7.56 (m, 1H), 4.40 (br s, 1H), 4.23 (br d, J=6.0 Hz, 2H), 2.11 (s, 3H), 1.21-1.16 (m, 6H). ESI [M+H]=580.8

Compound D13

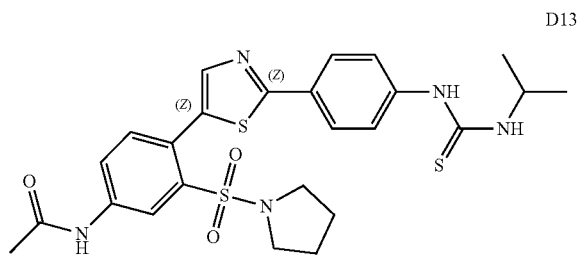 [SMILES: CC(=O)Nc1ccc(-c2cnc(-c3ccc(NC(=S)NC(C)C)cc3)s2)c(S(=O)(=O)N2CCCC2)c1]

¹H NMR (400 MHz, DMSO-d6) δ=10.46 (s, 1H), 9.58 (br s, 1H), 8.32 (s, 1H), 7.92-7.79 (m, 5H), 7.64 (d, J=8.6 Hz, 2H), 7.55 (s, 1H), 4.39 (br d, J=6.2 Hz, 1H), 3.10-3.01 (m, 4H), 2.11 (s, 3H), 1.82-1.75 (m, 4H), 1.18 (d, J=6.4 Hz, 6H). ESI [M+H]=543.9

Compound D14

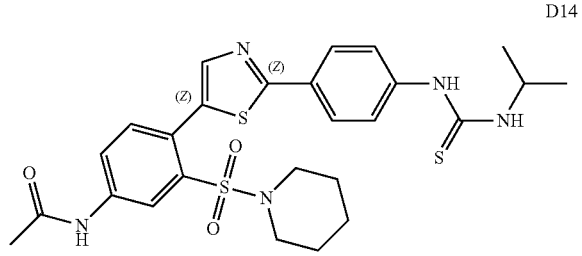 [SMILES: CC(=O)Nc1ccc(-c2cnc(-c3ccc(NC(=S)NC(C)C)cc3)s2)c(S(=O)(=O)N2CCCCC2)c1]

¹H NMR (400 MHz, DMSO-d6) δ=10.46 (s, 1H), 9.58 (br s, 1H), 8.32 (d, J=2.2 Hz, 1H), 7.96-7.80 (m, 5H), 7.63 (d, J=8.8 Hz, 2H), 7.56 (d, J=8.4 Hz, 1H), 4.39 (br d, J=6.2 Hz, 1H), 2.91 (br s, 4H), 2.10 (s, 3H), 1.38 (br s, 6H), 1.20-1.16 (m, 6H). ESI [M+H]=557.9

Compound D15

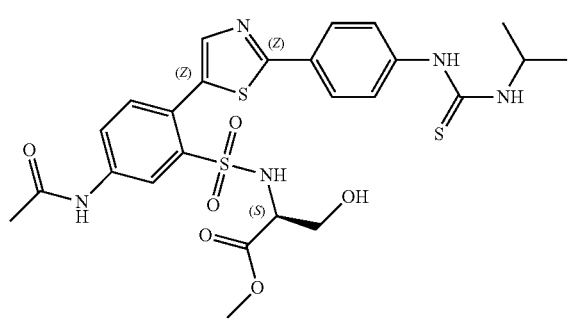

¹H NMR (400 MHz, DMSO-d6) δt=10.40 (s, 1H), 9.54 (s, 1H), 8.25 (s, 1H), 7.96-7.77 (m, 6H), 7.62 (d, J=8.4 Hz, 2H), 7.48 (d, J=8.2 Hz, 1H), 4.37 (s, 1H), 3.68 (br s, 1H), 3.53-3.51 (m, 2H), 3.43 (s, 3H), 2.07 (s, 3H), 1.20 (br s, 1H), 1.15 (d, J=6.6 Hz, 6H). ESI [M+H]=591.8

Compound D16

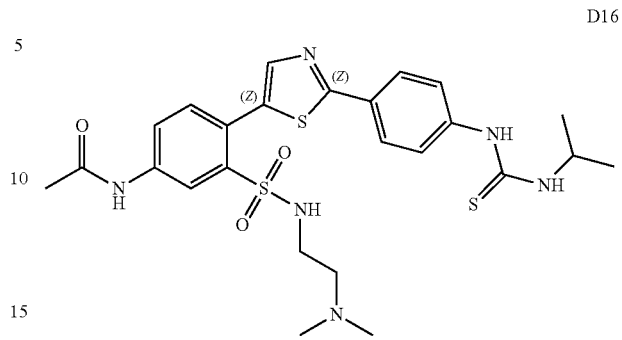

¹H NMR (400 MHz, DMSO-d6) δ=10.58-10.47 (m, 1H), 9.73 (br s, 1H), 9.44 (br s, 1H), 8.49-8.29 (m, 1H), 8.02-7.97 (m, 1H), 7.92-7.80 (m, 4H), 7.69 (d, J=8.6 Hz, 2H), 7.60-7.53 (m, 1H), 4.39 (br d, J=6.6 Hz, 1H), 3.20-3.07 (m, 4H), 2.76 (br s, 6H), 2.11 (s, 3H), 1.21-1.14 (m, 6H). ESI [M+H]=560.9

Compound D17

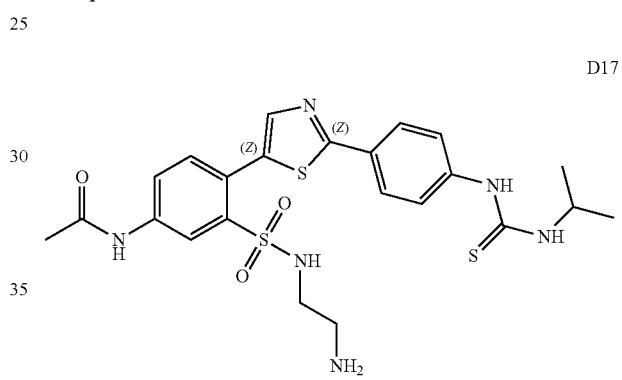

¹H NMR (400 MHz, DMSO-d6) δ=10.48 (s, 1H), 9.64 (br s, 1H), 8.42 (d, J=2.0 Hz, 1H), 7.93-7.85 (m, 3H), 7.81 (dd, J=2.2, 8.4 Hz, 1H), 7.76-7.65 (m, 5H), 7.57 (d, J=8.4 Hz, 1H), 4.46-4.32 (m, 1H), 3.01 (q, J=6.5 Hz, 2H), 2.82 (br d, J=5.5 Hz, 2H), 2.11 (s, 3H), 1.18 (d, J=6.6 Hz, 6H). ESI [M+H]=533.1

Compound D18

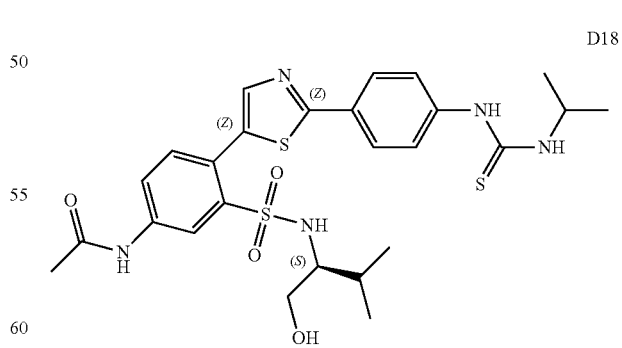

¹H NMR (400 MHz, DMSO-d6) δ=10.36 (s, 1H), 9.54 (br s, 1H), 8.28 (s, 1H), 7.87-7.81 (m, 5H), 7.69 (d, J=3.3 Hz, 1H), 7.60 (br d, J=6.0 Hz, 2H), 7.46 (d, J=8.4 Hz, 1H), 7.10 (d, J=9.0 Hz, 1H), 4.36 (br s, 1H), 3.28-3.13 (m, 2H), 2.88 (br s, 1H), 2.06 (s, 3H), 1.81-1.69 (m, 1H), 1.15 (br d, J=4.4 Hz, 6H), 0.71-0.60 (m, 6H). ESI [M+H]=575.9

Compound D19

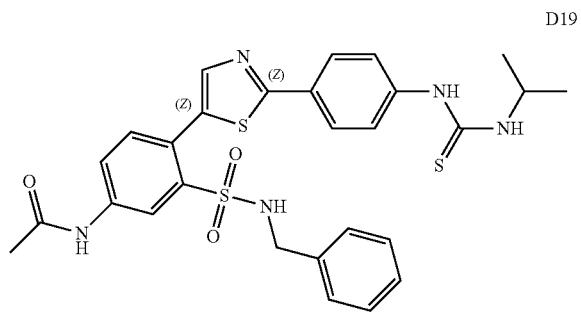 [SMILES: CC(=O)Nc1ccc(-c2cnc(-c3ccc(NC(=S)NC(C)C)cc3)s2)c(S(=O)(=O)NCc2ccccc2)c1]

¹H NMR (400 MHz, DMSO-d6) δ=10.43 (s, 1H), 9.57 (br s, 1H), 8.30 (s, 1H), 8.20-8.14 (m, 1H), 7.90-7.79 (m, 5H), 7.64 (d, J=8.6 Hz, 2H), 7.50 (d, J=8.2 Hz, 1H), 7.28-7.14 (m, 5H), 4.39 (br s, 1H), 4.03 (d, J=5.7 Hz, 2H), 2.11 (s, 3H), 1.18 (d, J=6.4 Hz, 6H). ESI [M+H]=580.1

Compound D20

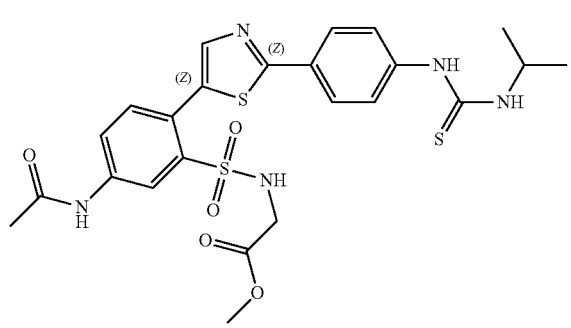

¹H NMR (400 MHz, DMSO-d6) δ=10.38 (s, 1H), 9.54 (br s, 1H), 8.19 (s, 1H), 8.05 (s, 1H), 7.91-7.75 (m, 5H), 7.62 (br d, J=8.6 Hz, 2H), 7.48 (d, J=8.2 Hz, 1H), 4.35 (s, 1H), 3.62 (br d, J=5.7 Hz, 2H), 3.49 (s, 3H), 2.07 (s, 3H), 1.15 (d, J=6.6 Hz, 6H). ESI [M+H]=561.8

Compound D21

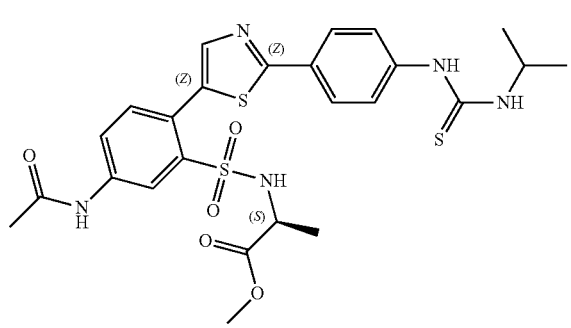

¹H NMR (400 MHz, DMSO-d6) δt=10.40 (s, 1H), 9.54 (br s, 1H), 8.28 (s, 1H), 8.22 (d, J=8.4 Hz, 1H), 7.88-7.79 (m, 5H), 7.62 (br d, J=8.8 Hz, 2H), 7.49 (d, J=8.2 Hz, 1H), 4.36 (br s, 1H), 3.74-3.66 (m, 1H), 3.46 (s, 3H), 2.07 (s, 3H), 1.20 (br d, J=7.3 Hz, 3H), 1.15 (d, J=6.4 Hz, 6H). ESI [M+H]=575.9

Compound D22

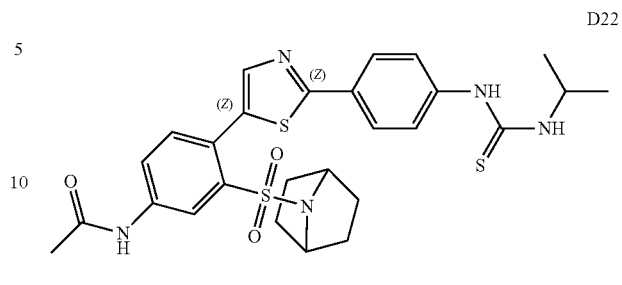

¹H NMR (400 MHz, DMSO-d₆) δ=10.46 (s, 1H), 9.61 (br s, 1H), 8.40 (d, J=2.2 Hz, 1H), 8.00-7.92 (m, 1H), 7.91-7.82 (m, 4H), 7.66-7.59 (m, 2H), 7.56 (d, J=8.4 Hz, 1H), 4.38 (br d, J=6.8 Hz, 1H), 3.84 (br s, 2H), 2.13-2.07 (m, 3H), 1.58 (br d, J=6.8 Hz, 4H), 1.34 (br d, J=6.8 Hz, 4H), 1.16 (d, J=6.6 Hz, 6H). ESI [M+H]=569.9

Compound D23

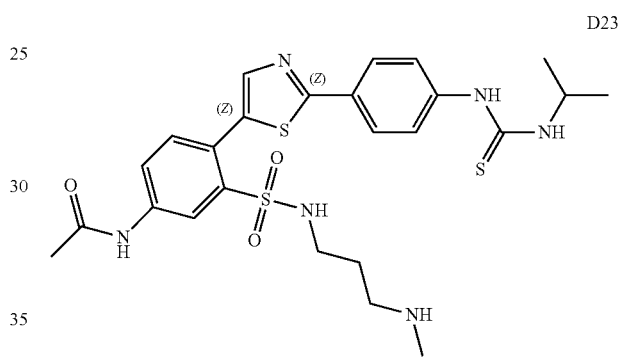

¹H NMR (400 MHz, DMSO-d6) δ=10.48 (s, 1H), 9.69 (br s, 1H), 8.39 (d, J=1.8 Hz, 1H), 8.31 (br s, 2H), 7.96 (br d, J=7.9 Hz, 1H), 7.91-7.85 (m, 3H), 7.84-7.79 (m, 1H), 7.75-7.65 (m, 3H), 7.55 (d, J=8.4 Hz, 1H), 4.39 (br d, J=6.2 Hz, 1H), 2.90-2.81 (m, 4H), 2.50 (s, 3H), 2.11 (s, 3H), 1.69 (quin, J=7.3 Hz, 2H), 1.18 (d, J=6.4 Hz, 6H). ESI [M+H]=561.3

Compound D24

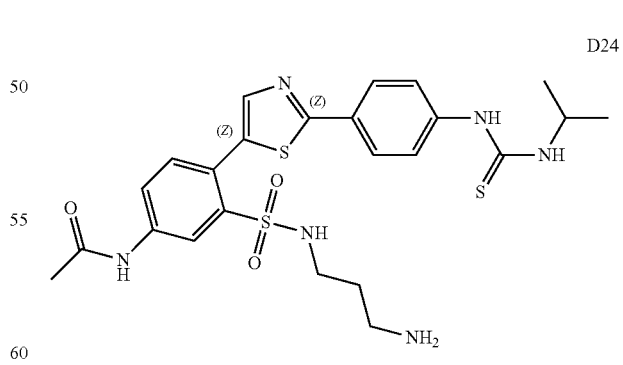

¹H NMR (400 MHz, DMSO-d6) δ=10.48 (s, 1H), 9.71 (br s, 1H), 8.37 (d, J=1.8 Hz, 1H), 7.98 (br d, J=7.7 Hz, 1H), 7.91-7.81 (m, 4H), 7.74-7.62 (m, 6H), 7.54 (d, J=8.4 Hz, 1H), 4.52-4.30 (m, 1H), 2.87 (q, J=6.5 Hz, 2H), 2.81-2.70 (m, 2H), 2.11 (s, 3H), 1.74-1.59 (m, 2H), 1.18 (d, J=6.6 Hz, 6H). ESI [M+H]=547.2

Compound D25

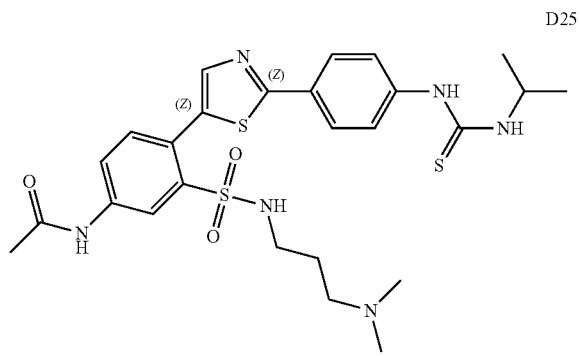 [SMILES: CC(=O)Nc1ccc(-c2cnc(-c3ccc(NC(=S)NC(C)C)cc3)s2)c(S(=O)(=O)NCCCN(C)C)c1]

$^1$H NMR (400 MHz, DMSO-d6) δ=10.45 (s, 1H), 9.67 (br s, 1H), 9.38 (br s, 1H), 8.36 (s, 1H), 7.94 (br d, J=7.7 Hz, 1H), 7.88-7.82 (m, 3H), 7.78 (br d, J=8.2 Hz, 1H), 7.72-7.63 (m, 3H), 7.52 (d, J=8.2 Hz, 1H), 4.36 (br d, J=6.6 Hz, 1H), 3.03-2.92 (m, 2H), 2.84 (q, J=6.3 Hz, 2H), 2.68 (d, J=4.4 Hz, 6H), 2.08 (s, 3H), 1.78-1.65 (m, 2H), 1.15 (d, J=6.4 Hz, 6H). ESI [M+H]=575.2

Compound D26

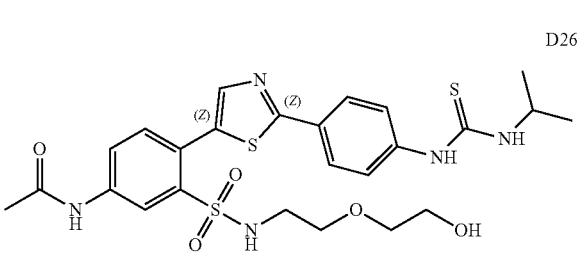 [SMILES: CC(=O)Nc1ccc(-c2cnc(-c3ccc(NC(=S)NC(C)C)cc3)s2)c(S(=O)(=O)NCCOCCO)c1]

$^1$H NMR (400 MHz, DMSO-d6) δ=10.42 (s, 1H), 9.58 (br s, 1H), 8.29 (d, J=2.2 Hz, 1H), 7.93-7.81 (m, 5H), 7.68-7.57 (m, 3H), 7.53 (d, J=8.4 Hz, 1H), 4.47-4.37 (m, 2H), 3.44-3.39 (m, 2H), 3.38-3.29 (m, 4H), 3.03-2.93 (m, 2H), 2.10 (s, 3H), 1.18 (d, J=6.6 Hz, 6H). ESI [M+H]=578.2

Compound D27

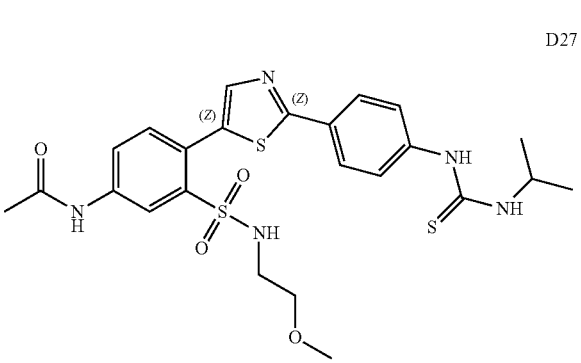 [SMILES: COCCNS(=O)(=O)c1cc(NC(C)=O)ccc1-c1cnc(-c2ccc(NC(=S)NC(C)C)cc2)s1]

$^1$H NMR (400 MHz, DMSO-d6) δ=10.42 (s, 1H), 9.58 (br s, 1H), 8.28 (d, J=2.2 Hz, 1H), 7.92-7.82 (m, 5H), 7.68-7.58 (m, 3H), 7.54-7.50 (m, 1H), 4.40 (br d, J=6.6 Hz, 1H), 4.00 (s, 3H), 3.26 (t, J=5.8 Hz, 2H), 3.02-2.93 (m, 2H), 2.10 (s, 3H), 1.20-1.16 (m, 6H). ESI [M+H]=548.2

Compound D28

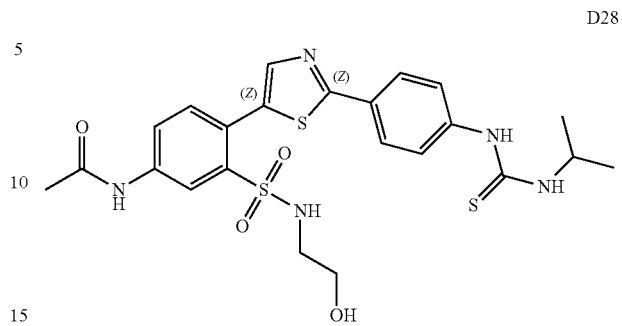

$^1$H NMR (400 MHz, DMSO-d6) δ=10.43 (s, 1H), 9.59 (br s, 1H), 8.29 (d, J=2.2 Hz, 1H), 7.98-7.79 (m, 5H), 7.70-7.61 (m, 2H), 7.53 (d, J=8.4 Hz, 1H), 7.44 (t, J=5.8 Hz, 1H), 4.69-4.47 (m, 2H), 3.33 (t, J=6.6 Hz, 2H), 2.91-2.80 (m, 2H), 2.10 (s, 3H), 1.18 (d, J=6.4 Hz, 6H). ESI [M+H]=534.2

Compound D29

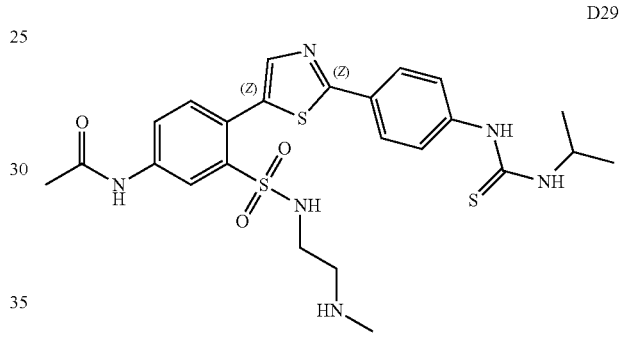

$^1$H NMR (400 MHz, DMSO-d6) δ=10.50 (s, 1H), 9.72 (br s, 1H), 8.41 (d, J=2.2 Hz, 2H), 7.98 (d, J=7.7 Hz, 1H), 7.91-7.86 (m, 3H), 7.84-7.77 (m, 2H), 7.72-7.67 (m, 2H), 7.57 (d, J=8.4 Hz, 1H), 4.48-4.27 (m, 1H), 3.12-3.01 (m, 2H), 2.95 (br s, 2H), 2.56-2.52 (m, 3H), 2.11 (s, 3H), 1.18 (d, J=6.4 Hz, 6H). ESI [M+H]=547.2

Compound D30

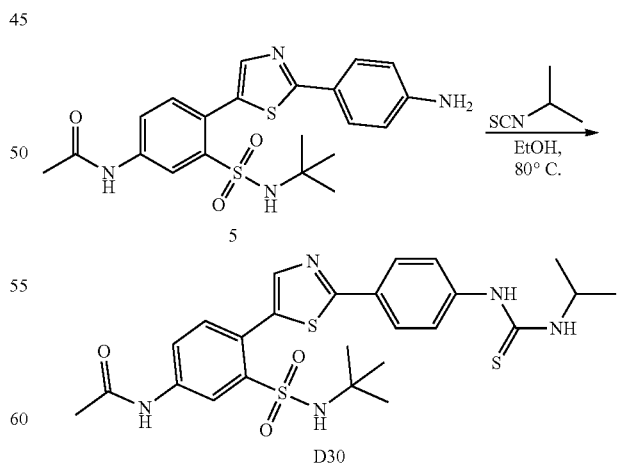

General method G. $^1$H NMR (400 MHz, METHANOL-d4) δ=8.48 (d, J=1.8 Hz, 1H), 7.95-7.82 (m, 4H), 7.57 (d, J=8.8 Hz, 2H), 7.49 (d, J=8.3 Hz, 1H), 4.53 (br s, 1H), 2.17 (s, 3H), 1.24 (d, J=6.6 Hz, 6H), 1.14 (s, 9H). ESI [M+H]=546.0

Scheme 4.1

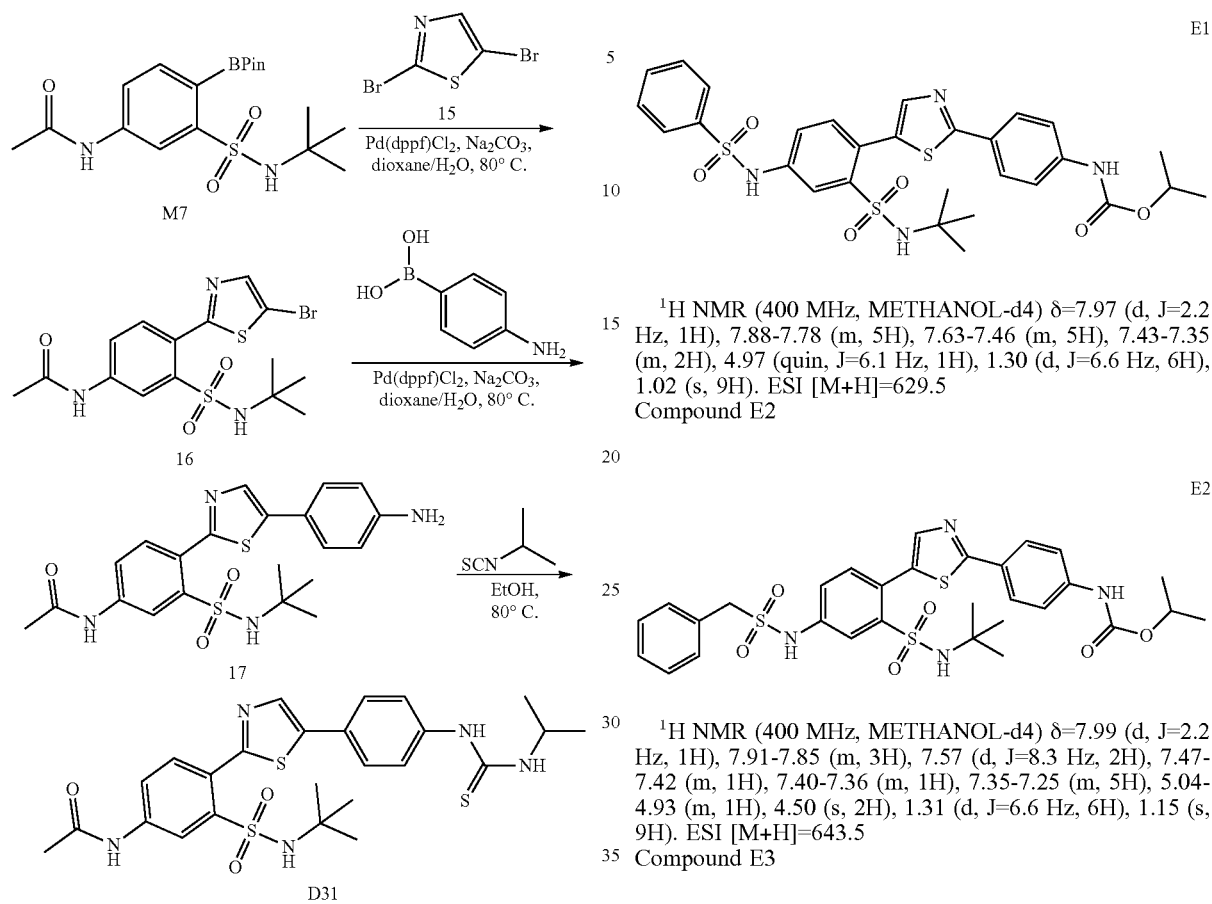

Compound D31

Compound D31 was prepared using the conditions set forth in general methods A and G.

$^1$H NMR (400 MHz, METHANOL-d4) δ=8.39 (d, J=1.1 Hz, 1H), 8.14 (s, 1H), 8.03-7.91 (m, 1H), 7.77 (d, J=8.6 Hz, 1H), 7.66 (br d, J=8.4 Hz, 2H), 7.49 (br d, J=8.4 Hz, 2H), 4.62-4.40 (m, 1H), 2.16 (s, 3H), 1.26 (s, 9H), 1.22 (d, J=6.6 Hz, 6H). ESI [M+H]=546.2

Example 5

The following compounds were synthesized via reacting intermediate 7 with different sulfonyl chlorides via general method C (shown in Example 1), unless otherwise noted.

Compound E1

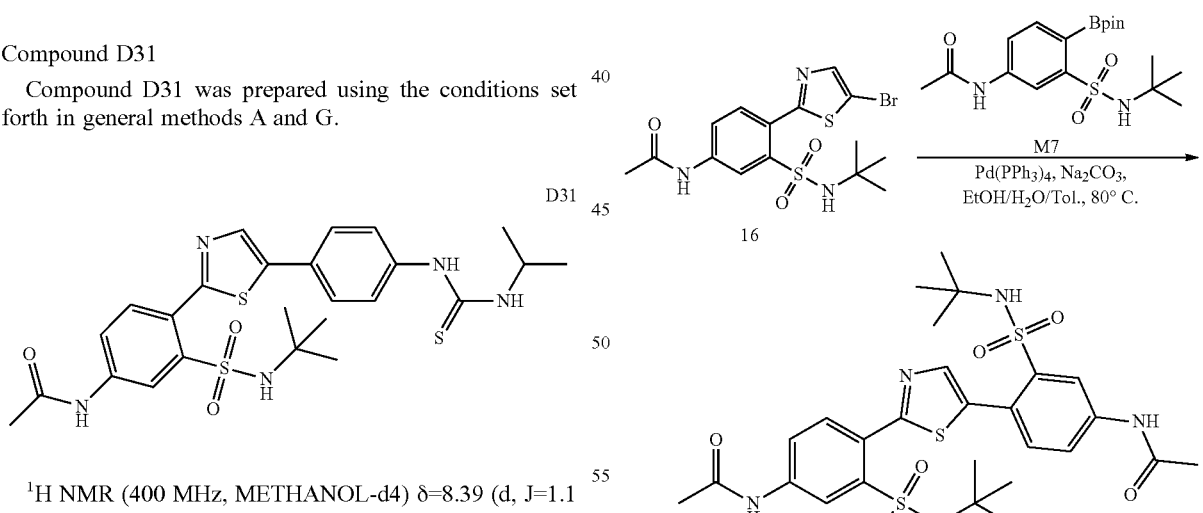

$^1$H NMR (400 MHz, METHANOL-d4) δ=7.97 (d, J=2.2 Hz, 1H), 7.88-7.78 (m, 5H), 7.63-7.46 (m, 5H), 7.43-7.35 (m, 2H), 4.97 (quin, J=6.1 Hz, 1H), 1.30 (d, J=6.6 Hz, 6H), 1.02 (s, 9H). ESI [M+H]=629.5

Compound E2

$^1$H NMR (400 MHz, METHANOL-d4) δ=7.99 (d, J=2.2 Hz, 1H), 7.91-7.85 (m, 3H), 7.57 (d, J=8.3 Hz, 2H), 7.47-7.42 (m, 1H), 7.40-7.36 (m, 1H), 7.35-7.25 (m, 5H), 5.04-4.93 (m, 1H), 4.50 (s, 2H), 1.31 (d, J=6.6 Hz, 6H), 1.15 (s, 9H). ESI [M+H]=643.5

Compound E3

A mixture of N-[3-(tert-butylsulfamoyl)-4-(4,4,5,5-tetramethyl-1,3,2-dioxaborolan-2-yl)phenyl]acetamide (285.99 mg, 721.62 µmol, 1.20 eq.), N-[4-(5-bromothiazol-2-yl)-3-(tert-butylsulfamoyl)phenyl]acetamide (260.00 mg, 601.35 µmol, 1.00 eq.), Na$_2$CO$_3$ (159.34 mg, 1.50 mmol, 2.50 eq.) and Pd(PPh$_3$)$_4$ (138.98 mg, 120.27 µmol, 0.20 eq.) in Tol. (1.50 mL)/EtOH (3.00 mL)/H$_2$O (1.50 mL) was degassed and purged with N$_2$ for 3 times, and then the mixture was stirred at 80° C. for 12 hrs under N₂ atmosphere. LCMS showed the reaction was complete. The reaction mixture was concentrated, diluted with H₂O (5 mL) and extracted with EtOAc (10 mL×3). The combined organic layers were washed with brine, dried over Na₂SO₄, filtered and concentrated. The residue was purified by prep-HPLC (TFA condition; 5-P1B, column: YMC-Actus Triart C18 150*30 5u; mobile phase: [water (0.1% TFA)-€]; B %: 40%-70%, 12 min) to give compound E3 (65.75 mg, 101.09 µmol, 16.81% yield, 95.6% purity) as a light yellow solid. ¹H NMR (400 MHz, METHANOL-d4) δ=8.44 (dd, J=2.2, 12.8 Hz, 2H), 8.01 (dd, J=2.2, 8.4 Hz, 1H), 7.98 (s, 1H), 7.92 (dd, J=2.4, 8.4 Hz, 1H), 7.79 (d, J=8.4 Hz, 1H), 7.54 (d, J=8.4 Hz, 1H), 2.18 (d, J=3.1 Hz, 6H), 1.29 (s, 9H), 1.12 (s, 9H). ESI [M+H]=622.3

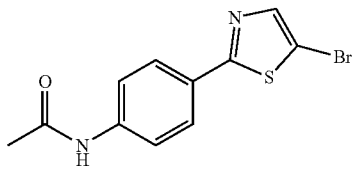

ESI [M+H]=298.8/296.8
Compound E4

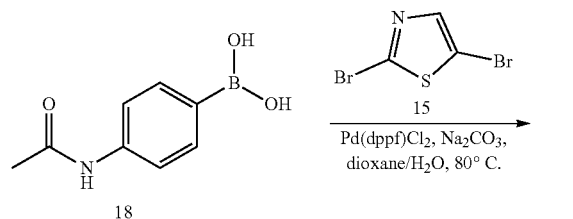

Scheme 5.1

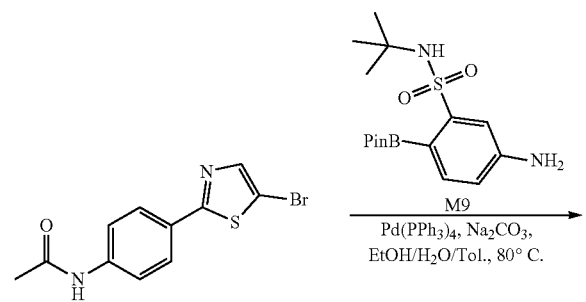

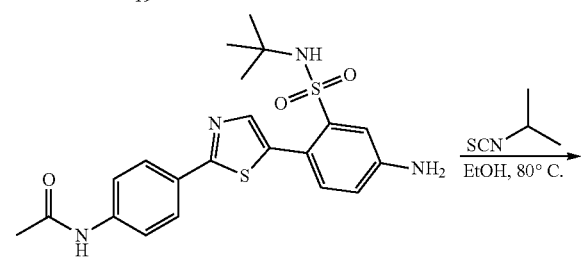

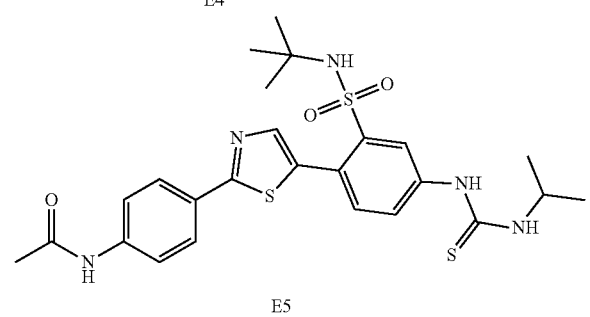

Intermediate Compound 19

Intermediate compound 19 was prepared via general method A (shown in Example 1).

To a solution of 5-amino-N-tert-butyl-2-(4,4,5,5-tetramethyl-1,3,2-dioxaborolan-2-yl)benzenesulfonamide (150.00 mg, 423.41 µmol, 1.00 eq.) in EtOH (2.00 mL), Tol. (1.00 mL) and H₂O (1.00 mL), were added N-[4-(5-bromothiazol-2-yl)phenyl] acetamide (150.99 mg, 508.09 µmol, 1.20 eq.), Pd(PPh₃)₄ (48.93 mg, 42.34 µmol, 0.10 eq.) and Na₂CO₃ (134.63 mg, 1.27 mmol, 3.00 eq.). The mixture was stirred at 80° C. for 16 hrs under N₂ and LCMS showed the reaction was complete. The mixture was concentrated and the residue was purified by acidic prep-HPLC to give compound E4 (47.72 mg, 107.34 µmol, 25.35% yield, 100% purity) as a yellow solid. ¹H NMR (400 MHz, DMSO-d6) δ=10.16 (s, 1H), 7.90-7.83 (m, 2H), 7.74-7.67 (m, 3H), 7.32 (d, J=2.4 Hz, 1H), 7.15 (d, J=8.2 Hz, 1H), 6.81 (s, 1H), 6.74 (dd, J=2.4, 8.2 Hz, 1H), 5.83 (br s, 1H), 2.07 (s, 3H), 1.06 (s, 9H). ESI [M+H]=445.2

Compound E5

Compound E5 was prepared via general method G (shown in Example 1).

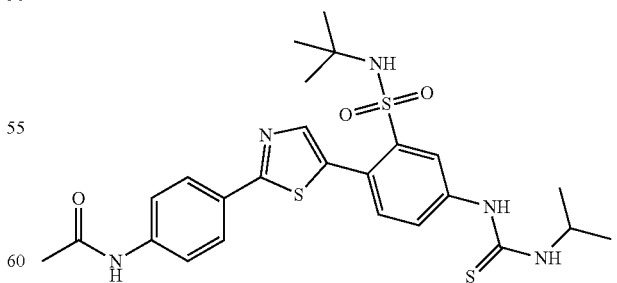

¹H NMR (400 MHz, DMSO-d6) δ=10.19 (s, 1H), 9.72 (br s, 1H), 8.36 (d, J=2.0 Hz, 1H), 7.90 (d, J=8.6 Hz, 3H), 7.84 (s, 1H), 7.77-7.69 (m, 3H), 7.46 (d, J=8.2 Hz, 1H), 7.16 (s, 1H), 4.38 (br d, J=5.3 Hz, 1H), 2.10-2.06 (m, 3H), 1.19 (d, J=6.6 Hz, 6H), 1.10 (s, 9H). ESI [M+H]=546.3

Scheme 5.2

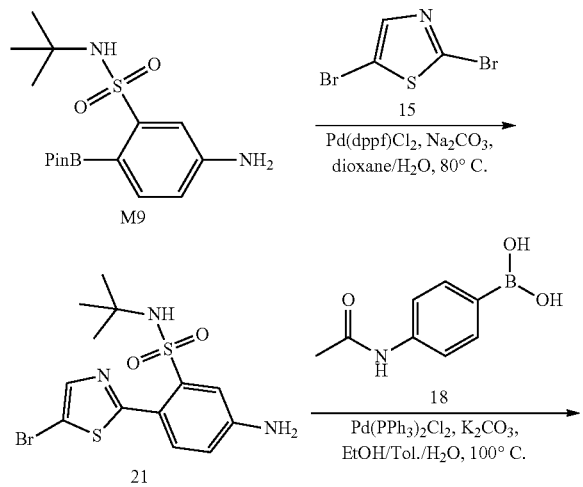

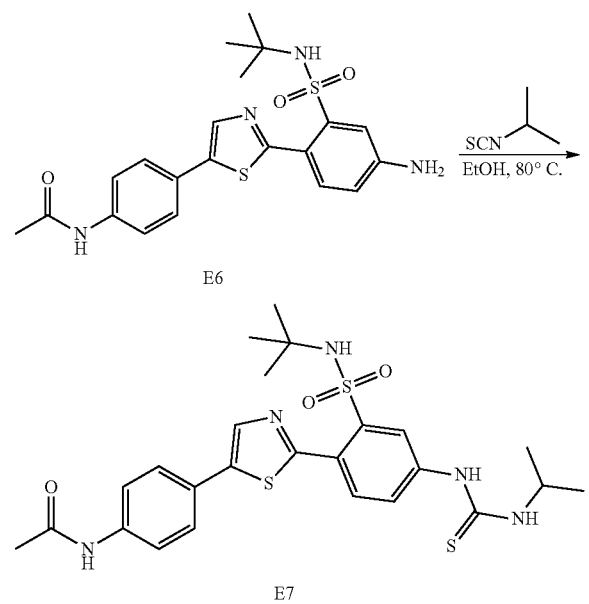

Intermediate Compound 21

Intermediate compound 21 was prepared via general method A (shown in Example 1).

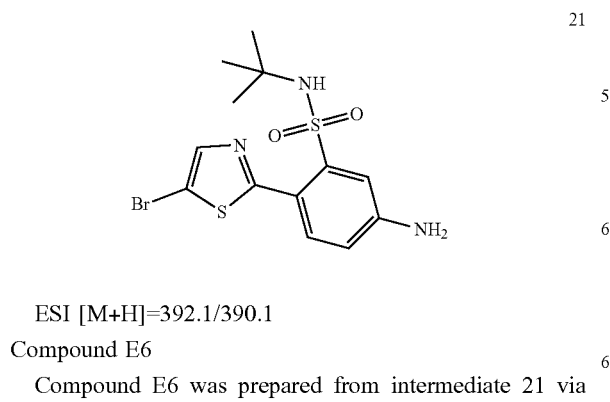

ESI [M+H]=392.1/390.1

Compound E6

Compound E6 was prepared from intermediate 21 via general method H.

$^1$H NMR (400 MHz, METHANOL-d4) δ=8.03 (s, 1H), 7.63 (d, J=3.5 Hz, 4H), 7.53 (d, J=8.3 Hz, 1H), 7.46-7.43 (m, 1H), 6.86 (br d, J=11.0 Hz, 1H), 2.14 (s, 3H), 1.27 (s, 9H). ESI [M+H]=445.2

Compound E7

Compound E7 was prepared from compound E6 via general method G.

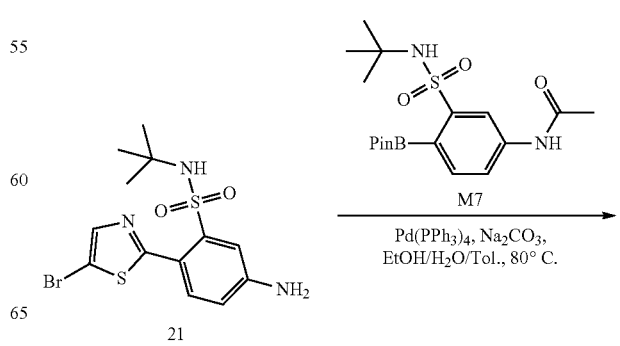

$^1$H NMR (400 MHz, METHANOL-d4) δ=8.42 (d, J=2.6 Hz, 1H), 8.13 (s, 1H), 7.85 (dd, J=2.2, 8.3 Hz, 1H), 7.75 (d, J=8.3 Hz, 1H), 7.65 (s, 4H), 4.53 (br s, 1H), 2.14 (s, 3H), 1.31-1.24 (m, 15H). ESI [M+H]=546.3

Scheme 5.3

-continued

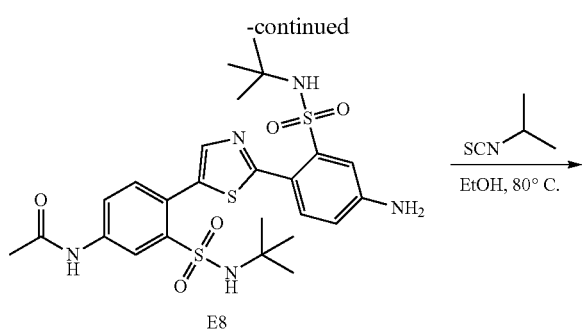

E8

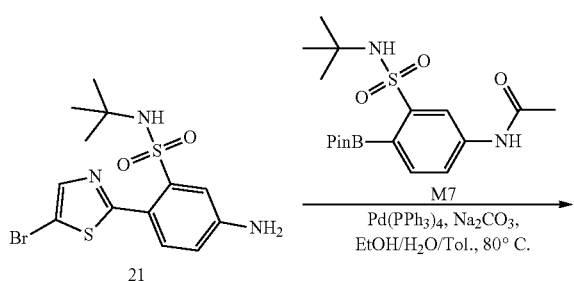

E9

Compound E8

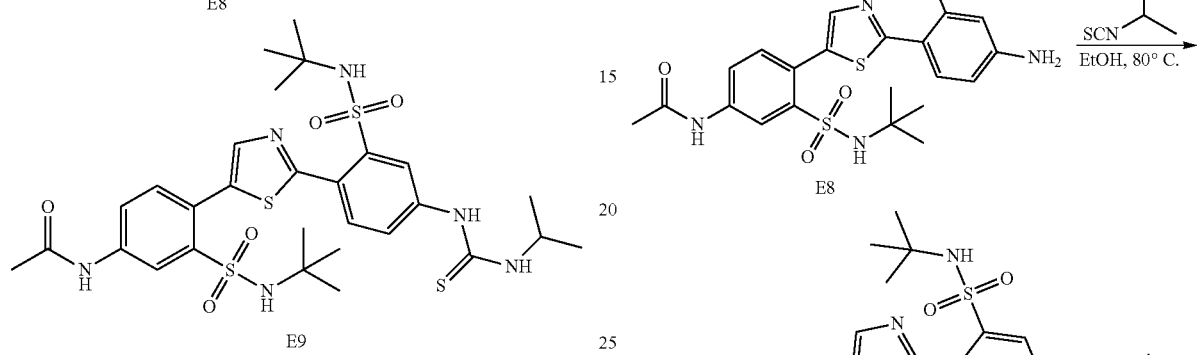

To a solution of 5-amino-2-(5-bromothiazol-2-yl)-N-tert-butyl-benzenesulfonamide (95.00 mg, 243.39 μmol, 1.00 eq.) in EtOH (2.00 mL), Tol. (1.00 mL) and H2O (1.00 mL) were added N-[3-(tert-butylsulfamoyl)-4-(4,4,5,5-tetramethyl-1,3,2-dioxaborolan-2-yl)phenyl]acetamide (106.10 mg, 267.73 μmol, 1.10 eq.), Pd(PPh3)4 (28.13 mg, 24.34 μmol, 0.10 eq.) and Na2CO3 (64.49 mg, 608.48 μmol, 2.50 eq.). The mixture was stirred at 80° C. for 16 hrs under N2 and LCMS showed the reaction was complete. The mixture was filtered and concentrated and the residue was purified by prep-HPLC to give compound E8 (11.00 mg, 17.04 μmol, 7.00% yield, 89.79% purity) as a yellow solid. $^1$H NMR (400 MHz, METHANOL-d4) δ=8.43 (s, 1H), 7.90 (s, 2H), 7.56-7.50 (m, 2H), 7.46 (s, 1H), 6.86 (br d, J=10.5 Hz, 1H), 2.17 (s, 3H), 1.28 (s, 9H), 1.10 (s, 9H). ESI [M+H]=580.2

Compound E9

Compound E9 was prepared from compound E8 via general method G (shown in Example 1).

$^1$H NMR (400 MHz, METHANOL-d4) δ=8.45 (s, 2H), 7.99 (s, 1H), 7.92 (br d, J=10.1 Hz, 1H), 7.87-7.83 (m, 1H), 7.79-7.75 (m, 1H), 7.54 (d, J=8.3 Hz, 1H), 4.52 (s, 1H), 2.17 (s, 3H), 1.31-1.24 (m, 15H), 1.12 (s, 9H). ESI [M+H]=681.3

Scheme 5.4

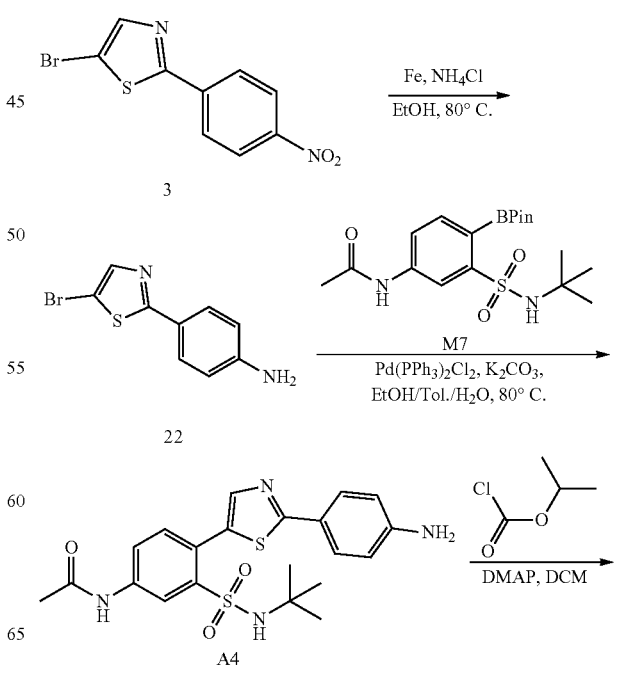

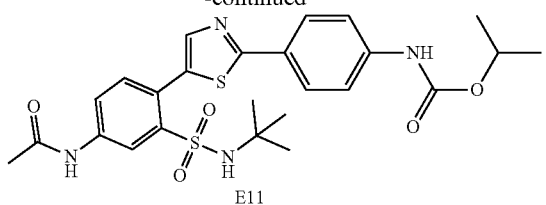

Intermediate Compound 22

Intermediate compound 22 was prepared from intermediate compound 3 via general method B (shown in Example 1).

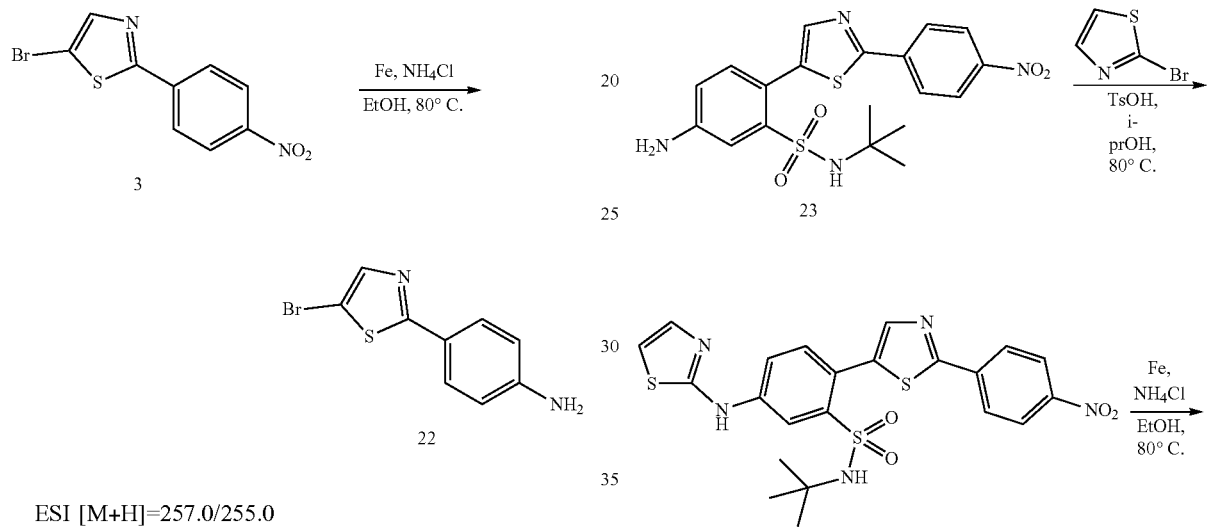

ESI [M+H]=257.0/255.0

Compound E11

Compound E11 was prepared from compound A4 via general method C (shown in Example 1).

$^1$H NMR (400 MHz, METHANOL-d4) δ=8.48 (d, J=1.8 Hz, 1H), 7.95-7.82 (m, 4H), 7.57 (d, J=8.8 Hz, 2H), 7.49 (d, J=8.3 Hz, 1H), 4.53 (br s, 1H), 2.17 (s, 3H), 1.24 (d, J=6.6 Hz, 6H), 1.14 (s, 9H). ESI [M+H]=531.1

Scheme 5.5

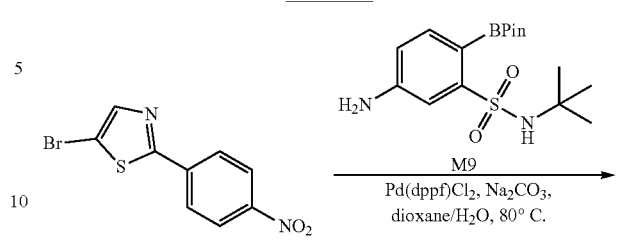

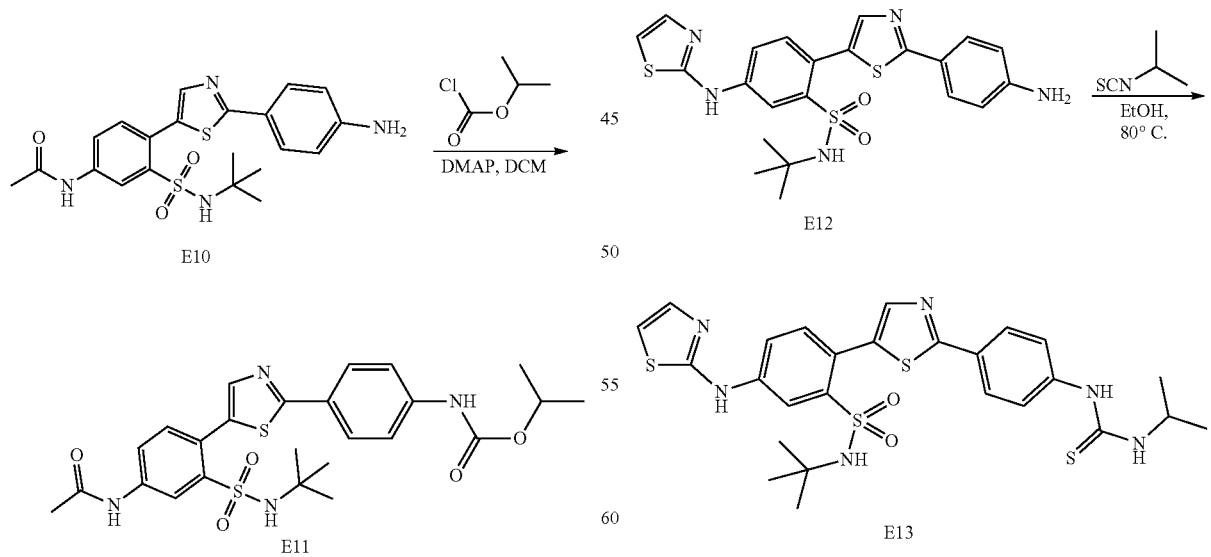

Intermediate Compound 23

Intermediate compound 23 was prepared from intermediate compound 3 via general method A (shown in Example 1).

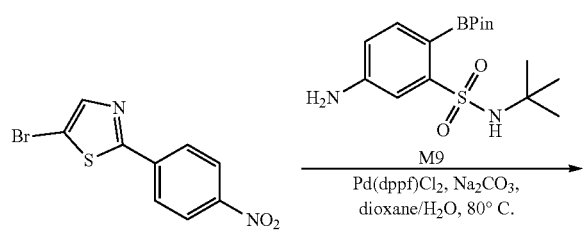

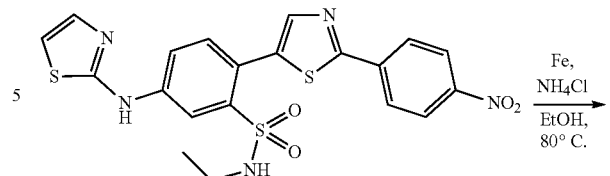

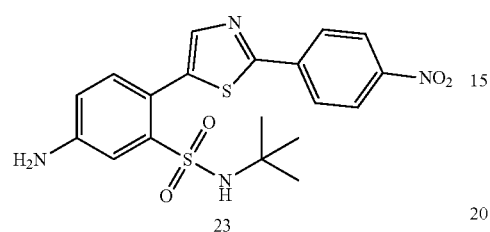

ESI [M+H]=433.1

Intermediate Compound 24

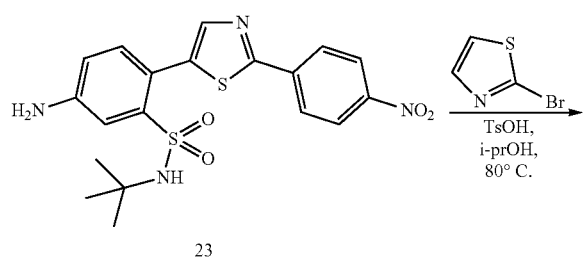

To a solution of 5-amino-N-tert-butyl-2-[2-(4-nitrophenyl)thiazol-5-yl] benzenesulfonamide (150.00 mg, 346.80 μmol, 1.00 eq.) in i-PrOH (5.00 mL), were added 2-bromothiazole (170.65 mg, 1.04 mmol, 93.76 ul, 3.00 eq.) and TsOH (179.16 mg, 1.04 mmol, 3.00 eq.). The mixture was stirred at 80° C. for 16 hrs and LCMS showed the reaction was complete. The mixture was concentrated and the residue was purified by prep-TLC (PE:EtOAc=1:1) to give intermediate compound 24 (100.00 mg, crude) as a yellow solid. ESI [M+H]=516.0

Compound E12

Compound E12 was prepared from intermediate 24 via general method B (shown in Example 1).

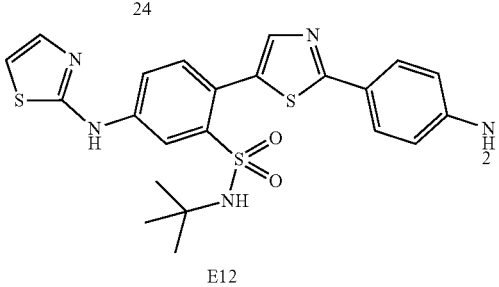

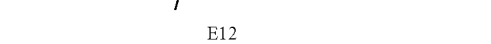

$^1$H NMR (400 MHz, DMSO-d6) δ=10.66 (br s, 1H), 8.47 (s, 1H), 7.88-7.79 (m, 1H), 7.72 (s, 1H), 7.65 (d, J=8.6 Hz, 2H), 7.43 (d, J=8.4 Hz, 1H), 7.30 (d, J=3.7 Hz, 1H), 7.10 (s, 1H), 7.00 (d, J=3.7 Hz, 1H), 6.70 (br d, J=7.9 Hz, 2H), 1.09 (s, 9H). ESI [M+H]=486.1

Compound E13

Compound E13 was prepared from compound E12 via general method G (shown in Example 1).

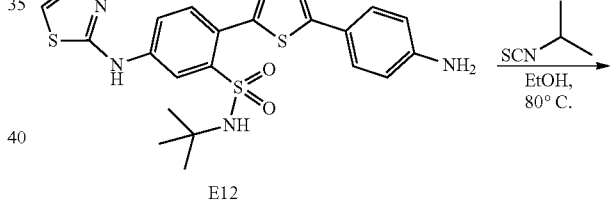

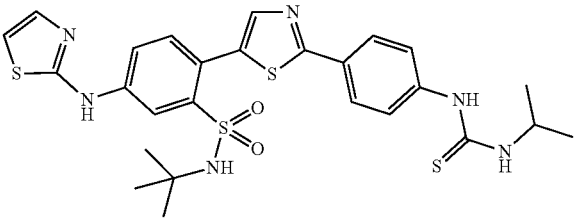

$^1$H NMR (400 MHz, DMSO-d6) δ=10.69 (s, 1H), 9.55 (br s, 1H), 8.49 (d, J=2.2 Hz, 1H), 7.91-7.77 (m, 5H), 7.61 (d, J=8.6 Hz, 2H), 7.47 (d, J=8.4 Hz, 1H), 7.31 (d, J=3.7 Hz, 1H), 7.15 (s, 1H), 7.01 (d, J=3.7 Hz, 1H), 4.37 (br d, J=6.6 Hz, 1H), 1.16 (d, J=6.6 Hz, 6H), 1.09 (s, 9H). ESI [M+H]=587.2

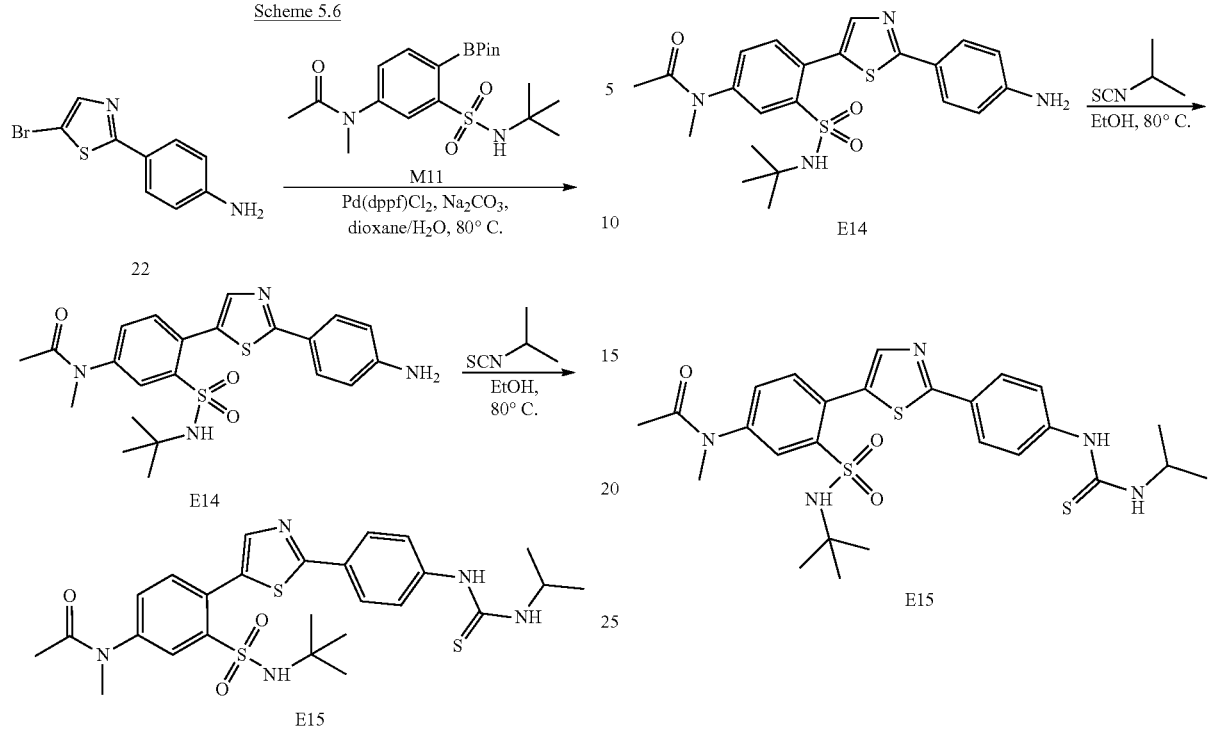
Compound E14
Compound E14 was prepared from intermediate compound 22 via general method A (shown in Example 1).
$^1$H NMR (400 MHz, DMSO-d6) δ=7.97 (s, 1H), 7.80 (s, 1H), 7.69 (d, J=8.3 Hz, 2H), 7.64-7.54 (m, 2H), 7.26 (s, 1H), 6.74 (d, J=8.3 Hz, 3H), 3.24 (br s, 3H), 1.92 (br s, 3H), 1.05 (s, 9H). ESI [M+H]=459.2
Compound E15
Compound E15 was prepared from compound E14 via general method G (shown in Example 1).
$^1$H NMR (400 MHz, DMSO-d$_6$) δ=9.56 (br s, 1H), 7.98 (d, J=2.0 Hz, 1H), 7.91-7.80 (m, 4H), 7.66-7.56 (m, 4H), 7.28 (s, 1H), 4.37 (br dd, J=6.6, 13.2 Hz, 1H), 3.23 (br s, 3H), 1.90 (br s, 3H), 1.16 (d, J=6.6 Hz, 6H), 1.04 (s, 9H). ESI [M+H]=559.9
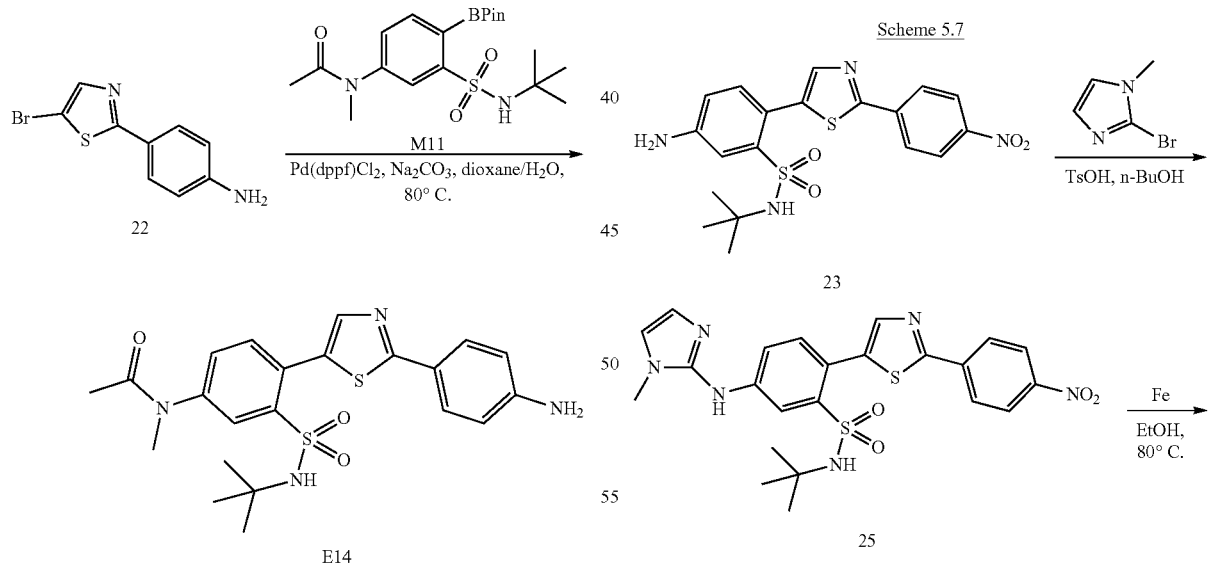

-continued

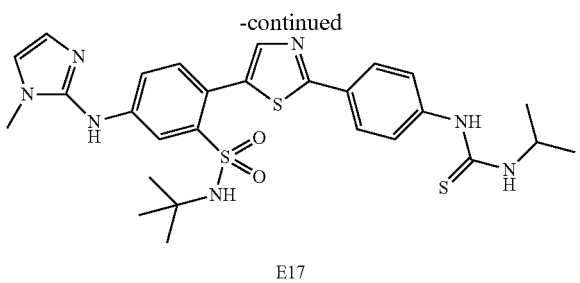

E17

Intermediate Compound 25

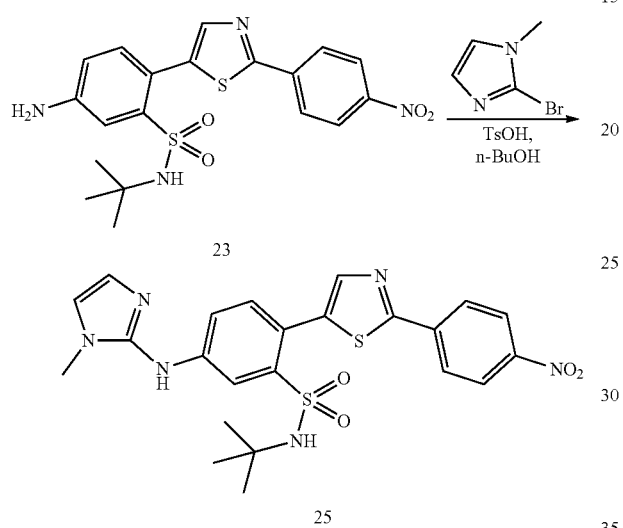

To a solution of 5-amino-N-tert-butyl-2-[2-(4-nitrophenyl)thiazol-5-yl] benzenesulfonamide (50.00 mg, 115.60 μmol, 1.00 eq.) in n-BuOH (2.00 mL) was added 2-bromo-1-methyl-imidazole (55.84 mg, 346.80 μmol, 3.00 eq.) and TsOH.H₂O (65.97 mg, 346.80 μmol, 3.00 eq.) and the mixture was stirred at 125° C. for 6 hrs. The mixture was concentrated and the residue was purified by prep-HPLC (TFA condition) to give intermediate compound 25 (45 mg, crude) as a yellow solid. ESI [M+H]=513.1

Compound E16

Compound E16 was prepared from intermediate compound 25 via general method B (shown in Example 1).

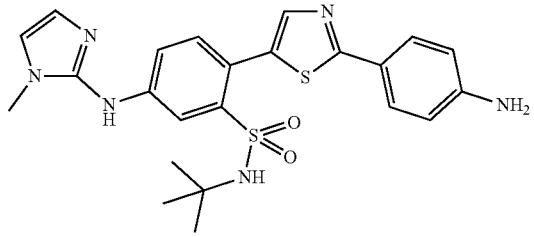

E16

¹H NMR (400 MHz, DMSO-d6) δ=10.07 (br s, 1H), 7.89 (s, 1H), 7.74 (s, 1H), 7.64 (d, J=8.3 Hz, 2H), 7.56-7.50 (m, 1H), 7.44 (br d, J=7.9 Hz, 1H), 7.35 (s, 1H), 7.24 (br s, 1H), 7.11 (s, 1H), 6.64 (d, J=8.8 Hz, 2H), 3.64 (s, 3H), 1.06 (s, 9H). ESI [M+H]=483.1

Compound E17

Compound E17 was prepared from compound E16 via general method G (shown in Example 1).

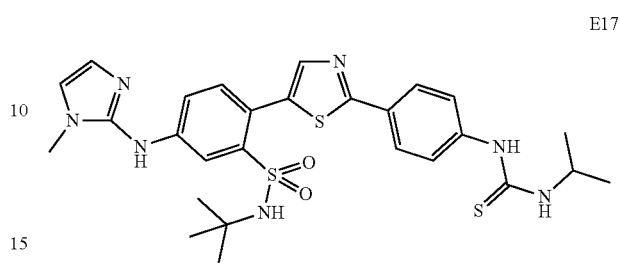

E17

¹H NMR (400 MHz, DMSO-d6) δ=10.10 (br s, 1H), 9.60 (br s, 1H), 7.94-7.82 (m, 5H), 7.66 (br d, J=8.3 Hz, 2H), 7.57 (d, J=8.8 Hz, 1H), 7.45 (br d, J=8.3 Hz, 1H), 7.36 (s, 1H), 7.26 (s, 1H), 7.17 (s, 1H), 4.38 (br s, 1H), 3.64 (s, 3H), 1.18 (d, J=6.6 Hz, 6H), 1.06 (s, 9H). ESI [M+H]=584.0

Scheme 5.8

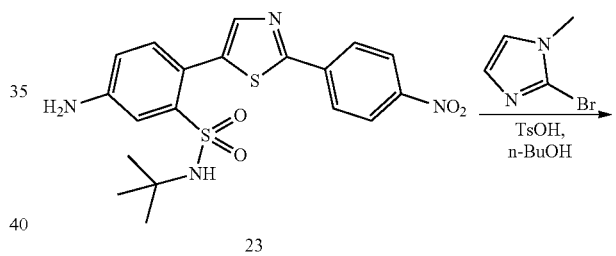

23

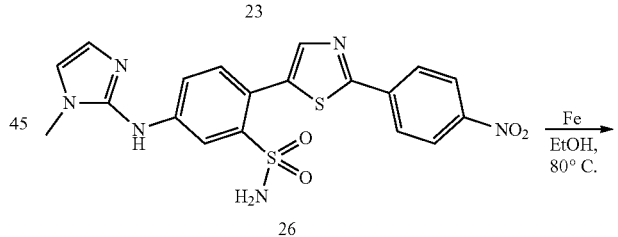

26

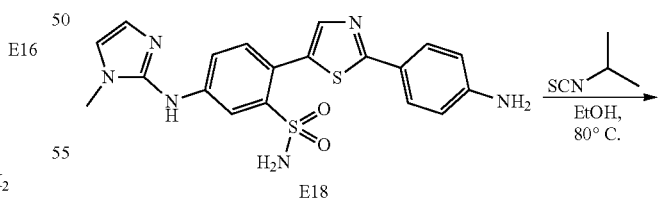

E18

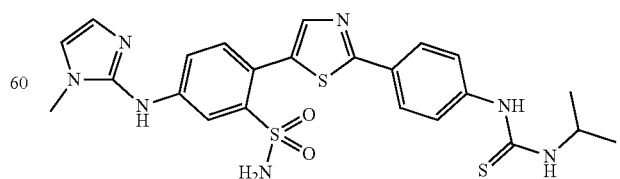

E19

Intermediate Compound 26

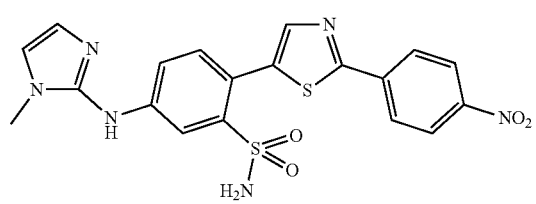

To a solution of 5-amino-N-tert-butyl-2-[2-(4-nitrophenyl)thiazol-5-yl] benzenesulfonamide (300.00 mg, 693.61 μmol, 1.00 eq.) in n-BuOH (5.00 mL) was added TsOH.H$_2$O (395.82 mg, 2.08 mmol, 3.00 eq.) and the mixture was stirred at 130° C. for 18 hrs. LCMS showed the reaction was complete. The mixture was concentrated and the residue was purified by prep-HPLC (TFA condition) to give intermediate compound 26 (140.00 mg, 291.35 μmol, 42.00% yield, 95% purity) as a yellow solid. $^1$H NMR (400 MHz, CHLOROFORM-d) δ=8.23 (br d, J=8.8 Hz, 2H), 8.05 (d, J=8.3 Hz, 2H), 7.93 (s, 1H), 7.79 (s, 1H), 7.39 (d, J=8.3 Hz, 1H), 7.23 (br d, J=8.3 Hz, 1H), 6.95-6.81 (m, 2H), 3.58 (s, 3H).

Compound E18

Compound E18 was prepared from intermediate compound 26 via general method B (shown in Example 1).

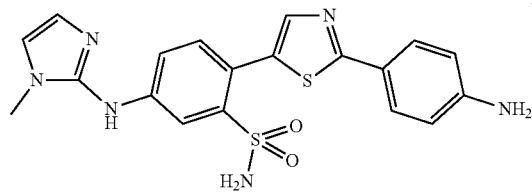

$^1$H NMR (400 MHz, DMSO-d6) δ=10.29 (br s, 1H), 7.83 (s, 1H), 7.78 (s, 1H), 7.66 (d, J=8.3 Hz, 2H), 7.56 (d, J=8.3 Hz, 1H), 7.46-7.38 (m, 4H), 7.29 (s, 1H), 6.68 (br d, J=7.5 Hz, 2H), 3.66 (s, 3H). ESI [M+H]=427.2

Compound E19

Compound E19 was prepared from compound E18 via general method G (shown in Example 1).

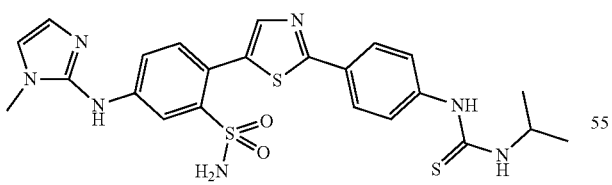

$^1$H NMR (400 MHz, DMSO-d6) δ=10.17 (br s, 1H), 9.62 (br s, 1H), 7.93-7.76 (m, 5H), 7.67 (br d, J=8.8 Hz, 2H), 7.59 (d, J=8.3 Hz, 1H), 7.51-7.40 (m, 3H), 7.38 (s, 1H), 7.28 (s, 1H), 4.40 (br s, 1H), 3.65 (s, 3H), 1.19 (d, J=6.6 Hz, 6H). ESI [M+H]=528.2

Compound E20

Compound E20 was prepared from compound E14 via general method C (shown in Example 1).

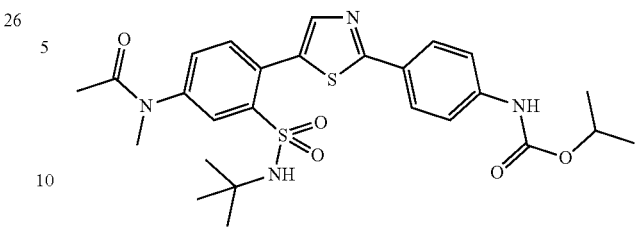

$^1$H NMR (400 MHz, DMSO-d6) δ=9.89 (s, 1H), 8.01 (s, 1H), 7.95-7.82 (m, 3H), 7.62 (br d, J=8.6 Hz, 4H), 7.32 (s, 1H), 4.93 (td, J=6.2, 12.5 Hz, 1H), 3.34-3.30 (m, 3H), 1.94 (br s, 3H), 1.28 (d, J=6.2 Hz, 6H), 1.07 (s, 9H). ESI [M+H]=544.9

Scheme 5.9

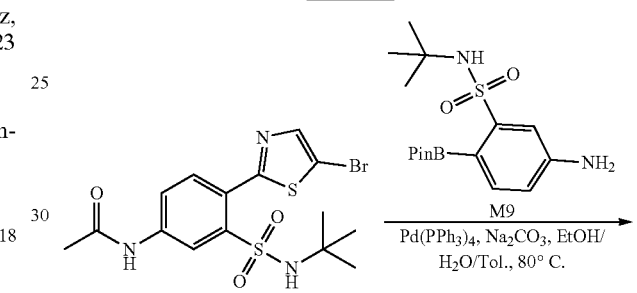

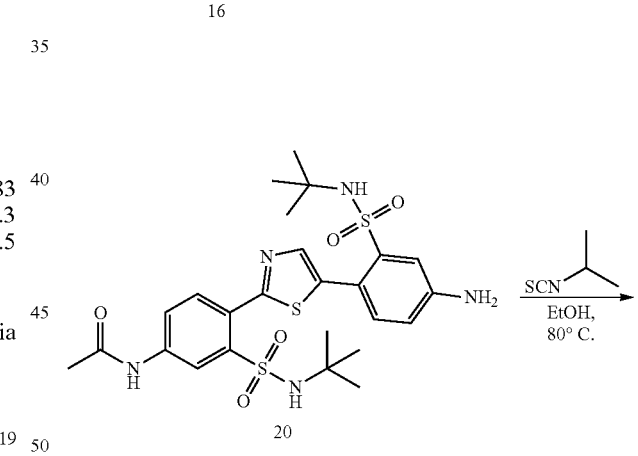

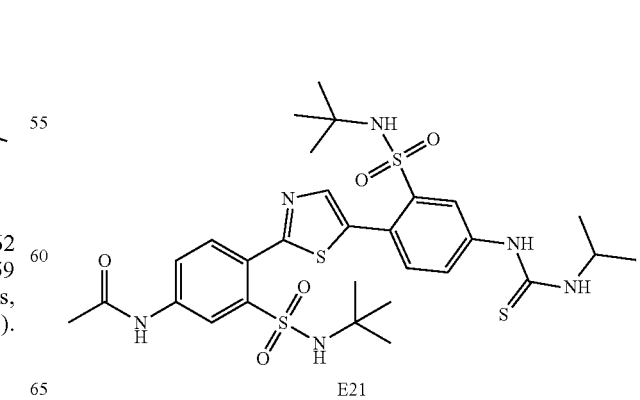

Intermediate Compound 20

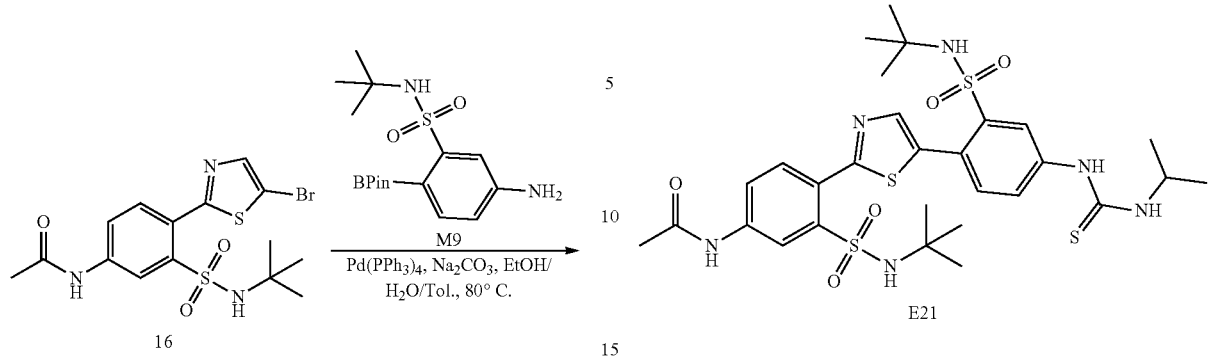

To a solution of N-[4-(5-bromothiazol-2-yl)-3-(tert-butylsulfamoyl)phenyl] acetamide (100.00 mg, 231.29 μmol, 1.00 eq.) in EtOH (2.00 mL), Tol. (1.00 mL) and H₂O (1.00 mL) were added 5-amino-N-tert-butyl-2-(4,4,5,5-tetramethyl-1,3,2-dioxaborolan-2-yl)benzenesulfonamide (90.13 mg, 254.42 μmol, 1.10 eq.), Pd(PPh₃)₄ (26.73 mg, 23.13 μmol, 0.10 eq.) and Na₂CO₃ (61.29 mg, 578.22 μmol, 2.50 eq.). The mixture was stirred at 80° C. for 16 hrs under N₂ and LCMS showed the reaction was complete. The mixture was filtered and concentrated and the residue was purified by prep-HPLC (TFA condition) to give intermediate compound 20 (25.00 mg, 36.58 μmol, 15.82% yield, 84.83% purity) as a yellow solid. ESI [M+H]=580.2

Compound E21

Compound E21 was prepared from intermediate compound 20 via general method G (shown in Example 1).

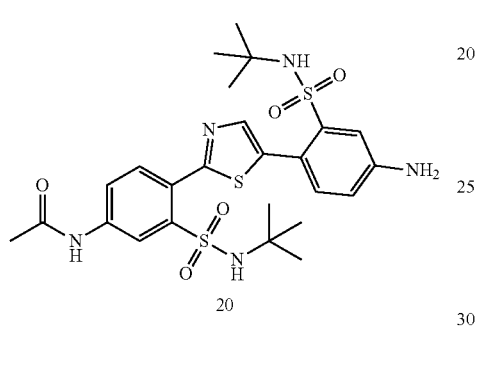

$^1$H NMR (400 MHz, METHANOL-d4) δ=8.40 (s, 2H), 8.02-7.95 (m, 2H), 7.78 (br d, J=8.4 Hz, 2H), 7.51 (d, J=8.4 Hz, 1H), 4.52 (br s, 1H), 2.17 (s, 3H), 1.30-1.21 (m, 15H), 1.12 (s, 9H). ESI [M+H]=681.3

Example 6

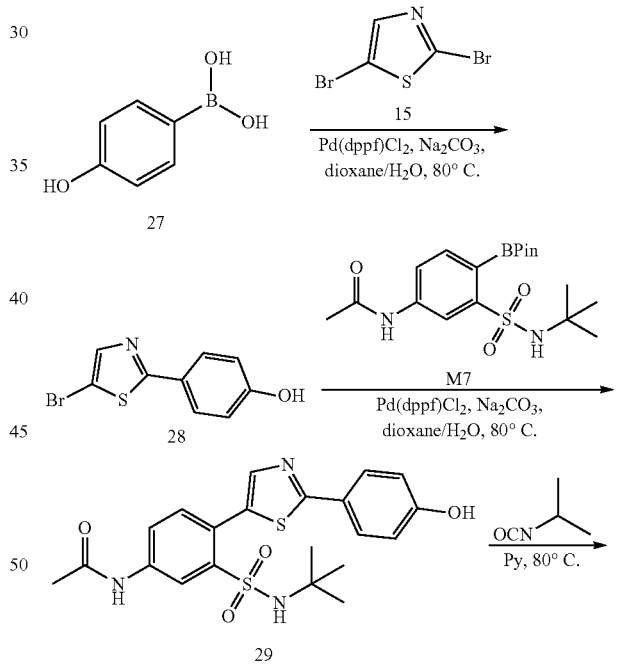

Intermediate Compound 28

Intermediate compound 28 was prepared from intermediate 27 via general method A (shown in Example 1).

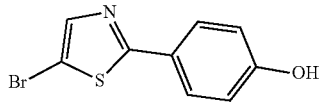

ESI [M+H]=257.9/255.7

Intermediate Compound 29

Intermediate compound 29 was prepared from intermediate compound 28 via general method A (shown in Example 1).

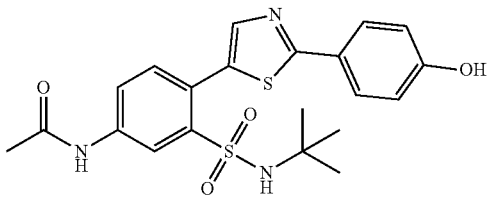

ESI [M+H]=446.1

Example 7

The following compounds were synthesized via reacting intermediate 5 with different acyl chloride via general method C (shown in Example 1), unless otherwise noted.

Compound G1

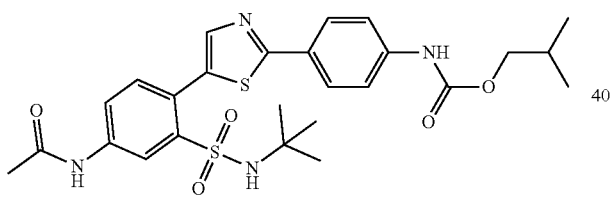

¹H NMR (400 MHz, METHANOL-d4) δ=8.48 (s, 1H), 7.92-7.84 (m, 4H), 7.59 (br d, J=8.8 Hz, 2H), 7.50 (d, J=8.3 Hz, 1H), 3.95 (d, J=6.6 Hz, 2H), 2.18 (s, 3H), 2.05-1.95 (m, 1H), 1.14 (s, 9H), 1.00 (d, J=6.6 Hz, 6H). ESI [M+H]=545.2

Compound G2

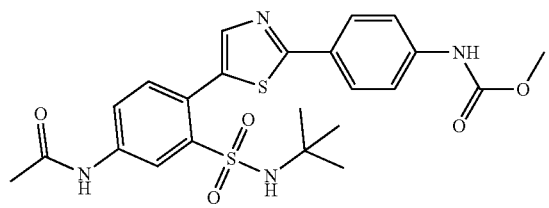

¹H NMR (400 MHz, METHANOL-d4) δ=8.48 (s, 1H), 7.92-7.84 (m, 4H), 7.58 (d, J=8.3 Hz, 2H), 7.50 (d, J=8.3 Hz, 1H), 3.76 (s, 3H), 2.17 (s, 3H), 1.14 (s, 9H). ESI [M+H]=503.3

Compound G3

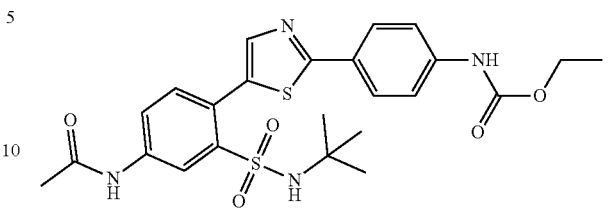

¹H NMR (400 MHz, METHANOL-d4) δ=8.48 (d, J=1.8 Hz, 1H), 7.91-7.85 (m, 4H), 7.58 (d, J=8.8 Hz, 2H), 7.50 (d, J=8.3 Hz, 1H), 4.21 (q, J=7.0 Hz, 2H), 2.18 (s, 3H), 1.32 (t, J=7.0 Hz, 3H), 1.14 (s, 9H). ESI [M+H]=517.2

Compound G4

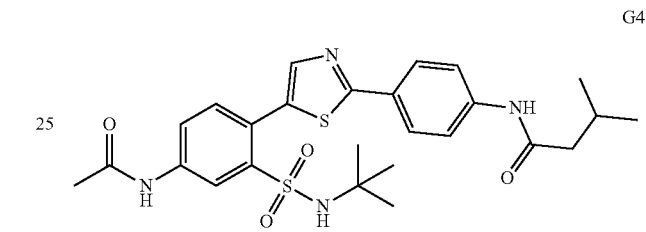

¹H NMR (400 MHz, METHANOL-d4) δ=8.48 (s, 1H), 7.93 (d, J=8.8 Hz, 2H), 7.89-7.85 (m, 2H), 7.72 (d, J=8.8 Hz, 2H), 7.50 (d, J=8.3 Hz, 1H), 2.30-2.25 (m, 2H), 2.18 (s, 3H), 1.14 (s, 10H), 1.03 (d, J=6.6 Hz, 6H). ESI [M+H]=529.2

Compound G5

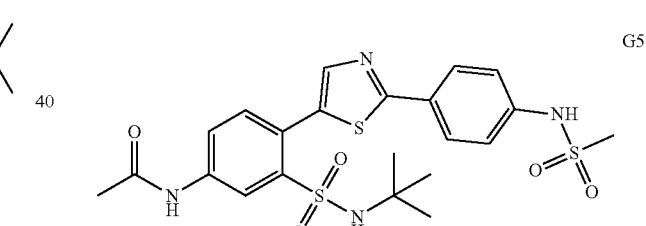

¹H NMR (400 MHz, DMSO-d₆) δ=10.38 (s, 1H), 10.10 (s, 1H), 8.39 (s, 1H), 7.90 (d, J=8.4 Hz, 2H), 7.84-7.78 (m, 2H), 7.46 (d, J=8.4 Hz, 1H), 7.29 (br d, J=8.6 Hz, 2H), 7.15 (s, 1H), 3.05 (s, 3H), 2.07 (s, 3H), 1.05 (s, 9H). [M+H]=523.0

Compound G6

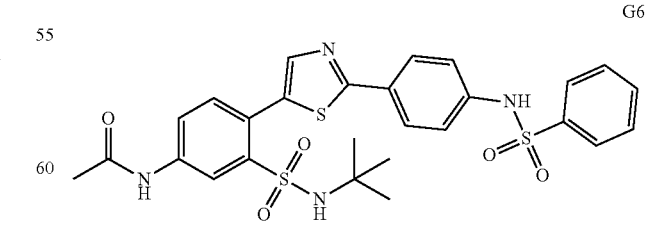

¹H NMR (400 MHz, DMSO-d6) δ=10.66 (s, 1H), 10.41 (s, 1H), 8.41 (s, 1H), 7.86-7.79 (m, 6H), 7.65-7.53 (m, 3H), 7.46 (d, J=8.2 Hz, 1H), 7.23 (br d, J=8.2 Hz, 2H), 7.15 (s, 1H), 2.09 (s, 3H), 1.06 (s, 9H). ESI [M+H]=585.0

Compound G7

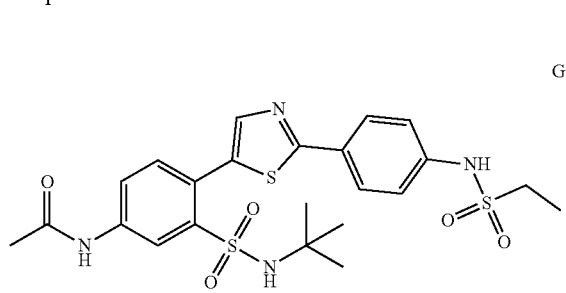

¹H NMR (400 MHz, DMSO-d6) δ=10.42 (s, 1H), 10.17 (s, 1H), 8.42 (s, 1H), 7.92 (d, J=8.6 Hz, 2H), 7.87-7.82 (m, 2H), 7.49 (d, J=8.4 Hz, 1H), 7.33 (d, J=8.8 Hz, 2H), 7.19 (s, 1H), 3.18 (q, J=7.2 Hz, 2H), 2.10 (s, 3H), 1.21 (t, J=7.3 Hz, 3H), 1.07 (s, 9H). ESI [M+H]=537.3

Compound G8

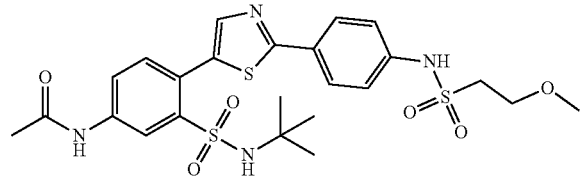

¹H NMR (400 MHz, DMSO-d6) δ=10.41 (s, 1H), 10.15 (s, 1H), 8.42 (s, 1H), 7.95-7.88 (m, 2H), 7.85-7.84 (m, 2H), 7.49 (d, J=8.3 Hz, 1H), 7.35-7.29 (m, J=8.4 Hz, 2H), 7.17 (s, 1H), 3.68 (t, J=5.9 Hz, 2H), 3.46-3.43 (m, 2H), 3.18 (s, 3H), 2.10 (s, 3H), 1.08 (s, 9H). ESI [M+H]=567.1

Compound G9

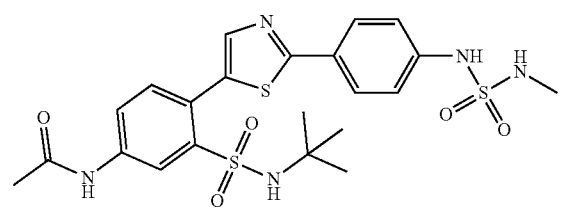

¹H NMR (400 MHz, METHANOL-d4) δ=8.48 (d, J=2.0 Hz, 1H), 7.99-7.85 (m, 4H), 7.50 (d, J=8.2 Hz, 1H), 7.29 (d, J=8.6 Hz, 2H), 2.60 (s, 3H), 2.18 (s, 3H), 1.14 (s, 9H). ESI [M+H]=538.1

Compound G10

Compound G10 was prepared from intermediate 5 via general method I (shown in Example 1).

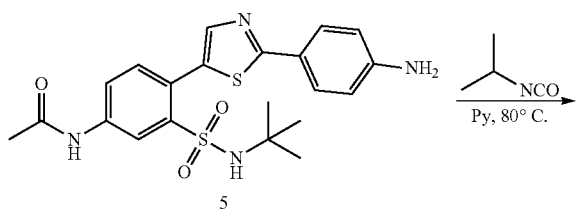

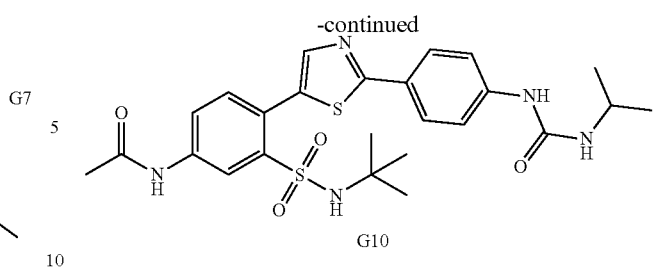

¹HNMR (400 MHz, METHANOL-d4) δ=8.48 (s, 1H), 7.91-7.84 (m, 4H), 7.50 (d, J=8.8 Hz, 3H), 3.94-3.82 (m, 1H), 2.18 (s, 3H), 1.20 (d, J=6.6 Hz, 6H), 1.14 (s, 9H). ESI [M+H]=530.2

Compound G11

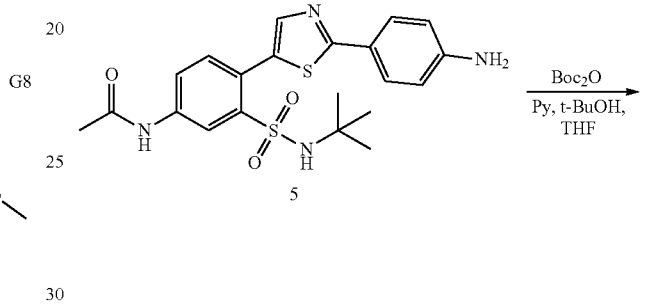

A mixture of N-[4-[2-(4-aminophenyl)thiazol-5-yl]-3-(tert-butylsulfamoyl) phenyl]acetamide (50.00 mg, 112.47 μmol, 1.00 eq.), Pyridine (25.00 mg, 316.04 μmol, 25.51 ul, 2.81 eq.) and Boc₂O (40.00 mg, 183.28 μmol, 42.11 ul, 1.63 eq.) in THF (2.00 mL) and t-BuOH (2.00 mL) was stirred at 20° C. for 14 hrs. LCMS showed the reaction was complete. The mixture was concentrated and the residue was purified by prep-HPLC (YMC-Actus Triart C18 150*30 5u; mobile phase: [water (10 mM NH₄HCO₃)-€]; B %: 55%-75%, 12 min) to give tert-butyl N-[4-[5-[4-acetamido-2-(tert-butylsulfamoyl) phenyl]thiazol-2-yl]phenyl]carbamate (20.01 mg, 35.05 μmol, 31.16% yield, 95.41% purity) as a yellow solid. ¹H NMR (400 MHz, DMSO-d6) δ=10.41 (s, 1H), 9.70-9.63 (m, 1H), 8.42 (d, J=2.2 Hz, 1H), 7.88-7.82 (m, 4H), 7.59 (d, J=8.8 Hz, 2H), 7.48 (d, J=8.4 Hz, 1H), 7.18 (s, 1H), 2.10 (s, 3H), 1.50-1.49 (m, 9H), 1.08 (s, 9H). ESI [M+H]=545.4

Example 8
Scheme 8.1
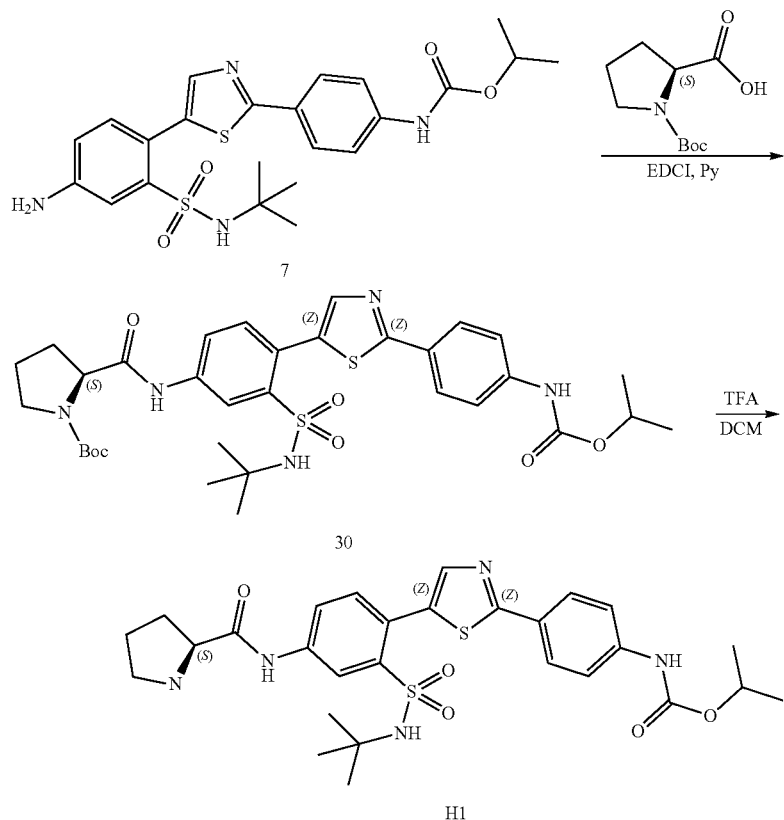
Intermediate Compound 30.
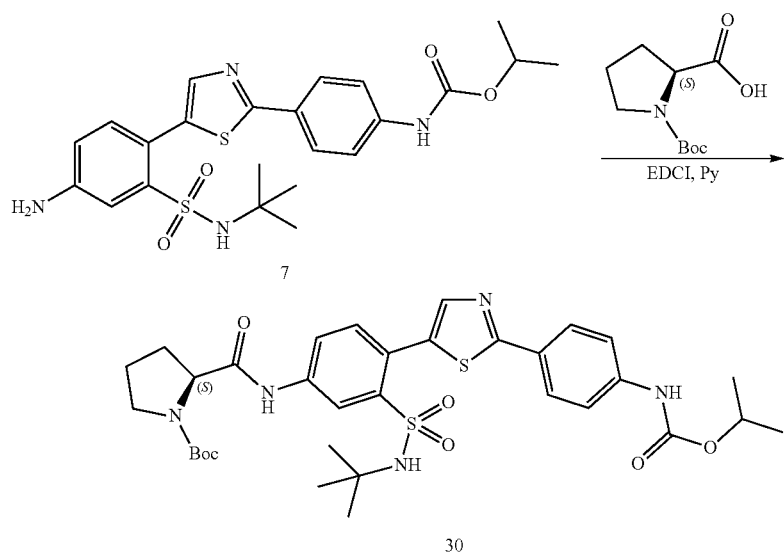
To a solution of isopropyl N-[4-[5-[4-amino-2-(tert-butylsulfamoyl)phenyl] thiazol-2-yl]phenyl]carbamate (20.00 mg, 40.93 μmol, 1.00 eq.) in Pyridine (2.00 mL) were added (2S)-1-tert-butoxycarbonylpyrrolidine-2-carboxylic acid (44.05 mg, 204.66 μmol, 5.00 eq.) and EDCI (9.42 mg, 49.12 μmol, 1.20 eq.) and the mixture was stirred at 20° C.

for 0.5 hour. LCMS showed the reaction was complete. The mixture was poured into IM HCl (10 mL) and extracted with DCM (10 mL×3). The organic phase was dried over Na$_2$SO$_4$, filtered and concentrated to give tert-butyl (2S)-2-[[3-(tert-butylsulfamoyl)-4-[2-[4-(isopropoxycarbonylamino)phenyl]thiazol-5-yl]phenyl]carbamoyl]pyrrolidine-1-carboxylate (30.00 mg, crude) as a yellow oil which was used without any purification. ESI [M+H]=686.2

Compound H1

Compound H1 was prepared from intermediate compound 30 via general method E (shown in Example 1).

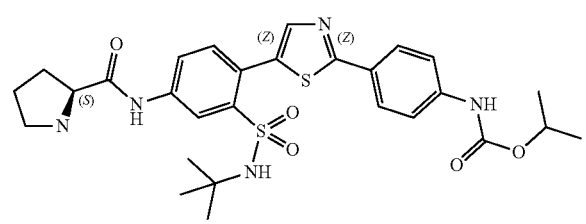

$^1$H NMR (400 MHz, METHANOL-d4) δ=8.55 (d, J=2.3 Hz, 1H), 7.96-7.88 (m, 4H), 7.63-7.56 (m, 3H), 5.00 (td, J=6.2, 12.5 Hz, 1H), 4.47 (dd, J=6.8, 8.6 Hz, 1H), 3.55-3.48 (m, 1H), 3.46-3.40 (m, 1H), 2.63-2.53 (m, 1H), 2.28-2.11 (m, 3H), 1.34 (d, J=6.2 Hz, 6H), 1.14 (s, 9H). ESI [M+H]=586.2

Compound H2

Compound H2 was synthesized via same method same as compound H1

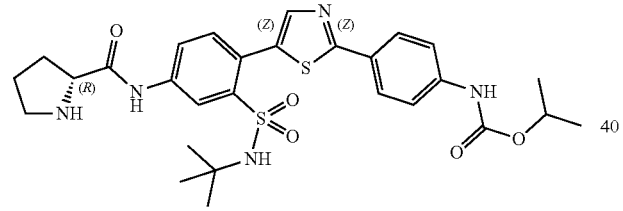

$^1$H NMR (400 MHz, METHANOL-d4) δ=8.54 (d, J=2.2 Hz, 1H), 7.95-7.91 (m, 2H), 7.90 (s, 2H), 7.61 (s, 1H), 7.60-7.56 (m, 2H), 5.07-4.95 (m, 1H), 4.50-4.42 (m, 1H), 3.54-3.48 (m, 1H), 3.46-3.39 (m, 2H), 2.65-2.54 (m, 1H), 2.20-2.13 (m, 2H), 1.34 (d, J=6.2 Hz, 6H), 1.14 (s, 9H). ESI [M+H]=586.2

The following compounds were synthesized via reacting intermediate compound 7 with different acyl chloride via general method C (shown in Example 1), unless otherwise noted.

Compound H3

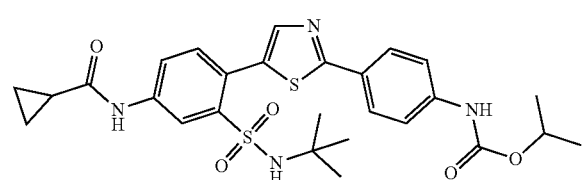

$^1$H NMR (400 MHz, METHANOL-d4) δ=8.49 (d, J=2.2 Hz, 1H), 7.94-7.87 (m, 4H), 7.59 (d, J=8.7 Hz, 2H), 7.51 (d, J=8.3 Hz, 1H), 5.06-4.95 (m, 1H), 1.87-1.77 (m, 1H), 1.34 (d, J=6.2 Hz, 6H), 1.15 (s, 9H), 1.05-0.99 (m, 2H), 0.96-0.89 (m, 2H). ESI [M+H]=557.1

Compound H4

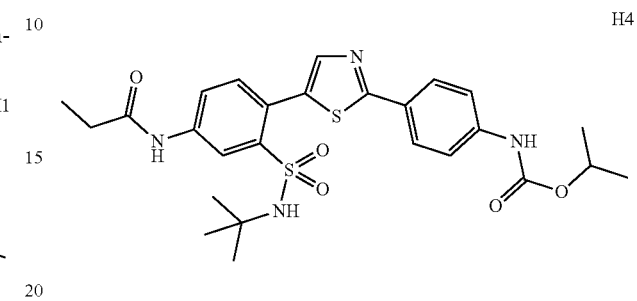

$^1$H NMR (400 MHz, METHANOL-d4) δ=8.48 (d, J=2.1 Hz, 1H), 7.91-7.85 (m, 4H), 7.57 (d, J=8.7 Hz, 2H), 7.49 (d, J=8.3 Hz, 1H), 5.04-4.92 (m, 1H), 2.45 (q, J=7.5 Hz, 2H), 1.32 (d, J=6.2 Hz, 6H), 1.23 (t, J=7.6 Hz, 3H), 1.14 (s, 9H). ESI [M+H]=545.1

Compound H5

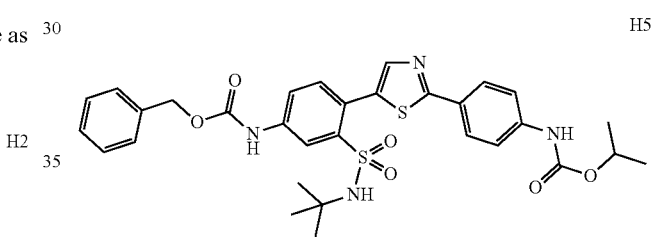

$^1$H NMR (400 MHz, METHANOL-d4) δ=8.36 (s, 1H), 7.88-7.82 (m, 3H), 7.71 (br d, J=7.3 Hz, 1H), 7.55 (br d, J=8.6 Hz, 2H), 7.47-7.39 (m, 3H), 7.39-7.28 (m, 3H), 5.20 (s, 2H), 4.96 (td, J=6.4, 12.5 Hz, 1H), 1.29 (d, J=6.2 Hz, 6H), 1.12 (s, 9H). ESI [M+H]=623.1

Compound H6

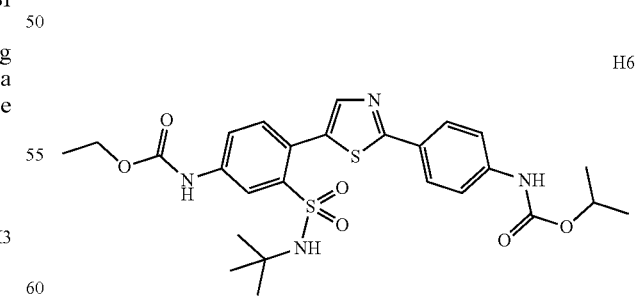

$^1$H NMR (400 MHz, METHANOL-d4) δ=8.35 (s, 1H), 7.89-7.82 (m, 3H), 7.69 (br d, J=8.2 Hz, 1H), 7.55 (br d, J=8.6 Hz, 2H), 7.44 (d, J=8.4 Hz, 1H), 4.96 (td, J=6.3, 12.6 Hz, 1H), 4.21 (q, J=7.1 Hz, 2H), 1.33-1.27 (m, 9H), 1.12 (s, 9H). ESI [M+H]=561.1

Compound H7

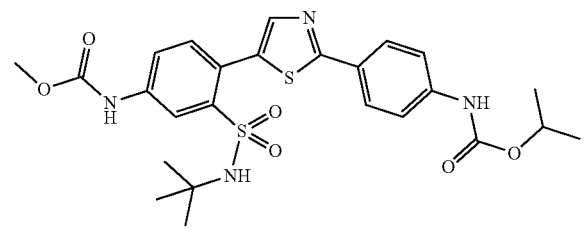

¹H NMR (400 MHz, METHANOL-d4) δ=8.35 (s, 1H), 7.90-7.83 (m, 3H), 7.70 (br d, J=8.4 Hz, 1H), 7.56 (d, J=8.6 Hz, 2H), 7.45 (d, J=8.4 Hz, 1H), 4.96 (quin, J=6.2 Hz, 1H), 3.76 (s, 3H), 1.29 (d, J=6.2 Hz, 6H), 1.12 (s, 9H). ESI [M+H]=547.1

Compound H8

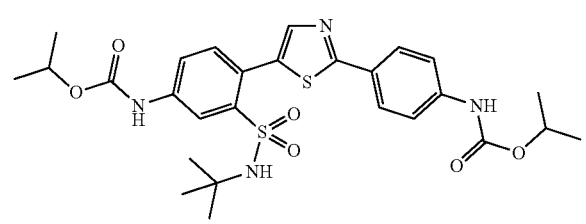

¹H NMR (400 MHz, METHANOL-d4) δ=8.37 (s, 1H), 7.91-7.82 (m, 3H), 7.70 (br d, J=8.2 Hz, 1H), 7.57 (br d, J=8.6 Hz, 2H), 7.45 (d, J=8.4 Hz, 1H), 5.04-4.91 (m, 2H), 1.32 (dd, J=3.6, 6.1 Hz, 12H), 1.14 (s, 9H). ESI [M+H]=575.2

Compound H9

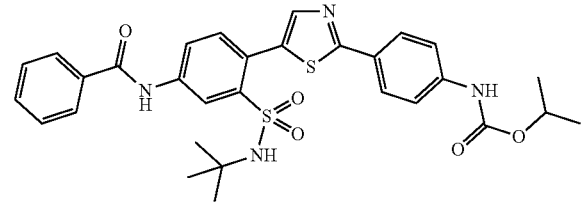

¹H NMR (400 MHz, METHANOL-d4) δ=8.70-8.67 (m, 1H), 8.06-7.95 (m, 3H), 7.94-7.85 (m, 3H), 7.65-7.48 (m, 6H), 5.02-4.93 (m, 1H), 1.32 (d, J=6.2 Hz, 6H), 1.16 (s, 9H). ESI [M+H]=593.2

Compound H10

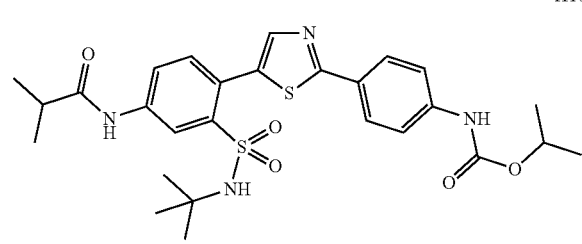

¹H NMR (400 MHz, METHANOL-d4) δ=8.49 (d, J=2.2 Hz, 1H), 7.92-7.86 (m, 4H), 7.57 (d, J=8.7 Hz, 2H), 7.50 (d, J=8.3 Hz, 1H), 4.98 (td, J=6.3, 12.5 Hz, 1H), 2.67 (spt, J=6.8 Hz, 1H), 1.32 (d, J=6.2 Hz, 6H), 1.23 (d, J=7.0 Hz, 6H), 1.14 (s, 9H). ESI [M+H]=559.2

Compound H11

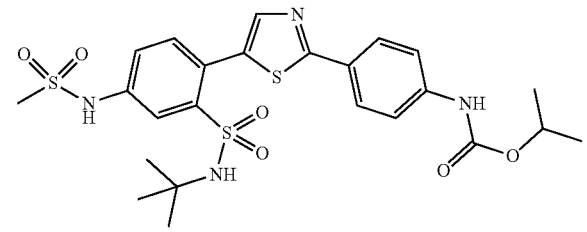

¹H NMR (400 MHz, METHANOL-d4) δ=8.09 (d, J=2.2 Hz, 1H), 7.92-7.84 (m, 3H), 7.63-7.44 (m, 4H), 4.98 (td, J=6.2, 12.5 Hz, 1H), 3.06 (s, 3H), 1.31 (d, J=6.2 Hz, 6H), 1.14 (s, 9H). ESI [M+H]=567.1

Example 9

Compound I1

A mixture of isopropyl N-[4-[5-[4-acetamido-2-(tert-butylsulfamoyl)phenyl] thiazol-2-yl]phenyl]carbamate (20.00 mg, 37.69 μmol, 1.00 eq.) in THF (200.00 ul) was added BH₃·Me₂S (10 M, 18.85 ul, 5.00 eq.) at 0° C. and then the mixture was stirred at 70° C. for 2 hrs under N₂ atmosphere. LCMS showed the reaction was complete. The mixture was quenched by addition of MeOH (5 mL) at 0° C. and then it was concentrated and the residue was purified by prep-HPLC (TFA condition) to give isopropyl N-[4-[5-[2-(tert-butylsulfamoyl)-4-(ethylamino)phenyl] thiazol-2-yl]phenyl]carbamate (3.92 mg, 7.59 μmol, 20.13% yield, 100% purity) as a pale yellow solid. ¹H NMR (400 MHz, METHANOL-d4) δ=7.84 (d, J=8.6 Hz, 2H), 7.76 (s, 1H), 7.54 (br d, J=8.6 Hz, 2H), 7.36 (d, J=2.2 Hz, 1H), 7.24 (d, J=8.4 Hz, 1H), 6.78 (dd, J=2.1, 8.5 Hz, 1H), 4.96 (td, J=6.2, 12.3 Hz, 1H), 3.18 (q, J=7.1 Hz, 2H), 1.29 (d, J=6.4 Hz, 6H), 1.25 (t, J=7.2 Hz, 3H), 1.10 (s, 9H). ESI [M+H]=517.1

Compound I2

Compound I3

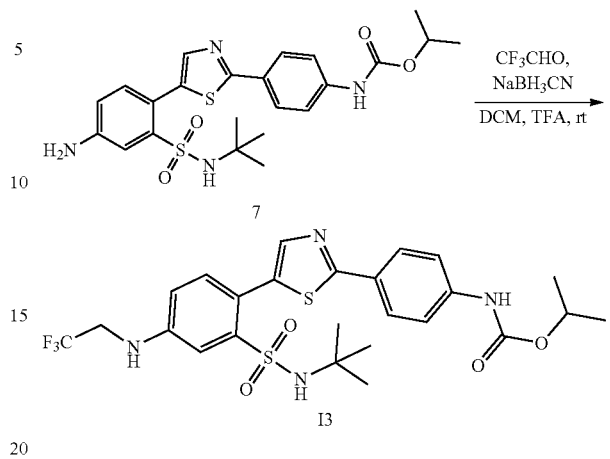

Isopropyl N-[4-[5-[4-amino-2-(tert-butylsulfamoyl)phenyl]thiazol-2-yl]phenyl] carbamate (20.00 mg, 40.93 µmol, 1.00 eq.) was dissolved into a solution of H₂SO₄ (40.14 mg, 409.30 mol, 21.82 ul, 10.00 eq.) in H₂O (1.00 mL). The mixture was cooled to −5° C., then added NaNO₂ (3.39 mg, 49.12 µmol, 2.67 ul, 1.20 eq.) in H₂O (500.00 ul) and the mixture was stirred at 0° C. for 30 min. Then H₂O (500.00 ul) was added and the mixture was stirred at 26° C. for 1.5 hrs. LCMS showed the reaction was complete. The mixture was concentrated and the residue was purified by acidic prep-HPLC to give isopropyl N-[4-[5-[2-(tert-butylsulfamoyl)-4-hydroxy-phenyl] thiazol-2-yl]phenyl]carbamate (3.04 mg, 6.02 µmol, 14.71% yield, 97% purity) as a brown solid. ¹H NMR (400 MHz, METHANOL-d4) δ=7.85 (d, J=8.6 Hz, 2H), 7.78 (s, 1H), 7.61-7.51 (m, 3H), 7.35 (d, J=8.2 Hz, 1H), 7.05-6.96 (m, 1H), 4.97-4.93 (m, 1H), 1.29 (d, J=6.2 Hz, 6H), 1.10 (s, 9H). ESI [M+H]=490.1

To solution of isopropyl N-[4-[5-[4-amino-2-(tert-butylsulfamoyl)phenyl] thiazol-2-yl]phenyl]carbamate (20.00 mg, 40.93 µmol, 1.00 eq.) and NaBH₃CN (5.14 mg, 81.86 µmol, 2.00 eq.) in DCM (2.00 mL) at 0° C. was added neat TFA (2.00 mL) and the mixture was stirred at 0° C. for 5 mins. 2,2,2-trifluoroacetaldehyde (10.03 mg, 102.33 µmol, 2.50 eq.) was then added at 0° C. and the mixture was stirred at 20° C. for 30 mins. LCMS showed the reaction was complete. The mixture was washed with sat.aq.NaHCO₃ (10 mL) and the aqueous phase was extracted with DCM (20 mL×3). The combined organic phase was dried, filtered and concentrated. The residue was purified by prep-HPLC (TFA condition) to give isopropyl N-[4-[5-[2-(tert-butylsulfamoyl)-4-(2,2,2-trifluoroethylamino)phenyl]thiazol-2-yl] phenyl]carbamate (4.68 mg, 8.20 µmol, 20.03% yield, 100% purity) as a pale yellow solid. ¹H NMR (400 MHz, METHANOL-d4) δ=7.77 (d, J=8.7 Hz, 2H), 7.69 (s, 1H), 7.47 (br d, J=8.7 Hz, 2H), 7.43 (d, J=2.4 Hz, 1H), 7.22 (d, J=8.4 Hz, 1H), 6.86 (dd, J=2.5, 8.4 Hz, 1H), 4.88 (td, J=6.2, 12.5 Hz, 1H), 3.83 (q, J=9.2 Hz, 2H), 1.22 (d, J=6.2 Hz, 6H), 1.02 (s, 9H). ESI [M+H]=571.1

Scheme 9.1

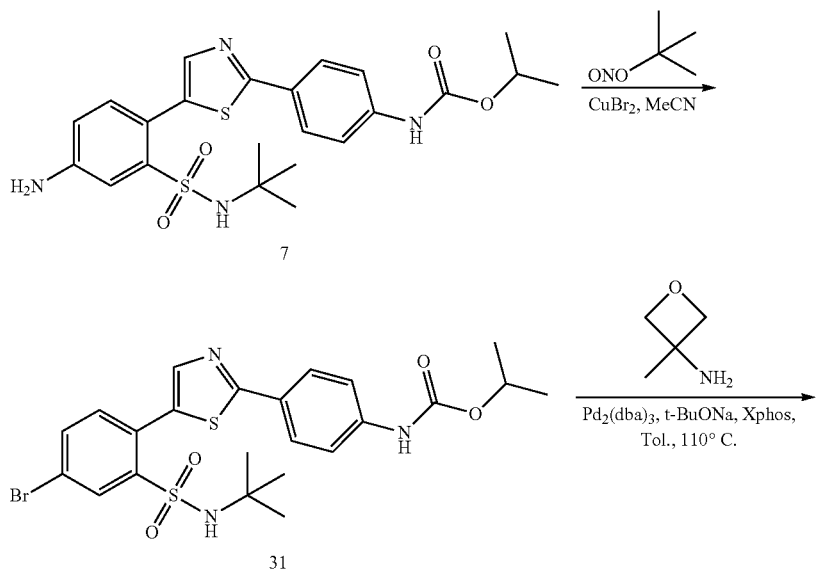

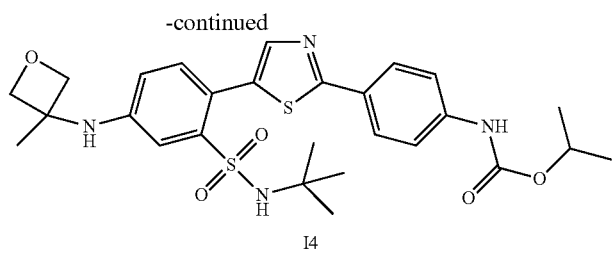

I4

Intermediate Compound 31

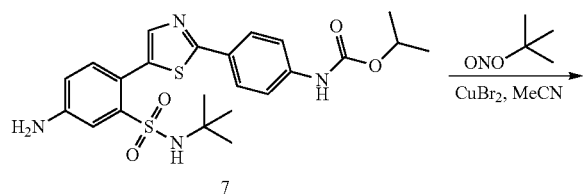

added tert-butyl nitrite (354.55 mg, 3.44 mmol, 407.53 ul, 2.00 eq.) and CuBr$_2$ (191.98 mg, 860.00 μmol, 40.25 ul, 0.50 eq.), then then the mixture was heated at 60° C. under N$_2$ for 1 hr. LCMS showed the reaction was complete. The mixture was diluted with water (50 mL) and extracted with EtOAc (50 mL×3). The combined organic phase was dried, filtered and concentrated. The residue was purified by silica gel column chromatography (Petroleum ether/Ethyl acetate=8:1) to give intermediate compound 31 (350.00 mg, 633.48 μmol, 36.83% yield) as a yellow solid. ESI [M+H]=554.0/552.0

Compound I4

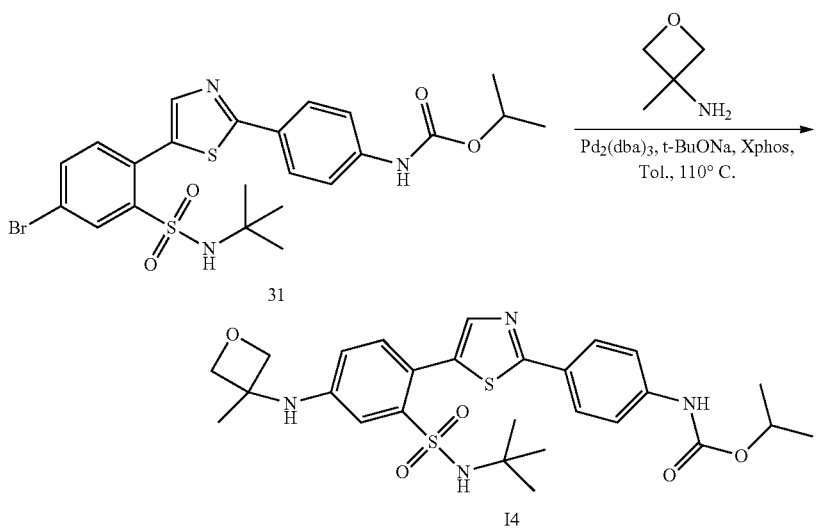

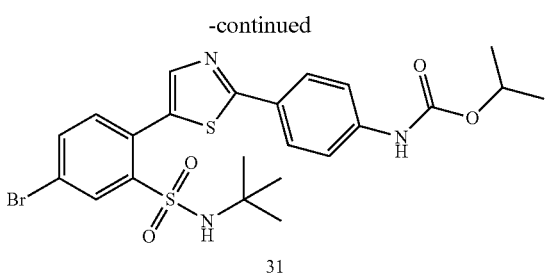

To a solution of isopropyl N-[4-[5-[4-amino-2-(tert-butylsulfamoyl)phenyl] thiazol-2-yl]phenyl]carbamate (840.00 mg, 1.72 mmol, 1.00 eq.) in € (30.00 mL) were A mixture of isopropyl N-[4-[5-[4-bromo-2-(tert-butylsulfamoyl)phenyl] thiazol-2-yl]phenyl]carbamate (30.00 mg, 54.30 μmol, 1.00 eq.), 3-methyloxetan-3-amine (23.65 mg, 271.49 μmol, 5.00 eq.), Pd$_2$(dba)$_3$ (4.97 mg, 5.43 μmol, 0.10 eq.), Xphos (3.88 mg, 8.14 mol, 0.15 eq.) and t-BuONa (5.74 mg, 59.73 μmol, 1.10 eq.) in toluene (2.00 mL) was stirred at 110° C. for 16 hrs under N$_2$. LCMS showed the reaction was complete. The mixture was washed with water (30 mL) and the aqueous phase was extracted with EtOAc (30 mL×3). The combined organic phase was dried, filtered and concentrated. The residue was purified by prep-TLC (PE:EtOAc=1:1) and prep-HPLC (TFA condition) to give compound I4 (2.78 mg, 4.94 μmol, 9.10% yield, 99.36% purity) as a brown solid. $^1$H NMR (400 MHz, METHANOL-d4) δ=7.88 (d, J=8.7 Hz, 2H), 7.80 (s, 1H), 7.58 (d, J=8.6 Hz, 2H), 7.30 (d, J=8.3 Hz, 1H), 7.23 (d, J=2.4 Hz, 1H), 6.67 (dd, J=2.4, 8.3 Hz, 1H), 5.00 (td, J=6.2, 12.5 Hz, 1H), 4.82 (d, J=6.0 Hz, 2H), 4.63 (d, J=6.0 Hz, 2H), 1.71 (s, 3H), 1.33 (d, J=6.2 Hz, 6H), 1.14 (s, 9H). ESI [M+H]=559.2

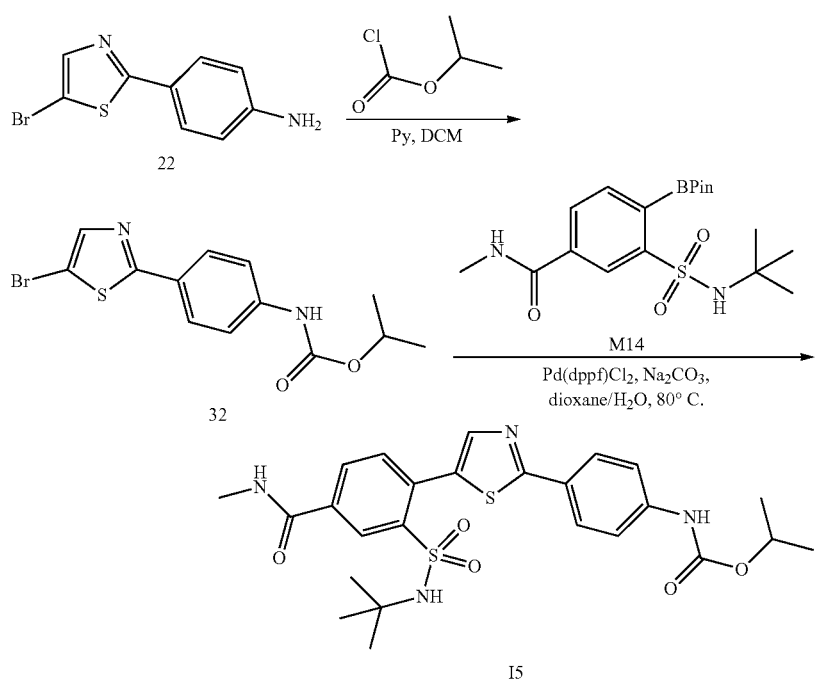
Intermediate Compound 32
Intermediate compound 32 was prepared from intermediate compound 22 via general method C (shown in Example 1).
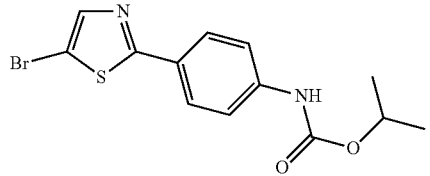
ESI [M+H]=343.1/341.1
Compound I5
Compound I5 was prepared from intermediate compound 32 via general method A (shown in Example 1).
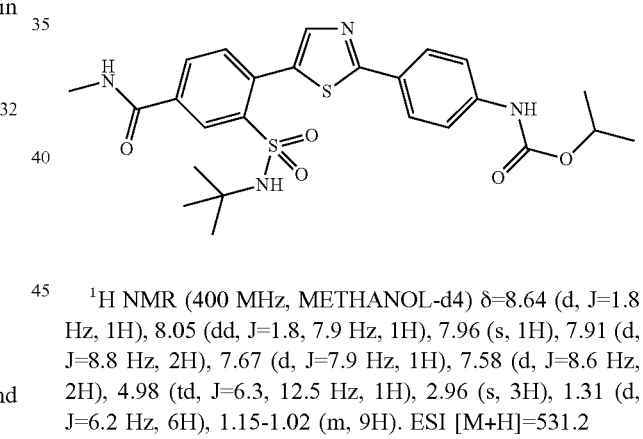
$^1$H NMR (400 MHz, METHANOL-d4) δ=8.64 (d, J=1.8 Hz, 1H), 8.05 (dd, J=1.8, 7.9 Hz, 1H), 7.96 (s, 1H), 7.91 (d, J=8.8 Hz, 2H), 7.67 (d, J=7.9 Hz, 1H), 7.58 (d, J=8.6 Hz, 2H), 4.98 (td, J=6.3, 12.5 Hz, 1H), 2.96 (s, 3H), 1.31 (d, J=6.2 Hz, 6H), 1.15-1.02 (m, 9H). ESI [M+H]=531.2
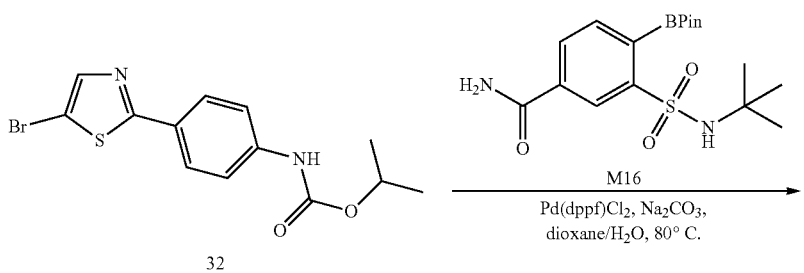

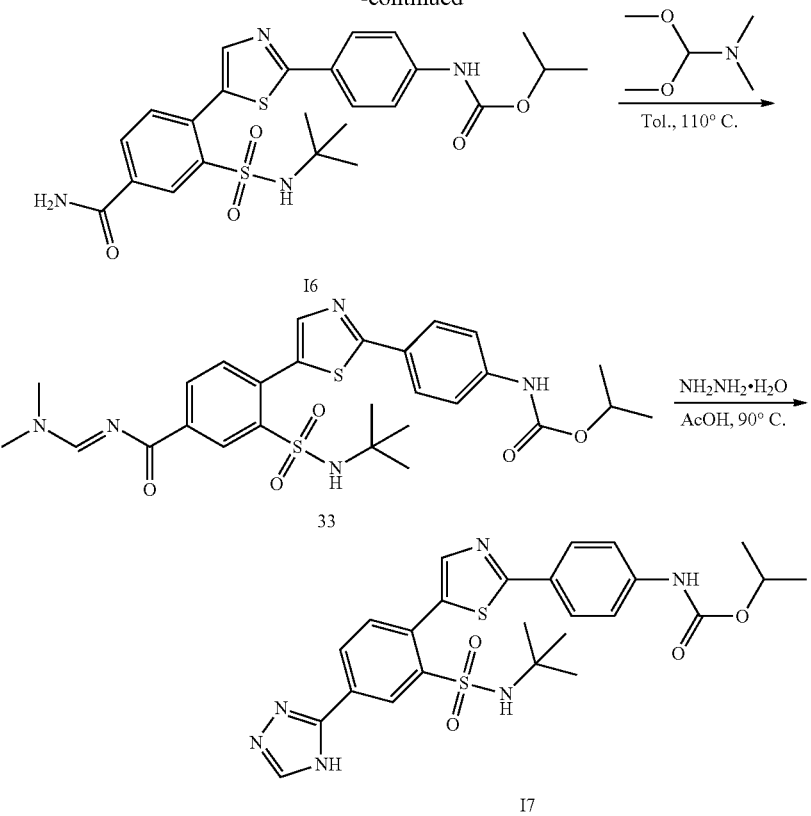

Compound I6

Compound I6 was prepared from intermediate compound 32 via general method A (shown in Example 1).

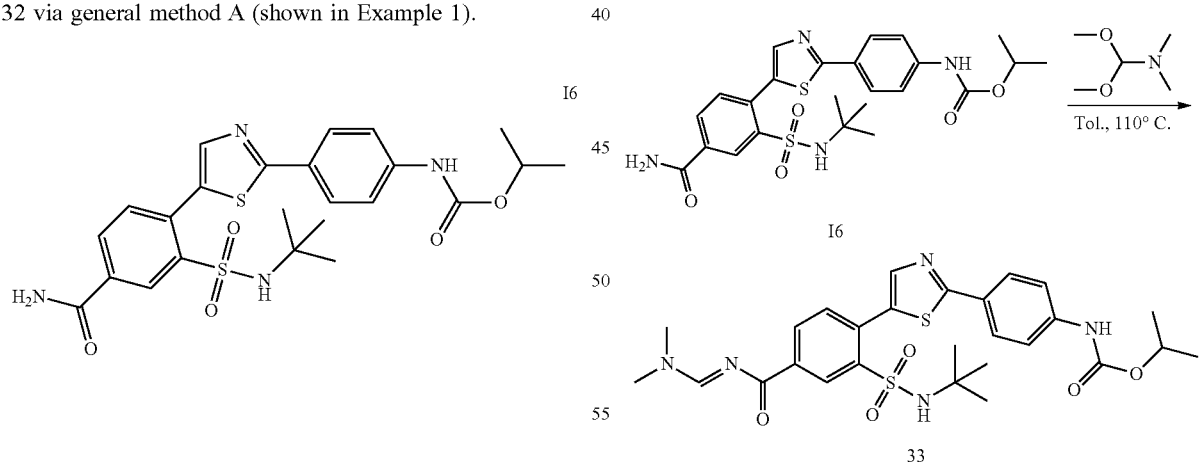

¹H NMR (400 MHz, DMSO-d6) δ=9.88 (s, 1H), 8.60 (d, J=2.0 Hz, 1H), 8.27 (br s, 1H), 8.13 (dd, J=2.0, 7.8 Hz, 1H), 7.99-7.86 (m, 3H), 7.65 (dd, J=8.3, 18.1 Hz, 4H), 7.28 (s, 1H), 4.93 (quin, J=6.4 Hz, 1H), 1.28 (d, J=5.9 Hz, 6H), 1.05 (s, 9H). ESI [M+H]=517.1

Intermediate Compound 33

To a solution of compound I6 (70.00 mg, 135.49 μmol, 1.00 eq.) in Tol. (2.00 mL) was added 1,1-dimethoxy-N,N-dimethyl-methanamine (48.44 mg, 406.48 μmol, 53.82 ul, 3.00 eq.). The mixture was stirred at 110° C. for 1 hr and LCMS showed the reaction was complete. The mixture was concentrated to give intermediate compound 33 (70.00 mg, crude) as a yellow solid. ESI [M+H]=572.2

Compound I7

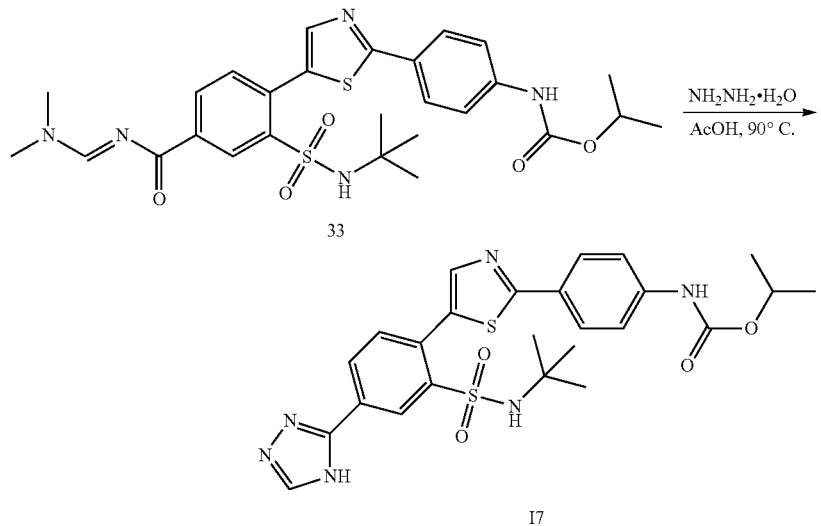

To a solution of intermediate compound 33 (70.00 mg, 122.44 μmol, 1.00 eq.) in AcOH (2.00 mL) was added NH₂NH₂·H₂O (9.38 mg, 183.66 μmol, 9.11 ul, 98% purity, 1.50 eq.). The mixture was stirred at 90° C. for 1 hr and LCMS showed the reaction was complete. The mixture was concentrated and the residue was purified by acidic prep-HPLC to give compound I7 (1.90 mg, 3.51 μmol, 2.87% yield, 100% purity) as a pale yellow solid. 1H NMR (400 MHz, METHANOL-d4) δ=8.89 (d, J=1.8 Hz, 1H), 8.54 (s, 1H), 8.29 (dd, J=1.8, 7.9 Hz, 1H), 7.97 (s, 1H), 7.91 (d, J=8.6 Hz, 2H), 7.69 (d, J=7.9 Hz, 1H), 7.58 (d, J=8.6 Hz, 2H), 4.98 (td, J=6.3, 12.6 Hz, 1H), 1.31 (d, J=6.2 Hz, 6H), 1.13 (s, 9H). ESI [M+H]=541.1

Example 10

Compound J1

Compound J1 was prepared from intermediate compound 32 via general method A

¹H NMR (400 MHz, METHANOL-d4) δ=8.19 (s, 1H), 7.91-7.86 (m, 3H), 7.64-7.51 (m, 4H), 4.97 (quin, J=6.2 Hz, 1H), 4.73 (s, 2H), 1.31 (d, J=6.2 Hz, 6H), 1.10 (s, 9H). ESI [M+H]=504.1

Scheme 10.1

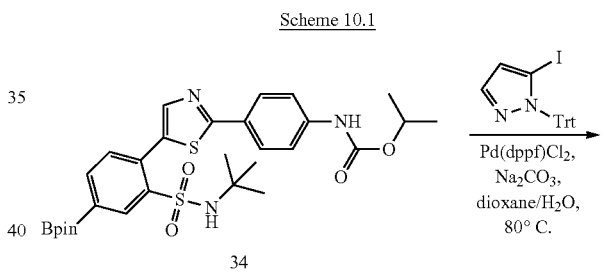

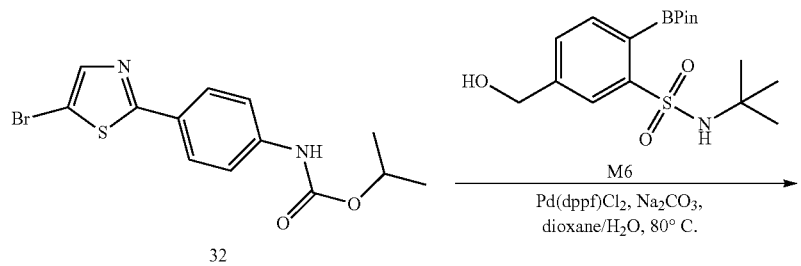

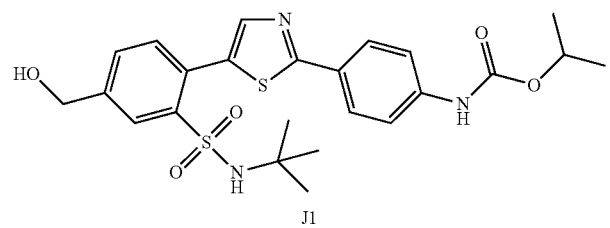

101

-continued

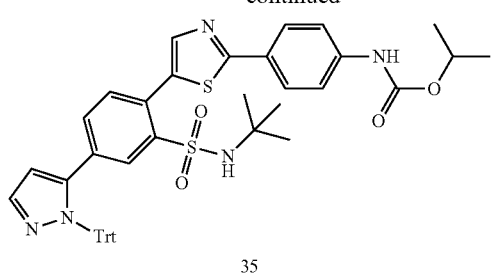
35

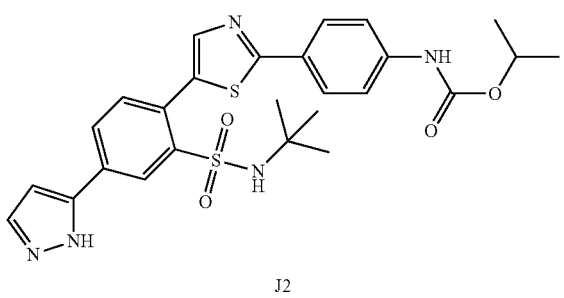
J2

Intermediate Compound 35

Intermediate compound 35 was prepared from intermediate compound 34 via general method A (shown in Example 1).

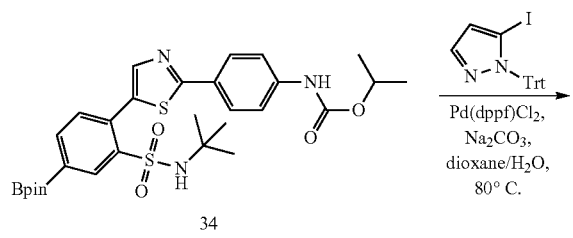
34

102

-continued

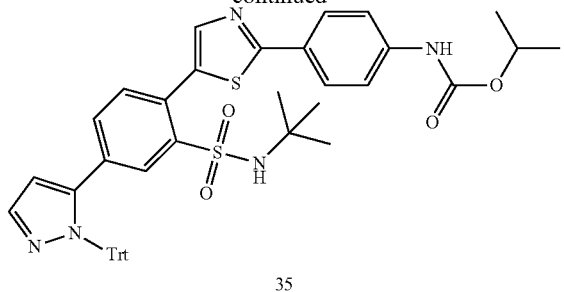
35

ESI [M+H]=782.4
Compound J2

Compound J2 was prepared from intermediate compound 34 via general method E (shown in Example 1).

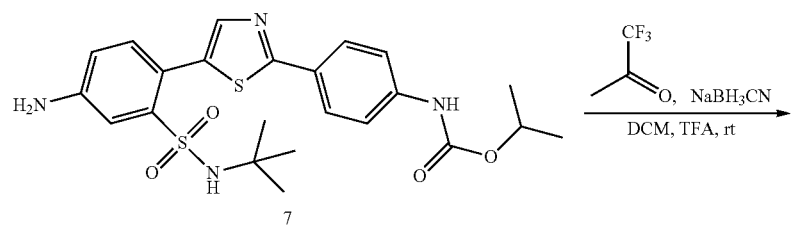
J2

$^1$H NMR (400 MHz, METHANOL-d4) δ=8.63 (s, 1H), 8.07 (dd, J=1.6, 7.9 Hz, 1H), 7.96 (s, 1H), 7.92 (br d, J=8.7 Hz, 2H), 7.77 (d, J=2.1 Hz, 1H), 7.65-7.58 (m, 3H), 6.82 (d, J=2.1 Hz, 1H), 5.00 (td, J=6.3, 12.5 Hz, 1H), 1.33 (d, J=6.2 Hz, 6H), 1.15 (s, 9H). ESI [M+H]=540.3
Compound J3

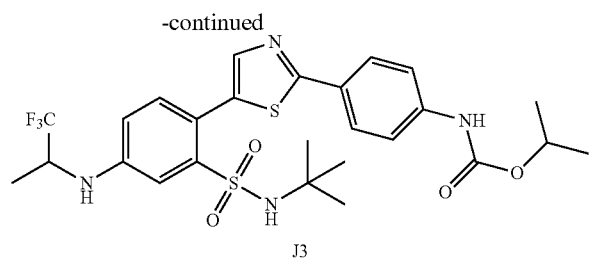

J3

To a solution of isopropyl N-[4-[5-[4-amino-2-(tert-butylsulfamoyl) phenyl]thiazol-2-yl]phenyl]carbamate (25.00 mg, 51.16 μmol, 1.00 eq.) and NaBH₃CN (6.43 mg, 102.32 μmol, 2.00 eq.) in DCM (2.00 mL) at 0° C. was added neat TFA (2.00 mL) and the mixture was stirred at 0° C. for 0.1 hr. Trifluoroacetone (14.33 mg, 127.90 μmol, 11.46 ul, 2.50 eq.) was added at 0° C. and the mixture was stirred at 20° C. for 1 hr. LCMS showed the reaction was complete. The mixture was washed with sat.aq. NaHCO₃ (10 mL) and the aqueous phase was extracted with DCM (20 mL×3). The combined organic phase was dried, filtered and concentrated. The residue was purified by prep-HPLC (TFA condition) to give isopropyl N-[4-[5-[2-(tert-butylsulfamoyl)-4-[(2,2,2-trifluoro-1-methyl-ethyl)amino]phenyl]thiazol-2-yl] phenyl]carbamate (3.97 mg, 6.75 μmol, 13.19% yield, 99.40% purity) as a yellow solid. ¹H NMR (400 MHz, METHANOL-d4) δ=7.88 (d, J=8.7 Hz, 2H), 7.81 (s, 1H), 7.58 (d, J=8.7 Hz, 2H), 7.54 (d, J=2.4 Hz, 1H), 7.32 (d, J=8.3 Hz, 1H), 6.97 (dd, J=2.6, 8.4 Hz, 1H), 5.00 (tt, J=6.3, 12.5 Hz, 1H), 4.31 (td, J=6.7, 13.4 Hz, 1H), 1.44 (d, J=6.8 Hz, 3H), 1.33 (d, J=6.2 Hz, 6H), 1.14 (s, 9H). ESI [M+H]=585.4

Scheme 10.3

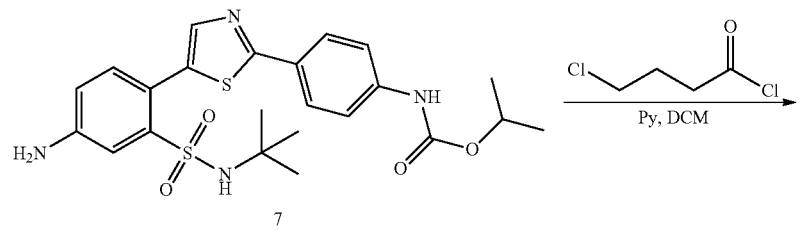

7

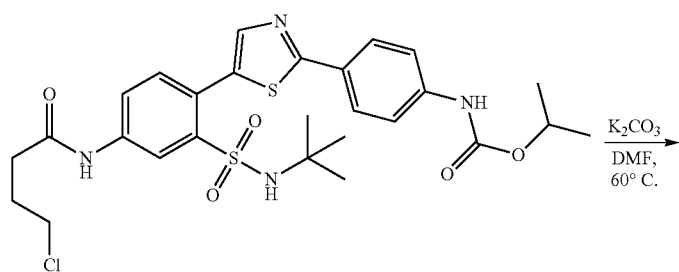

36

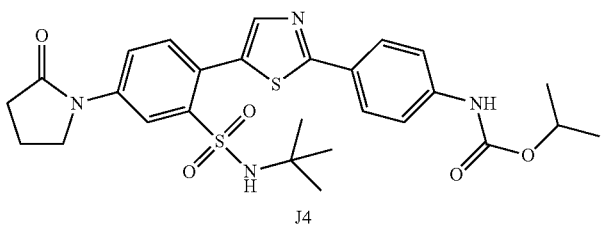

J4

Intermediate compound 36 was prepared from intermediate compound 7 via general method C (shown in Example 1).

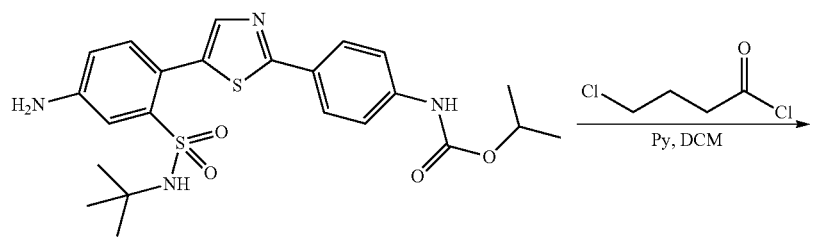

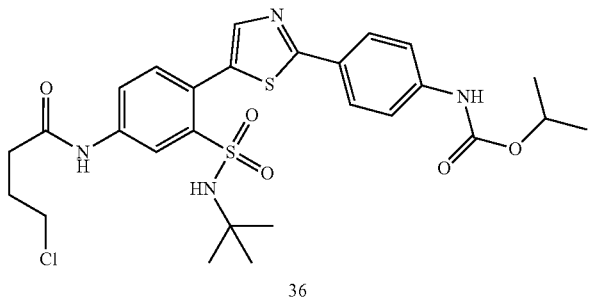

ESI [M+H]=593.2/595.2
Compound J4

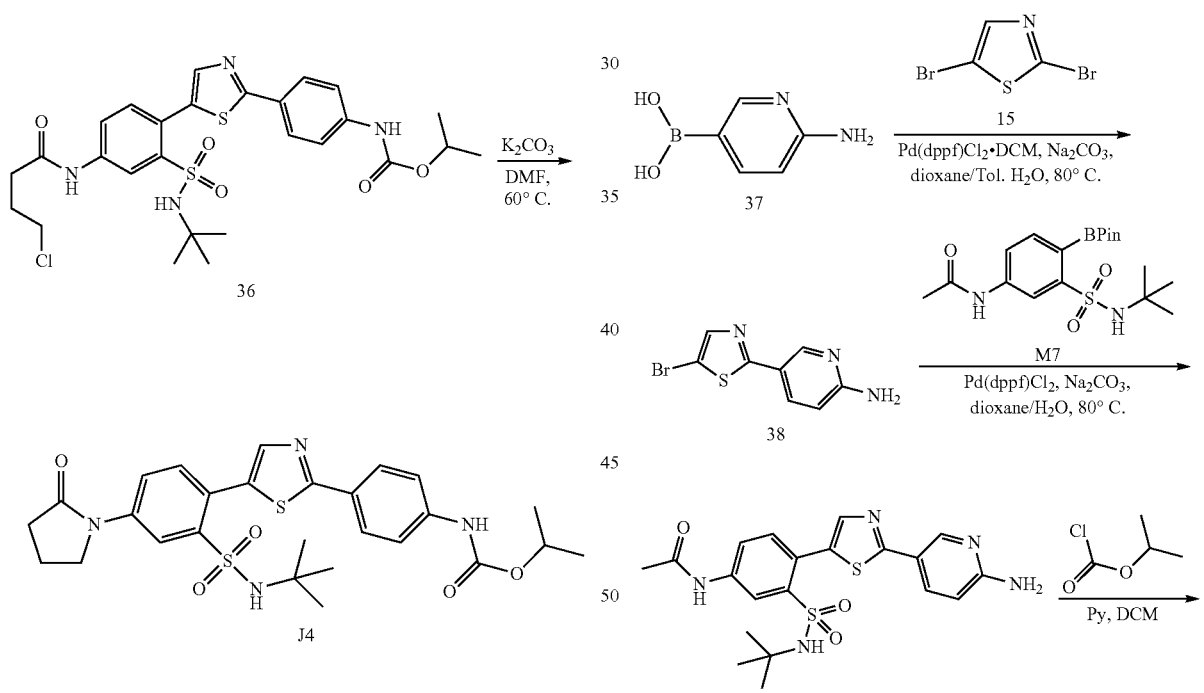

To a solution of intermediate compound 36 (15.00 mg, 25.29 μmol, 1.00 eq.) in DMF (150.00 ul) K$_2$CO$_3$ (10.49 mg, 75.87 μmol, 3.00 eq.) was added. The mixture was stirred at 60° C. for 2 hrs and LCMS showed the reaction was complete. The mixture was concentrated and the residue was purified by prep-HPLC (TFA condition) to give compound J3 (1.07 mg, 1.88 mol, 7.45% yield, 98% purity) as a white solid. $^1$H NMR (400 MHz, METHANOL-d4) δ=8.65 (d, J=2.4 Hz, 1H), 7.93-7.77 (m, 4H), 7.56 (dd, J=4.0, 8.6 Hz, 3H), 5.02-4.92 (m, 1H), 3.99 (t, J=7.1 Hz, 2H), 2.65 (t, J=8.0 Hz, 2H), 2.29-2.15 (m, 2H), 1.31 (d, J=6.2 Hz, 6H), 1.14 (s, 9H). ESI [M+H]=557.4

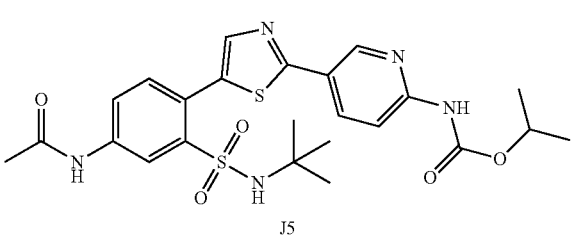

Intermediate Compound 38.

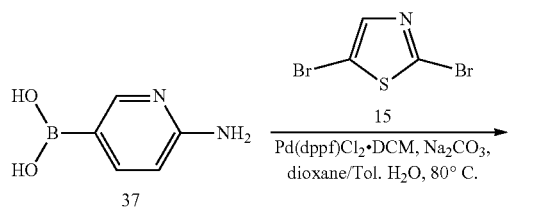

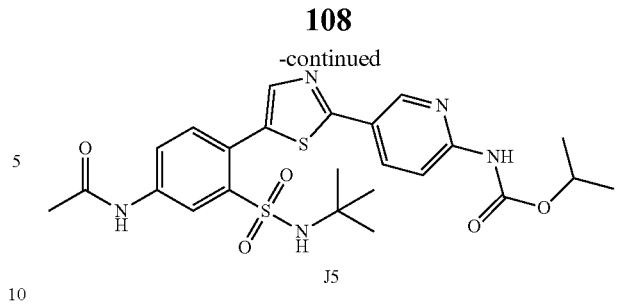

<sup>1</sup>H NMR (400 MHz, DMSO-d6) δ=10.38 (br d, J=19.0 Hz, 2H), 8.82 (s, 1H), 8.41 (s, 1H), 8.27 (br d, J=8.8 Hz, 1H), 7.97 (br d, J=9.0 Hz, 1H), 7.89-7.80 (m, 2H), 7.48 (br d, J=8.4 Hz, 1H), 7.17 (s, 1H), 5.01-4.85 (m, 1H), 2.08 (s, 3H), 1.25 (br d, J=6.0 Hz, 6H), 1.07 (s, 9H). ESI [M+H]=532.1

Compound J6

Compound J6 was prepared from intermediate compound 32 via general method A (shown in Example 1).

To a solution of (6-amino-3-pyridyl)boronic acid (200.00 mg, 1.45 mmol, 1.00 eq.) in dioxane (5.00 mL), Tol. (5.00 mL) and H₂O (2.00 mL) were added Pd(dppf)Cl₂.CH₂Cl2 (118.41 mg, 145.00 μmol, 0.10 eq.), Na₂CO₃ (461.06 mg, 4.35 mmol, 3.00 eq.) and 2,5-dibromothiazole (528.35 mg, 2.18 mmol, 1.50 eq.). The mixture was stirred at 80° C. for 16 hrs under N₂ and LCMS showed the reaction was complete. The mixture was concentrated and the residue was purified by prep-TLC (PE:EtOAc=1:2) to give 5-(5-bromothiazol-2-yl)pyridin-2-amine (100.00 mg, crude) as a yellow solid. ESI [M+H]=257.7/255.7

Intermediate compound 39 was prepared from intermediate compound 38 via general method A (shown in Example 1.

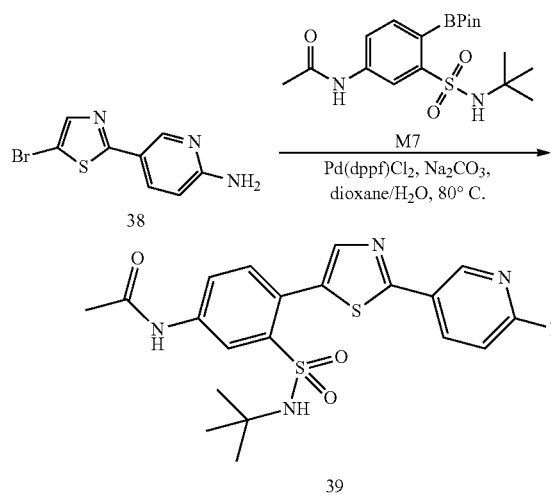

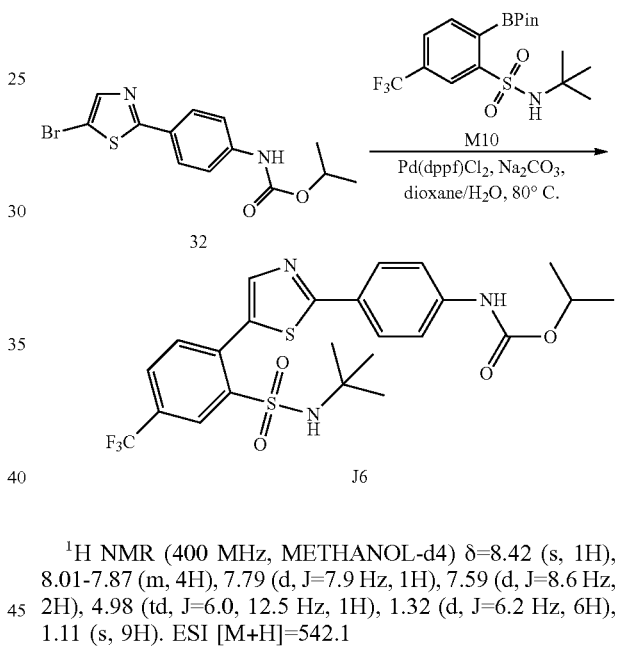

<sup>1</sup>H NMR (400 MHz, METHANOL-d4) δ=8.42 (s, 1H), 8.01-7.87 (m, 4H), 7.79 (d, J=7.9 Hz, 1H), 7.59 (d, J=8.6 Hz, 2H), 4.98 (td, J=6.0, 12.5 Hz, 1H), 1.32 (d, J=6.2 Hz, 6H), 1.11 (s, 9H). ESI [M+H]=542.1

Scheme 10.5

ESI [M+H]=446.1
Compound J5

Compound J5 was prepared from intermediate compound 39 via general method C (shown in Example 1).

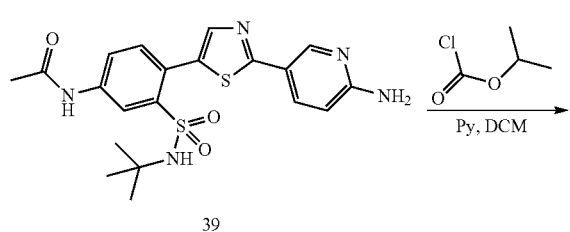

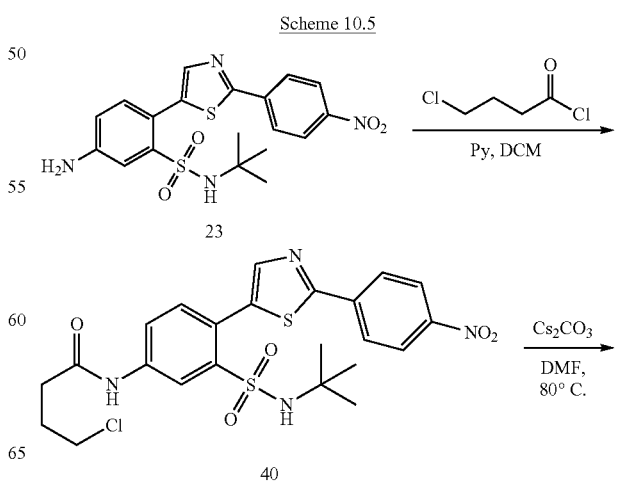

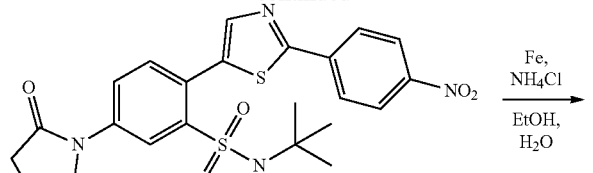

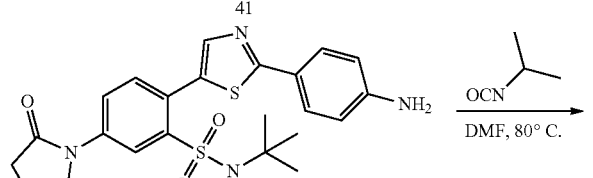

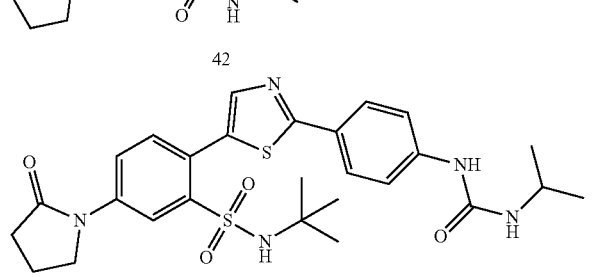

J7

Preparation of compound 40.

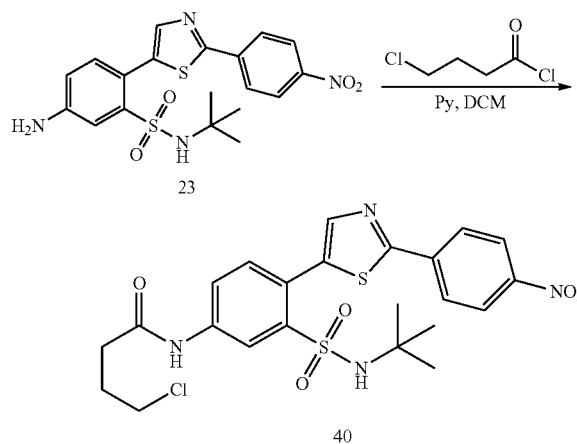

General method C, N-[3-(tert-butylsulfamoyl)-4-[2-(4-nitrophenyl)thiazol-5-yl]phenyl]-4-chloro-butanamide. ESI [M+H]=537.0

Preparation of compound 41.

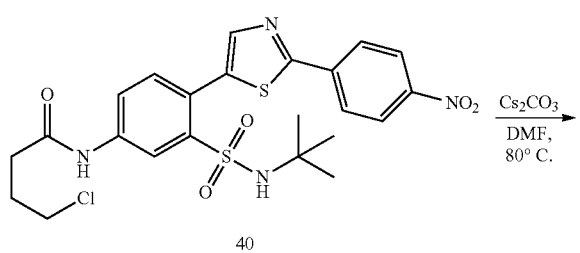

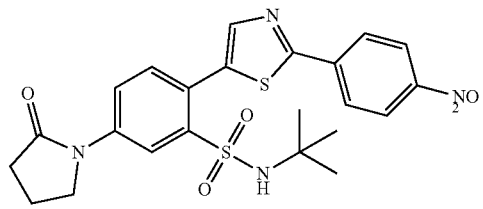

A mixture of N-[3-(tert-butylsulfamoyl)-4-[2-(4-nitrophenyl)thiazol-5-yl]phenyl]-4-chloro-butanamide (100.00 mg, 186.20 μmol, 1.00 eq.) and $Cs_2CO_3$ (75.00 mg, 542.65 μmol, 2.91 eq.) in DMF (2.00 mL) was stirred at 80° C. for 8 hrs and LCMS showed the reaction was complete. The mixture was diluted with $H_2O$ (10 mL) and extracted with EtOAc (10 mL). The organic phase was dried over $Na_2SO_4$, filtered and concentrated to give N-tert-butyl-2-[2-(4-nitrophenyl)thiazol-5-yl]-5-(2-oxopyrrolidin-1-yl) benzenesulfonamide (100.00 mg, crude) as a black brown solid, which was used directly. ESI [M+H]=501.1

Preparation of compound 42.

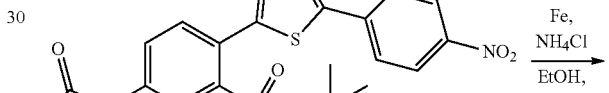

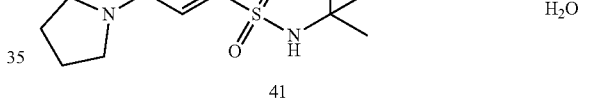

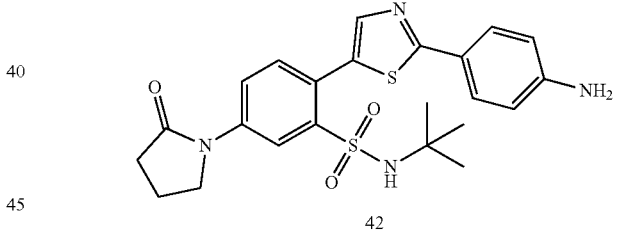

General method B, 2-[2-(4-aminophenyl)thiazol-5-yl]-N-tert-butyl-5-(2-oxopyrrolidin-1-yl)benzenesulfonamide. ESI [M+H]=471.1

Compound J7

Compound J7 was prepared from intermediate compound 42 via general method I (shown in Example 1).

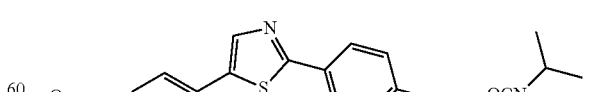

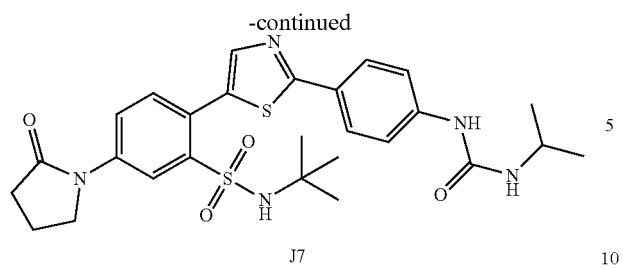

J7

¹H NMR (400 MHz, DMSO-d6) δ=8.67-8.58 (m, 2H), 7.86-7.73 (m, 4H), 7.59-7.49 (m, 3H), 7.26 (s, 1H), 6.14 (d, J=7.5 Hz, 1H), 3.90 (t, J=6.9 Hz, 2H), 3.77 (qd, J=6.6, 13.5 Hz, 1H), 2.59-2.54 (m, 2H), 2.11 (quin, J=7.3 Hz, 2H), 1.17-1.05 (m, 15H). ESI [M+H]=556.1

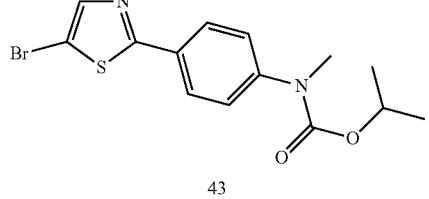

43

Scheme 10.6

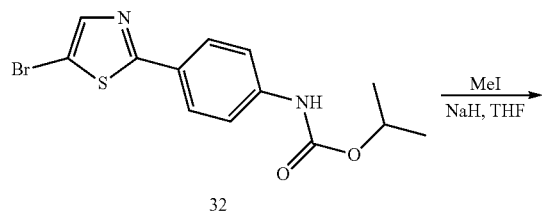

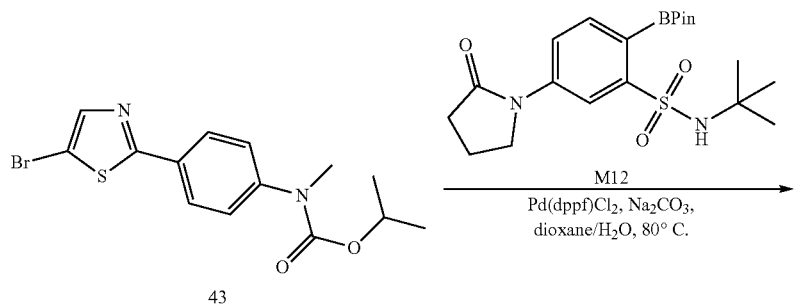

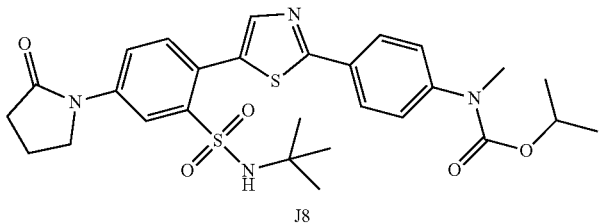

J8

Preparation of compound 43.

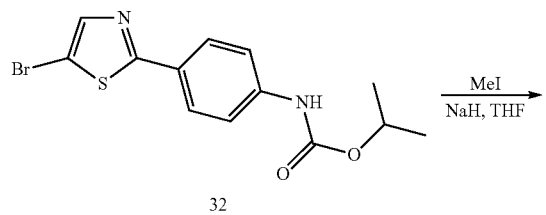

To a solution of NaH (11.72 mg, 293.06 μmol, 60% purity, 2.00 eq.) in THF (1.00 mL) wad added isopropyl N-[4-(5-bromothiazol-2-yl)phenyl]carbamate (50.00 mg, 146.53 μmol, 1.00 eq.) in THF (1.00 mL) at 0° C., followed by MeI (41.60 mg, 293.06 μmol, 18.25 ul, 2.00 eq.) in THF (1.00 mL). The mixture was stirred at 20° C. for 1 hr and LCMS showed the reaction was complete. The mixture was quenched by sat.aq.NH₄Cl (5 mL) and extracted with EtOAc (5 mL×3). The organic phase was dried over Na₂SO₄, filtered and concentrated to give isopropyl N-[4-(5-bromothiazol-2-yl)phenyl]-N-methyl-carbamate (65.00 mg, crude) as yellow oil. ESI [M+H]=357.0/355.0

Compound J8
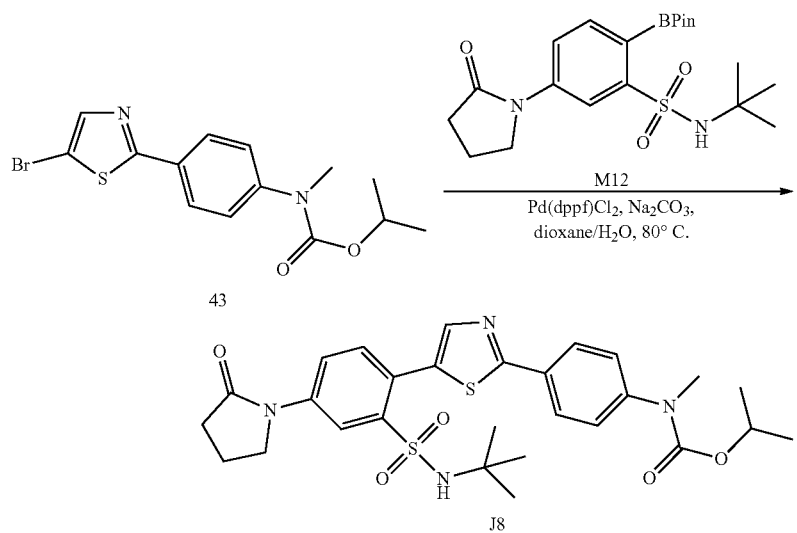
General method A, isopropyl N-[4-[5-[2-(tert-butylsulfamoyl)-4-(2-oxopyrrolidin-1-yl)phenyl]thiazol-2-yl]phenyl]-N-methyl-carbamate. $^1$H NMR (400 MHz, METHANOL-d4) δ=8.67 (s, 1H), 8.00-7.96 (m, 2H), 7.93 (s, 1H), 7.86 (br d, J=8.6 Hz, 1H), 7.58 (d, J=8.4 Hz, 1H), 7.43 (br d, J=8.6 Hz, 2H), 4.94 (br d, J=6.2 Hz, 1H), 4.00 (br t, J=6.8 Hz, 2H), 3.33 (s, 3H), 2.66 (br t, J=7.9 Hz, 2H), 2.29-2.19 (m, 2H), 1.26 (br d, J=6.2 Hz, 6H), 1.15 (s, 9H). ESI [M+H]=571.2
Scheme 10.7
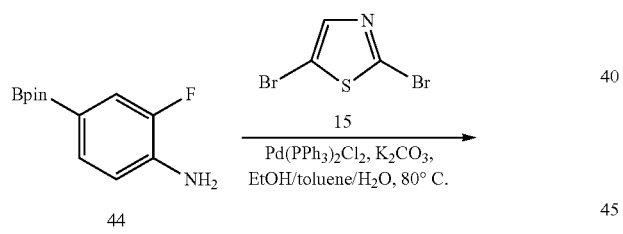
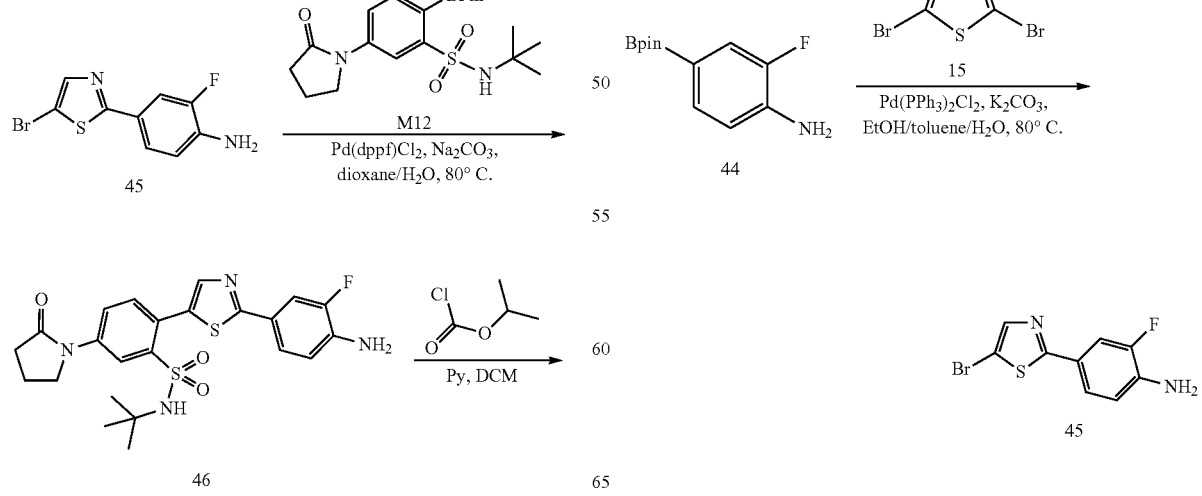
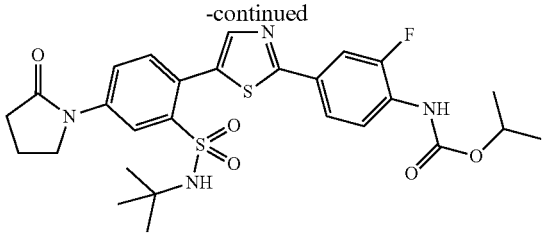
Preparation of compound 45.
General method H, 4-(5-bromothiazol-2-yl)-2-fluoro-aniline. ESI [M+H]=275.0/273.0

Preparation of compound 46.


General method A, 2-[2-(4-amino-3-fluoro-phenyl)thiazol-5-yl]-N-tert-butyl-5-(2-oxopyrrolidin-1-yl)benzenesulfonamide. ESI [M+H]=489.2

Compound J9


General method C, isopropyl N-[4-[5-[2-(tert-butylsulfamoyl)-4-(2-oxopyrrolidin-1-yl)phenyl]thiazol-2-yl]-2-fluoro-phenyl]carbamate. $^1$H NMR (400 MHz, METHANOL-d4) δ=8.66 (d, J=2.0 Hz, 1H), 8.08 (br t, J=8.2 Hz, 1H), 7.90 (s, 1H), 7.84 (dd, J=2.2, 8.4 Hz, 1H), 7.78-7.69 (m, 2H), 7.55 (d, J=8.4 Hz, 1H), 5.00 (quin, J=6.3 Hz, 1H), 3.99 (t, J=7.1 Hz, 2H), 2.65 (t, J=8.0 Hz, 2H), 2.22 (quin, J=7.6 Hz, 2H), 1.32 (d, J=6.2 Hz, 6H), 1.14 (s, 9H). ESI [M+H]=575.2

Scheme 10.8

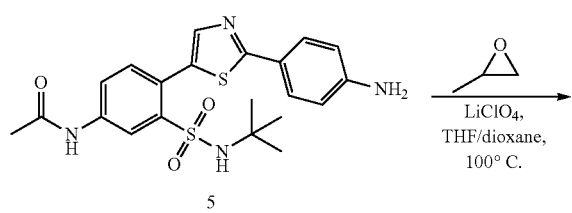

Compound J10

To a mixture of 2-methyloxirane (19.60 mg, 337.41 μmol, 23.61 ul, 1.50 eq.) in dioxane (1.00 mL) were added LiClO$_4$ (5 M, 1.00 mL, 22.23 eq.) in THF solution and N-[4-[2-(4-aminophenyl)thiazol-5-yl]-3-(tert-butylsulfamoyl)phenyl]acetamide (100.00 mg, 224.94 mol, 1.00 eq.). The mixture was stirred at 100° C. for 6 hrs and LCMS showed the reaction was complete. The mixture was diluted with H$_2$O (3 mL) and extracted with DCM (3 mL×3). The combined organic layers were dried over Na$_2$SO$_4$, filtered and concentrated. The residue was purified by prep-TLC to give N-[3-(tert-butylsulfamoyl)-4-[2-[4-(2-hydroxypropylamino)phenyl]thiazol-5-yl]phenyl]acetamide (40.00 mg, 75.60 μmol, 33.61% yield, 95% purity) as yellow oil. $^1$H NMR (400 MHz, METHANOL-d4) δ=8.50 (d, J=2.2 Hz, 1H), 7.93-7.87 (m, 2H), 7.81-7.75 (m, 2H), 7.53 (d, J=8.4 Hz, 1H), 6.83 (d, J=8.8 Hz, 2H), 4.04-3.92 (m, 1H), 3.29-3.11 (m, 2H), 2.19 (s, 3H), 1.27-1.24 (m, 3H), 1.17 (s, 9H). ESI [M+H]=503.1

Compound J11

Compound J11 was prepared from compound J0 via general method K (shown in Example 1).

Compound J12

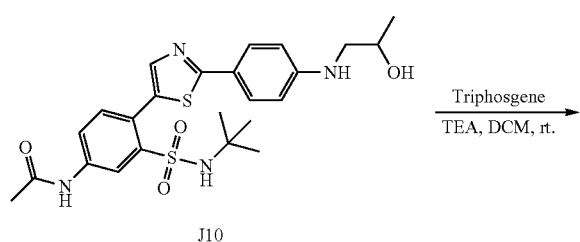

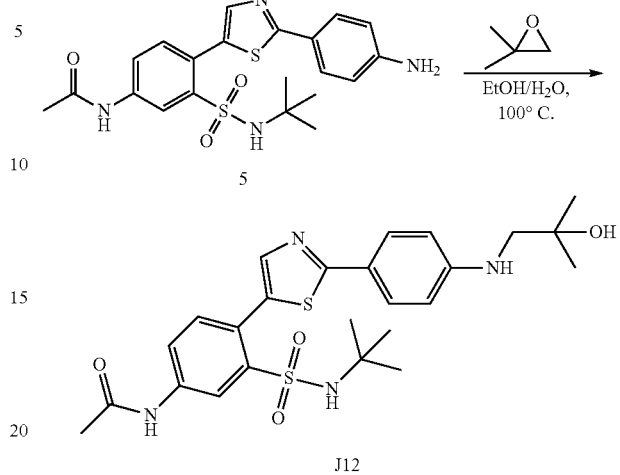

General method K, N-[3-(tert-butylsulfamoyl)-4-[2-[4-(2-hydroxypropylamino) phenyl]thiazol-5-yl]phenyl]acetamide. ¹H NMR (400 MHz, METHANOL-d4) δ=8.48 (d, J=2.2 Hz, 1H), 8.02-7.97 (m, 2H), 7.91-7.85 (m, 2H), 7.75-7.70 (m, 2H), 7.51 (d, J=8.4 Hz, 1H), 4.94-4.89 (m, 1H), 4.27 (t, J=8.6 Hz, 1H), 3.77 (dd, J=7.2, 8.9 Hz, 1H), 2.18 (s, 3H), 1.53 (d, J=6.2 Hz, 3H), 1.15 (s, 9H). ESI [M+H]=529.1

To a solution of N-[4-[2-(4-aminophenyl)thiazol-5-yl]-3-(tert-butylsulfamoyl) phenyl]acetamide (50.00 mg, 112.47 μmol, 1.00 eq.) in EtOH (900.00 ul) and H₂O (100.00 ul) was added 2,2-dimethyloxirane (810.00 mg, 11.23 mmol, 1.00 mL, 99.87 eq.). The mixture was heated at 100° C. for 1 hour and LCMS showed the reaction was complete. The mixture was concentrated and the residue was purified by prep-HPLC (TFA condition) to give N-[3-(tert-butylsulfamoyl)-4-[2-[4-[(2-hydroxy-2-methyl-propyl) amino]phenyl]thiazol-5-yl]phenyl]acetamide (60.00 mg, crude) as a yellow solid. ¹H NMR (400 MHz, METHANOL-d4) δ=8.46 (d, J=1.8 Hz, 1H), 7.87 (br d, J=6.4 Hz, 1H), 7.82 (s, 1H), 7.72 (d, J=8.8 Hz, 2H), 7.49 (d, J=8.4 Hz, 1H), 6.77 (d, J=8.6 Hz, 2H), 3.17 (s, 2H), 2.17 (s, 3H), 1.27 (s, 6H), 1.14 (s, 9H). ESI [M+H]=517.1

Compound J13

Compound J13 was prepared from compound J12 via general method K (shown in Example 1).

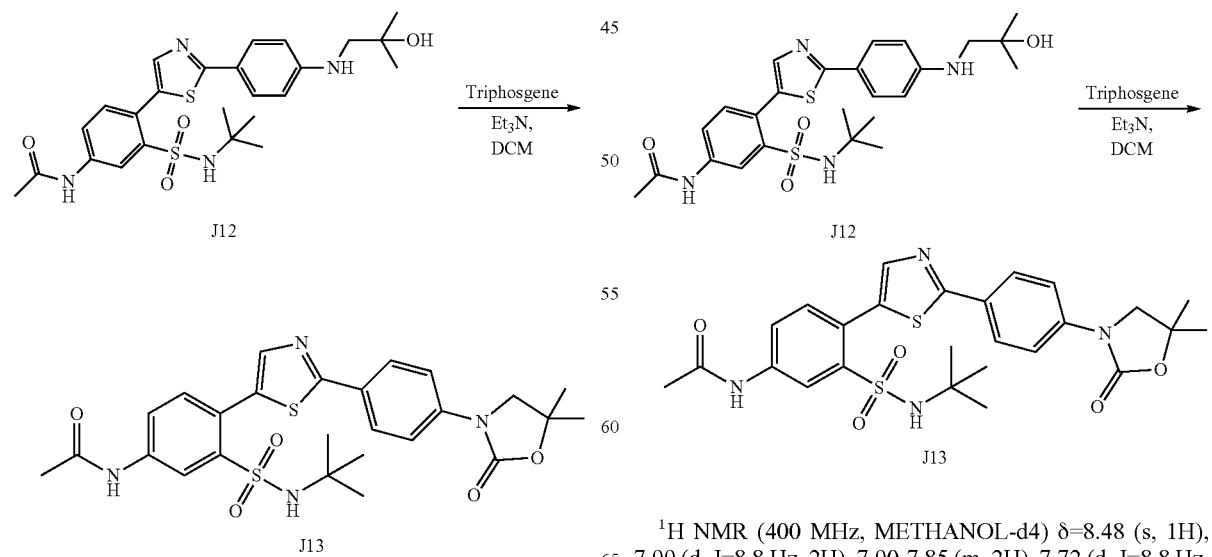

¹H NMR (400 MHz, METHANOL-d4) δ=8.48 (s, 1H), 7.99 (d, J=8.8 Hz, 2H), 7.90-7.85 (m, 2H), 7.72 (d, J=8.8 Hz, 2H), 7.50 (d, J=8.2 Hz, 1H), 3.94 (s, 2H), 2.17 (s, 3H), 1.56 (s, 6H), 1.14 (s, 9H). ESI [M+H]=543.2

Scheme 10.10

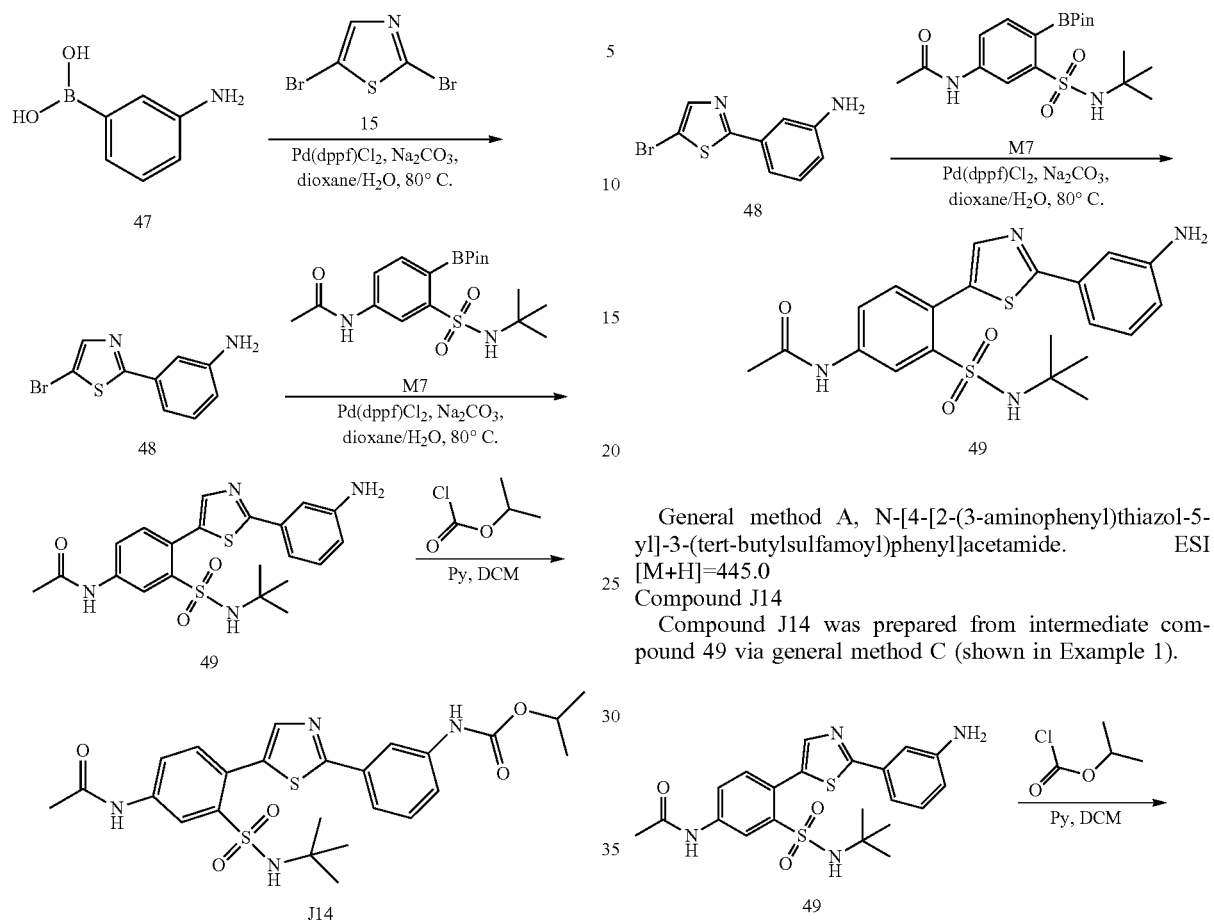

Preparation of compound 49.

General method A, N-[4-[2-(3-aminophenyl)thiazol-5-yl]-3-(tert-butylsulfamoyl)phenyl]acetamide. ESI [M+H]=445.0

Compound J14

Compound J14 was prepared from intermediate compound 49 via general method C (shown in Example 1).

¹H NMR (400 MHz, METHANOL-d4) δ=8.48 (d, J=2.0 Hz, 1H), 8.10 (s, 1H), 7.92-7.85 (m, 2H), 7.62 (d, J=7.5 Hz, 1H), 7.56-7.48 (m, 2H), 7.42-7.35 (m, 1H), 4.97 (td, J=6.3, 12.6 Hz, 1H), 2.17 (s, 3H), 1.31 (d, J=6.2 Hz, 6H), 1.14 (s, 9H). ESI [M+H]=531.2

Preparation of compound 48.

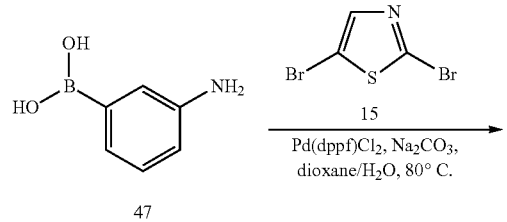

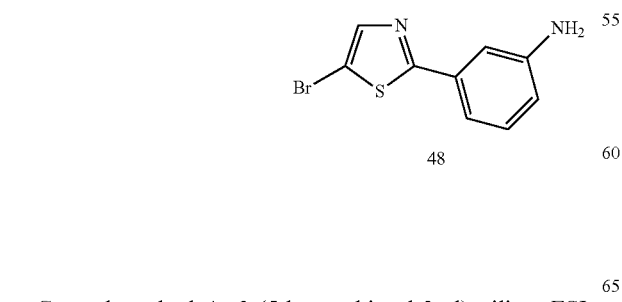

General method A, 3-(5-bromothiazol-2-yl)aniline. ESI [M+H]=255.0/257.0

Scheme 10.11

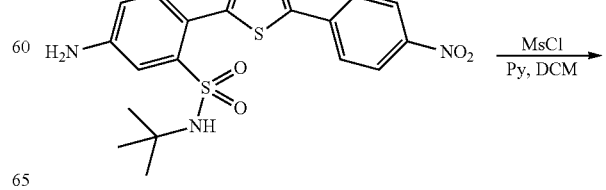

-continued

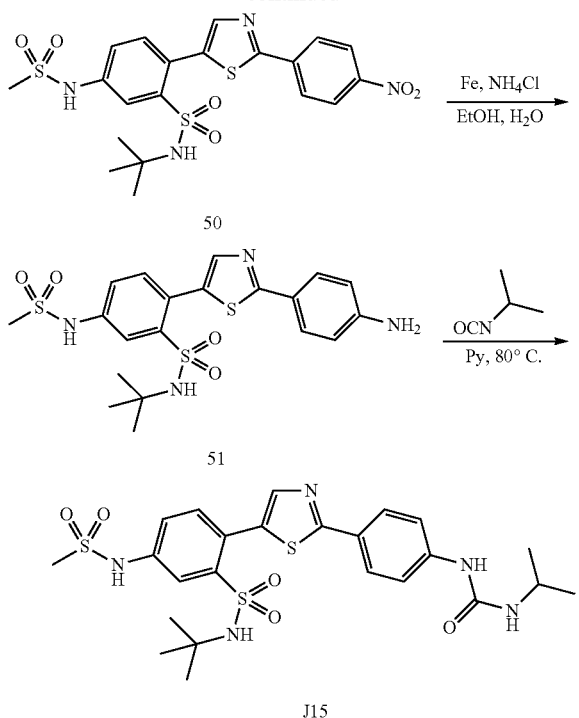

50

51

J15

Preparation of compound 50.

23

50

General method C, N-tert-butyl-5-(methanesulfonamido)-2-[2-(4-nitrophenyl)thiazol-5-yl]benzenesulfonamide. ESI [M+H]=511.1

Preparation of compound 51.

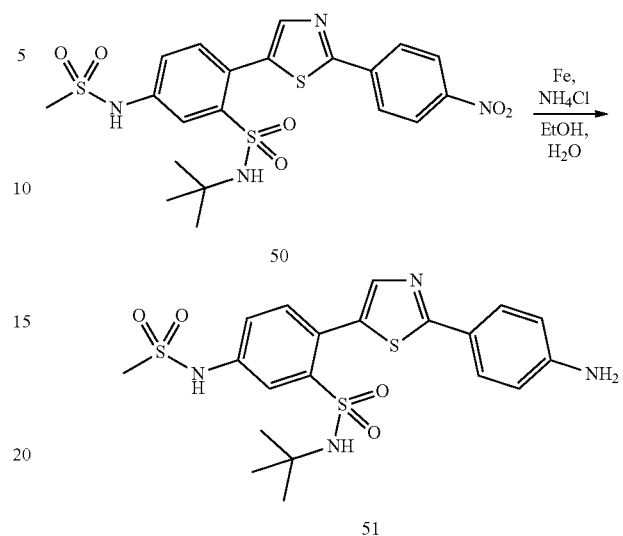

50

51

General method B, 2-[2-(4-aminophenyl)thiazol-5-yl]-N-tert-butyl-5-(methanesulfonamido)benzenesulfonamide. ESI [M+H]=481.2
Compound J15
Compound J15 was prepared from intermediate compound 51 via general method I (shown in Example 1).

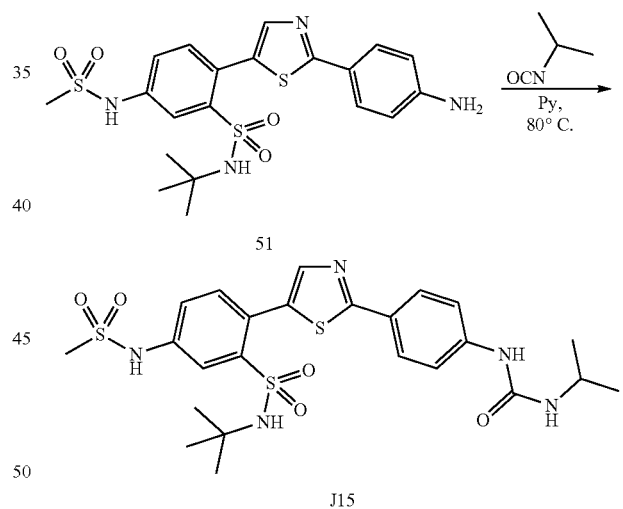

51

J15

$^1$H NMR (400 MHz, METHANOL-d4) δ=8.09 (d, J=2.2 Hz, 1H), 7.88-7.81 (m, 3H), 7.55-7.43 (m, 4H), 3.90 (td, J=6.7, 13.3 Hz, 1H), 1.20 (s, 3H), 1.18 (s, 6H), 1.14 (s, 9H). ESI [M+H]=566.1

Scheme 10.12

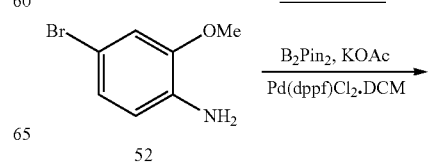

52

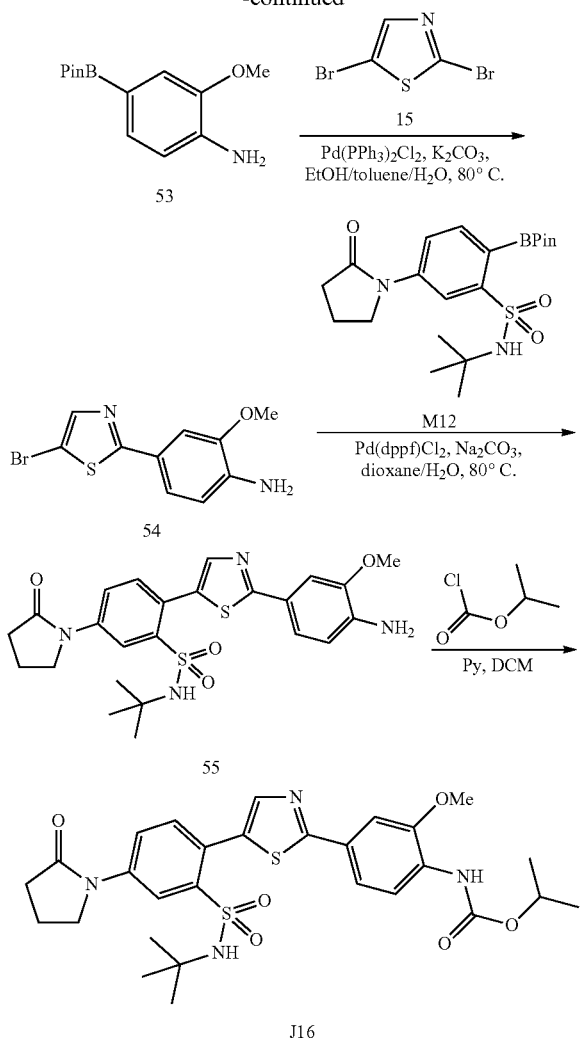

Preparation of compound 53.

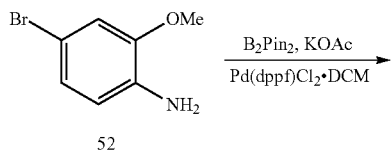

General method J, 2-methoxy-4-(4,4,5,5-tetramethyl-1,3,2-dioxaborolan-2-yl)aniline. H NMR (400 MHz, CHLOROFORM-d) δ=7.30 (dd, J=0.9, 7.5 Hz, 1H), 7.21 (s, 1H), 6.71 (d, J=7.9 Hz, 1H), 4.01 (br s, 2H), 3.90 (s, 3H), 1.34 (s, 12H)

Preparation of compound 54.

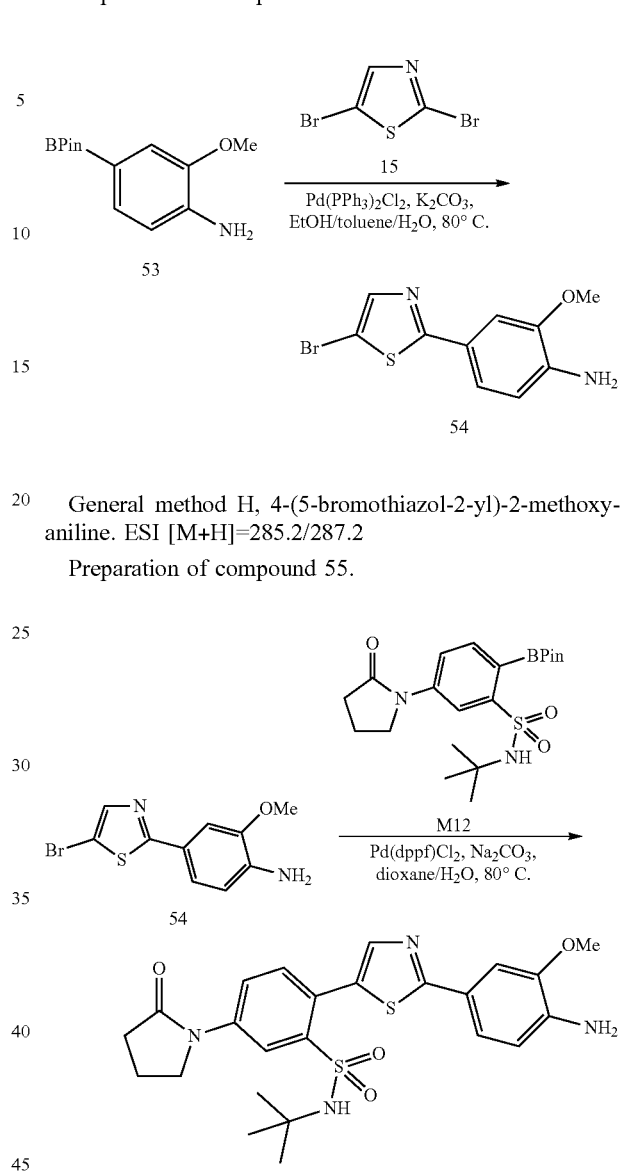

General method H, 4-(5-bromothiazol-2-yl)-2-methoxyaniline. ESI [M+H]=285.2/287.2

Preparation of compound 55.

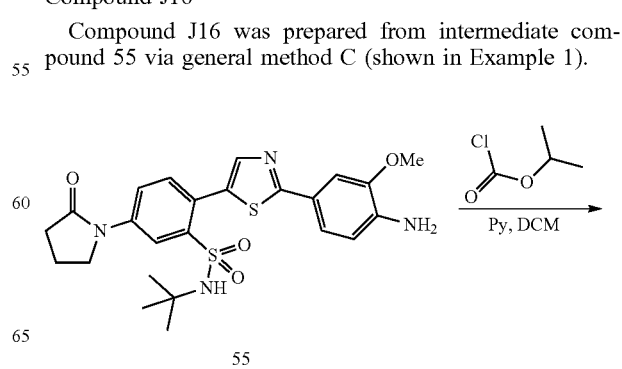

General method A, 2-[2-(4-amino-3-methoxy-phenyl)thiazol-5-yl]-N-tert-butyl-5-(2-oxopyrrolidin-1-yl)benzenesulfonamide. ESI [M+H]=501.2

Compound J16

Compound J16 was prepared from intermediate compound 55 via general method C (shown in Example 1).

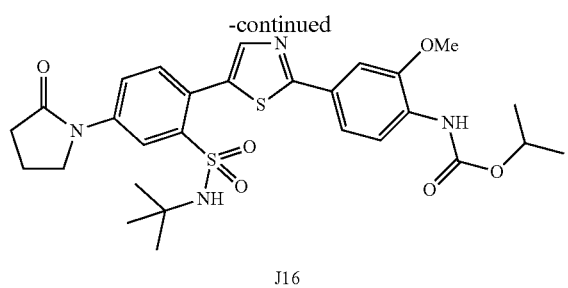

J16

¹H NMR (400 MHz, METHANOL-d4) δ=8.67 (d, J=2.2 Hz, 1H), 8.06 (d, J=8.4 Hz, 1H), 7.89 (s, 1H), 7.85 (dd, J=2.2, 8.6 Hz, 1H), 7.61 (s, 1H), 7.57 (d, J=8.5 Hz, 1H), 7.51 (d, J=8.6 Hz, 1H), 5.05-4.94 (m, 1H), 4.03-3.95 (m, 5H), 2.66 (t, J=8.0 Hz, 2H), 2.23 (quin, J=7.5 Hz, 2H), 1.32 (d, J=6.2 Hz, 6H), 1.15 (s, 9H). ESI [M+H]=587.1

Scheme 10.13

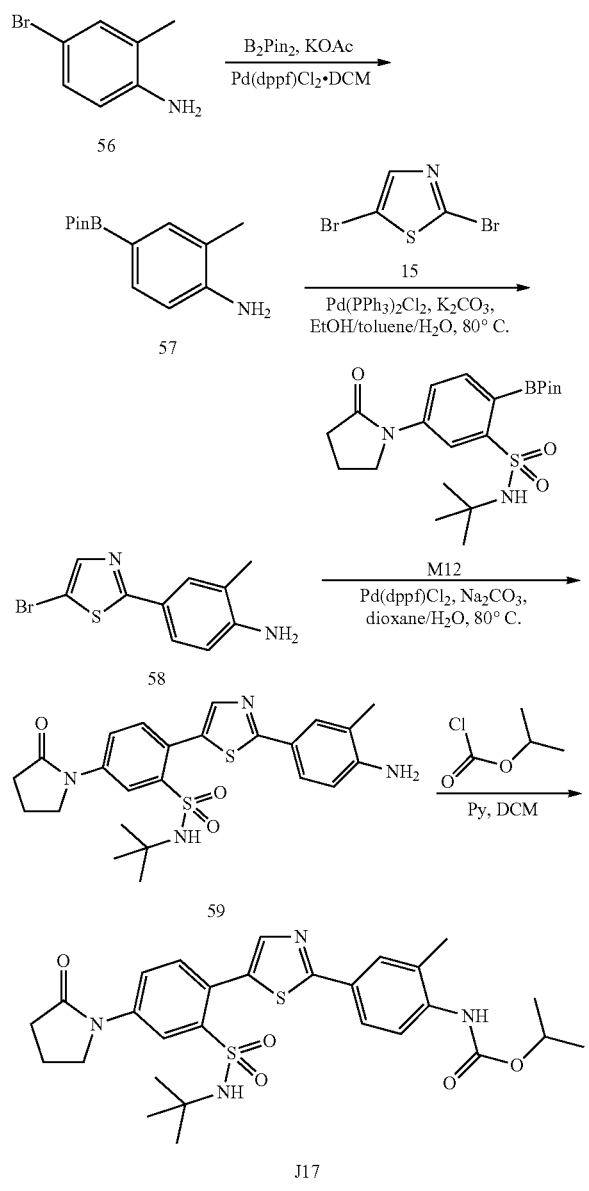

Preparation of compound 57.

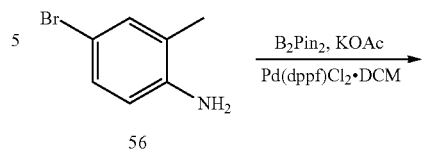

General method J, 2-methyl-4-(4,4,5,5-tetramethyl-1,3,2-dioxaborolan-2-yl) aniline. ¹H NMR (400 MHz, METHANOL-d4) δ=7.43-7.29 (m, 2H), 6.65 (d, J=7.8 Hz, 1H), 2.13 (s, 3H), 1.31 (s, 12H).

Preparation of compound 58.

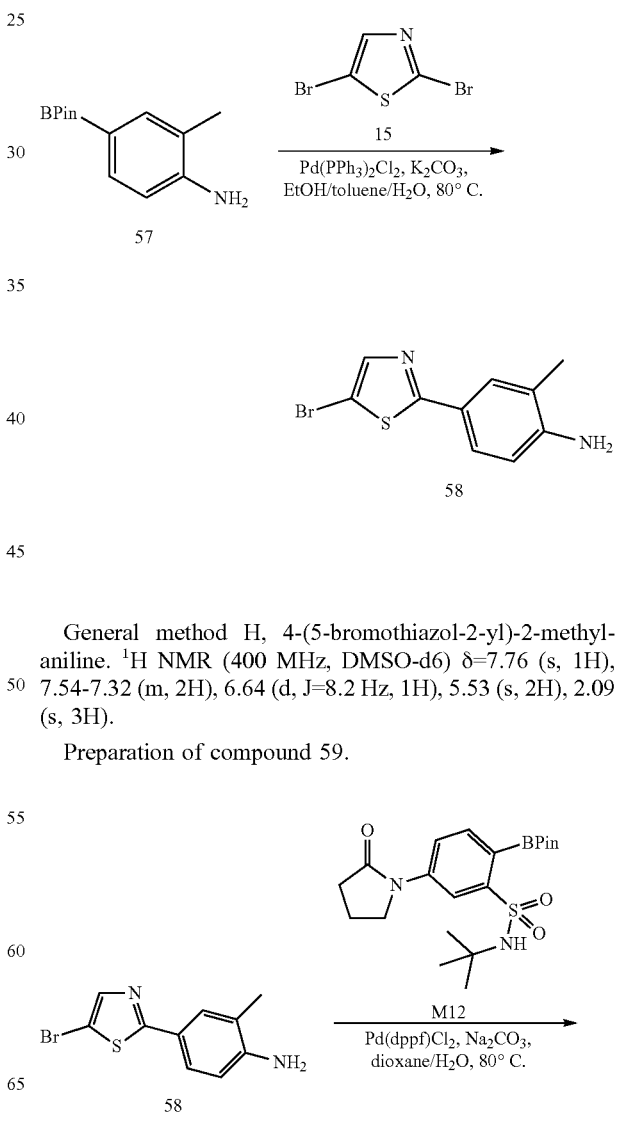

General method H, 4-(5-bromothiazol-2-yl)-2-methylaniline. ¹H NMR (400 MHz, DMSO-d6) δ=7.76 (s, 1H), 7.54-7.32 (m, 2H), 6.64 (d, J=8.2 Hz, 1H), 5.53 (s, 2H), 2.09 (s, 3H).

Preparation of compound 59.

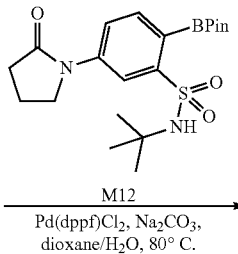

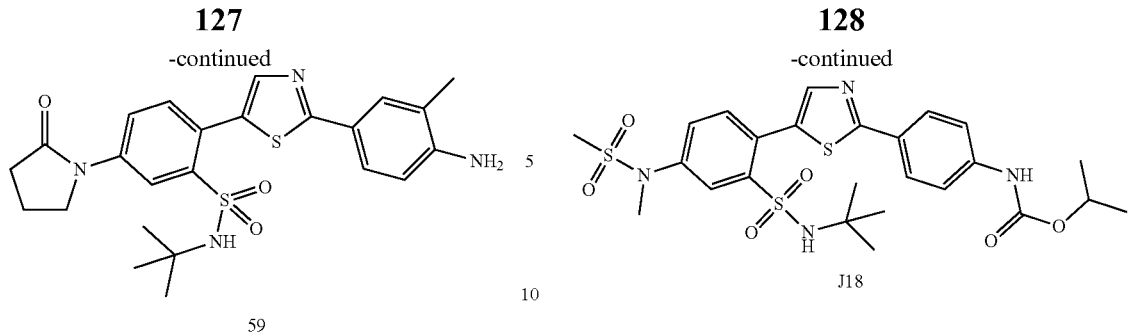

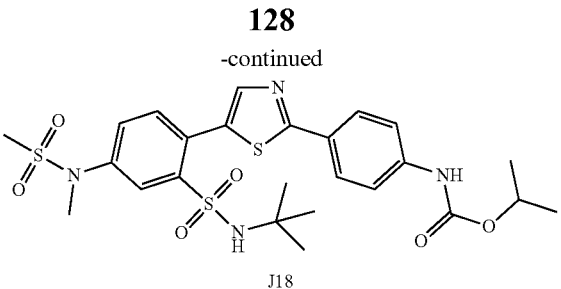

Preparation of compound 60.

General method A, 2-[2-(4-amino-3-methyl-phenyl)thiazol-5-yl]-N-tert-butyl-5-(2-oxopyrrolidin-1-yl)benzenesulfonamide. ESI [M+H]=485.1

Compound J17

Compound J17 was prepared from intermediate compound 59 via general method C (shown in Example 1).

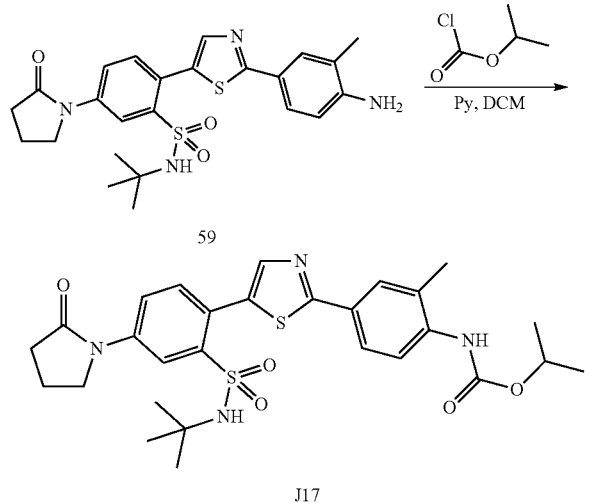

<sup>1</sup>HNMR (400 MHz, DMSO-d6) δ=8.90 (s, 1H), 8.64 (d, J=2.4 Hz, 1H), 7.87 (s, 1H), 7.80-7.74 (m, 3H), 7.59 (t, J=9.1 Hz, 2H), 7.24 (s, 1H), 4.90 (spt, J=6.2 Hz, 1H), 3.91 (t, J=7.0 Hz, 2H), 2.61-2.54 (m, 2H), 2.30 (s, 3H), 2.15-2.08 (m, 2H), 1.27 (d, J=6.2 Hz, 6H), 1.10 (s, 9H). ESI [M+H]=571.1

Scheme 10.14

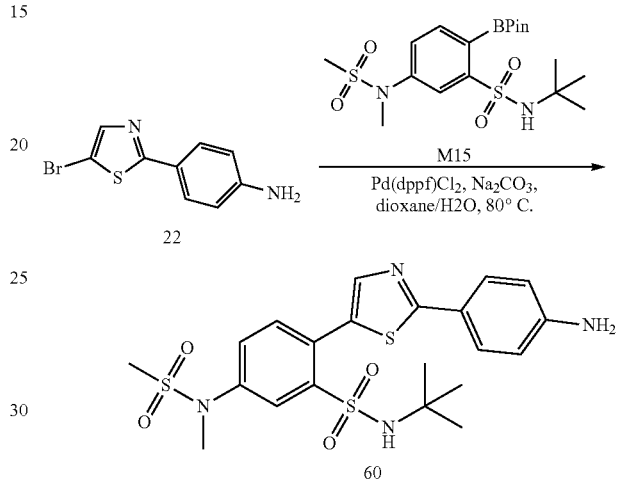

General method A, 2-[2-(4-aminophenyl)thiazol-5-yl]-N-tert-butyl-5-[methyl(methylsulfonyl)amino]benzenesulfonamide. ESI [M+H]=495.2

Compound J18

Compound J18 was prepared from intermediate compound 60 via general method C (shown in Example 1).

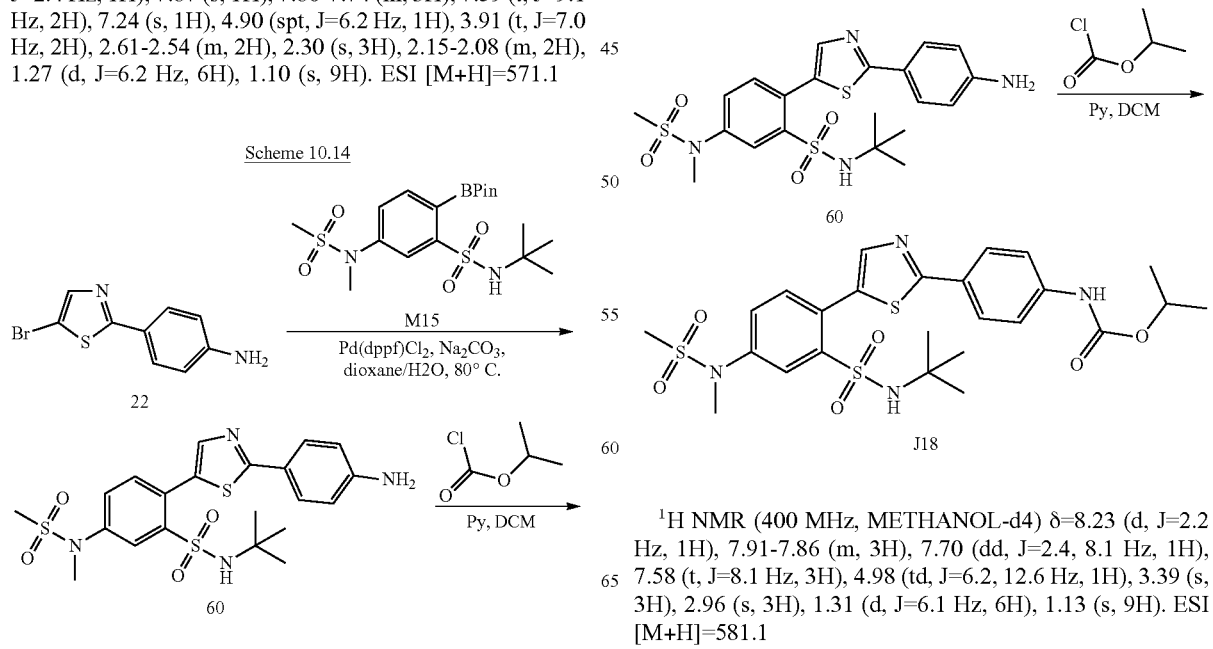

<sup>1</sup>H NMR (400 MHz, METHANOL-d4) δ=8.23 (d, J=2.2 Hz, 1H), 7.91-7.86 (m, 3H), 7.70 (dd, J=2.4, 8.1 Hz, 1H), 7.58 (t, J=8.1 Hz, 3H), 4.98 (td, J=6.2, 12.6 Hz, 1H), 3.39 (s, 3H), 2.96 (s, 3H), 1.31 (d, J=6.1 Hz, 6H), 1.13 (s, 9H). ESI [M+H]=581.1

Compound J18

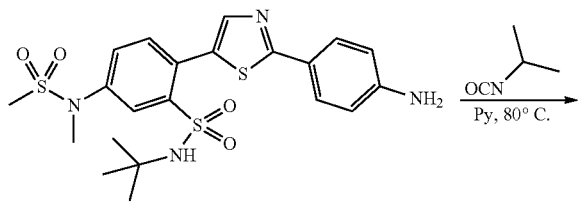

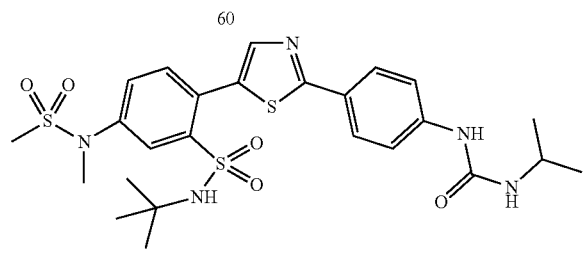

J18

General method I, 1-[4-[5-[2-(tert-butylsulfamoyl)-4-[methyl(methylsulfonyl) amino]phenyl]thiazol-2-yl]phenyl]-3-isopropyl-urea. ¹HNMR (400 MHz, METHANOL-d4) δ=8.23 (d, J=2.6 Hz, 1H), 7.90-7.84 (m, 3H), 7.71 (dd, J=2.6, 8.3 Hz, 1H), 7.60 (d, J=8.3 Hz, 1H), 7.50 (d, J=8.8 Hz, 2H), 3.90 (quin, J=6.5 Hz, 1H), 3.40 (s, 3H), 2.96 (s, 3H), 1.19 (d, J=6.6 Hz, 6H), 1.13 (s, 9H). ESI [M+H]=580.2

Scheme 10.15

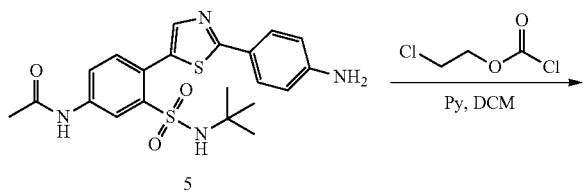

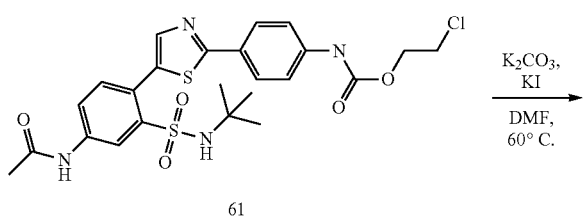

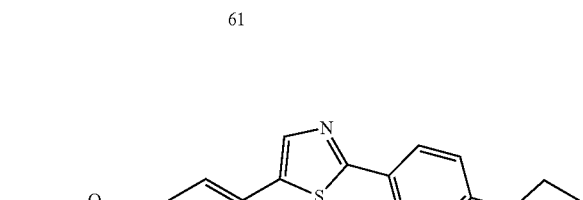

J19

Preparation of compound 61.

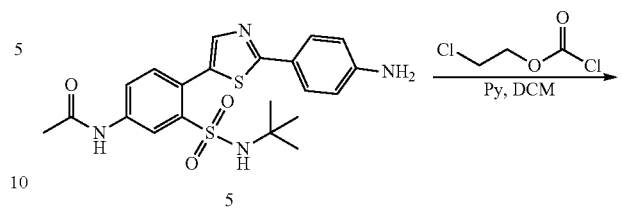

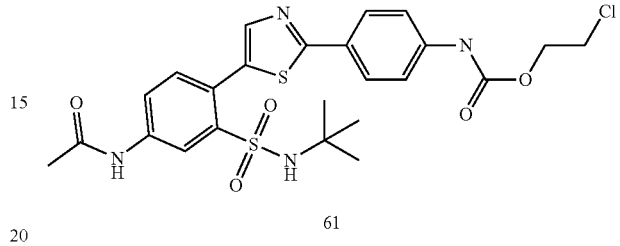

61

General method C, 2-chloroethyl N-[4-[5-[4-acetamido-2-(tert-butylsulfamoyl) phenyl]thiazol-2-yl]phenyl]carbamate. ESI [M+H]=551.1/553.0

Compound J19

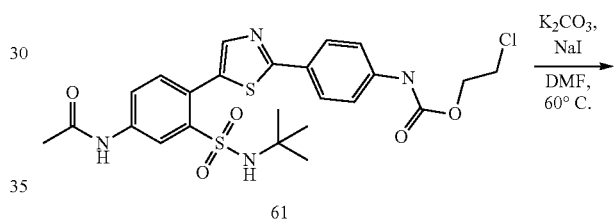

61

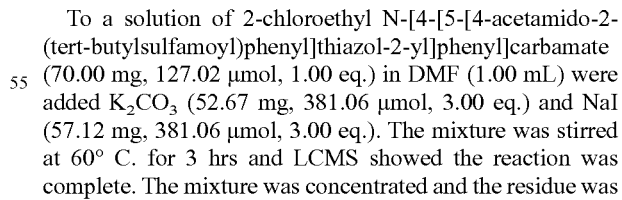

J19

To a solution of 2-chloroethyl N-[4-[5-[4-acetamido-2-(tert-butylsulfamoyl)phenyl]thiazol-2-yl]phenyl]carbamate (70.00 mg, 127.02 μmol, 1.00 eq.) in DMF (1.00 mL) were added K₂CO₃ (52.67 mg, 381.06 μmol, 3.00 eq.) and NaI (57.12 mg, 381.06 μmol, 3.00 eq.). The mixture was stirred at 60° C. for 3 hrs and LCMS showed the reaction was complete. The mixture was concentrated and the residue was purified by acidic prep-HPLC to give N-[3-(tert-butylsulfamoyl)-4-[2-[4-(2-oxooxazolidin-3-yl)phenyl]thiazol-5-yl]phenyl]acetamide (27.79 mg, 53.95 μmol, 42.47% yield, 99.9% purity) as a white solid. ¹H NMR (400 MHz, DMSO-d6) δ=10.38 (s, 1H), 8.39 (s, 1H), 7.96 (d, J=8.8 Hz, 2H), 7.86-7.78 (m, 2H), 7.69 (d, J=8.8 Hz, 2H), 7.47 (d, J=8.4 Hz, 1H), 7.18 (s, 1H), 4.44 (t, J=7.9 Hz, 2H), 4.15-4.04 (m, 2H), 2.07 (s, 3H), 1.05 (s, 9H). ESI [M+H]=515.3

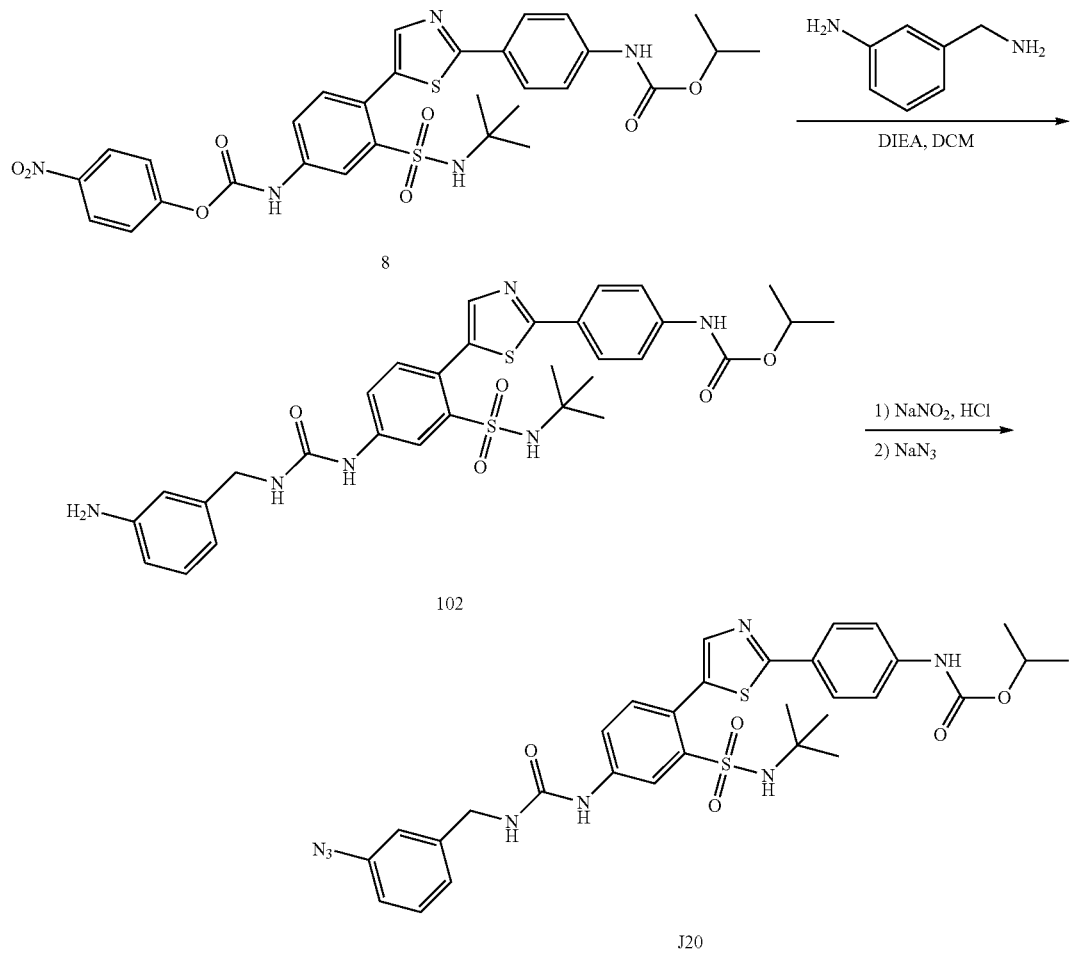
Preparation of compound 102.
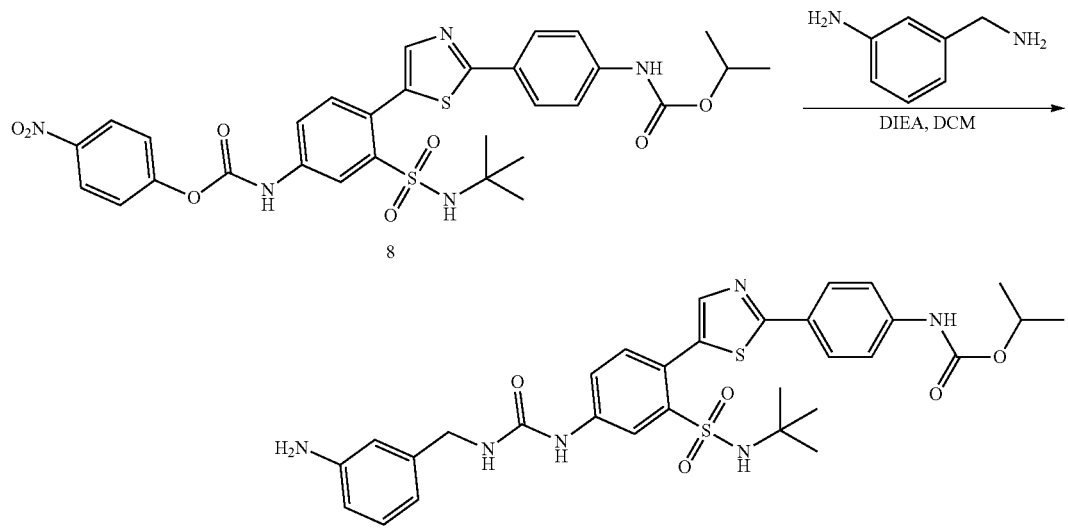

General method C, isopropyl (4-(5-(4-(3-(3-aminobenzyl)ureido)-2-(N-(tert-butyl)sulfamoyl)phenyl)thiazol-2-yl)phenyl)carbamate. ESI [M+H]=637.2
Compound J20

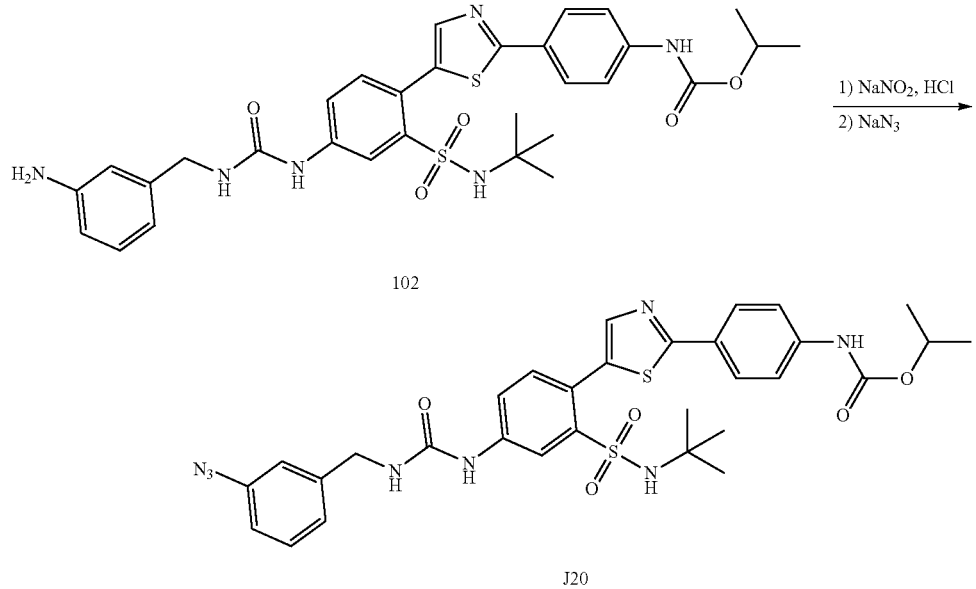

Isopropyl N-[4-[5-[4-[(3-aminophenyl)methylcarbamoylamino]-2-(tert-butylsulfamoyl) phenyl]thiazol-2-yl]phenyl]carbamate (0.05 g, 78.52 μmol, 1 eq.) was dissolved in conc.HCl (0.5 mL) and water (500.00 ul) and then cooled to 0° C. Aqueous NaNO$_2$ (8.13 mg, 117.78 μmol, 6.40 ul, 1.5 eq.) solution in water (0.5 mL) was added dropwise at such a rate that the temperature did not exceed 5° C. The mixture was stirred at 0° C. for 0.5 hr. A solution of NaN$_3$ (7.66 mg, 117.78 μmol, 1.5 eq.) and NaOAc (96.62 mg, 1.18 mmol, 15 eq.) in water (4 mL) was added at 0-5° C. and the mixture was stirred for an additional 0.5 hr at this temperature. The aqueous solution was extracted with EtOAc (30 mL×3) and the organic phase was dried, filtered and concentrated. The residue was purified by acidic prep-HPLC to give isopropyl N-[4-[5-[4-[(3-azidophenyl)methylcarbamoylamino]-2-(tert-butylsulfamoyl) phenyl]thiazol-2-yl]phenyl]carbamate (12.57 mg, 18.85 μmol, 24.01% yield, 99.39% purity) as a yellow solid. $^1$H NMR (400 MHz, METHANOL-d4) δ=8.27 (d, J=2.2 Hz, 1H), 7.90-7.83 (m, 3H), 7.72 (dd, J=2.2, 8.4 Hz, 1H), 7.57 (d, J=8.6 Hz, 2H), 7.43 (d, J=8.4 Hz, 1H), 7.38-7.33 (m, 1H), 7.16 (d, J=7.7 Hz, 1H), 7.06 (s, 1H), 6.97 (br d, J=7.9 Hz, 1H), 4.97 (td, J=6.3, 12.6 Hz, 1H), 4.41 (s, 2H), 1.31 (d, J=6.2 Hz, 6H), 1.13 (s, 9H). ESI [M+H]=663.4.

Compound J21

Compound J21 was prepared from intermediate compound 32 via general method A (shown in Example 1).

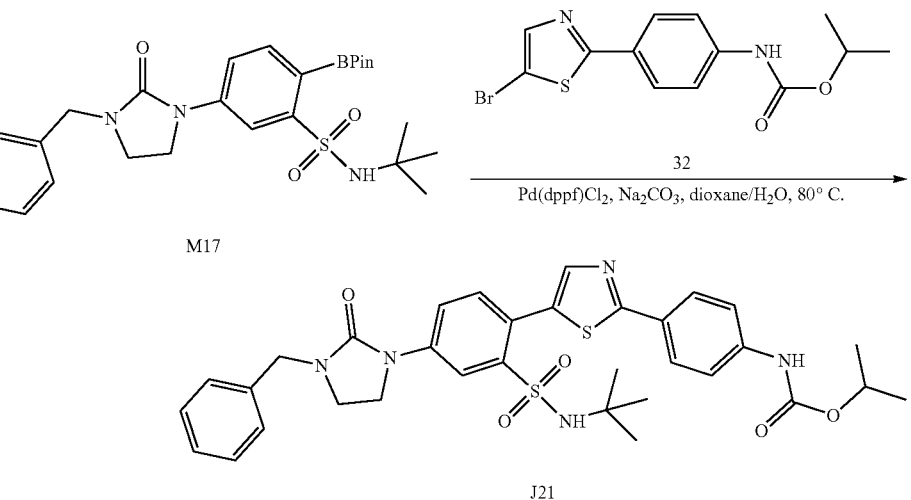

$^1$H NMR (400 MHz, DMSO-d6) δ=9.86 (s, 1H), 8.56 (s, 1H), 7.86 (d, J=8.6 Hz, 2H), 7.81 (s, 1H), 7.65 (br d, J=8.6

Hz, 1H), 7.59 (br d, J=8.4 Hz, 2H), 7.49 (d, J=8.4 Hz, 1H), 7.39-7.34 (m, 2H), 7.33-7.27 (m, 3H), 7.19 (s, 1H), 4.90 (td, J=6.0, 12.4 Hz, 1H), 4.42 (s, 2H), 3.88 (br t, J=7.9 Hz, 2H), 3.40 (br t, J=7.9 Hz, 2H), 1.26 (d, J=6.4 Hz, 6H), 1.08 (s, 9H). ESI [M+H]=648.2
Scheme 10.17
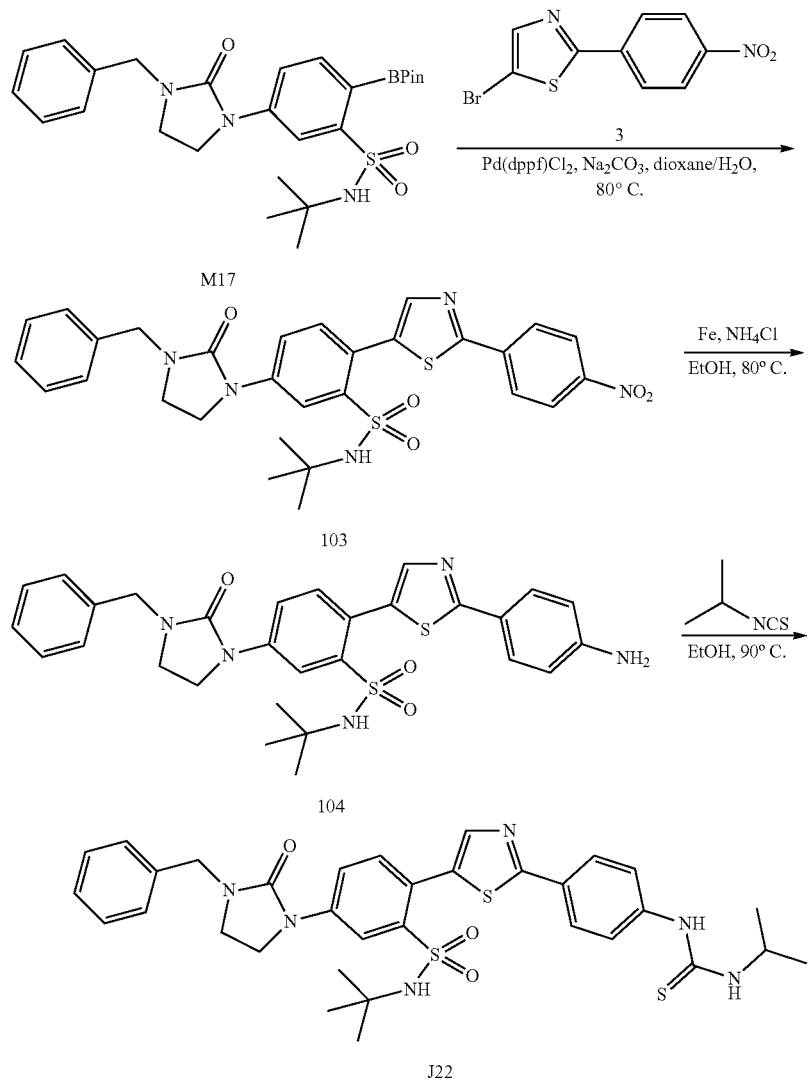
Preparation of compound 103.
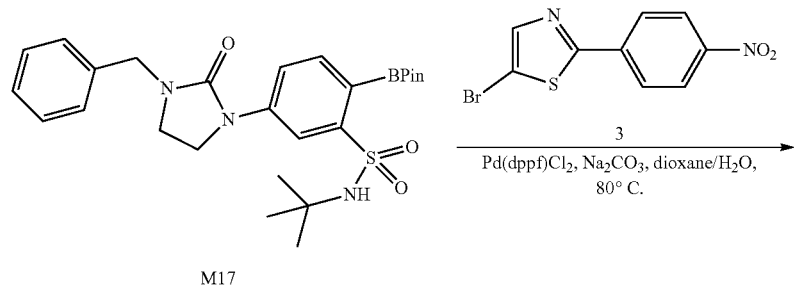

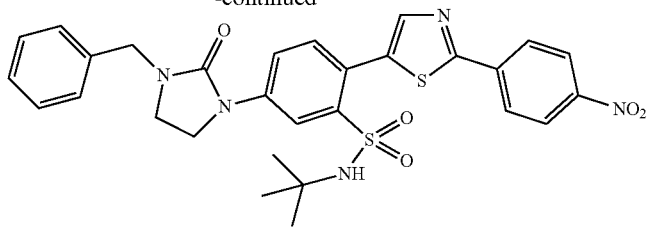
103
General method A, 5-(3-benzyl-2-oxoimidazolidin-1-yl)-N-(tert-butyl)-2-(2-(4-nitrophenyl) thiazol-5-yl)benzenesulfonamide. ESI [M+H]=591.9
Preparation of compound 104.
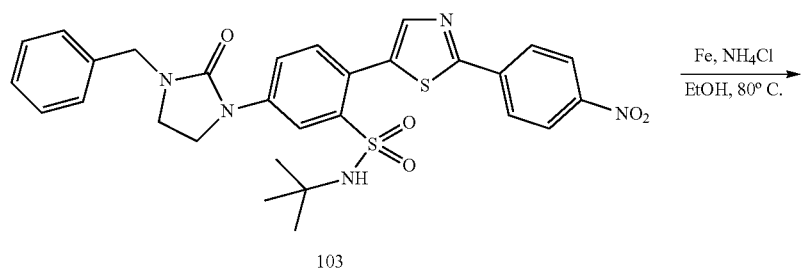
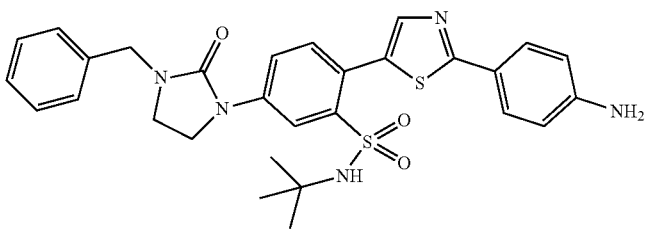
104
General method B, 2-(2-(4-aminophenyl)thiazol-5-yl)-5-(3-benzyl-2-oxoimidazolidin-1-yl)-N-(tert-butyl)benzenesulfonamide. ESI [M+H]=561.9
Compound J22
Compound J22 was prepared from intermediate compound 104 via general method G (shown in Example 1).
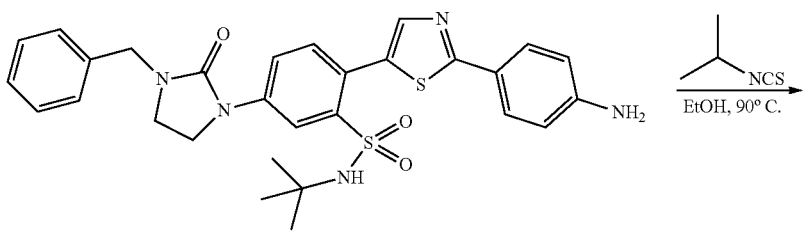
104

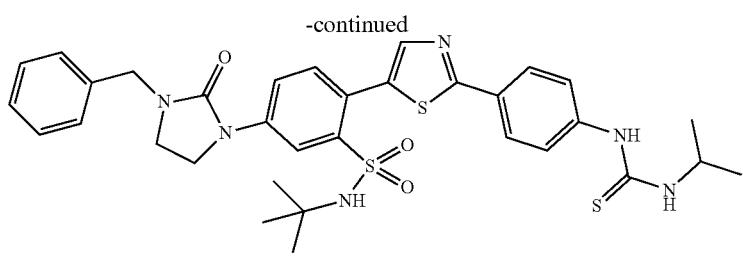
J22
¹H NMR (400 MHz, METHANOL-d4) δ=8.61 (d, J=2.0 Hz, 1H), 7.99-7.87 (m, 3H), 7.83-7.76 (m, 1H), 7.64-7.50 (m, 3H), 7.43-7.28 (m, 5H), 4.52 (s, 3H), 3.96 (br t, J=7.8 Hz, 2H), 3.57-3.43 (m, 2H), 1.27 (d, J=6.4 Hz, 6H), 1.18 (s, 9H). ESI [M+H]=663.2
Scheme 10.18
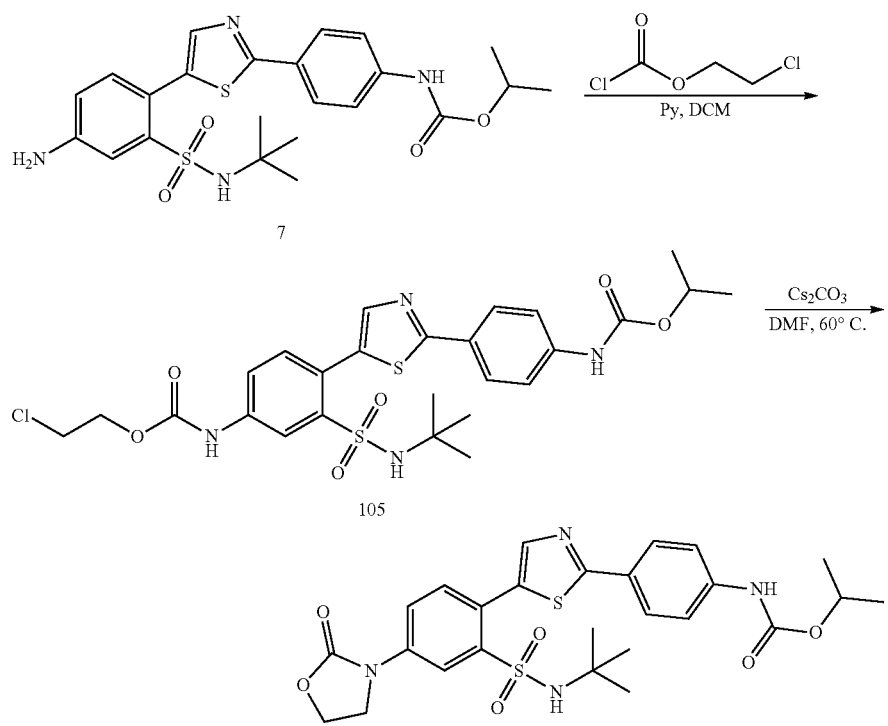
Preparation of compound 105.
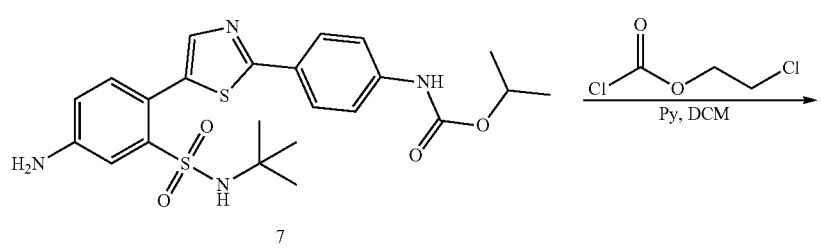

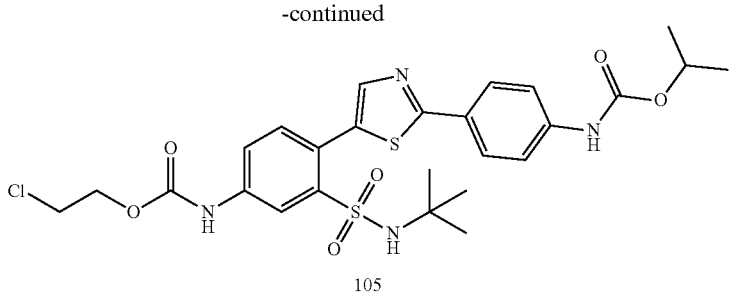

105

General method C, isopropyl N-[4-[5-[2-(tert-butylsulfamoyl)-4-(2-chloroethoxycarbonyl amino)phenyl]thiazol-2-yl]phenyl]carbamate. ESI [M+H]=595.3
Compound J23

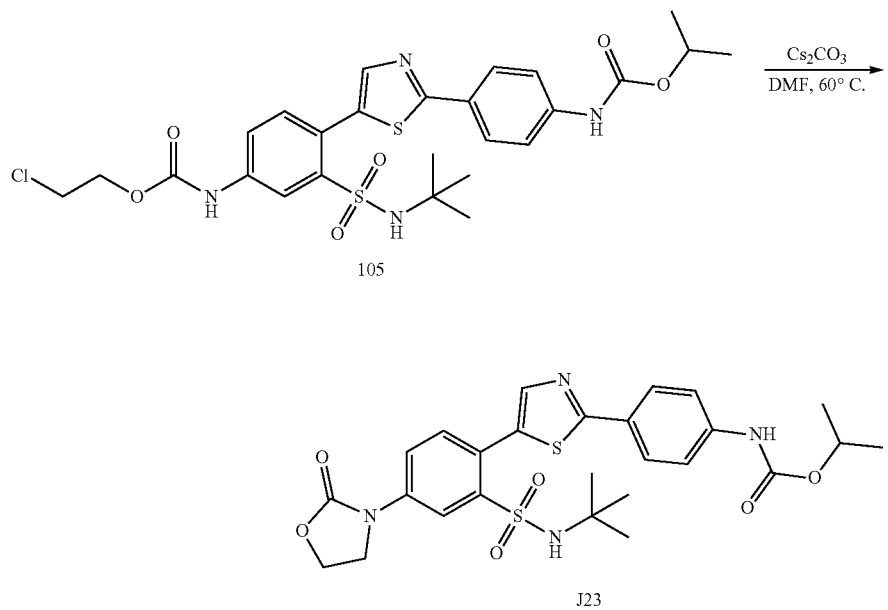

To a solution of isopropyl N-[4-[5-[2-(tert-butylsulfamoyl)-4-(2-chloroethoxycarbonylamino)phenyl]thiazol-2-yl]phenyl]carbamate (20.00 mg, 33.61 μmol, 1.00 eq.) in DMF (1.00 mL) was added Cs₂CO₃ (32.85 mg, 100.82 μmol, 3.00 eq.) and the mixture was stirred at 60° C. for 1 hr. The mixture was filtered and the filtrate was purified by acidic prep-HPLC to give isopropyl N-[4-[5-[2-(tert-butylsulfamoyl)-4-(2-oxooxazolidin-3-yl)phenyl]thiazol-2-yl]phenyl]carbamate (10.15 mg, 18.17 μmol, 54.06% yield, 100% purity) as a white solid. ¹H NMR (400 MHz, DMSO-d6) δ=9.88 (s, 1H), 8.51 (d, J=2.3 Hz, 1H), 7.98-7.79 (m, 3H), 7.71 (dd, J=2.3, 8.4 Hz, 1H), 7.65-7.57 (m, 3H), 7.31 (s, 1H), 5.02-4.85 (m, 1H), 4.51 (t, J=7.9 Hz, 2H), 4.16 (t, J=7.9 Hz, 2H), 1.29 (d, J=6.2 Hz, 6H), 1.11 (s, 9H). ESI [M+H]=559.1

Scheme 10.19

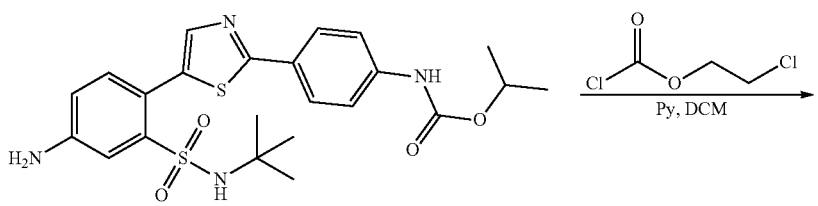

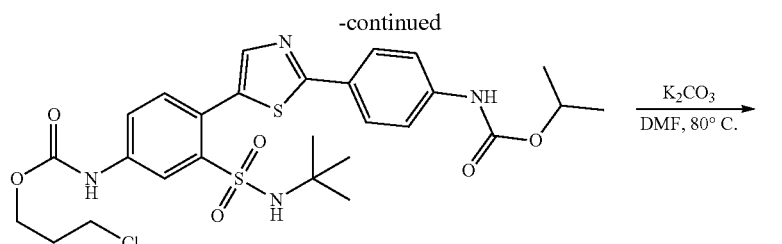

106

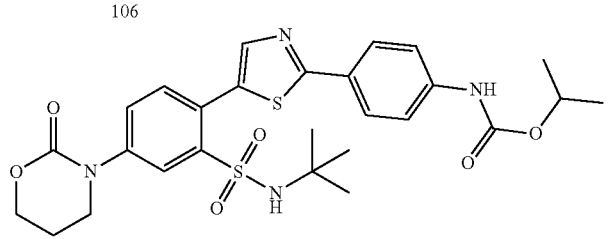

J24

Preparation of compound 106.

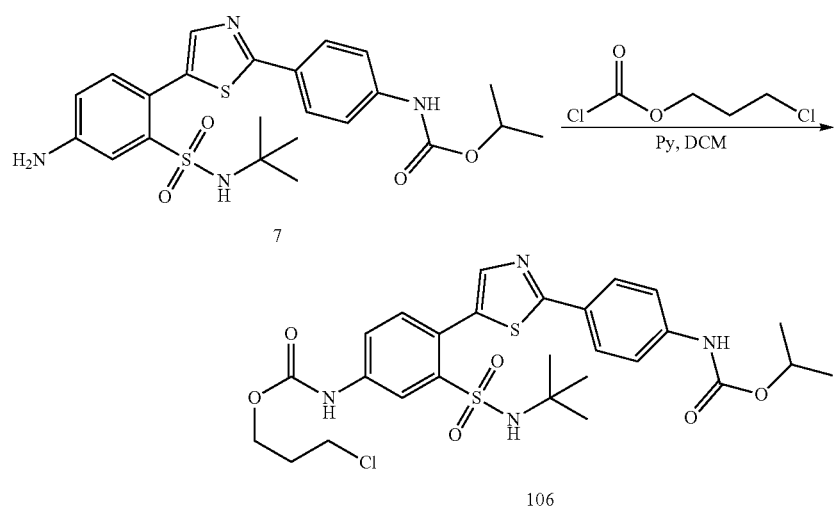

General method C, isopropyl N-[4-[5-[2-(tert-butylsulfamoyl)-4-(3-chloropropoxycarbonylamino)phenyl]thiazol-2-yl]phenyl]carbamate. ESI [M+H]=609.2
Compound J24

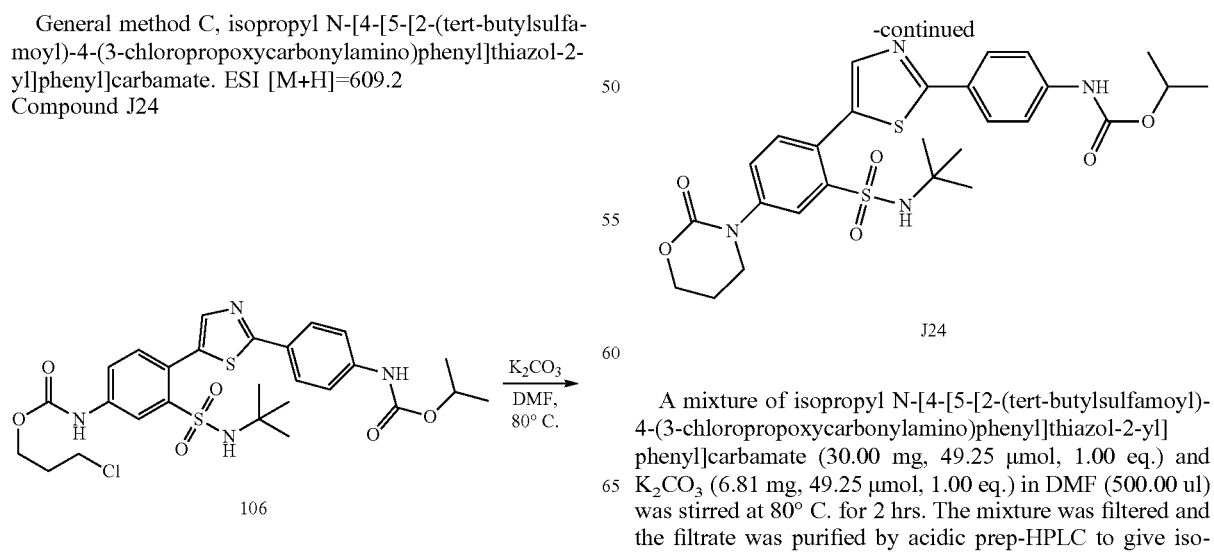

A mixture of isopropyl N-[4-[5-[2-(tert-butylsulfamoyl)-4-(3-chloropropoxycarbonylamino)phenyl]thiazol-2-yl]phenyl]carbamate (30.00 mg, 49.25 µmol, 1.00 eq.) and K₂CO₃ (6.81 mg, 49.25 µmol, 1.00 eq.) in DMF (500.00 ul) was stirred at 80° C. for 2 hrs. The mixture was filtered and the filtrate was purified by acidic prep-HPLC to give isopropyl N-[4-[5-[2-(tert-butylsulfamoyl)-4-(2-oxo-1,3-oxazinan-3-yl)phenyl]thiazol-2-yl]phenyl]carbamate (2.17 mg, 3.79 μmol, 7.70% yield) as a white solid. ¹H NMR (400 MHz, METHANOL-d4) δ=8.22 (d, J=2.0 Hz, 1H), 7.93-7.86 (m, 3H), 7.70-7.64 (m, 1H), 7.58 (dd, J=5.4, 8.3 Hz, 3H), 4.98 (td, J=6.3, 12.4 Hz, 1H), 4.49 (t, J=5.3 Hz, 2H), 3.84 (t, J=6.0 Hz, 2H), 2.26 (quin, J=5.6 Hz, 2H), 1.31 (d, J=6.4 Hz, 6H), 1.12 (s, 9H). ESI [M+H]=573.1

-continued

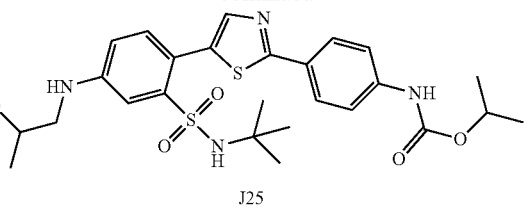

Scheme 10.20

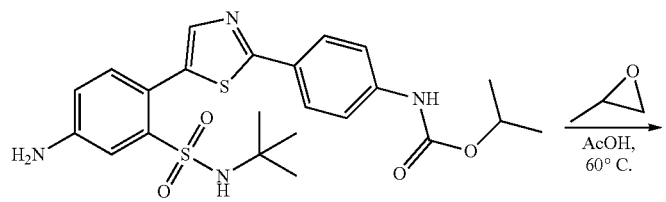

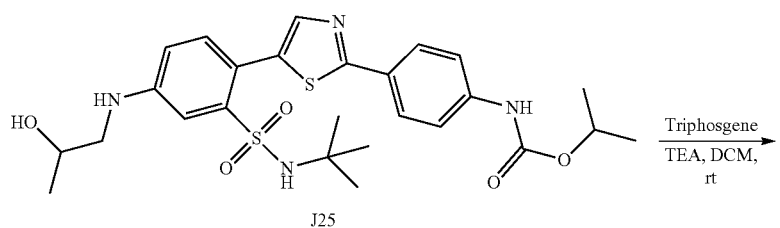

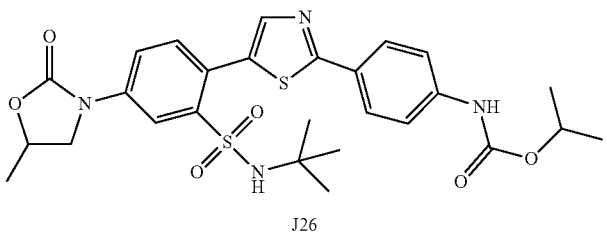

Compound J25

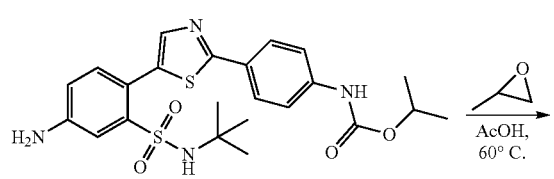

To a mixture of 2-methyloxirane (29.72 mg, 511.65 μmol, 35.80 ul, 5.00 eq.) in AcOH (500.00 ul) was added isopropyl N-[4-[5-[4-amino-2-(tert-butylsulfamoyl)phenyl]thiazol-2-yl]phenyl]carbamate (50.00 mg, 102.33 μmol, 1.00 eq.) and the mixture was stirred at 60° C. for 2 hrs. The mixture was diluted with H₂O (1 mL) and extracted with DCM (1 mL×3). The combined organic layers were washed with H₂O (1 mL), sat.aq.NaHCO₃, dried over Na₂SO₄, filtered and concentrated. The residue was purified acidic prep-HPLC to give isopropyl N-[4-[5-[2-(tert-butylsulfamoyl)-4-(2-hydroxypropylamino)phenyl]thiazol-2-yl]phenyl]carbamate (7.32 mg, 13.35 μmol, 26.06% yield, 99.7% purity) as a yellow solid.

¹H NMR (400 MHz, METHANOL-d4) δ=7.86 (d, J=8.8 Hz, 2H), 7.78 (s, 1H), 7.57 (d, J=8.6 Hz, 2H), 7.47-7.40 (m, 1H), 7.26 (d, J=8.4 Hz, 1H), 6.88-6.82 (m, 1H), 5.03-4.93 (m, 1H), 4.03-3.90 (m, 1H), 3.72-3.55 (m, 1H), 3.22-3.08 (m, 1H), 1.31 (d, J=6.2 Hz, 6H), 1.26-1.22 (m, 3H), 1.12 (s, 9H). ESI [M+H]=547.2

Compound J26
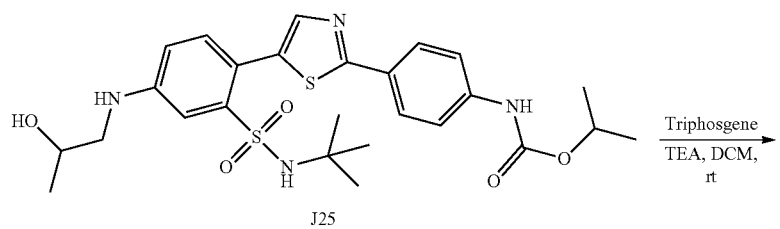
General method K, isopropyl (4-(5-(2-(N-(tert-butyl)sulfamoyl)-4-(5-methyl-2-oxooxazolidin-3-yl)phenyl)thiazol-2-yl)phenyl)carbamate. ¹H NMR (400 MHz, DMSO-d6) δ=9.86 (s, 1H), 8.46 (d, J=2.4 Hz, 1H), 7.87 (d, J=8.8 Hz, 2H), 7.83 (s, 1H), 7.65 (dd, J=2.4, 8.6 Hz, 1H), 7.58 (dd, J=8.7, 13.8 Hz, 3H), 7.26 (s, 1H), 4.97-4.77 (m, 2H), 4.22 (t, J=8.6 Hz, 1H), 3.73 (dd, J=7.3, 8.6 Hz, 1H), 1.43 (d, J=6.2 Hz, 3H), 1.26 (d, J=6.4 Hz, 6H), 1.07 (s, 9H). ESI [M+H]=573.2
Scheme 10.21
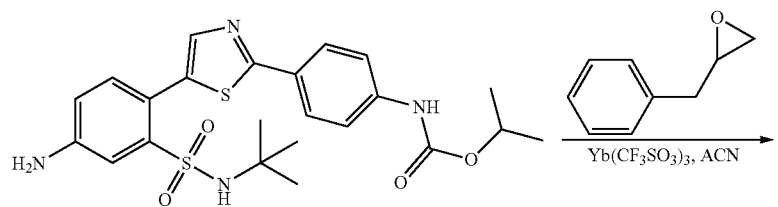
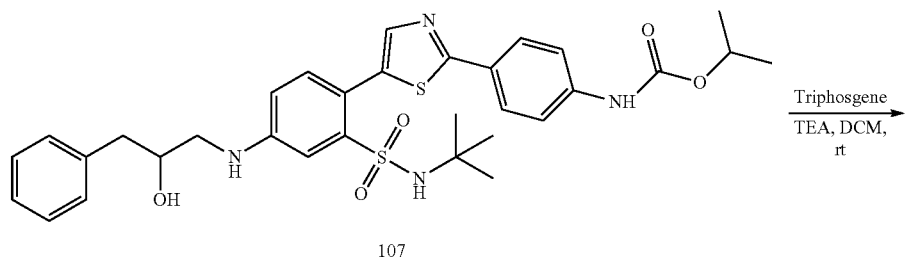
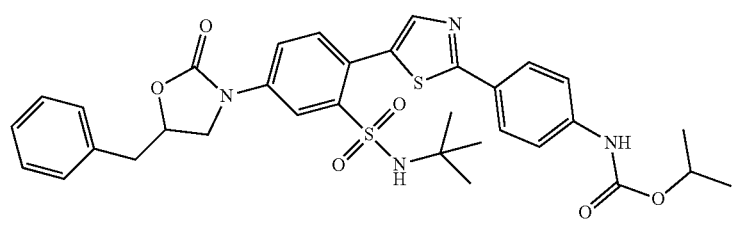

Preparation of compound 107.

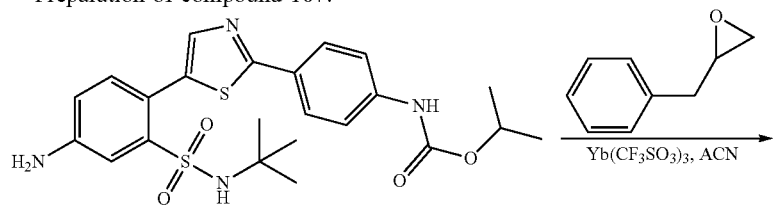

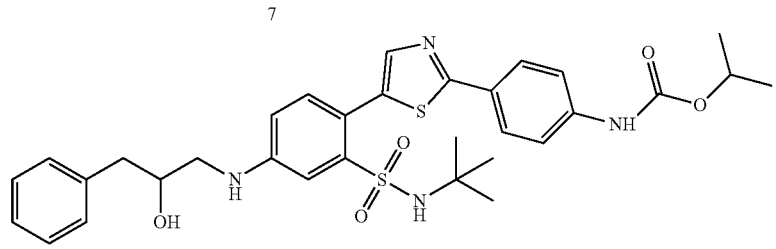

To a solution of isopropyl N-[4-[5-[4-amino-2-(tert-butylsulfamoyl)phenyl]thiazol-2-yl]phenyl]carbamate (200.00 mg, 409.32 μmol, 1.00 eq.) in ACN (5.00 mL) was added 2-benzyloxirane (219.67 mg, 1.64 mmol, 215.37 ul, 4.00 eq.) and tris(trifluoromethylsulfonyloxy)ytterbium (253.88 mg, 409.32 μmol, 1.00 eq.) and the mixture was stirred at 60° C. for 4 hrs. The mixture was concentrated and the residue was purified by acidic prep-HPLC to give isopropyl N-[4-[5-[2-(tert-butylsulfamoyl)-4-[(2-hydroxy-3-phenylpropyl)amino]phenyl]thiazol-2-yl]phenyl]carbamate (75.00 mg, 120.42 μmol, 29.42% yield) as a yellow solid. ESI [M+H]=623.1

Compound J27

Compound J27 was prepared from intermediate compound 107 via general method K (shown in Example 1).

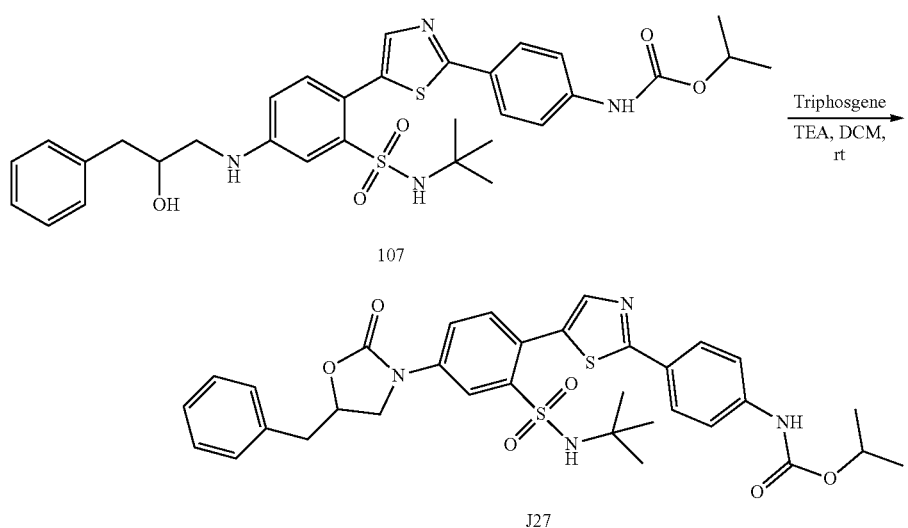 [SMILES: CC(C)OC(=O)Nc1ccc(-c2ncc(-c3ccc(NCC(O)Cc4ccccc4)cc3S(=O)(=O)NC(C)(C)C)s2)cc1 ; CC(C)OC(=O)Nc1ccc(-c2ncc(-c3ccc(N4CC(Cc5ccccc5)OC4=O)cc3S(=O)(=O)NC(C)(C)C)s2)cc1]

General method K, isopropyl (4-(5-(4-(5-benzyl-2-oxooxazolidin-3-yl)-2-(N-(tert-butyl) sulfamoyl)phenyl)thiazol-2-yl)phenyl)carbamate, $^1$H NMR (400 MHz, DMSO-d6) δ=9.88 (s, 1H), 8.41 (s, 1H), 7.94-7.80 (m, 3H), 7.67-7.59 (m, 3H), 7.55 (d, J=8.4 Hz, 1H), 7.34 (d, J=4.6 Hz, 4H), 7.29 (br d, J=17.4 Hz, 2H), 5.08-4.97 (m, 1H), 4.92 (td, J=6.3, 12.4 Hz, 1H), 4.20 (t, J=8.9 Hz, 1H), 3.88 (br t, J=7.9 Hz, 1H), 3.11 (d, J=6.2 Hz, 2H), 1.27 (d, J=6.2 Hz, 6H), 1.08 (s, 9H). ESI [M+H]=649.2

Compound J28
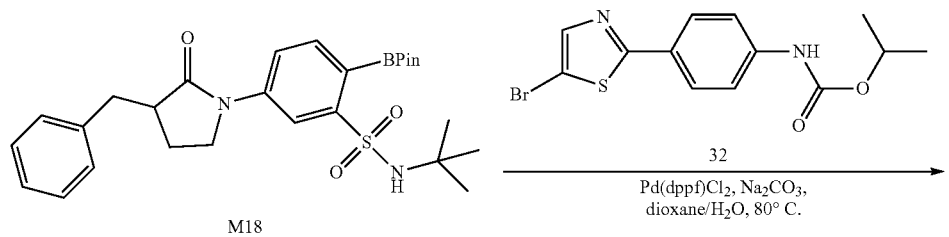
M18
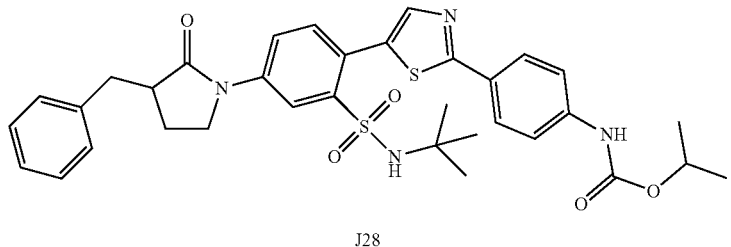
J28
General method A, isopropyl (4-(5-(4-(3-benzyl-2-oxopyrrolidin-1-yl)-2-(N-(tert-butyl)sulfamoyl)phenyl)thiazol-2-yl)phenyl)carbamate. ¹H NMR (400 MHz, DMSO-d6) δ=9.86 (s, 1H), 8.64 (d, J=2.2 Hz, 1H), 7.91-7.84 (m, 3H), 7.78 (dd, J=2.3, 8.4 Hz, 1H), 7.59 (dd, J=8.6, 19.4 Hz, 3H), 7.34-7.19 (m, 6H), 4.92 (spt, J=6.2 Hz, 1H), 3.83-3.65 (m, 2H), 3.15 (dd, J=4.2, 13.6 Hz, 1H), 3.02 (dq, J=4.2, 9.1 Hz, 1H), 2.76 (dd, J=9.4, 13.5 Hz, 1H), 2.16-2.07 (m, 1H), 1.89-1.78 (m, 1H), 1.28 (d, J=6.2 Hz, 6H), 1.11 (s, 9H). ESI [M+H]=647.2
Scheme 10.22
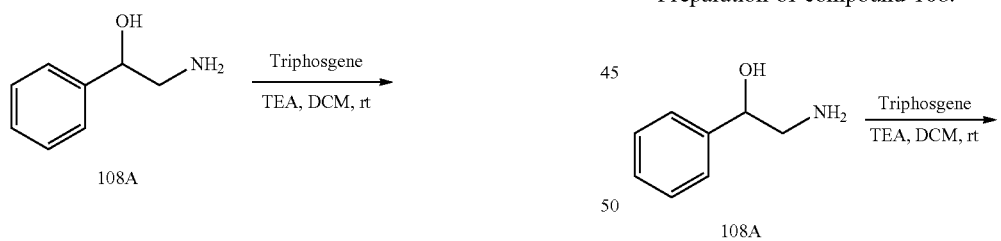
-continued
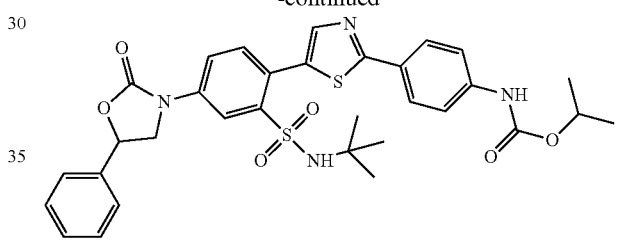
J29
Preparation of compound 108.
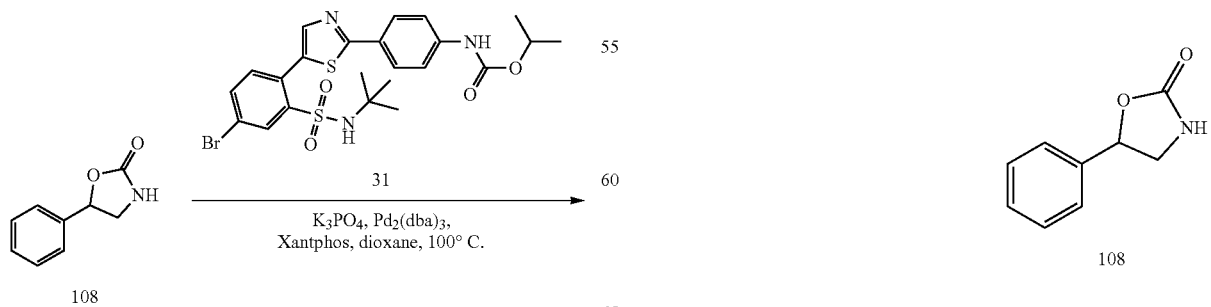
General method K, 5-phenyloxazolidin-2-one. ESI [M+H]=164.1

Compound J29

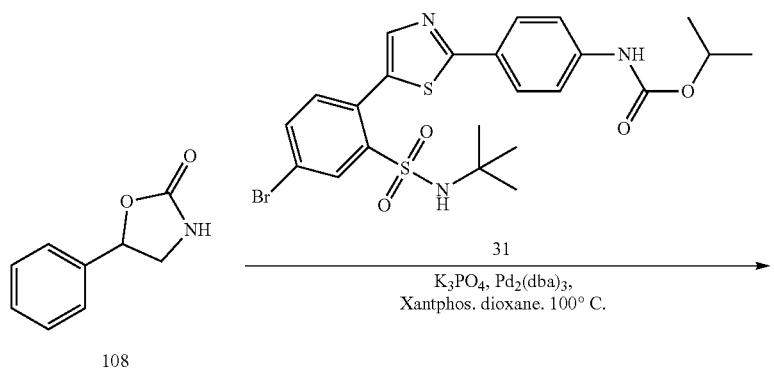

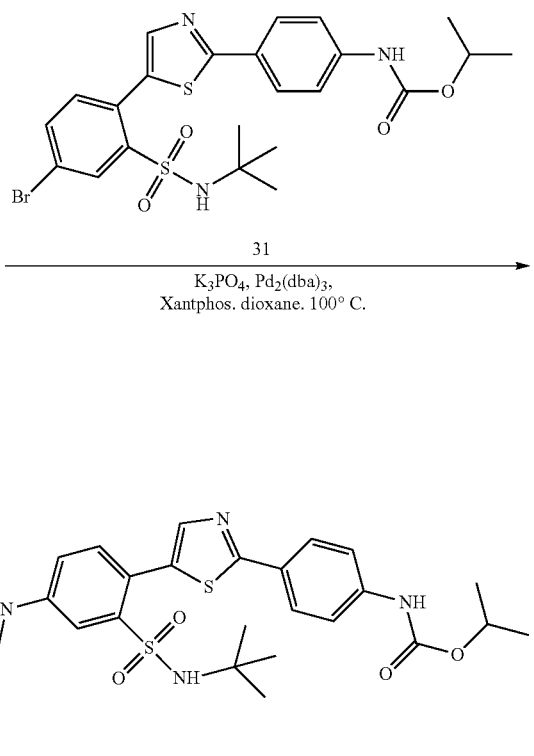

A mixture of isopropyl N-[4-[5-[4-bromo-2-(tert-butylsulfamoyl)phenyl]thiazol-2-yl]phenyl]carbamate (40.00 mg, 72.40 µmol, 1.00 eq.), 5-phenyloxazolidin-2-one (40.05 mg, 245.44 µmol, 3.39 eq.), Pd$_2$(dba)$_3$ (6.63 mg, 7.24 µmol, 0.10 eq.), K$_3$PO$_4$ (46.11 mg, 217.20 mol, 3.00 eq.) and Xantphos (4.19 mg, 7.24 µmol, 0.10 eq.) in dioxane (3.00 mL) was degassed and purged with N$_2$ for 3 times, stirred at 100° C. for 16 hrs under N$_2$ atmosphere. The mixture was poured into water (30 mL) and the aqueous phase was extracted with EtOAc (30 mL×3). The combined organic phase was dried, filtered and concentrated and the residue was purified by acidic prep-HPLC to give isopropyl N-[4-[5-[2-(tert-butylsulfamoyl)-4-(2-oxo-5-phenyl-oxazolidin-3-yl)-phenyl]thiazol-2-yl]phenyl]carbamate (28.54 mg, 44.96 mol, 62.10% yield, 100% purity) as a yellow solid. $^1$H NMR (400 MHz, METHANOL-d4) δ=9.42 (br s, 1H), 8.64 (br s, 1H), 7.88 (br s, 2H), 7.75 (br d, J=7.5 Hz, 1H), 7.62-7.54 (m, 1H), 7.57 (br d, J=7.7 Hz, 2H), 7.54-7.49 (m, 1H), 7.51 (br s, 1H), 7.46 (br d, J=7.5 Hz, 3H), 5.79 (br t, J=7.7 Hz, 1H), 5.00-4.93 (m, 1H), 4.58 (br t, J=8.8 Hz, 1H), 4.09 (br t, J=8.2 Hz, 1H), 1.31 (br d, J=6.0 Hz, 6H), 1.15 (s, 9H). ESI [M+H]=635.1

Example 11

The following compounds were synthesized via reacting intermediate compound 32 with different boronic esters via general method A (shown in Example 1), unless otherwise noted.

Compound K1

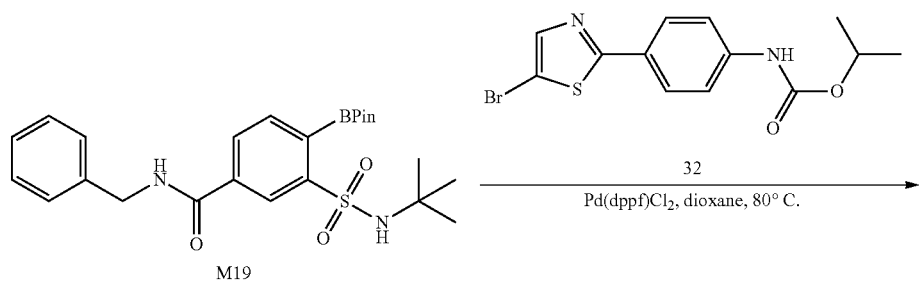

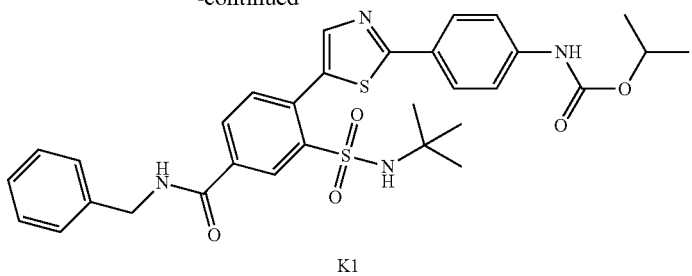
¹H NMR (400 MHz, METHANOL-d4) δ=8.67 (s, 1H), 8.08 (d, J=7.9 Hz, 1H), 7.96 (s, 1H), 7.90 (d, J=8.6 Hz, 2H), 7.67 (d, J=7.9 Hz, 1H), 7.58 (d, J=8.6 Hz, 2H), 7.41-7.30 (m, 4H), 7.29-7.21 (m, 1H), 4.97 (td, J=6.4, 12.3 Hz, 1H), 4.61 (s, 2H), 1.31 (d, J=6.4 Hz, 6H), 1.10 (s, 9H). ESI [M+H]=607.1
Compound K2
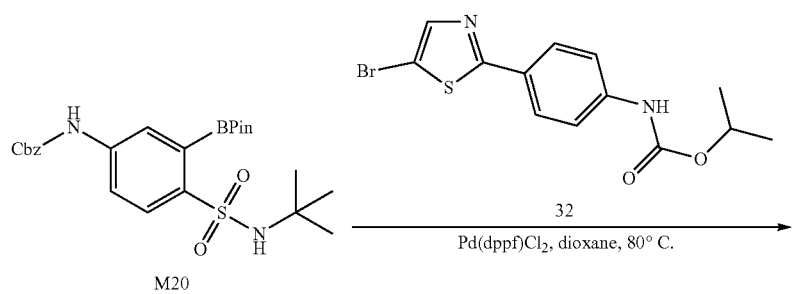
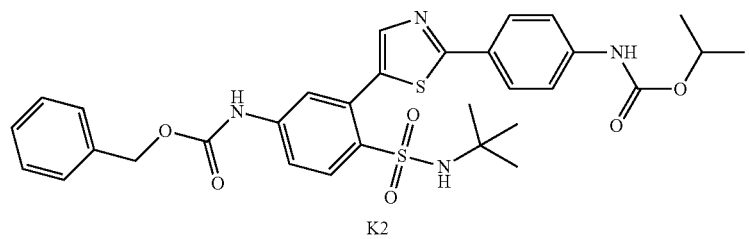
¹H NMR (400 MHz, METHANOL-d4) δ=8.08 (d, J=8.8 Hz, 1H), 7.96-7.86 (m, 3H), 7.76-7.65 (m, 2H), 7.59 (d, J=8.8 Hz, 2H), 7.49-7.42 (m, 2H), 7.41-7.29 (m, 3H), 5.23 (s, 2H), 5.00 (td, J=6.2, 12.6 Hz, 1H), 1.33 (d, J=6.4 Hz, 6H), 1.11 (s, 9H). ESI [M+H]=623.2
Example 12
Scheme 12.1
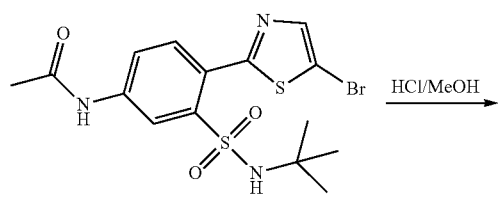

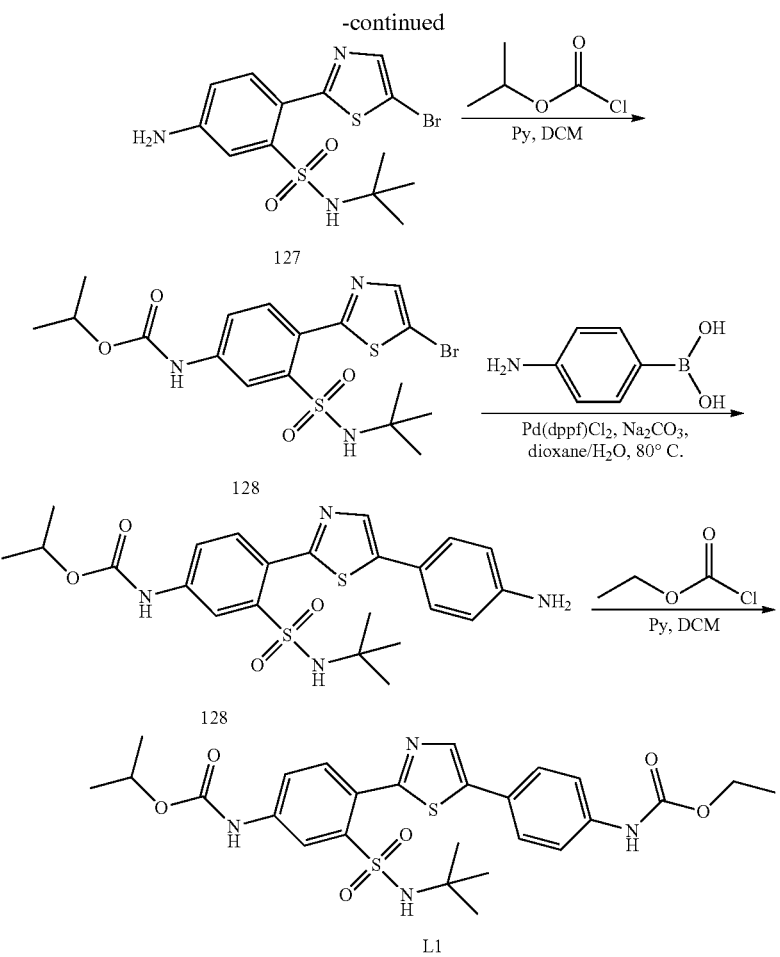

Preparation of compound 127.

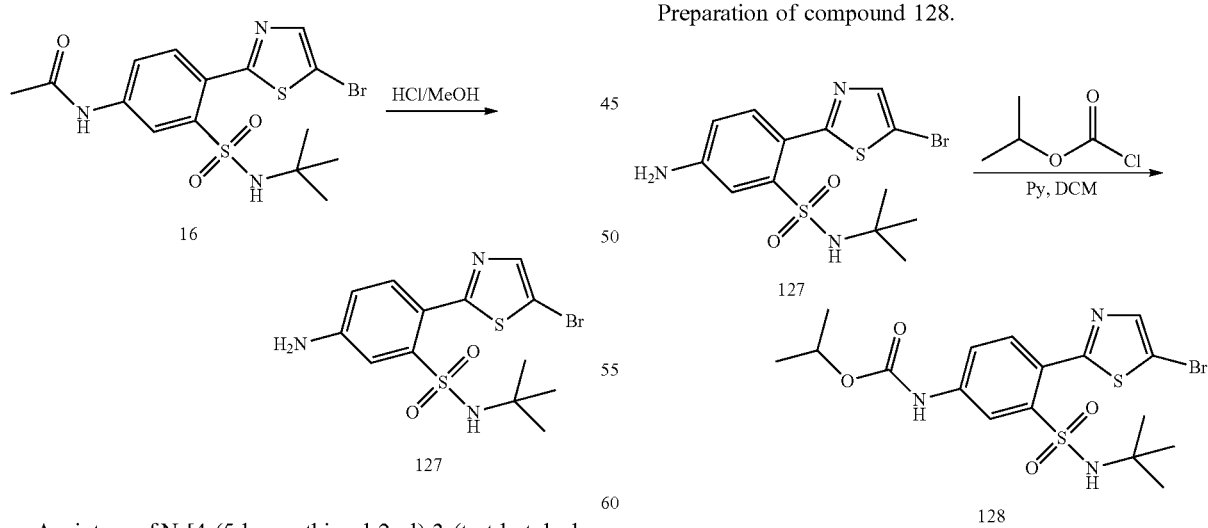

A mixture of N-[4-(5-bromothiazol-2-yl)-3-(tert-butylsulfamoyl)phenyl]acetamide (200.00 mg, 462.58 μmol, 1.00 eq.) in HCl/MeOH (5.00 mL, 4 M) was stirred at 40° C. for 20 mins, and then concentrated. The residue was partitioned between EtOAc (10 mL) and sat.aq.NaHCO₃ (10 mL). The organic layer was dried, filtered and concentrated to give 5-amino-2-(bromothiazol-2-yl)-N-tert-butyl-benzene-sulfonamide (200.00 mg, crude) as a yellow oil, which was used directly. ESI [M+H]=389.9/391.9

Preparation of compound 128.

General method C, isopropyl (4-(5-bromothiazol-2-yl)-3-(N-(tert-butyl)sulfamoyl)phenyl) carbamate. ESI [M+H]=475.9/477.9

Preparation of compound 129.

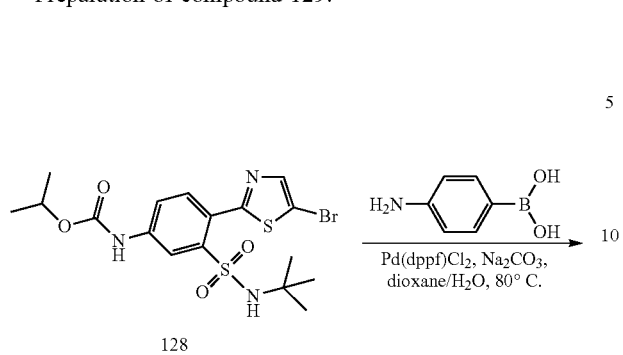

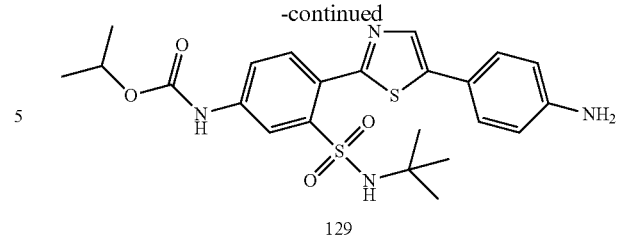

General method A, isopropyl (4-(5-(4-aminophenyl)thiazol-2-yl)-3-(N-(tert-butyl)sulfamoyl) phenyl)carbamate. ESI [M+H]=489.1

Compound L1

Compound L1 was prepared from intermediate compound 129 via general method C (shown in Example 1).

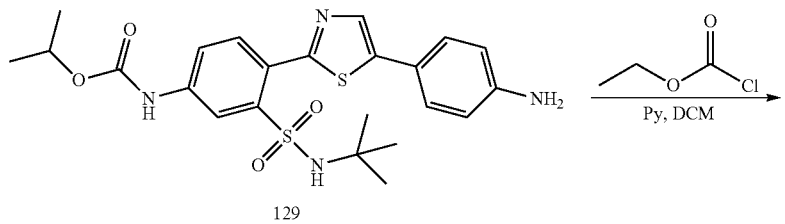

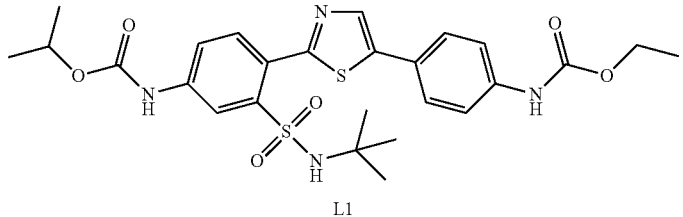

$^1$H NMR (400 MHz, DMSO-d6) δ=10.19 (s, 1H), 9.86 (s, 1H), 8.37 (s, 1H), 8.28 (s, 1H), 7.81 (s, 1H), 7.78-7.73 (m, 2H), 7.68-7.63 (m, 2H), 7.57 (d, J=8.6 Hz, 2H), 4.94 (spt, J=6.2 Hz, 1H), 4.15 (q, J=7.1 Hz, 2H), 1.30-1.23 (m, 9H), 1.20 (s, 9H). ESI [M+H]=561.2

Compound L2

Compound L2 was prepared from intermediate compound 129 via general method C (shown in Example 1).

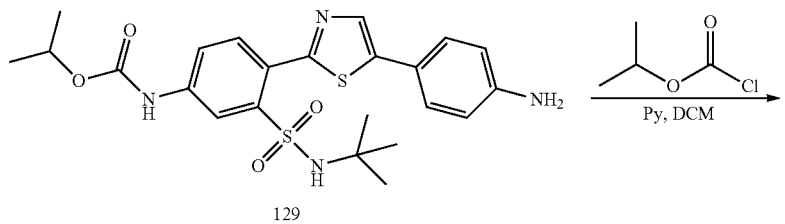

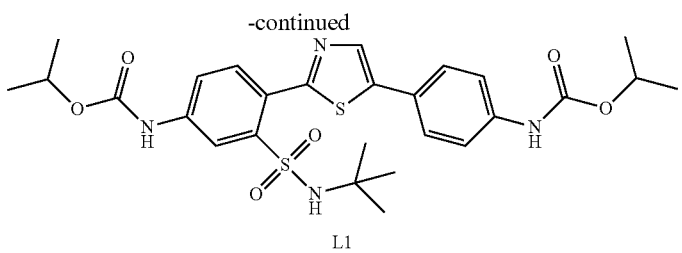

<sup>1</sup>H NMR (400 MHz, DMSO-d6) δ=10.19 (s, 1H), 9.80 (s, 1H), 8.37 (s, 1H), 8.28 (s, 1H), 7.81 (s, 1H), 7.76 (s, 2H), 7.68-7.63 (m, 2H), 7.59-7.53 (m, 2H), 5.00-4.85 (m, 2H), 1.28 (t, J=6.4 Hz, 12H), 1.20 (s, 9H). ESI [M+H]=575.2

Compound L3

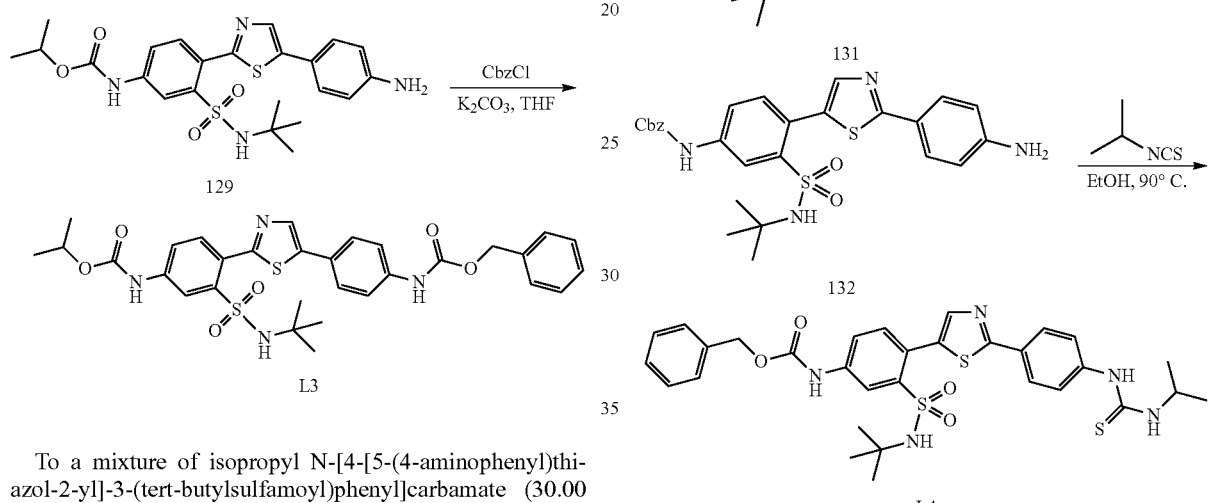

To a mixture of isopropyl N-[4-[5-(4-aminophenyl)thiazol-2-yl]-3-(tert-butylsulfamoyl)phenyl]carbamate (30.00 mg, 61.40 μmol, 1.00 eq.) and K$_2$CO$_3$ (20.00 mg, 144.71 μmol, 2.36 eq.) in THF (2.00 mL) and H$_2$O (500.00 ul) was added CbzCl (15.00 mg, 87.93 μmol, 1.43 eq.). The mixture was stirred at 15° C. for 1 hr and then concentrated. The residue was purified by acidic prep-HPLC to give isopropyl N-[4-[5-[4-(benzyloxycarbonylamino)phenyl]thiazol-2-yl]-3-(tert-butylsulfamoyl)phenyl]carbamate (30.92 mg, 49.45 μmol, 80.54% yield, 99.596% purity) as a pale yellow solid. <sup>1</sup>H NMR (400 MHz, DMSO-d6) δ=10.19 (s, 1H), 10.01 (s, 1H), 8.37 (s, 1H), 8.29 (s, 1H), 7.81 (s, 1H), 7.76 (s, 2H), 7.70-7.65 (m, 2H), 7.58 (d, J=8.8 Hz, 2H), 7.47-7.33 (m, 5H), 5.18 (s, 2H), 5.02-4.84 (m, 1H), 1.28 (d, J=6.2 Hz, 6H), 1.20 (s, 9H). ESI [M+H]=623.2

Scheme 12.2

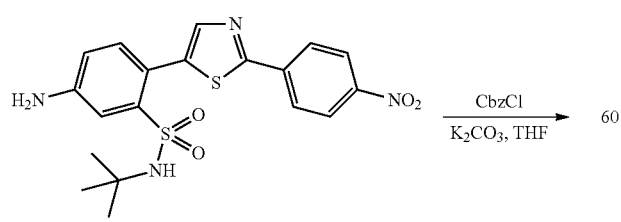

Preparation of compound 131.

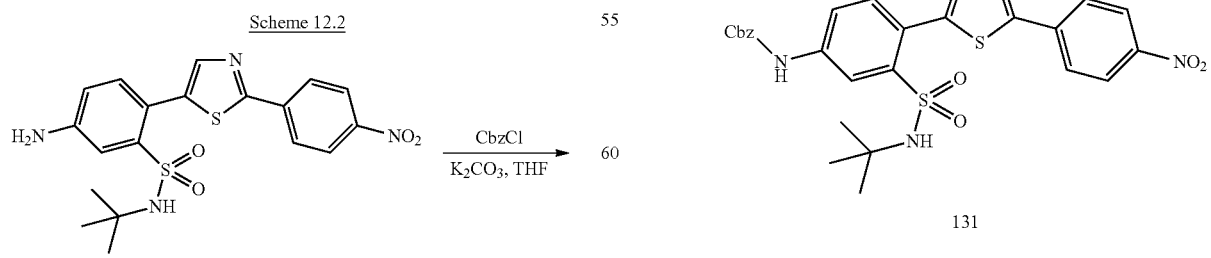

To a solution of 5-amino-N-tert-butyl-2-[2-(4-nitrophenyl)thiazol-5-yl]benzenesulfonamide (100.00 mg, 231.20 μmol, 1.00 eq.) in THF (3.00 mL) was added K$_2$CO$_3$ (63.91 mg, 462.41 μmol, 2.00 eq.) and benzyl carbonochloridate (197.20 mg, 1.16 mmol, 164.34 ul, 5.00 eq.). The mixture was stirred at 20° C. for 0.5 hr, then concentrated and purified by prep-TLC (SiO₂, Petroleum ether:EtOAc=2:1) to give benzyl N-[3-(tert-butylsulfamoyl)-4-[2-(4-nitrophenyl)thiazol-5-yl]phenyl]carbamate (90.00 mg) as a yellow solid.

Preparation of compound 132.

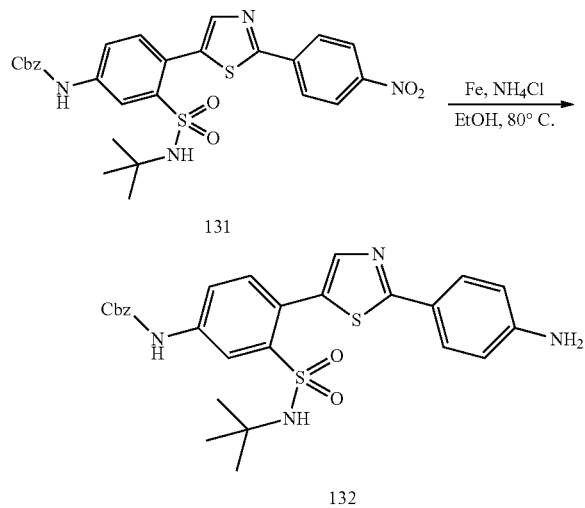

General method B, benzyl (4-(2-(4-aminophenyl)thiazol-5-yl)-3-(N-(tert-butyl)sulfamoyl)phenyl)carbamate. ESI [M+H]=537.2

Compound L4

Compound L4 was prepared from intermediate compound 132 via general method G (shown in Example 1).

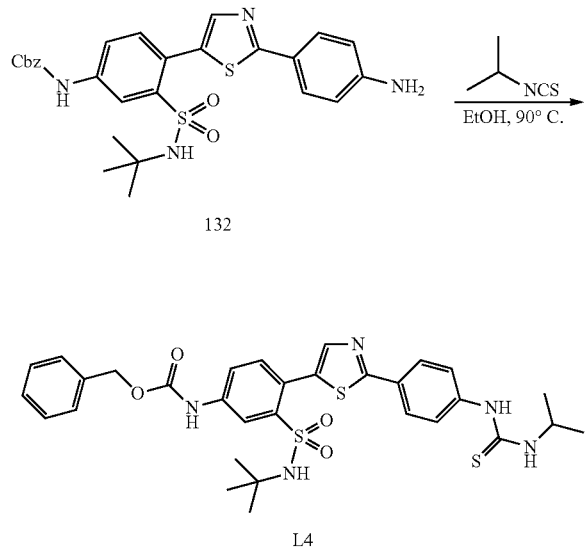

¹H NMR (400 MHz, METHANOL-d4) δ=8.41 (d, J=1.7 Hz, 1H), 7.95 (d, J=8.7 Hz, 2H), 7.90 (s, 1H), 7.79-7.71 (m, 1H), 7.60 (d, J=8.6 Hz, 2H), 7.50-7.45 (m, 3H), 7.43-7.34 (m, 3H), 5.25 (s, 2H), 4.56 (br s, 1H), 1.27 (d, J=6.6 Hz, 6H), 1.16 (s, 9H). ESI [M+H]=638.2

Scheme 12.3

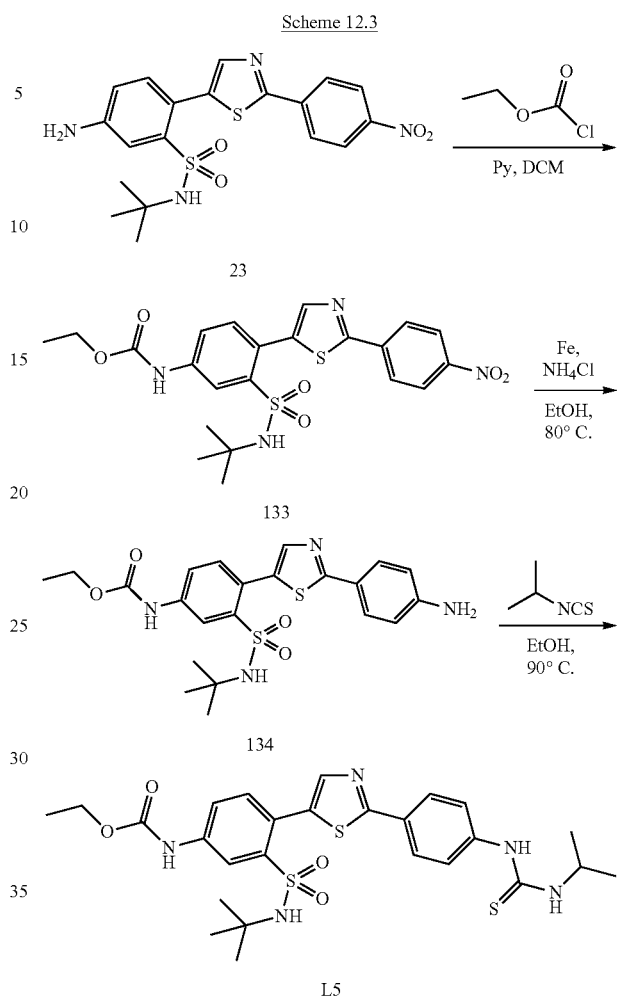

Preparation of compound 133.

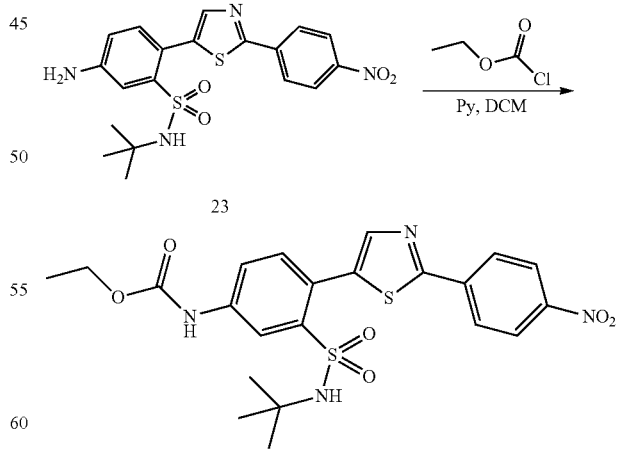

General method C, ethyl (3-(N-(tert-butyl)sulfamoyl)-4-(2-(4-nitrophenyl)thiazol-5-yl)phenyl)carbamate. ESI [M+H]=505.0

Preparation of compound 134.

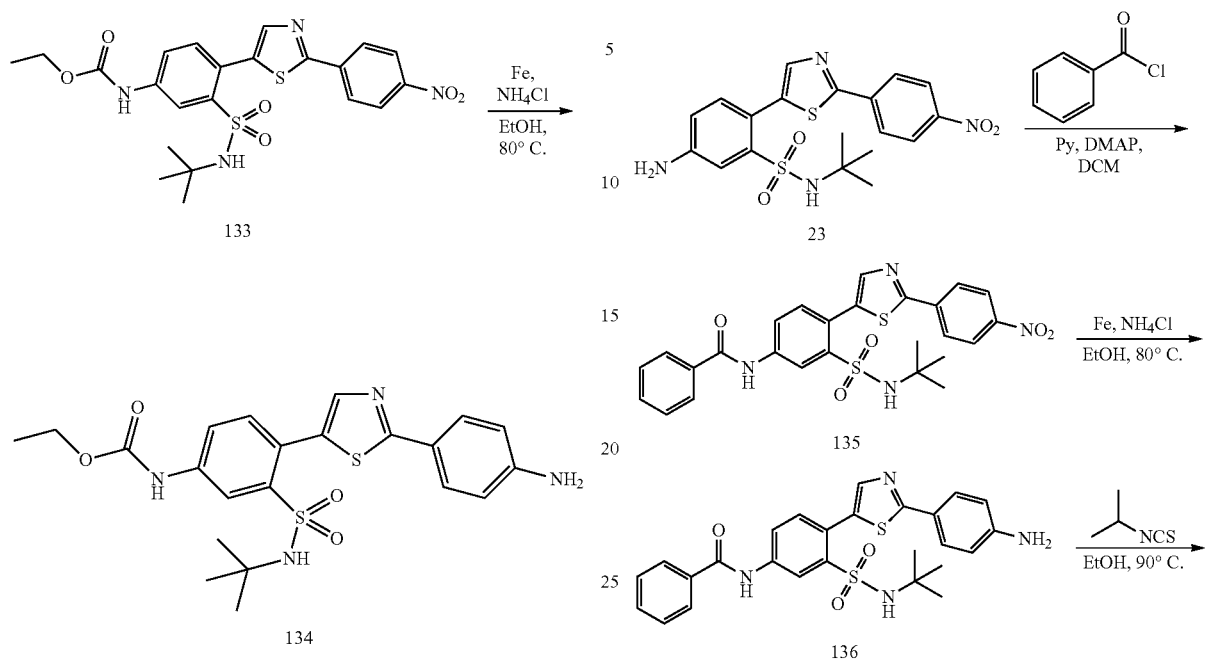

General method B, ethyl (4-(2-(4-aminophenyl)thiazol-5-yl)-3-(N-(tert-butyl)sulfamoyl)phenyl)carbamate. ESI [M+H]=475.0

Compound L5

Compound L5 was prepared from intermediate compound 134 via general method G (shown in Example 1).

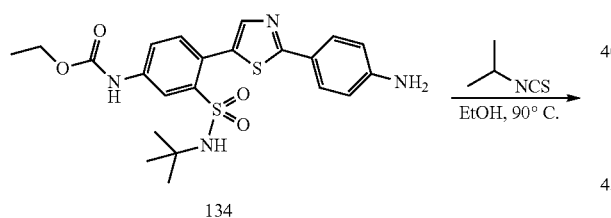

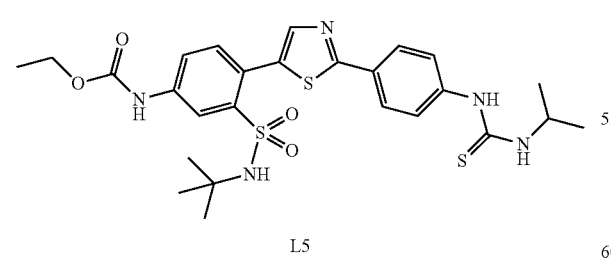

$^1$H NMR (400 MHz, DMSO-d$_6$) δ=10.18 (br s, 1H), 9.58 (br s, 1H), 8.35 (br s, 1H), 7.88 (br d, J=10.1 Hz, 4H), 7.76-7.59 (m, 3H), 7.49 (br s, 1H), 7.18 (br s, 1H), 4.39 (br s, 1H), 4.18 (br s, 2H), 1.27 (br d, J=7.0 Hz, 3H), 1.19 (br s, 6H), 1.09 (br s, 9H). ESI [M+H]=576.2

Preparation of compound 135.

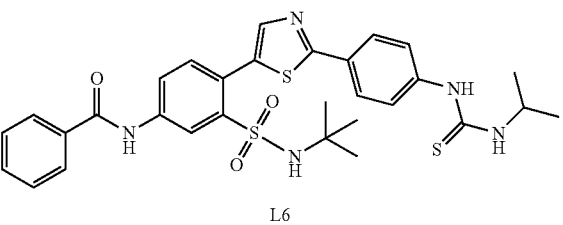

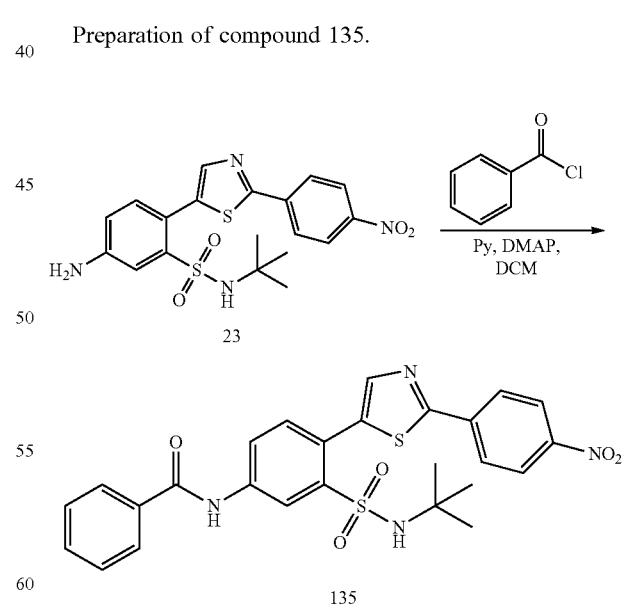

General method C, N-(3-(N-(tert-butyl)sulfamoyl)-4-(2-(4-nitrophenyl)thiazol-5-yl)phenyl) benzamide. ESI [M+H]=537.3

Preparation of compound 136.

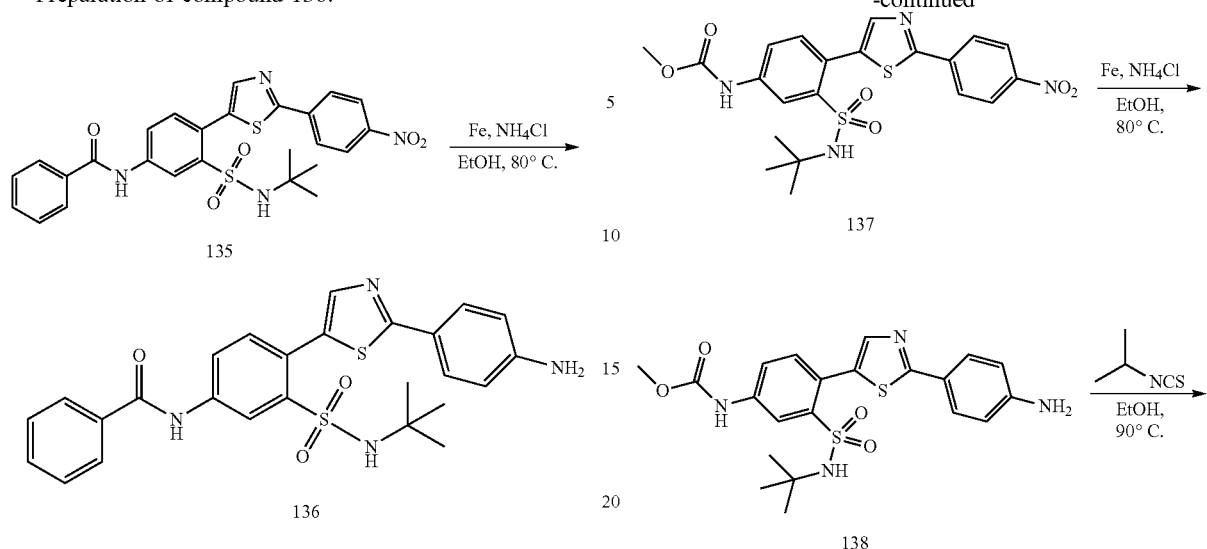

General method B, N-(4-(2-(4-aminophenyl)thiazol-5-yl)-3-(N-(tert-butyl)sulfamoyl)phenyl)benzamide. Compound L6

Compound L6 was prepared from intermediate compound 136 via general method G (shown in Example 1).

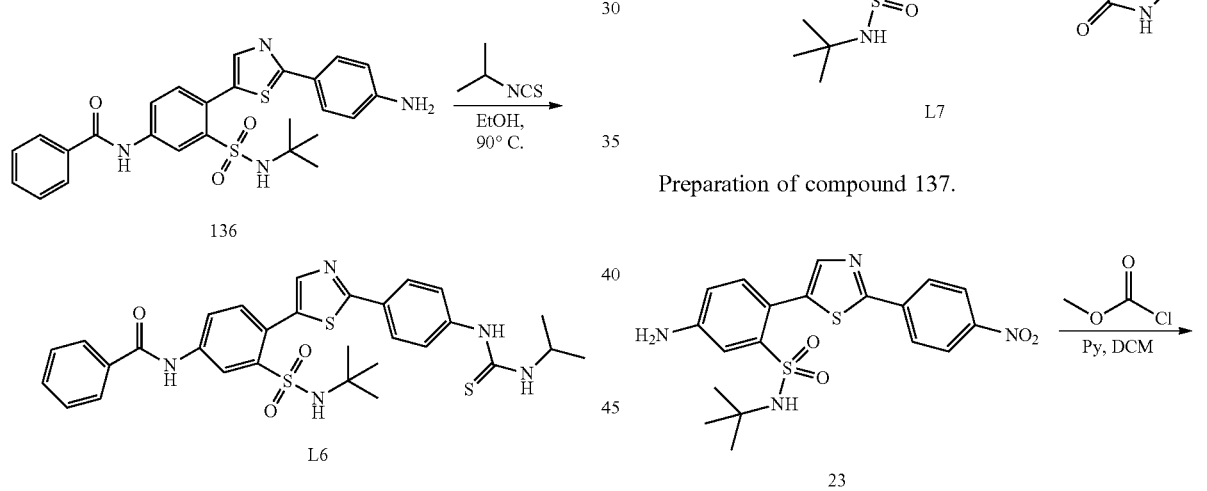

¹H NMR (400 MHz, METHANOL-d4) δ=8.69 (1H, s), 7.89-8.10 (6H, m), 7.49-7.62 (6H, m), 4.54 (1H, br s), 1.25 (6H, d, J=6.4 Hz), 1.16 (9H, s). ESI [M+H]=608.2

Scheme 12.5

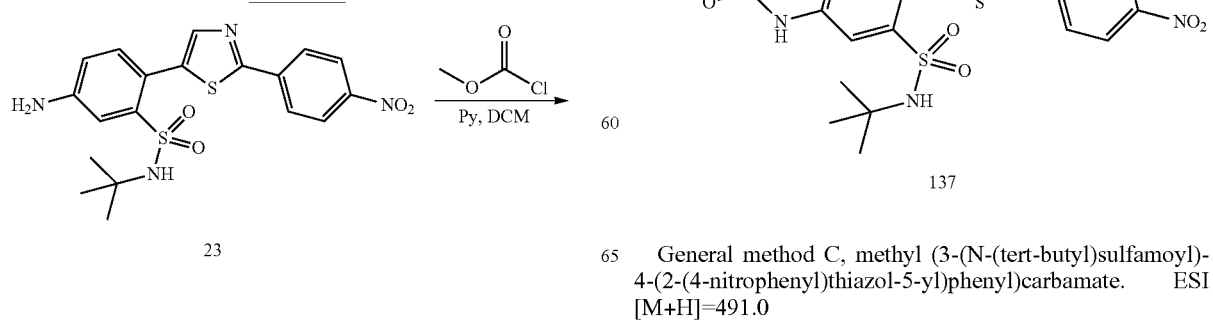

Preparation of compound 137.

General method C, methyl (3-(N-(tert-butyl)sulfamoyl)-4-(2-(4-nitrophenyl)thiazol-5-yl)phenyl)carbamate. ESI [M+H]=491.0

Preparation of compound 138.

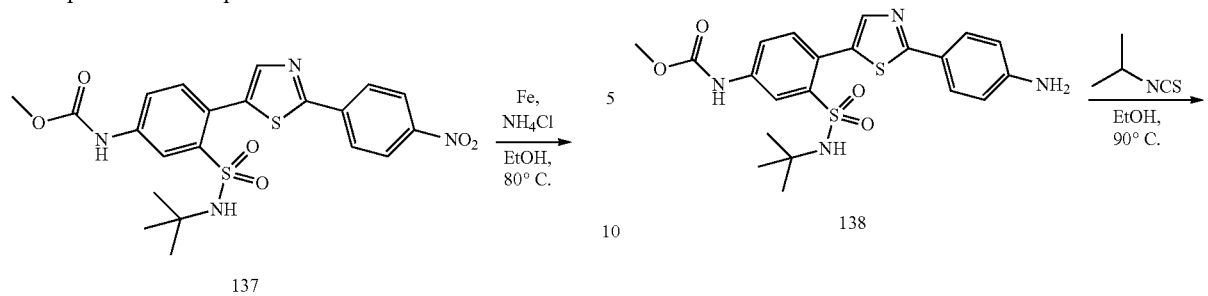

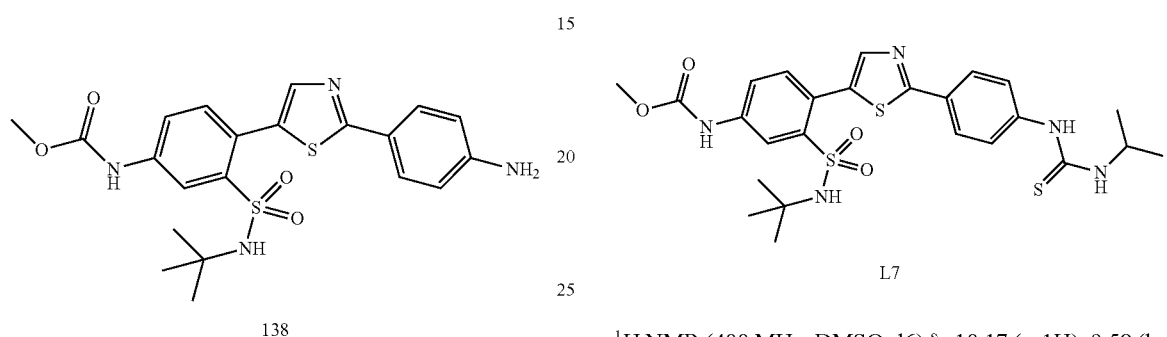

138

General method B, methyl (4-(2-(4-aminophenyl)thiazol-5-yl)-3-(N-(tert-butyl)sulfamoyl)phenyl)carbamate. ESI [M+H]=461.0

Compound L7

Compound L7 was prepared from intermediate compound 138 via general method G (shown in Example 1).

$^1$H NMR (400 MHz, DMSO-d6) δ=10.17 (s, 1H), 9.58 (br s, 1H), 8.34 (s, 1H), 7.93-7.80 (m, 4H), 7.74-7.61 (m, 3H), 7.50 (d, J=8.3 Hz, 1H), 7.17 (s, 1H), 4.40 (br d, J=5.9 Hz, 1H), 3.72 (s, 3H), 1.19 (d, J=6.5 Hz, 6H), 1.10 (s, 9H). ESI [M+H]=562.2

Compound L8

Compound L8 was prepared from intermediate compound 7 via general method G (shown in Example 1).

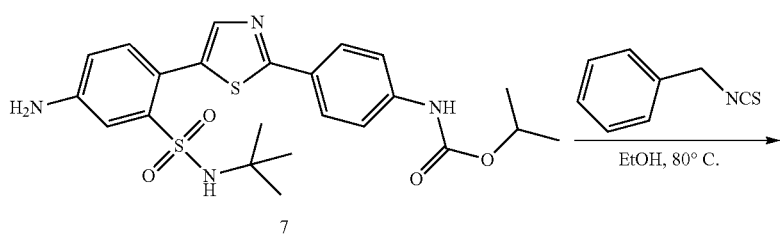

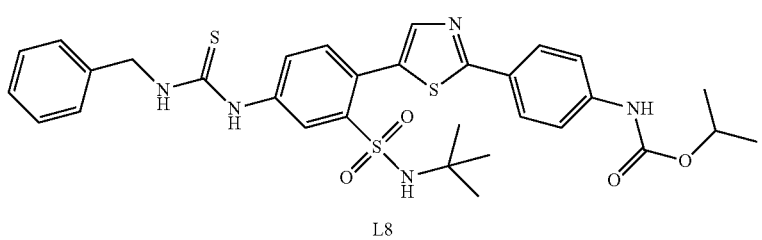

L8

$^1$H NMR (400 MHz, DMSO-d6) δ=10.05 (br s, 1H), 9.87 (s, 1H), 8.49-8.36 (m, 2H), 7.92-7.76 (m, 4H), 7.62 (br d, J=8.6 Hz, 2H), 7.49 (d, J=8.3 Hz, 1H), 7.40-7.33 (m, 4H), 7.29 (br d, J=3.1 Hz, 1H), 7.18 (s, 1H), 5.03-4.87 (m, 1H), 4.77 (br d, J=5.0 Hz, 2H), 1.28 (d, J=6.1 Hz, 6H), 1.11 (s, 9H). ESI [M+H]=638.2
Compound L9
Compound L9 was prepared from intermediate compound 7 via general method G (shown in Example 1).
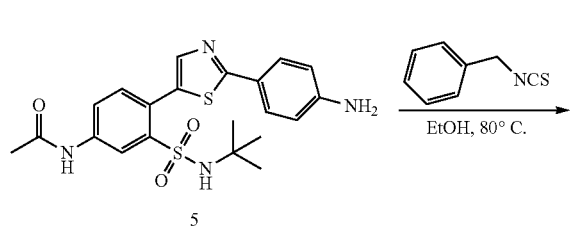
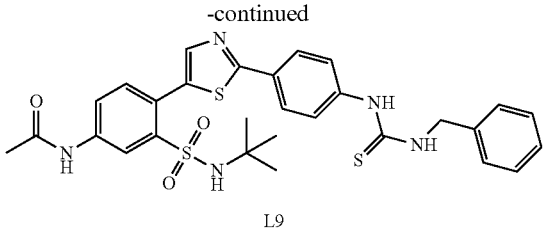
L9
$^1$H NMR (400 MHz, METHANOL-d4) δ=8.47 (s, 1H), 7.99-7.81 (m, 4H), 7.58 (d, J=8.6 Hz, 2H), 7.49 (d, J=8.2 Hz, 1H), 7.41-7.29 (m, 4H), 7.28-7.21 (m, 1H), 4.83 (br s, 2H), 2.17 (s, 3H), 1.13 (s, 9H). ESI [M+H]=594.2
Scheme 12.6
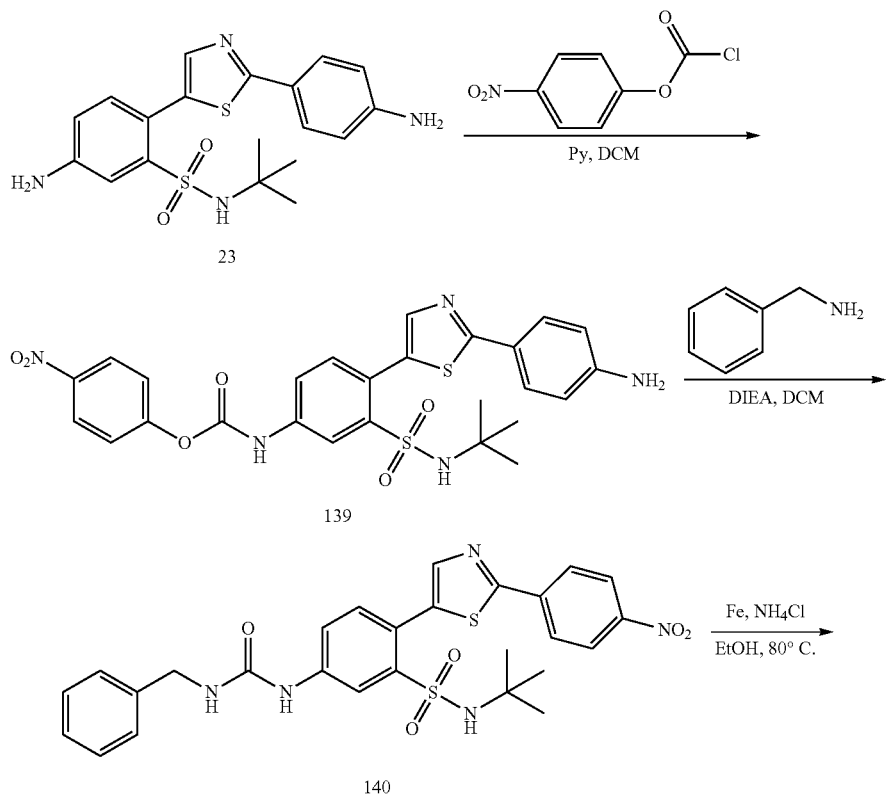
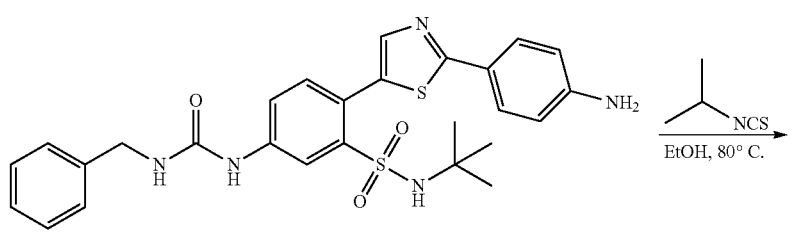

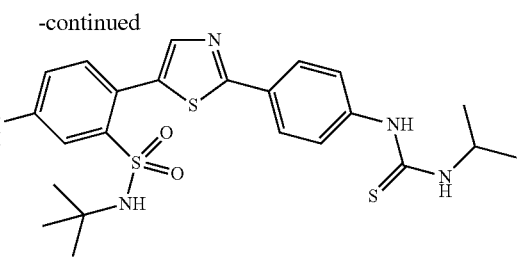

L10

Preparation of compound 139.

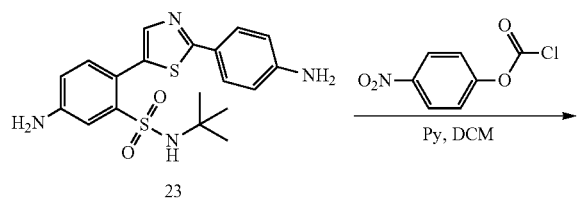

General method C, 4-nitrophenyl (3-(N-(tert-butyl)sulfamoyl)-4-(2-(4-nitrophenyl)thiazol-5-yl)phenyl)carbamate. ESI [M+H]=597.9

Preparation of compound 140.

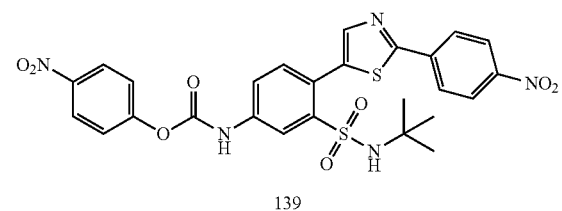

General method F, 5-(3-benzoylureido)-N-(tert-butyl)-2-(2-(4-nitrophenyl)thiazol-5-yl)benzenesulfonamide. ESI [M+H]=566.1

Preparation of compound 141.

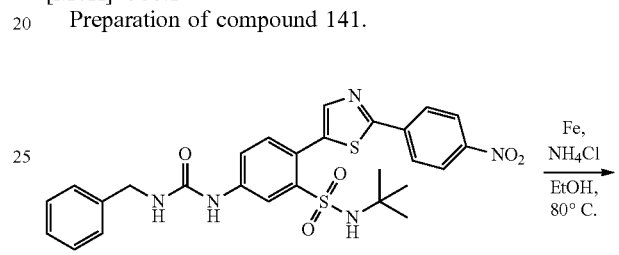

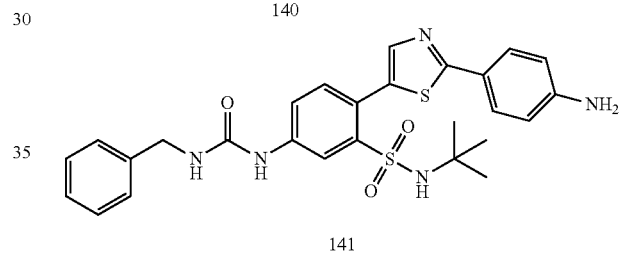

General method B, 2-(2-(4-aminophenyl)thiazol-5-yl)-5-(3-benzoylureido)-N-(tert-butyl)benzenesulfonamide. ESI [M+H]=536.3

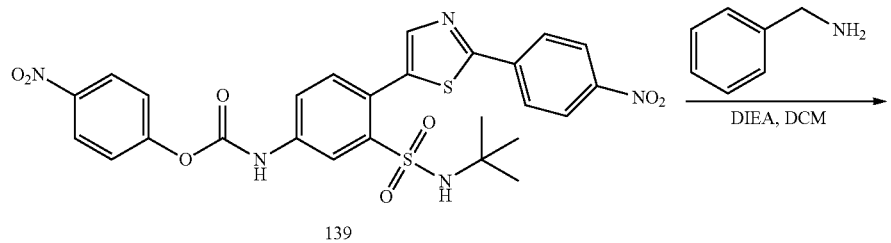

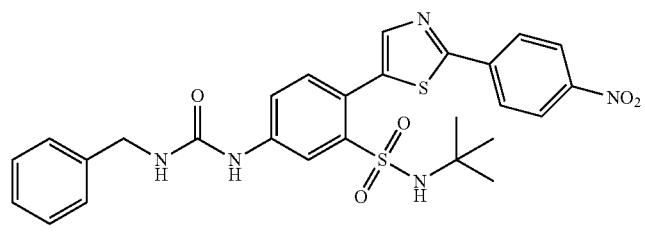

Compound L10

Compound L10 was prepared from intermediate compound 141 via general method G (shown in Example 1).

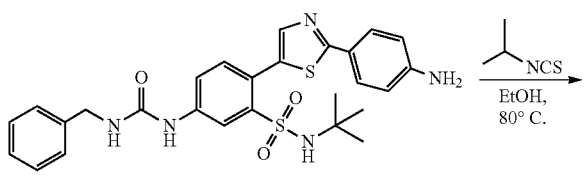

141

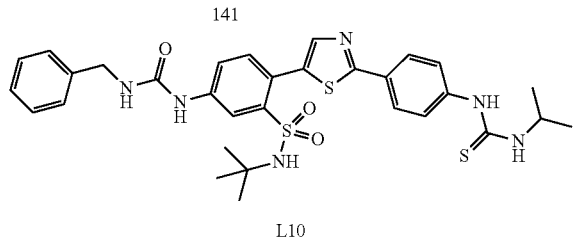

L10

$^1$H NMR (400 MHz, DMSO-d6) δ=9.56 (br s, 1H), 9.15 (s, 1H), 8.28 (d, J=2.2 Hz, 1H), 7.88 (d, J=8.7 Hz, 2H), 7.85-7.80 (m, 2H), 7.68-7.61 (m, 3H), 7.42 (d, J=8.3 Hz, 1H), 7.38-7.30 (m, 4H), 7.26 (dt, J=2.6, 6.1 Hz, 1H), 7.09 (s, 1H), 6.77 (br t, J=5.9 Hz, 1H), 4.45-4.36 (m, 1H), 4.33 (d, J=5.7 Hz, 2H), 1.19 (d, J=6.5 Hz, 6H), 1.08 (s, 9H). ESI [M+H]=637.3

Example 13

The following compounds were synthesized via reacting intermediate compound 139 with different amines and alcohols via general method F, B, G and E (shown in Example 1), unless otherwise noted.

Compound M1

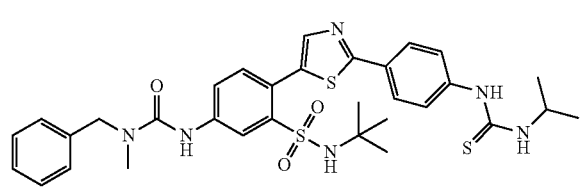

M1

$^1$H NMR (400 MHz, DMSO-d6) δ=9.57 (br s, 1H), 8.95 (s, 1H), 8.39 (d, J=2.2 Hz, 1H), 7.91-7.81 (m, 5H), 7.64 (d, J=8.7 Hz, 2H), 7.44 (d, J=8.4 Hz, 1H), 7.40-7.34 (m, 2H), 7.29 (br d, J=6.6 Hz, 3H), 7.02 (s, 1H), 4.59 (s, 2H), 4.40 (br d, J=6.7 Hz, 1H), 2.95 (s, 3H), 1.19 (d, J=6.6 Hz, 6H), 1.07 (s, 9H). ESI [M+H]=651.3

Compound M2

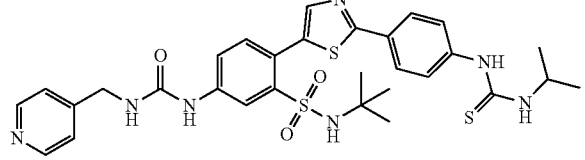

M2

$^1$H NMR (400 MHz, METHANOL-d4) δ=8.80 (d, J=6.5 Hz, 2H), 8.36 (d, J=2.2 Hz, 1H), 8.06 (d, J=6.4 Hz, 2H), 7.94 (d, J=8.6 Hz, 2H), 7.89 (s, 1H), 7.73 (dd, J=2.3, 8.4 Hz, 1H), 7.61 (d, J=8.6 Hz, 2H), 7.47 (d, J=8.3 Hz, 1H), 4.73 (s, 2H), 4.56 (br s, 1H), 1.27 (d, J=6.5 Hz, 6H), 1.13 (s, 9H). ESI [M+H]=638.3

Compound M3

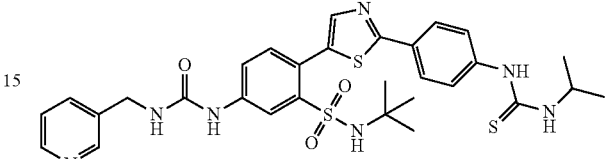

M3

$^1$H NMR (400 MHz, DMSO-d6) δ=9.61 (br s, 1H), 9.44 (s, 1H), 8.83-8.66 (m, 2H), 8.31-8.22 (m, 2H), 7.94-7.76 (m, 5H), 7.64 (br d, J=8.4 Hz, 3H), 7.42 (br d, J=8.3 Hz, 2H), 7.08 (s, 2H), 4.52-4.33 (m, 3H), 1.18 (d, J=6.5 Hz, 6H), 1.06 (s, 9H). ESI [M+H]=638.2

Compound M4

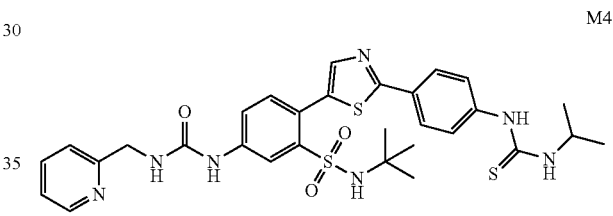

M4

$^1$H NMR (400 MHz, DMSO-d6) δ=9.57 (br s, 1H), 9.48 (s, 1H), 8.64 (br d, J=5.3 Hz, 1H), 8.27 (d, J=2.2 Hz, 1H), 8.07 (br t, J=7.5 Hz, 1H), 7.89-7.81 (m, 4H), 7.67-7.57 (m, 4H), 7.54 (br d, J=6.4 Hz, 1H), 7.41 (d, J=8.4 Hz, 1H), 7.09 (s, 1H), 7.00 (br t, J=5.6 Hz, 1H), 4.52 (br d, J=5.5 Hz, 2H), 4.37 (br s, 1H), 1.16 (d, J=6.4 Hz, 6H), 1.05 (s, 9H). ESI [M+H]=638.1

Compound M5

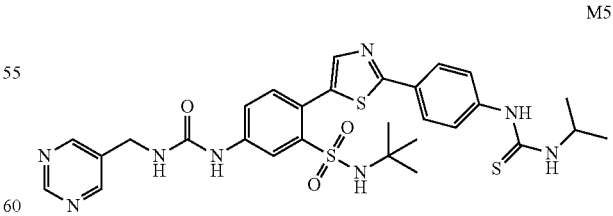

M5

$^1$H NMR (400 MHz, DMSO-d6) δ=9.60 (br s, 1H), 9.34 (s, 1H), 9.10 (s, 1H), 8.78 (s, 2H), 8.28 (d, J=2.1 Hz, 1H), 7.92-7.82 (m, 4H), 7.69-7.61 (m, 3H), 7.45-7.39 (m, 1H), 7.10 (s, 1H), 7.03-6.95 (m, 1H), 4.45-4.33 (m, 3H), 1.19 (d, J=6.6 Hz, 6H), 1.08 (s, 9H). ESI [M+H]=639.2

Compound M6
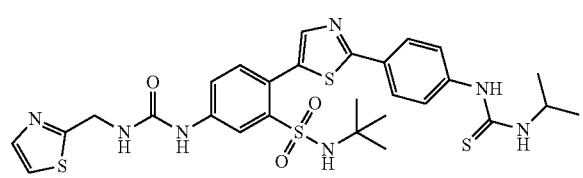
¹H NMR (400 MHz, DMSO-d6) δ=9.60 (br s, 1H), 9.43 (s, 1H), 8.31 (d, J=2.1 Hz, 1H), 7.94-7.82 (m, 4H), 7.75 (d, J=3.2 Hz, 1H), 7.71-7.62 (m, 4H), 7.44 (d, J=8.4 Hz, 1H), 7.20-7.09 (m, 2H), 4.63 (br d, J=5.9 Hz, 2H), 4.40 (br d, J=6.2 Hz, 1H), 1.19 (d, J=6.5 Hz, 6H), 1.09 (s, 9H). ESI [M+H]=644.1
Compound M7
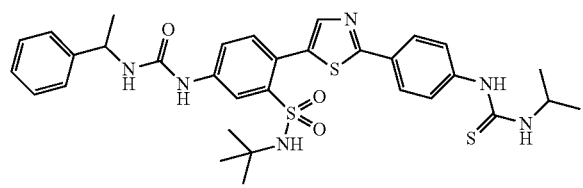
¹H NMR (400 MHz, METHANOL-d4) δ=8.22 (d, J=2.2 Hz, 1H), 7.91 (d, J=8.8 Hz, 2H), 7.85 (s, 1H), 7.68 (dd, J=2.4, 8.4 Hz, 1H), 7.56 (d, J=8.6 Hz, 2H), 7.45-7.32 (m, 5H), 7.28-7.21 (m, 1H), 4.93 (q, J=6.8 Hz, 1H), 4.53 (br s, 1H), 1.49 (d, J=7.1 Hz, 3H), 1.24 (d, J=6.6 Hz, 6H), 1.11 (s, 9H). ESI [M+H]=651.2
Compound M8
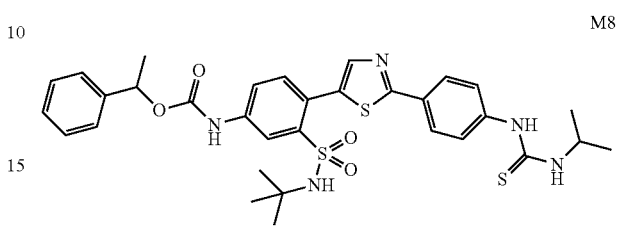
¹H NMR (400 MHz, METHANOL-d4) δ=8.35 (d, J=2.0 Hz, 1H), 7.91 (d, J=8.6 Hz, 2H), 7.86 (s, 1H), 7.70 (br d, J=8.4 Hz, 1H), 7.57 (d, J=8.6 Hz, 2H), 7.47-7.41 (m, 3H), 7.36 (t, J=7.4 Hz, 2H), 7.32-7.26 (m, 1H), 5.87 (q, J=6.6 Hz, 1H), 4.53 (br s, 1H), 1.59 (d, J=6.6 Hz, 3H), 1.24 (d, J=6.6 Hz, 6H), 1.12 (s, 9H). ESI [M+H]=652.2
Example 14
Scheme 14.1
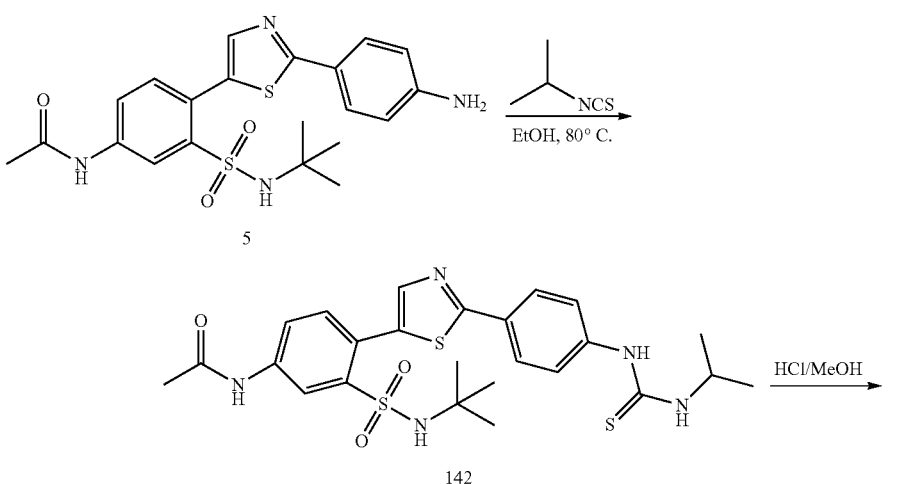
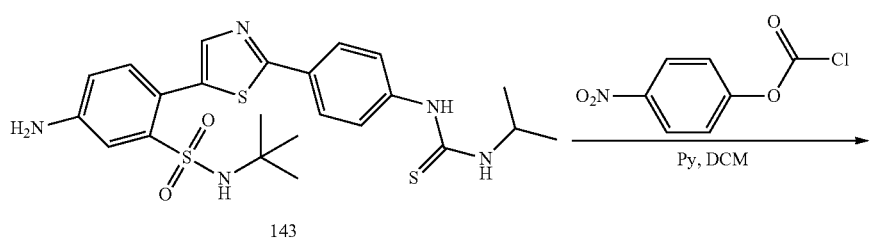

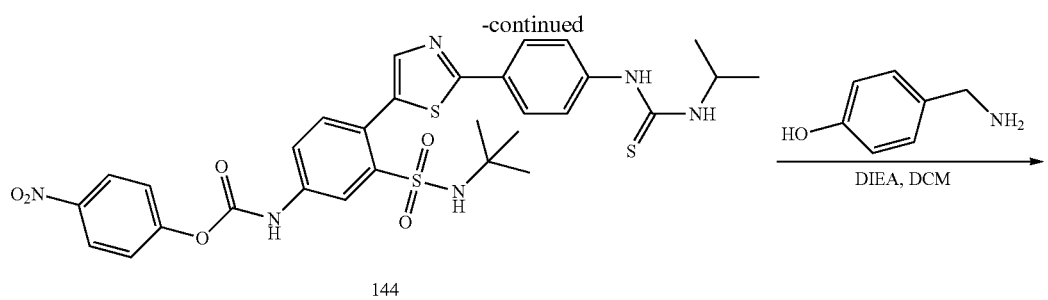

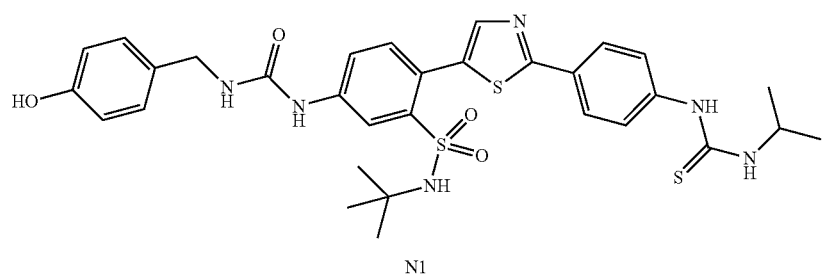

N1

Preparation of compound 142.

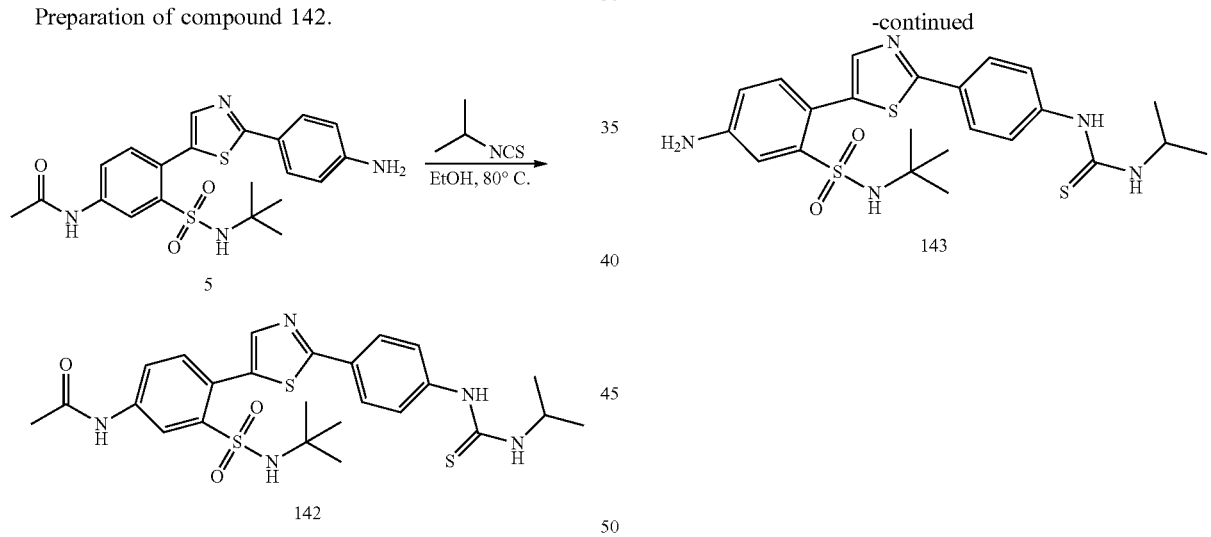

General method G, N-(3-(N-(tert-butyl)sulfamoyl)-4-(2-(4-(3-isopropylthioureido)phenyl)thiazol-5-yl)phenyl)acetamide. ESI [M+H]=546.4

Preparation of compound 143.

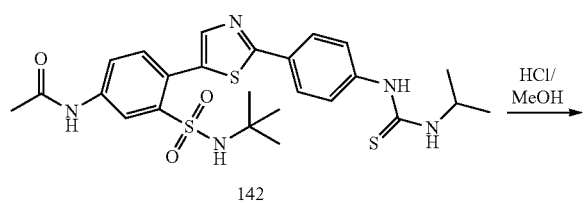

A mixture of N-[3-(tert-butylsulfamoyl)-4-[2-[4-(isopropylcarbamothioylamino)phenyl]thiazol-5-yl]phenyl]acetamide (g, 1.83 mmol, eq.) in HCl/MeOH (4 M, 50 mL) was stirred at 30° C. for 1 hr, and then concentrated. The residue was diluted with DCM (30 mL) and washed with sat.aq.$Na_2CO_3$ aq. (20 mL). The organic phase was dried over $Na_2SO_4$, filtered and concentrated to give 1-[4-[5-[4-amino-2-(tert-butylsulfamoyl)phenyl]thiazol-2-yl]phenyl]-3-isopropyl-thiourea (900 mg, crude) as a yellow solid. ESI [M+H]=504.0

Preparation of compound 144.

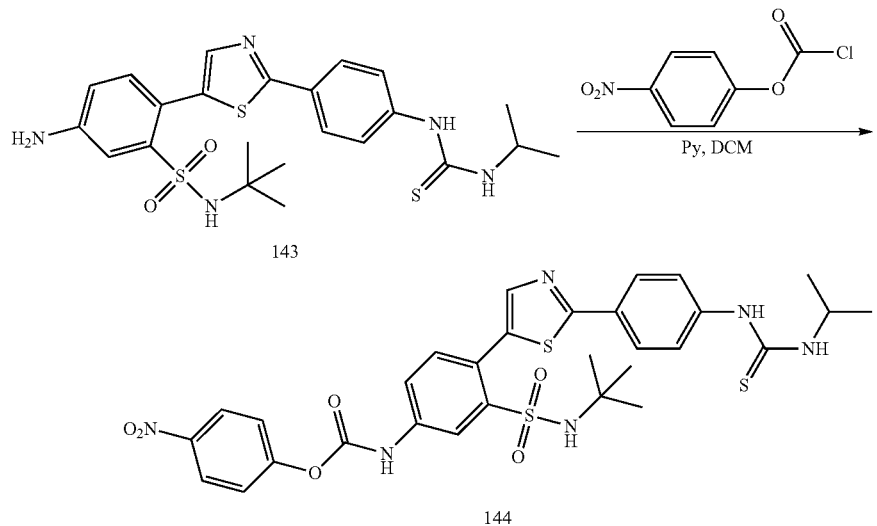

General method C, 4-nitrophenyl (3-(N-(tert-butyl)sulfamoyl)-4-(2-(4-(3-isopropylthioureido)phenyl)thiazol-5-yl)phenyl)carbamate.
Compound N1
Preparation of compound 145.

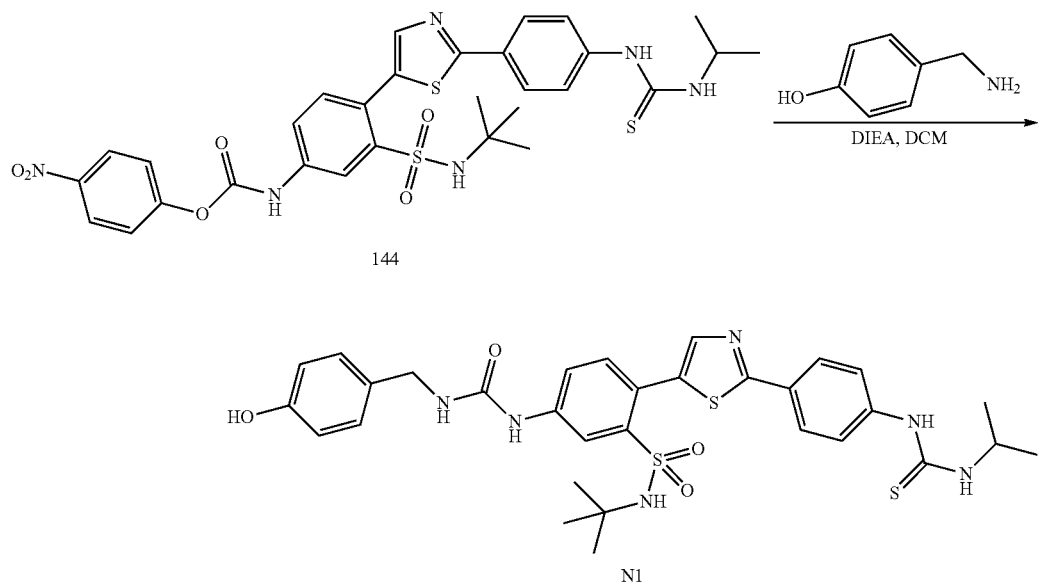

General method F, N-(tert-butyl)-5-(3-(4-hydroxybenzyl)ureido)-2-(2-(4-(3-isopropyl thioureido)phenyl)thiazol-5-yl)benzenesulfonamide. $^1$H NMR (400 MHz, METHANOL-d4) δ=8.30-8.25 (m, 1H), 7.96-7.89 (m, 2H), 7.86 (s, 1H), 7.70 (br d, J=6.6 Hz, 1H), 7.57 (br d, J=8.3 Hz, 2H), 7.42 (br d, J=8.3 Hz, 1H), 7.17 (br d, J=8.3 Hz, 2H), 6.75 (br d, J=8.3 Hz, 2H), 4.54 (br s, 1H), 4.30 (s, 2H), 1.24 (br d, J=6.6 Hz, 6H), 1.13 (s, 9H). ESI [M+H]=653.2

The following compounds were synthesized via reacting intermediate 144 with different amines similar to compound N1, unless otherwise noted.

Compound N2

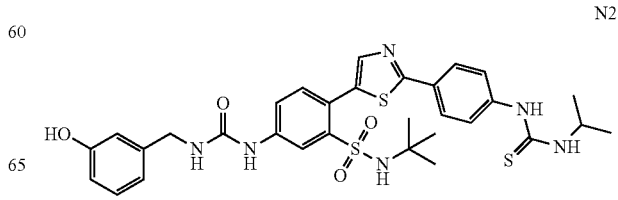

¹H NMR (400 MHz, DMSO-d6) δ=9.58 (br s, 1H), 9.35 (br s, 1H), 9.15 (s, 1H), 8.31-8.23 (m, 1H), 7.94-7.77 (m, 4H), 7.69-7.59 (m, 3H), 7.42 (br d, J=8.3 Hz, 1H), 7.15-7.07 (m, 2H), 6.72 (br s, 3H), 6.63 (br d, J=8.6 Hz, 1H), 4.46-4.31 (m, 1H), 4.24 (br d, J=5.4 Hz, 2H), 1.23-1.13 (m, 6H), 1.08 (s, 9H). ESI [M+H]=653.2
Compound N3

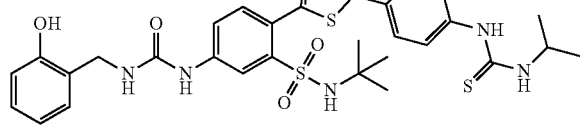

¹H NMR (400 MHz, METHANOL-d4) δ=8.26 (s, 1H), 7.96-7.85 (m, 3H), 7.69 (br d, J=8.3 Hz, 1H), 7.58 (br d, J=8.8 Hz, 2H), 7.42 (d, J=8.3 Hz, 1H), 7.21 (br d, J=7.0 Hz, 1H), 7.10 (br t, J=7.7 Hz, 1H), 6.83-6.74 (m, 2H), 4.54 (br s, 1H), 4.37 (s, 2H), 1.24 (d, J=6.6 Hz, 6H), 1.13 (s, 9H). ESI [M+H]=653.1
Compound N4

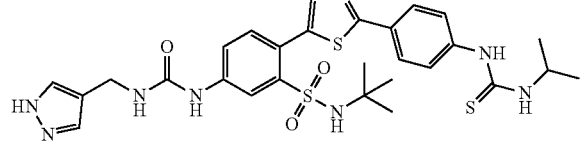

¹H NMR (400 MHz, DMSO-d6) δ=9.58 (br s, 1H), 9.02 (s, 1H), 8.27 (s, 1H), 7.93-7.79 (m, 4H), 7.64 (br d, J=8.4 Hz, 3H), 7.57 (s, 3H), 7.41 (br d, J=8.2 Hz, 1H), 7.11 (s, 1H), 6.51 (br s, 1H), 4.40 (br d, J=5.6 Hz, 1H), 4.18 (br d, J=4.2 Hz, 2H), 1.18 (br d, J=6.5 Hz, 6H), 1.08 (s, 9H). ESI [M+H]=627.2
Compound N5

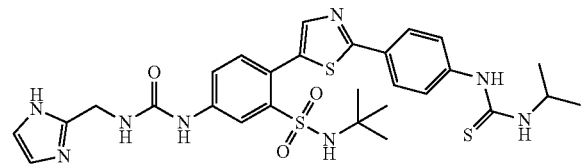

¹H NMR (400 MHz, DMSO-d6) δ=11.89 (br s, 1H), 9.57 (br s, 1H), 9.25 (s, 1H), 8.28 (s, 1H), 7.93-7.77 (m, 4H), 7.64 (br d, J=8.3 Hz, 3H), 7.42 (br d, J=8.4 Hz, 1H), 7.10 (s, 1H), 6.94 (br s, 2H), 6.69 (br t, J=5.0 Hz, 1H), 4.48-4.20 (m, 3H), 1.18 (br d, J=6.5 Hz, 6H), 1.08 (s, 9H). ESI [M+H]=627.1
Compound N6

¹H NMR (400 MHz, METHANOL-d4) δ=8.27 (d, J=2.4 Hz, 1H), 7.92 (d, J=8.6 Hz, 2H), 7.86 (s, 1H), 7.70 (dd, J=2.4, 8.4 Hz, 1H), 7.64 (s, 1H), 7.57 (d, J=8.6 Hz, 2H), 7.43 (d, J=8.4 Hz, 1H), 7.02 (s, 1H), 4.53 (br s, 1H), 4.36 (s, 2H), 1.24 (d, J=6.6 Hz, 6H), 1.12 (s, 9H). ESI [M+H]=627.2

Example 15

Scheme 15.1

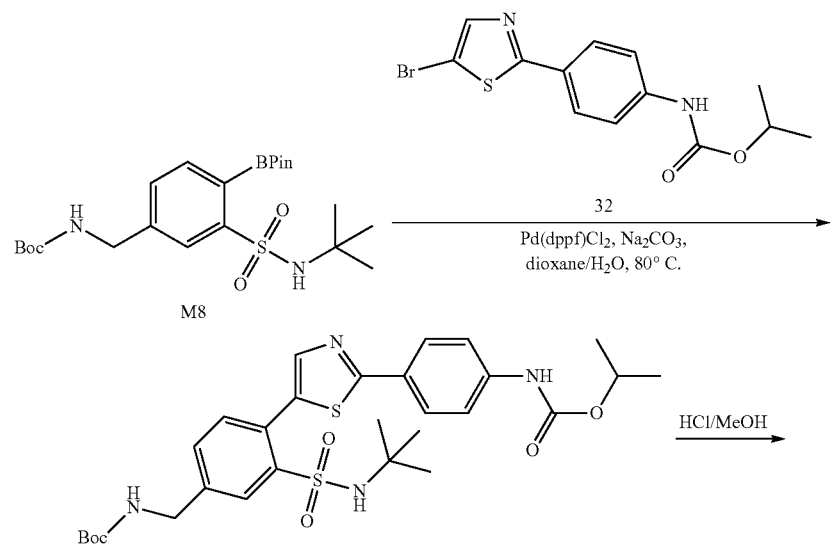

-continued
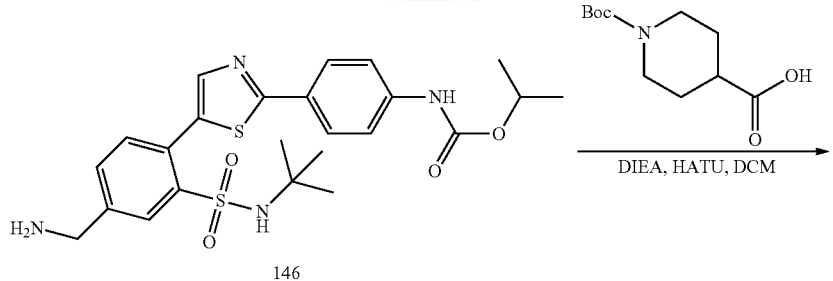
146
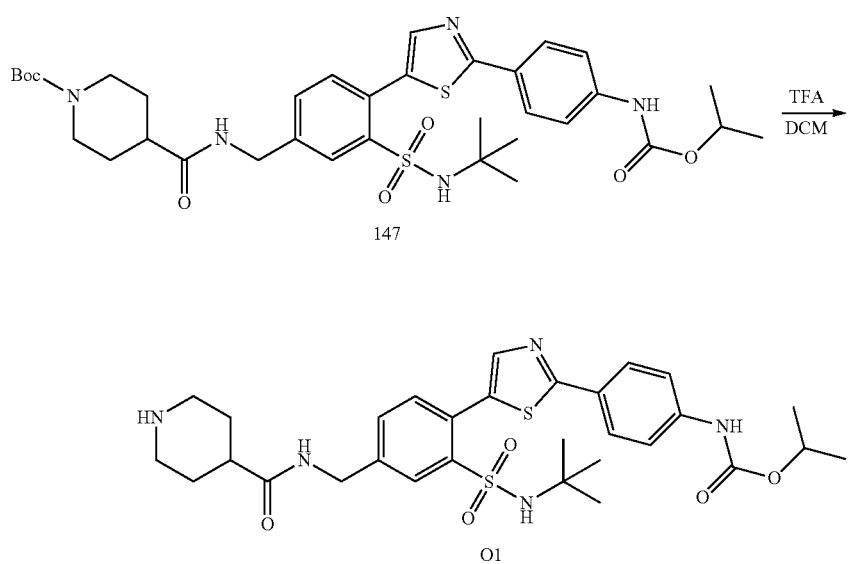
147
O1
Preparation of compound 145.
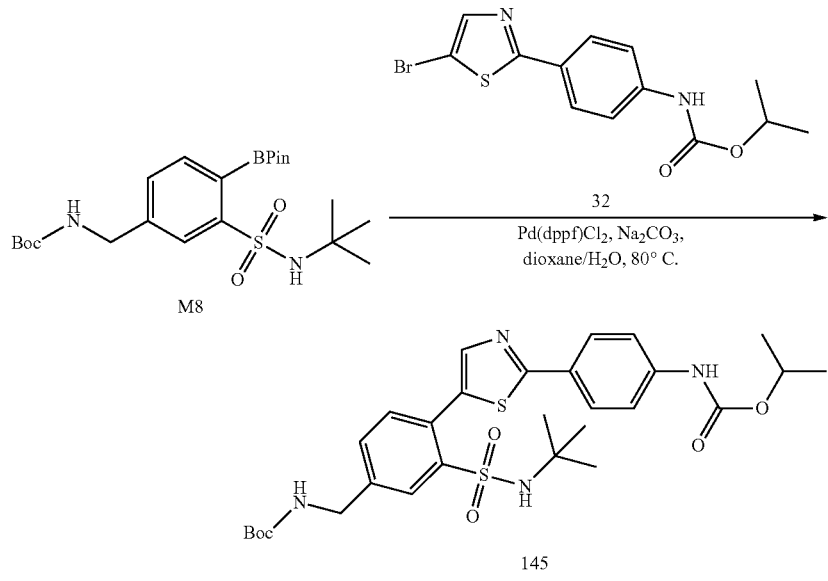
145

General method A, isopropyl N-[4-[5-[4-[(tert-butoxycarbonylamino)methyl]-2-(tert-butylsulfamoyl)phenyl]thiazol-2-yl]phenyl]carbamate. ESI [M+H]=603.3

Preparation of compound 146.

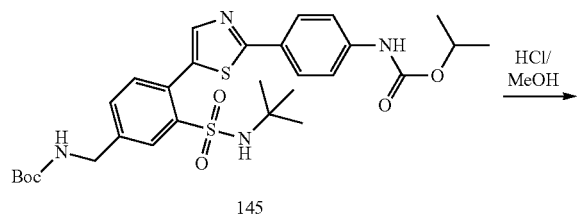
145

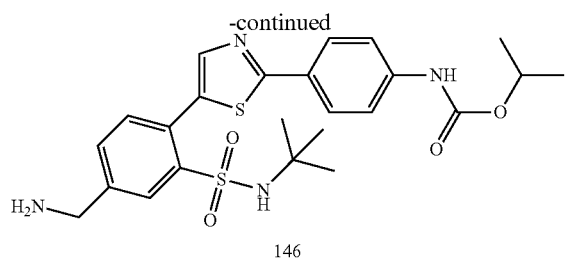
146

A solution of isopropyl N-[4-[5-[4-[(tert-butoxycarbonylamino)methyl]-2-(tert-butyl sulfamoyl)phenyl]thiazol-2-yl]phenyl]carbamate (2.20 g, 3.65 mmol, 1.00 eq.) in HCl/MeOH (20.00 mL) was stirred at 15° C. for 1 hr and then concentrated to give isopropyl N-[4-[5-[4-(aminomethyl)-2-(tert-butylsulfamoyl)phenyl]thiazol-2-yl]phenyl]carbamate (2.00 g, crude, HCl) as a yellow solid.

Preparation of compound 147.

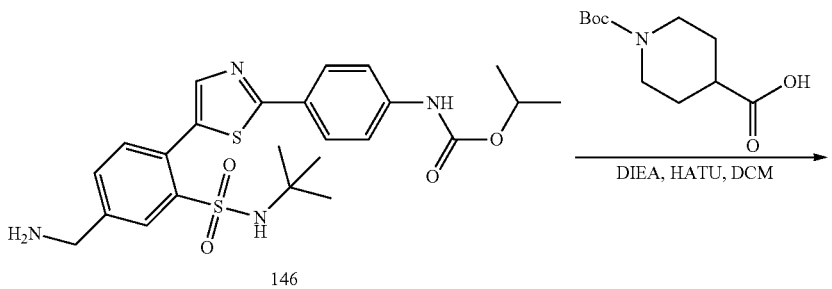

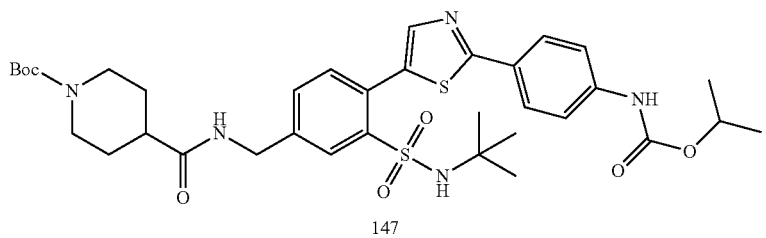
147

To a mixture of isopropyl N-[4-[5-[4-(aminomethyl)-2-(tert-butylsulfamoyl)phenyl]thiazol-2-yl]phenyl]carbamate (40.00 mg, 74.20 μmol, 1.00 eq., HCl), 1-tert-butoxycarbonyl piperidine-4-carboxylic acid (25.52 mg, 111.30 μmol, 1.50 eq.) and DIEA (47.95 mg, 371.00 mol, 64.62 ul, 5.00 eq.) in DCM (2.00 mL) was added HATU (36.68 mg, 96.46 μmol, 1.30 eq.). The mixture was stirred at 20° C. for 1 hr, then washed with 0.5N HCl (5 mL), sat.aq.Na$_2$CO$_3$ (5 mL), dried over Na$_2$SO$_4$, filtered and concentrated to give tert-butyl 4-[[3-(tert-butylsulfamoyl)-4-[2-[4-(isopropoxycarbonylamino)phenyl]thiazol-5-yl]phenyl]methylcarbamoyl]piperidine-1-carboxylate (50 mg, crude) as a yellow oil. ESI [M+H]=714.1

Compound O1

Compound O1 was prepared from intermediate compound 147 via general method E (shown in Example 1).

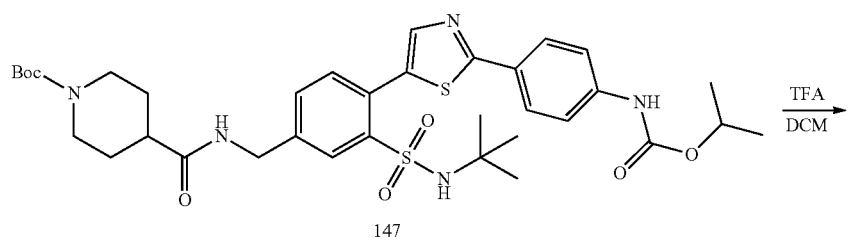

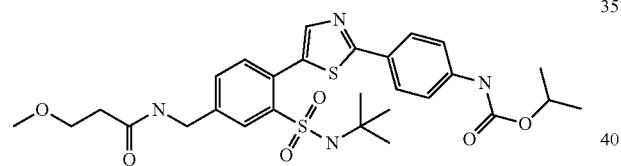

¹H NMR (400 MHz, METHANOL-d4) δ=8.09 (s, 1H), 7.91-7.86 (m, 3H), 7.60-7.50 (m, 4H), 4.98 (td, J=6.0, 12.5 Hz, 1H), 4.54-4.46 (m, 2H), 3.46 (br d, J=13.2 Hz, 2H), 3.11-3.01 (m, 2H), 2.69-2.58 (m, 1H), 2.11-1.89 (m, 4H), 1.31 (d, J=6.6 Hz, 6H), 1.07 (s, 9H). ESI [M+H]=614.2

The following compounds were synthesized via reacting intermediate 146 with different acids using a procedure similar to that used to synthesize compound O1.

Compound O2

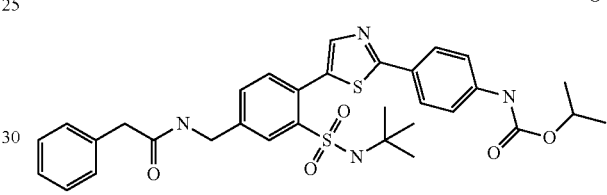

¹H NMR (400 MHz, METHANOL-d4) δ=8.11 (s, 1H), 7.92-7.81 (m, 3H), 7.60-7.46 (m, 4H), 5.02-4.92 (m, 1H), 4.50 (s, 2H), 3.68 (t, J=6.1 Hz, 2H), 3.35 (s, 3H), 2.52 (t, J=5.9 Hz, 2H), 1.31 (d, J=6.1 Hz, 6H), 1.09 (s, 9H). ESI [M+H]=589.2

Compound O3

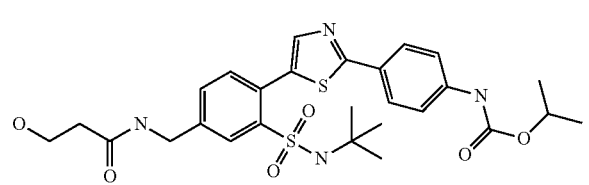

¹H NMR (400 MHz, METHANOL-d4) δ=8.12 (s, 1H), 7.96-7.83 (m, 3H), 7.59 (br d, J=8.2 Hz, 3H), 7.55-7.49 (m, 1H), 5.07-4.91 (m, 1H), 4.51 (s, 2H), 3.86 (t, J=6.2 Hz, 2H), 2.50 (t, J=6.2 Hz, 2H), 1.32 (d, J=6.1 Hz, 6H), 1.11 (s, 9H). ESI [M+H]=575.1

Compound O4

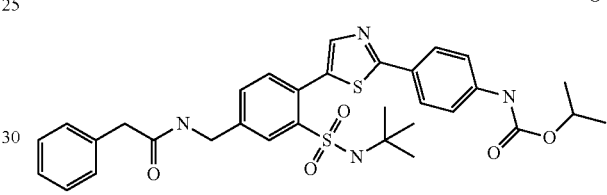

¹H NMR (400 MHz, METHANOL-d4) δ=8.10 (s, 1H), 7.92-7.85 (m, 3H), 7.62-7.43 (m, 4H), 7.35-7.18 (m, 5H), 4.97 (td, J=6.2, 12.6 Hz, 1H), 4.47 (s, 2H), 3.34-3.24 (m, 2H), 1.31 (d, J=6.1 Hz, 6H), 1.07 (s, 9H). ESI [M+H]=621.1

Compound O5

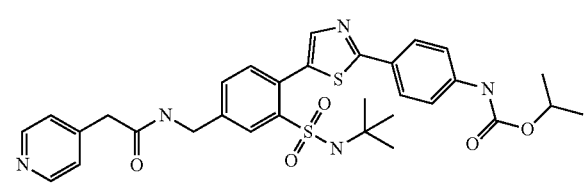

¹H NMR (400 MHz, METHANOL-d4) δ=8.81 (br d, J=6.0 Hz, 2H), 8.07 (br d, J=6.0 Hz, 2H), 8.01 (s, 1H), 7.93-7.87 (m, 3H), 7.63-7.51 (m, 4H), 5.00 (td, J=6.2, 12.5 Hz, 1H), 4.55 (s, 2H), 4.02 (s, 2H), 1.34 (d, J=6.2 Hz, 6H), 1.07 (s, 9H). ESI [M+H]=622.2

Compound O6

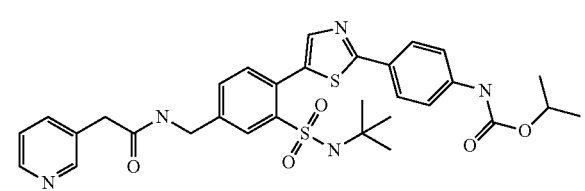

¹H NMR (400 MHz, METHANOL-d4) δ=8.85 (s, 1H), 8.78 (d, J=5.8 Hz, 1H), 8.57 (br d, J=7.9 Hz, 1H), 8.11-7.98

(m, 2H), 7.88 (d, J=7.9 Hz, 3H), 7.57 (br d, J=8.1 Hz, 3H), 7.54-7.49 (m, 1H), 5.03-4.93 (m, 1H), 4.53 (s, 2H), 3.93 (s, 2H), 1.31 (d, J=6.1 Hz, 6H), 1.05 (s, 9H). ESI [M+H]=622.2

Compound O7

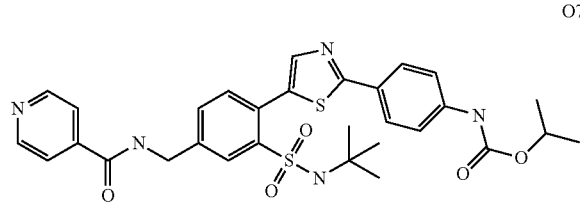 [SMILES: CC(C)OC(=O)Nc1ccc(-c2ncc(-c3ccc(CNC(=O)c4cncnc4)cc3S(=O)(=O)NC(C)(C)C)s2)cc1]

¹H NMR (400 MHz, METHANOL-d4) δ=8.88 (br d, J=5.3 Hz, 2H), 8.20 (s, 1H), 8.14 (d, J=5.5 Hz, 2H), 7.93-7.85 (m, 3H), 7.67 (br d, J=7.7 Hz, 1H), 7.61-7.54 (m, 3H), 4.98 (td, J=6.2, 12.4 Hz, 1H), 4.73 (s, 2H), 1.31 (d, J=6.2 Hz, 6H), 1.09 (s, 9H). ESI [M+H]=608.2

Compound O8

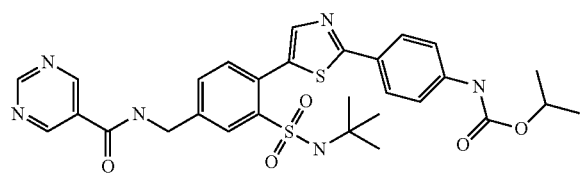

¹H NMR (400 MHz, METHANOL-d4) δ=9.29 (s, 1H), 9.21 (s, 2H), 8.20 (s, 1H), 7.88 (br d, J=6.0 Hz, 3H), 7.67 (br d, J=7.8 Hz, 1H), 7.62-7.52 (m, 3H), 5.06-4.92 (m, 1H), 4.75-4.69 (m, 2H), 1.31 (d, J=6.1 Hz, 6H), 1.09 (s, 9H). ESI [M+H]=609.1

Example 16

The following compounds were synthesized via reacting intermediate 146 with different acyl chlorides via general method C (shown in Example 1), unless otherwise noted.

Compound P1

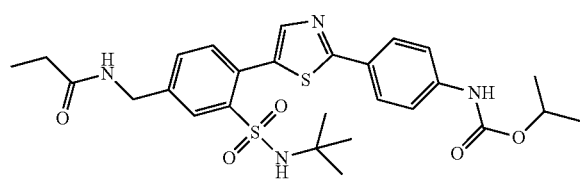

¹H NMR (400 MHz, METHANOL-d4) δ=8.13 (s, 1H), 7.96-7.86 (m, 3H), 7.65-7.51 (m, 4H), 5.00 (td, J=6.2, 12.3 Hz, 1H), 4.50 (s, 2H), 2.32 (q, J=7.6 Hz, 2H), 1.34 (d, J=6.2 Hz, 6H), 1.20 (br t, J=7.6 Hz, 3H), 1.15-1.09 (m, 9H). ESI [M+H]=559.2

Compound P2

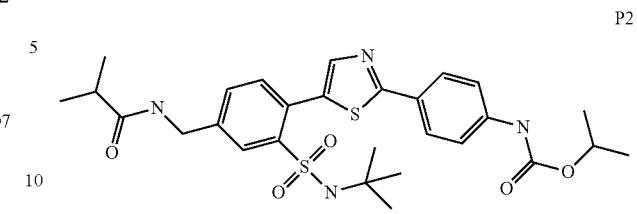

¹H NMR (400 MHz, METHANOL-d4) δ=8.11 (s, 1H), 7.95-7.83 (m, 3H), 7.63-7.47 (m, 4H), 5.00-4.95 (m, 1H), 4.47 (s, 2H), 2.68-2.43 (m, 1H), 1.32 (br d, J=6.2 Hz, 6H), 1.17 (br d, J=6.8 Hz, 6H), 1.09 (s, 9H). ESI [M+H]=573.2

Compound P3

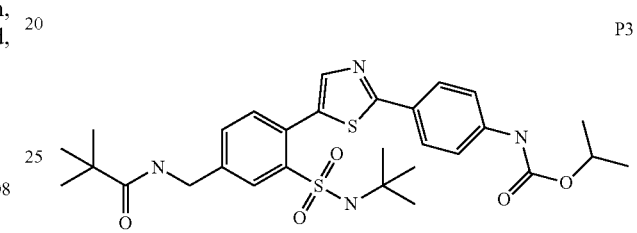

¹H NMR (400 MHz, METHANOL-d4) δ=8.11 (br s, 1H), 7.89 (br s, 3H), 7.65-7.44 (m, 4H), 5.00-4.94 (m, 1H), 4.47 (s, 2H), 1.32 (br d, J=6.0 Hz, 6H), 1.24 (s, 9H), 1.09 (s, 9H). ESI [M+H]=587.3

Compound P4

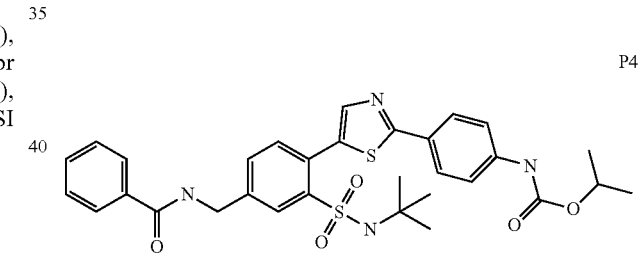

¹H NMR (400 MHz, DMSO-d6) δ=9.88 (br s, 1H), 9.23 (br s, 1H), 8.05 (br s, 1H), 7.88 (br dd, J=9.2, 18.6 Hz, 5H), 7.67-7.43 (m, 7H), 7.22 (s, 1H), 4.98-4.86 (m, 1H), 4.58 (br s, 2H), 1.27 (br d, J=6.2 Hz, 6H), 1.02 (s, 9H). ESI [M+H]=607.2

Compound P5

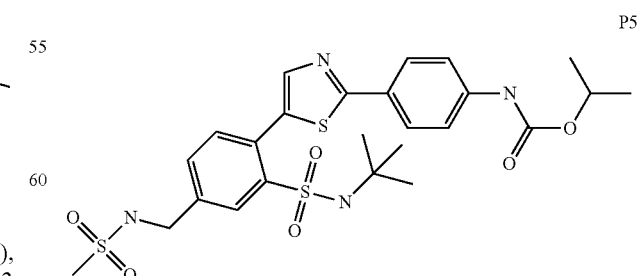

¹H NMR (400 MHz, METHANOL-d4) δ=8.23 (br s, 1H), 7.97-7.79 (m, 3H), 7.67 (br d, J=7.5 Hz, 1H), 7.62-7.52 (m,

3H), 4.97 (br dd, J=6.0, 12.1 Hz, 1H), 4.39 (s, 2H), 2.96 (s, 3H), 1.32 (br d, J=6.0 Hz, 6H), 1.12 (s, 9H). ESI [M+H]=581.2

Compound P6

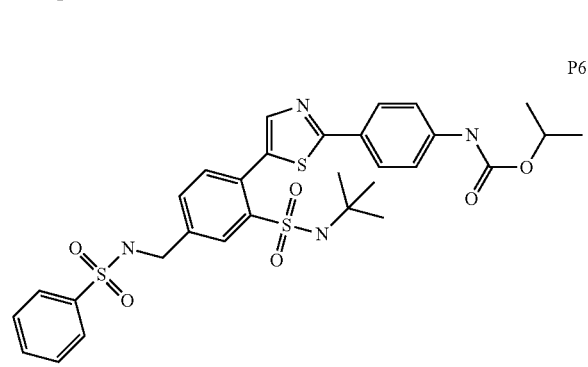 [SMILES: CC(C)OC(=O)Nc1ccc(-c2ncc(-c3ccc(CNS(=O)(=O)c4ccccc4)cc3S(=O)(=O)NC(C)(C)C)s2)cc1]

¹H NMR (400 MHz, METHANOL-d4) δ=8.10 (br s, 1H), 7.96-7.78 (m, 5H), 7.69-7.45 (m, 6H), 7.45-7.35 (m, 1H), 5.02-4.94 (m, 1H), 4.20 (s, 2H), 1.32 (br d, J=5.5 Hz, 6H), 1.10 (s, 9H). ESI [M+H]=643.2

Compound P7

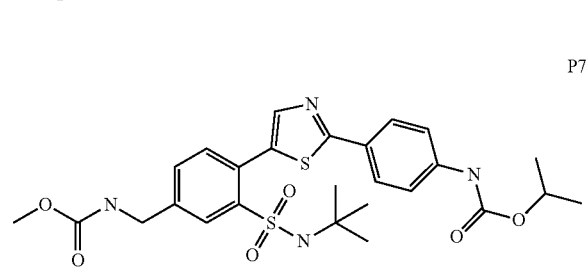 [SMILES: COC(=O)NCc1ccc(-c2cnc(-c3ccc(NC(=O)OC(C)C)cc3)s2)c(S(=O)(=O)NC(C)(C)C)c1]

¹H NMR (400 MHz, METHANOL-d4) δ=8.12 (br s, 1H), 7.94-7.85 (m, 3H), 7.65-7.46 (m, 4H), 5.03-4.94 (m, 1H), 4.40 (br s, 2H), 3.68 (s, 3H), 1.32 (br d, J=6.0 Hz, 6H), 1.12 (s, 9H). ESI [M+H]=561.2

Compound P8

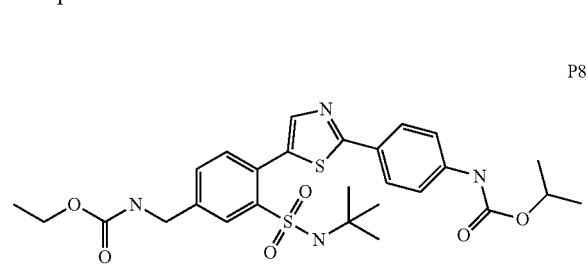

¹H NMR (400 MHz, METHANOL-d4) δ=8.12 (br s, 1H), 7.95-7.84 (m, 3H), 7.63-7.46 (m, 4H), 5.05-4.93 (m, 1H), 4.39 (br s, 2H), 4.12 (q, J=6.7 Hz, 2H), 1.32 (br d, J=6.2 Hz, 6H), 1.26 (br t, J=6.8 Hz, 3H), 1.11 (s, 9H). ESI [M+H]=575.2

Compound P9

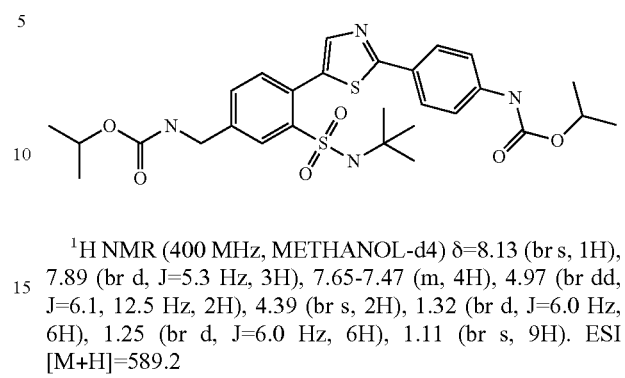

¹H NMR (400 MHz, METHANOL-d4) δ=8.13 (br s, 1H), 7.89 (br d, J=5.3 Hz, 3H), 7.65-7.47 (m, 4H), 4.97 (br dd, J=6.1, 12.5 Hz, 2H), 4.39 (br s, 2H), 1.32 (br d, J=6.0 Hz, 6H), 1.25 (br d, J=6.0 Hz, 6H), 1.11 (br s, 9H). ESI [M+H]=589.2

Example 17

Compound Q1

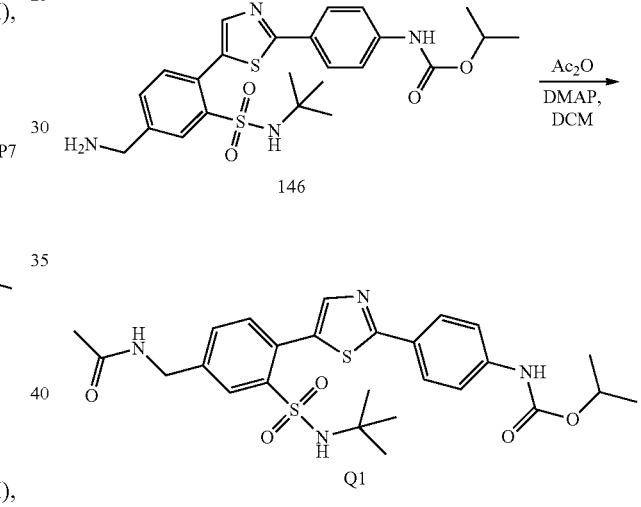

To a solution of isopropyl N-[4-[5-[4-(aminomethyl)-2-(tert-butylsulfamoyl)phenyl]thiazol-2-yl]phenyl]carbamate (75.00 mg, 69.56 µmol, 1.00 eq., HCl) in DCM (3.00 mL) were added DMAP (849.80 ug, 6.96 µmol, 0.10 eq.) and Ac₂O (8.52 mg, 83.47 µmol, 7.82 ul, 1.20 eq.) at 0° C. The mixture was stirred at 15° C. for 0.5 hr, then concentrated and the residue was purified by acidic prep-HPLC to give isopropyl N-[4-[5-[4-(acetamidomethyl)-2-(tert-butylsulfamoyl) phenyl]thiazol-2-yl]phenyl]carbamate (5.27 mg, 9.67 µmol, 13.90% yield, 99.9% purity) as a yellow solid. ¹H NMR (400 MHz, METHANOL-d4) δ=8.11 (s, 1H), 7.92-7.86 (m, 3H), 7.63-7.50 (m, 4H), 4.98 (quind, J=6.3, 12.4 Hz, 1H), 4.48 (s, 2H), 2.03 (s, 3H), 1.32 (d, J=6.2 Hz, 6H), 1.11 (s, 9H). ESI [M+H]=545.2

Compound O2

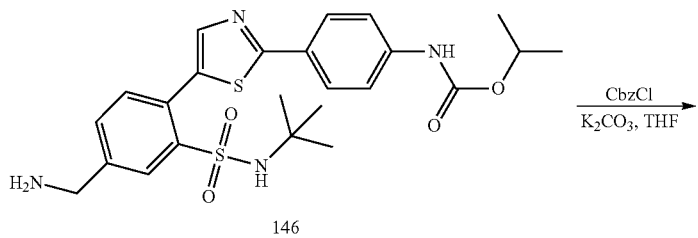

To a solution of isopropyl N-[4-[5-[4-(aminomethyl)-2-(tert-butylsulfamoyl)phenyl]thiazol-2-yl]phenyl]carbamate (20.00 mg, 37.10 μmol, 1.00 eq., HCl) in THF (3.00 mL) was added K$_2$CO$_3$ (10.26 mg, 74.20 μmol, 2.00 eq.) and benzyl carbonochloridate (31.64 mg, 185.50 μmol, 26.37 ul, 5.00 eq.). The mixture was stirred at 20° C. for 2 hrs, then concentrated and the residue was purified by acidic prep-HPLC to give isopropyl N-[4-[5-[4-(benzyloxycarbonylaminomethyl)-2-(tert-butylsulfamoyl)phenyl]thiazol-2-yl]phenyl]carbamate (17.54 mg, 27.27 μmol, 73.50% yield, 99% purity) as a gray solid. 1H NMR (400 MHz, METHANOL-d4) δ=8.14 (br s, 1H), 7.89 (br s, 3H), 7.66-7.45 (m, 4H), 7.42-6.99 (m, 5H), 5.12 (br s, 2H), 4.97 (br dd, J=6.3, 12.2 Hz, 1H), 4.42 (br s, 2H), 1.32 (br d, J=6.0 Hz, 6H), 1.10 (br s, 9H). ESI [M+H]=637.2

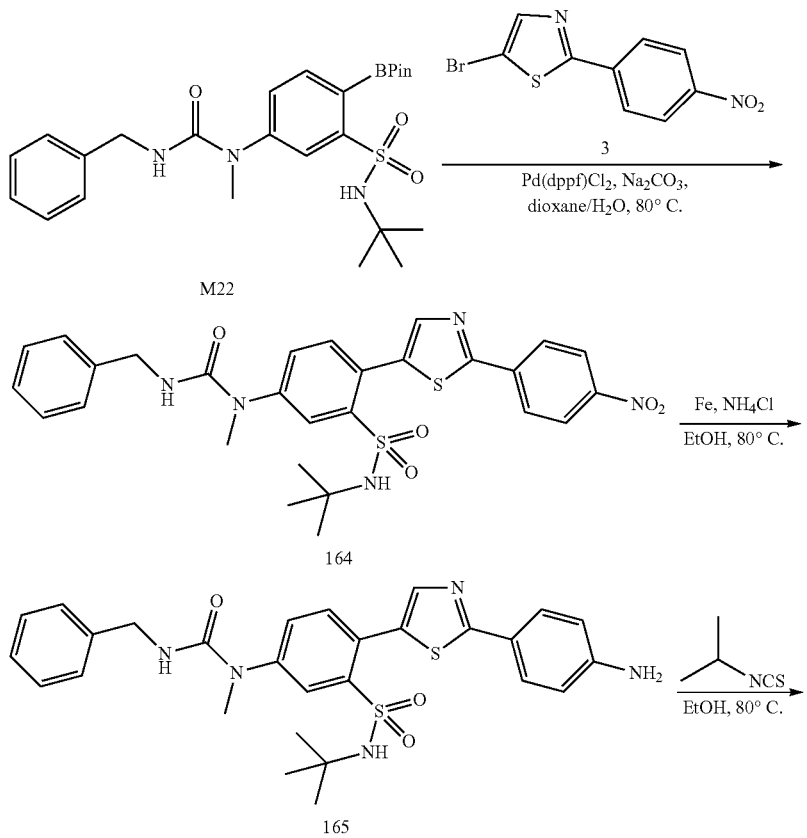

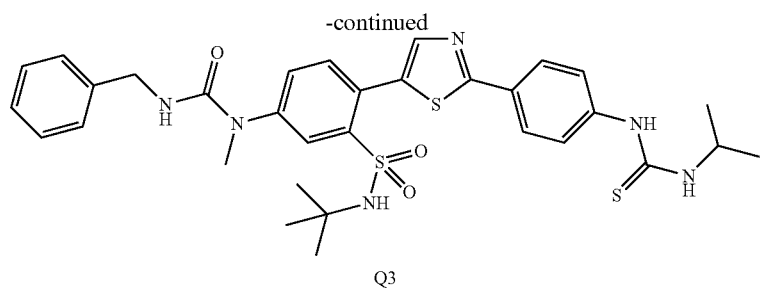
Q3
Preparation of compound 164.
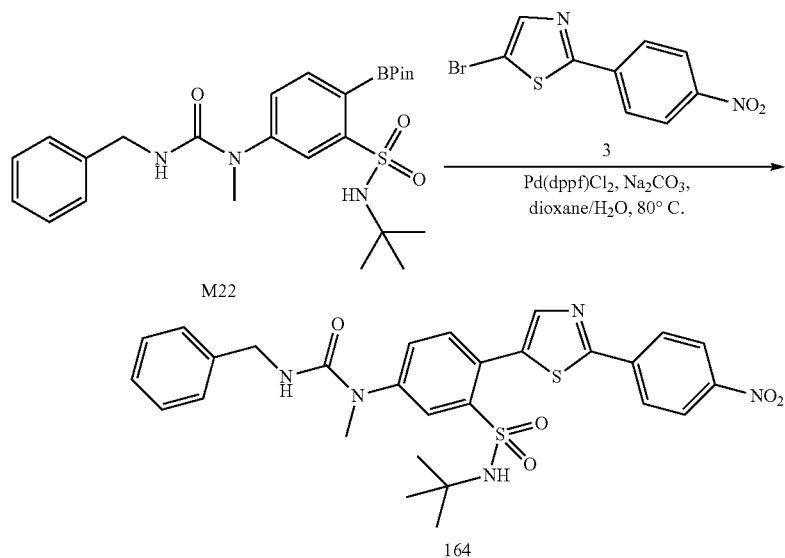
General method A, 5-(3-benzyl-1-methylureido)-N-(tert-butyl)-2-(2-(4-nitrophenyl)thiazol-5-yl)benzenesulfonamide. ESI [M+H]=580.3
Preparation of compound 165.
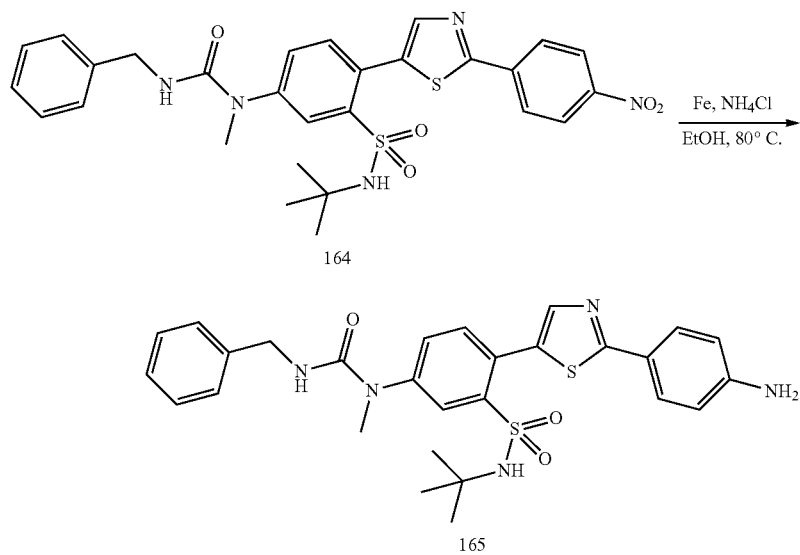

General method B, 2-(2-(4-aminophenyl)thiazol-5-yl)-5-(3-benzyl-1-methylureido)-N-(tert-butyl)benzenesulfonamide. ESI [M+H]=550.0
Compound Q3
Compound Q3 was prepared from intermediate compound 165 via general method G (shown in Example 1).
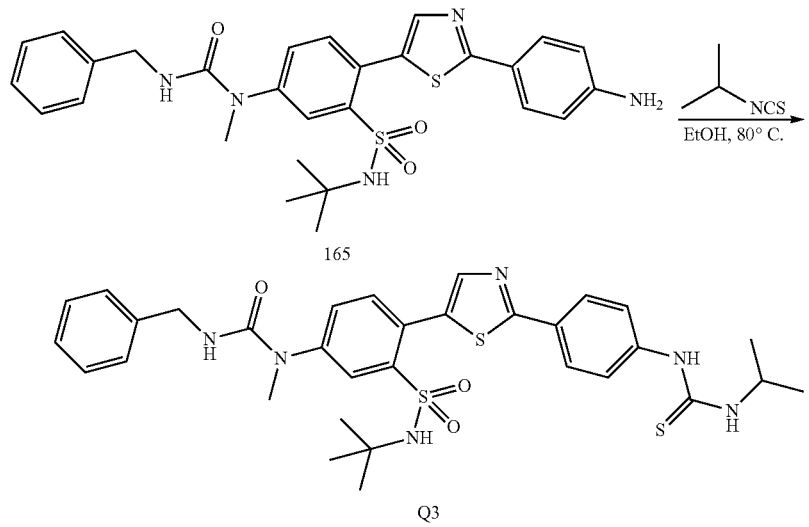
$^1$H NMR (400 MHz, METHANOL-d4) δ=8.12 (s, 1H), 7.98-7.92 (m, 3H), 7.63-7.59 (m, 4H), 7.33 (d, J=4.4 Hz, 4H), 7.28-7.21 (m, 1H), 4.56 (br s, 1H), 4.40 (s, 2H), 3.37 (s, 3H), 1.27 (d, J=6.5 Hz, 6H), 1.13 (s, 9H). ESI [M+H]=651.2
Scheme 17.2
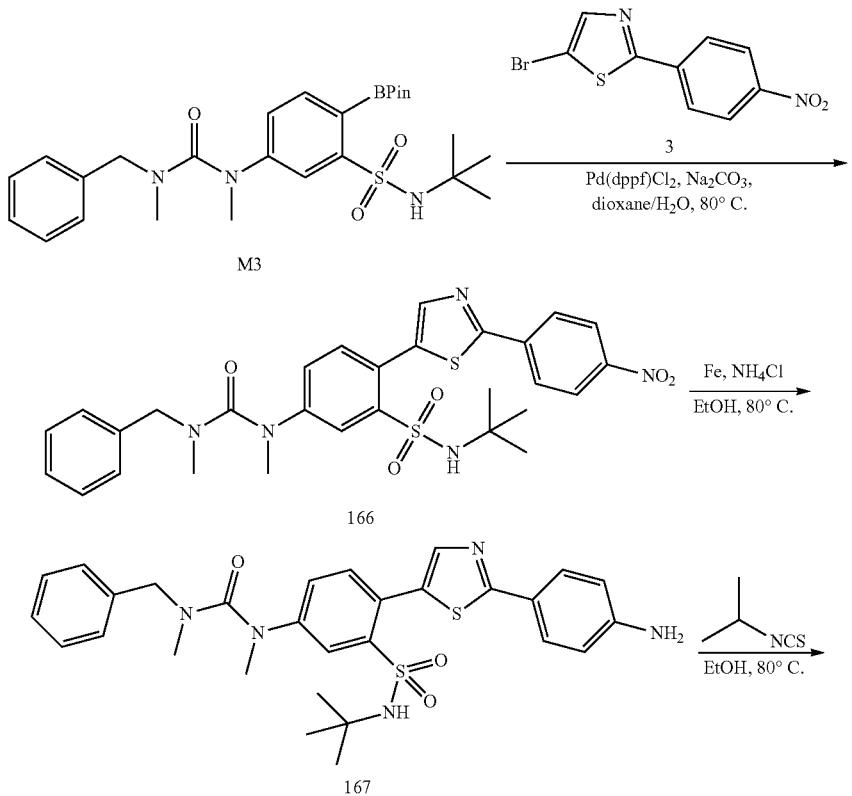

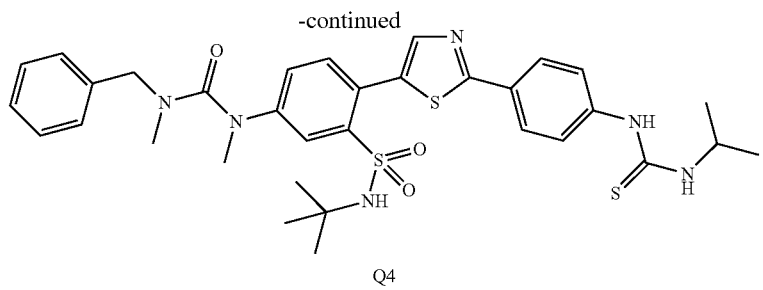
Q4
Preparation of compound 166.
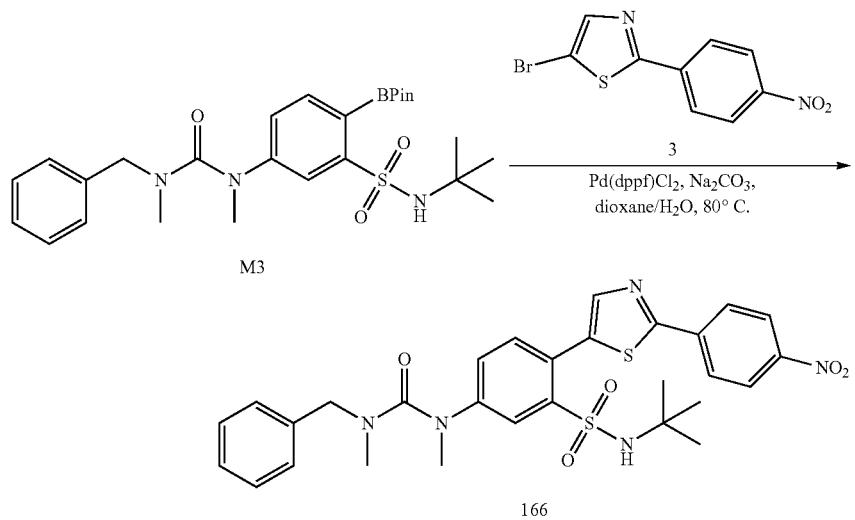
General method A, 5-(3-benzyl-1,3-dimethylureido)-N-(tert-butyl)-2-(2-(4-nitrophenyl)thiazol-5-yl)benzenesulfonamide. ESI [M+H]=593.9
Preparation of compound 167.
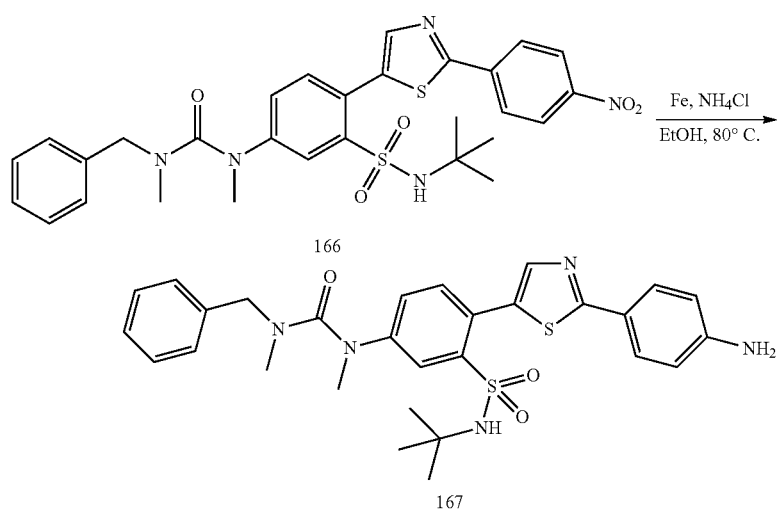
General method B, 2-(2-(4-aminophenyl)thiazol-5-yl)-5-(3-benzyl-1,3-dimethylureido)-N-(tert-butyl)benzenesulfonamide. ESI [M+H]=564.1

Compound Q4
Compound Q4 was prepared from intermediate compound 167 via general method G (shown in Example 1).
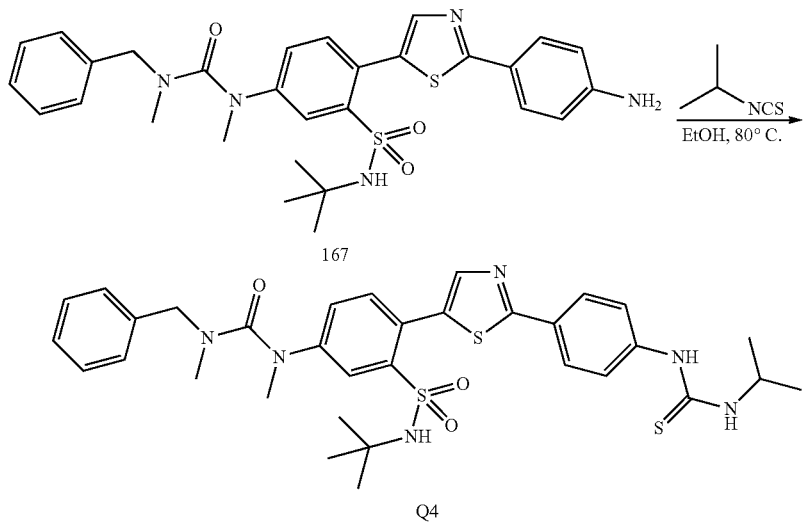
¹H NMR (400 MHz, METHANOL-d4) δ=7.98-7.86 (m, 4H), 7.58 (br d, J=8.6 Hz, 2H), 7.51 (d, J=8.4 Hz, 1H), 7.40-7.31 (m, 3H), 7.30-7.22 (m, 3H), 4.53 (br s, 1H), 4.45 (s, 2H), 3.28 (s, 3H), 2.65 (s, 3H), 1.24 (d, J=6.6 Hz, 6H), 1.08 (s, 9H). ESI [M+H]=665.2
Scheme 17.3
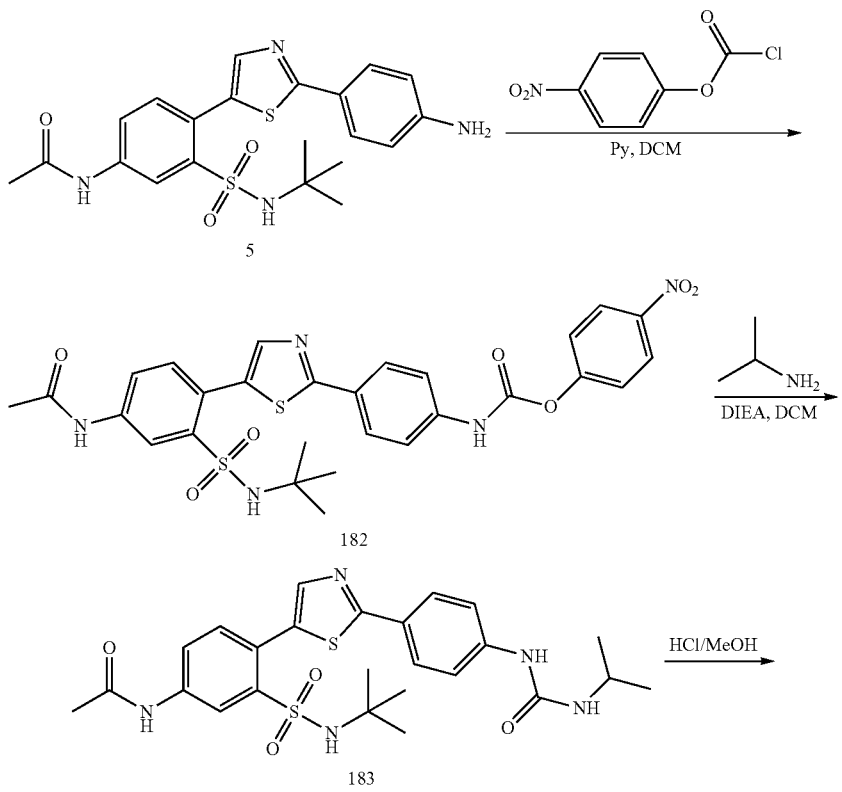

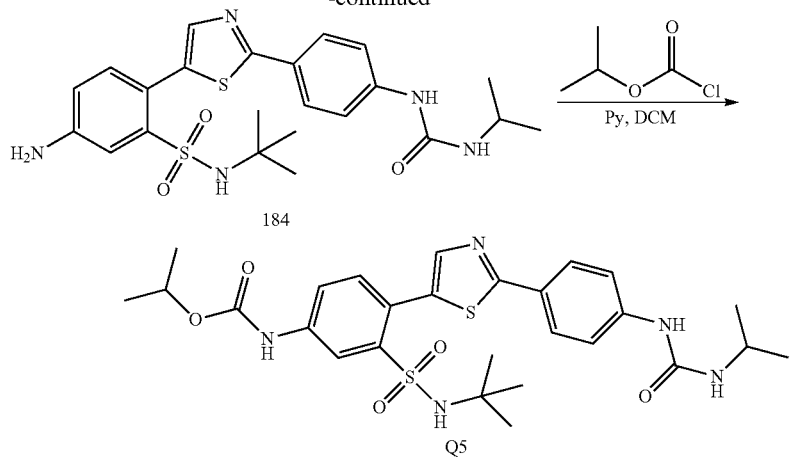
Preparation of compound 182.
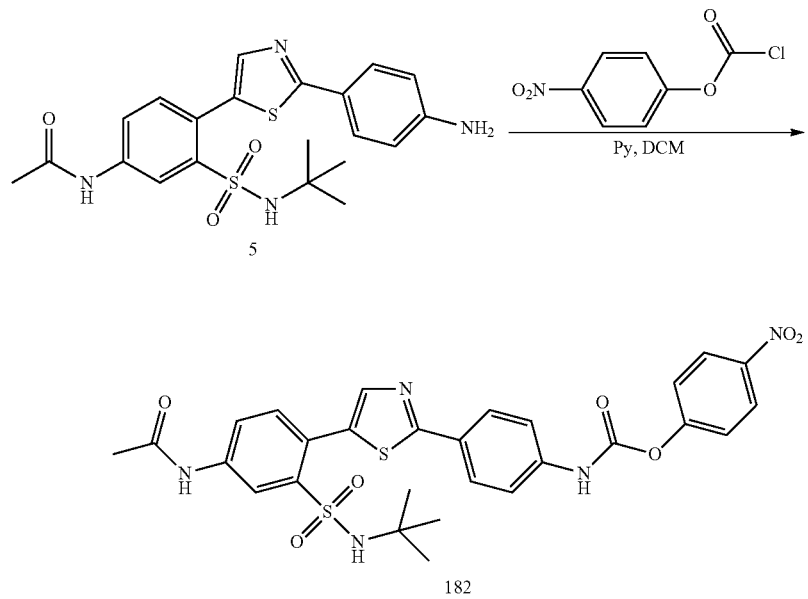 [SMILES: CC(=O)Nc1ccc(-c2cnc(-c3ccc(N)cc3)s2)c(S(=O)(=O)NC(C)(C)C)c1 ; O=C(Cl)Oc1ccc([N+](=O)[O-])cc1 ; CC(=O)Nc1ccc(-c2cnc(-c3ccc(NC(=O)Oc4ccc([N+](=O)[O-])cc4)cc3)s2)c(S(=O)(=O)NC(C)(C)C)c1]
General method C, 4-nitrophenyl (4-(5-(4-acetamido-2-(N-(tert-butyl)sulfamoyl)phenyl)thiazol-2-yl)phenyl)carbamate. ESI [M+H]=610.2
Preparation of compound 183.
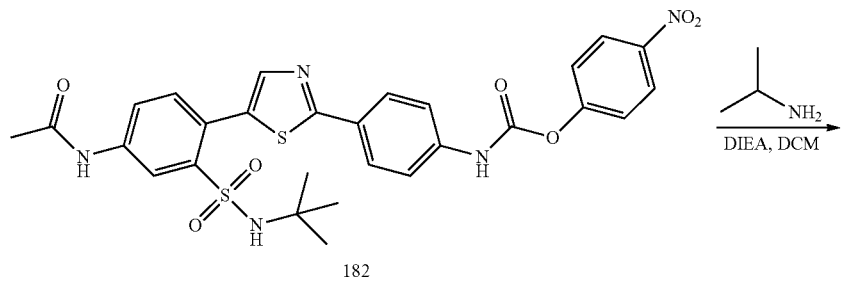

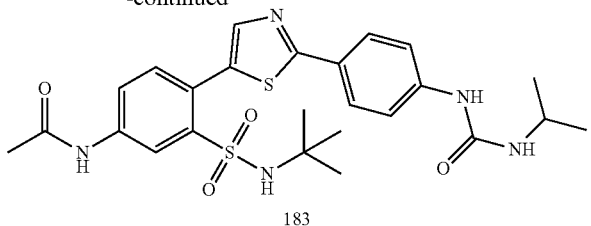

183

General method F, N-(3-(N-(tert-butyl)sulfamoyl)-4-(2-(4-(3-isopropylureido)phenyl)thiazol-5-yl)phenyl)acetamide. ESI [M+H]=530.2

Preparation of compound 184.

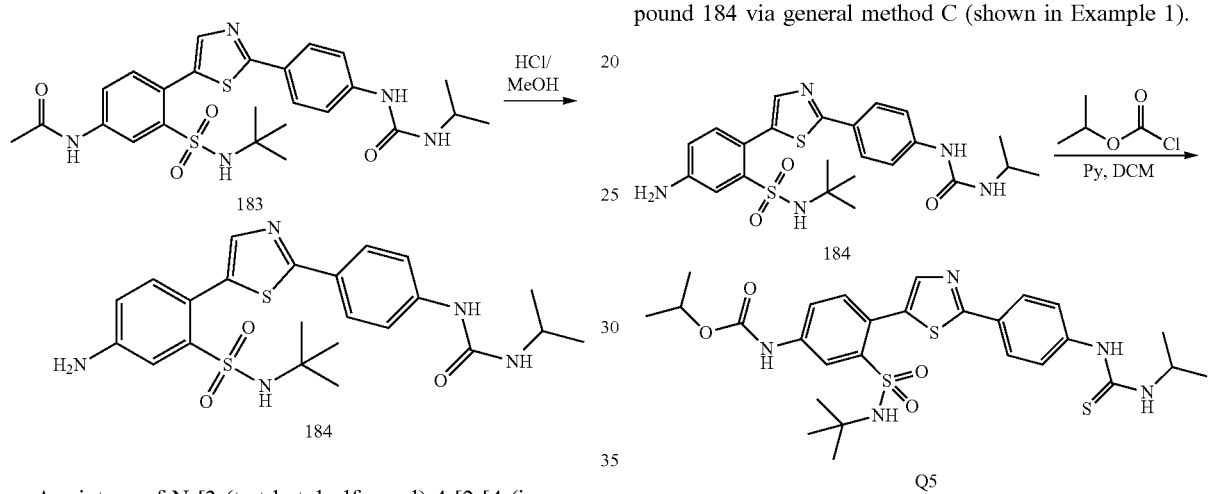

A mixture of N-[3-(tert-butylsulfamoyl)-4-[2-[4-(isopropylcarbamoylamino)phenyl]thiazol-5-yl]phenyl]acetamide (100 mg, 188.80 μmol, 1 eq.) in HCl/MeOH (4 M, 2 mL) was stirred at 30° C. for 1 hr. The mixture was concentrated, then diluted with EtOAc (50 mL) and washed with sat.aq.Na₂CO₃ (5 mL). The organic layer was dried over Na₂SO₄, filtered and concentrated to give 1-[4-[5-[4-amino-2-(tert-butylsulfamoyl)phenyl]thiazol-2-yl]phenyl]-3-isopropyl-urea (0.08 g, crude) as a yellow solid. ESI [M+H]=488.2

Compound Q5

Compound Q5 was prepared from intermediate compound 184 via general method C (shown in Example 1).

$^1$H NMR (400 MHz, METHANOL-d4) δ=8.39 (d, J=2.2 Hz, 1H), 7.83-7.91 (m, 3H), 7.73 (dd, J=8.4 Hz, J=2.1 Hz, 1H), 7.50-7.57 (m, 2H), 7.48 (d, J=8.3 Hz, 1H), 4.97-5.06 (m, 1H), 3.92 (quin, J=6.5 Hz, 1H), 1.34 (d, J=6.2 Hz, 6H), 1.21 (d, J=6.5 Hz, 6H), 1.16 (s, 9H). ESI [M+H]=574.2

Scheme 17.4

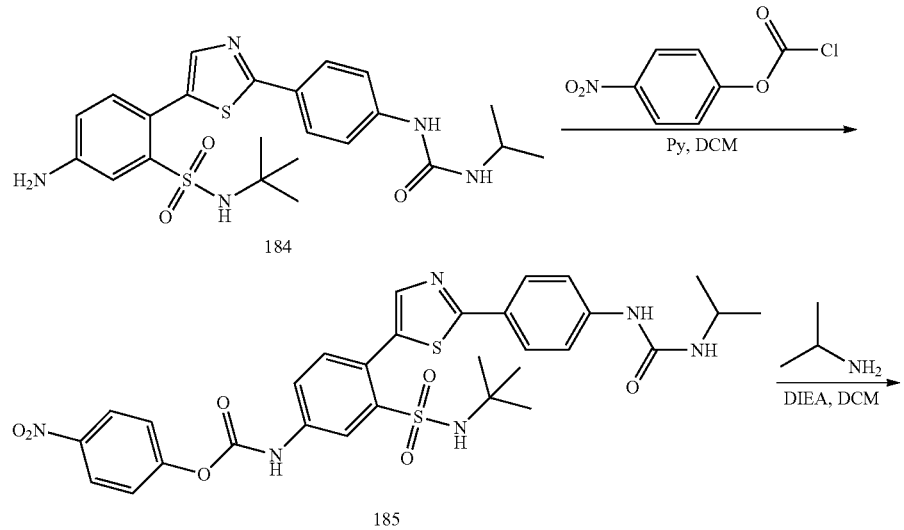

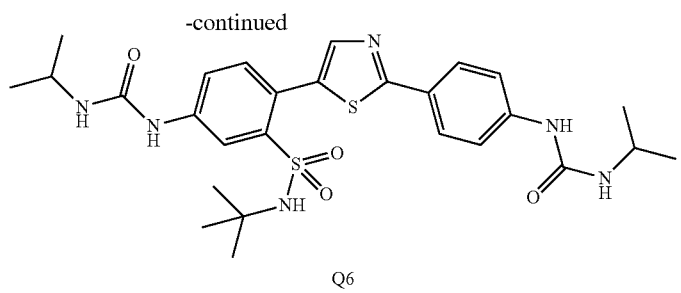
Q6
Preparation of compound 185.
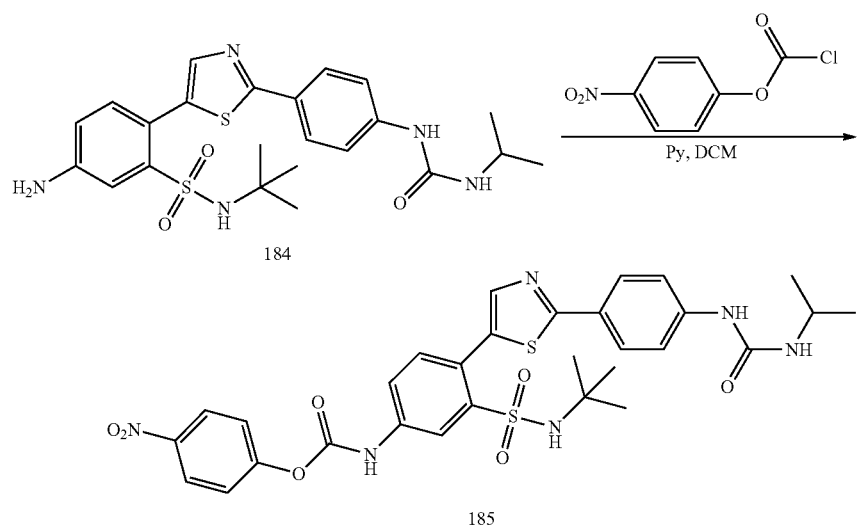
General method C, 4-nitrophenyl (3-(N-(tert-butyl)sulfamoyl)-4-(2-(4-(3-isopropylureido)phenyl)thiazol-5-yl)phenyl)carbamate. ESI [M+H]=653.1
Compound Q6
Compound Q6 was prepared from intermediate compound 185 via general method F (shown in Example 1).
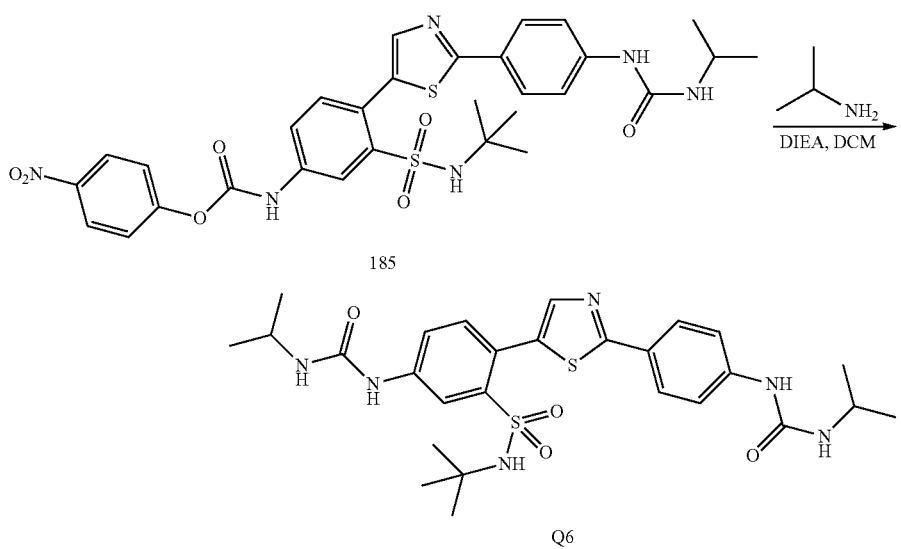

¹H NMR (400 MHz, METHANOL-d4) δ=8.25 (d, J=1.8 Hz, 1H), 7.79-7.87 (m, 3H), 7.66 (dd, J=8.3 Hz, J=1.3 Hz, 1H), 7.49 (br d, J=8.8 Hz, 2H), 7.41 (d, J=8.3 Hz, 1H), 3.90 (br dd, J=10.1 Hz, J=6.1 Hz, 2H), 1.19 (dd, J=6.1 Hz, J=2.2 Hz, 12H), 1.12 (s, 9H). ESI [M+H]=573.2

Example 18

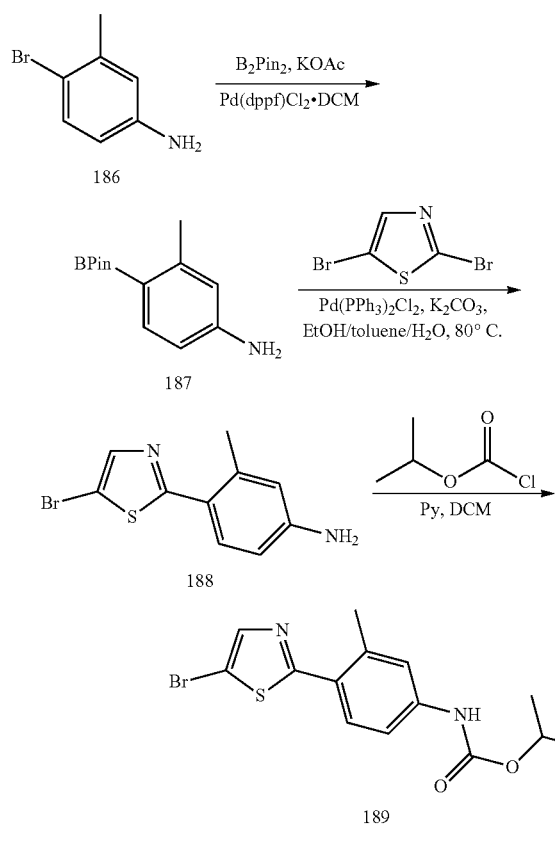

Preparation of compound 187.

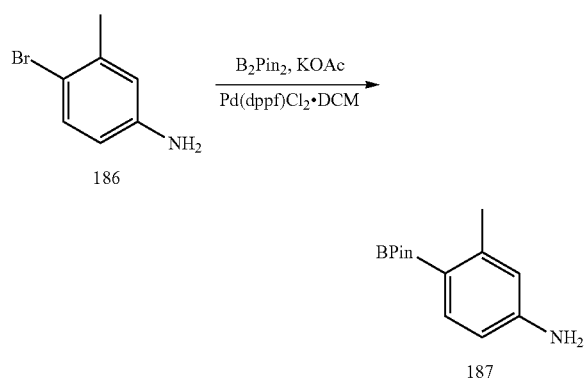

General method J, 3-methyl-4-(4,4,5,5-tetramethyl-1,3,2-dioxaborolan-2-yl)aniline. ESI [M+H]=234.2

Preparation of compound 188.

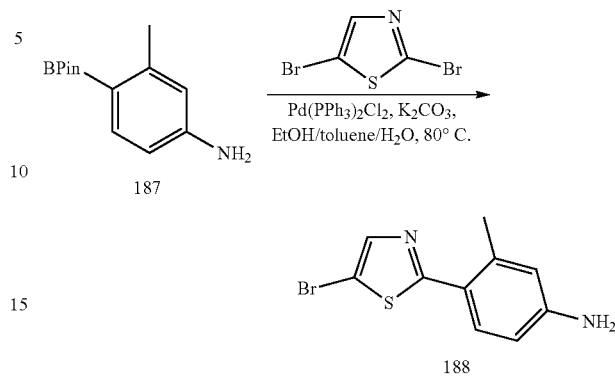

General method H, 4-(5-bromothiazol-2-yl)-3-methyl-aniline. ESI [M+H]=269.0/271.0

Preparation of compound 189.

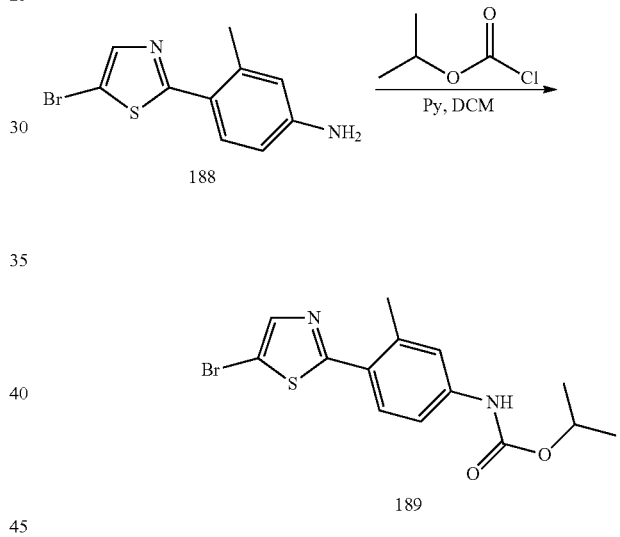

General method C, isopropyl N-[4-(5-bromothiazol-2-yl)-3-methyl-phenyl]carbamate. ESI [M+H]=355.0/357.0

The following compounds were synthesized with different bromides using a procedure similar to the used in the synthesis of intermediate compound 189.

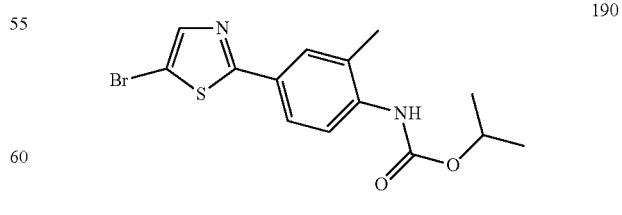

¹H NMR (400 MHz, METHANOL-d4) δ=7.75 (s, 1H), 7.72 (s, 1H), 7.68-7.65 (m, 2H), 4.97 (spt, J=6.3 Hz, 1H), 5.03-4.91 (m, 1H), 2.31 (s, 3H), 1.31 (d, J=6.2 Hz, 6H). ESI [M+H]=355.0/357.0

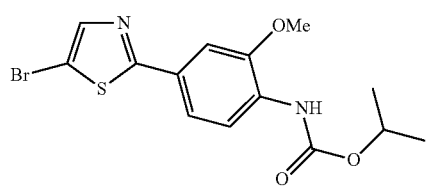
ESI [M+H]=370.7/372.7
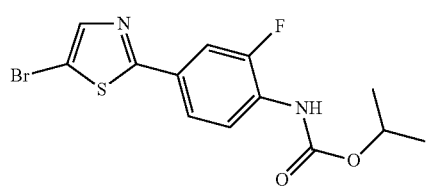
ESI [M+H]=358.9/360.9
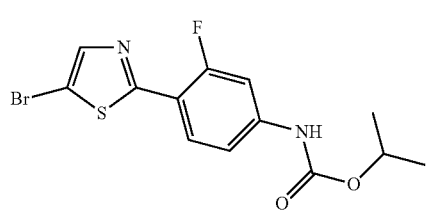
ESI [M+H]=358.8/360.8
General Scheme 18.2
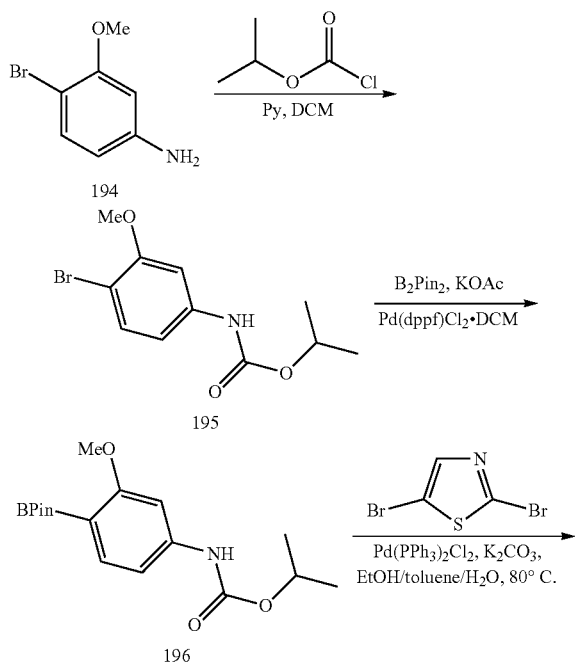
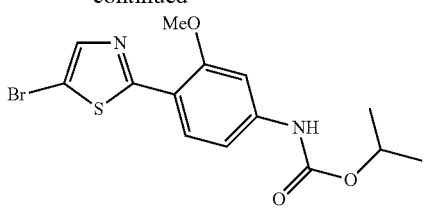
Preparation of compound 195.
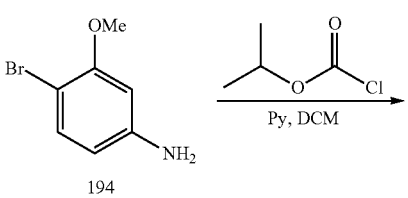
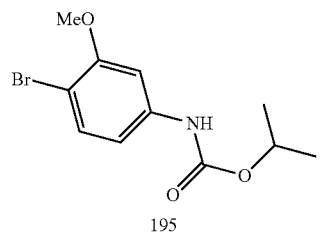
General method C, isopropyl (4-bromo-3-methoxyphenyl)carbamate. ESI[M+H]=288.0/290.0
Preparation of compound 196.
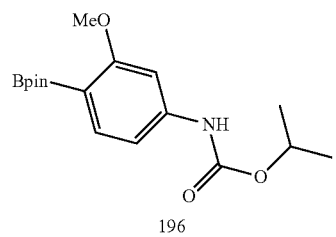
General method J, isopropyl N-[3-methoxy-4-(4,4,5,5-tetramethyl-1,3,2-dioxaborolan-2-yl)phenyl]carbamate. ESI [M+H]=336.2

Preparation of compound 197.

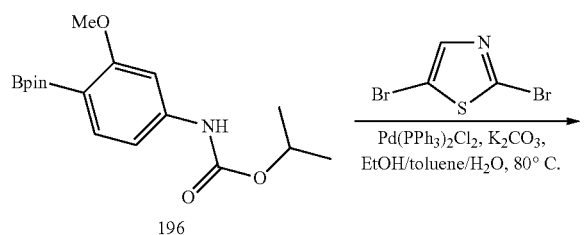

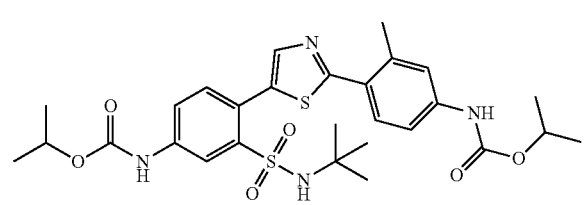

General method H, isopropyl N-[4-(5-bromothiazol-2-yl)-3-methoxy-phenyl]carbamate. ESI [M+H]=371.0/373.0

The following compounds were synthesized using intermediate compound M6 for the left hand side with different bromides for the right hand side via general method A (shown in Example 1), unless otherwise noted.

Compound R1

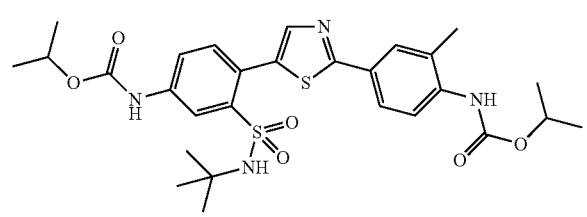

¹H NMR (400 MHz, METHANOL-d4) δ=8.40 (d, J=2.0 Hz, 1H), 7.94 (s, 1H), 7.78-7.62 (m, 2H), 7.52-7.39 (m, 3H), 5.09-4.95 (m, 2H), 2.59 (s, 3H), 1.34 (dd, J=4.4, 6.4 Hz, 12H), 1.17 (s, 9H). ESI [M+H]=589.2

Compound R2

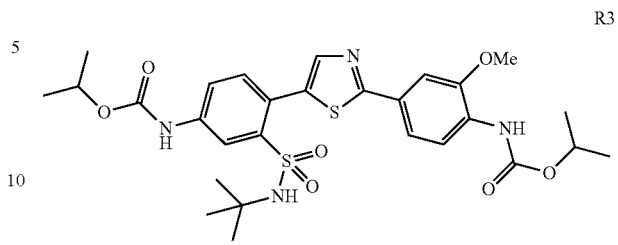

¹H NMR (400 MHz, METHANOL-d4) δ=8.37 (d, J=2.2 Hz, 1H), 7.86 (s, 1H), 7.82-7.74 (m, 2H), 7.72-7.63 (m, 2H), 7.45 (d, J=8.3 Hz, 1H), 5.03-4.94 (m, 2H), 2.33 (s, 3H), 1.32 (d, J=6.1 Hz, 12H), 1.13 (s, 9H). ESI [M+H]=589.2

Compound R3

¹H NMR (400 MHz, METHANOL-d4) δ=8.37 (d, J=2.2 Hz, 1H), 8.05 (d, J=8.4 Hz, 1H), 7.86 (s, 1H), 7.69 (dd, J=2.0, 8.4 Hz, 1H), 7.59 (d, J=1.8 Hz, 1H), 7.52-7.41 (m, 2H), 5.05-4.94 (m, 2H), 3.97 (s, 3H), 1.32 (dd, J=1.1, 6.2 Hz, 12H), 1.14 (s, 9H). ESI [M+H]=605.3

Compound R4

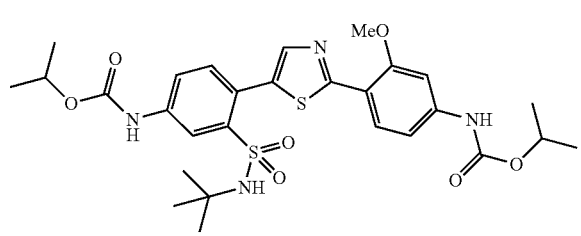

¹H NMR (400 MHz, METHANOL-d4) δ=8.37 (d, J=2.0 Hz, 1H), 8.08 (br t, J=8.2 Hz, 1H), 7.87 (s, 1H), 7.78-7.67 (m, 3H), 7.44 (d, J=8.4 Hz, 1H), 5.05-4.95 (m, 2H), 1.32 (dd, J=1.5, 6.4 Hz, 12H), 1.13 (s, 9H). ESI [M+H]=593.2

Compound R5

¹H NMR (400 MHz, DMSO-d6) δ=10.10 (s, 1H), 9.92 (s, 1H), 8.35 (d, J=1.5 Hz, 1H), 8.20 (d, J=8.8 Hz, 1H), 7.87 (s, 1H), 7.67 (dd, J=1.5, 8.3 Hz, 1H), 7.53 (s, 1H), 7.44 (d, J=8.3 Hz, 1H), 7.16 (br d, J=7.8 Hz, 1H), 7.08 (s, 1H), 4.94 (qd, J=6.3, 9.6 Hz, 2H), 3.96 (s, 3H), 1.28 (d, J=6.4 Hz, 12H), 1.09 (s, 9H). ESI [M+H]=605.2

Using intermediate compound M5 for the left hand side.
Compound R6

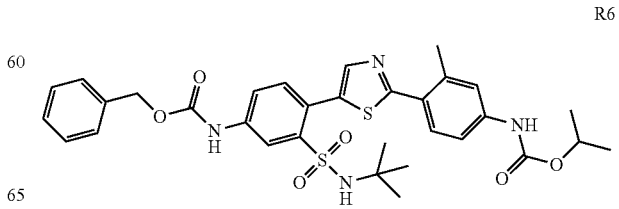

¹H NMR (400 MHz, METHANOL-d4) δ=8.39 (d, J=1.8 Hz, 1H), 7.92 (s, 1H), 7.73 (br d, J=8.3 Hz, 1H), 7.66 (d, J=8.3 Hz, 1H), 7.50-7.41 (m, 5H), 7.40-7.30 (m, 3H), 5.22 (s, 2H), 4.97 (td, J=6.5, 12.5 Hz, 1H), 2.56 (s, 3H), 1.31 (d, J=6.6 Hz, 6H), 1.14 (s, 9H). ESI [M+H]=637.4

Compound R7

R7

¹H NMR (400 MHz, METHANOL-d₄) δ=8.39 (d, J=2.2 Hz, 1H), 8.05 (d, J=8.6 Hz, 1H), 7.86 (s, 1H), 7.77-7.68 (m, 1H), 7.60 (d, J=1.5 Hz, 1H), 7.53-7.41 (m, 4H), 7.40-7.28 (m, 3H), 5.22 (s, 2H), 5.06-4.94 (m, 1H), 3.98 (s, 3H), 1.32 (d, J=6.2 Hz, 6H), 1.14 (s, 9H). ESI [M+H]=653.1

Compound R8

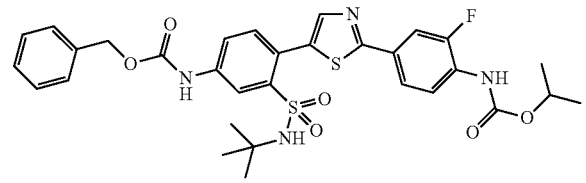

R8

¹H NMR (400 MHz, METHANOL-d4) δ=8.38 (s, 1H), 8.11-8.03 (m, 1H), 7.87 (s, 1H), 7.78-7.70 (m, 3H), 7.48-7.41 (m, 3H), 7.40-7.29 (m, 3H), 5.22 (s, 2H), 5.00 (td, J=6.4, 12.5 Hz, 1H), 1.32 (d, J=6.2 Hz, 6H), 1.13 (s, 9H). ESI [M+H]=641.2

Compound R9

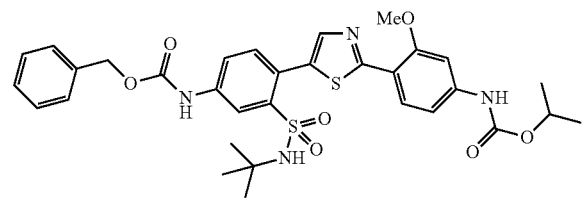

R9

¹H NMR (400 MHz, METHANOL-d4) δ=8.39 (d, J=2.2 Hz, 1H), 8.10 (d, J=8.8 Hz, 1H), 7.97 (s, 1H), 7.75 (dd, J=2.2, 8.4 Hz, 1H), 7.56 (d, J=1.5 Hz, 1H), 7.49-7.41 (m, 3H), 7.41-7.27 (m, 3H), 7.13 (dd, J=1.9, 8.7 Hz, 1H), 5.22 (s, 2H), 5.06-4.92 (m, 1H), 4.05 (s, 3H), 1.32 (d, J=6.2 Hz, 6H), 1.14 (s, 9H). ESI [M+H]=653.1

Using intermediate compound M4 for the left hand side.

Compound R10

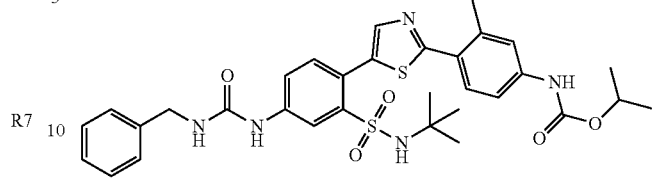

R10

¹H NMR (400 MHz, METHANOL-d4) δ=8.28 (d, J=2.2 Hz, 1H), 7.91 (s, 1H), 7.73 (dd, J=2.2, 8.3 Hz, 1H), 7.66 (d, J=8.3 Hz, 1H), 7.47-7.41 (m, 3H), 7.37-7.30 (m, 4H), 7.29-7.21 (m, 1H), 5.00-4.95 (m, 1H), 4.42 (s, 2H), 2.56 (s, 3H), 1.31 (d, J=6.1 Hz, 6H), 1.14 (s, 9H). ESI [M+H]=636.4

Compound R11

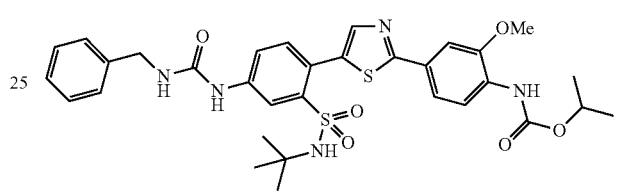

R11

¹H NMR (400 MHz, DMSO-d6) δ=9.17 (s, 1H), 8.45 (s, 1H), 8.29 (d, J=2.2 Hz, 1H), 7.91-7.83 (m, 2H), 7.66 (dd, J=2.3, 8.4 Hz, 1H), 7.56 (d, J=1.7 Hz, 1H), 7.51 (dd, J=1.7, 8.4 Hz, 1H), 7.42 (d, J=8.4 Hz, 1H), 7.38-7.31 (m, 4H), 7.29-7.23 (m, 1H), 7.14 (s, 1H), 6.80 (t, J=5.9 Hz, 1H), 4.91 (spt, J=6.2 Hz, 1H), 4.34 (d, J=5.9 Hz, 2H), 3.91 (s, 3H), 1.26 (d, J=6.2 Hz, 6H), 1.09 (s, 9H). ESI [M+H]=652.2

Compound R12

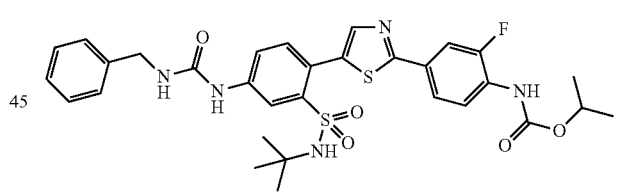

R12

¹H NMR (400 MHz, METHANOL-d4) δ=8.27 (d, J=2.2 Hz, 1H), 8.07 (br t, J=8.3 Hz, 1H), 7.86 (s, 1H), 7.78-7.69 (m, 3H), 7.43 (d, J=8.4 Hz, 1H), 7.36-7.29 (m, 4H), 7.28-7.22 (m, 1H), 5.00 (td, J=6.3, 12.5 Hz, 1H), 4.41 (s, 2H), 1.32 (d, J=6.2 Hz, 6H), 1.13 (s, 9H). ESI [M+H]=640.3

Compound R13

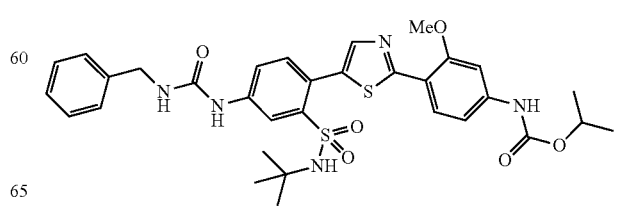

R13

$^1$H NMR (400 MHz, METHANOL-d4) δ=8.27 (d, J=2.2 Hz, 1H), 8.11 (d, J=8.8 Hz, 1H), 7.95 (s, 1H), 7.74 (dd, J=2.4, 8.4 Hz, 1H), 7.55 (d, J=1.5 Hz, 1H), 7.44 (d, J=8.6 Hz, 1H), 7.38-7.30 (m, 4H), 7.29-7.22 (m, 1H), 7.11 (dd, J=1.9, 8.7 Hz, 1H), 4.99 (td, J=6.2, 12.5 Hz, 1H), 4.42 (s, 2H), 4.05 (s, 3H), 1.32 (d, J=6.4 Hz, 6H), 1.13 (s, 9H). ESI [M+H]=652.2

Compound R14

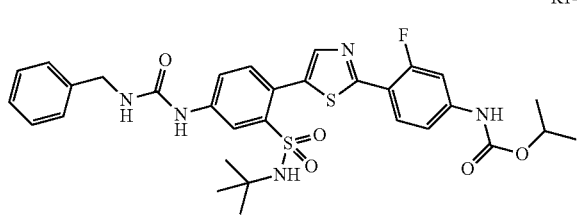

R14

$^1$H NMR (400 MHz, METHANOL-d4) δ=8.27 (d, J=2.2 Hz, 1H), 8.11 (t, J=8.6 Hz, 1H), 7.93 (d, J=2.2 Hz, 1H), 7.72 (dd, J=2.3, 8.3 Hz, 1H), 7.61 (br d, J=13.7 Hz, 1H), 7.42 (d, J=8.4 Hz, 1H), 7.37-7.31 (m, 4H), 7.29-7.22 (m, 2H), 4.99 (td, J=6.2, 12.7 Hz, 1H), 4.42 (s, 2H), 1.31 (d, J=6.2 Hz, 6H), 1.12 (s, 9H). ESI [M+H]=640.1

Biological Screen

Example 19

Compound Primary Screening
1. Materials and Supplies

Plastic ware and consumables needed for this experiment include: Cell Culture media; Evaporation Buffer media; 100% DMSO; 96 well U-bottom sterile culture plates; 250 mL bottle; 1.5 mL Opaque amber epi tubes; Epi Tube rack; 300 mL reservoirs; 25 mL reservoir; 25 mL serological pipette tips; 5 mL serological pipette tips P1000 Pipette Tips; and P200 Pipette Tips.

Equipment needed for this experiment include: Viaflo 384 liquid handler; Eppendorf serological pipette; Eppendorf P1000 Pipette; and Eppendorf P200 Pipette Daudi Cell Culture is also needed for this experiment.

Lastly, compounds (e.g., the compounds of this invention) to be tested are needed.
2. Procedure All steps were performed in a sterile environment inside the Biosafety cabinet.

A 96 well u-bottom plate was prepared by writing the experiment number, plate number, date and initials in the top right corner of the plate lid. With a sterile 300 ml reservoir, and 25 ml serological pipette, evaporation buffer media was pipetted into reservoir in 25 ml increments. Using the liquid handler, 150 ul of evaporation buffer media was pipetted from reservoir into rows A and H, and Columns 1 and 12 of the 96 well u-bottom plate. Cell cultures were counted to obtain the density of cells per ml, and the culture viability. The cell density information was used to obtain 1,000,000 cells from culture using a 5 mL serological pipette into an epi tube. The cell density information from the culture was used to calculate the number of cells and volume of media needed for the assay to seed 1250 cells in 130 ul of media per available culture well in the 96 well u-bottom plate. Rows B through F were used for cells (50 wells in total), with row G left for an empty media control. The calculation was overestimated by 10 mL to account for the dead volume in the 300 ml reservoir. Once the media volume was calculated, the appropriate volume of media was pipetted in 25 mL increments into the 250 mL bottle using a 25 mL serological pipette. The 250 ml bottle was capped tightly, and placed into a 37° C. water bath for 2 minutes. While the culture media was warming, 10 mL of fresh media was pipetted from the 500 mL culture media bottle into a sterile 25 mL reservoir. Using the Eppendorf multichannel pipette, 130 ul of media was pipetted from the 25 mL reservoir into row G of the 96 well u-bottom plate. Once the 250 mL bottle of media was warmed, the volume of culture needed was pipetted into the bottle, and mixed gently with a 25 mL serological pipette as to not create bubbles, and then the contents of the bottle were pipetted into a new 300 mL reservoir. Using the liquid handler, 130 ul of culture was pipetted from the 300 mL reservoir into rows B through F of the 96 well u-bottom plate. Once the culture was added, the plate was placed into a 37° C. incubator until the compound master plate was prepared for use.

Two 96 well u-bottom plates were prepared by writing the master plate name in the upper right corner of the plate lid. Labeling one DMSO master and the other Media Master. The compounds of interest were obtained from the laboratory freezer, and placed into a 25 well storage box with a lid, and set the box aside. The compounds were vortexed after thawing but before use. Using an automatic multichannel pipette, 20 ul of 100% DMSO was pipetted into wells B3-B11 through G3-G11 of the DMSO master plate. For each compound on the master plate, 50 ul of the compound were pipetted in the appropriate well of row 2 (reference plate map to determine appropriate well). A serial dilution was prepared beginning by aspirating 20 ul from row 2 and mixing with row 3, repeating until row 11 was reached. Using the liquid handler, 194 ul of Daudi media was dispensed into wells B2-B11 through G2-G11 of the Media master plate. Using the liquid handler, 6 ul from the DMSO master plate was aspirated and dispensed into the media master plate, mixing 100 ul twice.

Compounds from master plate were then added to the culture plate. The culture plates were removed from the incubator, and set inside the biosafety cabinet. Using a liquid handler, 20 ul from wells B2 to B11 through G2 to G11 of master plate were aspirated, and dispensed into wells B2 to B11 through G2 to G11 of culture plate. This set was continued with each culture plate. Once the culture plates acquired their 20 ul of compound dilutions, they were placed back into the incubator, until their reads on Day 7 of experiment.

Screening Data

TABLE 1

| No | Structure | EC50 (μM)<br>A = <1 μM<br>B = <5 μM<br>C = <10 μM<br>D = >10 μM |
|---|---|---|
| A2 | 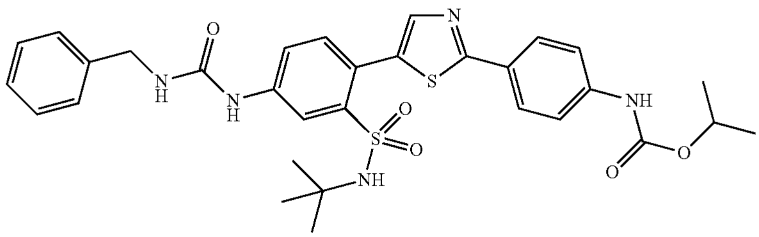 | A |
| A3 | 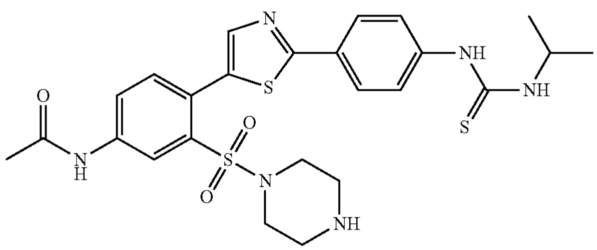 [SMILES: CC(=O)Nc1ccc(-c2cnc(-c3ccc(NC(=S)NC(C)C)cc3)s2)c(S(=O)(=O)N2CCNCC2)c1] | B |
| A4 | 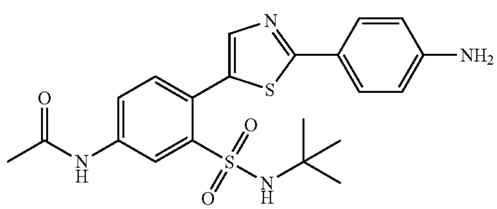 [SMILES: CC(=O)Nc1ccc(-c2cnc(-c3ccc(N)cc3)s2)c(S(=O)(=O)NC(C)(C)C)c1] | C |
| A5 | 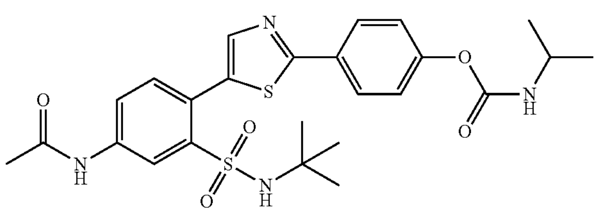 [SMILES: CC(=O)Nc1ccc(-c2cnc(-c3ccc(OC(=O)NC(C)C)cc3)s2)c(S(=O)(=O)NC(C)(C)C)c1] | B |
| A6 | 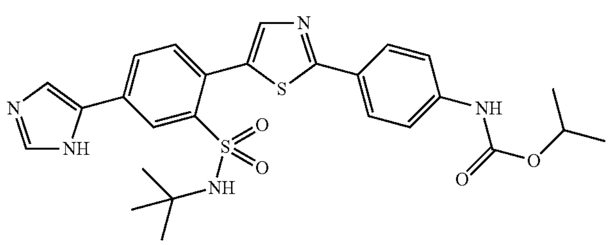 [SMILES: CC(C)OC(=O)Nc1ccc(-c2ncc(-c3ccc(-c4cnc[nH]4)cc3S(=O)(=O)NC(C)(C)C)s2)cc1] | B |
| A7 | 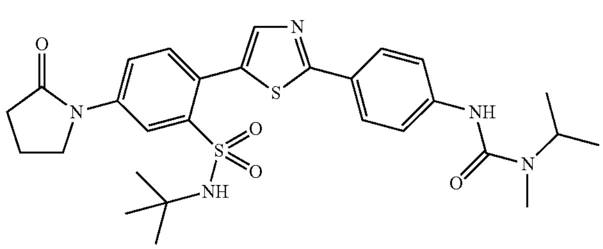 [SMILES: CC(C)N(C)C(=O)Nc1ccc(-c2ncc(-c3ccc(N4CCCC4=O)cc3S(=O)(=O)NC(C)(C)C)s2)cc1] | C |

TABLE 1-continued
| No | Structure | EC50 (μM)<br>A = <1 μM<br>B = <5 μM<br>C = <10 μM<br>D = >10 μM |
|---|---|---|
| B1 | 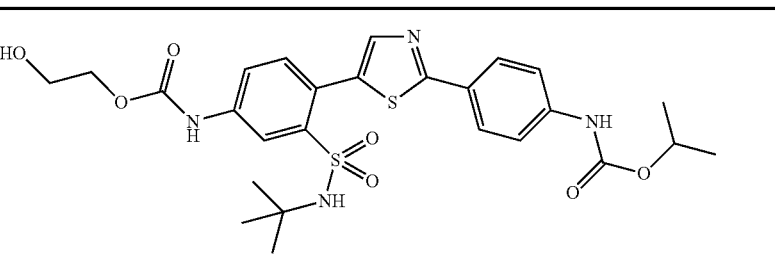 | B |
| B10 | 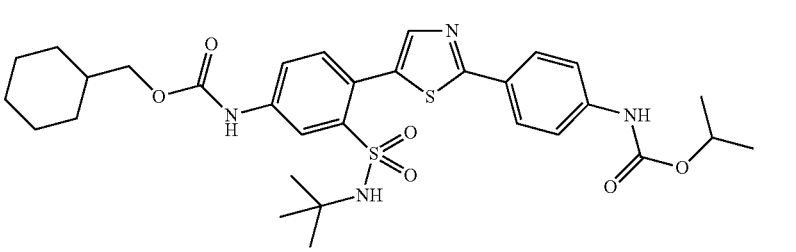 [SMILES: CC(C)OC(=O)Nc1ccc(-c2ncc(-c3ccc(NC(=O)OCC4CCCCC4)cc3S(=O)(=O)NC(C)(C)C)s2)cc1] | A |
| B11 | 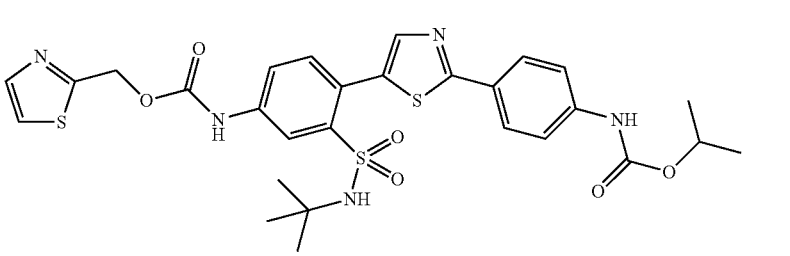 [SMILES: CC(C)OC(=O)Nc1ccc(-c2ncc(-c3ccc(NC(=O)OCc4nccs4)cc3S(=O)(=O)NC(C)(C)C)s2)cc1] | A |
| B12 | 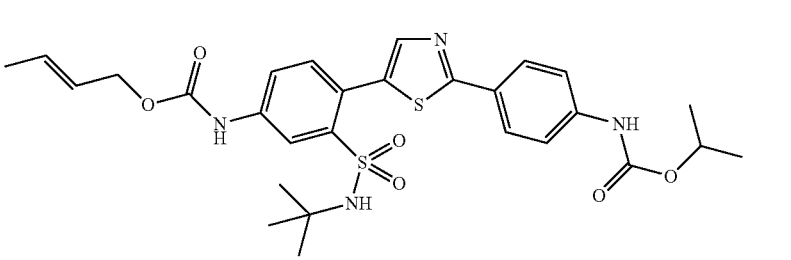 [SMILES: C/C=C/COC(=O)Nc1ccc(-c2cnc(-c3ccc(NC(=O)OC(C)C)cc3)s2)c(S(=O)(=O)NC(C)(C)C)c1] | A |
| B13 | 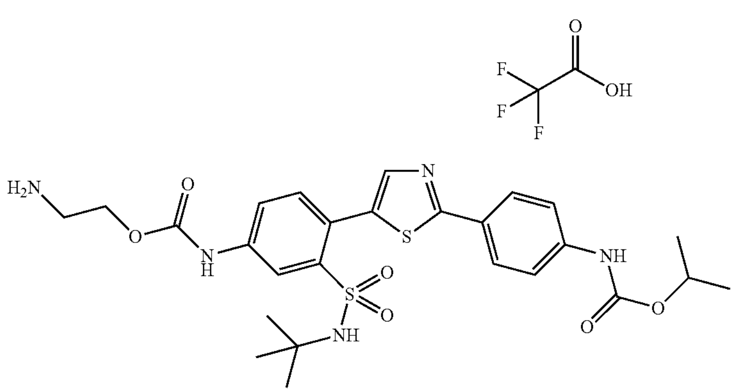 [SMILES: O=C(O)C(F)(F)F ; CC(C)OC(=O)Nc1ccc(-c2ncc(-c3ccc(NC(=O)OCCN)cc3S(=O)(=O)NC(C)(C)C)s2)cc1] | B |

TABLE 1-continued

| No | Structure | EC50 (μM)<br>A = <1 μM<br>B = <5 μM<br>C = <10 μM<br>D = >10 μM |
|---|---|---|
| B14 | 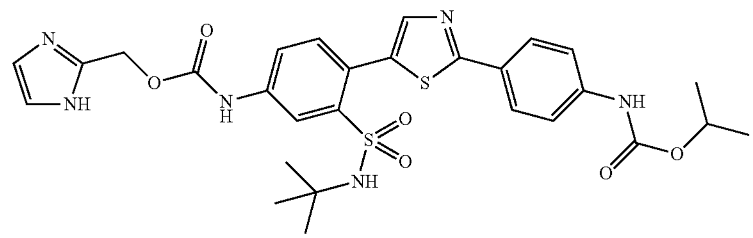 [SMILES: CC(C)OC(=O)Nc1ccc(-c2ncc(-c3ccc(NC(=O)OCc4ncc[nH]4)cc3S(=O)(=O)NC(C)(C)C)s2)cc1] | C |
| B15 | 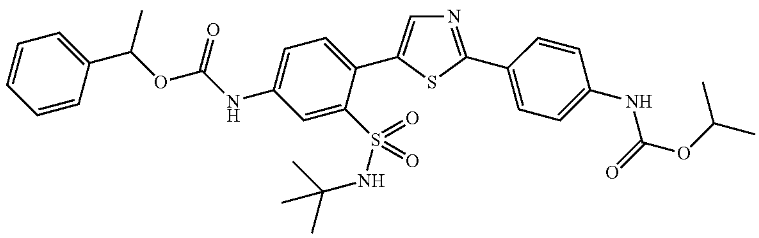 [SMILES: CC(C)OC(=O)Nc1ccc(-c2ncc(-c3ccc(NC(=O)OC(C)c4ccccc4)cc3S(=O)(=O)NC(C)(C)C)s2)cc1] | A |
| B2 | 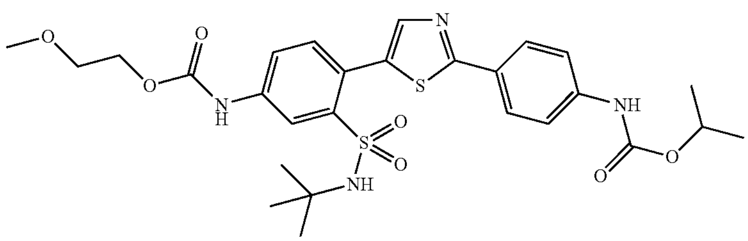 [SMILES: COCCOC(=O)Nc1ccc(-c2cnc(-c3ccc(NC(=O)OC(C)C)cc3)s2)c(S(=O)(=O)NC(C)(C)C)c1] | A |
| B3 | 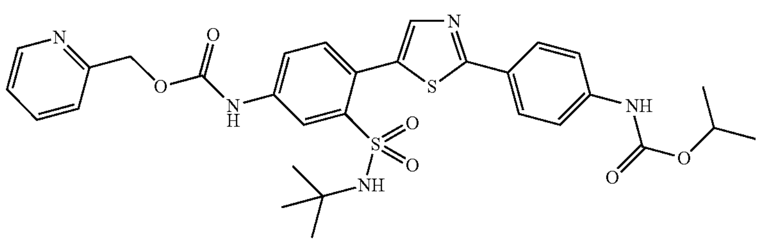 [SMILES: CC(C)OC(=O)Nc1ccc(-c2ncc(-c3ccc(NC(=O)OCc4ccccn4)cc3S(=O)(=O)NC(C)(C)C)s2)cc1] | A |
| B4 | 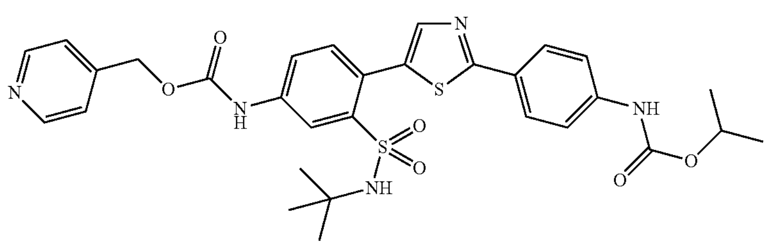 [SMILES: CC(C)OC(=O)Nc1ccc(-c2ncc(-c3ccc(NC(=O)OCc4ccncc4)cc3S(=O)(=O)NC(C)(C)C)s2)cc1] | A |
| B5 | 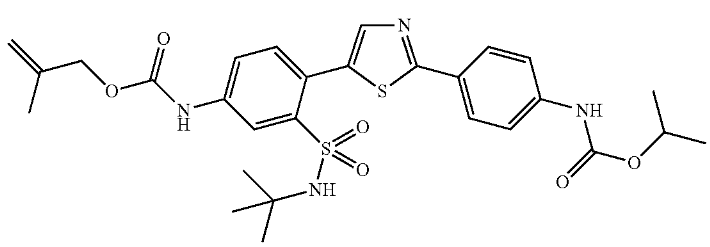 [SMILES: C=C(C)COC(=O)Nc1ccc(-c2cnc(-c3ccc(NC(=O)OC(C)C)cc3)s2)c(S(=O)(=O)NC(C)(C)C)c1] | A |

TABLE 1-continued

| No | Structure | EC50 (μM) A = <1 μM B = <5 μM C = <10 μM D = >10 μM |
|---|---|---|
| B6 | 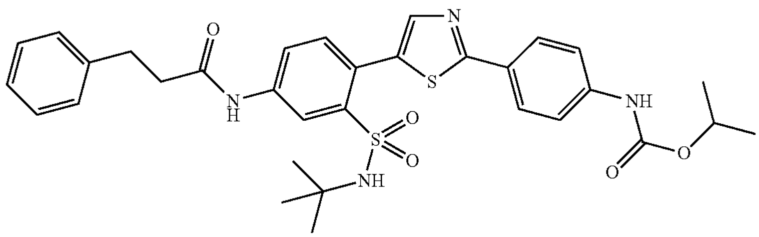 | A |
| B7 | 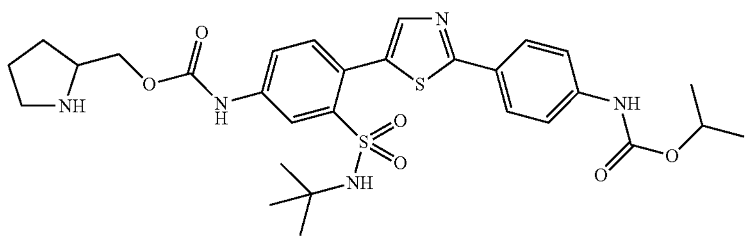 [SMILES: CC(C)OC(=O)Nc1ccc(-c2ncc(-c3ccc(NC(=O)OCC4CCCN4)cc3S(=O)(=O)NC(C)(C)C)s2)cc1] | B |
| B8 | 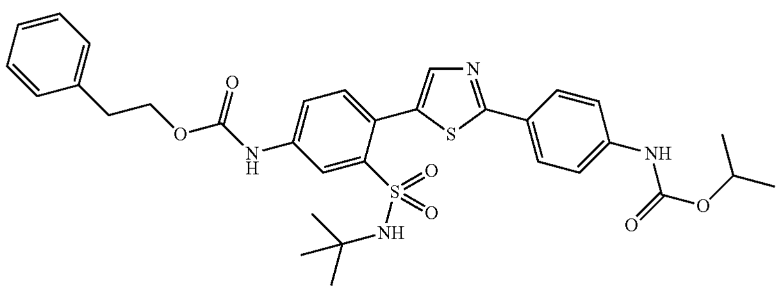 [SMILES: CC(C)OC(=O)Nc1ccc(-c2ncc(-c3ccc(NC(=O)OCCc4ccccc4)cc3S(=O)(=O)NC(C)(C)C)s2)cc1] | A |
| B9 | 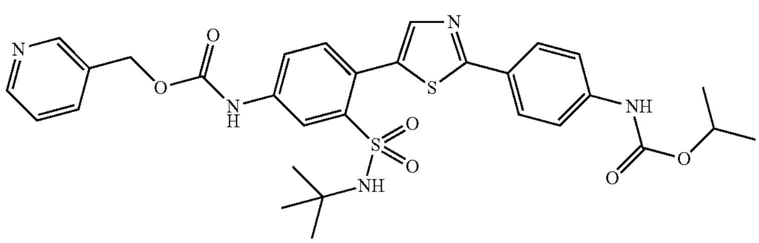 [SMILES: CC(C)OC(=O)Nc1ccc(-c2ncc(-c3ccc(NC(=O)OCc4cccnc4)cc3S(=O)(=O)NC(C)(C)C)s2)cc1] | A |
| C1 | 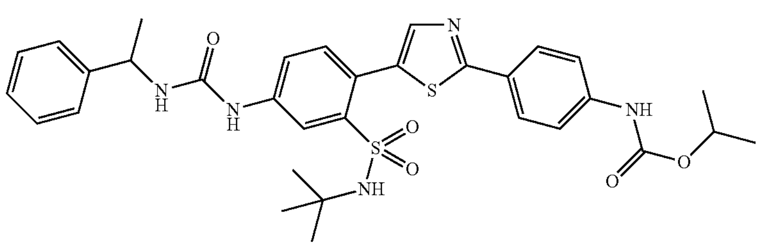 [SMILES: CC(C)OC(=O)Nc1ccc(-c2ncc(-c3ccc(NC(=O)NC(C)c4ccccc4)cc3S(=O)(=O)NC(C)(C)C)s2)cc1] | A |
| J19 | 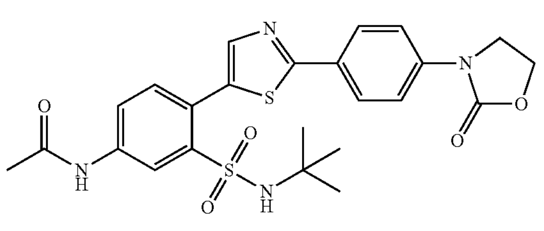 [SMILES: CC(=O)Nc1ccc(-c2cnc(-c3ccc(N4CCOC4=O)cc3)s2)c(S(=O)(=O)NC(C)(C)C)c1] | D |

TABLE 1-continued

| No | Structure | EC50 (μM)<br>A = <1 μM<br>B = <5 μM<br>C = <10 μM<br>D = >10 μM |
|---|---|---|
| H1 | 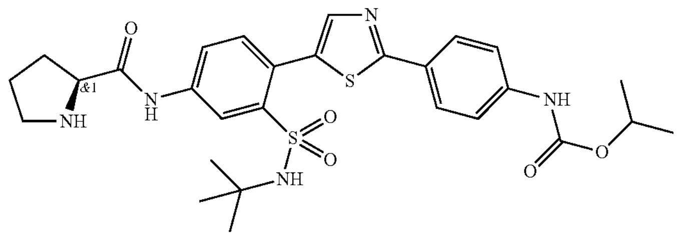 [SMILES: CC(C)OC(=O)Nc1ccc(-c2ncc(-c3ccc(NC(=O)[C@@H]4CCCN4)cc3S(=O)(=O)NC(C)(C)C)s2)cc1] | B |
| H2 | 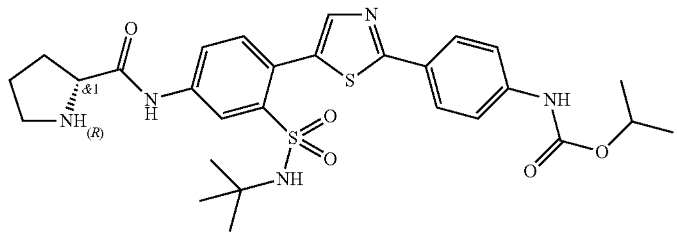 | B |
| I6 | 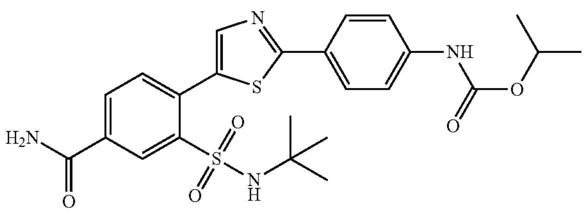 [SMILES: CC(C)OC(=O)Nc1ccc(-c2ncc(-c3ccc(C(N)=O)cc3S(=O)(=O)NC(C)(C)C)s2)cc1] | B |
| I7 | 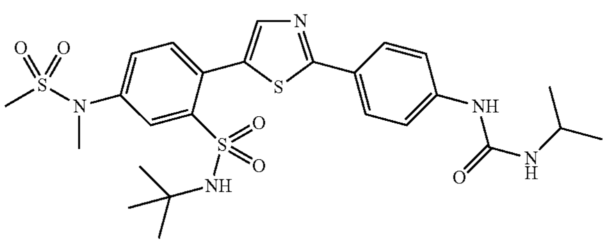 [SMILES: CC(C)NC(=O)Nc1ccc(-c2ncc(-c3ccc(N(C)S(C)(=O)=O)cc3S(=O)(=O)NC(C)(C)C)s2)cc1] | D |
| L4 | 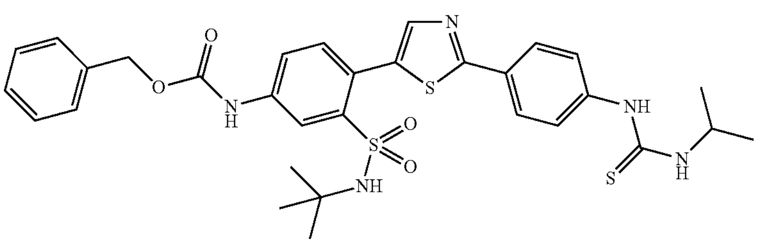 [SMILES: CC(C)NC(=S)Nc1ccc(-c2ncc(-c3ccc(NC(=O)OCc4ccccc4)cc3S(=O)(=O)NC(C)(C)C)s2)cc1] | D |
| L6 | 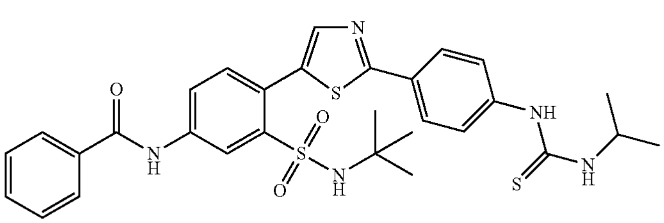 [SMILES: CC(C)NC(=S)Nc1ccc(-c2ncc(-c3ccc(NC(=O)c4ccccc4)cc3S(=O)(=O)NC(C)(C)C)s2)cc1] | B |

TABLE 1-continued

| No | Structure | EC50 (μM) A = <1 μM B = <5 μM C = <10 μM D = >10 μM |
|---|---|---|
| D1 | 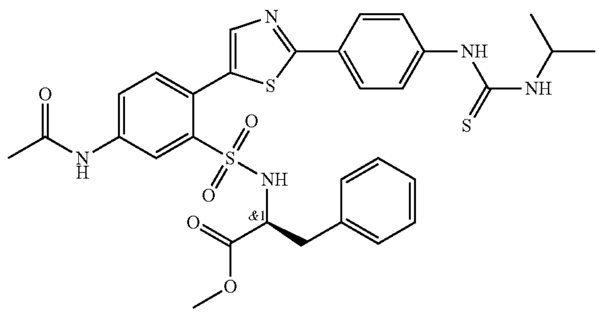 [SMILES: COC(=O)[C@H](Cc1ccccc1)NS(=O)(=O)c1cc(NC(C)=O)ccc1-c1cnc(-c2ccc(NC(=S)NC(C)C)cc2)s1] | D |
| D10 | 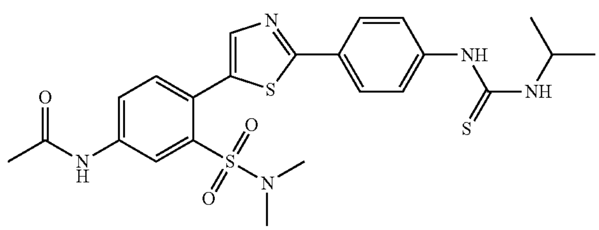 [SMILES: CC(=O)Nc1ccc(-c2cnc(-c3ccc(NC(=S)NC(C)C)cc3)s2)c(S(=O)(=O)N(C)C)c1] | A |
| D11 | 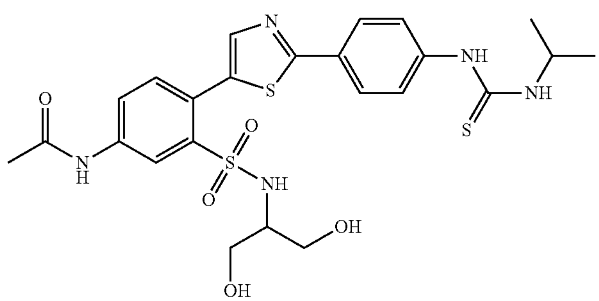 [SMILES: CC(=O)Nc1ccc(-c2cnc(-c3ccc(NC(=S)NC(C)C)cc3)s2)c(S(=O)(=O)NC(CO)CO)c1] | D |
| D12 | 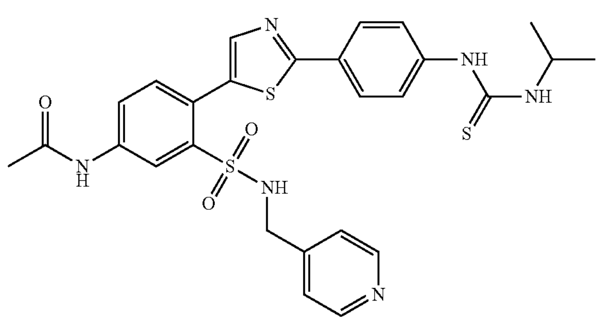 | D |
| D13 | 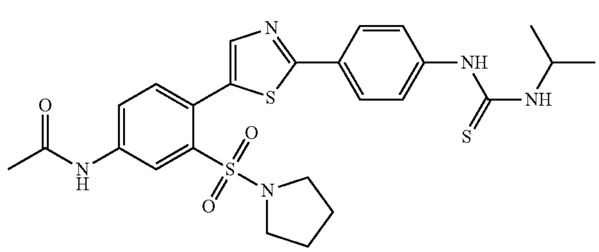 [SMILES: CC(=O)Nc1ccc(-c2cnc(-c3ccc(NC(=S)NC(C)C)cc3)s2)c(S(=O)(=O)N2CCCC2)c1] | D |

TABLE 1-continued

| No | Structure | EC50 (μM)<br>A = <1 μM<br>B = <5 μM<br>C = <10 μM<br>D = >10 μM |
|---|---|---|
| D14 | 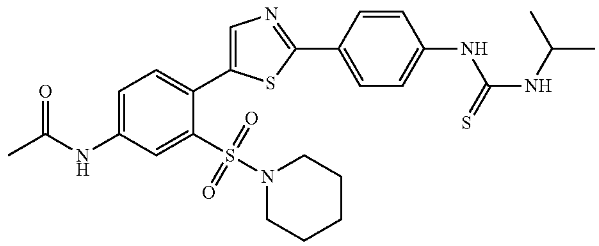 [SMILES: CC(=O)Nc1ccc(-c2cnc(-c3ccc(NC(=S)NC(C)C)cc3)s2)c(S(=O)(=O)N2CCCCC2)c1] | D |
| D15 | 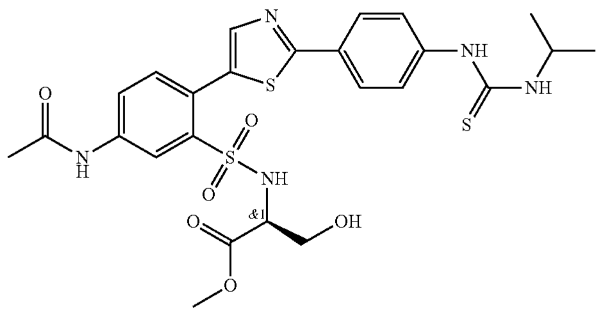 [SMILES: COC(=O)[C@H](CO)NS(=O)(=O)c1cc(NC(C)=O)ccc1-c1cnc(-c2ccc(NC(=S)NC(C)C)cc2)s1] | D |
| D16 | 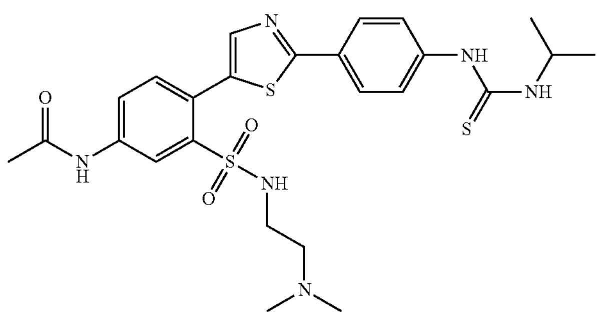 [SMILES: CC(=O)Nc1ccc(-c2cnc(-c3ccc(NC(=S)NC(C)C)cc3)s2)c(S(=O)(=O)NCCN(C)C)c1] | D |
| D17 | 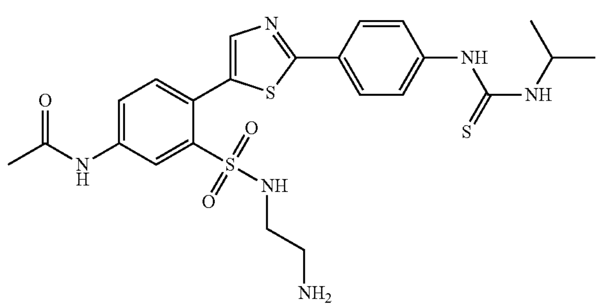 [SMILES: CC(=O)Nc1ccc(-c2cnc(-c3ccc(NC(=S)NC(C)C)cc3)s2)c(S(=O)(=O)NCCN)c1] | D |
| D18 | 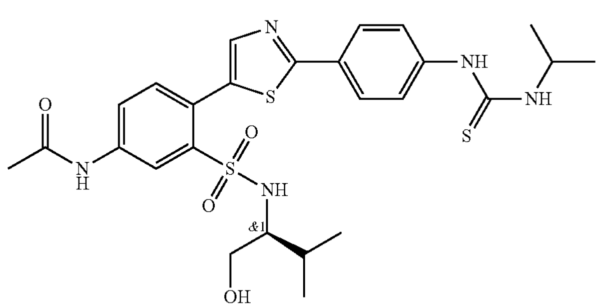 [SMILES: CC(=O)Nc1ccc(-c2cnc(-c3ccc(NC(=S)NC(C)C)cc3)s2)c(S(=O)(=O)N[C@H](CO)C(C)C)c1] | D |

TABLE 1-continued

| No | Structure | EC50 (μM)<br>A = <1 μM<br>B = <5 μM<br>C = <10 μM<br>D = >10 μM |
|---|---|---|
| D19 | 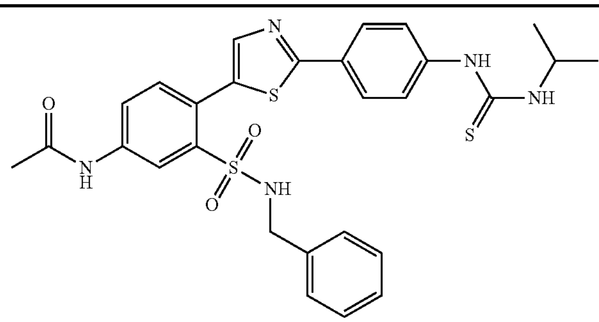 | D |
| D2 | 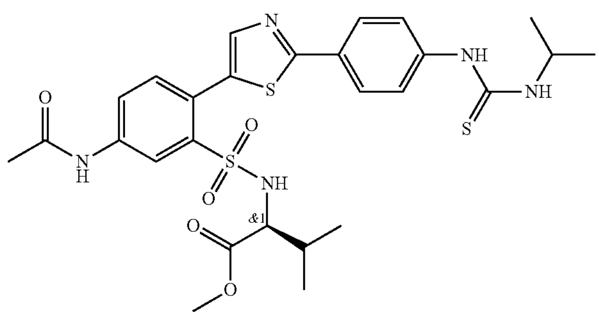 [SMILES: COC(=O)[C@@H](NS(=O)(=O)c1cc(NC(C)=O)ccc1-c1cnc(-c2ccc(NC(=S)NC(C)C)cc2)s1)C(C)C] | D |
| D20 | 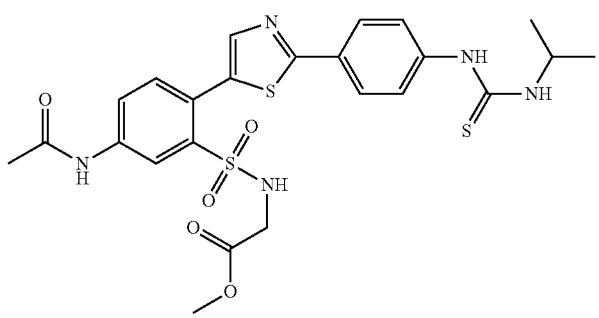 [SMILES: COC(=O)CNS(=O)(=O)c1cc(NC(C)=O)ccc1-c1cnc(-c2ccc(NC(=S)NC(C)C)cc2)s1] | D |
| D21 | 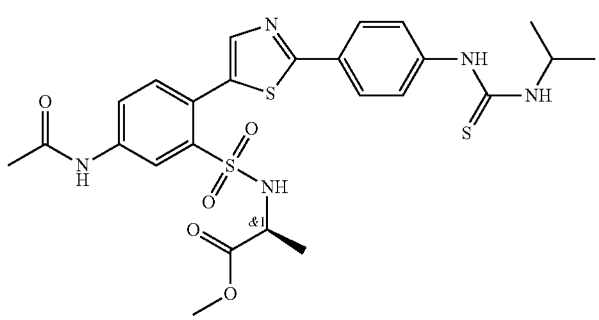 [SMILES: COC(=O)[C@H](C)NS(=O)(=O)c1cc(NC(C)=O)ccc1-c1cnc(-c2ccc(NC(=S)NC(C)C)cc2)s1] | D |
| D22 | 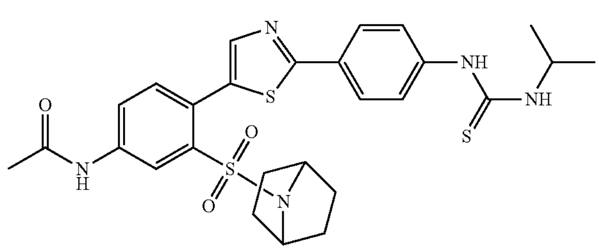 [SMILES: CC(=O)Nc1ccc(-c2cnc(-c3ccc(NC(=S)NC(C)C)cc3)s2)c(S(=O)(=O)N2C3CCC2CC3)c1] | A |

TABLE 1-continued

| No | Structure | EC50 (μM)<br>A = <1 μM<br>B = <5 μM<br>C = <10 μM<br>D = >10 μM |
|----|-----------|------|
| D23 | 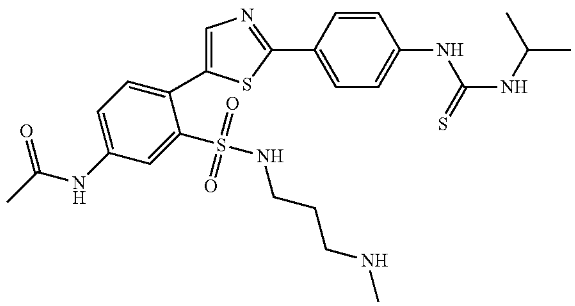 [SMILES: CNCCCNS(=O)(=O)c1cc(NC(C)=O)ccc1-c1cnc(-c2ccc(NC(=S)NC(C)C)cc2)s1] | D |
| D24 | 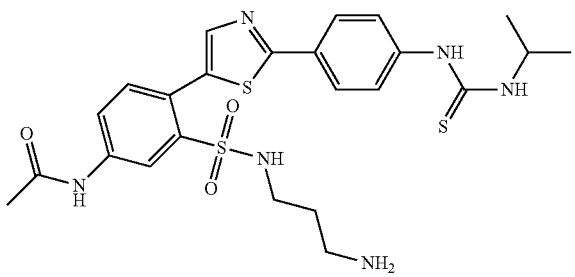 [SMILES: CC(=O)Nc1ccc(-c2cnc(-c3ccc(NC(=S)NC(C)C)cc3)s2)c(S(=O)(=O)NCCCN)c1] | D |
| D25 | 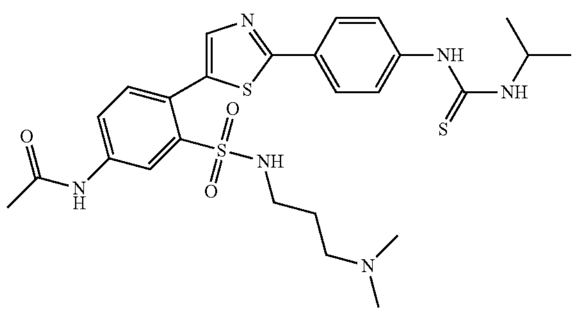 [SMILES: CC(=O)Nc1ccc(-c2cnc(-c3ccc(NC(=S)NC(C)C)cc3)s2)c(S(=O)(=O)NCCCN(C)C)c1] | A |
| D26 | 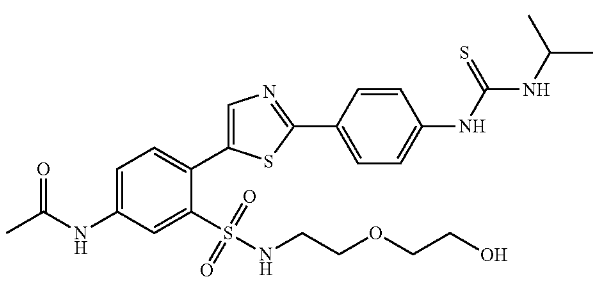 [SMILES: CC(=O)Nc1ccc(-c2cnc(-c3ccc(NC(=S)NC(C)C)cc3)s2)c(S(=O)(=O)NCCOCCO)c1] | D |
| D27 | 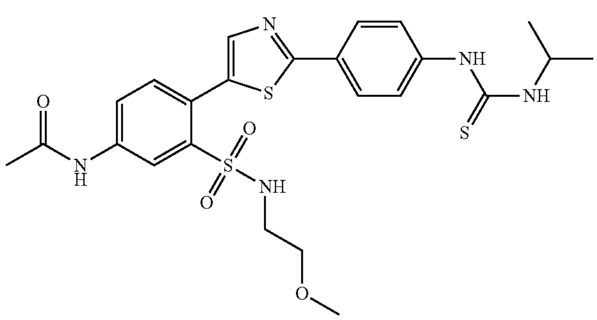 [SMILES: COCCNS(=O)(=O)c1cc(NC(C)=O)ccc1-c1cnc(-c2ccc(NC(=S)NC(C)C)cc2)s1] | D |

TABLE 1-continued

| No | Structure | EC50 (μM)<br>A = <1 μM<br>B = <5 μM<br>C = <10 μM<br>D = >10 μM |
|---|---|---|
| D28 | 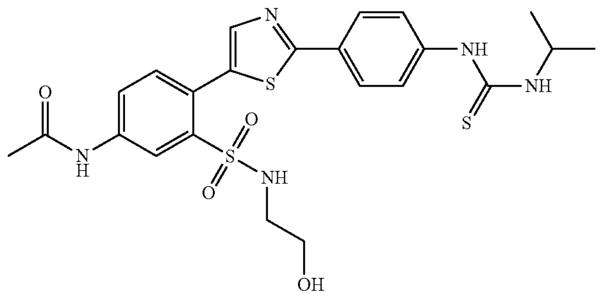 [SMILES: CC(=O)Nc1ccc(-c2cnc(-c3ccc(NC(=S)NC(C)C)cc3)s2)c(S(=O)(=O)NCCO)c1] | D |
| D29 | 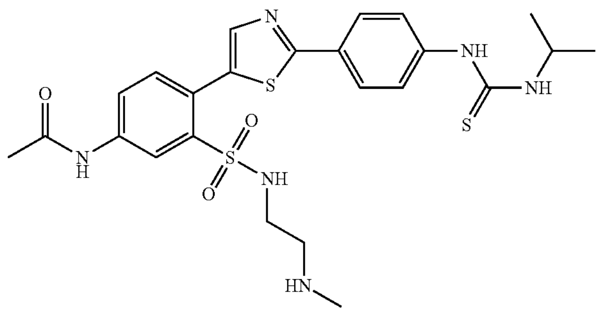 | D |
| D3 | 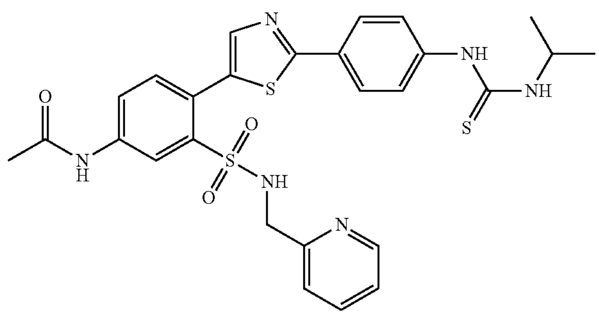 | D |
| D30 | 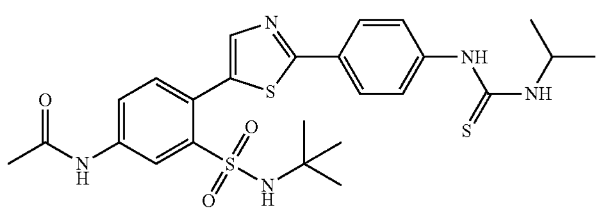 [SMILES: CC(=O)Nc1ccc(-c2cnc(-c3ccc(NC(=S)NC(C)C)cc3)s2)c(S(=O)(=O)NC(C)(C)C)c1] | B |
| D4 | 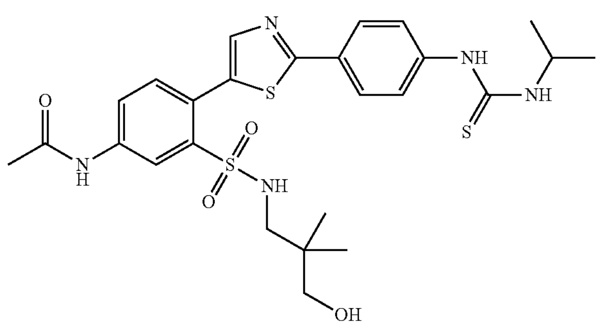 [SMILES: CC(=O)Nc1ccc(-c2cnc(-c3ccc(NC(=S)NC(C)C)cc3)s2)c(S(=O)(=O)NCC(C)(C)CO)c1] | D |

TABLE 1-continued

| No | Structure | EC50 (μM)<br>A = <1 μM<br>B = <5 μM<br>C = <10 μM<br>D = >10 μM |
|----|-----------|---|
| D5 | 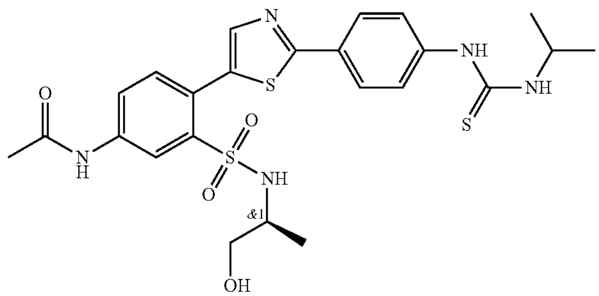 [SMILES: CC(=O)Nc1ccc(-c2cnc(-c3ccc(NC(=S)NC(C)C)cc3)s2)c(S(=O)(=O)N[C@@H](C)CO)c1] | D |
| D6 | 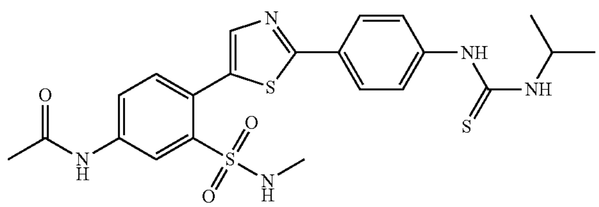 [SMILES: CNS(=O)(=O)c1cc(NC(C)=O)ccc1-c1cnc(-c2ccc(NC(=S)NC(C)C)cc2)s1] | D |
| D7 | 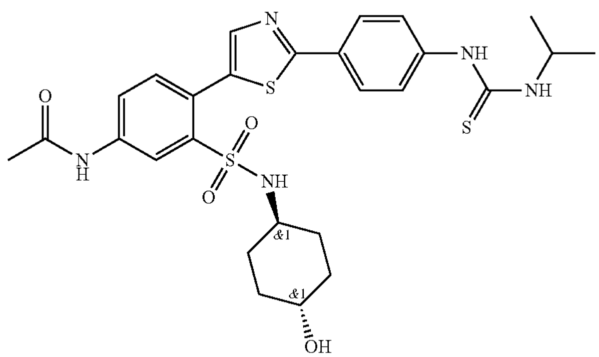 [SMILES: CC(=O)Nc1ccc(-c2cnc(-c3ccc(NC(=S)NC(C)C)cc3)s2)c(S(=O)(=O)N[C@H]2CC[C@H](O)CC2)c1] | D |
| D8 | 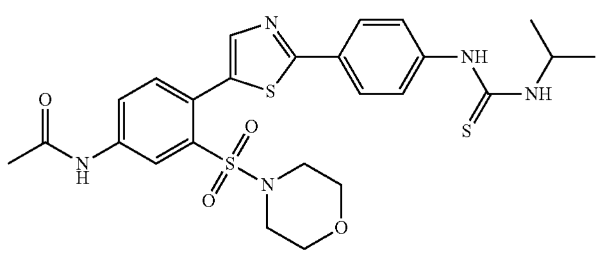 | D |
| D9 | 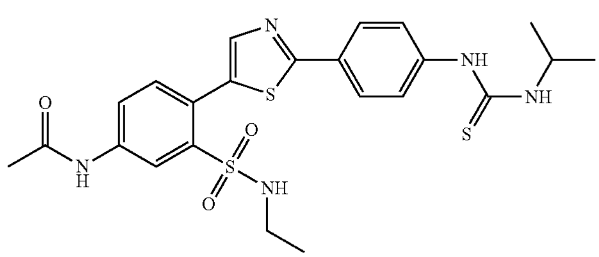 [SMILES: CCNS(=O)(=O)c1cc(NC(C)=O)ccc1-c1cnc(-c2ccc(NC(=S)NC(C)C)cc2)s1] | D |

TABLE 1-continued

| No | Structure | EC50 (μM) A = <1 μM B = <5 μM C = <10 μM D = >10 μM |
|---|---|---|
| E1 | 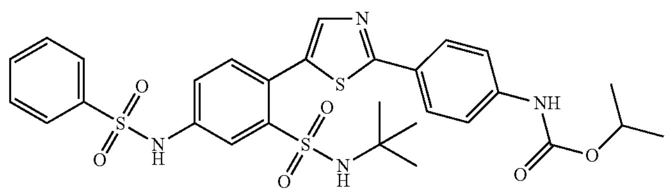 [SMILES: CC(C)OC(=O)Nc1ccc(-c2ncc(-c3ccc(NS(=O)(=O)c4ccccc4)cc3S(=O)(=O)NC(C)(C)C)s2)cc1] | D |
| E11 | 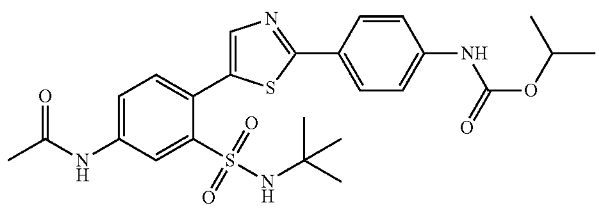 [SMILES: CC(=O)Nc1ccc(-c2cnc(-c3ccc(NC(=O)OC(C)C)cc3)s2)c(S(=O)(=O)NC(C)(C)C)c1] | B |
| E12 | 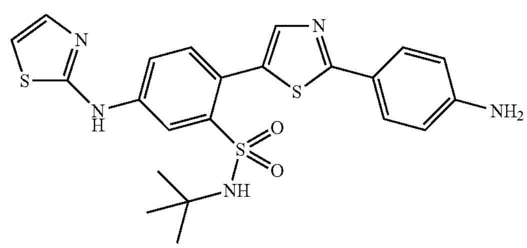 [SMILES: CC(C)(C)NS(=O)(=O)c1cc(Nc2nccs2)ccc1-c1cnc(-c2ccc(N)cc2)s1] | D |
| E14 | 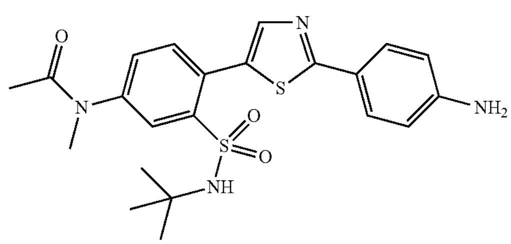 [SMILES: CC(=O)N(C)c1ccc(-c2cnc(-c3ccc(N)cc3)s2)c(S(=O)(=O)NC(C)(C)C)c1] | D |
| E15 | 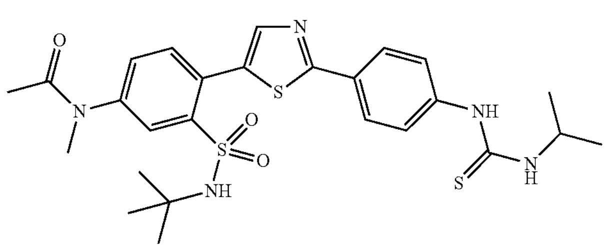 [SMILES: CC(=O)N(C)c1ccc(-c2cnc(-c3ccc(NC(=S)NC(C)C)cc3)s2)c(S(=O)(=O)NC(C)(C)C)c1] | D |
| E16 | 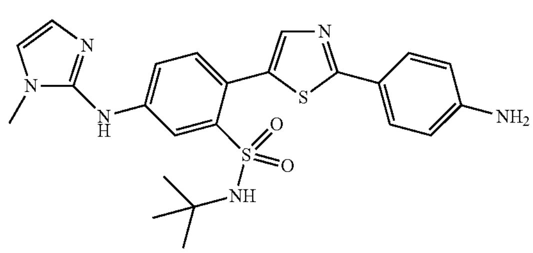 [SMILES: Cn1ccnc1Nc1ccc(-c2cnc(-c3ccc(N)cc3)s2)c(S(=O)(=O)NC(C)(C)C)c1] | D |

TABLE 1-continued

| No | Structure | EC50 (μM)<br>A = <1 μM<br>B = <5 μM<br>C = <10 μM<br>D = >10 μM |
|----|-----------|------|
| E17 | 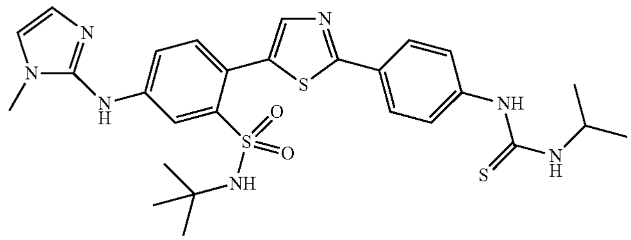 [SMILES: CC(C)NC(=S)Nc1ccc(-c2ncc(-c3ccc(Nc4nccn4C)cc3S(=O)(=O)NC(C)(C)C)s2)cc1] | D |
| E18 | 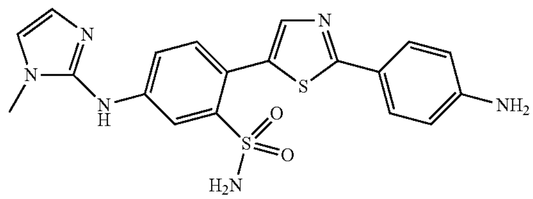 [SMILES: Cn1ccnc1Nc1ccc(-c2cnc(-c3ccc(N)cc3)s2)c(S(N)(=O)=O)c1] | D |
| E19 | 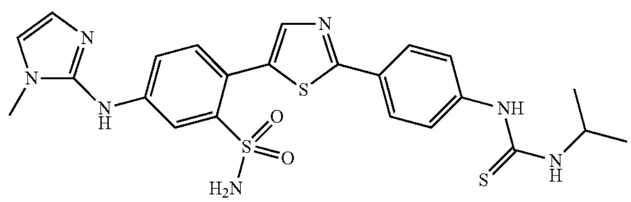 [SMILES: CC(C)NC(=S)Nc1ccc(-c2ncc(-c3ccc(Nc4nccn4C)cc3S(N)(=O)=O)s2)cc1] | D |
| E2 | 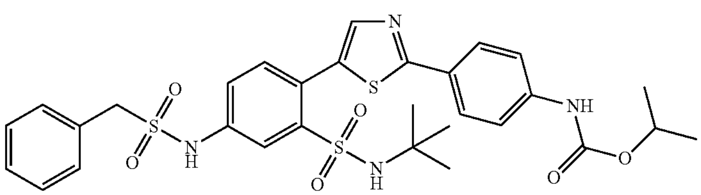 [SMILES: CC(C)OC(=O)Nc1ccc(-c2ncc(-c3ccc(NS(=O)(=O)Cc4ccccc4)cc3S(=O)(=O)NC(C)(C)C)s2)cc1] | D |
| E20 | 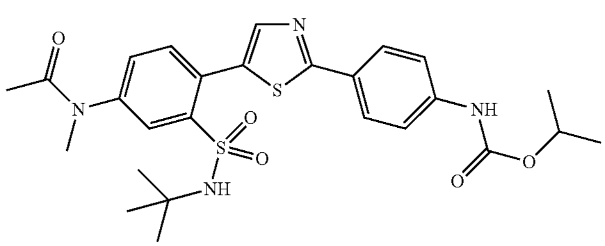 [SMILES: CC(=O)N(C)c1ccc(-c2cnc(-c3ccc(NC(=O)OC(C)C)cc3)s2)c(S(=O)(=O)NC(C)(C)C)c1] | C |
| E21 | 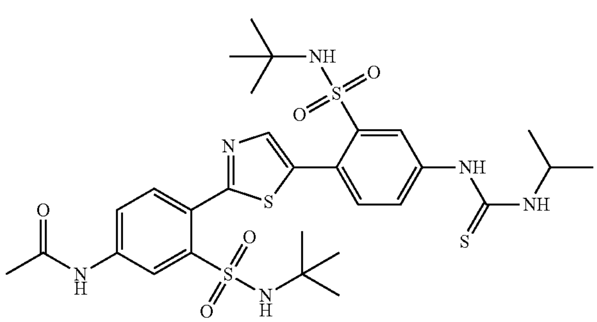 [SMILES: CC(=O)Nc1ccc(-c2ncc(-c3ccc(NC(=S)NC(C)C)cc3S(=O)(=O)NC(C)(C)C)s2)c(S(=O)(=O)NC(C)(C)C)c1] | B |

TABLE 1-continued

| No | Structure | EC50 (μM) A = <1 μM B = <5 μM C = <10 μM D = >10 μM |
|----|-----------|------|
| E3 | 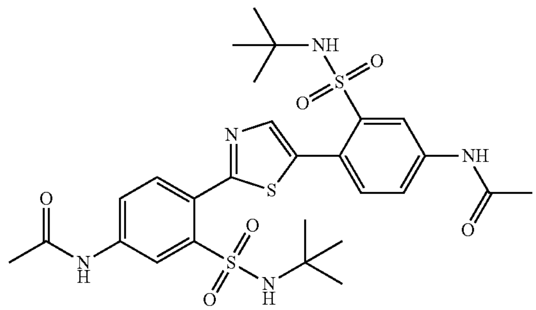 [SMILES: CC(=O)Nc1ccc(-c2cnc(-c3ccc(NC(C)=O)cc3S(=O)(=O)NC(C)(C)C)s2)c(S(=O)(=O)NC(C)(C)C)c1] | C |
| E4 | 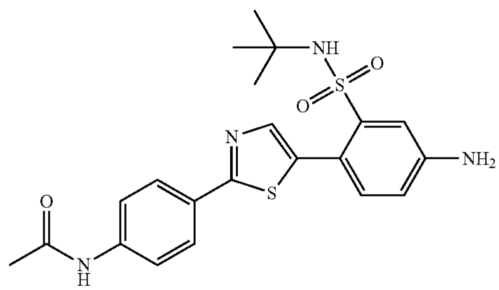 [SMILES: CC(=O)Nc1ccc(-c2ncc(-c3ccc(N)cc3S(=O)(=O)NC(C)(C)C)s2)cc1] | D |
| E5 | 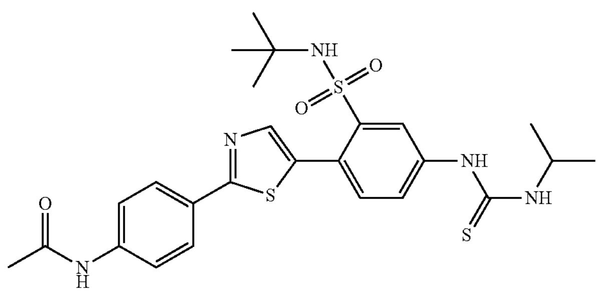 [SMILES: CC(=O)Nc1ccc(-c2ncc(-c3ccc(NC(=S)NC(C)C)cc3S(=O)(=O)NC(C)(C)C)s2)cc1] | C |
| E8 | 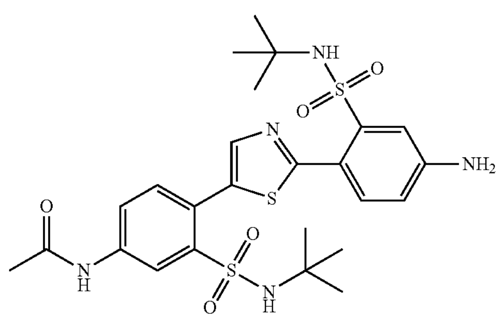 [SMILES: CC(=O)Nc1ccc(-c2cnc(-c3ccc(N)cc3S(=O)(=O)NC(C)(C)C)s2)c(S(=O)(=O)NC(C)(C)C)c1] | D |
| E9 | 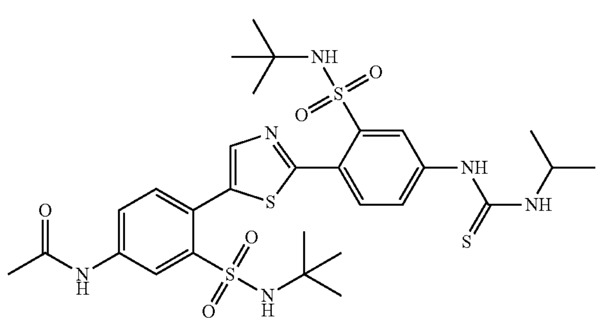 [SMILES: CC(=O)Nc1ccc(-c2cnc(-c3ccc(NC(=S)NC(C)C)cc3S(=O)(=O)NC(C)(C)C)s2)c(S(=O)(=O)NC(C)(C)C)c1] | A |

TABLE 1-continued

| No | Structure | EC50 (μM)<br>A = <1 μM<br>B = <5 μM<br>C = <10 μM<br>D = >10 μM |
|----|-----------|-----|
| G1 | 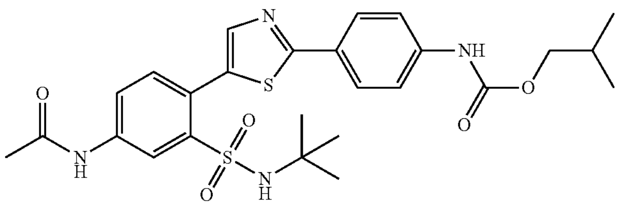 [SMILES: CC(=O)Nc1ccc(-c2cnc(-c3ccc(NC(=O)OCC(C)C)cc3)s2)c(S(=O)(=O)NC(C)(C)C)c1] | B |
| G10 | 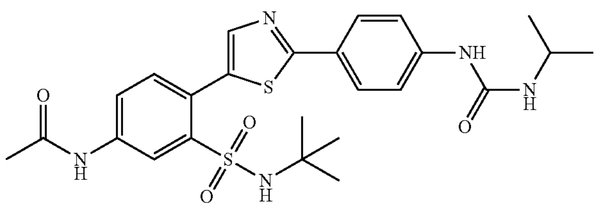 | C |
| G11 | 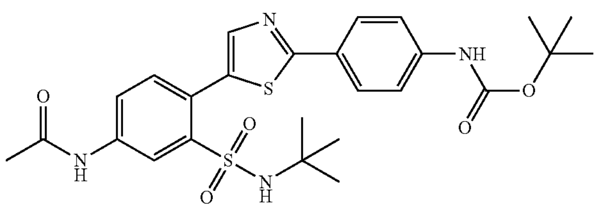 [SMILES: CC(=O)Nc1ccc(-c2cnc(-c3ccc(NC(=O)OC(C)(C)C)cc3)s2)c(S(=O)(=O)NC(C)(C)C)c1] | B |
| G2 | 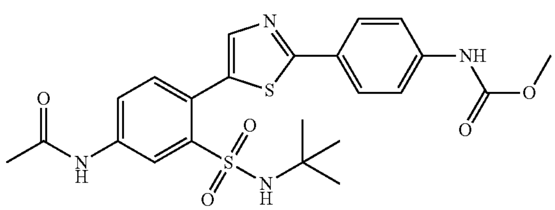 [SMILES: COC(=O)Nc1ccc(-c2ncc(-c3ccc(NC(C)=O)cc3S(=O)(=O)NC(C)(C)C)s2)cc1] | C |
| G3 | 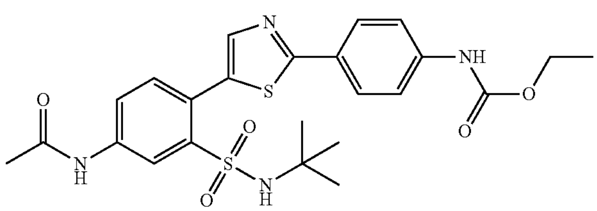 [SMILES: CCOC(=O)Nc1ccc(-c2ncc(-c3ccc(NC(C)=O)cc3S(=O)(=O)NC(C)(C)C)s2)cc1] | A |
| G4 | 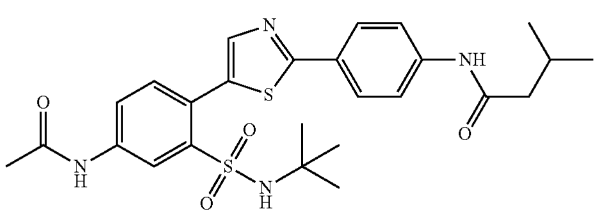 | D |
| G5 | 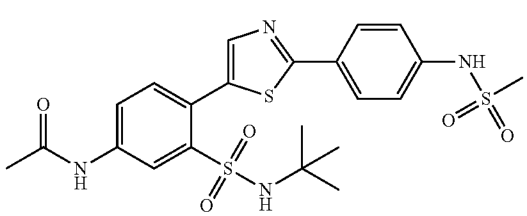 [SMILES: CC(=O)Nc1ccc(-c2cnc(-c3ccc(NS(C)(=O)=O)cc3)s2)c(S(=O)(=O)NC(C)(C)C)c1] | D |

TABLE 1-continued

| No | Structure | EC50 (µM)<br>A = <1 µM<br>B = <5 µM<br>C = <10 µM<br>D = >10 µM |
|---|---|---|
| G6 | 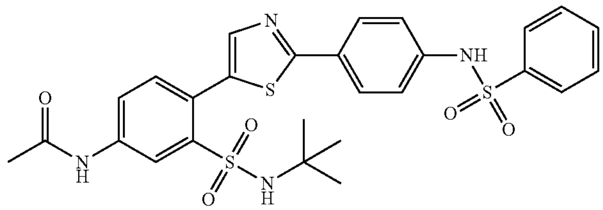 [SMILES: CC(=O)Nc1ccc(-c2cnc(-c3ccc(NS(=O)(=O)c4ccccc4)cc3)s2)c(S(=O)(=O)NC(C)(C)C)c1] | C |
| G7 | 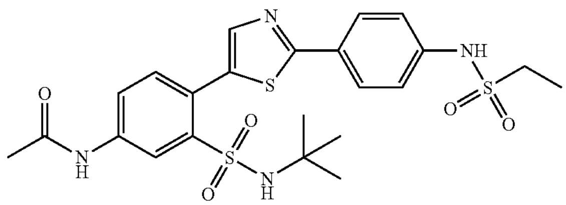 [SMILES: CCS(=O)(=O)Nc1ccc(-c2ncc(-c3ccc(NC(C)=O)cc3S(=O)(=O)NC(C)(C)C)s2)cc1] | D |
| G8 | 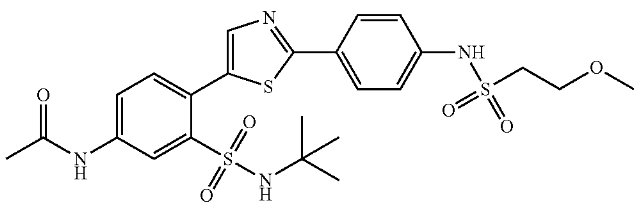 [SMILES: COCCS(=O)(=O)Nc1ccc(-c2ncc(-c3ccc(NC(C)=O)cc3S(=O)(=O)NC(C)(C)C)s2)cc1] | D |
| G9 | 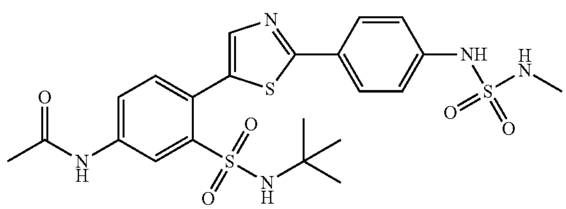 [SMILES: CNS(=O)(=O)Nc1ccc(-c2ncc(-c3ccc(NC(C)=O)cc3S(=O)(=O)NC(C)(C)C)s2)cc1] | D |
| H10 | 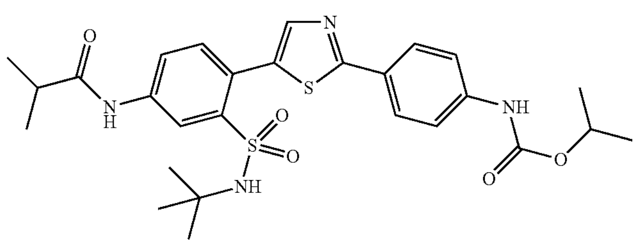 [SMILES: CC(C)OC(=O)Nc1ccc(-c2ncc(-c3ccc(NC(=O)C(C)C)cc3S(=O)(=O)NC(C)(C)C)s2)cc1] | A |
| H11 | 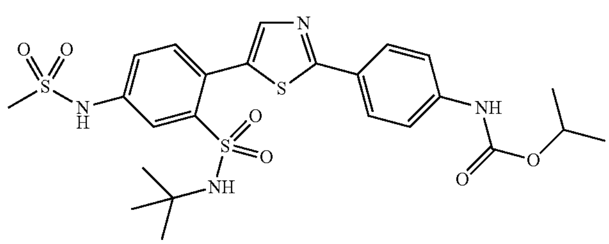 [SMILES: CC(C)OC(=O)Nc1ccc(-c2ncc(-c3ccc(NS(C)(=O)=O)cc3S(=O)(=O)NC(C)(C)C)s2)cc1] | D |
| H3 | 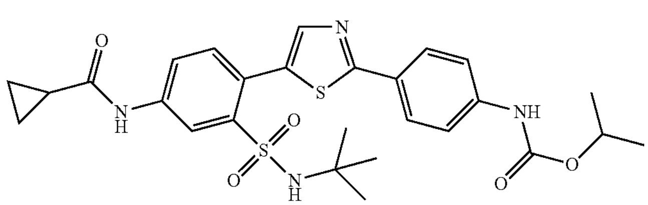 [SMILES: CC(C)OC(=O)Nc1ccc(-c2ncc(-c3ccc(NC(=O)C4CC4)cc3S(=O)(=O)NC(C)(C)C)s2)cc1] | B |

TABLE 1-continued

| No | Structure | EC50 (μM)<br>A = <1 μM<br>B = <5 μM<br>C = <10 μM<br>D = >10 μM |
|---|---|---|
| H4 | 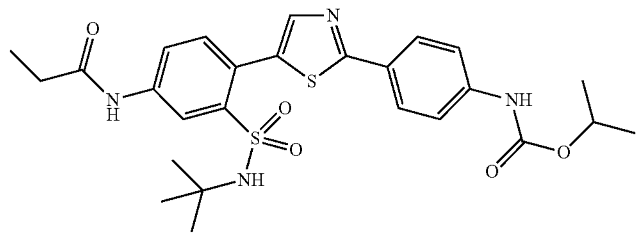 [SMILES: CCC(=O)Nc1ccc(-c2cnc(-c3ccc(NC(=O)OC(C)C)cc3)s2)c(S(=O)(=O)NC(C)(C)C)c1] | A |
| H5 | 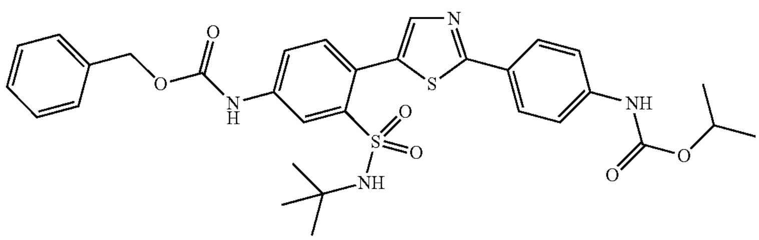 | A |
| H6 | 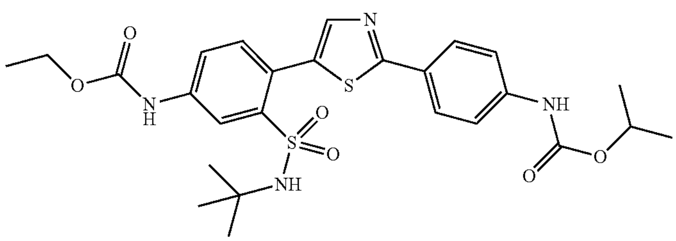 [SMILES: CCOC(=O)Nc1ccc(-c2cnc(-c3ccc(NC(=O)OC(C)C)cc3)s2)c(S(=O)(=O)NC(C)(C)C)c1] | A |
| H7 | 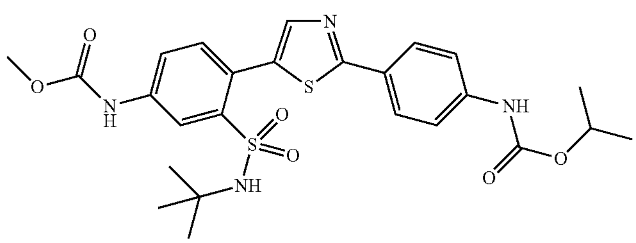 [SMILES: COC(=O)Nc1ccc(-c2cnc(-c3ccc(NC(=O)OC(C)C)cc3)s2)c(S(=O)(=O)NC(C)(C)C)c1] | A |
| H8 | 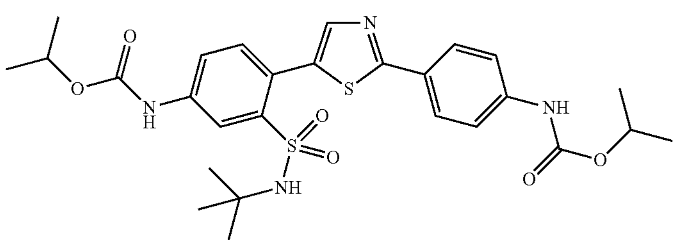 [SMILES: CC(C)OC(=O)Nc1ccc(-c2ncc(-c3ccc(NC(=O)OC(C)C)cc3S(=O)(=O)NC(C)(C)C)s2)cc1] | A |
| H9 | 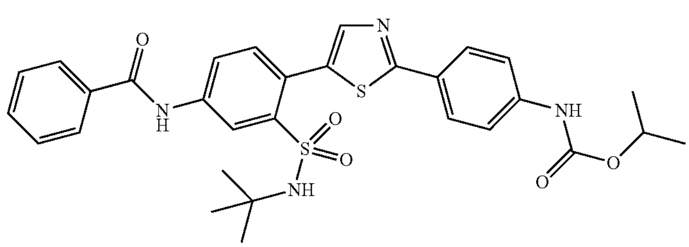 [SMILES: CC(C)OC(=O)Nc1ccc(-c2ncc(-c3ccc(NC(=O)c4ccccc4)cc3S(=O)(=O)NC(C)(C)C)s2)cc1] | A |

TABLE 1-continued

| No | Structure | EC50 (μM)<br>A = <1 μM<br>B = <5 μM<br>C = <10 μM<br>D = >10 μM |
|---|---|---|
| I1 | 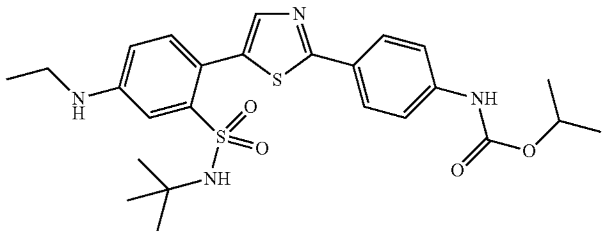 [SMILES: CCNc1ccc(-c2cnc(-c3ccc(NC(=O)OC(C)C)cc3)s2)c(S(=O)(=O)NC(C)(C)C)c1] | B |
| I2 | 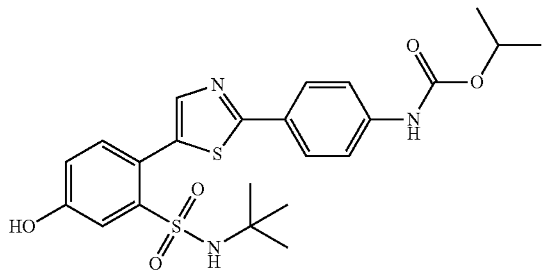 [SMILES: CC(C)OC(=O)Nc1ccc(-c2ncc(-c3ccc(O)cc3S(=O)(=O)NC(C)(C)C)s2)cc1] | B |
| I3 | 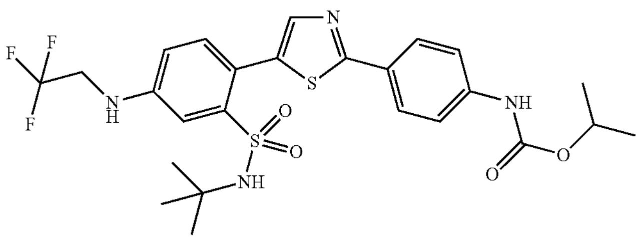 [SMILES: CC(C)OC(=O)Nc1ccc(-c2ncc(-c3ccc(NCC(F)(F)F)cc3S(=O)(=O)NC(C)(C)C)s2)cc1] | B |
| I4 | 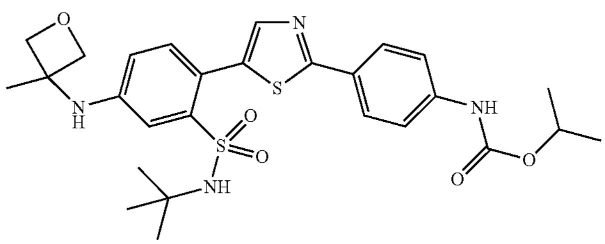 [SMILES: CC(C)OC(=O)Nc1ccc(-c2ncc(-c3ccc(NC4(C)COC4)cc3S(=O)(=O)NC(C)(C)C)s2)cc1] | B |
| I5 | 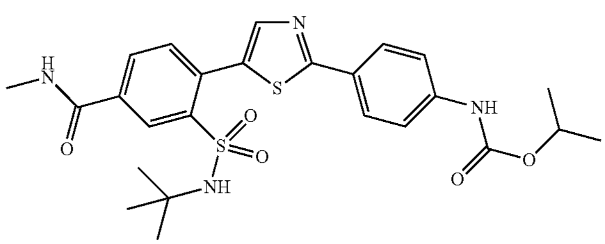 [SMILES: CNC(=O)c1ccc(-c2cnc(-c3ccc(NC(=O)OC(C)C)cc3)s2)c(S(=O)(=O)NC(C)(C)C)c1] | B |
| I7 | 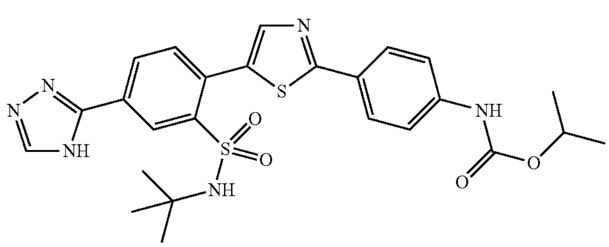 [SMILES: CC(C)OC(=O)Nc1ccc(-c2ncc(-c3ccc(-c4nnc[nH]4)cc3S(=O)(=O)NC(C)(C)C)s2)cc1] | B |

TABLE 1-continued

| No | Structure | EC50 (μM)<br>A = <1 μM<br>B = <5 μM<br>C = <10 μM<br>D = >10 μM |
|---|---|---|
| J1 | 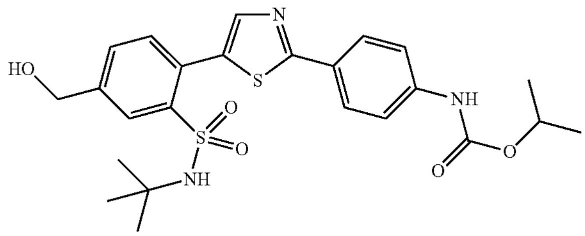 [SMILES: CC(C)OC(=O)Nc1ccc(-c2ncc(-c3ccc(CO)cc3S(=O)(=O)NC(C)(C)C)s2)cc1] | B |
| J10 | 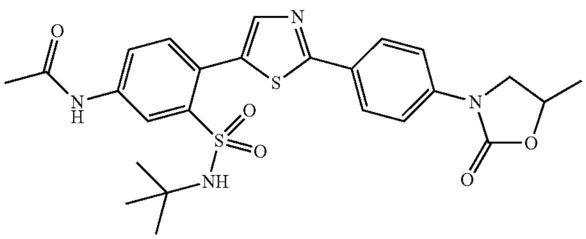 [SMILES: CC(=O)Nc1ccc(-c2cnc(-c3ccc(N4CC(C)OC4=O)cc3)s2)c(S(=O)(=O)NC(C)(C)C)c1] | D |
| J11 | 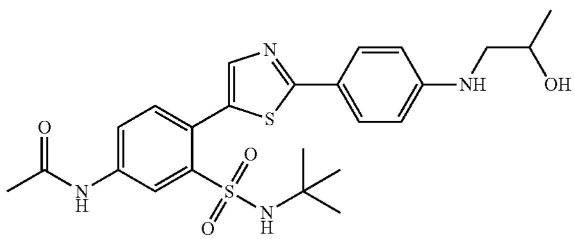 [SMILES: CC(=O)Nc1ccc(-c2cnc(-c3ccc(NCC(C)O)cc3)s2)c(S(=O)(=O)NC(C)(C)C)c1] | D |
| J12 | 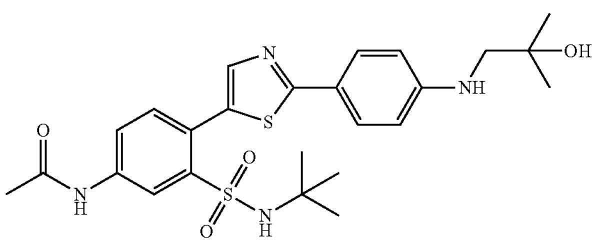 [SMILES: CC(=O)Nc1ccc(-c2cnc(-c3ccc(NCC(C)(C)O)cc3)s2)c(S(=O)(=O)NC(C)(C)C)c1] | D |
| J13 | 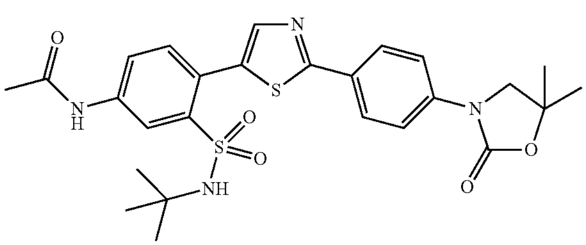 | D |
| J14 | 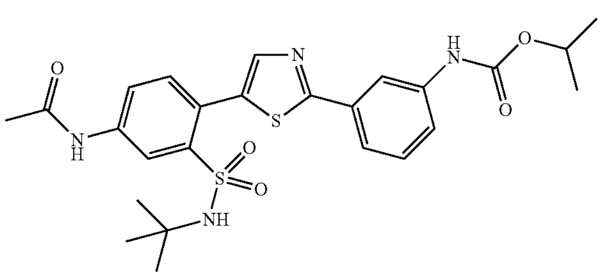 [SMILES: CC(=O)Nc1ccc(-c2cnc(-c3cccc(NC(=O)OC(C)C)c3)s2)c(S(=O)(=O)NC(C)(C)C)c1] | C |

TABLE 1-continued

| No | Structure | EC50 (μM)<br>A = <1 μM<br>B = <5 μM<br>C = <10 μM<br>D = >10 μM |
|----|-----------|------|
| J15 | 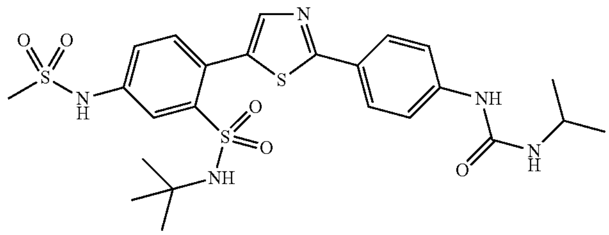 [SMILES: CC(C)NC(=O)Nc1ccc(-c2ncc(-c3ccc(NS(C)(=O)=O)cc3S(=O)(=O)NC(C)(C)C)s2)cc1] | D |
| J16 | 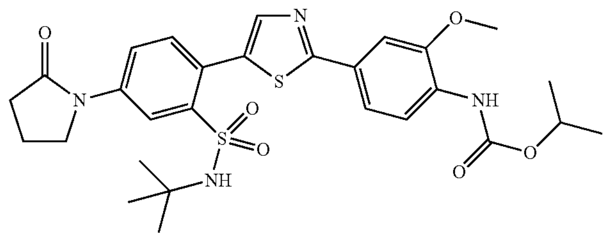 [SMILES: COc1cc(-c2ncc(-c3ccc(N4CCCC4=O)cc3S(=O)(=O)NC(C)(C)C)s2)ccc1NC(=O)OC(C)C] | C |
| J17 | 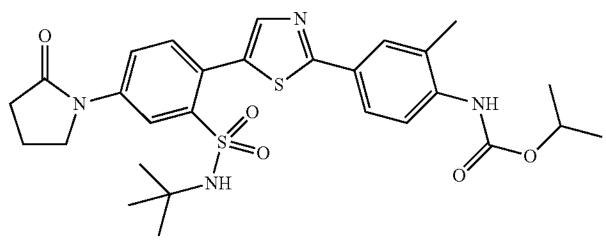 [SMILES: Cc1cc(-c2ncc(-c3ccc(N4CCCC4=O)cc3S(=O)(=O)NC(C)(C)C)s2)ccc1NC(=O)OC(C)C] | FAIL |
| J18 | 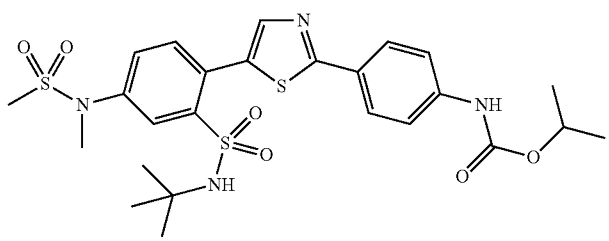 [SMILES: CC(C)OC(=O)Nc1ccc(-c2ncc(-c3ccc(N(C)S(C)(=O)=O)cc3S(=O)(=O)NC(C)(C)C)s2)cc1] | B |
| J2 | 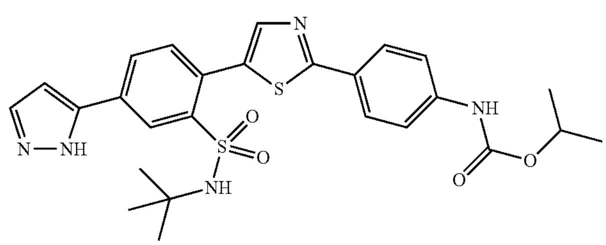 [SMILES: CC(C)OC(=O)Nc1ccc(-c2ncc(-c3ccc(-c4ccn[nH]4)cc3S(=O)(=O)NC(C)(C)C)s2)cc1] | B |
| J21 | 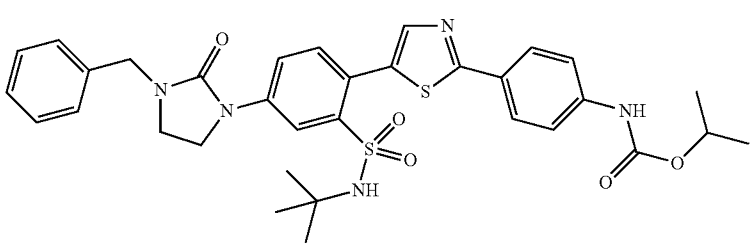 [SMILES: CC(C)OC(=O)Nc1ccc(-c2ncc(-c3ccc(N4CCN(Cc5ccccc5)C4=O)cc3S(=O)(=O)NC(C)(C)C)s2)cc1] | D |

TABLE 1-continued

| No | Structure | EC50 (μM)<br>A = <1 μM<br>B = <5 μM<br>C = <10 μM<br>D = >10 μM |
|---|---|---|
| J22 | 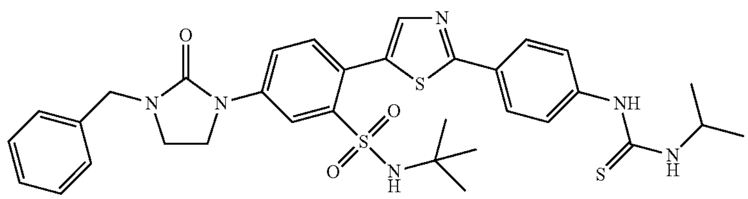 [SMILES: CC(C)NC(=S)Nc1ccc(-c2ncc(-c3ccc(N4CCN(Cc5ccccc5)C4=O)cc3S(=O)(=O)NC(C)(C)C)s2)cc1] | D |
| J23 | 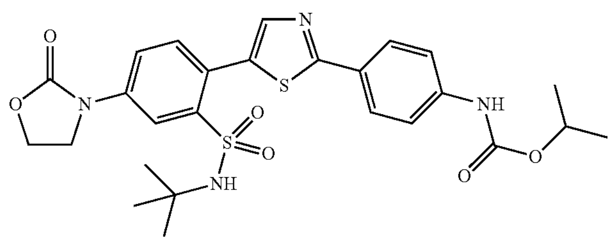 [SMILES: CC(C)OC(=O)Nc1ccc(-c2ncc(-c3ccc(N4CCOC4=O)cc3S(=O)(=O)NC(C)(C)C)s2)cc1] | B |
| J24 | 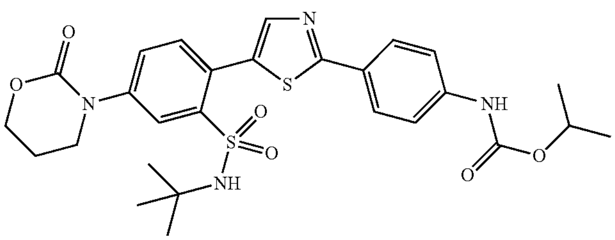 [SMILES: CC(C)OC(=O)Nc1ccc(-c2ncc(-c3ccc(N4CCCOC4=O)cc3S(=O)(=O)NC(C)(C)C)s2)cc1] | B |
| J25 | 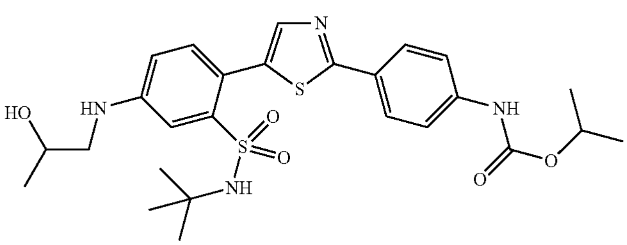 [SMILES: CC(O)CNc1ccc(-c2cnc(-c3ccc(NC(=O)OC(C)C)cc3)s2)c(S(=O)(=O)NC(C)(C)C)c1] | B |
| J26 | 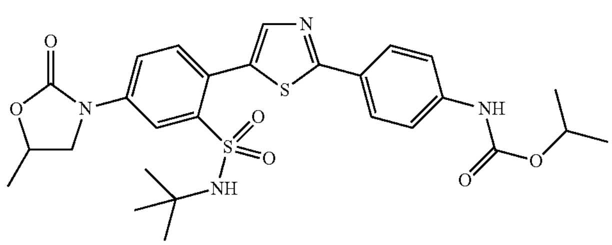 [SMILES: CC(C)OC(=O)Nc1ccc(-c2ncc(-c3ccc(N4CC(C)OC4=O)cc3S(=O)(=O)NC(C)(C)C)s2)cc1] | C |
| J27 | 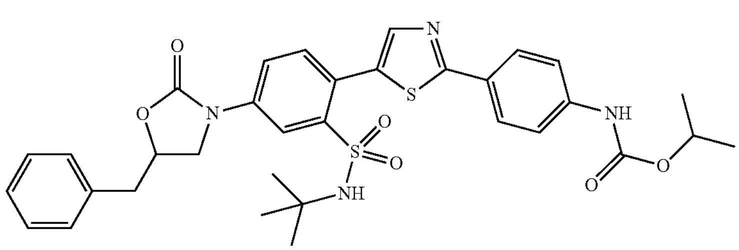 [SMILES: CC(C)OC(=O)Nc1ccc(-c2ncc(-c3ccc(N4CC(Cc5ccccc5)OC4=O)cc3S(=O)(=O)NC(C)(C)C)s2)cc1] | D |

TABLE 1-continued

| No | Structure | EC50 (µM) A = <1 µM B = <5 µM C = <10 µM D = >10 µM |
|---|---|---|
| J28 | 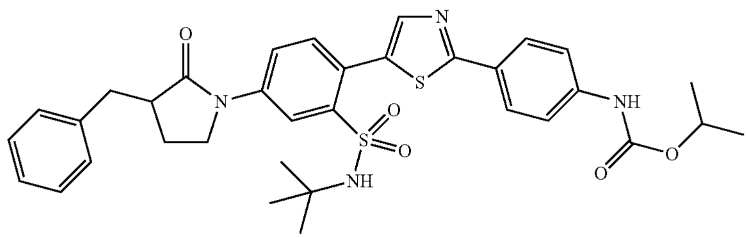 [SMILES: CC(C)OC(=O)Nc1ccc(-c2ncc(-c3ccc(N4CCC(Cc5ccccc5)C4=O)cc3S(=O)(=O)NC(C)(C)C)s2)cc1] | D |
| J29 | 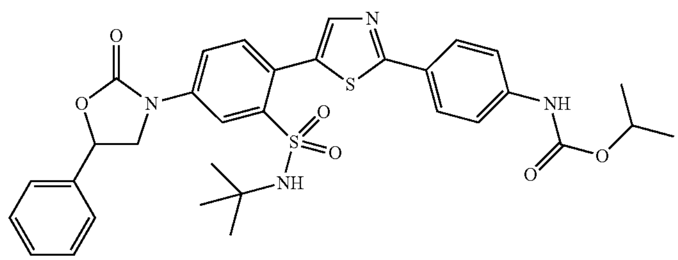 [SMILES: CC(C)OC(=O)Nc1ccc(-c2ncc(-c3ccc(N4CC(c5ccccc5)OC4=O)cc3S(=O)(=O)NC(C)(C)C)s2)cc1] | D |
| J3 | 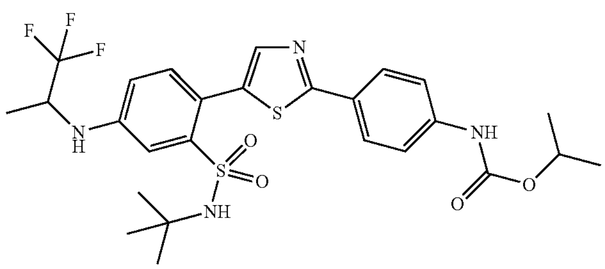 [SMILES: CC(C)OC(=O)Nc1ccc(-c2ncc(-c3ccc(NC(C)C(F)(F)F)cc3S(=O)(=O)NC(C)(C)C)s2)cc1] | B |
| J4 | 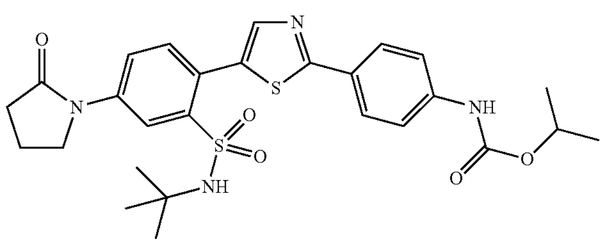 [SMILES: CC(C)OC(=O)Nc1ccc(-c2ncc(-c3ccc(N4CCCC4=O)cc3S(=O)(=O)NC(C)(C)C)s2)cc1] | B |
| J5 | 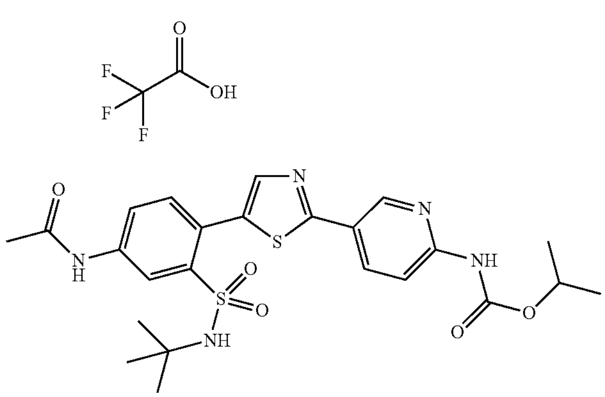 [SMILES: O=C(O)C(F)(F)F ; CC(=O)Nc1ccc(-c2cnc(-c3ccc(NC(=O)OC(C)C)nc3)s2)c(S(=O)(=O)NC(C)(C)C)c1] | A |

TABLE 1-continued

| No | Structure | EC50 (μM)<br>A = <1 μM<br>B = <5 μM<br>C = <10 μM<br>D = >10 μM |
|----|-----------|-----|
| J6 | 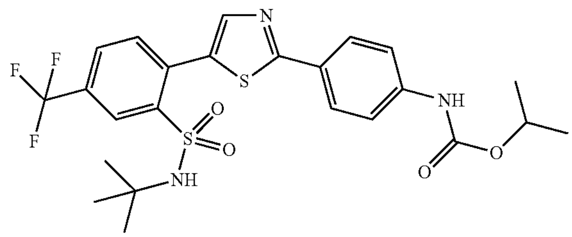 [SMILES: CC(C)OC(=O)Nc1ccc(-c2ncc(-c3ccc(C(F)(F)F)cc3S(=O)(=O)NC(C)(C)C)s2)cc1] | C |
| J7 | 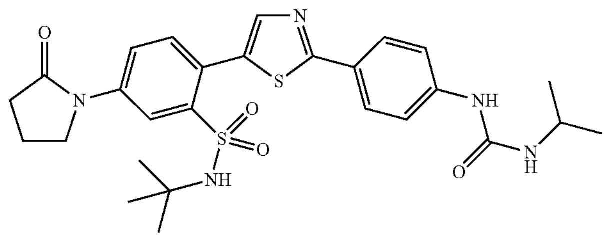 [SMILES: CC(C)NC(=O)Nc1ccc(-c2ncc(-c3ccc(N4CCCC4=O)cc3S(=O)(=O)NC(C)(C)C)s2)cc1] | C |
| J8 | 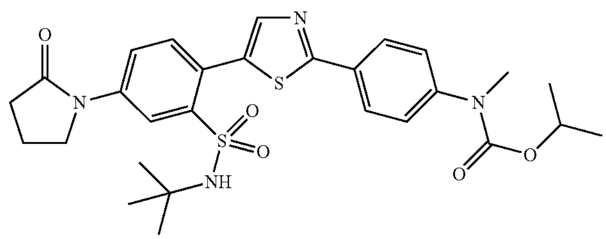 [SMILES: CC(C)OC(=O)N(C)c1ccc(-c2ncc(-c3ccc(N4CCCC4=O)cc3S(=O)(=O)NC(C)(C)C)s2)cc1] | C |
| J9 | 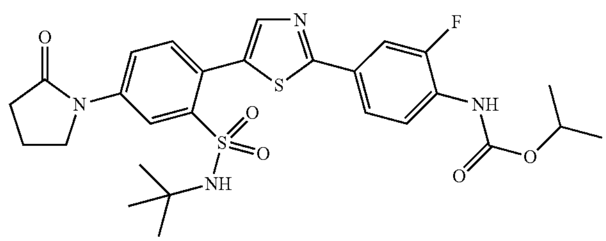 [SMILES: CC(C)OC(=O)Nc1ccc(-c2ncc(-c3ccc(N4CCCC4=O)cc3S(=O)(=O)NC(C)(C)C)s2)cc1F] | B |
| K1 | 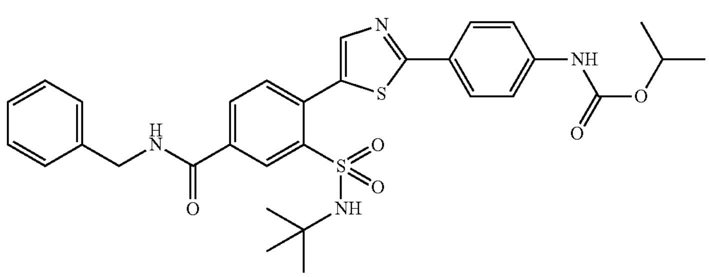 [SMILES: CC(C)OC(=O)Nc1ccc(-c2ncc(-c3ccc(C(=O)NCc4ccccc4)cc3S(=O)(=O)NC(C)(C)C)s2)cc1] | D |
| K2 | 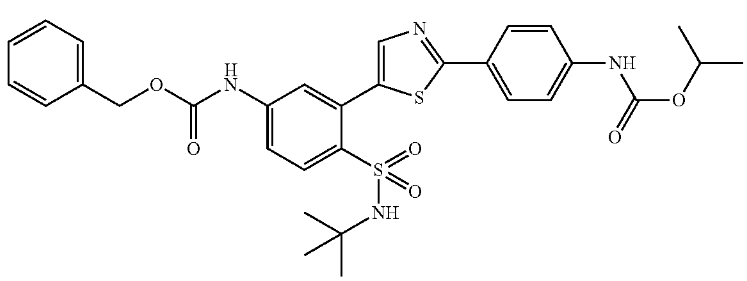 [SMILES: CC(C)OC(=O)Nc1ccc(-c2ncc(-c3cc(NC(=O)OCc4ccccc4)ccc3S(=O)(=O)NC(C)(C)C)s2)cc1] | D |

TABLE 1-continued

| No | Structure | EC50 (μM)<br>A = <1 μM<br>B = <5 μM<br>C = <10 μM<br>D = >10 μM |
|---|---|---|
| L10 | 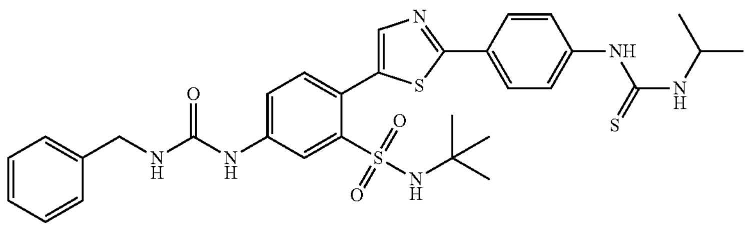 [SMILES: CC(C)NC(=S)Nc1ccc(-c2ncc(-c3ccc(NC(=O)NCc4ccccc4)cc3S(=O)(=O)NC(C)(C)C)s2)cc1] | B |
| L5 | 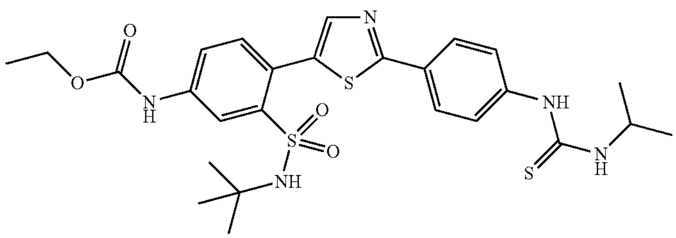 | B |
| L7 | 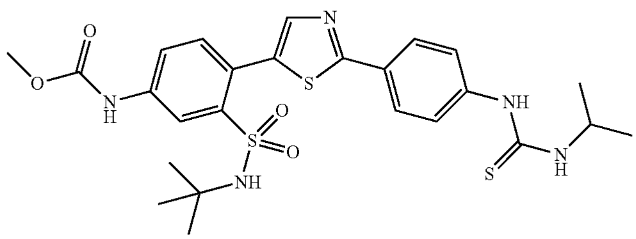 | D |
| L8 | 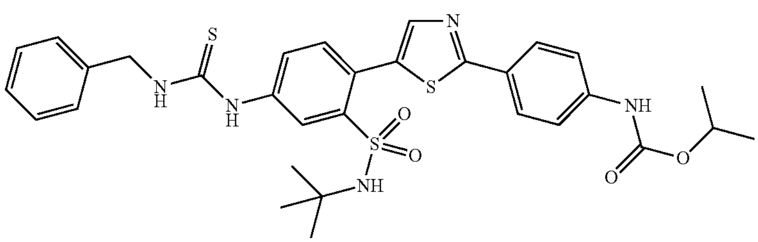 [SMILES: CC(C)OC(=O)Nc1ccc(-c2ncc(-c3ccc(NC(=S)NCc4ccccc4)cc3S(=O)(=O)NC(C)(C)C)s2)cc1] | A |
| L9 | 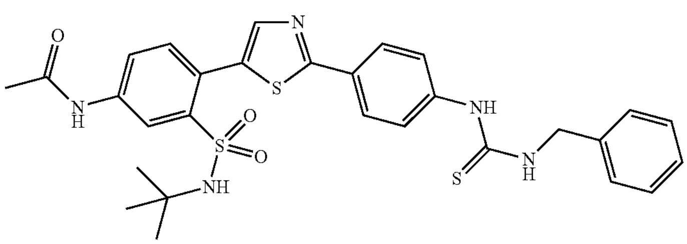 [SMILES: CC(=O)Nc1ccc(-c2cnc(-c3ccc(NC(=S)NCc4ccccc4)cc3)s2)c(S(=O)(=O)NC(C)(C)C)c1] | B |
| M1 | 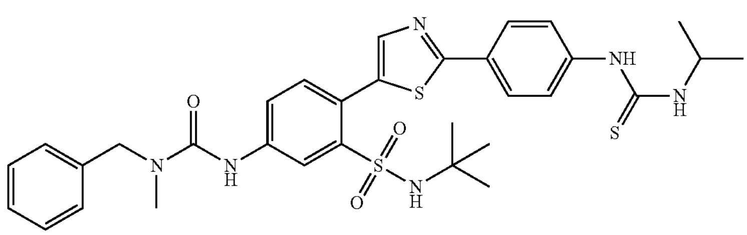 [SMILES: CC(C)NC(=S)Nc1ccc(-c2ncc(-c3ccc(NC(=O)N(C)Cc4ccccc4)cc3S(=O)(=O)NC(C)(C)C)s2)cc1] | D |

TABLE 1-continued

| No | Structure | EC50 (µM)<br>A = <1 µM<br>B = <5 µM<br>C = <10 µM<br>D = >10 µM |
|---|---|---|
| M2 | 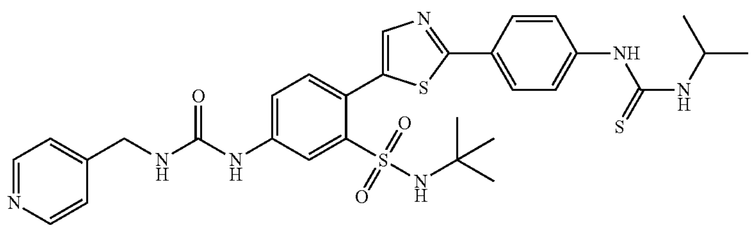 [SMILES: CC(C)NC(=S)Nc1ccc(-c2ncc(-c3ccc(NC(=O)NCc4ccncc4)cc3S(=O)(=O)NC(C)(C)C)s2)cc1] | B |
| M3 | 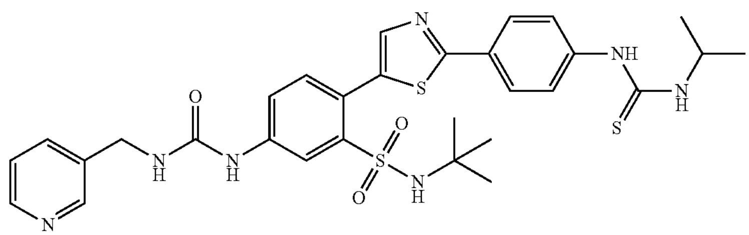 [SMILES: CC(C)NC(=S)Nc1ccc(-c2ncc(-c3ccc(NC(=O)NCc4cccnc4)cc3S(=O)(=O)NC(C)(C)C)s2)cc1] | C |
| M4 | 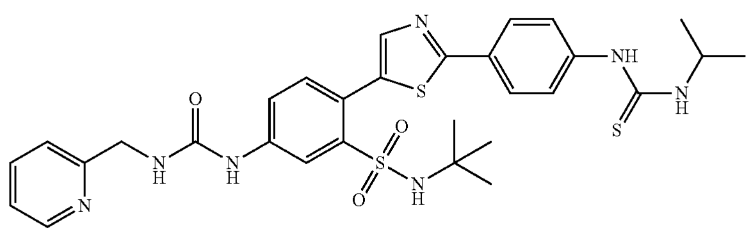 [SMILES: CC(C)NC(=S)Nc1ccc(-c2ncc(-c3ccc(NC(=O)NCc4ccccn4)cc3S(=O)(=O)NC(C)(C)C)s2)cc1] | C |
| M5 | 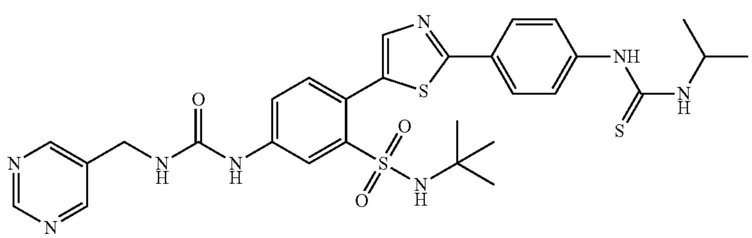 [SMILES: CC(C)NC(=S)Nc1ccc(-c2ncc(-c3ccc(NC(=O)NCc4cncnc4)cc3S(=O)(=O)NC(C)(C)C)s2)cc1] | D |
| M6 | 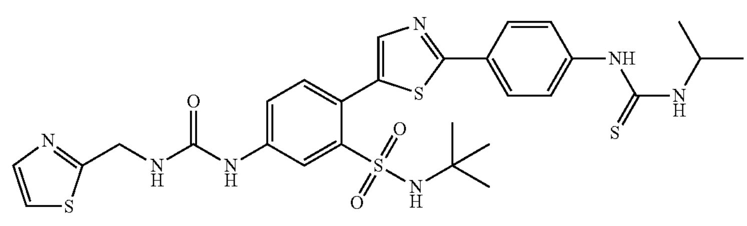 [SMILES: CC(C)NC(=S)Nc1ccc(-c2ncc(-c3ccc(NC(=O)NCc4nccs4)cc3S(=O)(=O)NC(C)(C)C)s2)cc1] | D |
| M7 | 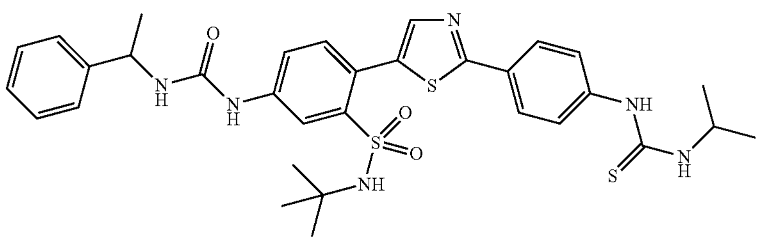 | C |

TABLE 1-continued

| No | Structure | EC50 (μM) A = <1 μM B = <5 μM C = <10 μM D = >10 μM |
|---|---|---|
| M8 | 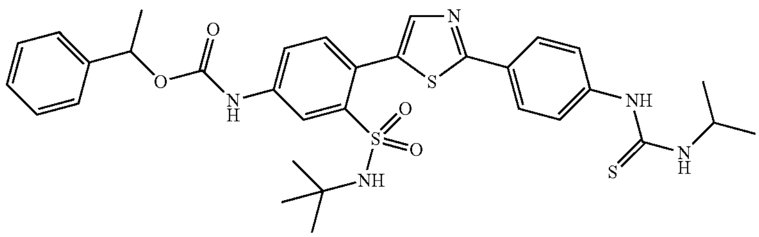 [SMILES: CC(C)NC(=S)Nc1ccc(-c2ncc(-c3ccc(NC(=O)OC(C)c4ccccc4)cc3S(=O)(=O)NC(C)(C)C)s2)cc1] | C |
| N1 | 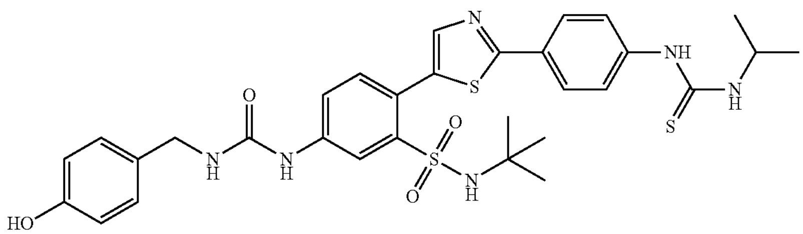 [SMILES: CC(C)NC(=S)Nc1ccc(-c2ncc(-c3ccc(NC(=O)NCc4ccc(O)cc4)cc3S(=O)(=O)NC(C)(C)C)s2)cc1] | C |
| N2 | 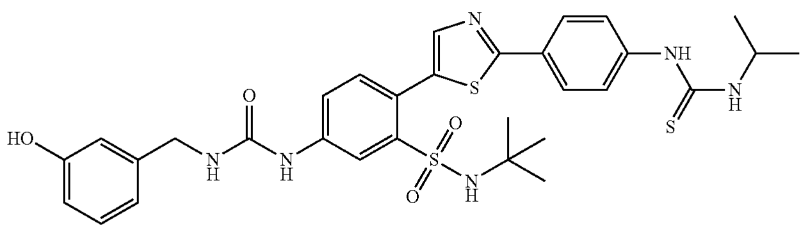 [SMILES: CC(C)NC(=S)Nc1ccc(-c2ncc(-c3ccc(NC(=O)NCc4cccc(O)c4)cc3S(=O)(=O)NC(C)(C)C)s2)cc1] | C |
| N4 | 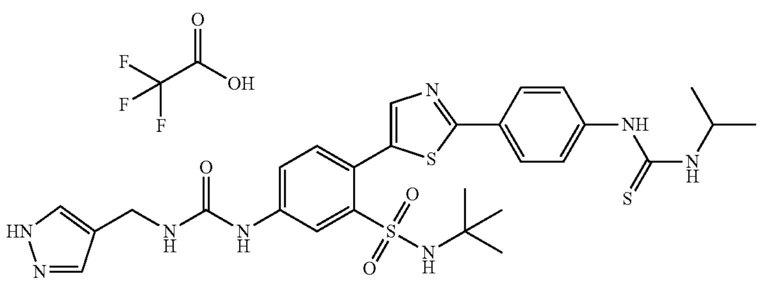 [SMILES: CC(C)NC(=S)Nc1ccc(-c2ncc(-c3ccc(NC(=O)NCc4cn[nH]c4)cc3S(=O)(=O)NC(C)(C)C)s2)cc1 ; O=C(O)C(F)(F)F] | D |
| N5 | 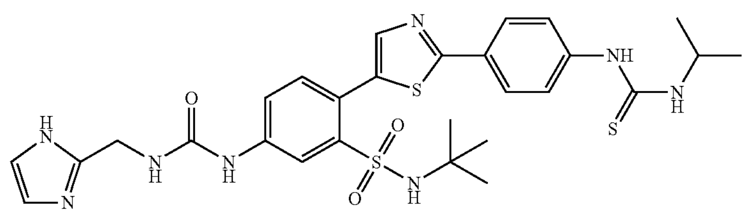 [SMILES: CC(C)NC(=S)Nc1ccc(-c2ncc(-c3ccc(NC(=O)NCc4ncc[nH]4)cc3S(=O)(=O)NC(C)(C)C)s2)cc1] | D |
| N6 | 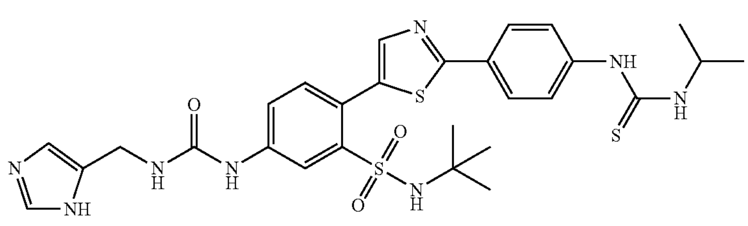 [SMILES: CC(C)NC(=S)Nc1ccc(-c2ncc(-c3ccc(NC(=O)NCc4cnc[nH]4)cc3S(=O)(=O)NC(C)(C)C)s2)cc1] | C |

TABLE 1-continued
| No | Structure | EC50 (μM)<br>A = <1 μM<br>B = <5 μM<br>C = <10 μM<br>D = >10 μM |
|---|---|---|
| O1 | 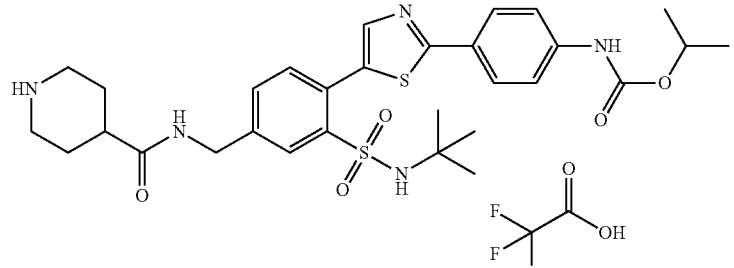 | C |
| O2 | 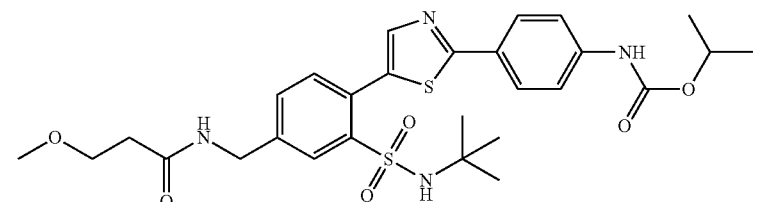 | D |
| O3 | 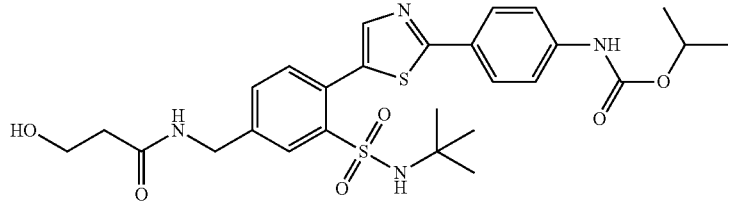 [SMILES: CC(C)OC(=O)Nc1ccc(-c2ncc(-c3ccc(CNC(=O)CCO)cc3S(=O)(=O)NC(C)(C)C)s2)cc1] | D |
| O4 | 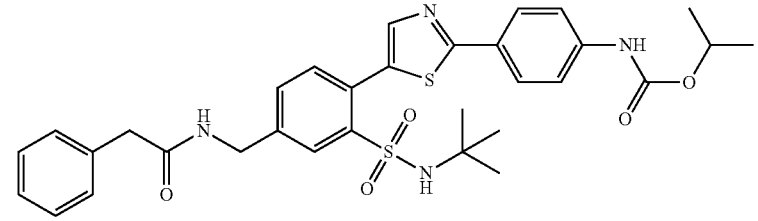 [SMILES: CC(C)OC(=O)Nc1ccc(-c2ncc(-c3ccc(CNC(=O)Cc4ccccc4)cc3S(=O)(=O)NC(C)(C)C)s2)cc1] | C |
| O5 | 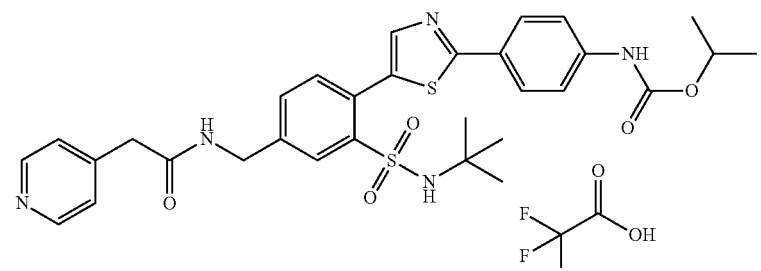 | B |
| O6 | 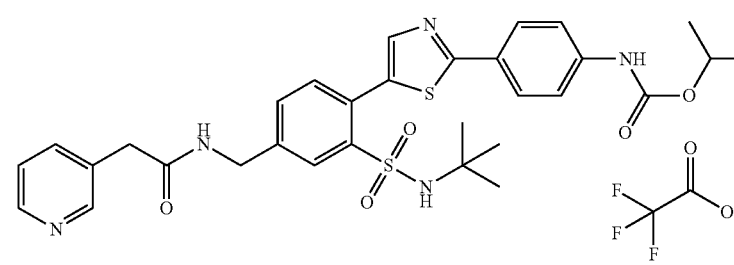 | D |

TABLE 1-continued

| No | Structure | EC50 (μM)<br>A = <1 μM<br>B = <5 μM<br>C = <10 μM<br>D = >10 μM |
|----|-----------|-----|
| O7 | 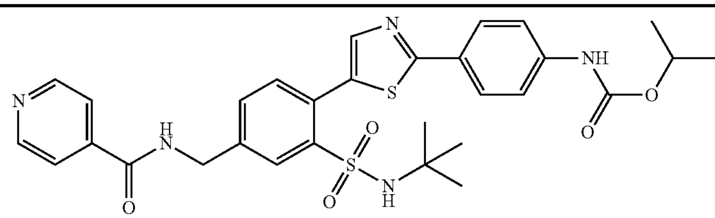 | B |
| O8 | 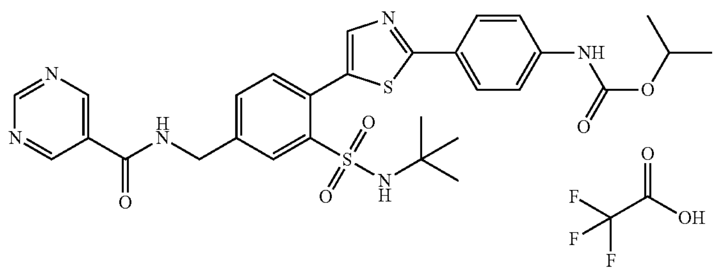 [SMILES: CC(C)OC(=O)Nc1ccc(-c2ncc(-c3ccc(CNC(=O)c4cncnc4)cc3S(=O)(=O)NC(C)(C)C)s2)cc1 ; O=C(O)C(F)(F)F] | C |
| P1 | 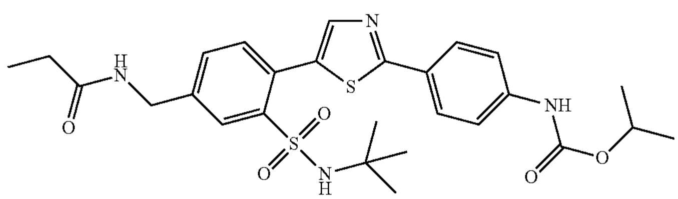 [SMILES: CCC(=O)NCc1ccc(-c2cnc(-c3ccc(NC(=O)OC(C)C)cc3)s2)c(S(=O)(=O)NC(C)(C)C)c1] | C |
| P2 | 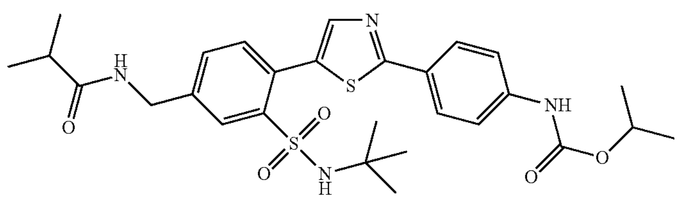 | B |
| P3 | 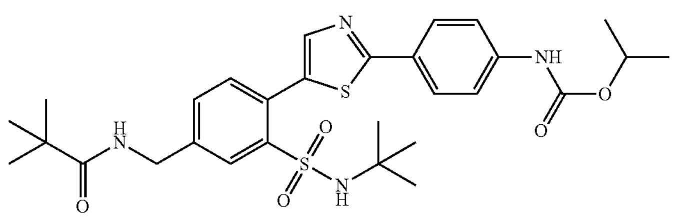 [SMILES: CC(C)OC(=O)Nc1ccc(-c2ncc(-c3ccc(CNC(=O)C(C)(C)C)cc3S(=O)(=O)NC(C)(C)C)s2)cc1] | D |
| P4 | 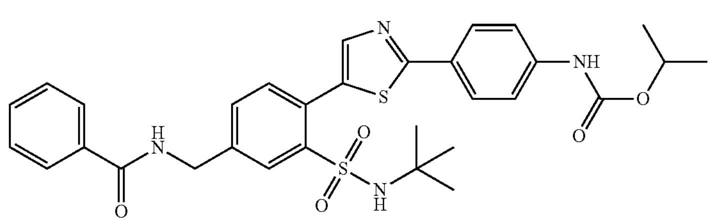 [SMILES: CC(C)OC(=O)Nc1ccc(-c2ncc(-c3ccc(CNC(=O)c4ccccc4)cc3S(=O)(=O)NC(C)(C)C)s2)cc1] | D |
| P5 | 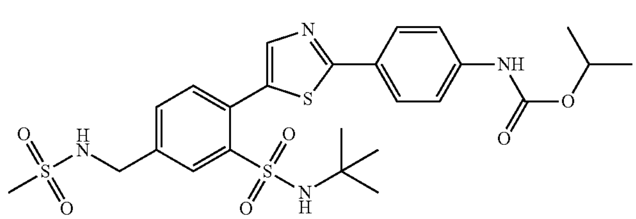 [SMILES: CC(C)OC(=O)Nc1ccc(-c2ncc(-c3ccc(CNS(C)(=O)=O)cc3S(=O)(=O)NC(C)(C)C)s2)cc1] | C |

TABLE 1-continued

| No | Structure | EC50 (μM)<br>A = <1 μM<br>B = <5 μM<br>C = <10 μM<br>D = >10 μM |
|---|---|---|
| P6 | 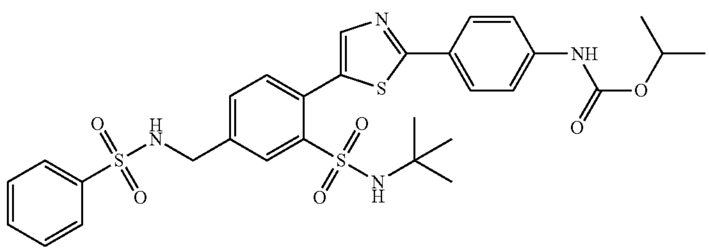 [SMILES: CC(C)OC(=O)Nc1ccc(-c2ncc(-c3ccc(CNS(=O)(=O)c4ccccc4)cc3S(=O)(=O)NC(C)(C)C)s2)cc1] | C |
| P7 | 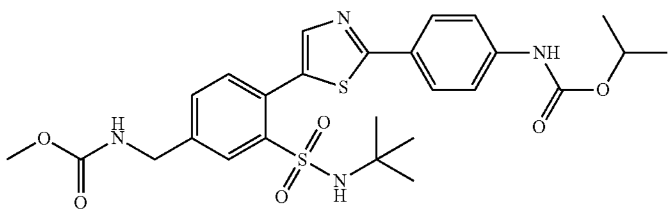 [SMILES: COC(=O)NCc1ccc(-c2cnc(-c3ccc(NC(=O)OC(C)C)cc3)s2)c(S(=O)(=O)NC(C)(C)C)c1] | C |
| P8 | 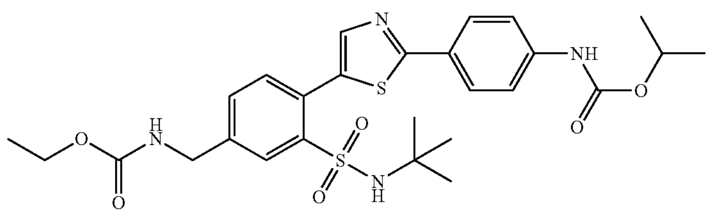 [SMILES: CCOC(=O)NCc1ccc(-c2cnc(-c3ccc(NC(=O)OC(C)C)cc3)s2)c(S(=O)(=O)NC(C)(C)C)c1] | C |
| P9 | 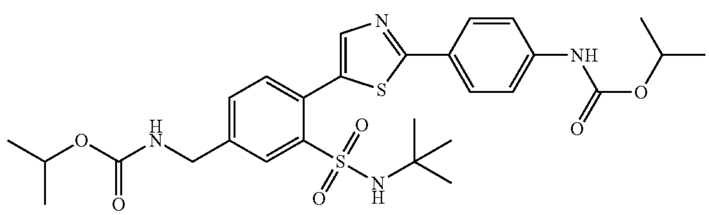 | D |
| Q1 | 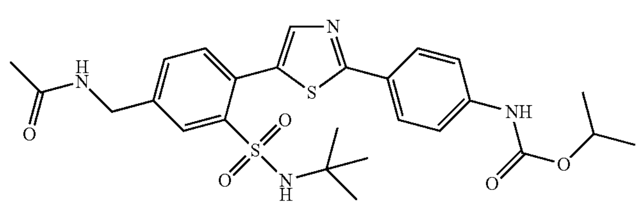 [SMILES: CC(=O)NCc1ccc(-c2cnc(-c3ccc(NC(=O)OC(C)C)cc3)s2)c(S(=O)(=O)NC(C)(C)C)c1] | C |
| Q2 | 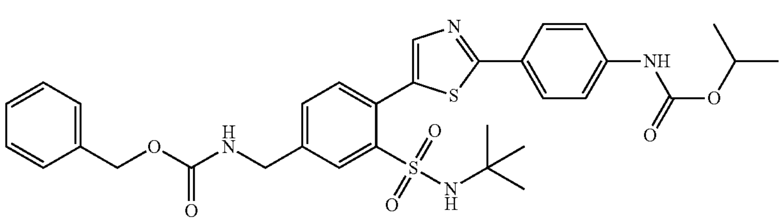 [SMILES: CC(C)OC(=O)Nc1ccc(-c2ncc(-c3ccc(CNC(=O)OCc4ccccc4)cc3S(=O)(=O)NC(C)(C)C)s2)cc1] | D |

TABLE 1-continued

| No | Structure | EC50 (μM)  A = <1 μM  B = <5 μM  C = <10 μM  D = >10 μM |
|---|---|---|
| Q3 | 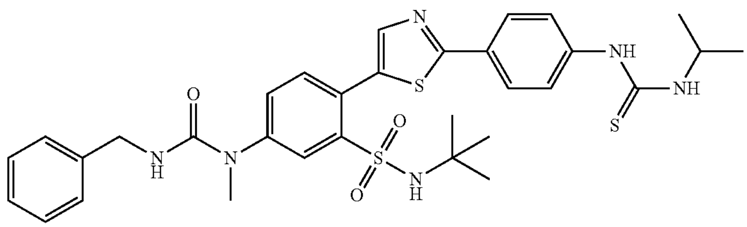 [SMILES: CC(C)NC(=S)Nc1ccc(-c2ncc(-c3ccc(N(C)C(=O)NCc4ccccc4)cc3S(=O)(=O)NC(C)(C)C)s2)cc1] | A |
| Q4 | 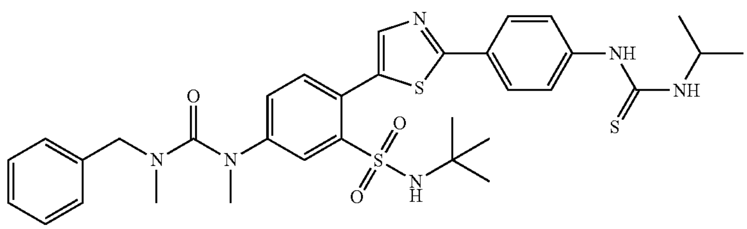 [SMILES: CC(C)NC(=S)Nc1ccc(-c2ncc(-c3ccc(N(C)C(=O)N(C)Cc4ccccc4)cc3S(=O)(=O)NC(C)(C)C)s2)cc1] | A |
| R1 | 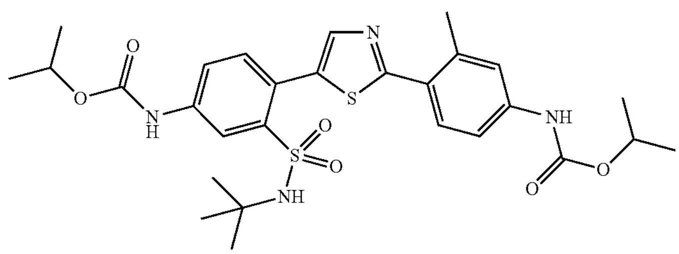 | A |
| R3 | 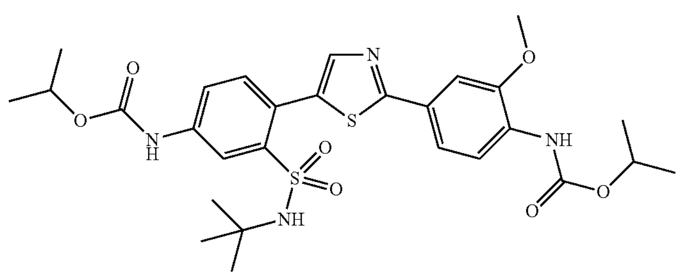 | B |
| R7 | 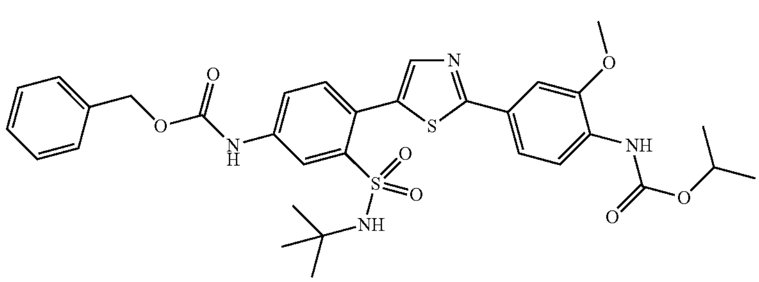 | A |

What is claimed is:

1. A compound represented by the following structural formula:

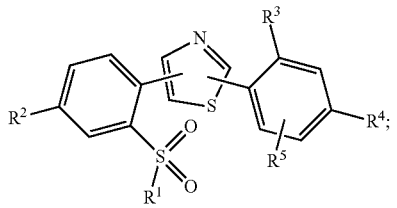

or a pharmaceutically acceptable salt thereof, wherein:
the thiazole ring is optionally substituted with —F or —Cl;
  $R^1$ is —$OR^a$, —$NH_2$, —$N((C_1-C_5)alkyl)_2$, —$NR^a(C_1-C_5)alkyl$, —$NR^a$—$(C_3-C_6)cycloalkyl$, —$NR^a$-phenyl, —$NR^a$-monocyclic 3-7 membered heterocyclic ring, —N-monocyclic 4-7 membered nitrogen containing heterocyclic ring (wherein the nitrogen atom of the heterocyclic ring is attached to the sulfur atom), or —N-5-8 membered nitrogen containing bridged bicyclic heterocyclyl (wherein the nitrogen atom of the bridged bicyclic heterocyclyl is attached to the sulfur atom),
    wherein the $(C_1-C_5)$alkyl in the group represented by $R^1$ is optionally substituted with —$OR^a$, —$OC(C_1-C_3)alkylene$—OH, —$CO(O)CH_3$, —$NR^aR^a$, —$(C_3-C_6)cycloalkyl$, phenyl, monocyclic 3-7 membered heterocyclic ring, or monocyclic 5-6 membered heteroaromatic ring, wherein the —$(C_3-C_6)cycloalkyl$ in the group represented by $R^1$ is optionally substituted with halogen or —$OR^a$, wherein the phenyl in the group represented by $R^1$ is optionally substituted with halogen, —$CH_3$, halomethyl, halomethoxy, —OH, or —$NH_2$;
  $R^2$ is —H, —$(C_1-C_4)alkyl$, —$NH_2$, —$NO_2$, $OR^a$, —$(CH_2)_mC(O)NH_2$, —$(CH_2)_mNR^aC(O)NH_2$, —$(CH_2)_mC(O)NR^a(C_1-C_4)alkyl$, —$(CH_2)_mC(O)NR^a(C_2-C_4)alkenyl$, —$(CH_2)_mC(O)NR^a$—$(C_3-C_6)cycloalkyl$, —$(CH_2)_mC(O)NR^a$-phenyl, —$(CH_2)_mC(O)NR^a$-monocyclic 3-7 membered heterocyclic ring —$(CH_2)_mC(O)NR^a$-5-10 membered heteroaromatic ring,
    —$(CH_2)_mNR^a(C_1-C_4)alkyl$, —$(CH_2)_mNR^a(C_2-C_4)alkenyl$, —$(CH_2)_mNR^a$—$(C_3-C_6)cycloalkyl$, —$(CH_2)_mNR^a$-phenyl —$(CH_2)_mNR^a$-monocyclic 3-7 membered heterocyclic ring, —$(CH_2)_mNR^a$-5-10 membered heteroaromatic ring,
    $(CH_2)_mNR^aC(O)(C_1-C_4)alkyl$, —$(CH_2)_mNR^aC(O)(C_2-C_4)alkenyl$, —$(CH_2)_mNR^aC(O)$—$(C_3-C_6)cycloalkyl$, —$(CH_2)_mNR^aC(O)$-phenyl —$(CH_2)_mNR^aC(O)$-monocyclic 3-7 membered heterocyclic ring, —$(CH_2)_mNR^aC(O)$-5-10 membered heteroaromatic ring,
    $(CH_2)_mNR^aC(O)O(C_1-C_4)alkyl$, —$(CH_2)_mNR^aC(O)O(C_2-C_4)alkenyl$, —$(CH_2)_mNR^aC(O)O$—$(C_3-C_6)cycloalkyl$, —$(CH_2)_mNR^aC(O)O$-phenyl —$(CH_2)_mNR^aC(O)O$-monocyclic 3-7 membered heterocyclic ring —$(CH_2)_mNR^aC(O)O$-5-10 membered heteroaromatic ring,
    $(CH_2)_mNR^aC(O)NR^a(C_1-C_4)alkyl$, —$(CH_2)_mNR^aC(O)NR^a(C_2-C_4)alkenyl$, —$(CH_2)_mNR^aC(O)NR^a$—$(C_3-C_6)cycloalkyl$, —$(CH_2)_mNR^aC(O)NR^a$— phenyl —$(CH_2)_mNR^aC(O)NR^a$-monocyclic 3-7 membered heterocyclic ring —$(CH_2)_mNR^aC(O)NR^a$-5-10 membered heteroaromatic ring,
    $(CH_2)_mNR^aC(S)(C_1-C_4)alkyl$, —$(CH_2)_mNR^aC(S)(C_2-C_4)alkenyl$, —$(CH_2)_mNR^aC(S)$—$(C_3-C_6)cycloalkyl$, —$(CH_2)_mNR^aC(S)$-phenyl —$(CH_2)_mNR^aC(S)$-monocyclic 3-7 membered heterocyclic ring —$(CH_2)_mNR^aC(S)$-5-10 membered heteroaromatic ring,
    $(CH_2)_mNR^aC(S)NR^a(C_1-C_4)alkyl$, —$(CH_2)_mNR^aC(S)NR^a(C_2-C_4)alkenyl$, —$(CH_2)_mNR^aC(S)NR^a$—$(C_3-C_6)cycloalkyl$, —$(CH_2)_mNR^aC(S)NR^a$— phenyl —$(CH_2)_mNR^aC(S)NR^a$-monocyclic 3-7 membered heterocyclic ring —$(CH_2)_mNR^aC(S)NR^a$-5-10 membered heteroaromatic ring,
    $(CH_2)_mNR^aS(O)_2$—$(C_1-C_4)alkyl$, —$(CH_2)_mNR^aS(O)_2$—$(C_2-C_4)alkenyl$, —$(CH_2)_mNR^aS(O)_2$—$(C_3-C_6)cycloalkyl$, —$(CH_2)_mNR^aS(O)_2$-phenyl —$(CH_2)_mNR^aS(O)_2$-monocyclic 3-7 membered heterocyclic ring —$(CH_2)_mNR^aS(O)_2$-5-10 membered heteroaromatic ring,
    monocyclic 3-10 membered heterocyclic ring or 5-10 membered heteroaromatic ring,
    wherein the $(C_1-C_4)$alkyl represented by $R^2$ or the $(C_1-C_4)$alkyl in the group represented by $R^2$ is optionally substituted with halogen, —$OR^a$, —$NR^aR^a$, —$(C_3-C_6)cycloalkyl$, phenyl, monocyclic 3-7 membered heterocyclic ring, or monocyclic 5-6 membered heteroaromatic ring, wherein the —$(C_3-C_6)cycloalkyl$ in the group represented by $R^2$ is optionally substituted with halogen, —$OR^a$ or —$NR^aR^a$, wherein the phenyl in the group represented by $R^2$ is optionally substituted with halogen, —$CH_3$, halomethyl, halomethoxy, —$OR^a$, or —$N_3$, wherein the heterocyclic ring represented by $R^2$ or the heterocyclic ring in the group represented by $R^2$ is optionally substituted with =O, —$CH_3$, halomethyl, halomethoxy, phenyl, or benzyl, wherein the heteroaromatic ring represented by $R^2$ or the heteroaromatic ring in the group represented by $R^2$ is optionally substituted with halogen, —$CH_3$, halomethyl, or halomethoxy;
  $R^4$ is —H, —$NH_2$, —$NO_2$, —$NR^a(C_1-C_4)alkyl$, —$NR^aC(O)(C_1-C_4)alkyl$, —$NR^aC(O)O(C_1-C_4)alkyl$, —$NR^aC(O)NR^a(C_1-C_4)alkyl$, —$NR^aC(S)NR^a(C_1-C_4)alkyl$, —$NR^aS(O)_2(C_1-C_4)alkyl$, —$NR^aS(O)_2NR^a(C_1-C_4)alkyl$, —$NR^aS(O)_2$-phenyl, —$OC(O)NR^a(C_1-C_4)alkyl$, $NR^aC(S)O(C_1-C_4)alkyl$, $NR^a$-monocyclic 5 or 6 membered nitrogen containing heteroaromatic ring, —$NR^aC(S)$—N-monocyclic 4-7 membered nitrogen containing heterocyclic ring —$NR^aC(S)NR^a$monocyclic 3-7 membered heterocyclic ring, —$NR^aC(S)NR^a$—monocyclic 5 or 6 membered nitrogen containing heteroaromatic ring, monocyclic 5 or 6 membered nitrogen containing heterocyclic ring, or —$NR^a$—$(C_3-C_6)cycloalkenyl$ optionally substituted with =O or —$NR^a(C_1-C_4)$alkyl,
    wherein the $(C_1-C_4)$alkyl in the group represented by $R^4$ is optionally substituted with —$OR^a$, phenyl, —$C(O)NR^aR^a$, or —$NR^aR^a$, wherein the heterocyclic ring represented by $R^4$ or the heterocyclic ring in the group represented by $R^4$ is optionally substituted with —$CH_3$, halomethyl, halomethoxy, or —$OR^a$;

each $R^5$ is independently —H, —($C_1$-$C_4$)alkyl, —O($C_1$-$C_4$)alkyl, halogen, —CN, halomethyl, halomethoxy, —OCH$_2$CH$_2$R$^1$, —C(O)O($C_1$-$C_4$)alkyl, —S(O)$_2$NH$_2$, or —SO$_2$NR$^a$($C_1$-$C_4$)alkyl;
$R^3$ is —H, halogen, —C(O)O($C_1$-$C_4$)alkyl, —S(O)$_2$NH$_2$, or —SO$_2$NR$^a$($C_1$-$C_4$)alkyl;
each $R^a$ is independently —H or —CH$_3$; and
m is 0 or 1.

2. The compound of claim 1, wherein the compound is represented by the following structural formula:

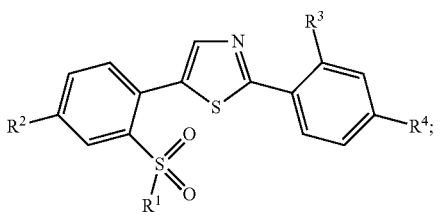

or a pharmaceutically acceptable salt thereof.

3. The compound of claim 1, or a pharmaceutically acceptable salt thereof, wherein:
the thiazole ring is optionally substituted with —F or —Cl;
$R^1$ is —NH$_2$, —NR$^a$($C_1$-$C_5$)alkyl, —NR$^a$—($C_3$-$C_6$)cycloalkyl, —N-monocyclic 4-7 membered nitrogen containing heterocyclic ring (wherein the nitrogen atom of the heterocyclic ring is attached to the sulfur atom), or —N-5-8 membered nitrogen containing bridged bicyclic heterocyclyl (wherein the nitrogen atom of the bridged bicyclic heterocyclyl is attached to the sulfur atom,
wherein the ($C_1$-$C_5$)alkyl in the group represented by $R^1$ is optionally substituted with —OR$^a$, —OC($C_1$-$C_3$)alkylene —OH, —CO(O)CH$_3$, —NR$^a$R$^a$, —($C_3$-$C_6$)cycloalkyl, phenyl, monocyclic 3-7 membered heterocyclic ring, or monocyclic 5-6 membered heteroaromatic ring, wherein the —($C_3$-$C_6$)cycloalkyl in the group represented by $R^1$ is optionally substituted with —OR$^a$;
$R^2$ is —H, —($C_1$-$C_4$)alkyl, —(CH$_2$)$_m$C(O)NH$_2$, —(CH$_2$)$_m$C(O)NR$^a$($C_1$-$C_4$)alkyl, —OR$^a$, —(CH$_2$)$_m$NR$^a$C(O)NR$^a$R$^a$, —(CH$_2$)$_m$NR$^a$($C_1$-$C_4$)alkyl, —(CH$_2$)$_m$NR$^a$C(O)($C_1$-$C_4$)alkyl, —(CH$_2$)$_m$NR$^a$C(O)O($C_1$-$C_4$)alkyl, —(CH$_2$)$_m$NR$^a$C(O)O($C_2$-$C_4$)alkenyl, —(CH$_2$)$_m$NR$^a$C(O)NR$^a$($C_1$-$C_4$)alkyl, —(CH$_2$)$_m$NR$^a$C(O)—($C_3$-$C_6$)cycloalkyl, —(CH$_2$)$_m$NR$^a$C(O)NR$^a$—($C_3$-$C_6$)cycloalkyl —(CH$_2$)$_m$NR$^a$C(O)-phenyl —(CH$_2$)$_m$NR$^a$C(O)O-phenyl, —(CH$_2$)$_m$NR$^a$-monocyclic 3-7 membered heterocyclic ring —(CH$_2$)$_m$NR$^a$-monocyclic 5-6 membered heteroaromatic ring —(CH$_2$)$_m$NR$^a$C(O)-monocyclic 3-7 membered heterocyclic ring —(CH$_2$)$_m$NR$^a$C(O)-monocyclic 5-6 membered heteroaromatic ring, (CH$_2$)$_m$NR$^a$C(O)O-monocyclic 3-7 membered heterocyclic ring —(CH$_2$)$_m$NR$^a$C(O)O-monocyclic 5-6 membered heteroaromatic ring monocyclic 3-7 membered heterocyclic ring monocyclic 5-6 membered heteroaromatic ring, —(CH$_2$)$_m$—NR$^a$C(O)NR$^a$-monocyclic 3-7 membered heterocyclic ring —(CH$_2$)$_m$—NR$^a$C(O)NR$^a$-monocyclic 5-6 membered heteroaromatic ring, —NR$^a$C(S)NR$^a$($C_1$-$C_4$)alkyl, —(CH$_2$)$_m$NR$^a$S(O)$_2$—($C_1$-$C_4$)alkyl, —CH$_2$NR$^a$S(O)$_2$-phenyl, wherein the ($C_1$-$C_4$)alkyl represented by $R^2$ or the ($C_1$-$C_4$)alkyl in the group represented by $R^2$ is optionally substituted with halogen, —OR$^a$, —NR$^a$R$^a$, —($C_3$-$C_6$)cycloalkyl, phenyl, monocyclic 3-7 membered heterocyclic ring, or monocyclic 5-6 membered heteroaromatic ring wherein the —($C_3$-$C_6$)cycloalkyl in the group represented by $R^2$ is optionally substituted with halogen, OR$^a$ or, —NR$^a$R$^a$, wherein the phenyl in the group represented by $R^2$ is optionally substituted with halogen, —CH$_3$, halomethyl, halomethoxy, —OR$^a$, or —N$_3$, wherein the monocyclic 3-7 membered heterocyclic ring represented by $R^2$ or the monocyclic 3-7 membered heterocyclic ring in the group represented by $R^2$ is optionally substituted with =O, —CH$_3$, halomethyl, halomethoxy, phenyl, or benzyl wherein the 5-6 membered heteroaromatic ring represented by $R^2$ or a 5-6 membered heteroaromatic ring in the group represented by $R^2$ is optionally substituted with halogen, —CH$_3$, halomethyl, or halomethoxy;
$R^3$, is —H, halogen, or —SO$_2$NR$^a$($C_1$-$C_4$)alkyl;
$R^4$ is —H, —NH$_2$, —NR$^a$($C_1$-$C_4$)alkyl, —NR$^a$C(O)($C_1$-$C_4$)alkyl, —NR$^a$C(O)O($C_1$-$C_4$)alkyl, —NR$^a$C(O)NR$^a$($C_1$-$C_4$)alkyl, —NR$^a$C(S)NR$^a$($C_1$-$C_4$)alkyl, —NR$^a$S(O)$_2$($C_1$-$C_4$)alkyl, —NR$^a$S(O)$_2$NR$^a$($C_1$-$C_4$)alkyl, —NR$^a$S(O)$_2$-phenyl —OC(O)NR$^a$($C_1$-$C_4$)alkyl, or monocyclic 5 or 6 membered nitrogen containing heterocyclic ring optionally substituted with methyl, wherein the ($C_1$-$C_4$)alkyl in the group represented by $R^4$ is optionally substituted with —OR$^a$ or phenyl;
each $R^a$ is independently —H or —CH$_3$; and
m is 0 or 1.

4. The compound of claim 3, or a pharmaceutically acceptable salt thereof, wherein:
$R^1$ is —NH$_2$, —NHCH$_3$, —NHCH$_2$CH$_3$, —N(CH$_3$)$_2$, —NHC(CH$_3$)$_3$, —NHCH$_2$CH$_2$NH$_2$, —NHCH$_2$CH$_2$NHCH$_3$, —NHCH$_2$CH$_2$N(CH$_3$)$_2$, —NHCH$_2$CH$_2$CH$_2$NH$_2$, —NHCH$_2$CH$_2$CH$_2$NHCH$_3$, —NHCH$_2$CH$_2$CH$_2$N(CH$_3$)$_2$, —NHCH$_2$C(O)OCH$_3$, —NHCH(CH(CH$_3$)$_2$)C(O)OCH$_3$, —NHCH$_2$-phenyl, —NHCH$_2$-pyridyl, —NHCH$_2$CH$_2$OH, —NHCH$_2$CH$_2$OCH$_3$, —NHCH$_2$C(CH$_3$)$_2$CH$_2$OH, —NHCH(CH$_3$)CH$_2$OH, —NHCH$_2$CH$_2$OCH$_2$CH$_2$OH, —NHCH(CH$_2$OH)C(O)OCH$_3$, —NHCH(CH$_2$OH)$_2$, —NH-cyclohexyl (wherein the cyclohexyl is optionally substituted with —OH), N-morpholinyl, N-piperidinyl, N-piperazinyl, N-pyrrolidinyl, or 7-azabicyclo[2.2.1]heptanyl;
$R^2$ is —H, CH$_2$OH, —CH$_2$NHC(O)CH$_3$, —CH$_2$NHC(O)OCH$_3$, —CH$_2$NHC(O)CH$_2$CH$_3$, —CH$_2$NHC(O)CH$_2$CH$_2$OH, —CH$_2$NHC(O)CH$_2$CH$_2$OCH$_3$, —CH$_2$NHC(O)OCH$_2$CH$_3$, —CH$_2$NHC(O)CH(CH$_3$)$_2$, —CH$_2$NHC(O)OCH(CH$_3$)$_2$, —CH$_2$NHC(O)C(CH$_3$)$_3$, —CH$_2$—CH(O)-phenyl, —CH$_2$NHC(O)-piperidinyl, —CH$_2$NHC(O)-pyridyl, —CH$_2$NHC(O)-pyrimidinyl, —CH$_2$NHC(O)CH$_2$-phenyl, —CH$_2$NHC(O)CH$_2$-pyridyl, —CH$_2$NHC(O)OCH$_2$-phenyl, —CH$_2$NHS(O)$_2$CH$_3$, —CH$_2$NHS(O)$_2$-phenyl, —CF$_3$, —C(O)NH$_2$, —C(O)NHCH$_3$, —C(O)NHCH$_2$-phenyl, —OH, —NHCH$_2$CH$_3$, —NHCH$_2$CF$_3$, —NHCH(CH$_3$)CF$_3$, —NHCH$_2$CH(OH)CH$_3$, —NH-oxetanyl substituted with methyl, —NHC(O)CH$_3$, —NHC(O)CH$_2$CH$_3$, —N(CH$_3$)C(O)CH$_3$, —NHC(O)CH(CH$_3$)$_2$, —NHC(O)-cyclopropyl, —NHC(O)-pyrrolidinyl, —NHC(O)-phenyl, —NHC(O)—CH$_2$—CH$_2$-phenyl, —NHC(O)NH—CH$_2$CH$_2$NH$_2$, —NHC(O)N(CH$_3$)$_2$, —NHC(O)NH—CH$_2$CH$_2$NHCH$_3$, —NHC(O)NH-azetidinyl, —NHC(O)NH-cyclohexyl (wherein the cyclohexyl is optionally substituted with —NH$_2$ or —N(CH$_3$)$_2$), —NHC(O)NHCH$_2$-azepanyl, —NHC(O)NHCH$_2$-azetidinyl, —NHC(O)NH—CH$_2$-phenyl (wherein the phenyl is optionally substituted with —OH or N$_3$), —NHC(O)NH—CH(CH$_3$)-phenyl, —NHC(O)N(CH$_3$)—CH$_2$-phenyl, —N(CH$_3$)C(O)NH—CH$_2$-phenyl, —N(CH$_3$)C(O)N(CH$_3$)—CH$_2$-Phenyl, —NHC(O —NH—CH$_2$-imidazolyl, —NHC(O)NH—CH$_2$-pyrazolyl, —NHC(O)NH—CH$_2$-pyridyl, —NHC(O)NH—CH$_2$-pyrimidinyl, —NHC(O)NH—CH$_2$-pyrrolidinyl (wherein the pyrrolidinyl is optionally substituted with —CH$_3$), —NHC(O)N(CH$_3$)—CH$_2$-pyrrolidinyl —NHC(O)NH—CH$_2$-thiazolyl, —NHC(O)OCH$_3$, —NHC(O)OCH$_2$CH$_3$, NHC(O)OCH(CH$_3$)$_2$, —NHC(O)OCH$_2$CH$_3$, —NHC(O)OCH$_2$CH$_2$NH$_2$, —NHC(O)OCH$_2$C(CH$_3$)—CH$_2$, —NHC(O)OCH=CH(CH$_3$), —NHC(O)OCH$_2$CH$_2$OH, —NHC(O)OCH$_2$CH$_2$OCH$_3$, —NHC(O)O—CH$_2$-cyclohexyl, —NHC(O)O—CH$_2$-imidazolyl, —NHC(O)O —CH$_2$-phenyl, —NHC(O)O—CH(CH$_3$)-phenyl, NHC(O)O—CH$_2$—CH$_2$-phenyl, —NHC(O)—CH$_2$-pyridyl, —NHC(O)O—CH$_2$-pyrrolidinyl, —NHC(O)O—CH$_2$—CH$_2$-thiazolyl, —NHC(S)NHCH(CH$_3$)$_2$, —NHC(S)NHCH$_2$-phenyl, —NH-thiazolyl, —NH-imidazolyl (substituted with methyl), —NHS(O)$_2$CH$_3$, —NHS(O)$_2$-phenyl, —NHS(O)$_2$—CH$_2$-phenyl, —N(CH$_3$)S(O)$_2$CH$_3$, imidazolyl, pyrazolyl, triazolyl,

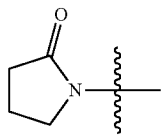 [SMILES: *N1CCCC1=O]

optionally substituted with benzyl,

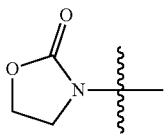 [SMILES: *N1CCOC1=O]

optionally substituted with methyl, phenyl, or benzyl, or

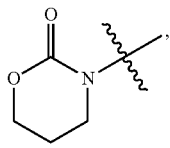

optionally substituted with benzyl,

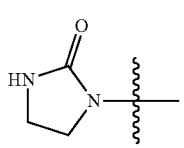 [SMILES: *N1CCNC1=O]

R$^3$ is —H, —F, or —SO$_2$NHC(CH$_3$)$_3$;

R$^4$ is —H, —NH$_2$, —NHCH$_2$CH(OH)CH$_3$, —NHCH$_2$C(CH)$_2$OH, —NHC(O)CH$_3$, —NHC(O)CH$_2$CH(CH$_3$)$_2$, —NHC(O)OCH$_3$, —NHC(O)OC(CH$_3$)$_3$, —NHC(O)OCH$_2$CH$_3$, —NHC(O)OCH(CH$_3$)$_2$, —NHC(O)OCH$_2$CH(CH$_3$)$_2$, —NHC(O)NHCH(CH$_3$)$_2$, —NHC(O)N(CH$_3$)CH(CH$_3$)$_2$, —N(CH$_3$)C(O)NHCH(CH$_3$)$_2$, —NHC(S)NHCH(CH$_3$)$_2$, —NHC(S)NHCH$_2$-phenyl, —NHS(O)$_2$CH$_3$, —NHS(O)$_2$CH$_2$CH$_3$, —NHS(O)$_2$CH$_2$CH$_2$OCH$_3$, —NHS(O)$_2$-phenyl, —NHS(O)$_2$NHCH$_3$, —OC(O)NHCH(CH$_3$)$_2$, or

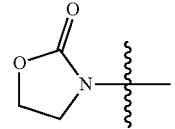

optionally substituted with one or two methyl.

5. The compound of claim 3, or a pharmaceutically acceptable salt thereof, wherein:

R$^1$ is —NH(C$_1$-C$_4$)alkyl, —N-monocyclic 5 or 6 membered nitrogen containing heterocyclic ring (wherein the nitrogen atom of the heterocyclic ring is attached to the sulfur atom), or —N-5-8 membered nitrogen containing bridged bicyclic heterocyclyl (wherein the nitrogen atom of the bridged bicyclic heterocyclyl is attached to the sulfur atom);

R$^2$ is —H, CH$_2$OR$^a$, —C(O)NR$^a$R$^a$, —OR$^a$, —(CH$_2$)$_m$NHC(O)(C$_1$-C$_4$)alkyl, —NHC(O)NR$^a$R$^a$, —NH(C$_1$-C$_4$)alkyl, —NHC(O)(C$_1$-C$_4$)alkyl, —NHC(O)NH(C$_1$-C$_4$)alkyl, —NHC(O)O(C$_1$-C$_4$)alkyl, —NHC(O)O(C$_2$-C$_4$)alkenyl, —NHC(O)—(C$_3$-C$_6$)cycloalkyl, NHC(O)OCH$_2$—(C$_3$-C$_6$)cycloalkyl, —NHC(O)NH—(CH$_2$)$_2$—(C$_3$-C$_6$)cycloalkyl, —NR$^a$C(O)—(CHR$^a$)$_n$-phenyl, —NR$^a$C(O)O—(CHR$^a$)$_n$-phenyl —NR$^a$C(O)NR$^a$—(CHR$^a$)$_n$-phenyl, —NR$^a$C(S)NR$^a$—(CH$_2$)-phenyl —NH-monocyclic 3-7 membered heterocyclic ring optionally substituted with —CH$_3$, —NH-monocyclic 5-6 membered heteroaromatic ring, NHC(O)-monocyclic 3-7 membered heterocyclic ring, —NHC(O)—monocyclic 5-6 membered heteroaromatic ring, —(CH$_2$)$_m$NHC(O)—(CH$_2$)$_n$-monocyclic 5 or 6 membered nitrogen containing heterocyclic or heteroaromatic ring, —NHC(O)O—(CH$_2$)$_n$-monocyclic 5 or 6 membered nitrogen containing heterocyclic or heteroaromatic ring optionally substituted with —CH$_3$, monocyclic 5 or 6 membered nitrogen containing heteroaromatic ring, —NR$^a$C(O)NR$^a$ —(CH$_2$)$_n$-monocyclic 3-7 membered heterocyclic ring, —NR$^a$C(O)NR$^a$—(CH$_2$)$_n$-monocyclic 5 or 6 membered nitrogen containing heteroaromatic ring —NR$^a$C(S)NR$^a$(C$_1$-C$_4$)alkyl, —NR$^a$C(S)NR$^a$—(CHR$^a$)$_n$-phenyl, or —NR$^a$S(O)$_2$—(C$_1$-C$_4$)alkyl;

wherein the (C$_1$-C$_4$)alkyl represented by R$^2$ or a (C$_1$-C$_4$)alkyl in the group represented by R$^2$ is optionally substituted with halogen, —OR$^a$, or —NR$^a$R$^a$; wherein the (C$_3$-C$_6$)cycloalkyl represented by R$^2$ or a (C$_3$-C$_6$)cycloalkyl in the group represented by R$^2$ is optionally substituted with —NR$^a$R$^a$; wherein the phenyl represented by R$^2$ or a phenyl in the group represented by R$^2$ is optionally substituted with halogen, —OR$^a$ or —N$_3$;

R$^3$ is —H or halogen;

R⁴ is —H, —NRᵃC(O)O(C₁-C₄)alkyl, —OC(O)NRᵃ(C₁-C₄)alkyl, or —NRᵃC(S)NRᵃ(C₁-C₄)alkyl optionally substituted with phenyl;
each Rᵃ is independently —H or —CH₃;
m is 0 or 1; and
n is 0, 1, or 2.

6. The compound of claim 1, or a pharmaceutically acceptable salt thereof, wherein:
R¹ is —N(CH₃)₂, —NHC(CH₃)₃, —N-piperazinyl, or 7-azabicyclo[2.2.1]heptanyl;
R² is —H, —CH₂OH, —CH₂NHC(O)CH(CH₃)₂, —CH₂NHC(O)-pyridyl, —CH₂NHC(O)CH₂-pyridyl, —C(O)NH₂, —C(O)NHCH₃, —OH, —NHCH₂CH₃, —NHCH₂CF₃, —NHCH(CH₃)CF₃, —NHCH₂CH(OH)CH₃, —NH-oxetanyl substituted with methyl, —NHC(O)CH₃, —NHC(O)CH₂CH₃, —NHC(O)CH(CH₃)₂, —NHC(O)-cyclopropyl, —NHC(O)-pyrrolidinyl, —NHC(O)-phenyl, —NHC(O)—CH₂—CH₂-phenyl, —NHC(O)NH—CH₂CH₂NH₂, —NHC(O)N(CH₃)₂, —NHC(O)NH—CH₂CH₂NHCH₃, —NHC(O)NH—azetidinyl, —NHC(O)NH-cyclohexyl (wherein the cyclohexyl is optionally substituted with —NH₂ or [—N(CH₃)₂), NHC(O)NHCH₂-azepanyl, —NHC(O)NHCH₂-azetidinyl, —NHC(O)NH—CH₂-phenyl (wherein the phenyl is optionally substituted with —OH or N₃), —NHC(O)NH—CH(CH₃)-phenyl, —N(CH₃)C(O)NH—CH₂-phenyl, —N(CH₃)C(O)N(CH₃)—CH₂-phenyl, —NHC(O)NH—CH₂-pyridyl, —NHC(O)NH—CH₂-pyrrolidinyl (wherein the pyrrolidinyl is optionally substituted with —CH₃), —NHC(O)N(CH₃)—CH₂-pyrrolidinyl, —NHC(O)OCH₃, —NHC(O)OCH₂CH₃, —NHC(O)OCH(CH₃)₂, —NHC(O)OCH₂CH₃, —NHC(O)OCH₂CH₂NH₂, —NHC(O)OCH₂C(CH₃)=CH₂, —NHC(O)OCH=CH(CH₃), —NHC(O)OCH₂CH₂OH, —NHC(O)OCH₂CH₂OCH₃, —NHC(O)O—CH₂-cyclohexyl, —NHC(O)O—CH₂-phenyl, —NHC(O)O—CH(CH₃)-phenyl, —NHC(O)O—CH₂—CH₂-phenyl, —NHC(O)O—CH₂-pyridyl, —NHC(O)O—CH₂-pyrrolidinyl, —NHC(O)O—CH₂—CH₂-thiazolyl, —NHC(S)NHCH(CH₃)₂, —NHC(S)NHCH₂-phenyl, —N(CH₃)S(O)₂CH₃, imidazolyl, pyrazolyl, or triazolyl,
R³ is —H or —F; and
R⁴ is —H, —NHC(O)OCH₂CH₃, —NHC(O)OCH(CH₃)₂, —NHC(O)OCH₂CH(CH₃)₂, —NHC(S)NHCH(CH₃)₂, —NHC(S)NHCH₂-phenyl, or —OC(O)NHCH(CH₃)₂.

7. The compound of claim 3, or a pharmaceutically acceptable salt thereof, wherein:
R¹ is —NH(C₁-C₄)alkyl or 7-azabicyclo[2.2.1]heptanyl;
R² is —H, —NHC(O)(C₁-C₄)alkyl, —NHC(O)O(C₁-C₄)alkyl, —NHC(O)O(C₂-C₄)alkenyl —NHC(O)OCH₂—(C₃-C₆)cycloalkyl, —NHC(O)NH—(CH₂)ₙ—(C₃-C₆)cycloalkyl, —NRᵃC(O)—(CHRᵃ)ₙ-phenyl, —NRᵃC(O)O—(CHRᵃ)ₙ-phenyl —NRᵃC(O)NRᵃ—(CHRᵃ)ₙ-phenyl, —NRᵃC(S)NRᵃ—(CHRᵃ)n-phenyl; —NHC(O)O—(CH₂)n-monocyclic 5 or 6 membered nitrogen containing heterocyclic or heteroaromatic ring optionally substituted with —CH₃, —NRᵃC(O)NRᵃ—(CH₂)ₙ-monocyclic 5 or 6 membered nitrogen containing heterocyclic or heteroaromatic ring,
wherein the (C₁-C₄)alkyl represented by R² or a (C₁-C₄)alkyl in the group represented by R² is optionally substituted with —ORᵃ; wherein the (C₃-C₆)cycloalkyl represented by R² or a (C₃-C₆)cycloalkyl in the group represented by R² is optionally substituted with —NRᵃ; wherein the phenyl represented by R² or a phenyl in the group represented by R² is optionally substituted with —ORᵃ or —N₃;
R³—H or halogen;
R⁴ is —H, —NRᵃC(O)O(C₁-C₄)alkyl, or —NRᵃC(S)NRᵃ(C₁-C₄)alkyl;
each Rᵃ is independently —H, or —CH₃; and
n is 0, 1, or 2.

8. The compound of claim 1, or a pharmaceutically acceptable salt thereof, wherein:
R¹ is —N(CH₃)₂, —NHC(CH₃)₃, or 7-azabicyclo[2.2.1]heptanyl;
R² is —H, —NHC(O)CH₃, —NHC(O)CH₂CH₃, —NHC(O)CH(CH₃)₂, —NHC(O)-phenyl —NHC(O)—CH₂—CH₂-phenyl —NHC(O)NH-cyclohexyl (wherein the cyclohexyl is optionally substituted with —NH₂ or —N(CH₃)₂), —NHC(O)NH—CH₂-phenyl (wherein the phenyl is optionally substituted with —OH or N₃, —NHC(O)NH—CH(CH₃)-phenyl, —N(CH₃)C(O)NH—CH₂-phenyl, —N(CH₃)C(O)N(CH₃)—CH₂-phenyl, —NHC(O)NH—CH₂-pyrrolidinyl (wherein the pyrrolidinyl is optionally substituted with —CH₃), —NHC(O)OCH₃, —NHC(O)OCH(CH₃)₂, —NHC(O)OCH₂CH₃, —NHC(O)OCH₂C(CH₃)=CH₂, —NHC(O)OCH=CH(CH₃), —NHC(O)OCH₂CH₂OCH₃, —NHC(O)O—CH₂-cyclohexyl —NHC(O)O—CH₂-phenyl —NHC(O)O—CH(CH₃)-phenyl, —NHC(O)O—CH₂—CH₂-phenyl —NHC(O)O—CH₂-pyridyl —NHC(O)O—CH₂—CH₂-thiazolyl, or —NHC(S)NHCH₂-phenyl;
R³ is —H or —F; and
R⁴ is —H, —NHC(O)OCH₂CH₃, —NHC(O)OCH(CH₃)₂, or —NHC(S)NHCH(CH₃)₂.

9. The compound of claim 1, wherein the compound is represented by a structural formula selected from:

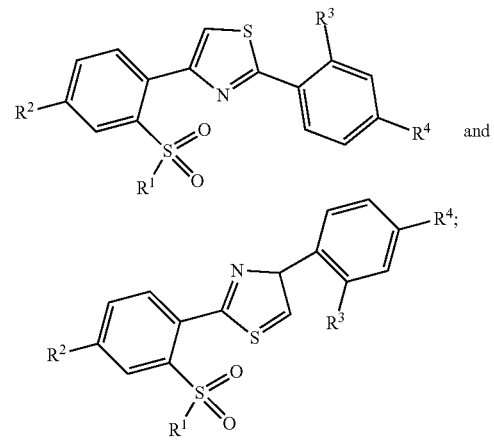

or a pharmaceutically acceptable salt thereof, wherein R³ is —H, halogen, —C(O)O(C₁-C₄)alkyl, —S(O)₂NH₂, or —SO₂NRᵃ(C₁-C₄)alkyl.

10. The compound of claim 9, or a pharmaceutically acceptable salt thereof, wherein:
the thiazole ring is optionally substituted with —F or —Cl;
R¹ is —NRᵃRᵃ, —NRᵃ(C₁-C₅)alkyl, or —N-monocyclic 4-7 membered nitrogen containing heterocyclic ring (wherein the nitrogen atom of the heterocyclic ring is attached to the sulfur atom);
wherein the (C₁-C₅)alkyl in the group represented by R¹ is optionally substituted with —ORᵃ, —OC(C₁-

$C_3$)alkylene-OH, —CO(O)CH$_3$, —NR$^a$R$^a$, —($C_3$-$C_6$)cycloalkyl, phenyl, or monocyclic 5-6 membered heteroaromatic ring;

R$^2$ is —H, —NH$_2$, —NO$_2$, —NR$^a$C(O)(C$_1$-C$_4$)alkyl, —NR$^a$C(O)O(C$_1$-C$_4$)alkyl, or —NR$^a$C(S)NR$^a$(C$_1$-C$_4$)alkyl;

R$^3$ is —H or —S(O)$_2$NR$^a$(C$_1$-C$_4$)alkyl;

R$^4$ is —H, —NH$_2$, —NO$_2$, —NR$^a$C(O)(C$_1$-C$_4$)alkyl, —NR$^a$C(O)O(C$_1$-C$_4$)alkyl, or —NR$^a$C(S)NR$^a$(C$_1$-C$_4$)alkyl; and each R$^a$ is independently —H, or —CH$_3$.

11. The compound of claim 10, or a pharmaceutically acceptable salt thereof, wherein:

the thiazole ring is optionally substituted with —F or —Cl;

R$^1$ is —NHCH$_3$, —NHCH$_2$CH$_3$, —N(CH$_3$)$_2$, —NHC(CH$_3$)$_3$, —NHCH$_2$CH$_2$OH, —NHCH(CH$_3$)CH$_2$OH, —NHCH$_2$C(CH$_3$)$_2$CH$_2$OH, —NHCH$_2$CH$_2$OCH$_3$, —NHCH$_2$C(O)OCH$_3$, —NHCH$_2$CH$_2$OCH$_2$CH$_2$OH, —NHCH(CH$_2$OH)$_2$, —NHCH$_2$CH$_2$NH$_2$, —NHCH$_2$CH$_2$NHCH$_3$, —NHCH$_2$CH$_2$N(CH$_3$)$_2$, —NHCH$_2$CH$_2$CH$_2$NH$_2$, —NHCH$_2$CH$_2$CH$_2$NHCH$_3$, —NHCH$_2$CH$_2$CH$_2$N(CH$_3$)$_2$, —NHCH$_2$-phenyl, —NHCH$_2$-pyridyl, —NH-cyclobutyl, or —N-pyrrolidinyl;

R$^2$ is —H, —NH$_2$, NO$_2$, —NHC(O)CH$_3$, —NHC(O)OCH(CH$_3$)$_2$, or —NHC(S)NHCH(CH$_3$)$_2$;

R$^3$ is —H or —S(O)$_2$NHCH(CH$_3$)$_3$; and

R$^4$ is —H, —NH$_2$, —NO$_2$, —NHC(O)CH$_3$, —NHC(O)OCH(CH$_3$)$_2$, or —NHC(S)NHCH(CH$_3$)$_2$.

12. A pharmaceutical composition comprising a pharmaceutically acceptable carrier or diluent and a compound of claim 1 or a pharmaceutically acceptable salt thereof.

13. A compound selected from:

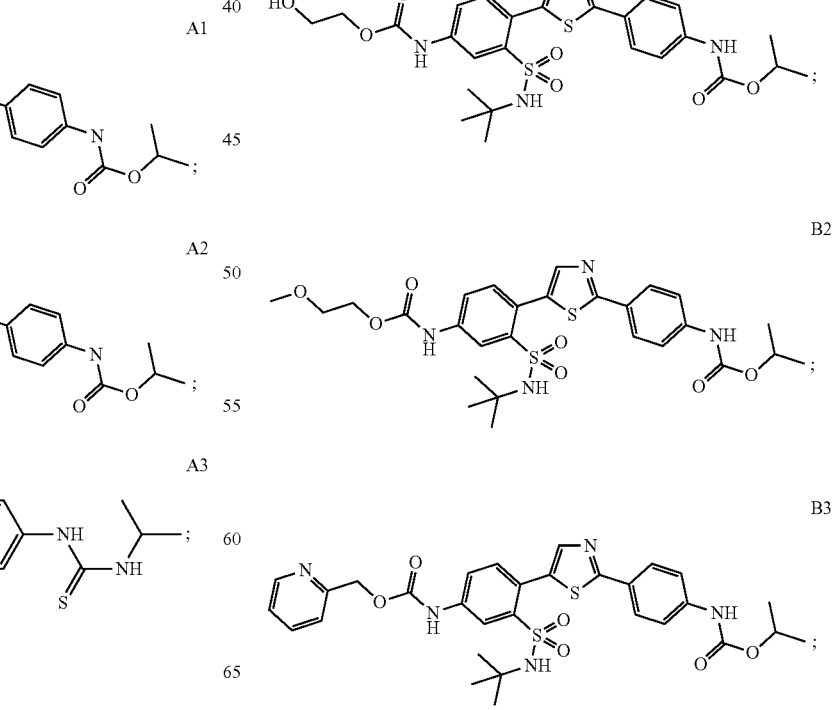

B4
B5
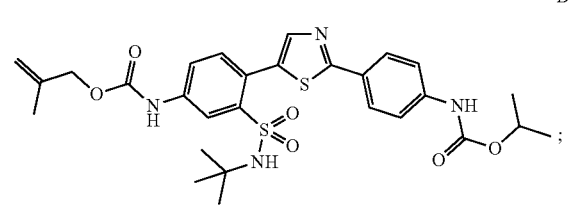
B6
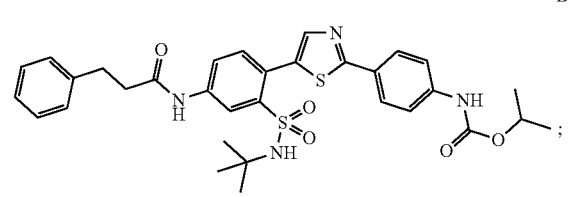
B7
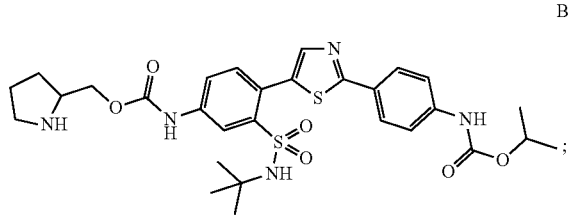
B8
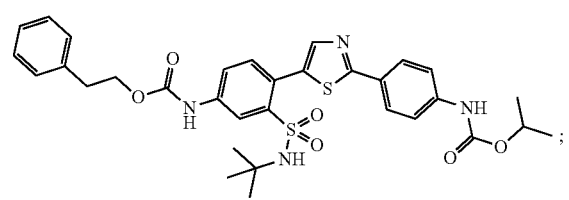
B9
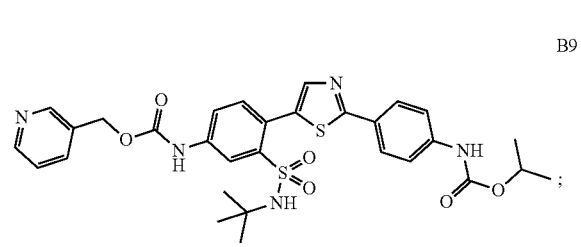
B10
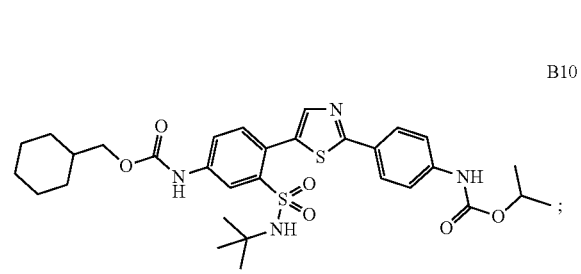
B11
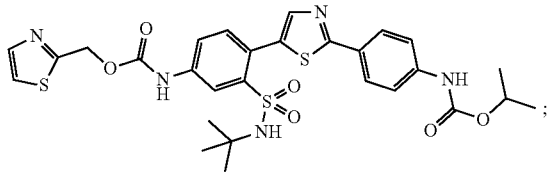
B12
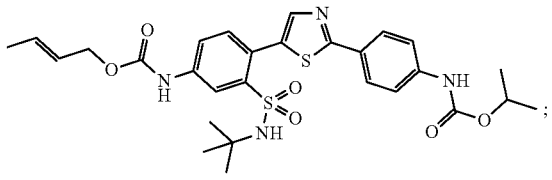
B13
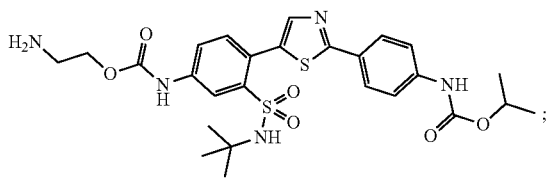
B14
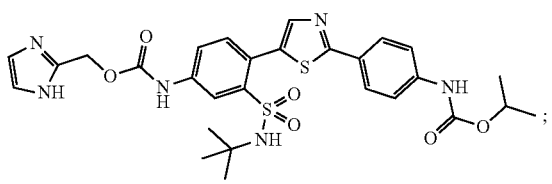
B15
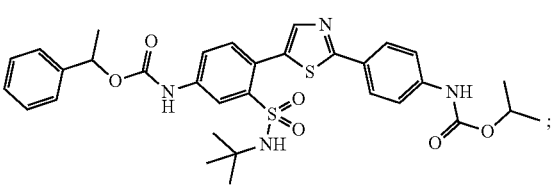
B16
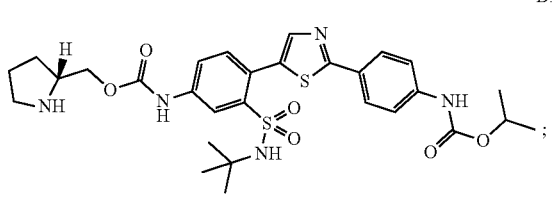
B17
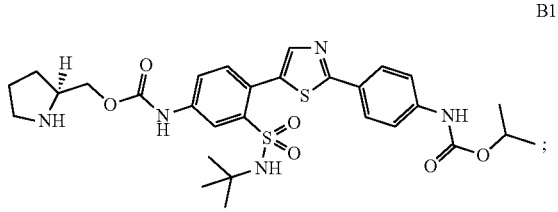
B18
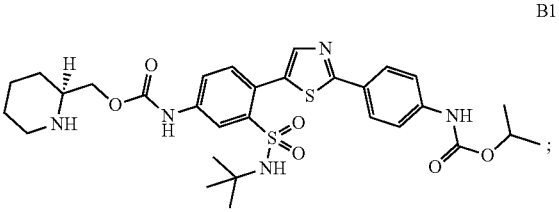

B19
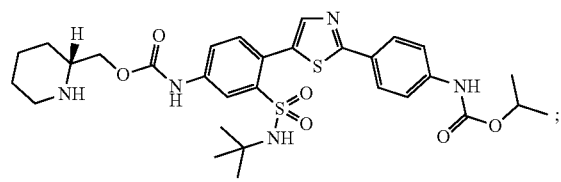
C1
C2
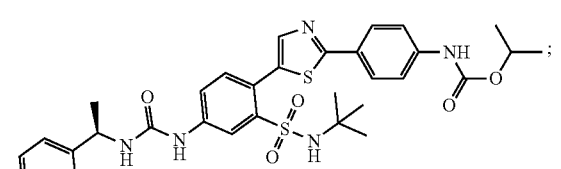
C3
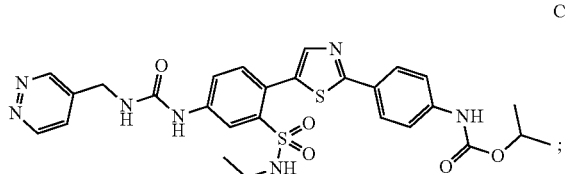
C4
C5
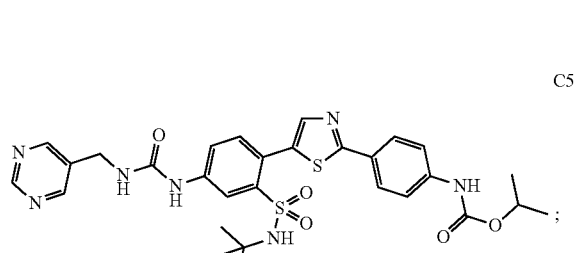
C6
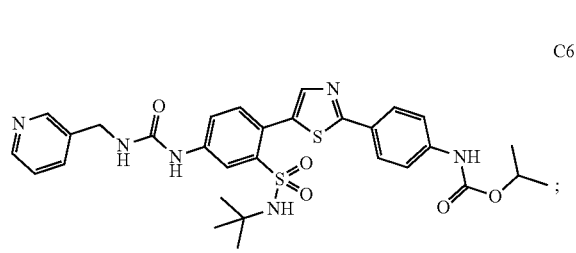
C7
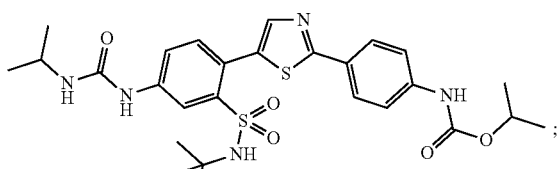
C8
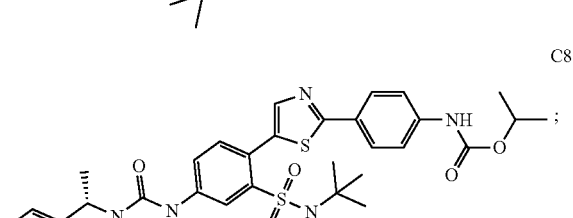
C9
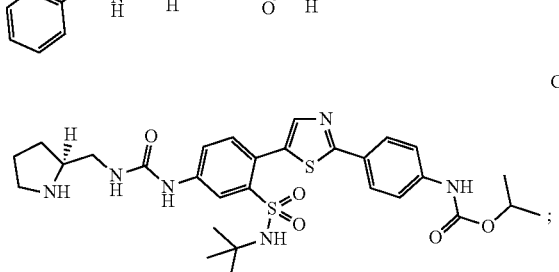
C10
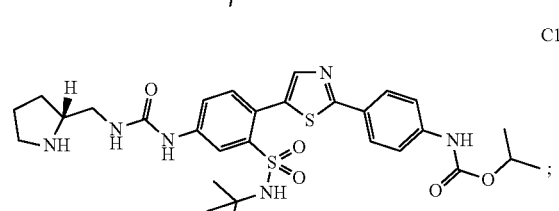
C11
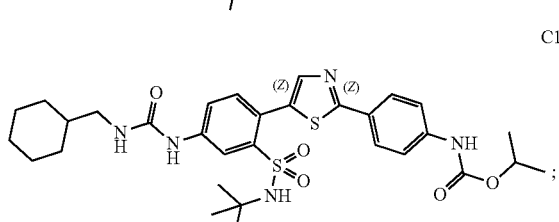
C12
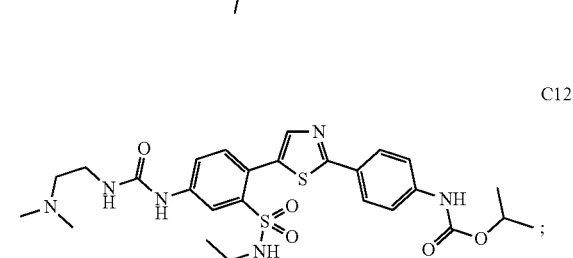
C13
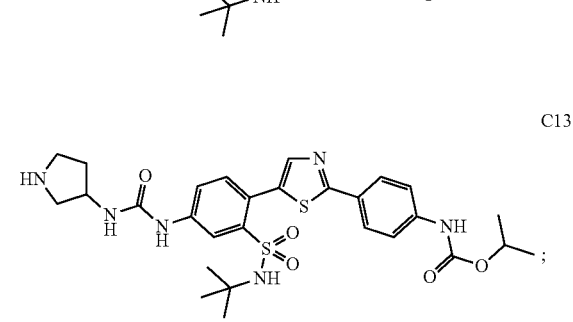

C14
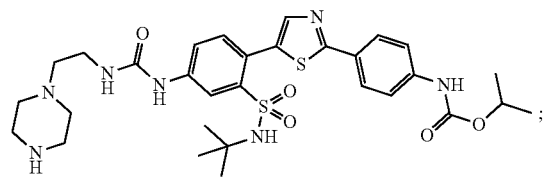
C15
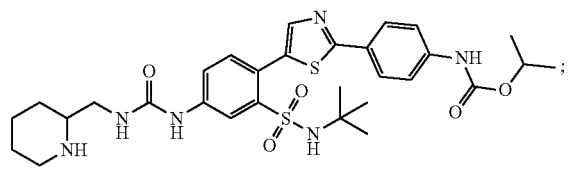
C16
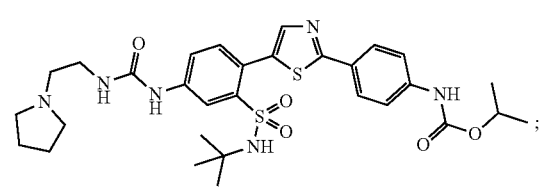
C17
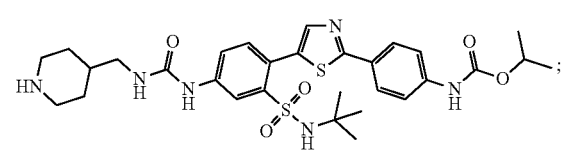
C18
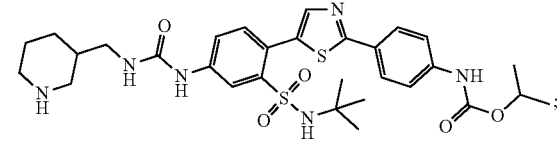
C19
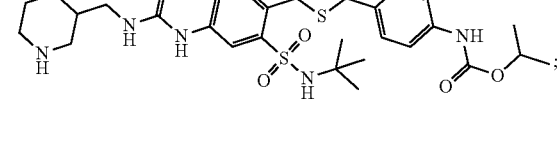
D1
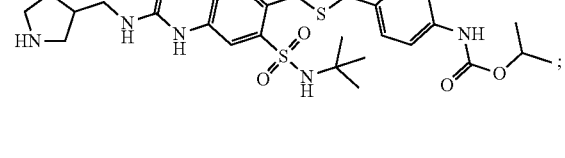
D2
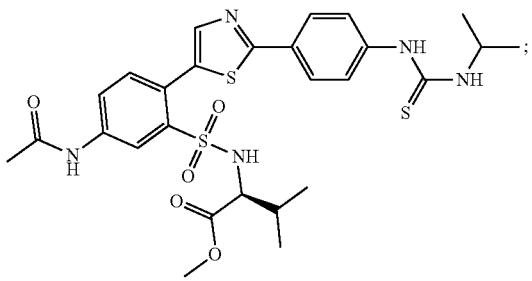
D3
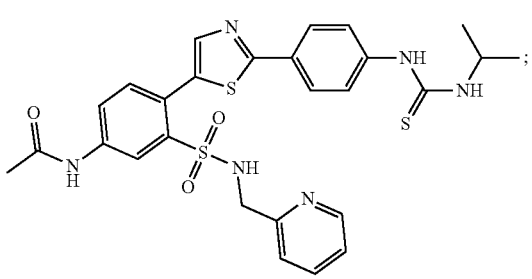
D4
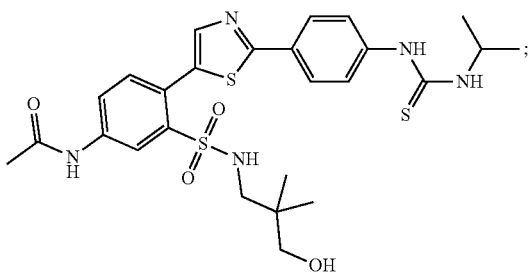
D5
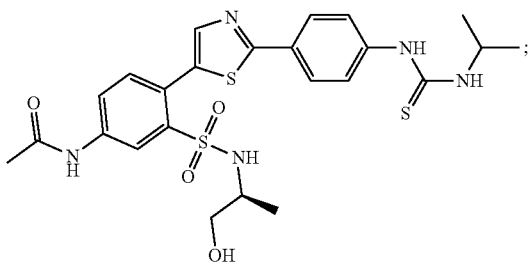
D6
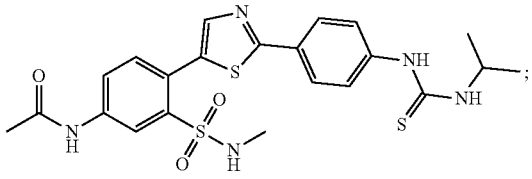

D7
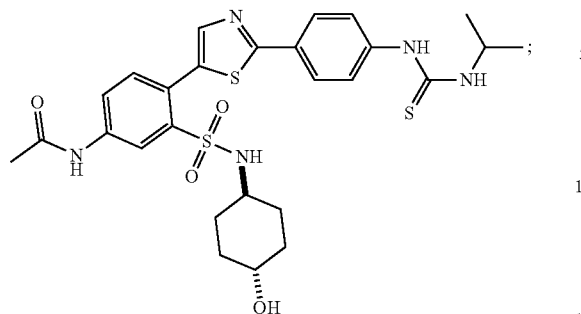
D8
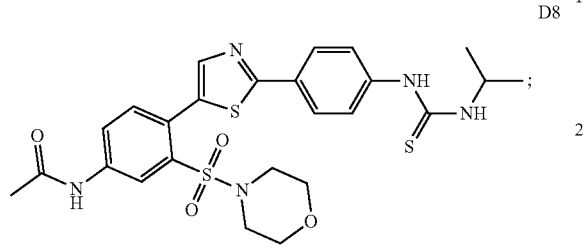
D9
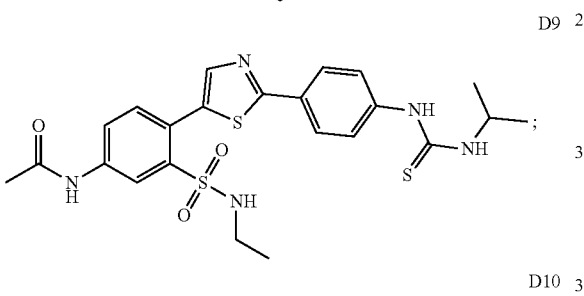
D10
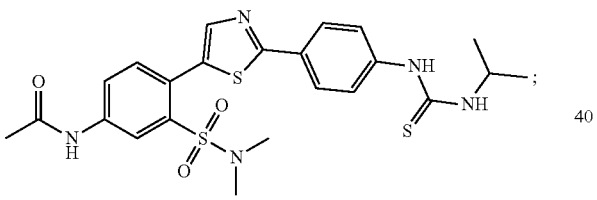
D11
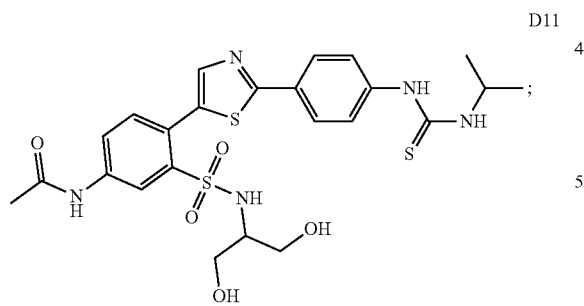
D12
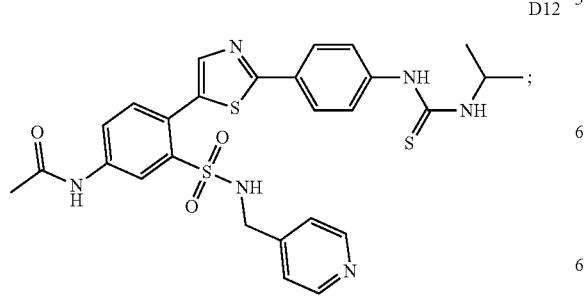
D13
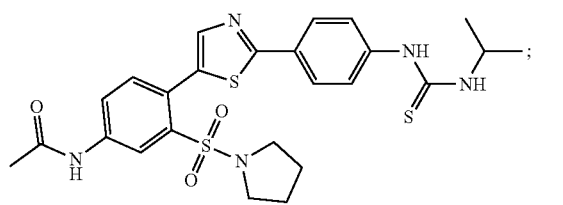
D14
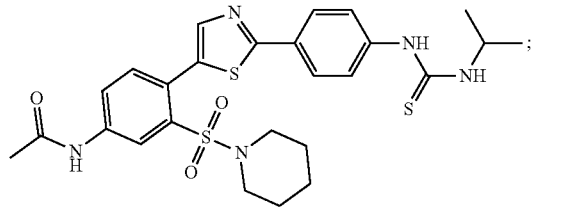
D15
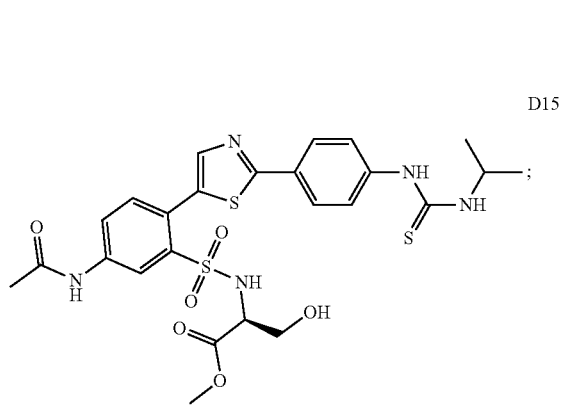
D16
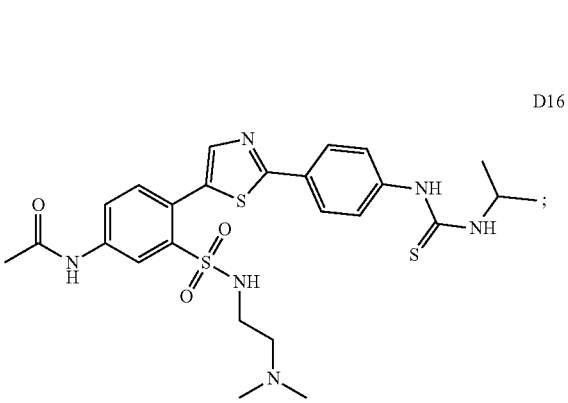
D17
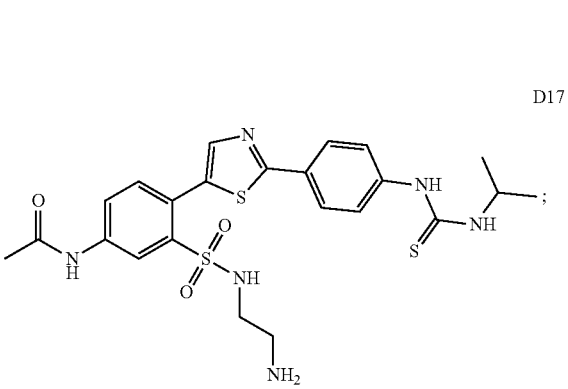

D18 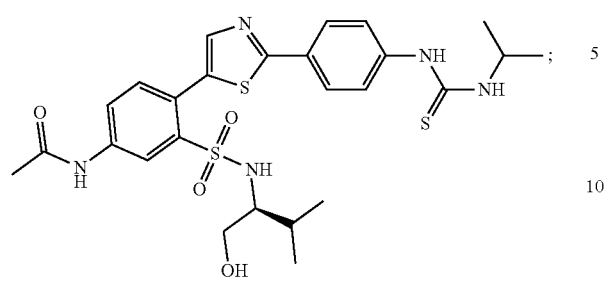
D19 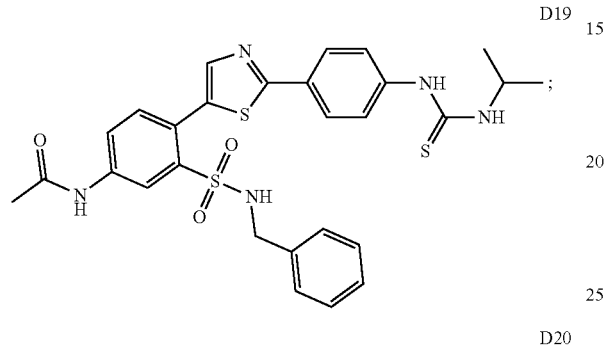
D20 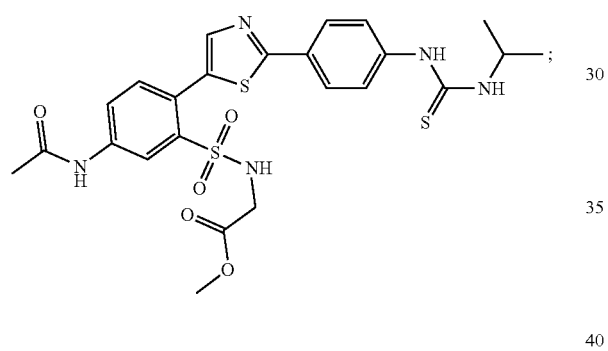
D21 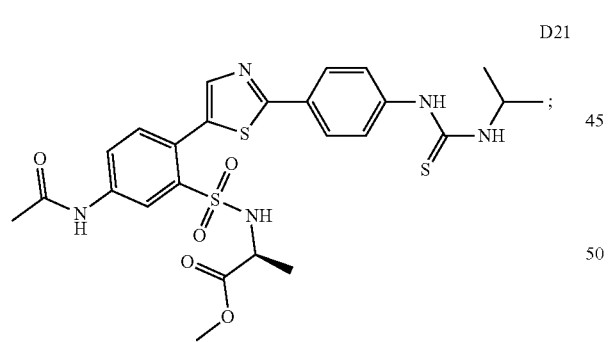
D22 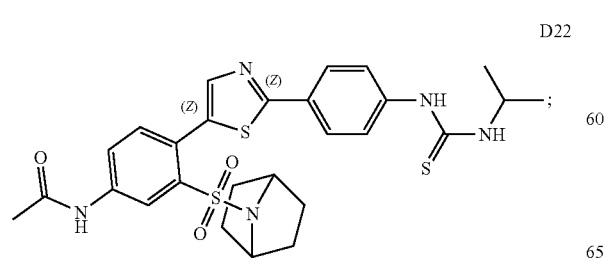
D23 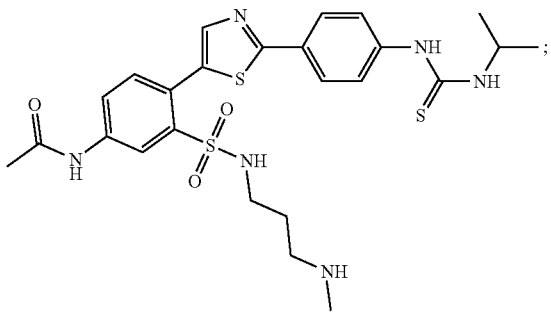
D24 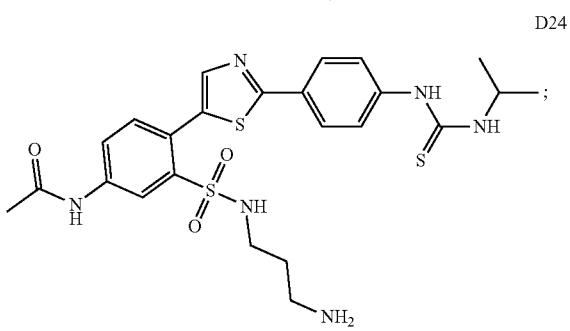
D25 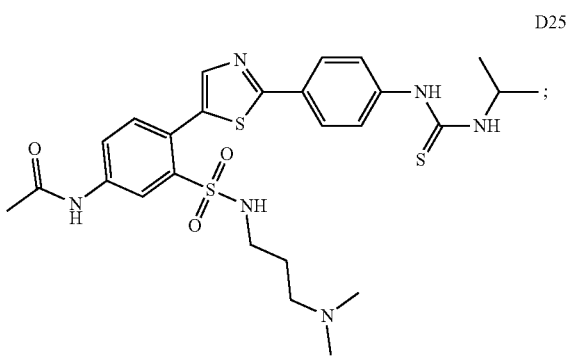
D26 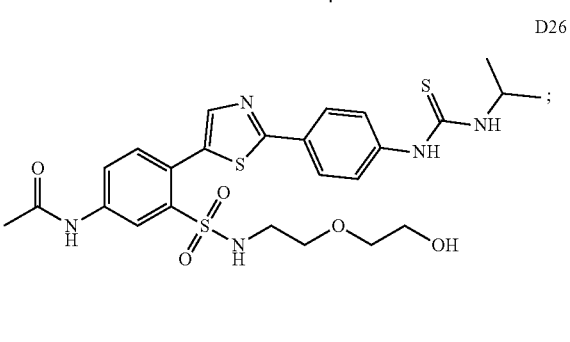
D27 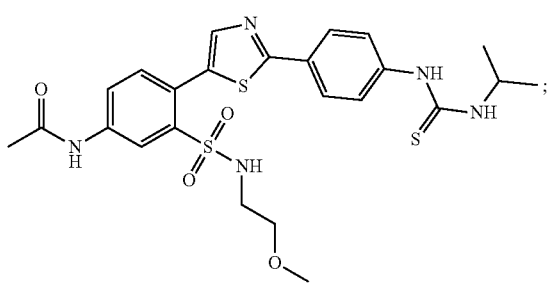

D28
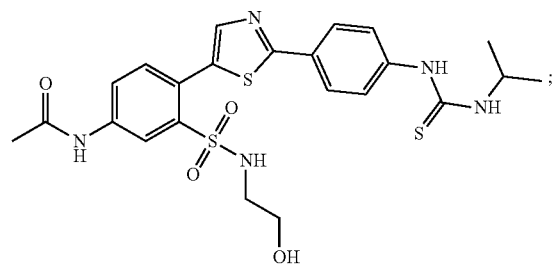
D29
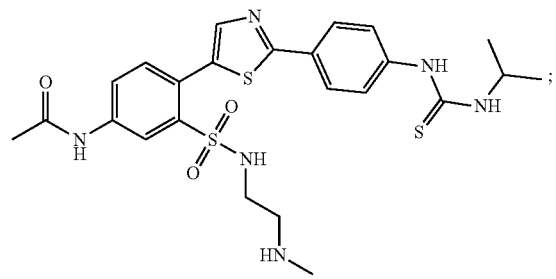
D30
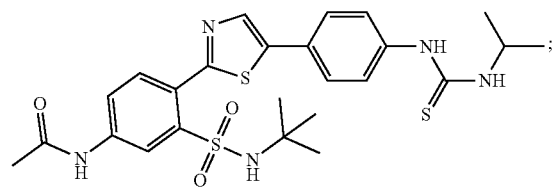
D31
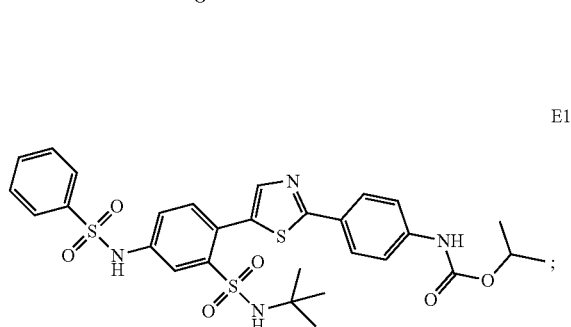
E1
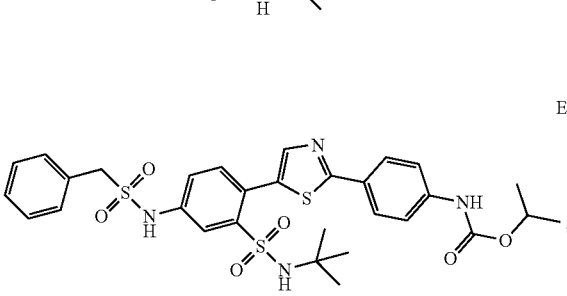
E2
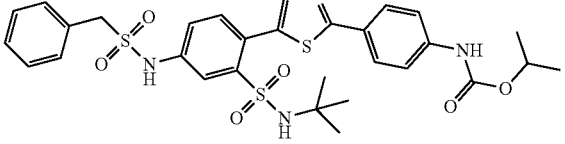
E3
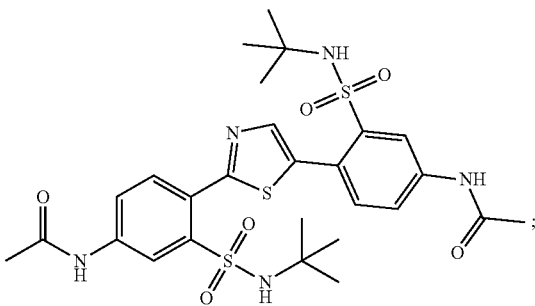
E4
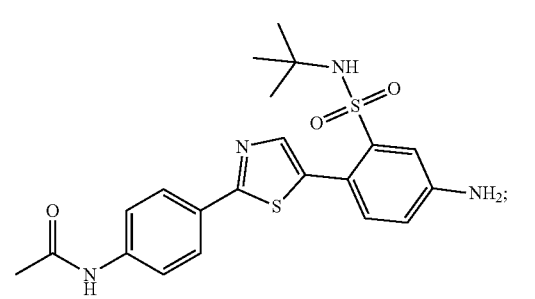
E5
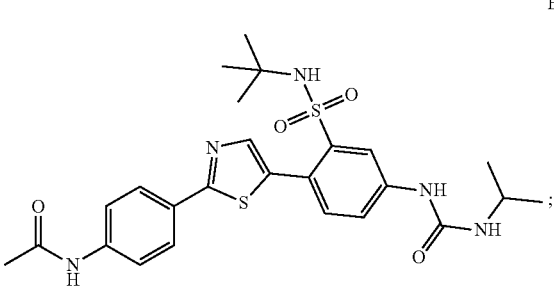
E6
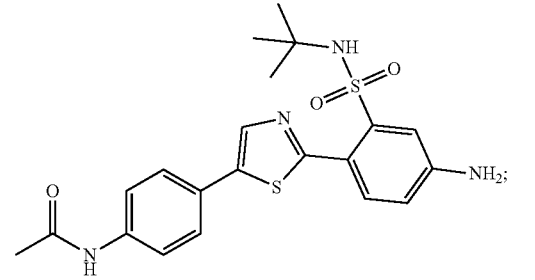
E7
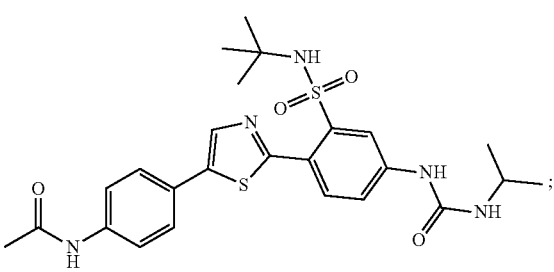

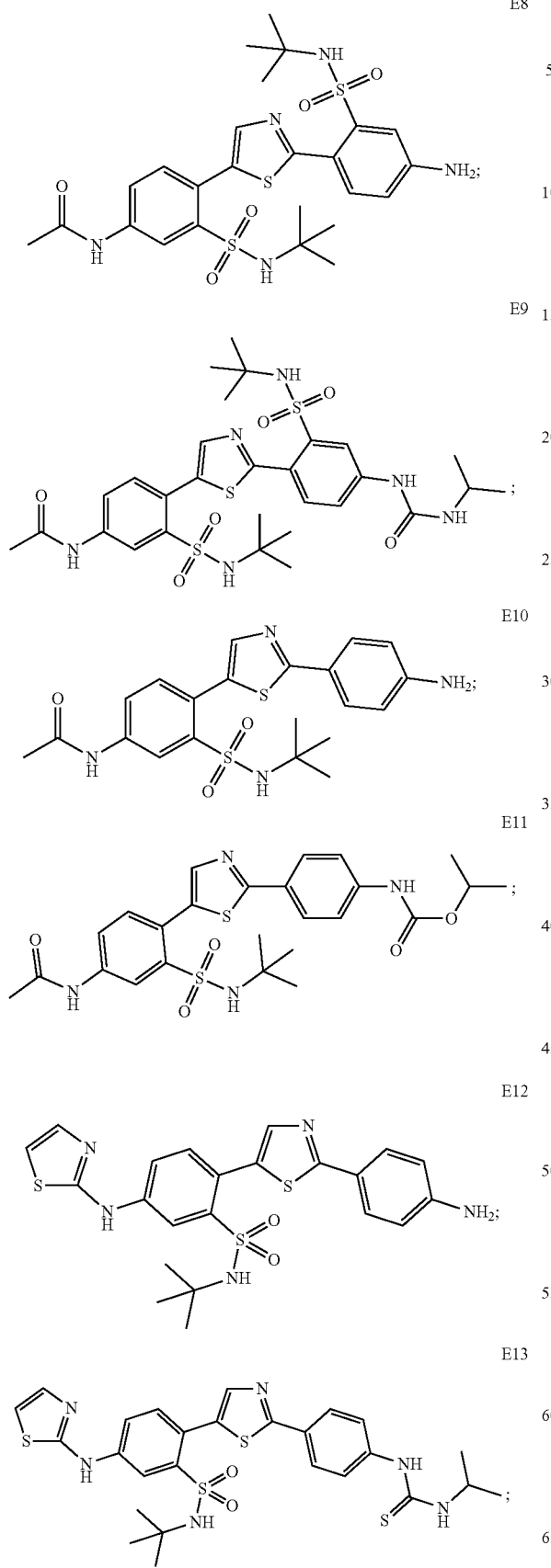
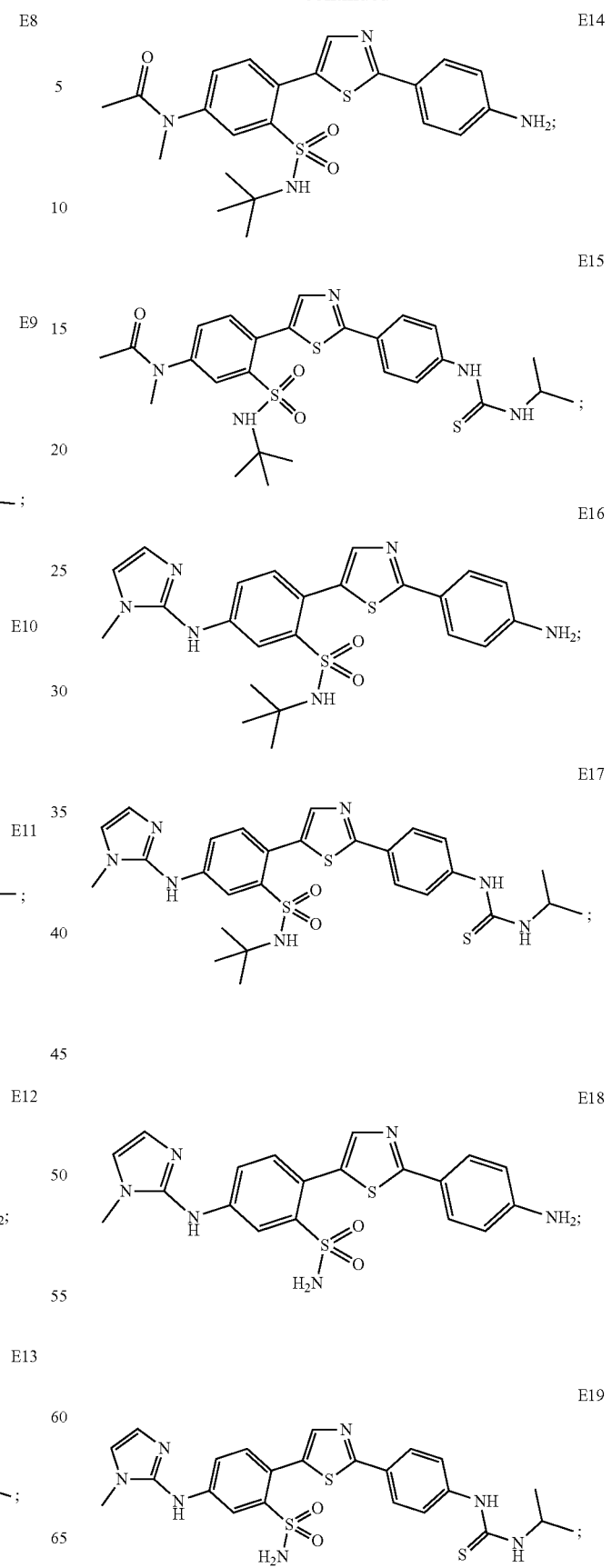

E20
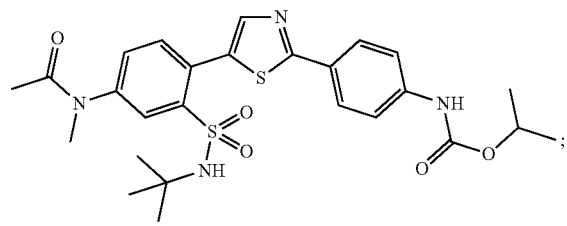
E21
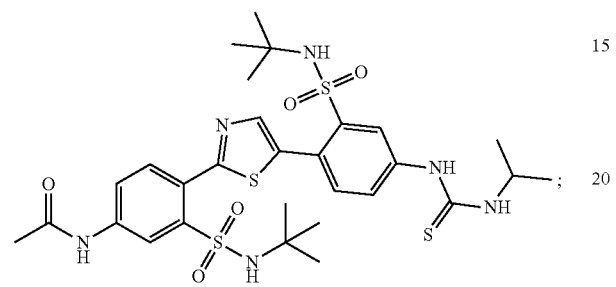
G1
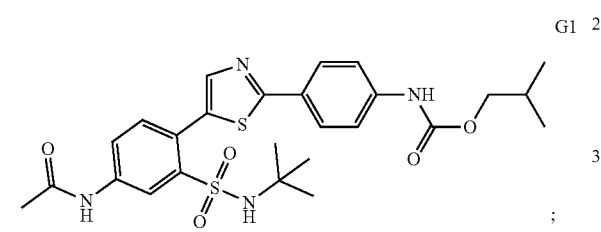
G2
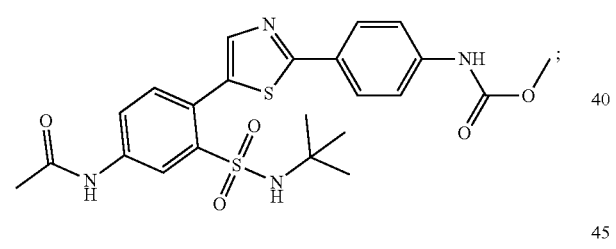
G3
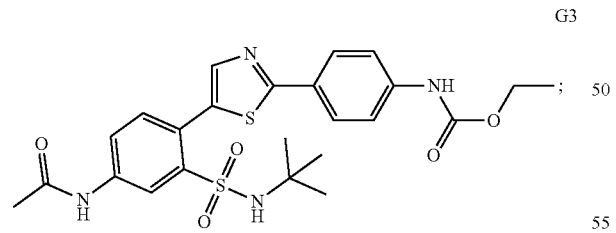
G4
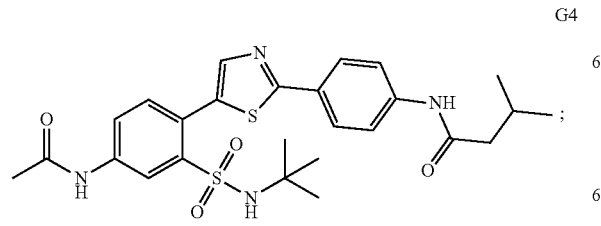
G5
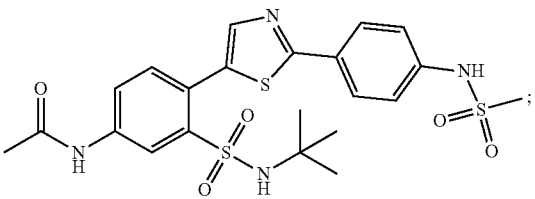
G6
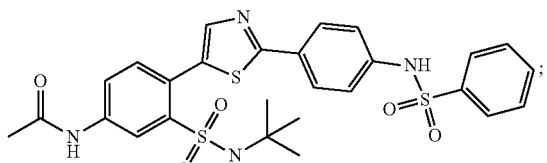
G7
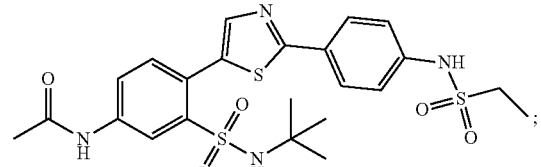
G8
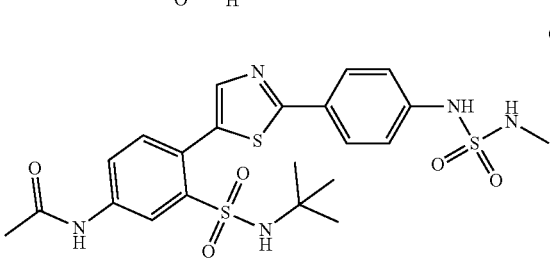
G9
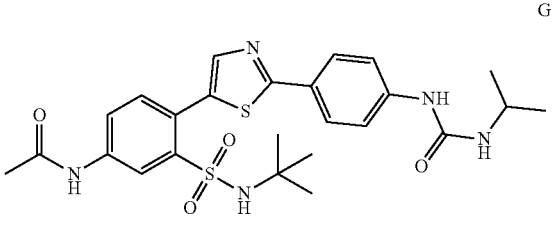
G10
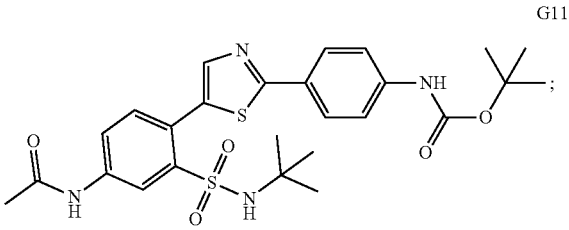
G11

H1 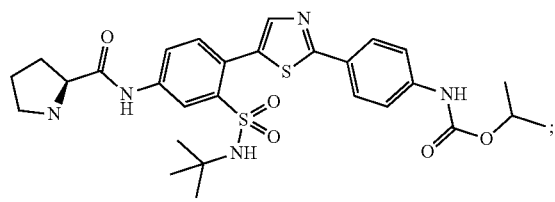
H2 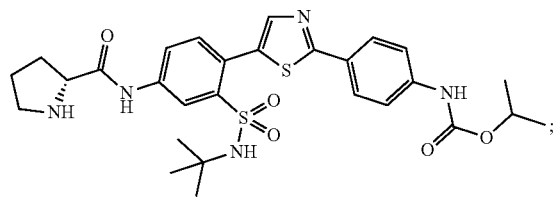
H3 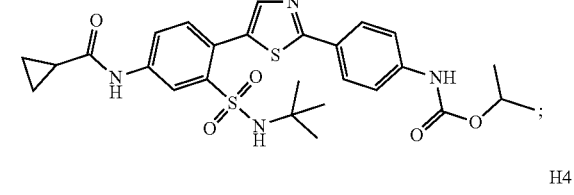
H4 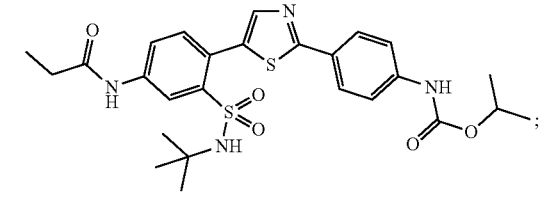
H5 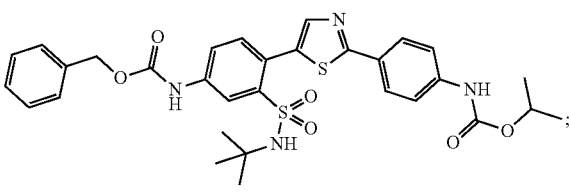
H6 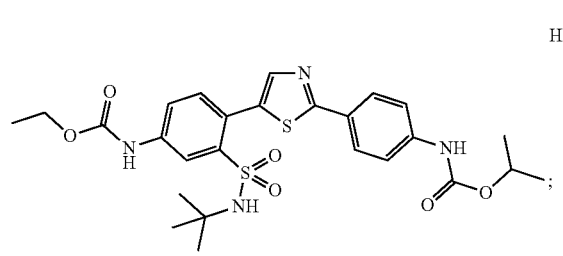
H7 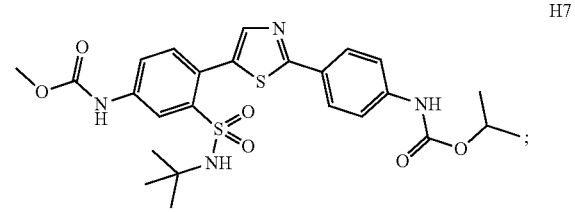
H8 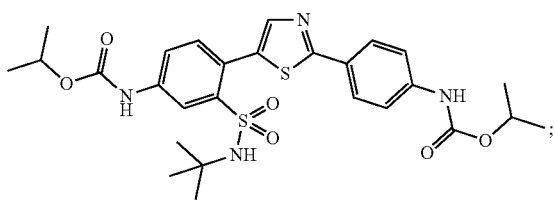
H9 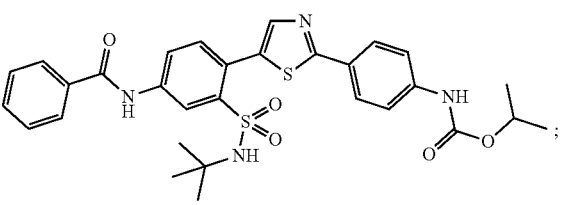
H10 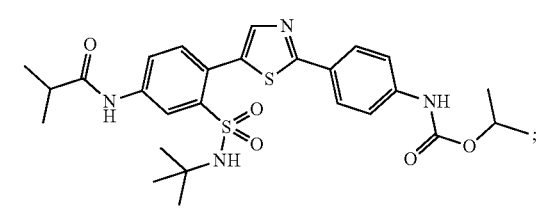
H11 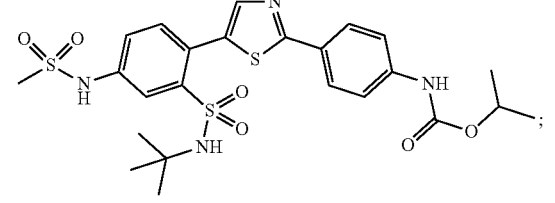
I1 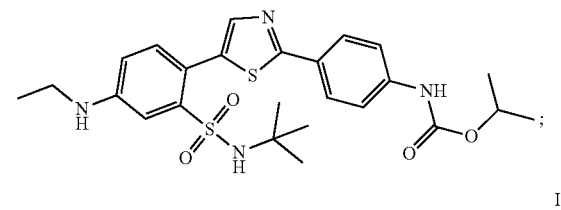
I2 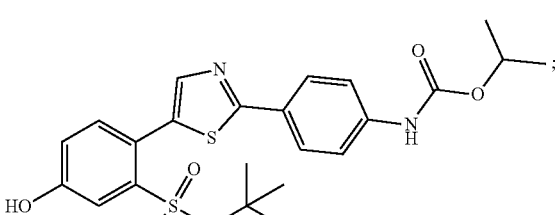
I3 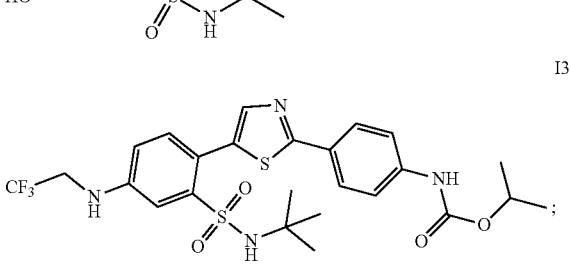

I4
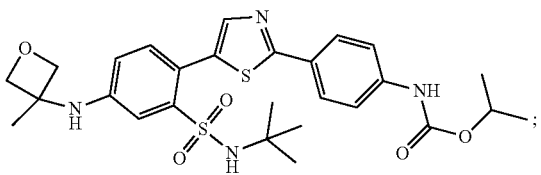
I5
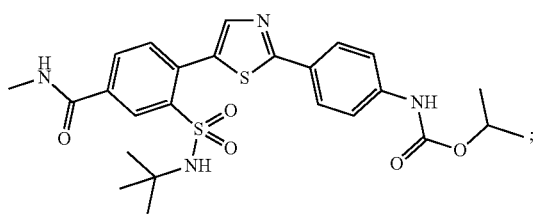
I6
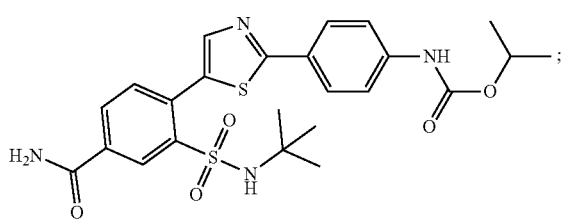
I7
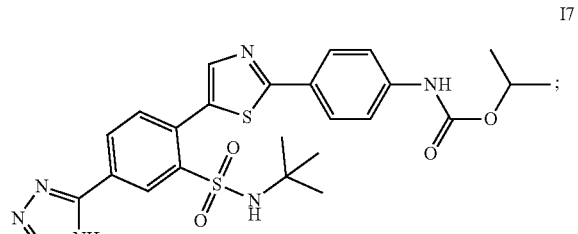
J1
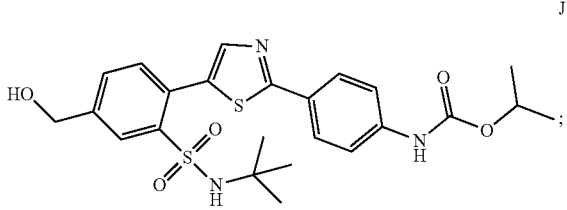
J2
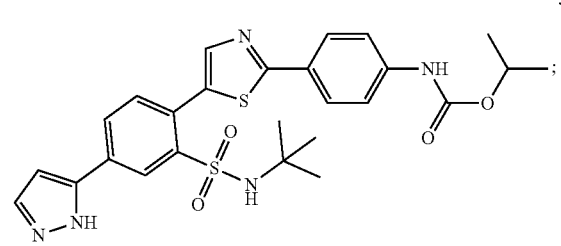
J3
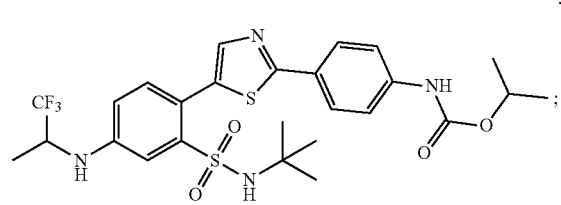
J4
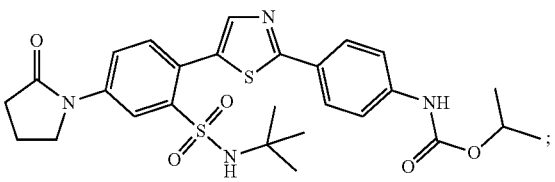
J6
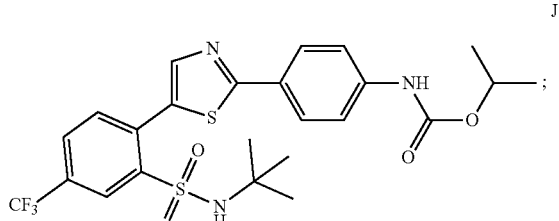
J7
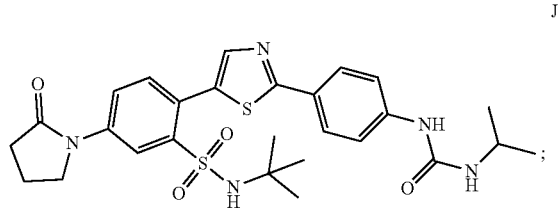
J8
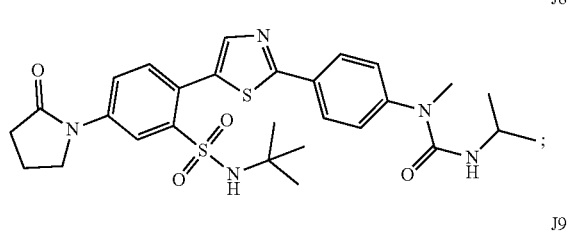
J9
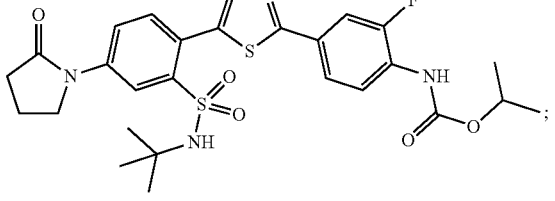
J10
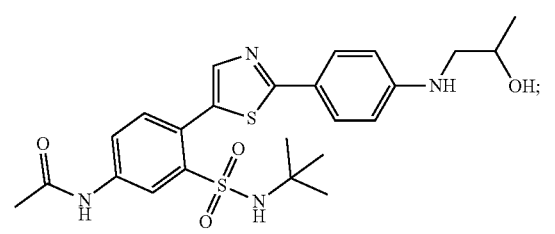
J11
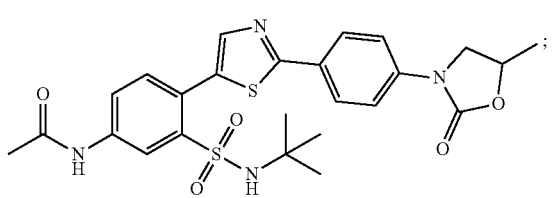

-continued
J12
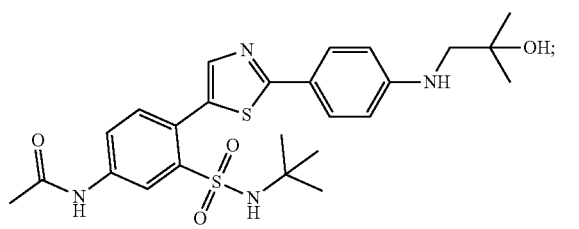
J13
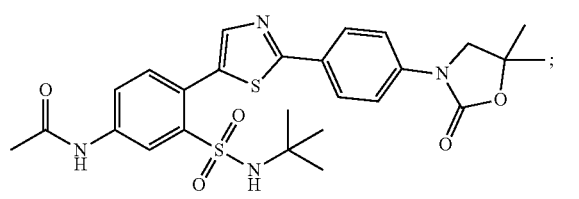
J15
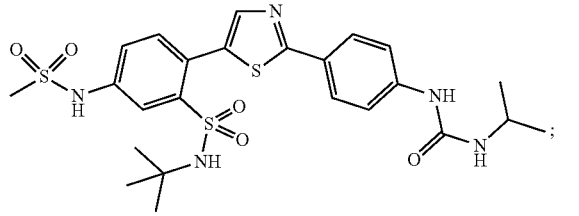
J16
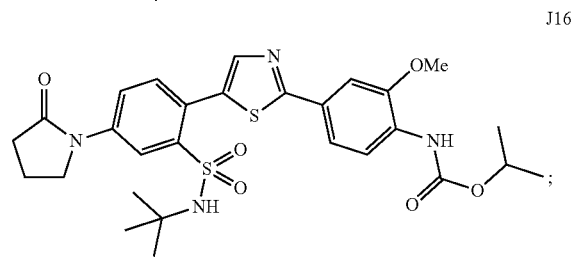
J17
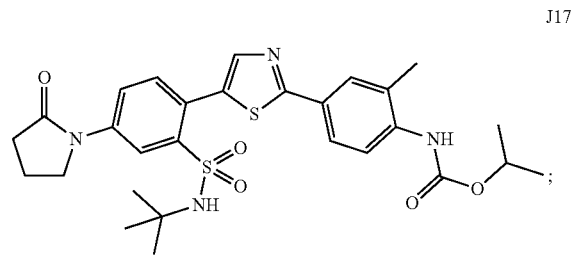
J18
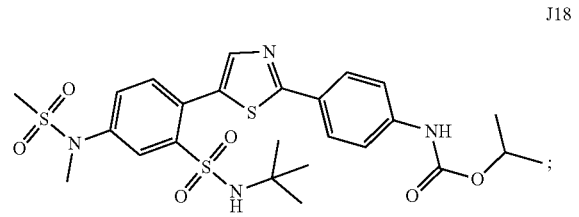
J18
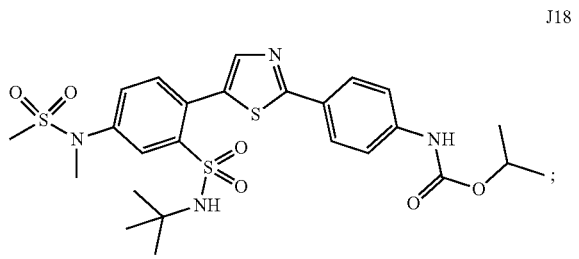
-continued
J19
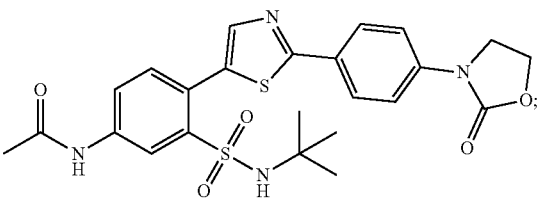
J20
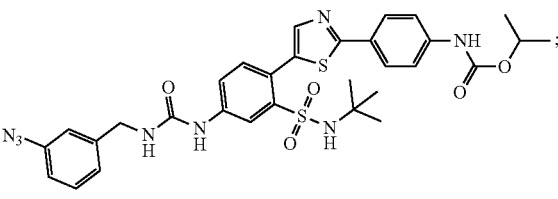
J21
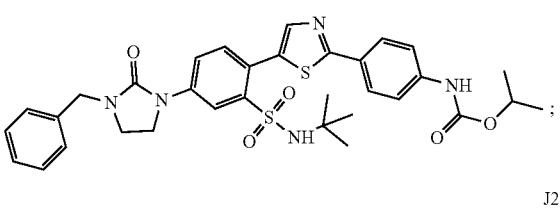
J22
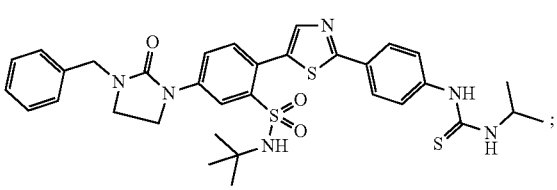
J23
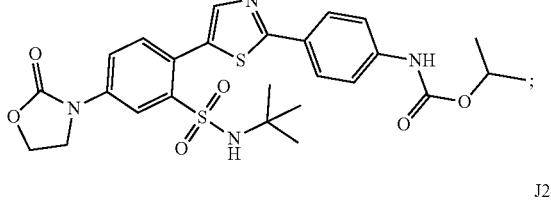
J24
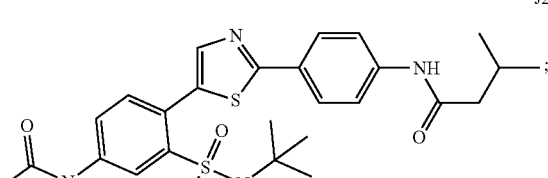
J25
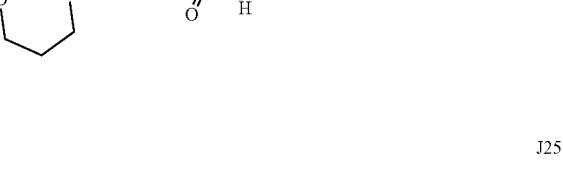

-continued
J26
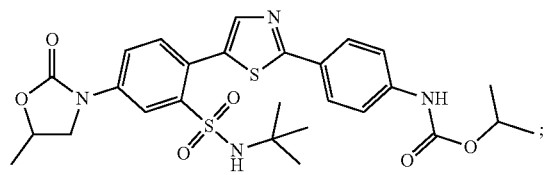
J27
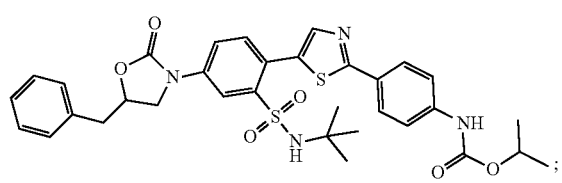
J28
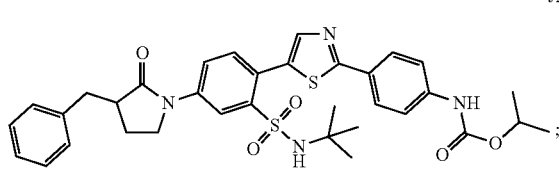
J29
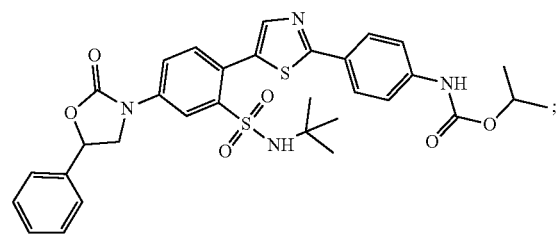
K1
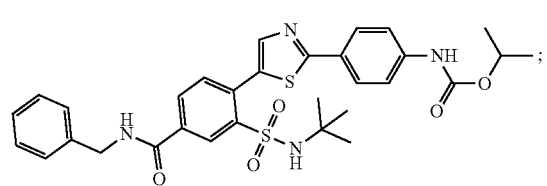
K2
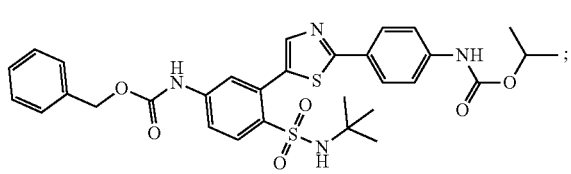
L1
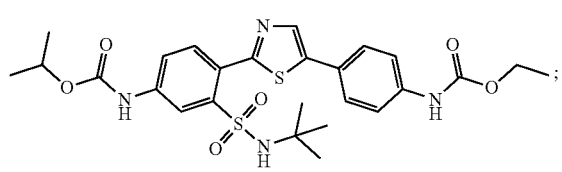
L2
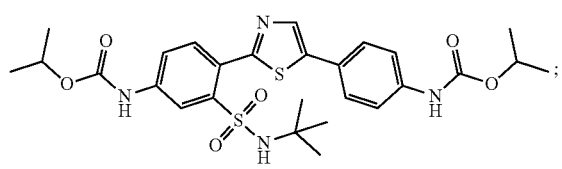
-continued
L3
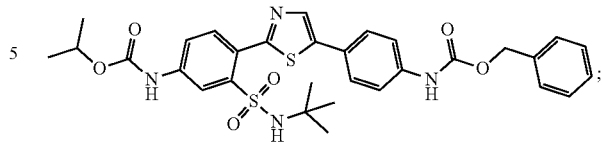
L4
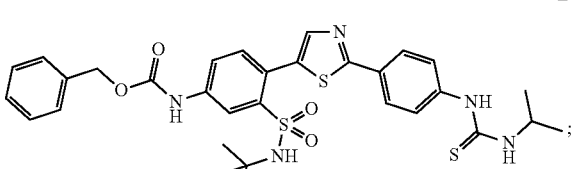
L5
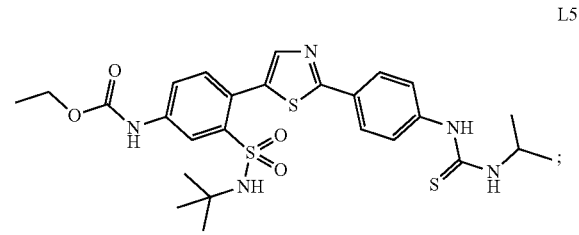
L6
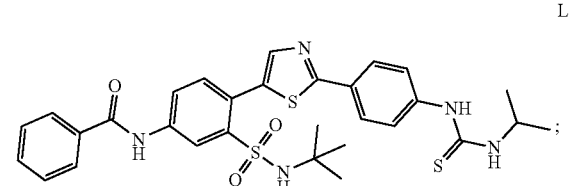
L7
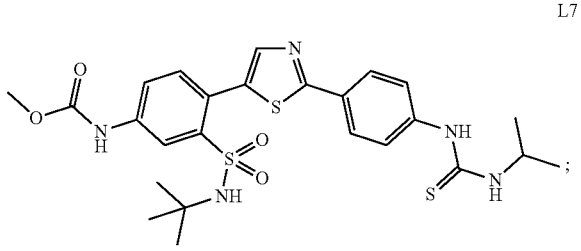
L8
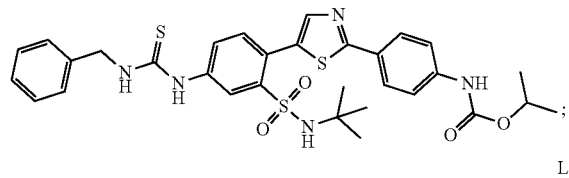
L9
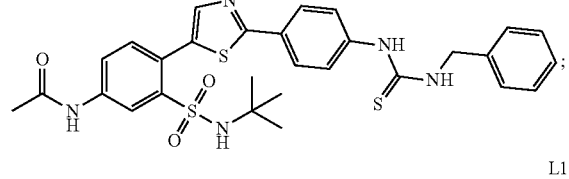
L10
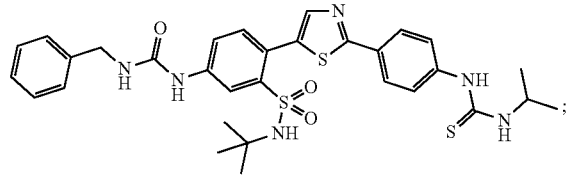

M1
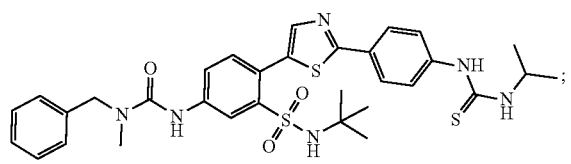
M2
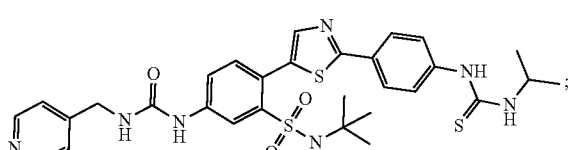
M3
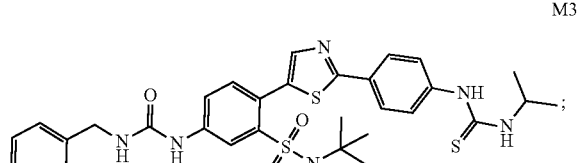
M4
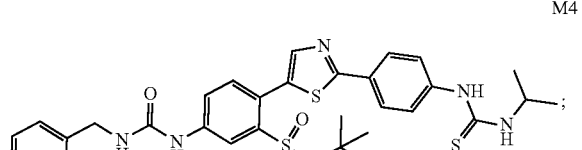
M5
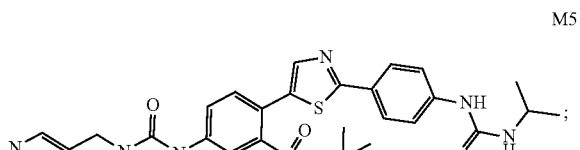
M6
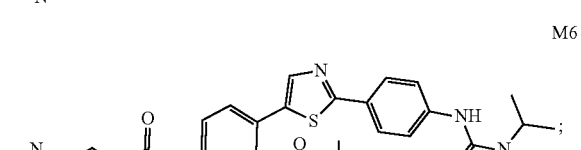
M7
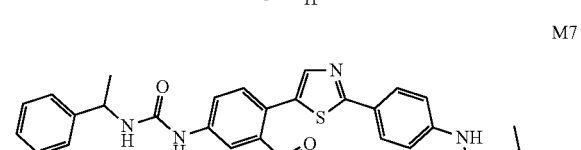
M8
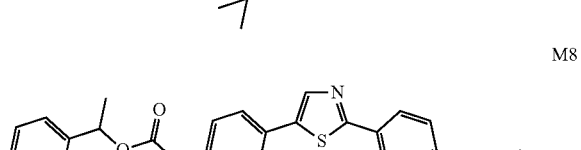
N1
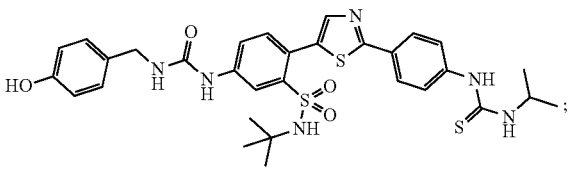
N2
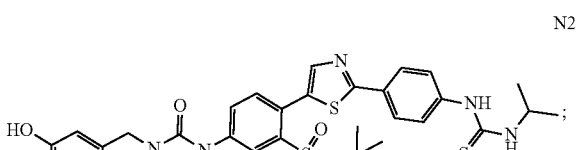
N3
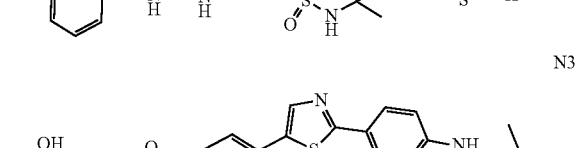
N4
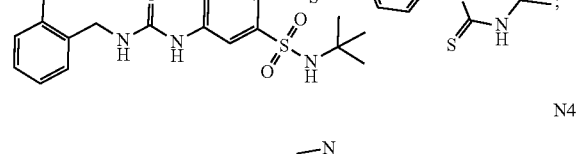
N5
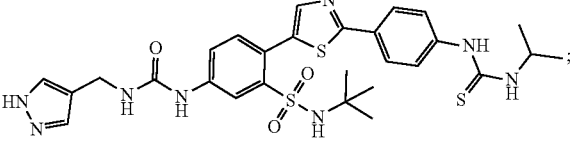
N6
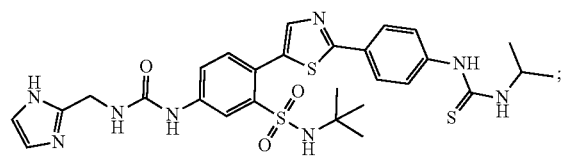
O1
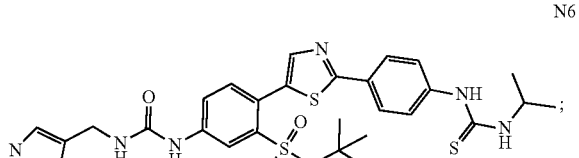
O2
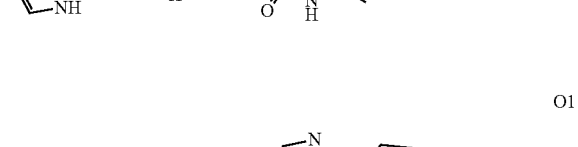

317
-continued
O3
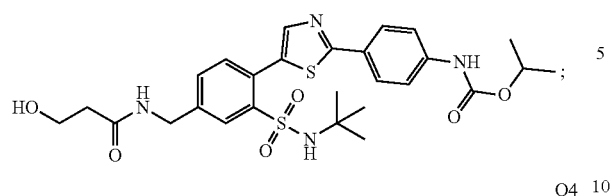
O4
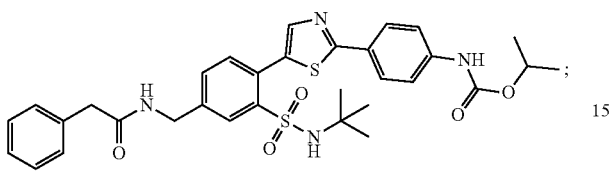
O5
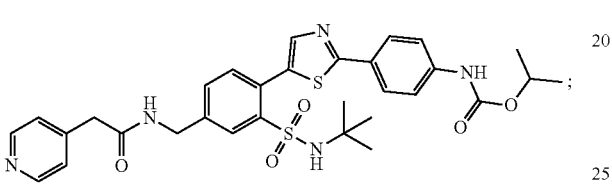
O6
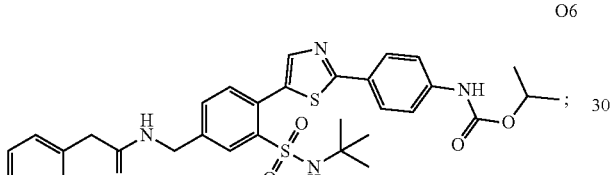
O7
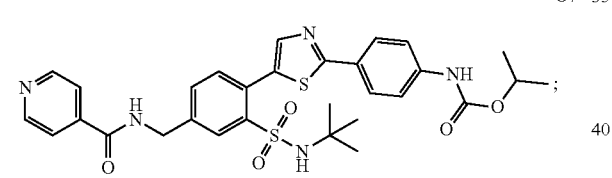
O8
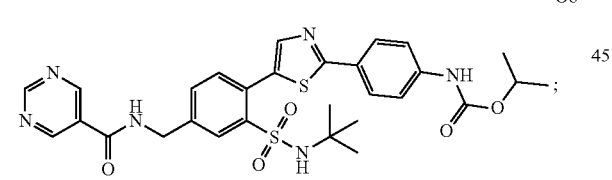
P1
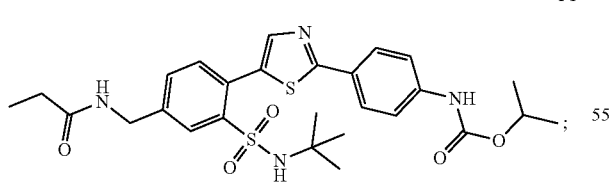
P2
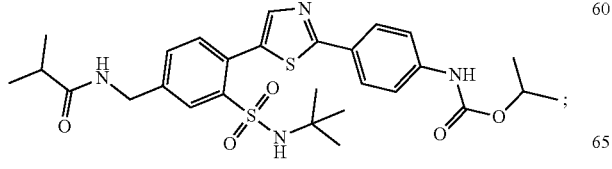
318
-continued
P3
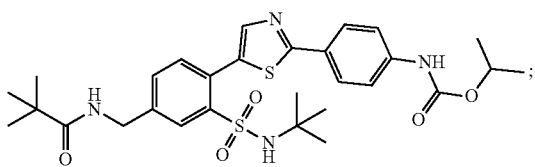
P4
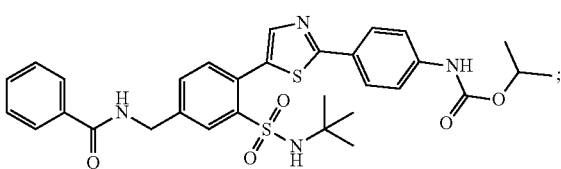
P5
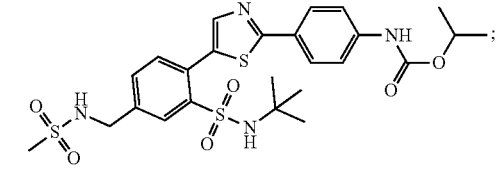
P6
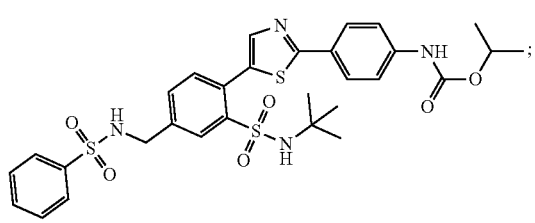
P7
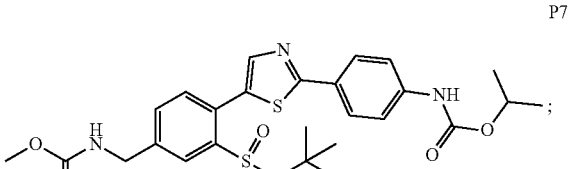
P8
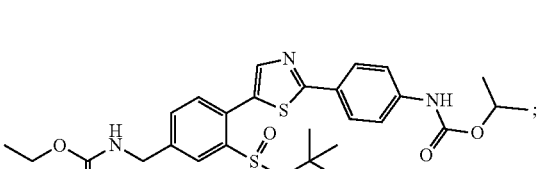
P9
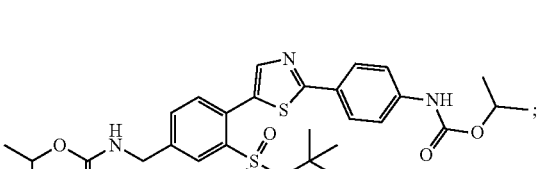
Q1
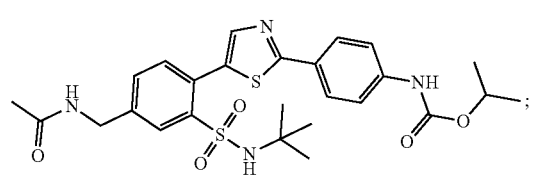

-continued
Q2
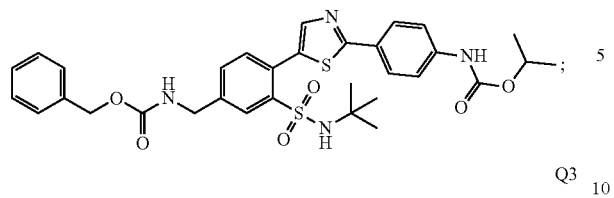
Q3
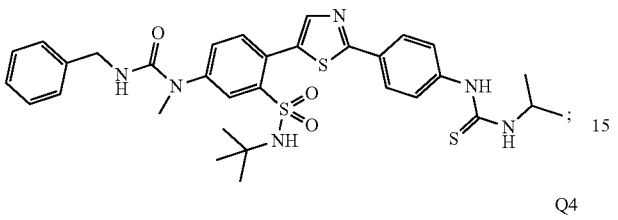
Q4
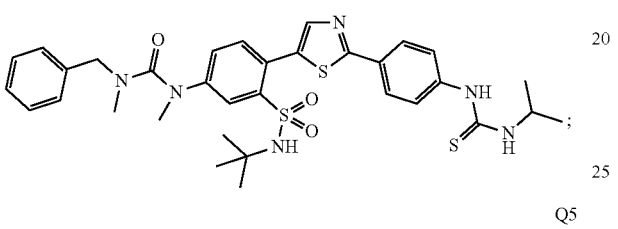
Q5
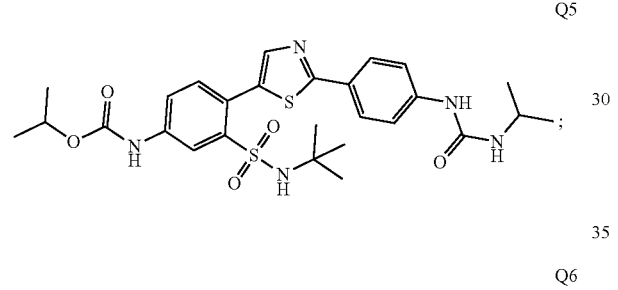
Q6
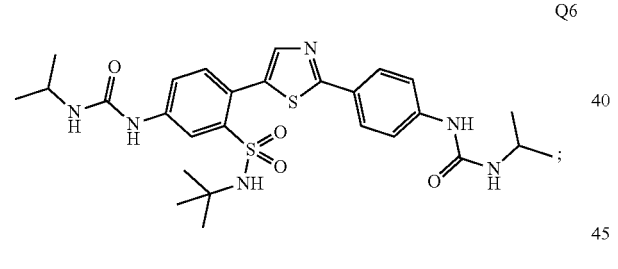
R1
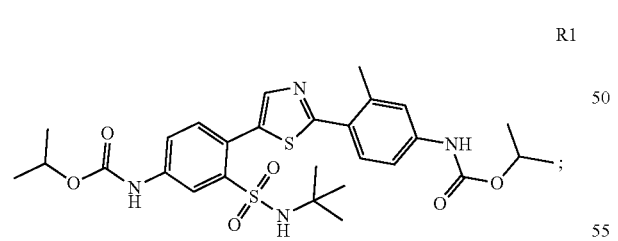
R2
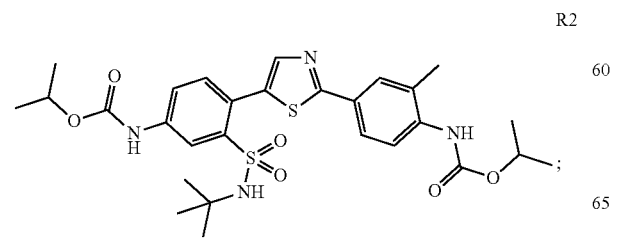
-continued
R3
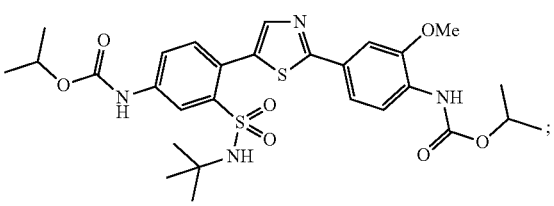
R4
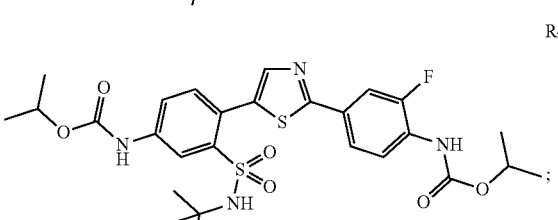
R5
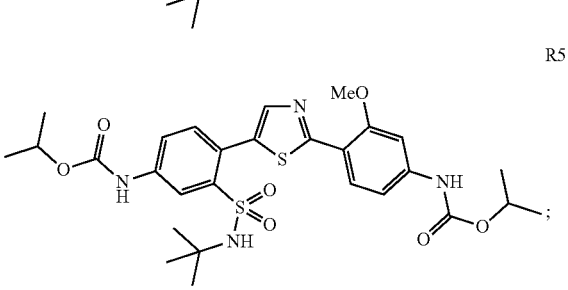
R6
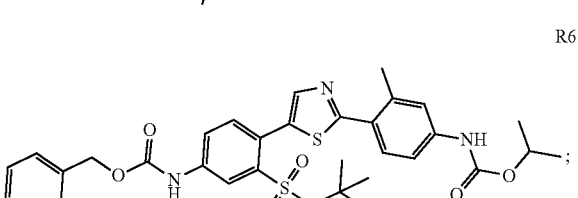
R7
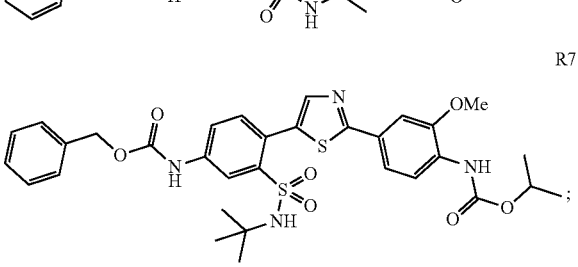
R8
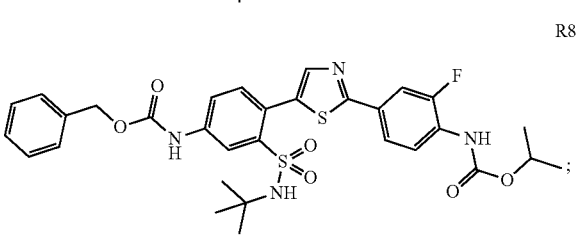
R9
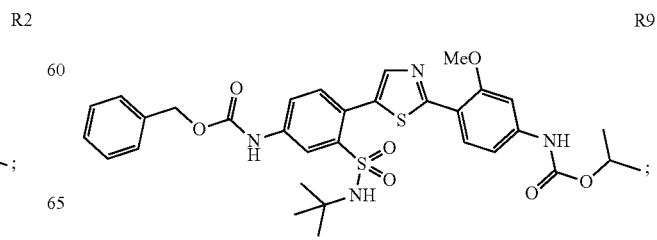

R10
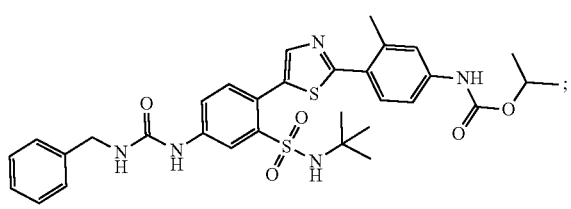

R11
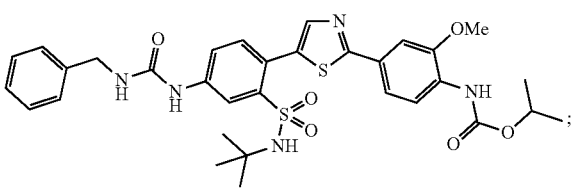

R12
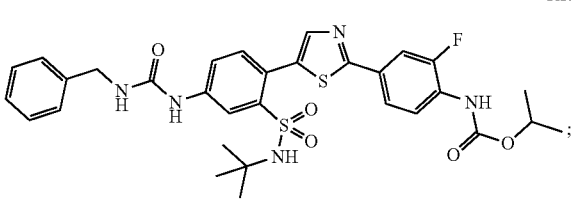

R13
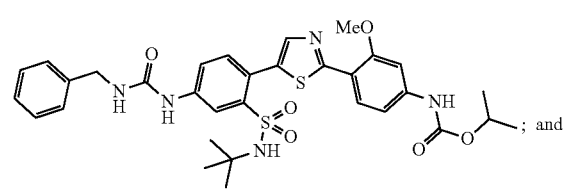 ; and

R14
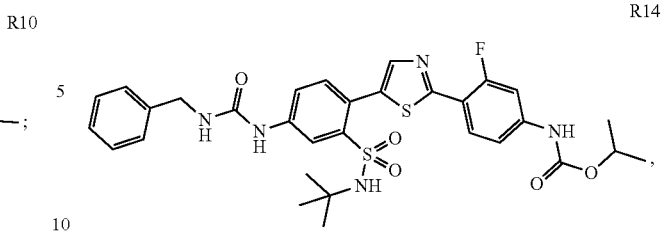

or a pharmaceutically acceptable salt thereof.

14. A method of treating cancer, autoimmune disease, immune deficiency, or neurodegenerative disease, the method comprising administering to a subject in need thereof an effective amount of a compound of claim 1 or a pharmaceutically acceptable salt thereof.

15. The method of claim 14, wherein the method is a method of treating cancer and the cancer is selected from the group consisting of lymphoma, leukemia, and a plasma cell neoplasm.

16. The method of claim 14, wherein the method is a method of treating cancer selected from the group consisting of epithelial cell cancer; colon cancer; liver cancer; gastric cancer; intestinal cancer; esophageal cancer; breast cancer; ovarian cancer; head and neck cancer; lung cancer; and thyroid cancer.

17. The method of claim 14, wherein the method is a method of treating autoimmune disease selected from the group consisting of lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; inflammatory chronic rhinosinusitis; colitis; celiac disease; inflammatory bowel disease; Barrett's esophagus; inflammatory gastritis; autoimmune nephritis; autoimmune vasculitis; autoimmune hepatitis; autoimmune carditis; autoimmune encephalitis; autoimmune diabetes; autoimmune diabetes nephritis; and autoimmune mediated hematological disease.

18. The method of claim 14, further comprising the step of co-administering to the subject an effective amount of a DNA damaging agent.

19. The method of claim 14, wherein the subject is determined to have an increased level and/or activity of a DNA damage process or DNA editing enzyme.

20. The method of claim 14, wherein blood cells obtained from the subject have been determined to have a detectable level of activation-induced cytidine deaminase (AID).

* * * * *

UNITED STATES PATENT AND TRADEMARK OFFICE
CERTIFICATE OF CORRECTION

PATENT NO. : 11,291,655 B2
APPLICATION NO. : 16/623850
DATED : April 5, 2022
INVENTOR(S) : Alfredo C. Castro et al.

It is certified that error appears in the above-identified patent and that said Letters Patent is hereby corrected as shown below:

In the Claims

At Column 284, Claim number 4, Line number 54, replace:
"–CH$_2$–CH(O)-phenyl"
With:
-- -CH$_2$NHC(O)-phenyl --

At Column 285, Claim number 4, Line number 17, replace:
"–NHC(O)OCH$_2$C(CH$_3$)–CH$_2$"
With:
-- -NHC(O)OCH$_2$C(CH$_3$)=CH$_2$ --

At Column 285, Claim number 4, Line number 23, replace:
"–NHC(O)–CH$_2$-pyridyl"
With:
-- -NHC(O)O-CH$_2$-pyridyl --

At Column 285, Claim number 4, Line number 50-65, replace:

" 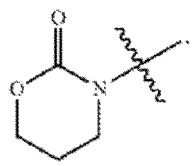

optionally substituted with benzyl,"
With:

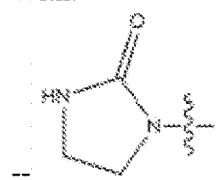

--

Signed and Sealed this
First Day of August, 2023

Katherine Kelly Vidal
*Director of the United States Patent and Trademark Office* optionally substituted with benzyl,

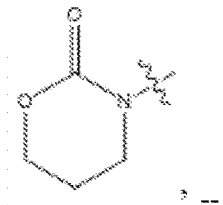

, --

At Column 286, Claim number 5, Line number 37, replace:
"(O)NH–(CH$_2$)$_2$–(C$_3$-C$_6$)cycloalkyl,"
With:
-- (O)NH-(CH$_2$)$_n$-(C$_3$-C$_6$)cycloalkyl, --

At Column 287, Claim number 6, Line number 23, replace:
"[–N(CH$_3$)$_2$),"
With:
-- -N(CH$_3$)$_2$), --

At Column 288, Claim number 7, Line number 3, replace:
"R$^3$ –H or halogen;"
With:
-- R$^3$ is -H or halogen; --

At Column 288, Claim number 8, Line number 18, replace:
"or N$_3$,"
With:
-- or N$_3$), --